US012054754B2

(12) United States Patent
Scott et al.

(10) Patent No.: US 12,054,754 B2
(45) Date of Patent: Aug. 6, 2024

(54) CRISPR-ASSOCIATED TRANSPOSON SYSTEMS AND COMPONENTS

(71) Applicant: Arbor Biotechnologies, Inc., Cambridge, MA (US)

(72) Inventors: David A. Scott, Cambridge, MA (US); David R. Cheng, Boston, MA (US); Winston X. Yan, Boston, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 701 days.

(21) Appl. No.: 16/761,206

(22) PCT Filed: Nov. 2, 2018

(86) PCT No.: PCT/US2018/059089
§ 371 (c)(1),
(2) Date: May 1, 2020

(87) PCT Pub. No.: WO2019/090173
PCT Pub. Date: May 9, 2019

(65) Prior Publication Data
US 2020/0291395 A1    Sep. 17, 2020

Related U.S. Application Data

(60) Provisional application No. 62/587,381, filed on Nov. 16, 2017, provisional application No. 62/580,880, filed on Nov. 2, 2017.

(51) Int. Cl.
| | |
|---|---|
| *C12N 9/22* | (2006.01) |
| *C12N 9/12* | (2006.01) |
| *C12N 15/10* | (2006.01) |
| *C12N 15/11* | (2006.01) |
| *C12N 15/113* | (2010.01) |
| *C12N 15/63* | (2006.01) |
| *C12N 15/70* | (2006.01) |
| *C12N 15/85* | (2006.01) |

(52) U.S. Cl.
CPC ............ *C12N 9/22* (2013.01); *C12N 9/1241* (2013.01); *C12N 15/102* (2013.01); *C12N 15/1058* (2013.01); *C12N 15/11* (2013.01); *C12N 15/113* (2013.01); *C12N 15/63* (2013.01); *C12N 15/70* (2013.01); *C12N 15/85* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 8,795,965 B2 | 8/2014 | Zhang et al. | |
| 8,871,445 B2 | 10/2014 | Cong et al. | |
| 10,947,534 B2 | 3/2021 | Sternberg et al. | |
| 10,995,327 B2* | 5/2021 | Chittoor | C12N 9/22 |
| 2002/0188105 A1 | 12/2002 | Craig | |
| 2010/0068815 A1 | 3/2010 | Ow et al. | |
| 2015/0079681 A1 | 3/2015 | Zhang et al. | |
| 2016/0202843 A1 | 7/2016 | Suggs | |
| 2020/0140893 A1 | 5/2020 | Baltes | |
| 2020/0190487 A1 | 6/2020 | Zhang et al. | |
| 2020/0255829 A1 | 8/2020 | Scott et al. | |
| 2020/0255830 A1 | 8/2020 | Scott et al. | |
| 2020/0283769 A1 | 9/2020 | Sternberg et al. | |
| 2020/0325474 A1 | 10/2020 | Sternberg et al. | |
| 2020/0377881 A1 | 12/2020 | Shrock et al. | |
| 2021/0166783 A1 | 6/2021 | Shmakov et al. | |
| 2023/0048564 A1 | 2/2023 | Jakimo et al. | |

FOREIGN PATENT DOCUMENTS

| | | | | |
|---|---|---|---|---|
| EP | 3009511 A2 | | 4/2016 | |
| WO | WO 2013/176772 | * | 11/2013 | ............. C12N 15/11 |
| WO | WO-2013/176772 A1 | | 11/2013 | |
| WO | WO-2013176772 A1 | * | 11/2013 | ........... A01H 6/4684 |
| WO | WO 2014/093622 A2 | | 6/2014 | |
| WO | WO 2015/070083 A1 | | 5/2015 | |
| WO | WO 2015/131101 A1 | | 9/2015 | |
| WO | WO 2016/094872 A1 | | 6/2016 | |
| WO | WO 2016/161207 | * | 10/2016 | ............... C12N 9/22 |
| WO | WO-2016/161207 A1 | | 10/2016 | |
| WO | WO-2016161207 A1 | * | 10/2016 | ........... C12N 15/111 |
| WO | WO 2016/205764 A1 | | 12/2016 | |
| WO | WO 2017/070605 A1 | | 4/2017 | |
| WO | WO 2017/137768 | * | 8/2017 | ............. C12N 15/90 |
| WO | WO-2017/137768 A1 | | 8/2017 | |

(Continued)

OTHER PUBLICATIONS

Xu et al. piggyBac Mediates Efficient in Vivo CRISPR Library Screening for Tumorigenesis in Mice. Proc Natl Acad Sci USA. 114(4):722-727. (Year: 2017).*
Gao et al. CRISPR/Cas9-based Pten Knock-out and Sleeping Beauty Transposon-mediated Nras Knock-in Induces Hepatocellular Carcinoma and Hepatic Lipid Accumulation in Mice. Cancer Biol Ther. 18(7): 505-512. (Year: 2017).*
Chunlong Xu et al: "piggyBac mediates efficient in vivo CRISPR library screening for tumorigenesis in mice", Proceedings of the National Academy of Sciences of the United States of America, vol. 114, No. 4, Jan. 6, 2017 (Jan. 6, 2017), pp. 722-727. (Year: 2017).*
Mingming Gao et al: CRISPR/Cas9-based Pten knock-out and Sleeping Beauty Transposon-mediated Nras_ knock-in induces hepatocellular carcinoma and hepatic lipid accumulation in mice, Cancer Biology & Therapy, vol. 18, No. 7, May 17, 2017 (May 17, 2017), pp. 505-512. (Year: 2017).*

(Continued)

*Primary Examiner* — Cynthia E Collins
(74) *Attorney, Agent, or Firm* — Wolf, Greenfield & Sacks, P.C.

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of DNA, RNA, and protein substrates. Each system includes one or more protein components and one or more nucleic acid components that together target DNA, RNA, or protein substrates.

21 Claims, 36 Drawing Sheets

Specification includes a Sequence Listing.

(56) References Cited

FOREIGN PATENT DOCUMENTS

| WO | WO-2017137768 A1 * | 8/2017 | ........... A61K 35/545 |
|---|---|---|---|
| WO | WO-2018/035250 A1 | 2/2018 | |
| WO | WO 2019/051278 A1 | 3/2019 | |
| WO | WO-2019/090174 A1 | 5/2019 | |
| WO | WO-2019/090175 A1 | 5/2019 | |
| WO | WO 2020/081438 A1 | 4/2020 | |
| WO | WO 2020/236972 A2 | 11/2020 | |
| WO | WO 2021/030756 A1 | 2/2021 | |
| WO | WO 2021/041922 A1 | 3/2021 | |
| WO | WO 2021/087394 A1 | 5/2021 | |
| WO | WO 2022/147321 A1 | 7/2022 | |
| WO | WO 2022/162622 A1 | 8/2022 | |
| WO | WO 2022/162623 A1 | 8/2022 | |

OTHER PUBLICATIONS

Whisstock J.C. et al. Prediction of protein function from protein sequence and structure. Q Rev Biophys. Aug. 2003;36(3):307-40. Review. (Year: 2003).*
Koonin et al. Mobile Genetic Elements and Evolution of CRISPR-Cas Systems: All the Way There and Back. Genome Biol. Evol. Oct. 1, 2017;9(10):2812-2825. (Year: 2017).*
Gao et al., "CRISPR/Cas9-based Pten Knock-Out and Sleeping Beauty Transposon-mediated Nras Knock-In Induces Hepatocellular Carcinoma and Hepatic Lipid Accumulation in Mice," Cancer Biol Ther. 18(7):505-512 (2017).
International Preliminary Report on Patentability for International Application No. PCT/US2018/059089, mailed May 14, 2020 (13 pages).
International Search Report and Written Opinion for International Application No. PCT/US2018/059089, mailed Mar. 1, 2019 (23 pages).
International Preliminary Report on Patentability for International Application No. PCT/US2018/059090, mailed May 14, 2020 (10 pages).
International Search Report and Written Opinion for International Application No. PCT/US2018/059090, mailed Feb. 25, 2019 (18 pages).
International Preliminary Report on Patentability for International Application No. PCT/US2018/059091, mailed May 5, 2020 (10 pages).
International Search Report and Written Opinion for International Application No. PCT/US2018/059091, mailed Feb. 5, 2019 (18 pages).
Nishimasu et al., "Crystal Structure of Cas9 in Complex with Guide RNA and Target DNA," Cell. 156(5):935-949 (2014) (23 pages).
Nishimasu et al., "Crystal Structure of *Staphylococcus aureus* Cas9," Cell. 162(5):1113-1126 (2015).
Peters et al., "Recruitment of CRISPR-Cas systems by Tn7-like transposons," Proc Natl Acad Sci U S A. 114(35):E7358-E7366 (2017).
Xu et al., "piggyBac Mediates Efficient in Vivo CRISPR Library Screening for Tumorigenesis in Mice," Proc Natl Acad Sci U S A. 114(4):722-727 (2017) (10 pages).
[No Author Listed], Full=Uncharacterized protein, UniProt Acc. No. A0A3S1A926. Apr. 10, 2019, entry version 1; Apr. 10, 2019, sequence version 1. Accessible at https://rest.uniprot.org/unisave/A0A3S1A926?format=txt&versions=1. 1 page.
[No Author Listed], Full=Uncharacterized protein, UniProt Acc. No. A0A3S1A926. Dec. 11, 2019, entry version 4; Apr. 10, 2019, sequence version 1. Accessible at https://rest.uniprot.org/unisave/A0A3S1A926?format=txt&versions=4. 1 page.
[No Author Listed], Lyngbya confervoides C2c5 homolog, SEQ ID 510, Acc. No. BIG55665. Oct. 29, 2020. (retrieved on Oct. 27, 2022). 1 page.
[No Author Listed], type V CRISPR-associated protein Cas12k [Trichormus variabilis], Genbank Acc. No. WP_127054896.1. Accessible at https://www.ncbi.nlm.nih.gov/protein/WP_127054896.1. Sep. 28, 2020. 2 pages.
[No Author Listed], Type V-U5 Crispr effector protein (1085045623), Acc. No. BFC60523. Apr. 19, 2018. (retrieved on Oct. 27, 2022). 1 page.
Aravind et al., The many faces of the helix-turn-helix domain: transcription regulation and beyond. FEMS Microbiol Rev. Apr. 2005;29(2):231-62. doi: 10.1016/j.femsre.2004.12.008.
Arias-Palomo et al., An Atypical AAA+ ATPase Assembly Controls Efficient Transposition through DNA Remodeling and Transposase Recruitment. Cell. Aug. 13, 2015;162(4):860-71. doi: 10.1016/j.cell.2015.07.037.
Chitilian et al., Critical components of the pluripotency network are targets for the p300/CBP interacting protein (p/CIP) in embryonic stem cells. Stem Cells. Jan. 2014;32(1):204-15. doi: 10.1002/stem.1564.
Halpin-Healy et al., Structural basis of DNA targeting by a transposon-encoded CRISPR-Cas system. Nature. Jan. 2020;577(7789):271-274. doi: 10.1038/s41586-019-1849-0. Epub Dec. 18, 2019. Erratum in: Nature. Sep. 2020;585(7825):E12.
Hou et al., CRISPR-Cas systems in multicellular cyanobacteria. RNA Biol. Apr. 2019;16(4):518-529. doi: 10.1080/15476286.2018.1493330. Epub Aug. 15, 2018.
Hou et al., Sleeping Beauty transposon system for genetic etiological research and gene therapy of cancers. Cancer Biol Ther. 2015;16(1):8-16. doi: 10.4161/15384047.2014.986944.
Ivics et al., Molecular reconstruction of Sleeping Beauty, a Tc1-like transposon from fish, and its transposition in human cells. Cell. Nov. 14, 1997;91(4):501-10. doi: 10.1016/s0092-8674(00)80436-5.
Jursch et al., Regulation of DNA transposition by CpG methylation and chromatin structure in human cells. Mob DNA. May 15, 2013;4(1):15. doi: 10.1186/1759-8753-4-15.
Kholodii et al., Four genes, two ends, and a res region are involved in transposition of Tn5053: a paradigm for a novel family of transposons carrying either a mer operon or an integron. Mol Microbiol. Sep. 1995;17(6):1189-200. doi: 10.1111/j.1365-2958.1995.mmi_17061189.x.
Klompe et al., Transposon-encoded CRISPR-Cas systems direct RNA-guided DNA integration. Nature. Jul. 11, 2019;571:219-25. Epub Jun. 12, 2019. Methods included. 24 pages.
Li et al., piggyBac transposase tools for genome engineering. Proc Natl Acad Sci U S A. Jun. 18, 2013;110(25):E2279-87. doi: 10.1073/pnas.1305987110. Epub May 30, 2013.
Ma et al., Transposon-Associated CRISPR-Cas System: A Powerful DNA Insertion Tool. Trends Microbiol. Jul. 2021;29(7):565-568. doi: 10.1016/j.tim.2021.01.017. Epub Feb. 18, 2021.
Miskey et al., The Frog Prince: a reconstructed transposon from Rana pipiens with high transpositional activity in vertebrate cells. Nucleic Acids Res. Dec. 1, 2003;31(23):6873-81. doi: 10.1093/nar/gkg910.
Peters et al., Heteromeric transposase elements: generators of genomic islands across diverse bacteria. Molecular Microbiology. 2014;93(6):1084-92. Epub Aug. 19, 2014.
Pflieger et al., Target capture during Mos1 transposition. J Biol Chem. Jan. 3, 2014;289(1):100-11. doi: 10.1074/jbc.M113.523894. Epub Nov. 22, 2013.
Rybarski et al., Metagenomic discovery of CRISPR-associated transposons. bioRxiv. Aug. 17, 2021; doi: https://doi.org/10.1101/2021.08.16.456562; Preprint. 13 pages.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.
Strecker et al., Response to Comment on "RNA-guided DNA insertion with CRISPR-associated transposases". Science. Jun. 5, 2020;368(6495):eabb2920. doi: 10.1126/science.abb2920.
Strecker et al., RNA-guided DNA insertion with CRISPR-associated transposases. Science. Jul. 5, 2019;365(6448):48-53. doi: 10.1126/science.aax9181. Epub Jun. 6, 2019.
Tenjo-Castaño et al., Structure of the TnsB transposase-DNA complex of type V-K CRISPR-associated transposon. Nat Commun. Oct. 2, 2022;13(1):5792. doi: 10.1038/s41467-022-33504-5.
Tenjo-Castaño et al., Transposons and CRISPR: Rewiring Gene Editing. Biochemistry. Sep. 21, 2022. doi: 10.1021/acs.biochem.2c00379. Epub ahead of print.

(56) References Cited

OTHER PUBLICATIONS

Urschitz et al., Transpositional transgenesis with piggyBac. Mob Genet Elements. May 1, 2013;3(3):e25167. doi: 10.4161/mge.25167. Epub May 24, 2013.
Verwaal et al., CRISPR/Cpf1 enables fast and simple genome editing of *Saccharomyces cerevisiae*. Yeast. Feb. 2018;35(2):201-211. doi: 10.1002/yea.3278. Epub Nov. 12, 2017.
Wang et al., Structural basis of a Tn7-like transposase recruitment and DNA loading to CRISPR-Cas surveillance complex. Cell Res. Feb. 2020;30(2):185-187. doi: 10.1038/s41422-020-0274-0. Epub Jan. 8, 2020.
Yant et al., Mutational analysis of the N-terminal DNA-binding domain of sleeping beauty transposase: critical residues for DNA binding and hyperactivity in mammalian cells. Mol Cell Biol. Oct. 2004;24(20):9239-47. doi: 10.1128/MCB.24.20.9239-9247.2004.
U.S. Appl. No. 18/058,694, filed Nov. 23, 2022, Scott et al.
U.S. Appl. No. 18/058,701, filed Nov. 23, 2022, Scott et al.
Carusillo, A., CRISPR-Associated Transposases—Precise Integration of Large Gene-Editing Cargos Without DNA Repair Requirements. CRISPR News Medicine. Sep. 20, 2021. https://crisprmedicinenews.com/news/crispr-associated-transposases-precise-integration-of-large-gene-editing-cargos-without-dna-repair/ [last accessed Oct. 16, 2023].

* cited by examiner

```
Scores for complete sequences (score includes all domains):
--- full sequence ---    --- best 1 domain ---    -#dom-
E-value  score  bias    E-value  score  bias    exp  N  Sequence              Description
-------  -----  ----    -------  -----  ----    ---  -  --------              -----------
0.00099   27.9   0.4    0.0011   27.7   0.4     1.0  1  D2RFI2.1_ARCPA/155-272 D2RFI2.1 PF01385.18; OrfB_IS605;
0.0046    25.7   0.2    0.0057   25.4   0.2     1.1  1  D2RHQ6_ARCPA/155-286   D2RHQ6.1 PF01385.18; OrfB_IS605;
------ inclusion threshold ------
```

FIG. 5

Scores for complete sequences (score includes all domains):

| --- full sequence --- | | | --- best 1 domain --- | | | --#dom-- | | Sequence | Description |
|---|---|---|---|---|---|---|---|---|---|
| E-value | score | bias | E-value | score | bias | exp | N | | |
| 1.1e-36 | 136.2 | 0.2 | 1.2e-36 | 136.1 | 0.2 | 1.0 | 1 | B7KIMO_CYAP7/6-77 | B7KIMO.1 PF13411.5; MerR_1; |
| 1.4e-36 | 135.9 | 0.1 | 1.5e-36 | 135.8 | 0.1 | 1.0 | 1 | A0A0C1UHR6_9CYAN/6-77 | A0A0C1UHR6.1 PF13411.5; MerR_1; |
| 1.4e-36 | 135.9 | 0.1 | 1.5e-36 | 135.7 | 0.1 | 1.0 | 1 | A0A0C1UV21_9CYAN/6-77 | A0A0C1UV21.1 PF13411.5; MerR_1; |
| 2.1e-36 | 135.3 | 0.2 | 2.2e-36 | 135.2 | 0.2 | 1.0 | 1 | L8LPZ2_9CHR0/6-77 | L8LPZ2.1 PF13411.5; MerR_1; |
| 2.7e-36 | 134.9 | 0.1 | 3e-36 | 134.8 | 0.1 | 1.0 | 1 | E0UFI8_CYAP2/9-80 | E0UFI8.1 PF13411.5; MerR_1; |
| 5.4e-36 | 134.0 | 0.1 | 5.8e-36 | 133.8 | 0.1 | 1.0 | 1 | Q8YR38_NOSS1/24-95 | Q8YR38.1 PF13411.5; MerR_1; |
| 5.9e-36 | 133.8 | 0.2 | 6.4e-36 | 133.7 | 0.2 | 1.0 | 1 | B2JZ4_NOSP7/6-77 | B2JZ4.1 PF13411.5; MerR_1; |
| 8.4e-36 | 133.3 | 0.2 | 9.2e-36 | 133.2 | 0.2 | 1.0 | 1 | K9WJ95_9CYAN/6-77 | K9WJ95.1 PF13411.5; MerR_1; |
| 1.5e-35 | 132.5 | 0.1 | 1.6e-35 | 132.4 | 0.1 | 1.0 | 1 | A0A0C1X7Q4_9CYAN/6-77 | A0A0C1X7Q4.1 PF13411.5; MerR_1; |
| 1.8e-35 | 132.2 | 0.2 | 2e-35 | 132.1 | 0.2 | 1.0 | 1 | K9WHA4_9CYAN/6-77 | K9WHA4.1 PF13411.5; MerR_1; |
| 5.1e-35 | 130.8 | 0.1 | 5.6e-35 | 130.7 | 0.1 | 1.0 | 1 | A0A0C2QDJ6_9CYAN/6-77 | A0A0C2QDJ6.1 PF13411.5; MerR_1; |
| 9.9e-35 | 129.9 | 0.1 | 1.1e-34 | 129.7 | 0.1 | 1.0 | 1 | A0A0D6KLX8_9CYAN/6-77 | A0A0D6KLX8.1 PF13411.5; MerR_1; |
| 1.2e-34 | 129.6 | 0.2 | 1.3e-34 | 129.5 | 0.2 | 1.0 | 1 | B1X1V0_CYAA5/6-77 | B1X1V0.1 PF13411.5; MerR_1; |
| 1.5e-34 | 129.3 | 0.1 | 1.6e-34 | 129.1 | 0.1 | 1.0 | 1 | A0A0K2M3D0_9NOST/6-77 | A0A0K2M3D0.1 PF13411.5; MerR_1; |
| 2.2e-34 | 128.7 | 0.2 | 2.4e-34 | 128.6 | 0.2 | 1.0 | 1 | B7K587_CYAP8/6-77 | B7K587.1 PF13411.5; MerR_1; |
| 3.2e-34 | 128.2 | 0.1 | 3.4e-34 | 128.1 | 0.1 | 1.0 | 1 | K9ZGE5_ANACC/6-77 | K9ZGE5.1 PF13411.5; MerR_1; |
| 3.4e-34 | 128.1 | 0.1 | 3.7e-34 | 128.0 | 0.1 | 1.0 | 1 | A0A0V7ZWT9_9CYAN/6-77 | A0A0V7ZWT9.1 PF13411.5; MerR_1; |
| 3.4e-34 | 128.1 | 0.1 | 3.7e-34 | 128.0 | 0.1 | 1.0 | 1 | D7E227_NOSA0/6-77 | D7E227.1 PF13411.5; MerR_1; |
| 1.4e-33 | 126.1 | 0.1 | 1.5e-33 | 126.0 | 0.1 | 1.0 | 1 | A0YWR7_LYNSP/30-101 | A0YWR7.1 PF13411.5; MerR_1; |
| 2.8e-33 | 125.1 | 0.1 | 3e-33 | 125.0 | 0.1 | 1.0 | 1 | K9W208_9CYAN/6-77 | K9W208.1 PF13411.5; MerR_1; |
| 8.1e-33 | 123.6 | 0.0 | 8.8e-33 | 123.5 | 0.0 | 1.0 | 1 | L8M4T0_9CYAN/12-81 | L8M4T0.1 PF13411.5; MerR_1; |
| 3.1e-32 | 121.7 | 0.1 | 3.4e-32 | 121.6 | 0.1 | 1.0 | 1 | K9Y9S9_HALP7/6-77 | K9Y9S9.1 PF13411.5; MerR_1; |

FIG. 8

| | | | | | |
|---|---|---|---|---|---|
| 3.7e-31 | 118.3 | 0.1 | | 4e-31 | 118.2 | 0.1 | 1.0 | 1 | K9PDE6_9CYAN/6-77 | K9PDE6.1 PF13411.5; MerR_1; |
| 2e-30 | 115.9 | 0.1 | 2.2e-30 | 115.8 | 0.1 | 1.0 | 1 | K9RJI0_9CYAN/6-77 | K9RJI0.1 PF13411.5; MerR_1; |
| 8.3e-29 | 110.6 | 0.0 | 8.9e-29 | 110.5 | 0.0 | 1.0 | 1 | K9Y_A75_HALP7/6-77 | K9Y_A75.1 PF13411.5; MerR_1; |
| 1.1e-23 | 94.0 | 0.1 | 1.2e-23 | 93.9 | 0.1 | 1.0 | 1 | A0A0D6AC54_9CHRO/3-68 | A0A0D6AC54.1 PF13411.5; MerR_1; |
| 2.8e-11 | 53.8 | 0.0 | 2.8e-11 | 53.8 | 0.0 | 1.0 | 1 | W5I_JI0_SCAIO/50-122 | W5I_JI0.1 PF13411.5; MerR_1; |
| 6e-11 | 52.7 | 0.0 | 6.2e-11 | 52.7 | 0.0 | 1.0 | 1 | A0A0J0UT29_9ACTN/18-90 | A0A0J0UT29.1 PF13411.5; MerR_1; |
| 6.8e-11 | 52.5 | 0.0 | 7.2e-11 | 52.5 | 0.0 | 1.0 | 1 | A0A094PPY8_9ACTN/8-80 | A0A094PPY8.1 PF13411.5; MerR_1; |
| 7.2e-11 | 52.4 | 0.0 | 7.4e-11 | 52.4 | 0.0 | 1.0 | 1 | A0A087AW05_9BIFI/34-106 | A0A087AW05.1 PF13411.5; MerR_1; |
| 1.2e-10 | 51.7 | 0.0 | 1.3e-10 | 51.7 | 0.0 | 1.0 | 1 | A0A0C1UD64_9ACTN/10-82 | A0A0C1UD64.1 PF13411.5; MerR_1; |
| 1.4e-10 | 51.5 | 0.0 | 1.5e-10 | 51.5 | 0.0 | 1.0 | 1 | A0A0H5CEP7_9PSEU/30-102 | A0A0H5CEP7.1 PF13411.5; MerR_1; |
| 1.5e-10 | 51.4 | 0.0 | 1.5e-10 | 51.4 | 0.0 | 1.0 | 1 | A0A0A7I7J2_9BIFI/30-102 | A0A0A7I7J2.1 PF13411.5; MerR_1; |
| 1.6e-10 | 51.3 | 0.0 | 1.8e-10 | 51.2 | 0.0 | 1.0 | 1 | E6J879_9ACTN/52-124 | E6J879.1 PF13411.5; MerR_1; |
| 2e-10 | 51.0 | 0.0 | 2.1e-10 | 50.9 | 0.0 | 1.0 | 1 | A0A0R2QBU2_9ACTN/6-78 | A0A0R2QBU2.1 PF13411.5; MerR_1; |
| 3.1e-10 | 50.4 | 0.0 | 3.2e-10 | 50.4 | 0.0 | 1.0 | 1 | S2VZ96_9ACTN/27-99 | S2VZ96.1 PF13411.5; MerR_1; |
| 4.4e-10 | 49.9 | 0.1 | 4.5e-10 | 49.9 | 0.1 | 1.0 | 1 | U1SE31_9BIFI/43-115 | U1SE31.1 PF13411.5; MerR_1; |
| 4.5e-10 | 49.9 | 0.0 | 4.8e-10 | 49.8 | 0.0 | 1.0 | 1 | A0A0R2R146_9ACTN/5-77 | A0A0R2R146.1 PF13411.5; MerR_1; |
| 5e-10 | 49.7 | 0.1 | 5e-10 | 49.7 | 0.1 | 1.0 | 1 | D6ZA50_SEGRD/53-125 | D6ZA50.1 PF13411.5; MerR_1; |
| 5e-10 | 49.7 | 0.0 | 5.1e-10 | 49.7 | 0.0 | 1.0 | 1 | A0A080N2N3_9BIFI/30-102 | A0A080N2N3.1 PF13411.5; MerR_1; |
| 5.2e-10 | 49.7 | 0.1 | 5.4e-10 | 49.6 | 0.1 | 1.0 | 1 | D1NTN6_9BIFI/46-118 | D1NTN6.1 PF13411.5; MerR_1; |
| 5.3e-10 | 49.6 | 0.1 | 5.6e-10 | 49.6 | 0.1 | 1.0 | 1 | D7GDZ0_PROFC/37-105 | D7GDZ0.1 PF13411.5; MerR_1; |
| 8.8e-10 | 48.9 | 0.0 | 8.8e-10 | 48.9 | 0.0 | 1.0 | 1 | A0A164M8F4_9NOCA/35-107 | A0A164M8F4.1 PF13411.5; MerR_1; |
| 8.9e-10 | 48.9 | 0.1 | 8.9e-10 | 48.9 | 0.1 | 1.0 | 1 | K4INF0_BIFAP/26-97 | K4INF0.1 PF13411.5; MerR_1; |

FIG. 8 (Cont.)

| full sequence E-value | score | bias | best 1 domain E-value | score | bias | #dom- exp | N | Sequence | Description |
|---|---|---|---|---|---|---|---|---|---|
| 9.7e-86 | 298.7 | 0.1 | 1.1e-85 | 298.5 | 0.0 | 1.0 | 1 | K9ZIY0_ANACC/187-323 | K9ZIY0.1 PF00665.25;rve; |
| 1.9e-85 | 297.7 | 0.1 | 2.1e-85 | 297.5 | 0.1 | 1.0 | 1 | A0A0C1UDH9_9CYAN/196-331 | A0A0C1UDH9.1 PF00665.25;rve; |
| 3.4e-85 | 296.9 | 0.1 | 3.7e-85 | 296.7 | 0.1 | 1.0 | 1 | Q8YR24_NOSS1/149-284 | Q8YR24.1 PF00665.25;rve; |
| 1.4e-83 | 291.5 | 0.0 | 1.6e-83 | 291.4 | 0.0 | 1.0 | 1 | A0A0D6KCA9_9CYAN/179-314 | A0A0D6KCA9.1 PF00665.25;rve; |
| 1.9e-83 | 291.1 | 0.0 | 2.1e-83 | 290.9 | 0.0 | 1.0 | 1 | E0UFJ1_CYAP2/186-321 | E0UFJ1.1 PF00665.25;rve; |
| ... | | | | | | | | | |
| 7.7e-30 | 114.0 | 0.2 | 8.4e-30 | 113.9 | 0.2 | 1.0 | 1 | B1WNW2_CYAA5/421-484 | B1WNW2.1 PF09299.10;Mu-transpos_C; |
| 9.5e-30 | 113.7 | 0.1 | 1e-29 | 113.6 | 0.1 | 1.0 | 1 | K9ZIY0_ANACC/399-463 | K9ZIY0.1 PF09299.10;Mu-transpos_C; |
| 3.4e-29 | 111.9 | 0.2 | 3.7e-29 | 111.8 | 0.2 | 1.0 | 1 | B2J811_NOSP7/407-470 | B2J811.1 PF09299.10;Mu-transpos_C; |
| 4.5e-29 | 111.5 | 0.5 | 4.9e-29 | 111.4 | 0.5 | 1.0 | 1 | A0A0D6AGG8_9CHR0/131-194 | A0A0D6AGG8.1 PF09299.10;Mu-transpos_C; |
| 4.8e-29 | 111.4 | 0.4 | 5.2e-29 | 111.3 | 0.4 | 1.0 | 1 | A0A0C2LP00_9CYAN/411-475 | A0A0C2LP00.1 PF09299.10;Mu-transpos_C; |
| ... | | | | | | | | | |
| 1e-15 | 67.4 | 0.0 | 1.1e-15 | 67.3 | 0.0 | 1.0 | 1 | B2J811_NOSP7/39-95 | B2J811.1 PF13384.5;HTH_23; |
| 1.1e-15 | 67.3 | 0.1 | 1.1e-15 | 67.3 | 0.1 | 1.0 | 1 | K9WKZ8_9CYAN/16-72 | K9WKZ8.1 PF13384.5;HTH_23; |
| 1.2e-15 | 67.1 | 0.2 | 1.3e-15 | 67.1 | 0.2 | 1.0 | 1 | B7K157_CYAP8/37-93 | B7K157.1 PF13384.5;HTH_23; |
| 1.3e-15 | 67.0 | 0.1 | 1.4e-15 | 66.9 | 0.1 | 1.0 | 1 | L8LU36_9CHR0/38-95 | L8LU36.1 PF13518.5;HTH_28; |
| 4.9e-15 | 65.1 | 0.1 | 5.2e-15 | 65.1 | 0.1 | 1.0 | 1 | E0UFJ1_CYAP2/30-87 | E0UFJ1.1 PF13384.5;HTH_23; |
| ... | | | | | | | | | |
| 2.5e-11 | 52.9 | 0.4 | 1.5e-06 | 37.1 | 0.1 | 2.9 | 2 | C8VZD6_DESAS/271-461 | C8VZD6.1 PF02914.14;DDE_2; |
| 1.4e-08 | 43.8 | 2.7 | 6.1e-08 | 41.7 | 2.7 | 2.1 | 1 | A0A150YHA9_9BACI/255-490 | A0A150YHA9.1 PF02914.14;DDE_2; |
| 2e-08 | 43.3 | 1.7 | 6.9e-08 | 41.5 | 1.7 | 2.0 | 1 | A0A150YHA7_9BACI/210-445 | A0A150YHA7.1 PF02914.14;DDE_2; |
| 1.5e-06 | 37.1 | 0.1 | 5.9e-06 | 35.2 | 0.1 | 1.7 | 1 | G9RTU5_9FIRM/258-450 | G9RTU5.1 PF02914.14;DDE_2; |
| 5.5e-06 | 35.3 | 3.0 | 0.00025 | 29.8 | 3.0 | 2.7 | 1 | J4TDJ0_9FIRM/266-453 | J4TDJ0.1 PF02914.14;DDE_2; |
| 3.1e-05 | 32.8 | 2.9 | 0.0087 | 24.7 | 2.9 | 2.8 | 1 | R5HI38_9SPIR/242-444 | R5HI38.1 PF02914.14;DDE_2; |

FIG. 11

Scores for complete sequences (score includes all domains):

| --- full sequence --- | | | --- best 1 domain --- | | | =#dom- | | | |
|---|---|---|---|---|---|---|---|---|---|
| E-value | score | bias | E-value | score | bias | exp | N | Sequence | Description |
| 4.2e-61 | 215.6 | 0.0 | 4.6e-61 | 215.4 | 0.0 | 1.0 | 1 | K9QJB5_9NOSO/10-128 | K9QJB5.1 PF06527.10;TniQ; |
| 7.8e-61 | 214.7 | 0.0 | 8.6e-61 | 214.5 | 0.0 | 1.0 | 1 | Q8YR26_N0SS1/11-129 | Q8YR26.1 PF06527.10;TniQ; |
| 1.5e-59 | 210.5 | 0.0 | 1.6e-59 | 210.4 | 0.0 | 1.0 | 1 | K9VZN2_9CYAN/8-126 | K9VZN2.1 PF06527.10;TniQ; |
| 3.3e-59 | 209.4 | 0.0 | 3.6e-59 | 209.3 | 0.0 | 1.0 | 1 | K9ZBU4_ANACC/25-145 | K9ZBU4.1 PF06527.10;TniQ; |
| 5.2e-59 | 208.8 | 0.0 | 5.7e-59 | 208.6 | 0.0 | 1.0 | 1 | K9WL29_9CYAN/11-129 | K9WL29.1 PF06527.10;TniQ; |
| 1.5e-58 | 207.2 | 0.0 | 1.7e-58 | 207.1 | 0.0 | 1.0 | 1 | A0A0C1Y3V0_9CYAN/10-128 | A0A0C1Y3V0.1 PF06527.10;TniQ; |
| 2.4e-58 | 206.6 | 0.1 | 2.6e-58 | 206.4 | 0.1 | 1.0 | 1 | K9UZ35_9CYAN/28-149 | K9UZ35.1 PF06527.10;TniQ; |
| 2.1e-57 | 203.5 | 0.0 | 2.3e-57 | 203.4 | 0.0 | 1.0 | 1 | A0A139X7R1_9CYAN/12-132 | A0A139X7R1.1 PF06527.10;TniQ; |
| 1.4e-55 | 197.6 | 0.0 | 1.5e-55 | 197.4 | 0.0 | 1.0 | 1 | K9RIW4_9CYAN/10-128 | K9RIW4.1 PF06527.10;TniQ; |
| 1.9e-55 | 197.2 | 0.0 | 2e-55 | 197.1 | 0.0 | 1.0 | 1 | A0A0D6KBW5_9CYAN/10-128 | A0A0D6KBW5.1 PF06527.10;TniQ; |
| 2.3e-55 | 196.9 | 0.0 | 2.5e-55 | 196.8 | 0.0 | 1.0 | 1 | A0A0S3PI18_9NOSO/25-145 | A0A0S3PI18.1 PF06527.10;TniQ; |
| 4.6e-55 | 195.9 | 0.1 | 5e-55 | 195.8 | 0.1 | 1.0 | 1 | B7K153_CYAP8/11-128 | B7K153.1 PF06527.10;TniQ; |
| 1.4e-54 | 194.4 | 0.0 | 1.5e-54 | 194.2 | 0.0 | 1.0 | 1 | B1WNWO_CYAA5/11-128 | B1WNWO.1 PF06527.10;TniQ; |
| 2.3e-54 | 193.6 | 0.0 | 2.5e-54 | 193.5 | 0.0 | 1.0 | 1 | A0A0K2M5O4_9NOST/10-131 | A0A0K2M5O4.1 PF06527.10;TniQ; |
| 5.8e-54 | 192.3 | 0.0 | 8.6e-54 | 191.8 | 0.0 | 1.3 | 1 | A0A0C2PXZ3_9CYAN/10-136 | A0A0C2PXZ3.1 PF06527.10;TniQ; |
| 9.2e-54 | 191.7 | 0.0 | 1e-53 | 191.5 | 0.0 | 1.0 | 1 | B7KIM4_CYAP7/11-129 | B7KIM4.1 PF06527.10;TniQ; |
| 6.5e-53 | 188.9 | 0.0 | 7.1e-53 | 188.8 | 0.0 | 1.0 | 1 | L8M3L9_9CYAN/11-129 | L8M3L9.1 PF06527.10;TniQ; |
| 1.7e-51 | 184.3 | 0.0 | 1.9e-51 | 184.1 | 0.0 | 1.0 | 1 | A0A0C1XIT2_9CYAN/10-131 | A0A0C1XIT2.1 PF06527.10;TniQ; |
| 1.8e-51 | 184.3 | 0.1 | 1.9e-51 | 184.1 | 0.1 | 1.0 | 1 | A0A0D6AGK4_9CHRO/9-125 | A0A0D6AGK4.1 PF06527.10;TniQ; |
| 4.5e-51 | 182.9 | 0.0 | 4.9e-51 | 182.8 | 0.0 | 1.0 | 1 | B7JWC7_CYAP8/7-128 | B7JWC7.1 PF06527.10;TniQ; |

FIG. 14

Scores for complete sequences (score includes all domains):
-- full sequence --     -- best 1 domain --     -#dom-

| E-value | score | bias | E-value | score | bias | exp | N | Sequence | Description |
|---|---|---|---|---|---|---|---|---|---|
| 5.4e-132 | 448.9 | 0.4 | 6e-132 | 448.8 | 0.4 | 1.0 | 1 | K9RK36_9CYAN/26-226 | K9RK36.1 PF05621.10;TniB; |
| 1.5e-129 | 440.9 | 1.8 | 1.7e-129 | 440.7 | 1.8 | 1.0 | 1 | B1WNW1_CYAA5/26-266 | B1WNW1.1 PF05621.10;TniB; |
| 8.7e-129 | 438.4 | 0.6 | 9.6e-129 | 438.3 | 0.6 | 1.0 | 1 | L8LWX5_9CHRO/20-265 | L8LWX5.1 PF05621.10;TniB; |
| 7.5e-128 | 435.3 | 0.1 | 8.4e-128 | 435.2 | 0.1 | 1.0 | 1 | B2J810_NOSP7/29-264 | B2J810.1 PF05621.10;TniB; |
| 1.8e-127 | 434.1 | 1.1 | 2.1e-127 | 433.9 | 1.1 | 1.0 | 1 | B7KIM5_CYAP7/20-264 | B7KIM5.1 PF05621.10;TniB; |
| 2.5e-19 | 79.4 | 0.0 | 2.7e-19 | 79.3 | 0.0 | 1.0 | 1 | E0UMY2_CYAP/65-197 | E0UMY2.1 PF13401.5;AAA_22; |
| 2.1e-18 | 76.3 | 0.0 | 2.3e-18 | 76.2 | 0.0 | 1.0 | 1 | B7JWD6_CYAP8/56-188 | B7JWD6.1 PF13401.5;AAA_22; |
| 7.2e-18 | 74.6 | 0.1 | 1.4e-17 | 73.6 | 0.1 | 1.5 | 1 | A0A0S3PGS0_9NOSO/57-176 | A0A0S3PGS0.1 PF13401.5;AAA_22; |
| 5.5e-13 | 58.6 | 0.0 | 5.8e-13 | 58.5 | 0.0 | 1.0 | 1 | K9WNX0_9CYAN/85-210 | K9WNX0.1 PF13401.5;AAA_22; |
| 1.6e-11 | 53.8 | 0.0 | 1.8e-11 | 53.6 | 0.0 | 1.0 | 1 | B7JWA3_CYAP8/56-176 | B7JWA3.1 PF13401.5;AAA_22; |

FIG. 17

SEQUENCE LISTING

<160> NUMBER OF SEQ ID NOS: 209

<210> SEQ ID NO 1
<211> LENGTH: 629
<212> TYPE: PRT
<213> ORGANISM: Alkalinema sp.

<400> SEQUENCE: 1

```
Met Ser Gln Ile Thr Ile Gln Cys Arg Leu Val Ala Pro Pro Thr Ala
1               5                   10                  15

Arg Gln His Leu Trp Thr Leu Ala Ala Glu Lys Asn Thr Pro Leu Ile
            20                  25                  30

Asn Thr Leu Ile Gln Glu Val Ala Asn His Glu Glu Phe Glu Thr Trp
        35                  40                  45

Arg Leu Lys Gly Lys His Pro Thr Lys Ile Val Ser Glu Ile Cys Arg
    50                  55                  60

Arg Leu Arg Thr Glu Ala Pro Phe Ser Gly Gln Pro Ala Arg Phe Tyr
65                  70                  75                  80

Thr Ser Ala Glu Lys Thr Val Asn Tyr Ile Phe Lys Ser Trp Phe Thr
                85                  90                  95

Leu Gln Ser Arg Leu Gln Arg Gln Leu Ser Arg Lys Gln Ile Trp Leu
            100                 105                 110

Ser Ile Leu Lys Ser Asp Pro Glu Leu Val Glu Leu Cys Gly His Pro
        115                 120                 125

Leu Glu Thr Ile Gln Asn Lys Ala Thr Gln Leu Leu Thr Gln Ile Glu
    130                 135                 140

Lys Thr Leu Ala Asp Ser Asn Pro Glu Asp Pro Gln Ser Pro Cys Thr
145                 150                 155                 160

Asn Asp Leu Ile Arg Ala Gln Leu Phe Lys Lys Tyr His Gly Ala Lys
                165                 170                 175

Thr Pro Leu Ile Arg Cys Ser Ile Ala Tyr Leu Ile Lys Asn Gly Gly
            180                 185                 190

Lys Leu Pro Lys Ser Pro Glu Ile Pro His Lys Phe Ala Gln Arg Arg
        195                 200                 205

Arg Lys Ala Glu Ile Gln Val Gln Arg Leu Gln Asp Gln Leu Glu Gly
    210                 215                 220

Arg Leu Pro Lys Gly Arg Asp Leu Thr Gly Gln Ala Trp Leu Ser Thr
225                 230                 235                 240
```

Leu Ile Thr Ala Thr Ser Thr Val Pro Lys Asp Asn His Glu Gln Lys
             245                 250                 255

Gln Trp Asn Asp Arg Leu Leu Ala Lys Pro Cys Thr Thr Pro Phe Pro
         260                 265                 270

Ile Leu Phe Glu Thr Asn Glu Asp Leu Asn Trp Ser Lys Asn His Thr
             275                 280                 285

Gly Arg Ile Cys Val Arg Phe Asn Gly Leu Ser Glu His Thr Phe Gln
         290                 295                 300

Val Tyr Cys Asp Gln Arg Gln Leu Pro Trp Phe Gln Arg Phe Leu Glu
305                 310                 315                 320

Asp Gln Gln Thr Lys His Thr Ser Lys Asn Gln His Ser Ser Ala Leu
             325                 330                 335

Phe Thr Leu Arg Ser Ala His Leu Ala Trp Gln Glu Thr His Ser Asn
             340                 345                 350

Gly Ala Gly Trp Asp Asn His Tyr Ile Thr Leu Tyr Cys Thr Val Asp
         355                 360                 365

Val Arg Leu Trp Thr Ala Glu Gly Thr Glu Val His Gln Glu Lys
         370                 375                 380

Ala Val Asp Ile Ala Lys Gln Leu Thr Tyr Leu Asp Gln Lys Glu Asp
385                 390                 395                 400

Leu Ser Glu Thr Gln Ala Ala Phe Ala Gln Arg Leu Thr Ser Thr Leu
             405                 410                 415

Asp Arg Leu Asn Lys Pro Phe Pro Arg Pro His Arg His Arg Ala Gln
         420                 425                 430

Gln His Ser His Ile Ile Val Gly Leu Ser Val Asp Trp Glu Ala Pro
         435                 440                 445

Leu Thr Leu Ala Ile Trp Asn Ala Asn Thr Gln Glu Val Leu Val Tyr
450                 455                 460

Arg Ser Leu Arg Gln Leu Leu Gly Lys Asp Tyr Pro Leu Phe Leu Gln
465                 470                 475                 480

His Arg Gln Glu Gln Gln Lys Gln Ser His Asn Arg His Lys Ala Gln
             485                 490                 495

Lys Arg Asn Lys Asn Cys Gln Phe Gly Thr Ser His Leu Gly Glu His
         500                 505                 510

Ile Asp Arg Leu Leu Ala Lys Ala Val Ile Thr Ile Ala Gln Gln Tyr
         515                 520                 525

Asn Ala Gly Ser Ile Ala Val Pro Asn Leu Asp Asn Ile Arg Glu Thr
         530                 535                 540

Leu Gln Ala Thr Ile Asp Ala Lys Ala Glu Gln Lys Ala Pro Gly Cys
545                 550                 555                 560

Ile Glu Ala Gln Lys Arg Tyr Thr Lys Gln Tyr Lys Ile Thr Ile His
             565                 570                 575

Arg Trp Ser Tyr Gly Arg Leu Ile Asp Gln Ile Ile Ser Lys Ala Lys
         580                 585                 590

Gln Val Gly Leu Gly Val Glu Glu Ala Lys Gln Pro Leu Ser Gly Asn
         595                 600                 605

Val Gln Glu Lys Ala Lys Leu Val Ala Ile Ser Ala Tyr Asn Ala Arg
610                 615                 620

Leu Ile Val Ala Phe
625

<210> SEQ ID NO 2
<211> LENGTH: 639

-continued

```
<212> TYPE: PRT
<213> ORGANISM: Anabaena sp.

<400> SEQUENCE: 2

Met Ser Gln Ile Thr Val Gln Cys Arg Leu Ile Ala Ser Glu Ser Thr
1               5                   10                  15

Arg Gln Gln Leu Trp Thr Leu Met Ala Glu Leu Asn Thr Pro Leu Ile
            20                  25                  30

Asn Glu Leu Leu Gln Gln Leu Ser Lys His Pro Asp Phe Glu Lys Trp
        35                  40                  45

Arg Lys Asp Gly Lys Phe Pro Ser Thr Val Val Ser Gln Leu Cys Gln
    50                  55                  60

Pro Leu Lys Thr Asp Pro Gln Phe Ala Gly Gln Pro Ser Arg Cys Tyr
65                  70                  75                  80

Leu Ser Ala Ile His Val Val Asp Tyr Ile Tyr Lys Ser Trp Leu Thr
                85                  90                  95

Ile Gln Lys Arg Leu Gln Gln Leu Asp Gly Lys Ile Arg Trp Leu
            100                 105                 110

Glu Met Leu Asn Ser Asp Ala Glu Leu Val Glu Thr Ser Gly Tyr Ser
        115                 120                 125

Leu Glu Ala Ile Arg Thr Lys Ala Ala Glu Ile Leu Ala Met Thr Thr
130                 135                 140

Pro Glu Ser Asp Thr Asn Val Pro Leu Thr Lys Lys Arg Asn Thr Lys
145                 150                 155                 160

Lys Ser Lys Lys Ser Ser Ala Ser Asn Pro Glu Pro Ser Leu Ser His
                165                 170                 175

Lys Leu Phe Asn Ala Tyr Gln Glu Thr Asp Asp Ile Leu Ser Arg Ser
            180                 185                 190

Ala Ile Ser Tyr Leu Leu Lys Asn Gly Cys Lys Leu Asn Asp Lys Glu
        195                 200                 205

Glu Asp Thr Glu Lys Phe Ala Lys Arg Arg Lys Val Glu Ile Gln
    210                 215                 220

Ile Gln Arg Leu Thr Asp Lys Leu Thr Ser Arg Ile Pro Lys Gly Arg
225                 230                 235                 240

Asp Leu Thr Asn Ser Lys Trp Leu Glu Thr Leu Phe Thr Ala Ile Thr
                245                 250                 255

Thr Val Pro Glu Asp Asn Ala Glu Ala Lys Arg Trp Gln Asp Ile Leu
            260                 265                 270

Ser Thr Arg Ser Ser Ser Leu Pro Phe Pro Leu Ile Phe Glu Thr Asn
        275                 280                 285

Glu Asp Leu Lys Trp Ser Thr Asn Glu Lys Gly Arg Leu Cys Val His
    290                 295                 300

Phe Asn Gly Leu Thr Asp Leu Thr Phe Glu Val Tyr Cys Asp Ser Arg
305                 310                 315                 320

Gln Leu His Trp Phe Lys Arg Phe Leu Glu Asp Gln Gln Thr Lys Arg
                325                 330                 335

Lys Ser Lys Asn Gln His Ser Ser Gly Leu Phe Thr Leu Arg Asn Gly
            340                 345                 350

Arg Leu Ala Trp Gln Glu Gly Glu Gly Lys Gly Glu Thr Trp Gln Ile
        355                 360                 365

His Arg Leu Thr Leu Ser Cys Cys Val Asp Asn Arg Leu Trp Thr Ala
    370                 375                 380

Glu Gly Thr Glu Gln Val Arg Gln Glu Lys Ala Glu Asp Ile Thr Lys
385                 390                 395                 400
```

```
Phe Ile Thr Lys Met Lys Glu Lys Ser Asp Leu Ser Asp Thr Gln Gln
                405                 410                 415

Ala Phe Ile Gln Arg Lys Gln Ser Thr Leu Thr Arg Ile Asn Asn Ser
            420                 425                 430

Phe Asp Arg Pro Cys Lys Pro Leu Tyr Gln Gly Gln Ser His Ile Leu
        435                 440                 445

Val Gly Val Ser Met Gly Leu Glu Lys Pro Ala Thr Val Ala Val Val
    450                 455                 460

Asp Ala Ser Ala Asn Lys Val Leu Thr Tyr Arg Ser Ile Lys Gln Ile
465                 470                 475                 480

Leu Gly Glu Asn Tyr Glu Leu Leu Asn Arg Gln Arg Arg Gln Gln Arg
                485                 490                 495

Ser Ser Ser His Glu Arg His Lys Ala Gln Lys Ser Phe Ser Pro Asn
            500                 505                 510

Gln Phe Gly Thr Ser Glu Leu Gly Gln Tyr Ile Asp Arg Leu Leu Ala
        515                 520                 525

Lys Glu Ile Val Ala Ile Ala Gln Thr Tyr Lys Ala Gly Ser Ile Val
    530                 535                 540

Leu Pro Lys Leu Gly Asp Met Arg Glu Asn Ile Gln Ser Glu Ile Gln
545                 550                 555                 560

Ala Ile Ala Glu Ile Lys Cys Pro Gly Ser Val Glu Ile Gln Gln Lys
                565                 570                 575

Tyr Ala Lys Gln Tyr Arg Ile Asn Val His Lys Trp Ser Tyr Gly Arg
            580                 585                 590

Leu Ile Gln Ser Ile Gln Ser Lys Ala Ala Gln Val Gly Ile Val Ile
        595                 600                 605

Glu Glu Gly Lys Gln Pro Val Arg Asp Ser Pro Gln Asp Lys Ala Lys
    610                 615                 620

Glu Leu Ala Leu Ser Thr Tyr His Leu Arg Leu Ala Lys Gln Ser
625                 630                 635

<210> SEQ ID NO 3
<211> LENGTH: 635
<212> TYPE: PRT
<213> ORGANISM: Anabaena variabilis

<400> SEQUENCE: 3

Met Ser Val Ile Thr Ile Gln Cys Arg Leu Val Ala Glu Glu Asp Ile
1               5                   10                  15

Leu Arg Gln Leu Trp Glu Leu Met Ala Glu Lys Asn Thr Pro Leu Ile
                20                  25                  30

Asn Glu Leu Leu Ala Gln Val Gly Lys His Pro Glu Phe Glu Thr Trp
            35                  40                  45

Leu Asp Lys Gly Arg Ile Pro Thr Glu Leu Leu Lys Thr Leu Val Asn
        50                  55                  60

Ser Phe Lys Thr Gln Glu Arg Phe Ala Asp Gln Pro Gly Arg Phe Tyr
65                  70                  75                  80

Thr Ser Ala Ile Ala Leu Val Asp Tyr Val Tyr Lys Ser Trp Phe Ala
                85                  90                  95

Leu Gln Lys Arg Arg Lys Arg Gln Ile Glu Gly Lys Glu Arg Trp Leu
            100                 105                 110

Thr Ile Leu Lys Ser Asp Leu Gln Leu Glu Gln Glu Ser Gln Cys Asn
        115                 120                 125

Leu Asn Val Ile Arg Thr Lys Ala Asn Glu Ile Leu Thr Gln Phe Thr
```

-continued

```
            130                 135                 140
Pro Gln Ser Asp Gln Asn Lys Asn Pro Arg Lys Ser Lys Ala Lys
145                 150                 155                 160

Lys Ser Ala Lys Leu Gln Lys Ser Ser Leu Phe Gln Ile Leu Leu Asn
                165                 170                 175

Thr His Glu Gln Thr Gln Glu Thr Leu Thr Arg Cys Ala Ile Ala Tyr
                180                 185                 190

Leu Leu Lys Asn Asn Cys Gln Ile Ser Glu Arg Asp Glu Asp Pro Glu
                195                 200                 205

Glu Phe Asn Arg Asn Arg Arg Thr Lys Glu Ile Glu Ile Glu Arg Leu
        210                 215                 220

Lys Asp Gln Leu Gln Ser Arg Ile Pro Lys Gly Arg Asp Leu Thr Gly
225                 230                 235                 240

Glu Glu Trp Leu Glu Thr Leu Glu Ile Ala Thr Val Asn Val Pro Gln
                245                 250                 255

Asn Glu Lys Glu Ala Lys Ala Trp Gln Ala Ala Leu Leu Arg Lys Thr
            260                 265                 270

Ala Asp Val Pro Phe Pro Val Ala Tyr Glu Ser Asn Glu Asp Met Thr
        275                 280                 285

Trp Leu Gln Asn Asp Lys Asp Arg Leu Phe Val Arg Phe Asn Gly Leu
    290                 295                 300

Gly Lys Met Thr Phe Glu Val Tyr Cys Asp Lys Arg His Leu His Tyr
305                 310                 315                 320

Phe Lys Arg Phe Leu Glu Asp Gln Glu Ile Lys Arg Asn Ser Lys Asn
                325                 330                 335

Gln Tyr Ser Ser Ser Leu Phe Thr Leu Arg Ser Gly Arg Leu Ala Trp
            340                 345                 350

Leu Pro Gly Lys Gln Lys Gly Leu Pro Trp Lys Ile Asn Gln Leu His
        355                 360                 365

Leu Tyr Cys Thr Leu Asp Thr Arg Met Trp Thr Ala Glu Gly Thr Gln
    370                 375                 380

Gln Val Val Asn Glu Lys Ile Thr Lys Ile Thr Glu Thr Leu Thr Lys
385                 390                 395                 400

Ala Lys Gln Lys Asp Glu Leu Asn Asp Lys Gln Gln Ala Phe Ile Thr
                405                 410                 415

Arg Gln Gln Ser Thr Leu Asp Arg Ile Asn Asn Pro Phe Pro Arg Pro
            420                 425                 430

Ser Gln Pro Asn Tyr Gln Gly Arg Pro Ser Ile Leu Val Gly Val Ser
        435                 440                 445

Phe Gly Leu Glu Lys Pro Val Thr Leu Ala Val Val Asp Val Val Lys
    450                 455                 460

Asn Glu Val Leu Ala Tyr Arg Ser Val Lys Gln Leu Leu Gly Lys Asn
465                 470                 475                 480

Tyr Asn Leu Leu Asn Arg Gln Arg Gln Gln Gln Arg Leu Ser His
                485                 490                 495

Glu Arg His Lys Ala Gln Lys Gln Asn Ala Pro Asn Ser Phe Gly Glu
            500                 505                 510

Ser Glu Leu Gly Gln Tyr Val Asp Arg Leu Leu Ala Asp Glu Ile Val
        515                 520                 525

Ala Ile Ala Lys Thr Tyr Gln Ala Gly Ser Ile Val Ile Pro Lys Leu
    530                 535                 540

Arg Asp Met Arg Glu Gln Ile Ser Ser Glu Ile Gln Ser Arg Ala Glu
545                 550                 555                 560
```

-continued

Lys Lys Cys Pro Gly Tyr Lys Glu Val Gln Gln Lys Tyr Ala Lys Glu
            565                 570                 575

Tyr Arg Met Ser Val His Arg Trp Ser Tyr Gly Arg Leu Ile Glu Ser
            580                 585                 590

Ile Lys Ser Gln Ala Ala Lys Ala Gly Ile Phe Thr Glu Ile Gly Thr
            595                 600                 605

Gln Pro Ile Arg Gly Ser Pro Gln Glu Lys Ala Arg Asp Leu Ala Val
            610                 615                 620

Phe Ala Tyr Gln Glu Arg Gln Ala Ala Leu Ile
625                 630                 635

<210> SEQ ID NO 4
<211> LENGTH: 643
<212> TYPE: PRT
<213> ORGANISM: Anabaena variabilis

<400> SEQUENCE: 4

Met Ser Val Ile Thr Ile Gln Cys Arg Leu Ile Ala Ser Glu Ala Thr
1               5                   10                  15

Arg Ser Tyr Leu Trp Gln Leu Met Ala Gln Lys Asn Thr Pro Leu Ile
            20                  25                  30

Asn Glu Leu Ile Glu Gln Leu Gly Ile His Pro Glu Ile Glu Gln Trp
            35                  40                  45

Leu Lys Lys Gly Lys Leu Pro Asp Gly Val Val Lys Pro Leu Cys Asp
        50                  55                  60

Ser Leu Ile Thr Gln Glu Ser Phe Ala Asn Gln Pro Lys Arg Phe Asn
65                  70                  75                  80

Lys Ser Ala Ile Glu Val Val Glu Tyr Ile Tyr Lys Ser Trp Leu Ala
                85                  90                  95

Leu Gln Lys Glu Arg Gln Gln Thr Ile Asp Arg Lys Glu His Trp Leu
            100                 105                 110

Lys Met Leu Lys Ser Asp Val Glu Leu Glu Gln Glu Ser Lys Cys Thr
            115                 120                 125

Leu Asp Ala Ile Arg Ser Gln Ala Thr Lys Ile Leu Pro Lys Tyr Leu
        130                 135                 140

Ala Gln Ser Glu Gln Asn Asn Asn Gln Thr Gln Ser Gln Asn Lys Lys
145                 150                 155                 160

Lys Ser Lys Lys Ser Lys Thr Lys Asn Glu Asn Ser Thr Leu Phe Asp
                165                 170                 175

Ile Leu Phe Lys Ala Tyr Asp Lys Ala Lys Asn Pro Leu Asn Arg Cys
            180                 185                 190

Thr Leu Ala Tyr Leu Leu Lys Asn Asn Cys Gln Val Ser Gln Lys Asp
        195                 200                 205

Glu Asp Pro Asn Gln Tyr Ala Leu Arg Arg Ser Lys Lys Glu Lys Glu
210                 215                 220

Ile Glu Arg Leu Lys Lys Gln Leu Gln Ser Arg Lys Pro Asn Gly Arg
225                 230                 235                 240

Asp Leu Thr Gly Arg Glu Trp Gln Gln Thr Leu Ile Met Ala Thr Ser
            245                 250                 255

Ser Val Pro Glu Ser Asn Asp Glu Ala Asn Ile Trp Gln Lys Arg Leu
            260                 265                 270

Leu Lys Lys Asp Ile Ser Leu Pro Phe Pro Ile Arg Phe Arg Thr Asn
        275                 280                 285

Glu Asp Leu Ile Trp Ser Lys Asn Glu Glu Gly Arg Ile Cys Val Ser 290                 295                 300
Phe Ser Gly Glu Gly Leu Asn Asp His Ile Phe Glu Ile Tyr Cys Gly
305                 310                 315                 320

Asn Arg Gln Ile His Trp Phe Gln Arg Phe Leu Glu Asp Gln Asn Ile
                325                 330                 335

Lys Asn Asp Asn Asn Asp Gln His Ser Ser Ala Leu Phe Thr Leu Arg
                340                 345                 350

Ser Ala Ile Leu Ala Trp Gln Glu Asn Lys Gln His Lys Glu Asn Ser
            355                 360                 365

Leu Pro Trp Asn Thr Arg Arg Leu Thr Leu Tyr Cys Thr Leu Asp Thr
    370                 375                 380

Arg Leu Trp Thr Thr Asp Gly Thr Glu Lys Val Lys Gln Glu Lys Val
385                 390                 395                 400

Asp Glu Phe Thr Gln Gln Leu Ala Asn Met Glu Gln Lys Glu Asn Leu
                405                 410                 415

Asn Gln Asn Gln Gln Asn Tyr Val Lys Arg Leu Gln Ser Thr Leu Asn
                420                 425                 430

Lys Leu Asn Asn Ala Tyr Pro Arg His Asn His Asp Leu Tyr Gln Gly
            435                 440                 445

Lys Pro Ser Ile Leu Val Gly Val Ser Leu Gly Leu Glu Lys Pro Ala
    450                 455                 460

Thr Leu Ala Ile Val Asp Ser Ser Thr Asn Ile Val Leu Ala Tyr Arg
465                 470                 475                 480

Ser Ile Lys Gln Leu Leu Gly Asp Asn Tyr Lys Leu Leu Asn Arg Gln
                485                 490                 495

Arg Gln Gln Gln Arg Asn Ser His Glu Arg His Lys Ala Gln Lys
                500                 505                 510

Ser Asn Met Pro Asn Lys Leu Ser Glu Ser Asp Leu Gly Lys Tyr Ile
            515                 520                 525

Asp Asn Leu Leu Ala Gln Ala Ile Ile Ala Leu Ala Lys Asn Tyr Gln
    530                 535                 540

Ala Gly Ser Ile Val Leu Pro Thr Met Lys Asn Val Arg Glu Ser Ile
545                 550                 555                 560

Gln Ser Glu Ile Glu Ala Arg Ala Val Lys Arg Cys Pro Asn Tyr Lys
                565                 570                 575

Glu Gly Gln Gln Gln Tyr Ala Lys Gln Tyr Arg Gln Ser Ile His Arg
                580                 585                 590

Trp Ser Tyr Asn Arg Leu Met Gln Phe Ile Gln Ser Gln Ala Val Lys
            595                 600                 605

Ala Asn Ile Ser Ile Glu Gln Gly Pro Gln Pro Ile Arg Gly Ser Ser
    610                 615                 620

Gln Glu Lys Ala Arg Asp Leu Ala Ile Ala Ala Tyr Tyr Leu Arg Gln
625                 630                 635                 640

Asn Lys Ser

<210> SEQ ID NO 5
<211> LENGTH: 642
<212> TYPE: PRT
<213> ORGANISM: Anabaena variabilis

<400> SEQUENCE: 5

Met Ser Gln Ile Thr Ile Gln Cys Arg Leu Val Ala Ser Glu Pro Ser
1               5                   10                  15

Arg His Gln Leu Trp Lys Leu Met Val Asp Leu Asn Thr Pro Leu Ile

```
                    20                  25                  30
Asn Glu Leu Leu Val Gln Val Ala Gln His Pro Glu Phe Glu Thr Trp
                35                  40                  45

Arg Gln Lys Gly Lys His Pro Ala Lys Ile Val Lys Glu Leu Cys Glu
            50                  55                  60

Pro Leu Arg Thr Asp Pro Arg Phe Ile Gly Gln Pro Gly Arg Phe Tyr
 65                 70                  75                  80

Thr Ser Ala Ile Ala Thr Val Asn Tyr Ile Tyr Lys Ser Trp Phe Ala
                85                  90                  95

Leu Met Lys Arg Ser Gln Ser Gln Leu Glu Gly Lys Met Arg Trp Trp
                100                 105                 110

Glu Met Leu Lys Ser Asp Ala Glu Leu Val Glu Val Ser Gly Val Thr
            115                 120                 125

Leu Glu Ser Leu Arg Thr Lys Ala Ala Glu Ile Leu Ser Gln Phe Ala
            130                 135                 140

Pro Gln Pro Asp Thr Val Glu Ala Gln Pro Ala Lys Gly Lys Lys Arg
145                 150                 155                 160

Lys Lys Thr Lys Lys Ser Asp Gly Asp Cys Ala Glu Arg Thr Leu Arg
                165                 170                 175

Glu Arg Ser Ile Ser Asp Tyr Leu Phe Glu Ala Tyr Arg Asp Thr Glu
                180                 185                 190

Glu Ile Leu Thr Arg Cys Ala Ile Asn Tyr Leu Leu Lys Asn Gly Cys
                195                 200                 205

Lys Ile Ser Asn Lys Glu Glu Asn Ala Glu Lys Phe Ala Lys Arg Arg
            210                 215                 220

Arg Lys Leu Glu Ile Gln Ile Glu Arg Leu Arg Glu Lys Leu Glu Ala
225                 230                 235                 240

Arg Ile Pro Lys Gly Arg Asp Leu Thr Asp Ala Lys Trp Leu Glu Thr
                245                 250                 255

Leu Leu Leu Ala Thr Leu Asn Val Pro Glu Asn Glu Ala Glu Ala Lys
                260                 265                 270

Ser Trp Gln Asp Ser Leu Leu Lys Lys Ser Ile Thr Val Pro Phe Pro
            275                 280                 285

Val Ala Tyr Glu Thr Asn Glu Asp Met Thr Trp Phe Lys Asn Glu Arg
            290                 295                 300

Gly Arg Ile Cys Val Lys Phe Ser Gly Leu Ser Glu His Thr Phe Gln
305                 310                 315                 320

Val Tyr Cys Asp Ser Arg Gln Leu Gln Trp Phe Gln Arg Phe Leu Glu
                325                 330                 335

Asp Gln Gln Ile Lys Arg Asn Ser Lys Asn Gln His Ser Ser Ser Leu
                340                 345                 350

Phe Thr Leu Arg Ser Gly Arg Ile Ala Trp Gln Glu Gly Glu Gly Lys
            355                 360                 365

Ser Glu Pro Trp Lys Val Asn Arg Leu Ile Leu Tyr Cys Ser Val Asp
            370                 375                 380

Thr Arg Leu Trp Thr Ala Glu Gly Thr Asn Leu Val Arg Glu Glu Lys
385                 390                 395                 400

Ala Glu Glu Ile Ala Lys Ala Ile Ala Gln Thr Lys Ala Lys Gly Lys
                405                 410                 415

Leu Asn Asp Lys Gln Gln Ala His Ile Lys Arg Lys Asn Ser Ser Leu
            420                 425                 430

Ala Arg Ile Asn Asn Leu Phe Pro Arg Pro Ser Lys Pro Leu Tyr Lys
            435                 440                 445
```

-continued

```
Gly Gln Ser His Ile Leu Val Gly Val Ser Leu Gly Leu Glu Lys Pro
            450                 455                 460

Thr Thr Leu Ala Val Val Asp Gly Ser Ile Gly Lys Val Leu Thr Tyr
465                 470                 475                 480

Arg Asn Ile Lys Gln Leu Leu Gly Asp Asn Tyr Arg Leu Leu Asn Arg
                485                 490                 495

Gln Arg Gln Gln Lys His Thr Leu Ser His Gln Arg Gln Val Ala Gln
                500                 505                 510

Ile Leu Ala Ser Pro Asn Gln Leu Gly Glu Ser Glu Leu Gly Gln Tyr
                515                 520                 525

Val Asp Arg Leu Leu Ala Lys Glu Ile Val Ala Ile Thr Gln Thr Tyr
530                 535                 540

Lys Ala Gly Ser Ile Val Leu Pro Lys Leu Gly Asp Met Arg Glu Gln
545                 550                 555                 560

Val Gln Ser Glu Ile Gln Ala Lys Ala Glu Gln Lys Ser Asp Leu Ile
                565                 570                 575

Glu Val Gln Gln Lys Tyr Ser Lys Gln Tyr Arg Val Ser Val His Gln
                580                 585                 590

Trp Ser Tyr Gly Arg Leu Ile Ala Ser Ile Arg Ser Ser Ala Ala Lys
            595                 600                 605

Val Gly Ile Val Ile Glu Glu Ser Lys Gln Pro Ile Arg Gly Ser Pro
610                 615                 620

Gln Glu Lys Ala Arg Glu Leu Ala Ile Ala Ala Tyr Asn Ser Arg Arg
625                 630                 635                 640

Arg Thr

<210> SEQ ID NO 6
<211> LENGTH: 641
<212> TYPE: PRT
<213> ORGANISM: Lyngbya confervoides

<400> SEQUENCE: 6

Met Ser Lys Ile Thr Ile Gln Cys Arg Leu Val Ala Ser Glu Ala Thr
1               5                   10                  15

Arg Gln Tyr Leu Trp His Leu Met Ala Asp Ile Tyr Thr Pro Phe Val
            20                  25                  30

Asn Glu Ile Leu Arg Gln Ile Arg Glu Asp Asp Asn Phe Glu Gln Trp
        35                  40                  45

Arg Gln Ser Gly Lys Ile Pro Ala Ser Val Phe Glu Asp Tyr Arg Lys
    50                  55                  60

Thr Leu Lys Thr Glu Ser Arg Phe Gln Gly Met Pro Gly Arg Trp Tyr
65              70                  75                  80

Tyr Ala Gly Arg Glu Glu Val Lys Arg Ile Tyr Lys Ser Trp Leu Ala
                85                  90                  95

Leu Arg Arg Arg Leu Arg Asn Gln Leu Ala Gly Gln Asn Arg Trp Leu
            100                 105                 110

Glu Val Leu Gln Ser Asp Glu Thr Leu Met Glu Val Ser Gly Leu Asp
        115                 120                 125

Leu Ser Ala Leu Gln Ala Glu Ala Ser Gln Leu Leu Asn Ile Leu Gly
    130                 135                 140

Ser Lys Asn Lys Thr Ser Lys Asn Arg Ser Lys Ala Lys Gly Lys
145                 150                 155                 160

Pro Lys Gly Lys Ser Ala Lys Asp Pro Thr Leu Tyr Gln Ala Leu Trp
                165                 170                 175
```

```
Glu Leu Tyr Arg Glu Thr Glu Asp Ile Ala Lys Lys Cys Val Ile Ala
            180                 185                 190

Tyr Leu Leu Lys His Lys Cys Gln Val Pro Asp Lys Pro Glu Asp Pro
        195                 200                 205

Lys Lys Phe Arg His Arg Arg Glu Ala Glu Ile Arg Ala Glu Arg
210                 215                 220

Leu Asn Glu Gln Leu Ile Lys Thr Arg Leu Pro Lys Gly Arg Asp Leu
225                 230                 235                 240

Thr Asn Glu Gln Trp Leu Gln Val Leu Glu Ile Ala Thr Arg Gln Val
                245                 250                 255

Pro Lys Asp Glu Asp Glu Ala Ala Ile Trp Gln Ser Arg Leu Leu Thr
            260                 265                 270

Asp Ala Ala Lys Phe Pro Phe Pro Val Ala Tyr Glu Thr Asn Glu Asp
        275                 280                 285

Leu Lys Trp Phe Leu Asn Gly Lys Gly Arg Leu Cys Val Ser Phe Asn
290                 295                 300

Gly Leu Ser Glu His Thr Phe Glu Val Tyr Cys Gly Gln Arg Gln Leu
305                 310                 315                 320

Tyr Trp Phe Asn Arg Phe Leu Glu Asp Gln Gln Ile Lys Lys Glu Asn
                325                 330                 335

Gln Gly Glu Arg Ser Ala Gly Leu Phe Thr Leu Arg Ser Gly Arg Leu
            340                 345                 350

Val Trp Lys Pro Tyr Ser Ser Asp Ala Ser Arg Ser Asp Pro Trp Met
        355                 360                 365

Ala Asn Gln Leu Thr Leu Gln Cys Ser Val Asp Thr Arg Leu Trp Thr
370                 375                 380

Ala Glu Gly Thr Glu Gln Val Arg Gln Glu Lys Ala Thr Ser Ile Ala
385                 390                 395                 400

Lys Val Ile Ala Gly Thr Lys Ala Lys Gly Asn Leu Asn Gln Lys Gln
                405                 410                 415

Gln Asp Phe Ile Thr Lys Arg Glu Lys Thr Leu Glu Leu Leu His Asn
            420                 425                 430

Pro Phe Pro Arg Pro Ser Lys Pro Leu Tyr Gln Gly Lys Pro Ser Ile
        435                 440                 445

Ile Ala Ala Val Ser Phe Gly Leu Glu Lys Pro Ala Thr Leu Ala Ile
450                 455                 460

Val Asp Ile Val Thr Asp Lys Ala Ile Thr Tyr Arg Ser Ile Arg Gln
465                 470                 475                 480

Leu Leu Gly Gln Asn Tyr Lys Leu Phe Thr Lys His Arg Leu Lys Gln
                485                 490                 495

Gln Gln Cys Ala His Gln Arg His Gln Asn Gln Val Glu Ser Ala Glu
            500                 505                 510

Asn Arg Ile Ser Glu Gly Gly Leu Gly Glu His Leu Asp Ser Leu Ile
        515                 520                 525

Ala Lys Ala Ile Leu Glu Thr Ala Ala Glu Tyr Gly Ala Ser Ser Ile
530                 535                 540

Val Leu Pro Glu Leu Gly Asn Ile Arg Glu Ile Ile His Ala Glu Ile
545                 550                 555                 560

Gln Ala Lys Ala Glu Arg Lys Ile Pro Gly Leu Lys Glu Lys Gln Asp
                565                 570                 575

Glu Tyr Ala Ala Lys Phe Arg Ala Ser Val His Arg Trp Ser Tyr Gly
            580                 585                 590
```

Arg Leu Ala Gln Lys Val Thr Thr Lys Ala Ser Leu His Gly Leu Glu
            595                 600                 605

Thr Glu Ser Thr Arg Gln Ser Leu Gln Gly Thr Pro Gln Glu Lys Ala
    610                 615                 620

Arg Asn Leu Ala Ile Ser Ala Tyr Glu Ser Arg Lys Val Ala Gln Arg
625                 630                 635                 640

Ala

<210> SEQ ID NO 7
<211> LENGTH: 649
<212> TYPE: PRT
<213> ORGANISM: Calothrix sp.

<400> SEQUENCE: 7

Met Ser Ile Ile Thr Ile Gln Cys Arg Leu Val Ala Asn Asp Arg Thr
1               5                   10                  15

Leu Gln His Leu Trp Glu Leu Met Ala Glu Lys Asn Thr Pro Leu Ile
            20                  25                  30

Ser Glu Leu Leu Glu Gln Leu Gly Lys His Pro Asp Phe Glu Thr Trp
        35                  40                  45

Leu Lys Asn Gly Lys Val Pro Lys Asp Thr Ile Lys Ile Leu Cys Asp
50                  55                  60

Ser Leu Lys Thr Gln Ser Arg Phe Ala Gly Gln Pro Gly Arg Phe Tyr
65                  70                  75                  80

Thr Ser Ala Ile Ser Gln Val Lys Glu Ile Tyr Lys Ser Trp Leu Thr
                85                  90                  95

Leu Gln Lys Arg Arg Gln Arg Gln Ile Glu Gly Lys Gln Arg Trp Leu
            100                 105                 110

Gly Met Leu Lys Ser Asp Val Glu Leu Gln Glu Glu Ser Asn Cys Ser
        115                 120                 125

Leu Glu Lys Ile Arg Ala Lys Gly Thr Glu Ile Leu Ala Glu Phe Val
130                 135                 140

Ser Lys Phe Thr Lys Asp Thr Thr Lys Lys Ser Lys Thr Lys Ile Lys
145                 150                 155                 160

Ser Thr Lys Lys Ser Asn Lys Lys Thr Lys Lys Asp Thr Glu Glu Ser
                165                 170                 175

Asn Ser Thr Leu Phe Gln Ala Leu Cys Asp Ile Tyr Asp Lys Thr Glu
            180                 185                 190

Asp Thr Leu Ser Lys Cys Ala Ile Ile Tyr Leu Leu Lys Asn Asn Cys
        195                 200                 205

Gln Val Ile Asp Thr Glu Glu Asn Pro Asp Thr Phe Leu Lys Arg Lys
210                 215                 220

Arg Ala Lys Glu Ile Glu Ile Lys Arg Leu Gln Asp Gln Ile Val Gly
225                 230                 235                 240

Arg Ile Pro Lys Gly Arg Asp Leu Thr Asp Lys Lys Trp Leu Asp Thr
                245                 250                 255

Ile Lys Leu Ala Ser Ser Gln Val Pro Gln Asp Glu Asn Glu Ala Lys
            260                 265                 270

Ser Trp Gln Asn Gln Leu Leu Lys Thr Ser Ser Val Pro Tyr Ser
        275                 280                 285

Val Asp Tyr Glu Thr Asn Thr Asp Ile Lys Trp Val Lys His Asn Asn
290                 295                 300

Gly Ser Ile Phe Val Asn Phe Asn Gly Leu Gly Glu His Gln Phe Glu
305                 310                 315                 320

Val Tyr Cys Asp Ser Arg Gln Leu Pro Tyr Phe Gln Arg Phe Cys Glu
            325                 330                 335

Asp Met Gln Ile Trp His Asn Asp Glu Glu Lys Tyr Ser Ser Ala Leu
        340                 345                 350

Phe Met Leu Arg Ser Ala Arg Leu Val Trp Leu Glu Lys Lys Gly Arg
        355                 360                 365

Gly Lys Pro Trp Asn Val Asn Tyr Leu Tyr Leu His Cys Ser Leu Asp
        370                 375                 380

Thr Ser Leu Trp Thr Ala Glu Gly Thr Glu Gln Ile Arg Ile Asn Lys
385                 390                 395                 400

Ile Asn Glu Thr Asp Glu Ala Ile Ala Lys Ala Lys Thr Lys Asp Lys
                405                 410                 415

Gln Glu Leu Thr Glu Asn Gln Leu Ala Tyr Leu Gln Arg Gln Gln Ser
            420                 425                 430

Thr Arg Asn Lys Leu Asn Asn Ser Phe Pro Gly Arg Pro Ser Lys Pro
        435                 440                 445

Ile Tyr Lys Gly Asn Ser His Ile Leu Val Gly Val Ser Leu Gly Leu
        450                 455                 460

Glu Lys Pro Val Thr Val Ala Ala Val Asp Val Val Ser Asn Lys Val
465                 470                 475                 480

Leu Ala Tyr Arg Ser Val Lys Gln Leu Leu Gly Gln Asn Tyr Lys Leu
                485                 490                 495

Leu Asn Arg Gln Arg Gln Gln Lys His Leu Ala Gln Lys Arg His
            500                 505                 510

Glu Ser Gln Lys Lys Gln Ala Pro Asn Gln Phe Gly Glu Ser Glu Leu
        515                 520                 525

Gly Leu Tyr Val Asp Arg Leu Leu Ala Lys Ser Ile Ile Asn Phe Ala
        530                 535                 540

Lys Thr Tyr Gln Ala Ser Ser Ile Ala Leu Pro Lys Leu Arg Asp Met
545                 550                 555                 560

Arg Glu Ile Ile Gln Ser Glu Ile Gln Ala Lys Ala Glu Ser Lys Ile
                565                 570                 575

Pro Gly Tyr Lys Glu Gly Gln Glu Lys Tyr Ala Lys Glu Tyr Arg Met
            580                 585                 590

Ser Val His Arg Trp Ser Tyr Gly Arg Leu Ile Gly Asn Ile Gln Ala
        595                 600                 605

Gln Ala Ala Gln Ala Gly Ile Leu Ile Glu Thr Ser Ser Gly Gln Ile
        610                 615                 620

Arg Gly Ser Pro Gln Glu Gln Ala Lys His Leu Ala Ile Ser Ala Tyr
625                 630                 635                 640

Ile Glu Arg Gln Thr Ile Leu Asn Lys
                645

<210> SEQ ID NO 8
<211> LENGTH: 682
<212> TYPE: PRT
<213> ORGANISM: Cyanothece sp.

<400> SEQUENCE: 8

Met Thr Leu Lys Thr Leu Glu Cys Arg Leu Tyr Ala Pro Ser Asp Thr
1               5                   10                  15

Leu Arg Tyr Leu Trp Leu Leu Met Ala Glu Lys Asn Thr Pro Leu Ile
            20                  25                  30

Asn Glu Ile Ile Asn His Leu Ser Glu His Pro Asp Phe Asp Gln Trp
        35                  40                  45

```
Phe Lys Ala Lys Gln Ile Pro Lys Ser Ala Ile Ser Asp Ile Cys Asn
 50                  55                  60

Asp Leu Lys Ser Gln Glu Asn Tyr Gln Asn Gln Pro Gly Arg Phe Tyr
 65                  70                  75                  80

Ser Ser Ala Ile Ser Leu Thr His Tyr Met Phe Lys Ser Trp Phe Ala
                 85                  90                  95

Val His Lys Gln Leu Gln Arg Arg Ile Glu Gly Lys Arg Arg Trp Leu
             100                 105                 110

Asn Leu Leu Lys Ser Asp Gln Glu Leu Glu Gln Asn Cys Gly Gln Ser
         115                 120                 125

Leu Glu Ile Ile Ile Gln Lys Ala Glu Glu Ile Leu Lys Leu Met Asp
     130                 135                 140

Ser Glu Lys Ser Gln Ser Ser Ser Lys Pro Lys Lys Pro Lys Lys Pro
145                 150                 155                 160

Lys Lys Lys Lys Ser Ser Ser Glu Glu Thr Ile Thr Leu Phe Asp
                165                 170                 175

Arg Leu Phe Lys Ala Tyr Asn Gln Gly Asn Asp Ser Leu Glu Ser Tyr
             180                 185                 190

Ala Leu Ala Tyr Leu Leu Lys Asn Asn Gly Gln Ile Pro Glu Asp Asp
         195                 200                 205

Glu Asp Leu Asp Lys Phe Ala Leu Arg Lys Arg Lys Glu Ile Glu
    210                 215                 220

Ile Glu Arg Leu Gln Gln Gln Leu Glu Asn Arg Ile Pro Leu Gly Arg
225                 230                 235                 240

Asp Leu Thr Gly Glu Leu Trp Gln Glu Met Leu Thr Ile Val Asn Glu
                245                 250                 255

Ser Ile Pro Gln Asp Glu Asn Glu Ala Ser Ala Trp Gln Ala Lys Leu
             260                 265                 270

Leu Lys Lys Ser His Asn Ile Pro Tyr Pro Val Ala Tyr Glu Thr Asn
         275                 280                 285

Thr Asp Leu Lys Trp Ser Lys Asp Ser Arg Gly His Leu Leu Val Thr
    290                 295                 300

Phe Asn Gly Leu Val Glu Ser Leu Lys Lys Leu Asn Leu Asn Pro Glu
305                 310                 315                 320

Phe Glu Ile Arg Cys Asp Arg Arg His Leu Pro Trp Phe Gln Arg Phe
                325                 330                 335

Cys Lys Asp Gln Glu Ile Lys Ala Asn Asn Asp Gln His Ser Ser Ala
             340                 345                 350

Leu Phe Val Leu Arg Ser Ala Arg Leu Ile Trp Arg Glu Gly Gln Gly
         355                 360                 365

Lys Glu Asp Pro Trp Lys Ile His Gln Leu Tyr Leu Gln Cys Ser Val
    370                 375                 380

Glu Thr Gln Leu Trp Thr Glu Ala Gly Thr Lys Gln Val Gln Ser Glu
385                 390                 395                 400

Lys Met Val Glu Phe Gln Leu Asn Gln Leu Arg Met Lys Pro Glu Leu
                405                 410                 415

Thr Phe Pro Ile Phe Phe Arg Ser Gln Ser Leu Pro Thr Tyr Phe Asn
             420                 425                 430

Leu Trp Lys Val Ile Thr Ser Tyr Arg Ile Leu Lys Phe Leu Glu Lys
         435                 440                 445

Gly Asp Phe Thr Lys Ala Gln Lys Asn Phe Gln Asp Ala Ile Lys Arg
    450                 455                 460
```

```
Thr Glu Ser Cys Leu Glu Asn Leu Gln Ser Ser Tyr Leu Thr Ser Gln
465                 470                 475                 480

Lys Ser Leu Tyr Gln Gly Asn Pro Glu Ile Ile Met Gly Val Ala Met
            485                 490                 495

Gly Leu Ser Gln Pro Ala Thr Ile Ala Val Val Asn Val Val Thr Gln
            500                 505                 510

Glu Val Leu Thr Tyr Arg Ser Leu Lys Gln Leu Leu Gly Lys Asn Tyr
            515                 520                 525

Asn Leu Leu Asn Arg Gln Arg Gln Gln Lys Gln Lys Leu Ser His Gln
            530                 535                 540

Arg His Lys Ala Gln Lys Lys Asp Ala Phe Asn Gln Tyr Gly Glu Ser
545                 550                 555                 560

Glu Leu Gly Gln Tyr Val Asp Arg Leu Ile Ala Lys Ala Ile Val Gln
            565                 570                 575

Val Ala Lys Glu Tyr Gln Ala Asp Ser Ile Ala Val Pro Lys Ile Arg
            580                 585                 590

Gln Met Arg Glu Ile Ile Gln Ser Glu Val Gln Ala Arg Ala Glu Arg
            595                 600                 605

Lys Ile Gln Gly Tyr Lys Glu Gly Gln Lys Lys Tyr Ala Gln Gln Tyr
            610                 615                 620

Arg Glu Asn Val His Gln Trp Ser Tyr Gly Arg Leu Ile Glu Ser Ile
625                 630                 635                 640

His Gln Ala Ser Ala Lys Phe Gly Ile Arg Val Glu Ile Ala Ser Gln
            645                 650                 655

Ser Tyr Gln Gly Ser Phe Gln Glu Gln Ala Gln Asn Leu Ala Ile Ala
            660                 665                 670

Ala Tyr Thr Asn Arg Leu Glu Ala Val Gly
            675                 680

<210> SEQ ID NO 9
<211> LENGTH: 660
<212> TYPE: PRT
<213> ORGANISM: Cyanothece sp.

<400> SEQUENCE: 9

Met Thr His Ile Thr Val Val Gln Cys Arg Leu Ile Ala Pro Glu Ser
1               5                   10                  15

Thr Leu Gln His Ile Trp Lys Met Met Ala Gln Gln Thr Pro Leu
            20                  25                  30

Ile Asn Gln Leu Leu His Asp Ile Asn Thr His Pro Asp Ile Asn Thr
            35                  40                  45

Trp Leu Thr Ala Asn Gln Leu Pro Ser Lys Leu Val Glu Thr Leu Ala
50                  55                  60

Gln Pro Leu Lys Thr Gln Ser Pro Tyr Gln Gly Leu Pro Gly Arg Phe
65                  70                  75                  80

Ile Thr Ser Ala Ile Ile Leu Val Lys Glu Met Tyr Ala Ser Trp Phe
            85                  90                  95

Ala Ile Gln Thr Gln Lys Arg Leu Ser Leu Glu Gly Lys Lys Arg Phe
            100                 105                 110

Leu Thr Ile Leu Lys Ser Asp Lys Gln Leu Ile Gln Asp Ser Gln Thr
            115                 120                 125

Asp Phe Leu Thr Leu Cys Tyr Lys Ala Gln Gln Leu Leu Lys Arg Thr
            130                 135                 140

Gln Asn Lys Leu Lys Leu Asp Glu Pro Gln His Ser Glu Lys Ala His
145                 150                 155                 160
```

```
Trp Ser Ile Ile Asn Ala Leu Tyr Pro Ala Tyr Asn Ala Lys Thr
            165                 170                 175

Pro Ile Ser Arg Ala Ala Phe Ala Leu Leu Ile Lys Asn Asn Gly Gln
            180                 185                 190

Val Pro Asp Thr Pro Glu Asn Pro Asp Tyr Tyr Gln Gln Arg Arg Lys
            195                 200                 205

Arg Lys Glu Ile Gln Ile Arg Arg Leu Glu Glu Gln Leu Lys Ala Ser
210                 215                 220

Leu Pro Lys Gly Arg Ile Leu Asp Ser Lys His Trp Glu Asn Thr Leu
225                 230                 235                 240

Lys Leu Ala Gln Thr Pro Ile Thr Thr Ile Glu Glu Ile Thr Ser Leu
                245                 250                 255

Gln Thr Gln Leu Leu Gln Lys Tyr Ser His Leu Pro Phe Pro Val Phe
                260                 265                 270

Tyr Gly Thr Asn Thr Asp Leu Thr Trp Phe Lys Asn Pro Gln Gly Arg
            275                 280                 285

Ile Cys Val Lys Phe Asn Gly Leu Asn Gln Tyr Pro Phe Gln Ile Ala
            290                 295                 300

Cys Asn Lys Arg Gln Tyr Pro Trp Phe Gln Arg Phe Phe Thr Asp Tyr
305                 310                 315                 320

Gln Ser Tyr Lys Ser His Lys Gln Gln Val Pro Thr Gly Leu Met Val
                325                 330                 335

Leu Arg Ser Ala Arg Leu Leu Trp Gln Pro Thr Asn Gly Gln Gly Glu
                340                 345                 350

Pro Trp Asn Thr His His Leu Ser Leu His Cys Ala Ile Asp Asn Asp
            355                 360                 365

Leu Trp Thr Ile Ser Gly Ile Gln Gln Val Lys Gln Gln Lys Ile Leu
            370                 375                 380

Gln Thr Glu Gln Lys Ile Ala Asn Phe His Ser Lys Ala Leu Glu Lys
385                 390                 395                 400

Glu Leu Thr Pro Asn Gln Gln Arg Leu Lys Ala Ser Gln Thr Ser
                405                 410                 415

Leu Asn Leu Leu Lys Thr Phe Asp Ile Asn Glu Phe Phe Pro Ser Lys
                420                 425                 430

Cys Ser Leu Tyr Gln Gly Ser Pro Asp Ile Ile Leu Gly Val Ser Ile
            435                 440                 445

Gly Leu Glu Asn Pro Ala Thr Ile Ala Ile Ile Asn Ile Ser Thr Gln
450                 455                 460

Glu Ile Leu Thr Tyr Arg Thr Thr Lys Gln Leu Leu Ser Arg Thr Arg
465                 470                 475                 480

Lys Val Arg Asn Lys Lys Pro Asn Ser Asn Asn Ser Asn Gln Ser Leu
                485                 490                 495

Ser Ser Ala Tyr Lys Gln Ile Ser Asn Tyr Glu Leu Phe Leu Gln Tyr
            500                 505                 510

Gln Gln Gln Lys His His Asn Gln His Gln Arg His Asn Ala Gln Ile
            515                 520                 525

Asn Asp Ala Asn Asn Tyr Gly Glu Ala Asn Leu Gly Leu Tyr Leu
530                 535                 540

Asn Arg Leu Leu Ala Lys Ala Ile Leu Glu Leu Ala Gln Tyr Gln
545                 550                 555                 560

Val Ser Leu Ile Ile Leu Pro Ser Leu Lys Asn Lys Arg Glu Leu Ile
                565                 570                 575
```

-continued

```
Glu Ser Glu Ile Arg Ala Lys Ala Glu Leu Lys Tyr Pro Gly Cys Lys
            580                 585                 590

Glu Lys Gln Asp Ser Tyr Ala Lys Asp Tyr Arg Thr Asn Val His Gln
        595                 600                 605

Trp Ser Tyr Gln Gln Leu Ile Lys Cys Ile Glu Ser Lys Ala Ala Gln
    610                 615                 620

Ile Gly Ile Asp Thr Ala Thr Gly Lys Gln Met Asn Leu Glu Thr Ser
625                 630                 635                 640

Gln Asp Gln Ala Arg Asn Leu Val Leu Asn Phe Cys Gln Lys Phe Ser
                645                 650                 655

Pro Thr Gln Val
            660

<210> SEQ ID NO 10
<211> LENGTH: 616
<212> TYPE: PRT
<213> ORGANISM: Geminocystis sp.

<400> SEQUENCE: 10

Met Ala His Val Thr Ile Gln Cys Arg Leu Ile Ala Ser Arg Asp Thr
1               5                   10                  15

Arg Gln Phe Leu Trp Gln Leu Met Ala Gln Lys Asn Thr Pro Leu Ile
            20                  25                  30

Asn Glu Ile Leu Leu Arg Ile Lys Gln His Pro Asp Phe Pro His Trp
        35                  40                  45

Arg Thr Lys Lys Arg Leu Pro Lys Asp Phe Leu Ala Arg Gln Ile Ala
    50                  55                  60

Glu Leu Lys Asn Asn Tyr Pro Phe Glu Glu Gln Pro Ser Arg Phe Tyr
65                  70                  75                  80

Ala Ser Val Asn Lys Val Ile Asp Tyr Ile Tyr Lys Ser Trp Phe Glu
                85                  90                  95

Val Gln Lys Ala Leu Asp Trp Lys Leu Gln Gly Asn Leu Arg Trp Val
            100                 105                 110

Glu Met Leu Leu Pro Asp Thr Glu Leu Ile Lys His Phe Asp Asn Ser
        115                 120                 125

Leu Glu Ser Leu Gln Gln Gln Ala Thr Leu Ile Leu Asp Ser Ile Asp
    130                 135                 140

Ser Thr Val Ser His Asp Arg Ile Ser Thr Ile Leu Phe Glu Lys Cys
145                 150                 155                 160

Gly Lys Thr Lys Lys Pro Glu Ile Lys Ser Ala Ile Ile Tyr Leu Leu
                165                 170                 175

Lys Asn Gly Cys Thr Ile Pro Lys Lys Pro Glu Thr Thr Glu Lys Tyr
            180                 185                 190

Gln Asp Leu Lys Arg Lys Val Glu Ile Lys Ile Thr Lys Leu His Arg
        195                 200                 205

Gln Ile Glu Ser Arg Ile Pro Leu Gly Arg Asp Leu Glu Asp Lys Lys
    210                 215                 220

Trp Leu Asp Thr Leu Ile Thr Ala Ser Thr Thr Ala Pro Ile Asp Gln
225                 230                 235                 240

Thr Glu Ala Asn Thr Trp Phe Ser Ile Leu Lys Gln Asn Gln Ser Ser
                245                 250                 255

Ile Pro Tyr Pro Ile Leu Tyr Glu Thr Asn Glu Asp Leu Lys Trp Ser
            260                 265                 270

Leu Asn Glu Lys Asn Arg Leu Ser Ile Arg Phe Ser Gly Leu Gly Glu
        275                 280                 285
```

```
His Ser Phe Gln Leu Cys Cys Asp His Arg Gln Leu Pro Tyr Phe Gln
    290                 295                 300

Arg Phe Tyr Glu Asp Gln Glu Leu Lys Lys Ala Ser Lys Asp Gln Leu
305                 310                 315                 320

Ser Ser Ala Leu Phe Thr Leu Arg Ser Ala Met Ile Leu Trp Lys Glu
                325                 330                 335

Asp Glu Gly Lys Gly Glu Leu Trp Asp Arg His Lys Leu Tyr Leu His
                340                 345                 350

Cys Thr Phe Glu Thr Arg Cys Leu Thr Ala Glu Gly Thr Ser Thr Ile
                355                 360                 365

Val Glu Glu Lys Gln Lys Glu Val Thr Lys Ile Ile Asp Leu Met Lys
370                 375                 380

Ala Lys Glu Glu Leu Ser Asp Ser Gln Gln Ala Phe Ile Arg Arg Lys
385                 390                 395                 400

Asn Ser Thr Leu Ala Lys Leu Asn Asn Thr Phe Pro Arg Pro Ser Lys
                405                 410                 415

Pro Val Tyr Gln Gly Lys Pro Asn Val His Leu Gly Ile Ala Met Gly
                420                 425                 430

Leu Glu Gln Pro Val Thr Ile Ala Ile Val Asp Ile Glu Thr Asp Lys
                435                 440                 445

Val Ile Thr Tyr Arg Asn Thr Lys Gln Leu Leu Arg Glu Asp Tyr Arg
450                 455                 460

Leu Leu Arg Arg Arg Ile Glu Lys Gln Lys Leu Ser His Gln Asn
465                 470                 475                 480

His Lys Ala Arg Lys Arg Phe Asn Phe Gln Gln Lys Gly Glu Ser Asn
                485                 490                 495

Leu Gly Glu Tyr Leu Asp Arg Leu Ile Ala Lys Ala Ile Leu Thr Val
                500                 505                 510

Ala Gln Glu Tyr Gln Val Ser Thr Ile Leu Ile Pro Arg Leu Arg Asp
                515                 520                 525

Met Arg Ser Ile Thr Glu Ala Glu Ile Gln Leu Arg Ala Glu Lys Lys
530                 535                 540

Ile Pro Glu Tyr Lys Glu Gly Gln Lys Tyr Ala Gln Asp Tyr Arg
545                 550                 555                 560

Val Gln Val His Gln Trp Ser Tyr Gly Arg Leu Ile Glu Asn Val Lys
                565                 570                 575

Leu Ile Cys Glu Lys Val Gly Ile Val Val Glu Ala Lys Gln Pro
                580                 585                 590

Lys Gln Gly Thr Leu Thr Glu Lys Ala Leu Gln Leu Val Leu Ser Ala
                595                 600                 605

Thr Glu Lys Asn Leu Lys Lys Lys
610                 615
```

<210> SEQ ID NO 11
<211> LENGTH: 636
<212> TYPE: PRT
<213> ORGANISM: Leptolyngbya boryana

<400> SEQUENCE: 11

```
Met Ser Val Ile Thr Ile Gln Cys Lys Leu Val Ala Thr Glu Glu Thr
1               5                   10                  15

Arg Arg Ala Leu Trp His Leu Met Ala Glu Lys His Thr Pro Leu Ile
                20                  25                  30

Asn Glu Leu Leu Lys His Ile Ala Gln Asp Ser Arg Phe Glu Glu Trp
```

```
            35                  40                  45
Ser Leu Thr Gly Lys Leu Pro Arg Leu Val Ser Glu Ala Cys Asn
 50                  55                  60

Gln Leu Lys Gln Asp Pro Gln Phe Ser Gly Gln Pro Gly Arg Phe Tyr
 65                  70                  75                  80

Ser Ser Ala Ile Ser Thr Val His Arg Ile Phe Leu Ser Trp Leu Ala
                 85                  90                  95

Leu Gln Thr Arg Leu Arg Asn Gln Ile Ser Gly Gln Thr Arg Trp Leu
                100                 105                 110

Ala Met Leu Gln Ser Asp Asn Glu Leu Thr Ile Ala Ser Gln Thr Asp
                115                 120                 125

Ile Asn Thr Leu Arg Leu Lys Ala Ser Glu Leu Leu Thr His Leu Asn
130                 135                 140

Glu Pro Ile Ser Glu Ser Asp Gln Pro Glu Val Lys Lys Thr Arg Ser
145                 150                 155                 160

Lys Lys Lys Asn Gln Thr Ser Asn Gln Ala Gly Ala Asn Val Ser Arg
                165                 170                 175

Thr Leu Phe Lys Leu Tyr Asp Glu Thr Glu Asp Pro Leu Thr Arg Cys
                180                 185                 190

Ala Ile Ala Tyr Leu Leu Lys Asn Gly Cys Lys Leu Pro Asp Gln Asn
                195                 200                 205

Glu Asn Pro Glu Lys Phe Ile Lys Arg Arg Lys Thr Glu Ile Arg
210                 215                 220

Leu Glu Arg Leu Met Asn Thr Phe Gln Thr Thr Arg Ile Pro Arg Gly
225                 230                 235                 240

Arg His Leu Ser Trp His Ser Trp Ile Glu Ala Leu Glu Thr Ala Thr
                245                 250                 255

Ser His Ile Pro Glu Asn Glu Glu Ala Ala Gly Trp Gln Ala Arg
                260                 265                 270

Leu Leu Thr Lys Pro Ala Ile Leu Pro Phe Pro Val Asn Tyr Glu Thr
                275                 280                 285

Asn Glu Asp Leu Arg Trp Ser Leu Asn Ser Gln Gly Arg Ile Cys Val
290                 295                 300

Ser Phe Asn Gly Leu Ser Glu His Phe Phe Glu Val Tyr Cys Asp Gln
305                 310                 315                 320

Arg Asp Leu His Trp Phe Asn Arg Phe Leu Glu Asp Gln Glu Thr Lys
                325                 330                 335

Lys Ala Ser Lys Asn Gln His Ser Ser Ser Leu Phe Ser Leu Arg Ser
                340                 345                 350

Gly Gln Ile Ala Trp Gln Glu Gly Lys Gly Asp Ala Glu His Trp Val
                355                 360                 365

Val His Arg Leu Val Leu Ser Cys Ser Ile Glu Thr Asp Thr Trp Thr
                370                 375                 380

Gln Glu Gly Thr Glu Glu Ile Arg Gln Lys Lys Ala Ser Asp Cys Ala
385                 390                 395                 400

Lys Val Ile Ala Ser Thr Lys Ala Lys Glu Asn Arg Ser Gln Asn Gln
                405                 410                 415

Asp Ala Phe Ile Arg Arg Arg Glu Arg Met Leu Glu Leu Leu Glu Asn
                420                 425                 430

Gln Phe Pro Arg Pro Ser Tyr Pro Leu Tyr Gln Gly Gln Pro Ser Ile
                435                 440                 445

Leu Ala Gly Val Ser Tyr Gly Leu Asp Lys Pro Ala Thr Leu Ala Ile
                450                 455                 460
```

```
Val Asn Ile Gln Thr Gly Lys Ala Ile Thr Tyr Arg Ser Ile Arg Gln
465                 470                 475                 480

Ile Leu Gly Lys Asn Tyr Lys Leu Leu Asn Arg Tyr Arg Leu Asn Gln
                485                 490                 495

Gln Arg Asn Ala His Lys Arg His Asn Asn Gln Arg Lys Gly Gly Ser
            500                 505                 510

Ser Gln Leu Arg Glu Ser Asn Gln Gly Gln Tyr Leu Asp Arg Leu Ile
        515                 520                 525

Ala His Glu Ile Val Ala Ile Ala Gln Glu Tyr Gln Val Ser Ser Leu
    530                 535                 540

Ala Leu Pro Asp Leu Gly Asp Ile Arg Glu Ile Val Gln Ser Glu Val
545                 550                 555                 560

Gln Ala Arg Ala Glu Gln Lys Ile Leu Gly Ser Ile Glu Gln Gln Arg
                565                 570                 575

Lys Tyr Ala Arg Gln Tyr Arg Ala Ser Val His Arg Trp Arg Tyr Ala
            580                 585                 590

Gln Leu Thr Gln Phe Ile Gln Ser Gln Ala Ala Gln Val Gly Ile Ser
        595                 600                 605

Ile Glu Ile Thr Lys Gln Pro Leu Ser Gly Thr Pro Gln Glu Lys Ala
    610                 615                 620

Arg Asn Leu Ala Ile Ala Ala Tyr Gln Ser Arg Lys
625                 630                 635

<210> SEQ ID NO 12
<211> LENGTH: 615
<212> TYPE: PRT
<213> ORGANISM: Myxosarcina sp.

<400> SEQUENCE: 12

Met Ser Gln Asn Ala Ile Gln Cys Arg Leu Ile Ala Pro Glu Thr Thr
1               5                   10                  15

Arg Arg Gln Gln Trp Gln Leu Met Ala Glu Lys Asn Thr Pro Leu Ile
                20                  25                  30

Asn Glu Leu Leu Lys Gln Leu Ala Glu His Pro Glu Leu Glu Thr Trp
            35                  40                  45

Lys Arg Lys Gly Lys Ile Pro Pro Gly Thr Val Lys Asn Leu Cys Gln
        50                  55                  60

Pro Leu Arg Thr Cys Pro Gln Tyr Ile Asn Gln Pro Gly Arg Phe Tyr
65                  70                  75                  80

Ser Ser Val Ile Ser Leu Ala Glu Tyr Ile Tyr Arg Ser Trp Leu Lys
                85                  90                  95

Leu Gln Arg Arg Leu Ile Phe Arg Leu Asn Gly Gln Gln Arg Trp Leu
            100                 105                 110

Gln Met Leu Lys Ser Asp Glu Glu Leu Val Ala Glu Ser Gly Arg Ser
        115                 120                 125

Leu Lys Glu Ile Glu Ala Lys Ala Ser Glu Ala Leu Asp Arg Leu Asn
    130                 135                 140

Arg Glu Glu Asn Pro Ser Ile Ser Asn Arg Leu Phe Asp Leu Tyr Asp
145                 150                 155                 160

Glu Thr Glu Asp Ile Leu Ile Arg Ser Ala Ile Val Tyr Leu Leu Lys
                165                 170                 175

Asn Gly Cys Lys Ile Arg Gln Lys Pro Glu Asp Pro Lys Lys Phe Ala
            180                 185                 190

Arg Arg Arg Arg Lys Thr Glu Ile Arg Val Lys Arg Leu Gln Glu Lys
```

-continued

```
                195                 200                 205
Leu Asn Gly Lys Ala Pro Gln Gly Arg Asp Leu Thr Gly Glu Lys Trp
210                 215                 220

Leu Asn Thr Leu Phe Thr Ala Thr Ser Gln Val Pro Gln Asp Glu Ala
225                 230                 235                 240

Gln Ala Lys Ser Trp Gln Asp Ile Leu Leu Thr Lys Ser Lys Leu Val
                245                 250                 255

Pro Tyr Pro Ile Val Tyr Glu Ser Asn Glu Asp Leu Thr Trp Ser Lys
            260                 265                 270

Asn Glu Arg Gly Arg Leu Cys Val Lys Phe Asn Gly Leu Ser Asp His
        275                 280                 285

Thr Phe Gln Ile Tyr Cys Asp Arg Arg Gln Leu Lys Ile Phe Asn Arg
    290                 295                 300

Phe Tyr Glu Asp Gln Gln Ile Lys Lys Ala Ser Lys Asn Ser His Ser
305                 310                 315                 320

Ser Ala Leu Phe Thr Leu Arg Ser Ala Thr Ile Ala Trp Gln Glu Gly
                325                 330                 335

Lys Gly Lys Gly Glu Pro Trp Asn Val Asn Arg Leu Ile Leu Tyr Cys
            340                 345                 350

Thr Phe Asp Asn Leu Leu Leu Thr Thr Glu Gly Thr Glu Val Val Arg
        355                 360                 365

Gln Glu Lys Ala Glu Ala Ile Ala Asn Thr Leu Thr Lys Ile Lys Glu
    370                 375                 380

Lys Gly Asp Leu Asn Gln Lys Gln Gln Ala Phe Ile Arg Arg Lys Glu
385                 390                 395                 400

Thr Ser Leu Ser Arg Ile Asn Asn Pro Phe Pro Arg Pro Ser Arg Pro
                405                 410                 415

Leu Tyr Lys Gly Lys Ser Asn Ile Leu Leu Gly Val Ala Ile Arg Leu
            420                 425                 430

Asp Lys Pro Ala Thr Val Ala Ile Val Asp Gly Ala Thr Asp Lys Ala
        435                 440                 445

Ile Ala Tyr Leu Ser Thr Lys Gln Leu Leu Gly Lys Asn Tyr His Leu
    450                 455                 460

Leu Asn Arg Lys Arg Gln Gln Gln His Ile Leu Ser His Gln Arg Asn
465                 470                 475                 480

Val Ala Gln Arg His His Ala Asn Asn Lys Phe Gly Glu Ser Glu Leu
                485                 490                 495

Gly Gln Tyr Ile Asp Arg Leu Leu Ala Lys Ala Ile Ile Gln Leu Ala
            500                 505                 510

Lys Asp Tyr Arg Val Gly Ser Ile Val Val Pro Tyr Met Glu Asp Thr
        515                 520                 525

Arg Glu Ile Ile Gln Ala Glu Val Gln Ala Arg Glu Ala Lys Ile
    530                 535                 540

Pro Gly Cys Ile Glu Lys Gln Lys Glu Tyr Ala Lys Lys Tyr Arg Thr
545                 550                 555                 560

Asn Ile His Lys Trp Ser Tyr Gly Arg Leu Ile Asp Leu Ile Lys Ala
                565                 570                 575

Gln Ala Ala Lys Ala Gly Ile Val Ile Glu Glu Ser Lys Gln Ser Ile
            580                 585                 590

Arg Gly Asp Pro Lys Lys Gln Ala Lys Glu Ile Ala Val Cys Ala Tyr
        595                 600                 605

Arg Asp Arg Ile Val Pro Phe
    610                 615
```

<210> SEQ ID NO 13
<211> LENGTH: 639
<212> TYPE: PRT
<213> ORGANISM: Nostoc punctiforme

<400> SEQUENCE: 13

```
Met Ser Gln Ile Thr Ile Gln Cys Arg Leu Ile Ala Ser Glu Ser Thr
1               5                   10                  15

Arg Gln Lys Leu Trp Lys Leu Met Ala Thr Leu Asn Thr Pro Leu Ile
            20                  25                  30

Asn Glu Leu Ile Glu Gln Leu Gly Lys His Pro Asp Phe Glu Asn Trp
        35                  40                  45

Arg Gln Gln Gly Lys Leu Pro Thr Thr Val Val Ser Gln Leu Cys Gln
    50                  55                  60

Pro Leu Lys Thr Asp Pro Arg Phe Val Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Leu Asp Gly Lys Met Arg Trp Leu
            100                 105                 110

Glu Met Leu Asn Ser Asp Val Glu Leu Val Glu Thr Ser Gly Ser Ser
        115                 120                 125

Met Gly Ala Ile Arg Thr Lys Ala Ser Glu Ile Leu Ala Lys Ala Met
    130                 135                 140

Pro Thr Ser Asp Ser Asp Ser Ser Gln Pro Lys Thr Lys Lys Gly Lys
145                 150                 155                 160

Glu Ala Lys Lys Ser Ser Ser Ser Ser Asp Arg Ser Leu Ser Asn
                165                 170                 175

Lys Leu Phe Glu Ala Tyr Gln Glu Thr Glu Asp Ile Leu Ser Arg Ser
            180                 185                 190

Ala Ile Ser Tyr Leu Leu Lys Asn Gly Cys Lys Leu Ser Asp Lys Glu
        195                 200                 205

Glu Asp Ser Glu Lys Phe Ala Lys Arg Arg Gln Val Glu Ile Gln
    210                 215                 220

Ile Gln Arg Leu Thr Glu Lys Leu Ile Ser Arg Met Pro Lys Gly Arg
225                 230                 235                 240

Asp Leu Thr Asn Arg Lys Trp Leu Glu Thr Leu Phe Thr Ala Thr Thr
                245                 250                 255

Thr Phe Pro Glu Asp Asn Ala Glu Ala Lys Arg Trp Gln Asp Ile Leu
            260                 265                 270

Leu Thr Arg Pro Ser Ser Leu Pro Phe Pro Leu Val Phe Glu Thr Asn
        275                 280                 285

Glu Asp Met Val Trp Ser Lys Asn Gln Lys Gly Arg Leu Cys Val His
    290                 295                 300

Phe Asn Gly Leu Ser Asp Leu Ser Phe Glu Val Tyr Cys Asp Asn Arg
305                 310                 315                 320

Gln Leu His Trp Phe Gln Arg Phe Leu Glu Asp Gln Thr Lys Arg
                325                 330                 335

Gln Ser Lys Ser Gln Tyr Ser Ser Gly Leu Phe Thr Leu Arg Asn Gly
            340                 345                 350

His Leu Val Trp Gln Glu Gly Glu Gly Lys Ser Glu Pro Trp Asn Leu
        355                 360                 365

Asn Arg Leu Asn Leu Tyr Cys Cys Val Asp Asn Arg Leu Trp Thr Ala
```

370                 375                 380
Asp Gly Thr Glu Gln Val Arg Gln Lys Ala Glu Ile Ser Lys
385                 390                 395                 400

Leu Ile Thr Lys Met Lys Glu Lys Ser Asp Leu Lys Asp Thr Gln Lys
                405                 410                 415

Ala Phe Ile Gln Arg Lys Glu Ser Thr Leu Asn Arg Met Asn Asn Ser
                420                 425                 430

Phe Glu Arg Pro Ser Gln Pro Leu Tyr Gln Gly Gln Ser His Ile Leu
                435                 440                 445

Val Gly Val Ser Leu Gly Leu Glu Lys Pro Ala Thr Val Ala Val Val
            450                 455                 460

Asp Ala Ile Ala Gly Lys Val Leu Ala Tyr Arg Ser Ile Arg Gln Leu
465                 470                 475                 480

Leu Gly Asp Asn Tyr Glu Leu Leu Asn Arg Gln Arg Arg Gln Gln Arg
                485                 490                 495

Ser Ser Ser His Glu Arg His Lys Ala Gln Lys Ser Phe Ser Pro Asn
            500                 505                 510

Gln Phe Gly Thr Ser Glu Leu Gly Gln Tyr Val Asp Arg Leu Leu Ala
            515                 520                 525

Lys Glu Ile Ile Ala Ile Ala Gln Thr Tyr Lys Ala Gly Asn Ile Val
            530                 535                 540

Leu Pro Lys Leu Gly Asp Met Arg Glu Ile Val Gln Ser Glu Ile Gln
545                 550                 555                 560

Ala Ile Ala Glu Ala Lys Cys Pro Gly Ser Val Glu Val Gln Gln Lys
                565                 570                 575

Tyr Ala Lys Gln Tyr Arg Val Asn Val His Lys Trp Ser Tyr Gly Arg
                580                 585                 590

Leu Ile Gln Ser Ile Gln Ser Lys Gly Ser Gln Ala Gly Ile Val Ile
            595                 600                 605

Glu Glu Gly Lys Gln Pro Val Arg Gly Ser Pro His Glu Gln Ala Lys
            610                 615                 620

Glu Leu Ala Leu Ser Ala Tyr His Asp Arg Leu Ala Arg Arg Ser
625                 630                 635

<210> SEQ ID NO 14
<211> LENGTH: 648
<212> TYPE: PRT
<213> ORGANISM: Nostoc sp.

<400> SEQUENCE: 14

Met Cys Phe Val Trp Tyr Phe Ile Phe Met Ser Gln Lys Thr Ile Gln
1               5                   10                  15

Cys Arg Leu Ile Ala Ser Glu Ser Thr Arg Gln Lys Leu Trp Lys Leu
            20                  25                  30

Met Ala Glu Ser Asn Thr Pro Leu Ile Asn Glu Leu Leu Gln Gln Leu
        35                  40                  45

Ser Lys His Pro Asp Phe Glu Lys Trp Arg Arg Asn Gly Lys Leu Pro
    50                  55                  60

Ser Thr Val Val Ser Gln Leu Cys Gln Pro Leu Lys Thr Asp Pro Ser
65                  70                  75                  80

Phe Thr Gly Gln Pro Ser Arg Phe Tyr Ile Ser Ala Ile His Ile Val
                85                  90                  95

Asp Tyr Ile Tyr Lys Ser Trp Leu Thr Ile Gln Lys Arg Leu Gln Gln
            100                 105                 110

-continued

```
Gln Leu Asp Gly Lys Leu Arg Trp Ile Glu Met Phe Asn Ser Asp Val
            115                 120                 125

Glu Leu Val Glu Ile Ser Gly Phe Ser Leu Glu Ala Ile Arg Thr Lys
        130                 135                 140

Ala Ser Glu Ile Leu Ala Ile Thr Thr Pro Glu Ser Asp Pro Lys Thr
145                 150                 155                 160

Leu Leu Thr Lys Arg Gly Lys Thr Lys Gln Ser Lys Lys Ser Ser Ala
                165                 170                 175

Ser Asn Pro Asp Arg Ser Leu Ser Arg Lys Leu Phe Asp Ala Tyr Gln
            180                 185                 190

Glu Thr Asp Asp Ile Leu Ser Arg Ser Ala Ile Ser Tyr Leu Leu Lys
        195                 200                 205

Asn Gly Cys Lys Leu Asn Asp Lys Glu Glu Asn Pro Glu Lys Phe Ala
210                 215                 220

Lys Arg Arg Arg Lys Val Glu Ile Gln Ile Gln Arg Leu Thr Asp Lys
225                 230                 235                 240

Leu Thr Ser Arg Ile Pro Lys Gly Arg Asp Leu Thr Tyr Ser Lys Trp
                245                 250                 255

Leu Glu Thr Leu Phe Thr Ala Thr Thr Thr Val Pro Glu Asn Asn Ala
        260                 265                 270

Glu Ala Lys Arg Trp Gln Asp Ile Leu Leu Thr Arg Ser Ser Ser Ile
        275                 280                 285

Pro Phe Pro Val Val Phe Glu Thr Asn Glu Asp Leu Val Trp Ser Thr
290                 295                 300

Asn Glu Lys Gly Arg Leu Cys Val His Phe Asn Gly Leu Ser Asp Leu
305                 310                 315                 320

Ile Phe Glu Val Tyr Cys Asp Ser Arg Gln Leu Tyr Trp Phe Lys Arg
                325                 330                 335

Phe Leu Glu Asp Gln Gln Thr Lys Arg Lys Ser Lys Asn Gln His Ser
            340                 345                 350

Ser Gly Leu Phe Thr Leu Arg Asn Gly Arg Leu Ala Trp Gln Gln Gly
        355                 360                 365

Glu Gly Lys Gly Glu Pro Trp Asn Ile Gly His Leu Ala Leu Tyr Cys
370                 375                 380

Cys Val Asp Asn Arg Leu Trp Thr Ala Glu Gly Thr Glu Gln Val Arg
385                 390                 395                 400

Gln Glu Lys Ala Glu Glu Ile Thr Lys Phe Ile Thr Lys Met Lys Asp
                405                 410                 415

Lys Ser Asp Leu Ser Glu Thr Gln Leu Ala Phe Ile Lys Arg Lys Glu
            420                 425                 430

Ser Thr Leu Thr Arg Ile Asn Asn Ser Phe Asp Arg Pro Ser Lys Pro
        435                 440                 445

Leu Tyr Gln Gly Gln Ser His Ile Leu Val Gly Val Ser Leu Gly Leu
        450                 455                 460

Glu Lys Pro Ala Thr Ile Ala Val Val Asp Ala Ile Ala Gly Lys Val
465                 470                 475                 480

Leu Thr Tyr Arg Ser Leu Arg Gln Leu Leu Gly Asp Asn Tyr Glu Leu
                485                 490                 495

Leu Asn Arg Gln Arg Arg Gln Arg Ser Leu Ser His Glu Arg His
            500                 505                 510

Lys Ala Gln Lys Ser Phe Ser Pro Asn Gln Phe Gly Ala Ser Glu Leu
        515                 520                 525

Gly Gln Tyr Val Asp Arg Leu Leu Ala Lys Glu Ile Val Ala Ile Ala
```

```
                   530                 535                 540
Gln Thr Tyr Lys Ala Gly Ser Ile Val Leu Pro Lys Leu Gly Asp Ile
545                 550                 555                 560

Arg Glu Ile Val Gln Ser Glu Ile Gln Ala Ile Ala Glu Ala Lys Cys
                565                 570                 575

Pro Ser Ser Ser Glu Ile Gln Lys Tyr Ala Lys Gln Tyr Arg Val
                580                 585                 590

Asn Val His Gln Trp Ser Tyr Gly Arg Leu Ile Gln Ser Ile Gln Ser
                595                 600                 605

Lys Ala Ala Gln Ile Gly Ile Val Ile Glu Glu Gly Lys Gln Pro Ile
                610                 615                 620

Arg Gly Ser Pro Gln Asp Lys Ala Lys Glu Leu Ala Leu Tyr Ala Tyr
625                 630                 635                 640

Ser Leu Arg Leu Ala Arg Arg Ser
                645

<210> SEQ ID NO 15
<211> LENGTH: 639
<212> TYPE: PRT
<213> ORGANISM: Nostoc sp.

<400> SEQUENCE: 15

Met Ser Gln Lys Thr Ile Gln Cys Arg Leu Ile Ala Ser Glu Ser Thr
1               5                   10                  15

Arg Gln Lys Leu Trp Lys Leu Met Ala Glu Ser Asn Thr Pro Leu Ile
                20                  25                  30

Asn Glu Leu Leu Gln Gln Leu Ser Lys His Pro Asp Phe Glu Lys Trp
            35                  40                  45

Arg Arg Asn Gly Lys Leu Pro Ser Thr Val Val Ser Gln Leu Cys Gln
50                  55                  60

Pro Leu Lys Thr Asp Pro Ser Phe Thr Gly Gln Pro Ser Arg Phe Tyr
65                  70                  75                  80

Ile Ser Ala Ile His Ile Val Asp Tyr Ile Tyr Lys Ser Trp Leu Thr
                85                  90                  95

Ile Gln Lys Arg Leu Gln Gln Gln Leu Asp Gly Lys Leu Arg Trp Ile
                100                 105                 110

Glu Met Phe Asn Ser Asp Val Glu Leu Val Glu Ile Ser Gly Phe Ser
            115                 120                 125

Leu Glu Ala Ile Arg Thr Lys Ala Ser Glu Ile Leu Ala Ile Thr Thr
130                 135                 140

Pro Glu Ser Asp Pro Lys Thr Leu Leu Thr Lys Arg Gly Lys Thr Lys
145                 150                 155                 160

Gln Ser Lys Lys Ser Ser Ala Ser Asn Pro Asp Arg Ser Leu Ser Arg
                165                 170                 175

Lys Leu Phe Asp Ala Tyr Gln Glu Thr Asp Asp Ile Leu Ser Arg Ser
            180                 185                 190

Ala Ile Ser Tyr Leu Leu Lys Asn Gly Cys Lys Leu Asn Asp Lys Glu
            195                 200                 205

Glu Asn Pro Glu Lys Phe Ala Lys Arg Arg Lys Val Glu Ile Gln
            210                 215                 220

Ile Gln Arg Leu Thr Asp Lys Leu Thr Ser Arg Ile Pro Lys Gly Arg
225                 230                 235                 240

Asp Leu Thr Tyr Ser Lys Trp Leu Glu Thr Leu Phe Thr Ala Thr Thr
                245                 250                 255
```

```
Thr Val Pro Glu Asn Asn Ala Glu Ala Lys Arg Trp Gln Asp Ile Leu
            260                 265                 270

Leu Thr Arg Ser Ser Ser Ile Pro Phe Pro Val Val Phe Glu Thr Asn
        275                 280                 285

Glu Asp Leu Val Trp Ser Thr Asn Glu Lys Gly Arg Leu Cys Val His
    290                 295                 300

Phe Asn Gly Leu Ser Asp Leu Ile Phe Glu Val Tyr Cys Asp Ser Arg
305                 310                 315                 320

Gln Leu Tyr Trp Phe Lys Arg Phe Leu Glu Asp Gln Thr Lys Arg
            325                 330                 335

Lys Ser Lys Asn Gln His Ser Ser Gly Leu Phe Thr Leu Arg Asn Gly
            340                 345                 350

Arg Leu Ala Trp Gln Gln Gly Glu Gly Lys Gly Glu Pro Trp Asn Ile
            355                 360                 365

Gly His Leu Ala Leu Tyr Cys Cys Val Asp Asn Arg Leu Trp Thr Ala
            370                 375                 380

Glu Gly Thr Glu Gln Val Arg Gln Glu Lys Ala Glu Glu Ile Thr Lys
385                 390                 395                 400

Phe Ile Thr Lys Met Lys Asp Lys Ser Asp Leu Ser Glu Thr Gln Leu
                405                 410                 415

Ala Phe Ile Lys Arg Lys Glu Ser Thr Leu Thr Arg Ile Asn Asn Ser
            420                 425                 430

Phe Asp Arg Pro Ser Lys Pro Leu Tyr Gln Gly Gln Ser His Ile Leu
            435                 440                 445

Val Gly Val Ser Leu Gly Leu Glu Lys Pro Ala Thr Ile Ala Val Val
450                 455                 460

Asp Ala Ile Ala Gly Lys Val Leu Thr Tyr Arg Ser Leu Arg Gln Leu
465                 470                 475                 480

Leu Gly Asp Asn Tyr Glu Leu Leu Asn Arg Gln Arg Gln Gln Arg
                485                 490                 495

Ser Leu Ser His Glu Arg His Lys Ala Gln Lys Ser Phe Ser Pro Asn
            500                 505                 510

Gln Phe Gly Ala Ser Glu Leu Gly Gln Tyr Val Asp Arg Leu Leu Ala
            515                 520                 525

Lys Glu Ile Val Ala Ile Ala Gln Thr Tyr Lys Ala Gly Ser Ile Val
            530                 535                 540

Leu Pro Lys Leu Gly Asp Ile Arg Glu Ile Val Gln Ser Glu Ile Gln
545                 550                 555                 560

Ala Ile Ala Glu Ala Lys Cys Pro Ser Ser Glu Ile Gln Gln Lys
            565                 570                 575

Tyr Ala Lys Gln Tyr Arg Val Asn Val His Gln Trp Ser Tyr Gly Arg
            580                 585                 590

Leu Ile Gln Ser Ile Gln Ser Lys Ala Ala Gln Ile Gly Ile Val Ile
            595                 600                 605

Glu Glu Gly Lys Gln Pro Ile Arg Gly Ser Pro Gln Asp Lys Ala Lys
            610                 615                 620

Glu Leu Ala Leu Tyr Ala Tyr Ser Leu Arg Leu Ala Arg Arg Ser
625                 630                 635
```

<210> SEQ ID NO 16
<211> LENGTH: 641
<212> TYPE: PRT
<213> ORGANISM: Nostoc sp.

<400> SEQUENCE: 16

```
Met Ser Val Ile Thr Ile Gln Cys Arg Leu Val Ala Ser Glu Asp Thr
1               5                   10                  15

Arg Arg His Leu Trp Gln Leu Met Ala Glu Lys Asn Thr Pro Leu Ile
            20                  25                  30

Asn Glu Leu Leu Lys Gln Val Arg Ile His Pro Asp Met Glu Gln Trp
        35                  40                  45

Leu Lys Lys Gly Lys Leu Pro Asp Gly Val Ile Lys Pro Leu Cys Asp
    50                  55                  60

Ser Leu Ser Thr Gln Glu Cys Phe Val Asn Gln Pro Lys Arg Phe Tyr
65                  70                  75                  80

Lys Ser Ala Ile Glu Val Val Glu Tyr Ile Tyr Lys Ser Trp Leu Ala
                85                  90                  95

Leu Gln Lys Glu Arg Gln Gln Lys Ile Asp Lys Lys Glu His Trp Leu
            100                 105                 110

Asn Met Leu Lys Ser Asp Ile Glu Leu Glu Gln Glu Ser Asn Phe Ser
        115                 120                 125

Leu Asn Ile Ile Arg Ala Lys Ala Ile Lys Val Leu Ala His Tyr Ile
    130                 135                 140

Ala Lys Val Glu Glu Asn His Lys Gln Asp Ile Thr Asn Lys Asn Val
145                 150                 155                 160

Asn Lys Arg Lys Lys Ser Lys Ser Lys Asn Asn Asn Tyr Thr Leu Phe
                165                 170                 175

Asp Ile Leu Phe Lys Ala Tyr Asp Gln Ala Lys Val Ser Leu Asn Arg
            180                 185                 190

Cys Ala Ile Ala Tyr Leu Leu Lys Asn Asn Cys Gln Val Ser Glu Glu
        195                 200                 205

Glu Glu Asp Pro Asn Arg Tyr Ala Leu Arg Arg Ser Lys Lys Leu Lys
    210                 215                 220

Glu Ile Glu Arg Leu Lys Glu Gln Leu Lys Ser Arg Ile Pro Ser Gly
225                 230                 235                 240

Arg Asp Leu Thr Gly Gln Glu Trp Leu Gln Ser Leu Leu Val Ala Thr
            245                 250                 255

Thr Asn Val Pro Glu Ser Glu Asn Gln Phe Lys Ile Trp Gln Lys His
        260                 265                 270

Leu Leu Gln Asn Ser Ser Ser Ile Pro Phe Pro Val Gln Phe Thr Ser
    275                 280                 285

Asn Glu Asp Leu Ile Trp Ser Lys Asn Glu Lys Gly Arg Ile Cys Val
290                 295                 300

Ser Phe Ser Gly Glu Glu Phe Asn Asn His Ile Phe Glu Ile Tyr Cys
305                 310                 315                 320

Asp Lys Lys Gln Ile Tyr Trp Phe Gln Arg Phe Leu Glu Asp Gln Ser
            325                 330                 335

Ile Lys Arg Asn Asn Lys Lys Gln Tyr Ser Ser Leu Phe Thr Leu
        340                 345                 350

Arg Ser Gly Arg Leu Ala Trp Gln Asp Asn Lys Gly Asn Asp Leu Pro
    355                 360                 365

Trp Lys Ile His Arg Leu Thr Leu Tyr Cys Ser Val Asp Thr Arg Leu
370                 375                 380

Trp Thr Ile Glu Gly Thr Gln Glu Phe Arg Arg Glu Lys Val Asp Glu
385                 390                 395                 400

Ile Thr Glu Lys Leu Ala Asp Met Glu Lys Lys Glu Asn Leu Asn Lys
            405                 410                 415
```

-continued

```
Asn Gln Gln Ile Tyr Val Lys Arg Leu Asn Ser Thr Leu Thr Lys Ile
                420                 425                 430

Asp Thr Ala Tyr Pro Arg Pro Asn Gln Asn Leu Tyr Gln Gly Lys Thr
            435                 440                 445

Ser Ile Leu Ile Gly Val Ser Leu Gly Leu Glu Lys Pro Ala Thr Ile
        450                 455                 460

Ala Ile Val Asp Cys Pro Thr Asn Lys Val Leu Ala Tyr Arg Ser Val
465                 470                 475                 480

Lys Gln Leu Leu Gly Asp Asn Tyr Asn Leu Asn Arg Gln Arg Gln
                485                 490                 495

Gln Gln Gln Arg Asn Ser His Glu Arg His Lys Ala Gln Lys Ser Asn
            500                 505                 510

Thr Gln Ile Lys Leu Ser Glu Leu Glu Leu Gly Lys His Ile Asp Asn
        515                 520                 525

Leu Leu Ala Gln Ala Ile Ile Thr Leu Ala Lys Ser Tyr Gln Ala Gly
530                 535                 540

Ser Ile Val Leu Pro Thr Met Lys Asn Val Arg Glu Ser Ile Gln Ser
545                 550                 555                 560

Glu Ile Glu Ala Arg Ala Val Lys Arg Cys Pro Asn Tyr Lys Glu Gly
                565                 570                 575

Gln Gln Gln Tyr Ala Lys Gln Tyr Arg Gln Ser Ile His Arg Trp Ser
            580                 585                 590

Tyr Asn Arg Leu Ile Gly Cys Ile Lys Ser Gln Ala Ala Lys Ala Asn
        595                 600                 605

Ile Ser Ile Glu Gln Gly Pro Gln Pro Ile Arg Asp Ser Pro Gln Glu
610                 615                 620

Lys Ala Arg Asp Leu Ala Ile Ala Ala Tyr His Phe Arg Gln Asn Lys
625                 630                 635                 640

Ser

<210> SEQ ID NO 17
<211> LENGTH: 639
<212> TYPE: PRT
<213> ORGANISM: Scytonema hofmanni

<400> SEQUENCE: 17

Met Ser Gln Ile Thr Ile Gln Ala Arg Leu Ile Ser Phe Glu Ser Asn
1               5                   10                  15

Arg Gln Gln Leu Trp Lys Leu Met Ala Asp Leu Asn Thr Pro Leu Ile
                20                  25                  30

Asn Glu Leu Leu Cys Gln Leu Gly Gln His Pro Asp Phe Glu Lys Trp
            35                  40                  45

Gln Gln Lys Gly Lys Leu Pro Ser Thr Val Ser Gln Leu Cys Gln
50                  55                  60

Pro Leu Lys Thr Asp Pro Arg Phe Ala Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Gln Leu Asp Gly Lys Thr Arg Trp Leu
            100                 105                 110

Glu Met Leu Asn Ser Asp Ala Glu Leu Val Glu Leu Ser Gly Asp Thr
        115                 120                 125

Leu Glu Ala Ile Arg Val Lys Ala Ala Glu Ile Leu Ala Ile Ala Met
    130                 135                 140
```

```
Pro Ala Ser Glu Ser Asp Ser Ala Ser Pro Lys Gly Lys Gly Lys
145                 150                 155                 160

Lys Glu Lys Lys Pro Ser Ser Ser Pro Lys Arg Ser Leu Ser Lys
            165                 170                 175

Thr Leu Phe Asp Ala Tyr Gln Glu Thr Glu Asp Ile Lys Ser Arg Ser
            180                 185                 190

Ala Ile Ser Tyr Leu Leu Lys Asn Gly Cys Lys Leu Thr Asp Lys Glu
        195                 200                 205

Glu Asp Ser Glu Lys Phe Ala Lys Arg Arg Gln Val Glu Ile Gln
    210                 215                 220

Ile Gln Arg Leu Thr Glu Lys Leu Ile Ser Arg Met Pro Lys Gly Arg
225                 230                 235                 240

Asp Leu Thr Asn Ala Lys Trp Leu Glu Thr Leu Leu Thr Ala Thr Thr
            245                 250                 255

Thr Val Ala Glu Asp Asn Ala Gln Ala Lys Arg Trp Gln Asp Ile Leu
        260                 265                 270

Leu Thr Arg Ser Ser Ser Leu Pro Phe Pro Leu Val Phe Glu Thr Asn
    275                 280                 285

Glu Asp Met Val Trp Ser Lys Asn Gln Lys Gly Arg Leu Cys Val His
290                 295                 300

Phe Asn Gly Leu Ser Asp Leu Ile Phe Glu Val Tyr Cys Gly Asn Arg
305                 310                 315                 320

Gln Leu His Trp Phe Gln Arg Phe Leu Glu Asp Gln Thr Lys Arg
            325                 330                 335

Lys Ser Lys Asn Gln His Ser Ser Gly Leu Phe Thr Leu Arg Asn Gly
            340                 345                 350

His Leu Val Trp Leu Glu Gly Glu Lys Gly Glu Pro Trp Asn Leu
            355                 360                 365

His His Leu Thr Leu Tyr Cys Cys Val Asp Asn Arg Leu Trp Thr Glu
    370                 375                 380

Glu Gly Thr Glu Ile Val Arg Gln Glu Lys Ala Asp Glu Ile Thr Lys
385                 390                 395                 400

Phe Ile Thr Asn Met Lys Lys Lys Ser Asp Leu Ser Asp Thr Gln Gln
            405                 410                 415

Ala Leu Ile Gln Arg Lys Gln Ser Thr Leu Thr Arg Ile Asn Asn Ser
        420                 425                 430

Phe Glu Arg Pro Ser Gln Pro Leu Tyr Gln Gly Gln Ser His Ile Leu
    435                 440                 445

Val Gly Val Ser Leu Gly Leu Glu Lys Pro Ala Thr Val Ala Val Val
450                 455                 460

Asp Ala Ile Ala Asn Lys Val Leu Ala Tyr Arg Ser Ile Lys Gln Leu
465                 470                 475                 480

Leu Gly Asp Asn Tyr Glu Leu Leu Asn Arg Gln Arg Gln Gln Gln
            485                 490                 495

Tyr Leu Ser His Glu Arg His Lys Ala Gln Lys Asn Phe Ser Pro Asn
            500                 505                 510

Gln Phe Gly Ala Ser Glu Leu Gly Gln His Ile Asp Arg Leu Leu Ala
        515                 520                 525

Lys Ala Ile Val Ala Leu Ala Arg Thr Tyr Lys Ala Gly Ser Ile Val
            530                 535                 540

Leu Pro Lys Leu Gly Asp Met Arg Glu Val Val Gln Ser Glu Ile Gln
545                 550                 555                 560

Ala Ile Ala Glu Gln Lys Phe Pro Gly Tyr Ile Glu Gly Gln Gln Lys
```

```
                565                 570                 575
Tyr Ala Lys Gln Tyr Arg Val Asn Val His Arg Trp Ser Tyr Gly Arg
            580                 585                 590

Leu Ile Gln Ser Ile Gln Ser Lys Ala Ala Gln Thr Gly Ile Val Ile
            595                 600                 605

Glu Glu Gly Lys Gln Pro Ile Arg Gly Ser Pro His Asp Lys Ala Lys
            610                 615                 620

Glu Leu Ala Leu Ser Ala Tyr Asn Leu Arg Leu Thr Arg Arg Ser
625                 630                 635

<210> SEQ ID NO 18
<211> LENGTH: 690
<212> TYPE: PRT
<213> ORGANISM: Scytonema sp.

<400> SEQUENCE: 18

Met Ser Val Ile Thr Ile Gln Cys Arg Leu Val Ala Glu Glu Asn Thr
1               5                   10                  15

Leu Arg Gln Leu Trp Glu Leu Met Ala Glu Lys Asn Thr Pro Leu Ile
            20                  25                  30

Asn Glu Leu Leu Glu Gln Val Gly Gln His Pro Asn Phe Glu Lys Trp
        35                  40                  45

Leu Lys Lys Gly Glu Val Pro Glu Ala Ile Asp Thr Ile Lys Lys
    50                  55                  60

Ser Leu Ile Thr Gln Glu Pro Phe Ala Gly Gln Pro Gly Arg Phe Tyr
65                  70                  75                  80

Thr Ser Ala Val Thr Leu Val Lys Glu Ile Tyr Lys Ser Trp Phe Ala
                85                  90                  95

Leu Gln Gln Glu Arg Gln Arg Lys Ile Glu Gly Lys Glu Arg Trp Leu
            100                 105                 110

Lys Met Leu Lys Ser Asp Ile Glu Leu Gln Gln Glu Ser Gln Cys Asn
        115                 120                 125

Leu Asp Ile Ile Arg Asn Lys Ala Asn Glu Ile Leu Thr Ser Phe Val
    130                 135                 140

Ala Asn Phe Thr Glu Asn Arg Asn Gln Gln Phe Lys Lys Lys Gly Asn
145                 150                 155                 160

Lys Thr Lys Lys Asn Lys Lys Glu Glu Glu Ser Thr Leu Phe Asn
                165                 170                 175

Ala Leu Phe Lys Ile Tyr Asp Lys Thr Lys Asp Cys Leu Ser Gln Cys
            180                 185                 190

Ala Leu Ala Tyr Leu Leu Lys Asn Asn Cys Gln Val Ser Glu Ile Asp
        195                 200                 205

Glu Asp Pro Glu Glu Tyr Val Lys Arg Arg Arg Lys Glu Ile Glu
    210                 215                 220

Ile Glu Arg Leu Arg Lys Gln Leu Lys Ser Arg Lys Pro Lys Gly Arg
225                 230                 235                 240

Asp Leu Thr Gly Glu Lys Trp Leu Thr Ala Leu Lys Glu Ala Thr Asn
                245                 250                 255

Gln Val Pro Val Asp Gln Leu Glu Ala Lys Ser Trp Gln Ala Ser Leu
            260                 265                 270

Leu Lys Val Thr Ser Asp Ile Pro Tyr Pro Val Asp Tyr Glu Ser Asn
        275                 280                 285

Thr Asp Leu Asp Trp Leu Ile His Ser Asn Asp Asp Ile Lys Lys
    290                 295                 300
```

```
Lys Val Ile Leu Val Trp Gln Ile Tyr Phe Leu Lys Gln Leu Ile Lys
305                 310                 315                 320

Ser Gly Ser Tyr Ser Phe Ile Lys Tyr Leu Tyr Phe Gln Arg Gly Cys
                325                 330                 335

Leu Pro Lys Arg Asp Val Asn Trp Leu Asn Leu Lys Asn Lys Ala Gly
                340                 345                 350

Arg Ile Phe Val Lys Phe Asn Gly Leu Arg Lys Asn Ile Ile Asn Pro
                355                 360                 365

Glu Phe Tyr Ile Cys Cys Asp Ser Arg Gln Arg His Tyr Phe Gln Arg
                370                 375                 380

Leu Cys Gln Asp Trp Gln Val Trp His Asp Asn Glu Glu Thr Tyr Ser
385                 390                 395                 400

Ser Ser Leu Phe Phe Leu Arg Ser Ala Arg Leu Leu Trp Gln Lys Arg
                405                 410                 415

Lys Gly Thr Gly Ala Pro Trp Lys Val Asn Arg Leu Ile Leu Gln Cys
                420                 425                 430

Ser Ile Glu Thr Arg Leu Trp Thr Glu Glu Thr Glu Leu Val Arg
                435                 440                 445

Ile Glu Lys Ile Asn Gln Ala Glu Thr Glu Ile Arg Glu Ser Glu Gln
450                 455                 460

Lys Gly Lys Pro Lys Gln Lys Val Leu Ser His Arg Gln Lys Leu Asn
465                 470                 475                 480

Asn Leu Phe Pro Asn Arg Pro Ser Lys Pro Ile Tyr Lys Gly Lys Pro
                485                 490                 495

Asn Ile Ile Val Gly Val Ser Phe Gly Leu Asp Lys Pro Ala Thr Val
                500                 505                 510

Ala Val Val Asp Val Ala Asn Lys Lys Val Leu Ala Tyr Arg Ser Thr
                515                 520                 525

Lys Gln Leu Leu Gly Lys Asn Tyr Asn Leu Leu Asn Arg Gln Arg Gln
530                 535                 540

Gln Gln Gln Arg Leu Ser His Glu Arg His Lys Ala Gln Lys Arg Asn
545                 550                 555                 560

Ala Pro Asn Ser Phe Gly Glu Ser Glu Leu Gly Gln Tyr Val Asp Arg
                565                 570                 575

Leu Leu Ala Asp Ala Ile Ile Ala Ile Ala Lys Thr Tyr Gln Ala Gly
                580                 585                 590

Ser Ile Val Ile Pro Lys Leu Arg Asp Met Arg Glu Gln Ile Thr Ser
                595                 600                 605

Glu Ile Gln Ser Arg Ala Glu Lys Lys Cys Pro Gly Tyr Lys Glu Ala
610                 615                 620

Gln Gln Lys Tyr Ala Lys Glu Tyr Arg Leu Ser Val His Arg Trp Ser
625                 630                 635                 640

Tyr Gly Arg Leu Ile Glu Ser Ile Lys Ser Gln Ala Ala Lys Val Gly
                645                 650                 655

Ile Ser Thr Glu Ile Gly Thr Gln Pro Ile Arg Gly Ser Pro Glu Glu
                660                 665                 670

Lys Ala Arg Asp Leu Ala Val Phe Ala Tyr Gln Glu Arg Gln Ala Ala
                675                 680                 685

Leu Val
    690

<210> SEQ ID NO 19
<211> LENGTH: 627
<212> TYPE: PRT
```

-continued

<213> ORGANISM: Spirulina major

<400> SEQUENCE: 19

Met Ser Gln Ile Thr Ile Gln Cys Arg Leu Val Ala Ser Glu Ala Thr
1               5                   10                  15

Arg Gln Val Leu Trp Thr Leu Met Ala Glu Arg Asn Thr Pro Leu Ile
            20                  25                  30

Asn Glu Leu Leu Ala Gln Met Ala Gln His Pro Asp Leu Glu Glu Trp
        35                  40                  45

Arg Gln Lys Gly Lys Pro Thr Pro Gly Val Val Lys Lys Leu Cys Asp
    50                  55                  60

Pro Leu Arg Gln Asp Pro Arg Phe Met Gly Gln Pro Gly Arg Phe Tyr
65                  70                  75                  80

Ser Ser Ala Ile Ala Leu Val Glu Tyr Ile Tyr Lys Ser Trp Leu Lys
                85                  90                  95

Leu Gln Gln Arg Leu Gln Arg Lys Leu Glu Gly Gln Gln Arg Trp Leu
            100                 105                 110

Gly Met Leu Lys Ser Asp Pro Glu Leu Cys Glu Glu Asn His Cys Thr
        115                 120                 125

Leu Asp Thr Leu Arg Asp Lys Ala Ala Glu Ile Leu Ala Ser Leu Glu
    130                 135                 140

Ser Pro Gln Pro Lys Gln Gly Lys Val Lys Thr Lys Lys Ala Lys Ala
145                 150                 155                 160

Gln Ser Ser Pro Arg Gln Ser Leu Phe Glu Met His Asp Gly Ala Glu
                165                 170                 175

Asp Gly Phe Val Lys Ser Ala Ile Ala Tyr Leu Leu Lys Asn Gly Gly
            180                 185                 190

Lys Leu Pro Thr His Glu Glu Asp Pro Lys Lys Phe Ala Lys Arg Arg
        195                 200                 205

Arg Lys Ala Glu Val Lys Val Glu Arg Leu Ile His Gln Ile Thr Ala
    210                 215                 220

Ser Leu Pro Lys Gly Arg Asp Leu Thr Gly Glu Arg Trp Leu Glu Thr
225                 230                 235                 240

Leu Leu Thr Ala Ser Tyr Thr Ala Pro Lys Asp Ala Gln Gln Thr Lys
                245                 250                 255

Val Trp Gln Ser Ile Leu Leu Thr Lys Thr Lys Ala Val Pro Tyr Pro
            260                 265                 270

Ile Asn Tyr Glu Thr Asn Glu Asp Leu Thr Trp Ser Lys Asn Glu Lys
        275                 280                 285

Gly Arg Leu Cys Val Arg Phe Asn Gly Leu Ser Glu His Thr Phe Gln
    290                 295                 300

Ile Tyr Cys Asp Gln Arg Gln Leu Lys Trp Phe Gln Arg Phe Tyr Glu
305                 310                 315                 320

Asp Gln Glu Val Lys Arg Thr Ser Lys Asn Gln His Ser Thr Ser Leu
                325                 330                 335

Phe Thr Leu Arg Ser Gly Arg Ile Val Trp Gln Glu Ser Asp Arg Asn
            340                 345                 350

Asp Lys Pro Trp Thr Ala Asn His Ile Thr Leu Cys Cys Thr Leu Asp
        355                 360                 365

Thr Arg Leu Trp Ser Ala Glu Gly Thr Glu Val Arg Thr Glu Lys
    370                 375                 380

Ala Ile Asp Ile Ala Lys Thr Leu Thr Asn Met Asn Glu Lys Gly Asp
385                 390                 395                 400

-continued

```
Leu Asn Asp Lys Gln Gln Ala Phe Ile Lys Arg Lys Thr Ala Thr Leu
                405                 410                 415

Asp Arg Ile Asn Asn Pro Tyr Pro Arg Pro Ser Lys Pro Leu Tyr His
            420                 425                 430

Gly Gln Ser His Ile Leu Val Gly Val Ala Leu Gly Leu Asp Lys Pro
        435                 440                 445

Ala Thr Val Ala Val Val Asp Gly Thr Thr Gly Lys Ala Ile Thr Tyr
    450                 455                 460

Arg Asn Leu Lys Gln Leu Leu Gly Glu Asn Tyr Lys Leu Val Asn Arg
465                 470                 475                 480

Gln Arg Gln Gln Lys Gln Ala Gln Ser His Gln Arg His Lys Ala Gln
                485                 490                 495

Lys Arg Ser Gly Thr Asp Gln Phe Gly Asp Ser Glu Leu Gly Gln His
            500                 505                 510

Ile Asp Arg Leu Leu Ala Lys Ala Ile Val Ala Phe Ala His Ser Gln
        515                 520                 525

Ser Ala Gly Ser Ile Val Val Pro Lys Leu Glu Asp Ile Arg Glu Ile
    530                 535                 540

Val Gln Ser Glu Ile Gln Ala Arg Ala Glu Glu Lys Val Pro Gly Tyr
545                 550                 555                 560

Ile Glu Gly Gln Lys Gln Tyr Ala Lys Arg Tyr Arg Val Gln Val His
                565                 570                 575

Gln Trp Ser Tyr Gly Arg Leu Ile Asp Ser Ile Lys Ser Lys Ala Thr
            580                 585                 590

Gln Gln Gln Val Val Ile Glu Glu Gly Lys Gln Pro Val Arg Gly Ser
        595                 600                 605

Pro Glu Ala Gln Ala Thr Glu Leu Ala Ile Ser Thr Tyr His Leu Arg
    610                 615                 620

Ala Ser Ser
625

<210> SEQ ID NO 20
<211> LENGTH: 608
<212> TYPE: PRT
<213> ORGANISM: Geminocystis sp.

<400> SEQUENCE: 20

Met Ala Val Ile Thr Ile His Cys Arg Leu Ile Ser Ser Lys Ser Asn
1               5                   10                  15

Arg His Gln Leu Trp Asn Leu Met Val Gln Lys Asn Thr Pro Leu Ile
            20                  25                  30

Asn Glu Leu Leu Leu Glu Leu Ser Gln His Glu Asp Leu Glu Gln Trp
        35                  40                  45

Cys Glu Leu Gly Lys Leu Pro Ser Gly Leu Ile Ser Lys Leu Cys Asp
    50                  55                  60

Gln Leu Lys Gln Arg Ala Glu Phe Glu Gly Gln Pro Ser Arg Phe Tyr
65                  70                  75                  80

Ala Ser Ala Ile Asn Leu Val Asp Tyr Ile Tyr Lys Ser Tyr Leu Arg
                85                  90                  95

Thr Gln Arg Arg Leu Arg Phe Arg Leu Gln Gly Gln Asn Arg Trp Phe
            100                 105                 110

Glu Met Phe Lys Ser Asp Thr Glu Phe Lys Asn Glu Thr Asn Phe Ser
        115                 120                 125

Leu Thr Asp Ile Arg Val Lys Ala Arg Glu Leu Leu Asp Lys Asp Leu
    130                 135                 140
```

-continued

```
Lys Asp Ser Ser Pro Asp Asp Tyr Phe Lys Thr Tyr Glu Ser Thr Ser
145                 150                 155                 160

Asp Leu Leu Thr Arg Ser Ala Ile Ser Tyr Leu Leu Lys Asn Gly Arg
            165                 170                 175

Lys Leu Pro Glu Lys Pro Glu Asp Tyr Gln Lys Phe Gln Lys Arg Arg
        180                 185                 190

Arg Lys Leu Gln Ile Lys Ile Glu Lys Leu Gln Lys Lys Ile Asp Ser
    195                 200                 205

Ser Pro Pro Met Gly Arg Asn Leu Thr Asn Asp Ser Trp Leu Gly Met
210                 215                 220

Leu Asn Leu Val Ser Asn Thr Ile Pro Gln Thr Asp Glu Glu Ala Lys
225                 230                 235                 240

Gln Trp Gln Asp Gln Leu Leu Arg Gln Ser Lys Ser Val Pro Tyr Pro
                245                 250                 255

Val Met Phe Asn Thr Asn Glu Asp Leu Arg Trp Ser Lys Asn Lys Lys
            260                 265                 270

Gly Arg Leu Cys Val Thr Phe Asn Gly Leu Gly Lys Leu Val Phe Glu
        275                 280                 285

Ile Tyr Cys Asp Gln Gln Gln Leu Lys Trp Phe Glu Arg Phe Tyr Glu
    290                 295                 300

Asp Gln Glu Val Lys Arg Lys Gly Lys Asn Gln His Ser Ser Ala Leu
305                 310                 315                 320

Phe Thr Leu Arg Ser Gly Met Leu Leu Trp Gln Glu His Glu Gly Lys
                325                 330                 335

Gln Glu Ala Trp Gln Asn Asn His Leu Thr Leu Tyr Cys Ser Leu Asp
            340                 345                 350

Thr Cys Phe Glu Thr Ala Glu Gly Thr Glu Leu Val Arg Gln Lys Lys
        355                 360                 365

Val Lys Glu Val Val Asn Leu Ile Asp Ala Met Asn Asn Lys Ser Glu
370                 375                 380

Arg Thr Lys Thr Gln Asp Ala Phe Ile Lys Arg Lys Gln Ser Thr Leu
385                 390                 395                 400

Ala Arg Leu Asp Asn Ser Phe Pro Arg Pro Ser Lys Pro Leu Tyr Gln
                405                 410                 415

Gly Asn Gln Asn Ile Val Val Ala Val Ser Met Ser Leu Glu Tyr Pro
            420                 425                 430

Ala Thr Ile Ala Met Phe Asn Met Ser Ser Gln Glu Val Leu Thr Tyr
        435                 440                 445

Arg Ser Thr Lys Gln Leu Leu Asp Asn Asn Tyr His Leu Leu Asn Arg
    450                 455                 460

Gln Arg Asn Gln Lys Gln Arg Leu Ser His Gln Arg His Lys Thr Gln
465                 470                 475                 480

Arg Gln Asn Ser Ser Asp Phe Phe Thr Gln Gln Glu Ser Glu Leu Gly
                485                 490                 495

Gln Tyr Leu Asp Arg Leu Leu Ala Gln Ser Ile Val Ser Ile Ala Lys
            500                 505                 510

Gln Tyr Gln Ala Ser Thr Ile Leu Leu Pro Asn Leu Lys Asn Ile Arg
        515                 520                 525

Asp Ser Ile Gln Ala Glu Ile Glu Ala Lys Ala Glu Ala Lys Ile Pro
    530                 535                 540

Asn Cys Lys Glu Ala Gln Lys Lys Tyr Leu Lys Asn Tyr Arg Ile Asn
545                 550                 555                 560
```

```
Ile His His Trp Ser Tyr Gly Arg Leu Ile Asp Ser Ile Gln Leu Gln
                565                 570                 575

Ala Ser Lys Leu Asp Ile Leu Ile Gln Glu Val Lys Gln Pro Ile Arg
            580                 585                 590

Gly Ser Pro Gln Glu Lys Ala Lys Gln Met Ala Ile Leu Thr Leu Glu
        595                 600                 605

<210> SEQ ID NO 21
<211> LENGTH: 635
<212> TYPE: PRT
<213> ORGANISM: Nostoc sp.

<400> SEQUENCE: 21

Met Ser Val Ile Thr Ile Gln Cys Arg Leu Val Ala Glu Glu Asp Thr
1               5                   10                  15

Leu Arg Gln Val Trp Glu Leu Met Thr Asp Lys Asn Thr Pro Leu Val
            20                  25                  30

Asn Glu Leu Leu Ala Gln Val Gly Lys His Pro Glu Phe Glu Thr Trp
        35                  40                  45

Leu Glu Lys Gly Lys Ile Pro Thr Glu Phe Leu Lys Thr Leu Val Asn
    50                  55                  60

Ser Leu Lys Asn Gln Glu Arg Phe Ser Asp Gln Pro Gly Arg Phe Tyr
65                  70                  75                  80

Thr Ser Ala Ile Ala Leu Val Asp Tyr Val Tyr Lys Ser Trp Phe Ala
                85                  90                  95

Leu Gln Lys Arg Arg Lys Arg Gln Ile Glu Gly Lys Glu Arg Trp Leu
            100                 105                 110

Ile Ile Leu Lys Ser Asp Leu Gln Leu Glu Gln Glu Ser Gln Cys Ser
        115                 120                 125

Leu Asn Val Ile Arg Thr Glu Ala Asn Glu Ile Leu Ala Lys Phe Thr
    130                 135                 140

Pro Gln Ser Asp Gln Asn Lys Asn Gln Arg Lys Ser Lys Arg Thr Arg
145                 150                 155                 160

Lys Ser Ala Lys Leu Gln Thr Pro Ser Leu Phe Gln Asn Leu Leu Asn
                165                 170                 175

Thr Tyr Glu Gln Thr Gln Glu Thr Leu Thr Arg Cys Ala Ile Ala Tyr
            180                 185                 190

Leu Leu Lys Asn Asn Cys Gln Ile Ser Glu Arg Asp Glu Asp Pro Glu
        195                 200                 205

Glu Phe Asn Arg Asn Arg Arg Lys Lys Glu Ile Glu Ile Glu Arg Leu
    210                 215                 220

Lys Asp Gln Leu Gln Ser Arg Ile Pro Lys Gly Arg Asp Leu Thr Gly
225                 230                 235                 240

Glu Glu Trp Leu Lys Thr Leu Glu Ile Ala Thr Thr Asn Val Pro Gln
                245                 250                 255

Asn Glu Asn Glu Ala Lys Ala Trp Gln Ala Ala Leu Leu Arg Lys Pro
            260                 265                 270

Ala Asp Val Pro Phe Pro Val Ala Tyr Glu Ser Asn Glu Asp Met Thr
        275                 280                 285

Trp Leu Gln Asn Asp Lys Gly Arg Leu Phe Val Arg Phe Asn Gly Leu
    290                 295                 300

Gly Lys Leu Thr Phe Glu Ile Tyr Cys Asp Lys Arg His Leu His Tyr
305                 310                 315                 320

Phe Lys Arg Phe Leu Glu Asp Gln Glu Leu Lys Arg Asn Ser Lys Asn
                325                 330                 335
```

```
Gln His Ser Ser Leu Phe Thr Leu Arg Ser Gly Arg Ile Ala Trp
            340                 345                 350

Ser Leu Gly Glu Lys Gly Glu Pro Trp Lys Val Asn Lys Leu His
            355                 360                 365

Leu Tyr Cys Thr Leu Asp Thr Arg Met Trp Thr Ile Glu Gly Thr Gln
    370                 375                 380

Gln Val Val Ser Glu Lys Thr Thr Lys Ile Thr Glu Thr Leu Asn Gln
385                 390                 395                 400

Ala Lys Arg Lys Asp Val Leu Asn Asp Lys Gln Gln Ala Phe Val Thr
                405                 410                 415

Arg Gln Gln Ser Thr Leu Asp Arg Ile Asn Asn Pro Phe Pro Arg Pro
            420                 425                 430

Ser Lys Pro Asn Tyr Gln Gly Gln Pro Ser Ile Leu Val Gly Val Ser
            435                 440                 445

Phe Gly Leu Glu Lys Pro Val Thr Leu Ala Val Val Asp Val Ile Lys
    450                 455                 460

Asn Glu Val Leu Ala Tyr Arg Thr Val Lys Gln Leu Leu Gly Lys Asn
465                 470                 475                 480

Tyr Asn Leu Leu Asn Arg Gln Arg Gln Gln Gln Arg Leu Ser His
                485                 490                 495

Glu Arg His Lys Val Gln Lys Arg Asn Ala Pro Asn Ser Phe Gly Glu
            500                 505                 510

Ser Glu Leu Gly Gln Tyr Val Asp Arg Leu Leu Ala Asp Ala Ile Ile
            515                 520                 525

Ala Ile Ala Lys Thr Tyr Gln Ala Gly Ser Ile Val Ile Pro Lys Leu
    530                 535                 540

Arg Asp Met Arg Glu Gln Ile Ser Ser Glu Ile Gln Ser Arg Ala Glu
545                 550                 555                 560

Lys Lys Cys Pro Gly Tyr Lys Glu Val Gln Gln Lys Tyr Ala Lys Glu
                565                 570                 575

Tyr Arg Met Ser Val His Arg Trp Gly Tyr Gly Arg Leu Ile Glu Ser
            580                 585                 590

Ile Lys Ser Gln Ala Ala Lys Ala Gly Ile Phe Thr Glu Ile Gly Thr
            595                 600                 605

Gln Pro Ile Arg Gly Ser Pro Gln Glu Lys Ala Arg Asp Leu Ala Val
    610                 615                 620

Phe Ala Tyr Gln Glu Arg Gln Ala Ala Leu Ile
625                 630                 635

<210> SEQ ID NO 22
<211> LENGTH: 667
<212> TYPE: PRT
<213> ORGANISM: Cyanothece sp.

<400> SEQUENCE: 22

Met Ser Thr Ile Thr Ile Gln Cys Arg Leu Val Ala Pro Glu Ala Thr
1               5                   10                  15

Arg Gln Ala Leu Trp Gln Leu Met Ala Gln Lys Asn Thr Pro Leu Val
            20                  25                  30

Ser Glu Leu Leu Arg Gln Val Ala Gln His Pro Asp Phe Glu Thr Trp
        35                  40                  45

Arg Gln Gln Gly Lys Leu Glu Ala Gly Ile Ile Lys Lys Leu Cys Glu
    50                  55                  60

Pro Leu Lys Lys Asp Pro Arg Phe Asn Glu Gln Pro Ala Arg Phe Tyr
```

-continued

```
               65                  70                  75                  80
Thr Ser Ala Ile Ala Leu Val Asp Tyr Ile Tyr Lys Ser Trp Leu Lys
                        85                  90                  95

Leu Gln Gln Arg Leu Gln Arg Lys Leu Glu Gly Gln Asn Arg Trp Leu
            100                 105                 110

Ala Met Leu Lys Ser Asp Asp Glu Leu Ile Gln Ile Ser Gln Thr Asn
            115                 120                 125

Ile Glu Ile Ile Gln Ala Lys Ala Thr Glu Ile Leu Ser Thr Leu Gln
        130                 135                 140

Pro Gln Asp Arg Glu Gln Ser Ser Lys Lys Ala Lys Lys Cys Lys
145                 150                 155                 160

Lys Ser Thr Asn Lys Asn Ser Leu Phe Ser Gln Leu Asp Lys Leu Tyr
                165                 170                 175

Asn Glu Ile Asn Asn Asn Leu Thr His Cys Ala Ile Arg Tyr Leu Leu
            180                 185                 190

Lys Asn Gly Gly Lys Ile Pro Gln Arg Pro Glu Asp Thr Glu Lys Phe
                195                 200                 205

Ala Gln Arg Arg Arg Lys Val Glu Ile Lys Ile Glu Arg Ile Ile Glu
        210                 215                 220

Gln Ile Glu Ser Ser Ile Pro Gln Gly Arg Asp Leu Thr Gly Asp Ser
225                 230                 235                 240

Trp Leu Glu Thr Leu Ile Ile Ala Ala Asn Thr Ala Thr Val Glu Ala
                245                 250                 255

Glu Asp Val Lys Ser Trp Gln Asp Lys Leu Leu Ser Gln Ser Lys Ser
            260                 265                 270

Ile Pro Tyr Pro Val Ala Tyr Glu Thr Asn Glu Asp Leu Thr Trp Ser
        275                 280                 285

Ile Asn Glu Lys Gly Arg Leu Cys Val Arg Phe Asn Gly Leu Gly Lys
        290                 295                 300

His Thr Phe Gln Ile Tyr Cys Asp Gln Arg Gln Leu Lys Trp Phe Gln
305                 310                 315                 320

Arg Phe Tyr Glu Asp Gln Gln Ile Lys Lys Asp Gly Lys Asp His His
                325                 330                 335

Ser Ser Ala Leu Phe Ser Leu Arg Ser Gly Arg Ile Val Trp Gln Glu
            340                 345                 350

Gly Leu Gly Lys Gly Lys Pro Trp Asn Ile His Arg Leu Thr Leu His
        355                 360                 365

Cys Ser Leu Asp Thr Arg Phe Trp Thr Glu Glu Gly Thr Gln Gln Val
    370                 375                 380

Gln Gln Glu Lys Ser Lys Lys Phe Gln Thr Asn Arg Leu Arg Met Lys
385                 390                 395                 400

Pro Glu Leu Thr Phe Ser Ile Phe Phe Arg Ser Gln Thr Leu Glu Thr
                405                 410                 415

Tyr Leu Gln Val Trp Leu Val Ile Thr Ala Tyr Arg Leu Gln Ser Phe
            420                 425                 430

Leu Asp Lys Gly Asn Val Ala Lys Ala His Gln Glu Phe Gln Lys Ala
        435                 440                 445

Ile Lys Arg Asn Glu Ser Ser Leu Gln Lys Ile Thr Ser Ser Tyr Asn
    450                 455                 460

Arg Pro His Lys Thr Leu Tyr Gln Gly Lys Ser His Ile Phe Val Gly
465                 470                 475                 480

Val Ala Met Gly Leu Glu Lys Pro Ala Thr Val Ala Val Val Asp Gly
                485                 490                 495
```

```
Thr Thr Gly Lys Ala Ile Ala Tyr Arg Ser Leu Lys Gln Leu Leu Gly
            500                 505                 510

Asn Asn Tyr His Leu Phe Asn Arg Gln Gly Lys Gln Lys Gln Asn Thr
            515                 520                 525

Ser His Gln Arg His Lys Ser Gln Lys His Phe Ala Asp Asn Gln Phe
        530                 535                 540

Gly Glu Ser Gln Leu Gly Gln Tyr Ile Asp Cys Leu Leu Ala Lys Ala
545                 550                 555                 560

Ile Ile Ser Val Ala Gln Thr Tyr Cys Ala Gly Ser Ile Val Val Pro
                565                 570                 575

Lys Leu Lys Asp Met Arg Glu Leu Ile Gln Ser Glu Ile Gln Ala Lys
            580                 585                 590

Ala Glu Ala Lys Ile Pro Gly Tyr Val Glu Gly Gln Ala Lys Tyr Ala
            595                 600                 605

Lys Ser Tyr Arg Val Gln Val His Gln Trp Ser His Gly Arg Leu Ile
        610                 615                 620

Asp Asn Ile Thr Ser Gln Ala Ser Lys Phe Asn Ile Thr Val Glu Glu
625                 630                 635                 640

Gly Glu Gln Pro His Gln Gly Asn Pro Gln Asp Lys Ala Lys Leu Leu
                645                 650                 655

Ala Ile Ala Ala Tyr His Ser Arg Leu Cys Ala
            660                 665

<210> SEQ ID NO 23
<211> LENGTH: 639
<212> TYPE: PRT
<213> ORGANISM: Calothrix sp.

<400> SEQUENCE: 23

Met Ser Val Ile Thr Ile Gln Cys Arg Leu Val Ala Asp Glu Glu Thr
1               5                   10                  15

Leu Arg His Leu Trp Thr Leu Met Ala Glu Lys Asn Thr Pro Phe Ala
            20                  25                  30

Asn Glu Ile Leu Glu Gln Leu Ala Gln His Ala Glu Phe Glu Ser Trp
        35                  40                  45

Val Lys Asn Ser Arg Val Pro Ala Thr Val Ile Lys Glu Leu Cys Asp
50                  55                  60

Ser Leu Lys Asn Gln Glu Leu Phe Ala Gly Gln Pro Gly Arg Phe Tyr
65                  70                  75                  80

Thr Ser Ala Thr Thr Leu Val Thr Tyr Ile Tyr Lys Ser Trp Leu Ala
            85                  90                  95

Val Asn Lys Arg Leu Gln Arg Lys Ile Glu Gly Lys Lys Gln Trp Leu
            100                 105                 110

Asp Met Leu Arg Ser Asp Thr Glu Leu Glu Gln Glu Ser Asn Ser Asn
        115                 120                 125

Leu Glu Lys Ile Arg Ala Lys Ala Thr Glu Ile Leu Asp Ser Phe Ala
        130                 135                 140

Thr Arg Gln Ile Asn Gln Val Asn Ser Lys Ser Lys Thr Ser Lys Asn
145                 150                 155                 160

Asn Lys Asn Lys Gln Glu Lys Glu Val Lys Ser Leu Ser Ile Gln Ser
                165                 170                 175

Asn Ile Leu Phe Glu Thr Tyr Arg Gln Thr Glu Asp Asn Leu Thr Lys
            180                 185                 190

Cys Ala Ile Val Tyr Leu Leu Lys Asn Asn Cys Glu Val Asn Asp Val
```

```
                195                 200                 205
Glu Glu Asp Ile Glu Glu Tyr Glu Lys Asn Lys Arg Lys Lys Glu Ile
210                 215                 220

Gln Ile Lys Arg Leu Glu Asp Gln Leu Lys Ser Arg Val Pro Lys Gly
225                 230                 235                 240

Arg Asp Leu Thr Gly Glu Lys Trp Val Glu Val Leu Glu Lys Ala Val
                245                 250                 255

Asn Ser Val Pro Glu Ser Glu Asn Glu Ala Lys Ser Trp Gln Ala Ser
                260                 265                 270

Leu Leu Arg Lys Ser Ser Gln Ile Pro Phe Pro Val Val Tyr Glu Thr
            275                 280                 285

Asn Glu Asp Ile Lys Trp Ser Ile Asn Glu Lys Gly Arg Ile Phe Val
290                 295                 300

Ser Phe Asn Gly Leu Gly Lys Leu Lys Phe Glu Ile Phe Cys Asp Lys
305                 310                 315                 320

Arg His Leu His Tyr Phe Gln Arg Phe Leu Glu Asp Gln Asp Ile Lys
                325                 330                 335

Arg Gln Gly Lys Asn Gln His Ser Ser Leu Phe Thr Leu Arg Ser
            340                 345                 350

Gly Arg Ile Ser Trp Leu Glu Gln Pro Gly Lys Gly Lys Pro Trp Asn
            355                 360                 365

Ile Asn Arg Leu Leu Leu Phe Cys Ser Ile Asp Thr Arg Met Leu Thr
370                 375                 380

Ala Glu Gly Thr Gln Gln Val Ile Glu Glu Lys Ile Ala Asp Thr Gln
385                 390                 395                 400

Asn Lys Ile Ala Lys Ala Gln Glu Lys Cys Glu Gly Glu Leu Asn Pro
                405                 410                 415

Asn Gln Gln Ala His Ile Asn Arg Lys Lys Ser Thr Leu Ala Arg Ile
            420                 425                 430

Asn Thr Pro Phe Pro Arg Pro Ser Lys Pro Leu Tyr Gln Gly Lys Ser
            435                 440                 445

His Ile Val Val Gly Val Ser Leu Gly Leu Lys Ala Thr Ala Thr Ile
        450                 455                 460

Ala Val Phe Asp Ala Met Asn Asn Gln Val Leu Ala Tyr Arg Ser Thr
465                 470                 475                 480

Lys Gln Leu Leu Gly Asp Asn Tyr Lys Leu Leu Asn Arg Gln Gln Gln
                485                 490                 495

Gln Lys Gln Arg Leu Ser Gln Arg His Lys Ser Gln Lys Gln Phe
            500                 505                 510

Ala Ser Asn Ser Phe Gly Glu Ser Glu Leu Gly Gln Tyr Val Asp Arg
        515                 520                 525

Leu Leu Ala Lys Glu Ile Val Ala Val Ala Lys Asn Phe Gly Ala Gly
            530                 535                 540

Ser Ile Val Leu Pro Lys Leu Gly Asp Met Arg Glu Ile Ile Gln Ser
545                 550                 555                 560

Glu Val Gln Ala Lys Ala Glu Lys Lys Ile Pro Gly Phe Ile Glu Leu
                565                 570                 575

Gln Lys Asn Tyr Ala Lys Glu Tyr Arg Lys Ser Ala His Asn Trp Ser
            580                 585                 590

Tyr Gly Arg Leu Ile Glu Asn Ile Gln Ser Gln Ala Thr Lys Glu Gly
            595                 600                 605

Ile Glu Ile Glu Thr Gly Lys Gln Pro Thr Arg Gly Ile Pro Gln Glu
610                 615                 620
```

Gln Ala Arg Asp Leu Ala Leu Phe Ala Tyr Gln Cys Arg Ile Ala
625                 630                 635

<210> SEQ ID NO 24
<211> LENGTH: 635
<212> TYPE: PRT
<213> ORGANISM: Anabaena cylindrica

<400> SEQUENCE: 24

Met Ser Gln Ile Thr Ile Gln Cys Arg Leu Val Ala Ser Glu Thr Thr
1               5                   10                  15

Arg Gln Gln Leu Trp Gln Leu Met Ala Glu Lys Asn Thr Pro Leu Ile
            20                  25                  30

Asn Glu Leu Leu Ser Gln Ile Gly Lys His Pro Glu Phe Glu Thr Trp
        35                  40                  45

Arg Gln Lys Gly Lys His Pro Thr Gly Ile Val Lys Glu Leu Cys Glu
    50                  55                  60

Pro Leu Lys Thr Asp Pro Arg Phe Ile Gly Gln Pro Ala Arg Phe Tyr
65                  70                  75                  80

Thr Ser Ala Thr Ala Ser Val Asn Tyr Ile Tyr Glu Ser Trp Phe Ala
                85                  90                  95

Leu Met Lys Arg Tyr Gln Ser Gln Leu Asp Gly Lys Leu Arg Trp Leu
            100                 105                 110

Glu Met Phe Asn Ser Asp Ala Glu Leu Val Glu His Ser Gly Val Ser
        115                 120                 125

Leu Asp Thr Leu Arg Ala Thr Ser Ala Glu Ile Leu Ala Gln Phe Ala
    130                 135                 140

Pro Gln Asp Thr Asn Arg Asp Thr Ser Asn Lys Gly Lys Lys Ser Lys
145                 150                 155                 160

Met Gly Lys Lys Ser Gln Lys Ser Asp Ser Glu Gly Asn Leu Ser Lys
                165                 170                 175

Lys Leu Phe Asp Ala Tyr Ser Ser Ala Glu Asp Asn Leu Thr Arg Cys
            180                 185                 190

Ala Ile Ser His Leu Leu Lys Asn Gly Cys Lys Val Ser Asn Lys Glu
        195                 200                 205

Glu Asn Ser Glu Lys Phe Thr Gln Arg Arg Lys Leu Glu Ile Gln
    210                 215                 220

Ile Gln Arg Leu Thr Glu Lys Leu Ala Ala Arg Ile Pro Lys Gly Arg
225                 230                 235                 240

Asp Leu Thr Asp Thr Gln Trp Leu Glu Thr Leu Phe Thr Ala Thr Tyr
                245                 250                 255

Asn Val Pro Glu Asp Glu Thr Glu Ala Lys Leu Trp Gln Asn Ser Leu
            260                 265                 270

Leu Arg Lys Phe Ser Ser Leu Pro Phe Pro Val Ala Tyr Glu Thr Asn
        275                 280                 285

Glu Asp Leu Val Trp Ser Lys Asn Arg Phe Gly Arg Ile Cys Leu Thr
    290                 295                 300

Phe Pro Thr Leu Arg Glu His Ile Phe Gln Ile Tyr Cys Asp Ser Arg
305                 310                 315                 320

Gln Leu His Trp Phe Gln Arg Phe Leu Glu Asp Gln Glu Ile Lys Lys
                325                 330                 335

Asn Ser Lys Asn Gln His Ser Ser Ala Leu Phe Thr Leu Arg Ser Gly
            340                 345                 350

Arg Ile Ala Trp Gln Glu Gly Glu Gly Lys Gly Glu Pro Trp Asp Ile

```
            355                 360                 365
His His Leu Thr Leu Tyr Cys Cys Val Asp Thr Arg Leu Trp Thr Glu
    370                 375                 380

Glu Gly Thr Asn Leu Val Lys Glu Lys Ala Glu Ile Ala Lys
385                 390                 395                 400

Thr Ile Thr Gln Thr Lys Ala Lys Gly Asp Leu Asn Asp Lys Gln Gln
                405                 410                 415

Ala His Leu Lys Arg Lys Asn Ser Ser Leu Ala Arg Ile Asn Asn Pro
            420                 425                 430

Phe Pro Arg Pro Ser Gln Pro Leu Tyr Lys Gly Gln Ser His Ile Leu
        435                 440                 445

Leu Gly Val Ser Leu Gly Leu Glu Lys Pro Ala Thr Val Ala Val Val
    450                 455                 460

Asp Gly Thr Thr Gly Lys Val Leu Thr Tyr Arg Asn Ile Lys Gln Leu
465                 470                 475                 480

Leu Gly Asp Asn Tyr Lys Leu Leu Asn Arg Gln Arg Gln Gln Lys His
                485                 490                 495

Leu Leu Ser His Gln Arg His Ile Ala Gln Arg Ile Ala Ala Pro Asn
            500                 505                 510

Asn Phe Gly Asp Ser Glu Leu Gly Glu Tyr Ile Asp Arg Leu Leu Ala
        515                 520                 525

Lys Glu Ile Ile Ala Ile Ala Gln Thr Tyr Gln Ala Gly Ser Ile Val
    530                 535                 540

Leu Pro Asn Leu Gly Asp Met Arg Glu Gln Ile Gln Ser Glu Ile Lys
545                 550                 555                 560

Ala Lys Ala Glu Gln Lys Ser Asp Leu Val Glu Val Gln Lys Lys Tyr
                565                 570                 575

Ala Lys Gln Tyr Pro Asn Ser Val His Gln Trp Ser Tyr Gly Arg Leu
            580                 585                 590

Ile Thr Asn Ile Gln Ser Gln Ser Lys Lys Ala Gly Ile Val Ile Glu
        595                 600                 605

Glu Gly Lys Gln Gln Ile Arg Ala Ser Pro Leu Glu Lys Ala Lys Glu
    610                 615                 620

Leu Ala Ile Asn Ala Tyr Gln Ser Arg Lys Ala
625                 630                 635

<210> SEQ ID NO 25
<211> LENGTH: 642
<212> TYPE: PRT
<213> ORGANISM: Anabaena cylindrica

<400> SEQUENCE: 25

Met Ser Val Ile Thr Ile Gln Cys Arg Leu Val Ala Glu Glu Asp Ser
1               5                   10                  15

Leu Arg Gln Leu Trp Glu Leu Met Ser Glu Lys Asn Thr Pro Phe Ile
            20                  25                  30

Asn Glu Ile Leu Leu Gln Ile Gly Lys His Pro Glu Phe Glu Thr Trp
        35                  40                  45

Leu Glu Lys Gly Arg Ile Pro Ala Glu Leu Leu Lys Thr Leu Gly Asn
    50                  55                  60

Ser Leu Lys Thr Gln Glu Pro Phe Thr Gly Gln Pro Gly Arg Phe Tyr
65                  70                  75                  80

Thr Ser Ala Ile Thr Leu Val Asp Tyr Leu Tyr Lys Ser Trp Phe Ala
                85                  90                  95
```

-continued

```
Leu Gln Lys Arg Arg Lys Gln Gln Ile Glu Gly Lys Gln Arg Trp Leu
                100                 105                 110
Lys Met Leu Lys Ser Asp Gln Glu Leu Glu Gln Glu Ser Gln Ser Ser
            115                 120                 125
Leu Glu Val Ile Arg Asn Lys Ala Thr Glu Leu Phe Ser Lys Phe Thr
        130                 135                 140
Pro Gln Ser Asp Ser Glu Ala Leu Arg Arg Asn Gln Asn Asp Lys Gln
145                 150                 155                 160
Lys Lys Val Lys Lys Thr Lys Lys Ser Thr Lys Pro Lys Thr Ser Ser
                165                 170                 175
Ile Phe Lys Ile Phe Leu Ser Thr Tyr Glu Glu Ala Glu Pro Leu
            180                 185                 190
Thr Arg Cys Ala Leu Ala Tyr Leu Leu Lys Asn Asn Cys Gln Ile Ser
        195                 200                 205
Glu Leu Asp Glu Asn Pro Glu Glu Phe Thr Arg Asn Lys Arg Arg Lys
210                 215                 220
Glu Ile Glu Ile Glu Arg Leu Lys Asp Gln Leu Gln Ser Arg Ile Pro
225                 230                 235                 240
Lys Gly Arg Asp Leu Thr Gly Glu Glu Trp Leu Glu Thr Leu Glu Ile
                245                 250                 255
Ala Thr Phe Asn Val Pro Gln Asn Glu Asn Glu Ala Lys Ala Trp Gln
            260                 265                 270
Ala Ala Leu Leu Arg Lys Thr Ala Asn Val Pro Phe Pro Val Ala Tyr
        275                 280                 285
Glu Ser Asn Glu Asp Met Thr Trp Leu Lys Asn Asp Lys Asn Arg Leu
    290                 295                 300
Phe Val Arg Phe Asn Gly Leu Gly Lys Leu Thr Phe Glu Ile Tyr Cys
305                 310                 315                 320
Asp Lys Arg His Leu His Tyr Phe Gln Arg Phe Leu Glu Asp Gln Glu
                325                 330                 335
Ile Leu Arg Asn Ser Lys Arg Gln His Ser Ser Ser Leu Phe Thr Leu
            340                 345                 350
Arg Ser Gly Arg Ile Ala Trp Leu Pro Gly Glu Glu Lys Gly Glu His
        355                 360                 365
Trp Lys Val Asn Gln Leu Asn Phe Tyr Cys Ser Leu Asp Thr Arg Met
    370                 375                 380
Leu Thr Thr Glu Gly Thr Gln Gln Val Val Glu Glu Lys Val Thr Ala
385                 390                 395                 400
Ile Thr Glu Ile Leu Asn Lys Thr Lys Gln Lys Asp Asp Leu Asn Asp
                405                 410                 415
Lys Gln Gln Ala Phe Ile Thr Arg Gln Gln Ser Thr Leu Ala Arg Ile
            420                 425                 430
Asn Asn Pro Phe Pro Arg Pro Ser Lys Pro Asn Tyr Gln Gly Lys Ser
        435                 440                 445
Ser Ile Leu Ile Gly Val Ser Phe Gly Leu Glu Lys Pro Val Thr Val
    450                 455                 460
Ala Val Val Asp Val Val Lys Asn Lys Val Ile Ala Tyr Arg Ser Val
465                 470                 475                 480
Lys Gln Leu Leu Gly Glu Asn Tyr Asn Leu Leu Asn Arg Gln Arg Gln
                485                 490                 495
Gln Gln Gln Arg Leu Ser His Glu Arg His Lys Ala Gln Lys Gln Asn
            500                 505                 510
Ala Pro Asn Ser Phe Gly Glu Ser Glu Leu Gly Gln Tyr Val Asp Arg
```

```
                515                 520                 525
Leu Leu Ala Asp Ala Ile Ile Ala Ile Ala Lys Lys Tyr Gln Ala Gly
        530                 535                 540
Ser Ile Val Leu Pro Lys Leu Arg Asp Met Arg Glu Gln Ile Ser Ser
545                 550                 555                 560
Glu Ile Gln Ser Arg Ala Glu Asn Gln Cys Pro Gly Tyr Lys Glu Gly
                565                 570                 575
Gln Gln Lys Tyr Ala Lys Glu Tyr Arg Ile Asn Val His Arg Trp Ser
        580                 585                 590
Tyr Gly Arg Leu Ile Glu Ser Ile Lys Ser Gln Ala Ala Gln Ala Gly
                595                 600                 605
Ile Ala Ile Glu Thr Gly Lys Gln Ser Ile Arg Gly Ser Pro Gln Glu
        610                 615                 620
Lys Ala Arg Asp Leu Ala Val Phe Thr Tyr Gln Glu Arg Gln Ala Ala
625                 630                 635                 640
Leu Ile

<210> SEQ ID NO 26
<211> LENGTH: 679
<212> TYPE: PRT
<213> ORGANISM: Nostoc sp.

<400> SEQUENCE: 26

Met Ser Ser Asp Arg Lys Lys Ser Thr Ile Pro Val His Arg Thr
1               5                   10                  15

Ile Arg Cys His Leu Asp Ala Ser Glu Asp Ile Leu Arg Lys Val Trp
                20                  25                  30

Glu Glu Met Thr Gln Lys Asn Thr Pro Leu Ile Leu Lys Leu Leu Lys
        35                  40                  45

Ser Val Ser Glu Gln Pro Glu Phe Glu Ala Asn Lys Glu Lys Gly Glu
    50                  55                  60

Ile Thr Lys Lys Glu Ile Val Lys Leu Arg Lys Asn Val Thr Lys Asn
65                  70                  75                  80

Pro Glu Leu Glu Glu Gln Ser Gly Arg Leu Arg Ser Ser Ala Glu Ser
                85                  90                  95

Phe Val Lys Glu Val Tyr Ser Ser Trp Leu Thr Leu Tyr Gln Lys Arg
                100                 105                 110

Lys Arg Gln Lys Glu Gly Lys Glu Tyr Phe Leu Lys Asn Ile Leu Lys
        115                 120                 125

Ser Asp Val Glu Leu Ile Asp Glu Ser Asn Cys Asp Leu Glu Thr Ile
    130                 135                 140

Arg Ser Lys Ala Gln Glu Val Leu Ser Gln Pro Glu Glu Phe Ile Lys
145                 150                 155                 160

Gln Leu Thr Ile Asn Asp Glu Asp Val Lys Pro Thr Lys Ser Ala Arg
                165                 170                 175

Lys Arg Val Asn Lys Asn Ile Asn Asn Lys Ser Thr Asp Ala Glu Gln
                180                 185                 190

Arg Lys Asp Ser Ser Ser Thr Asn Asn Val Asp Lys Asn Lys Leu Glu
        195                 200                 205

Thr Leu Thr Asn Ile Leu Tyr Glu Ile His Lys Gln Thr Gln Asp Ile
    210                 215                 220

Leu Thr Arg Cys Thr Val Ala Tyr Leu Ile Lys Asn His Asn Lys Ile
225                 230                 235                 240

Ser Asn Leu Glu Glu Asp Ile Gln Lys Leu Lys Lys Arg Arg Asn Glu
```

```
                245                 250                 255
Lys Ile Val Gln Ile Lys Arg Leu Glu Asn Gln Ile Gln Asp Asn Arg
            260                 265                 270

Leu Pro Ser Gly Arg Asp Ile Thr Gly Glu Arg Tyr Ser Glu Ala Phe
        275                 280                 285

Gly Asn Leu Ile Asn Gln Val Pro Lys Asn Asn Gln Glu Trp Glu Asp
290                 295                 300

Trp Ile Ala Asn Leu Ser Lys Lys Ile Ser His Leu Pro Tyr Pro Ile
305                 310                 315                 320

Asp Tyr Leu Tyr Gly Asp Leu Ser Trp Tyr Lys Asn Asp Val Gly Asn
                325                 330                 335

Ile Phe Val Tyr Phe Asn Gly Trp Ser Glu Tyr His Phe Lys Ile Cys
                340                 345                 350

Cys Asn Lys Arg Gln Arg His Phe Phe Glu Arg Phe Leu Glu Asp Tyr
                355                 360                 365

Lys Ala Phe Lys Val Ser Gln Lys Gly Glu Glu Lys Leu Ser Gly Ser
370                 375                 380

Leu Ile Thr Leu Arg Ser Ala Gln Leu Leu Trp Gln Gln Gly Glu Gly
385                 390                 395                 400

Lys Gly Glu Pro Trp Lys Val His Lys Leu Ala Leu His Cys Thr Tyr
                405                 410                 415

Asp Ser Arg Leu Trp Thr Ala Glu Gly Thr Glu Glu Val Arg Lys Glu
                420                 425                 430

Lys Thr Asp Lys Ala Gln Lys Arg Val Ser Lys Ala Glu Glu Asn Glu
                435                 440                 445

Lys Leu Asp Asp Ile Gln Gln Thr Gln Leu Asn Lys Asp Lys Ser Ser
450                 455                 460

Leu Ser Arg Leu Lys Asn Ser Phe Asn Arg Pro Gly Lys Leu Ile Tyr
465                 470                 475                 480

Gln Ser Gln Ser Asn Ile Ile Val Gly Ile Ser Phe His Pro Ile Glu
                485                 490                 495

Leu Ala Thr Val Ala Ile Val Asp Ile Asn Thr Lys Lys Val Leu Ala
                500                 505                 510

Cys Asn Thr Val Lys Gln Leu Leu Gly Asn Ala Phe His Leu Leu Ser
                515                 520                 525

Arg Arg Arg Arg Gln Gln Val His Leu Ser Lys Glu Arg Lys Lys Ala
                530                 535                 540

Gln Lys Lys Asp Ser Pro Cys Asn Ile Gly Glu Ser Lys Leu Gly Glu
545                 550                 555                 560

Tyr Ile Asp Lys Leu Leu Ala Lys Arg Ile Val Glu Ile Ala Lys Phe
                565                 570                 575

Tyr Gln Ala Gly Cys Ile Ile Leu Pro Arg Leu Lys Asp Met Lys Glu
                580                 585                 590

Ile Arg Thr Ser Ala Ile Gln Ala Lys Ala Glu Ala Lys Ile Pro Gly
                595                 600                 605

Asp Val Asn Ala Gln Lys Leu Tyr Val Lys Glu Tyr Asn Arg Gln Ile
                610                 615                 620

His Asn Trp Ser Tyr Asn Arg Leu Gln Glu Ser Ile Lys Ser Lys Ala
625                 630                 635                 640

Ala Glu Phe Lys Ile Ser Ile Glu Phe Gly Ile Gln Pro His Tyr Gly
                645                 650                 655

Thr Leu Glu Glu Gln Ala Lys Asp Leu Ala Phe Tyr Ala Tyr Gln Ser
                660                 665                 670
```

Arg Asn His Thr Leu Gly Arg
            675

<210> SEQ ID NO 27
<211> LENGTH: 632
<212> TYPE: PRT
<213> ORGANISM: Anabaena sp.

<400> SEQUENCE: 27

Met Ser Val Ile Thr Ile Gln Cys Arg Leu Val Ala Glu Glu Asp Thr
1               5                   10                  15

Leu Arg Thr Leu Trp Glu Leu Met Ala Asp Lys Asn Thr Pro Leu Ile
            20                  25                  30

Asn Glu Ile Leu Ala Gln Val Gly Lys His Pro Glu Phe Glu Thr Trp
        35                  40                  45

Leu Glu Lys Gly Lys Ile Pro Thr Glu Leu Leu Lys Thr Leu Val Asn
    50                  55                  60

Ser Leu Lys Thr Gln Glu Arg Phe Ala Ser Gln Pro Gly Arg Phe Tyr
65                  70                  75                  80

Thr Ser Ala Ile Ala Leu Val Asp Tyr Val Tyr Lys Ser Trp Phe Ala
                85                  90                  95

Leu Gln Lys Arg Arg Lys Arg Gln Ile Glu Gly Lys Glu Arg Trp Leu
            100                 105                 110

Thr Ile Leu Lys Ser Asp Leu Glu Leu Gln Glu Ser Gln Cys Ser
        115                 120                 125

Leu Asn Ile Ile Arg Thr Lys Ala Thr Glu Ile Ile Thr Glu Phe Thr
130                 135                 140

Pro Gln Ser Asp Gln Asn Asn Ser Gln Lys Lys Arg Lys Lys Thr Thr
145                 150                 155                 160

Lys Ser Thr Lys Pro Ser Leu Phe Gln Ile Leu Leu Asn Asn Tyr Glu
                165                 170                 175

Glu Thr Gln Asp Ile Leu Thr Arg Cys Ala Leu Ala Tyr Leu Leu Lys
            180                 185                 190

Asn Asn Cys Gln Ile Ser Glu Arg Asp Glu Asn Pro Glu Glu Phe Thr
        195                 200                 205

Arg Asn Arg Arg Lys Lys Glu Ile Glu Ile Glu Arg Leu Lys Asp Gln
    210                 215                 220

Leu Gln Ser Arg Ile Pro Lys Gly Arg Asp Leu Thr Gly Glu Glu Trp
225                 230                 235                 240

Leu Lys Thr Leu Glu Val Val Arg Ala Asn Val Thr Gln Asn Glu Asn
                245                 250                 255

Glu Ala Lys Ala Trp Gln Ala Ala Ile Leu Arg Lys Ser Ala Asp Val
            260                 265                 270

Pro Phe Pro Val Ala Tyr Glu Ser Asn Glu Asp Met Thr Trp Leu Gln
        275                 280                 285

Asn Asp Lys Gly Arg Leu Phe Val Arg Phe Asn Gly Leu Gly Lys Leu
    290                 295                 300

Thr Phe Glu Ile Tyr Cys Asp Lys Arg His Leu His Tyr Phe Lys Arg
305                 310                 315                 320

Phe Leu Glu Asp Gln Glu Leu Lys Arg Asn Ser Lys Asn Gln Tyr Ser
                325                 330                 335

Ser Ser Leu Phe Thr Leu Arg Ser Gly Arg Leu Ala Trp Ser Pro Gly
            340                 345                 350

Glu Glu Lys Gly Glu Pro Trp Lys Val Asn Gln Leu His Leu Tyr Cys

```
                355                 360                 365
Thr Leu Asp Thr Arg Met Trp Thr Ile Glu Gly Thr Gln Gln Val Val
    370                 375                 380
Asp Glu Lys Ser Thr Lys Ile Thr Glu Thr Leu Thr Lys Ala Lys Gln
385                 390                 395                 400
Lys Asp Asp Leu Asn Asp Lys Gln Gln Ala Phe Val Thr Arg Gln Gln
                405                 410                 415
Ser Thr Leu Asn Arg Ile Asn Asn Leu Phe Pro Arg Pro Ser Lys Ser
            420                 425                 430
Arg Tyr Gln Gly Gln Pro Ser Ile Leu Val Gly Val Ser Phe Gly Leu
            435                 440                 445
Glu Asn Pro Val Thr Leu Ala Val Val Asp Val Val Lys Asn Glu Val
            450                 455                 460
Leu Ala Tyr Arg Ser Val Lys Gln Leu Leu Gly Lys Asn Tyr Asn Leu
465                 470                 475                 480
Leu Asn Arg Gln Arg Gln Gln Gln Arg Leu Ser His Lys Arg His
                485                 490                 495
Lys Ala Gln Lys Arg Asn Ala Pro Asn Ser Phe Gly Glu Ser Glu Leu
            500                 505                 510
Gly Gln Tyr Val Asp Arg Leu Leu Ala Asp Ala Ile Ala Ile Ala
            515                 520                 525
Lys Thr Tyr Gln Ala Gly Ser Ile Val Ile Pro Lys Leu Arg Asp Met
    530                 535                 540
Arg Glu Gln Ile Ser Ser Glu Ile Gln Ser Arg Ala Glu Lys Lys Phe
545                 550                 555                 560
Pro Gly Tyr Lys Glu Ala Gln Gln Lys Tyr Ala Lys Glu Tyr Arg Met
                565                 570                 575
Ser Val His Arg Trp Ser Tyr Gly Arg Leu Ile Glu Ser Ile Lys Ser
            580                 585                 590
Gln Ala Ala Lys Ala Gly Ile Ser Thr Glu Ile Gly Thr Gln Pro Ile
            595                 600                 605
Arg Gly Ser Pro Gln Glu Lys Ala Arg Asp Leu Ala Val Phe Ala Tyr
    610                 615                 620
Gln Glu Arg Gln Ala Ala Leu Ile
625                 630

<210> SEQ ID NO 28
<211> LENGTH: 150
<212> TYPE: PRT
<213> ORGANISM: Anabaena sp.

<400> SEQUENCE: 28

Met Glu Gly Lys Phe Tyr Thr Ser Thr Glu Ala Ala Glu Ile Thr Asn
1               5                   10                  15
Cys Ser Arg Arg Gln Leu Gln Tyr Trp Arg Glu Lys Gly Val Ile Val
            20                  25                  30
Pro Thr Val Asn Ala Ser Gly Lys Gly Arg Asn Val Tyr Tyr Ser Lys
        35                  40                  45
Ala Asp Leu Leu Ala Leu Ser Val Met Glu His Leu Leu Ser Ile Gly
    50                  55                  60
Leu Asn Phe Glu Met Cys His Val Ala Leu Glu Thr Leu Arg Lys Arg
65                  70                  75                  80
Glu Pro Trp Leu Phe Glu Glu Ser Val Thr Glu Asp Lys Met Lys Arg
                85                  90                  95
```

```
Leu Met Phe Leu Pro Ser Lys Ser Pro Glu Gln Pro Leu Gln Leu Ala
            100                 105                 110

Glu Phe Asp Gln Gln Ala Ala Leu Glu Ala Leu Cys Glu Gly Gln Thr
        115                 120                 125

Val Ile Pro Phe Trp Gly Asp Arg Ile His Glu Leu Leu His Gln Asn
    130                 135                 140

Leu Lys Arg Phe Thr Glu
145                 150

<210> SEQ ID NO 29
<211> LENGTH: 150
<212> TYPE: PRT
<213> ORGANISM: Anabaena variabilis

<400> SEQUENCE: 29

Met Gln Glu Thr Phe Phe Thr Ser Lys Glu Ala Ser Lys Ile Thr Gly
1               5                   10                  15

Cys Thr Leu Arg Gln Leu Gln Tyr Trp Arg Glu Lys Gly Val Val Val
            20                  25                  30

Pro Val Ile Ser Asp Thr Gly Thr Gly Arg Ser Ile Tyr Tyr Ser Lys
        35                  40                  45

Thr Asn Leu Val Glu Leu Ala Ala Met Val Tyr Trp Leu Ser Val Gly
    50                  55                  60

Leu Ser Phe Asp Ile Ala Cys Glu Thr Leu Lys Thr Leu Lys Asp Gln
65                  70                  75                  80

Glu Pro Glu Leu Phe Ser Ser Gly Thr Gly Arg Arg Phe Met Leu Leu
                85                  90                  95

Ser Glu Ala Gln Glu Arg Ser Pro Leu Gly Ala Pro Lys Ile Ser Leu
            100                 105                 110

Glu Leu Met Glu Phe Asp Arg Thr Lys Ala Ile Ala Ser Leu Asp Glu
        115                 120                 125

Gly Lys Pro Val Ile Pro Val Trp Leu Asp Glu Ile Tyr Gln Gln Leu
    130                 135                 140

Gln Gln Lys Leu Lys Ala
145                 150

<210> SEQ ID NO 30
<211> LENGTH: 139
<212> TYPE: PRT
<213> ORGANISM: Geminocystis sp.

<400> SEQUENCE: 30

Met Lys Glu Arg Phe Phe Ser Ser Lys Gln Thr Ser Leu Ile Thr Gly
1               5                   10                  15

Cys Ser Leu Arg Gln Leu Gln Tyr Trp Arg Asp Lys Glu Val Ile Val
            20                  25                  30

Pro Phe Ile Gln Gly Thr Gly Thr Gly Lys Thr Ile Tyr Tyr Ser Pro
        35                  40                  45

Ala Glu Leu Val Glu Ile Ser Ile Met Val Tyr Leu Leu Ser Val Gly
    50                  55                  60

Leu Ser Phe Glu Ile Gly Gln Ile Ile Leu Ser Asp Leu Lys Glu Lys
65                  70                  75                  80

Glu Arg Asn Phe Arg Asn Pro Asp Tyr Lys Gly Arg Phe Met Ile Ile
                85                  90                  95

Pro Arg Asp Gly Lys Met Ser Leu Leu Ser Tyr Glu Arg Glu Lys Ala
            100                 105                 110
```

Ile Glu Leu Leu Asp Gln Gly Thr Ser Ile Val Pro Leu Trp Leu Asp
            115                 120                 125

Arg Ile His Glu Gln Leu Lys Glu Thr Leu Gly
    130                 135

<210> SEQ ID NO 31
<211> LENGTH: 164
<212> TYPE: PRT
<213> ORGANISM: Myxosarcina sp.

<400> SEQUENCE: 31

Met Gly Glu Pro Phe Tyr Thr Ser Thr Glu Ala Ser Leu Ile Thr Gly
1               5                   10                  15

Cys Ser Arg Arg Gln Leu Gln Tyr Trp Arg Lys Gln Gly Val Val
            20                  25                  30

Pro Thr Val Asn Pro Gly Gly Lys Gly Arg Asn Val Tyr Tyr Thr Glu
            35                  40                  45

Ser Asp Leu Leu Ile Leu Ser Val Met Lys Tyr Leu Leu Ser Leu Gly
    50                  55                  60

Leu Asn Phe Asp Val Ser Leu Lys Val Leu Glu Thr Leu Arg Glu Lys
65                  70                  75                  80

Glu Ile Leu Cys Phe Leu Asp Trp Ser Leu Ser Lys Asn Thr Lys Lys
                85                  90                  95

Arg Phe Met Leu Val Leu Asp Thr Glu Glu Lys Asn Thr Ile His Ile
            100                 105                 110

Thr Asn Phe Asp Thr Glu Leu Ala Val Gln Lys Leu Gln Glu Gly Phe
        115                 120                 125

Ala Ile Ala Pro Phe Gly Arg Asp Arg Ile Tyr Gln Lys Leu Gln Asp
    130                 135                 140

Asn Leu Gln Ala Phe Tyr Arg Asn Arg Lys Ser Leu Lys Gly Asp Arg
145                 150                 155                 160

Arg Thr Lys Asn

<210> SEQ ID NO 32
<211> LENGTH: 150
<212> TYPE: PRT
<213> ORGANISM: Nostoc punctiforme

<400> SEQUENCE: 32

Met Glu Glu Lys Phe Tyr Thr Ser Thr Glu Ala Ala Glu Ile Thr Asn
1               5                   10                  15

Cys Ser Arg Arg Gln Leu Gln Tyr Trp Arg Asp Lys Gly Val Val Ile
            20                  25                  30

Pro Thr Val Asn Thr Thr Gly Lys Gly Arg Asn Val Tyr Tyr Ser Val
            35                  40                  45

Ala Asp Leu Leu Thr Leu Thr Val Met His Tyr Leu Leu Ser Val Gly
    50                  55                  60

Leu Ser Phe Glu Val Cys Arg Glu Ala Leu Ala Met Leu Gln Asp Lys
65                  70                  75                  80

Glu Pro Trp Leu Phe Glu Glu Phe Val Ser Lys Lys Met Arg Arg
                85                  90                  95

Leu Met Leu Ile Ser Asn Ala Ser Gln Gln Lys Tyr Leu Thr Leu Ala
            100                 105                 110

Glu Phe Asp Lys Glu Ala Ala Leu Glu Ala Leu Cys Gln Gly Gln Thr
        115                 120                 125

Val Ile Pro Phe Trp Cys Asp Arg Ile His Glu Val Leu His Gln Asn

```
                130                 135                 140
Leu Lys Arg Phe Ser Glu
145                 150

<210> SEQ ID NO 33
<211> LENGTH: 168
<212> TYPE: PRT
<213> ORGANISM: Nostoc sp.

<400> SEQUENCE: 33

Met Leu Tyr Lys Ala Leu Met Cys Phe Arg Arg Cys Phe Tyr Arg Met
1               5                   10                  15

Phe Leu Met Glu Gly Lys Phe Tyr Thr Ser Thr Glu Ala Ser Glu Ile
                20                  25                  30

Thr His Cys Ser Arg Arg Gln Leu Gln Tyr Trp Arg Glu Lys Gly Val
            35                  40                  45

Ile Val Pro Thr Val Asn Ser Ser Gly Lys Gly Arg Asn Val Tyr Tyr
        50                  55                  60

Ser Lys Ala Asp Leu Leu Ala Leu Thr Val Met Glu Gln Leu Leu Ser
65                  70                  75                  80

Thr Gly Leu Asn Phe Asp Leu Cys Tyr Ala Ala Leu Gln Thr Leu Arg
                85                  90                  95

Lys Gln Glu Pro Trp Leu Phe Asp Glu Ser Val Pro Glu Glu Lys Met
            100                 105                 110

Lys Arg Leu Met Leu Leu Pro Thr Arg Ser Pro Glu Gln Pro Leu Gln
        115                 120                 125

Leu Ala Glu Phe Asp Lys Gln Ala Ala Leu Glu Ala Leu Cys His Gly
    130                 135                 140

Gln Thr Val Ile Pro Phe Trp Ser Asp Arg Ile His Gln Gln Leu Arg
145                 150                 155                 160

Glu Asn Leu Lys Ser Phe Ser Ser
                165

<210> SEQ ID NO 34
<211> LENGTH: 150
<212> TYPE: PRT
<213> ORGANISM: Scytonema hofmanni

<400> SEQUENCE: 34

Met Glu Gly Lys Phe Tyr Thr Ser Thr Glu Ala Ala Gln Ile Thr Asn
1               5                   10                  15

Cys Ser Arg Arg Gln Leu Gln Tyr Trp Arg Asp Lys Gly Val Val Val
                20                  25                  30

Pro Thr Val Asn Thr Thr Gly Lys Gly Arg Asn Val Tyr Tyr Ser Ile
            35                  40                  45

Ser Asp Leu Leu Val Leu Thr Val Met His Tyr Leu Leu Ser Val Gly
        50                  55                  60

Leu Ser Phe Glu Val Ser Arg Gln Thr Leu Val Ile Leu Arg Gln Lys
65                  70                  75                  80

Glu Pro Trp Leu Phe Glu Glu Phe Val Pro Lys Glu Lys Met Lys Arg
                85                  90                  95

Leu Met Leu Leu Thr Thr Cys Ser Leu Glu Gln Pro Leu Thr Leu Ala
            100                 105                 110

Glu Phe Asp Lys Glu Ala Ala Leu Glu Ala Leu Cys Gln Gly Gln Thr
        115                 120                 125

Val Ile Pro Phe Trp Cys Asp Arg Ile His Gln Gln Leu Arg Asp Asn
```

Leu Lys Ser Phe Ser Ser
145                 150

<210> SEQ ID NO 35
<211> LENGTH: 143
<212> TYPE: PRT
<213> ORGANISM: Spirulina major

<400> SEQUENCE: 35

Met Glu Gln Pro Phe Phe Ser Ser Arg Glu Ala Ala Asp Ile Thr Gly
1               5                   10                  15

Cys Thr Leu Arg Gln Leu Gln Tyr Trp Arg Lys Glu Val Val Ile
            20                  25                  30

Pro Thr Ile Asn Ala Thr Gly Thr Gly Arg Ser Ile Tyr Tyr Ser Gln
            35                  40                  45

Ala Asn Leu Val Glu Leu Ser Val Met Ala Tyr Trp Leu Ser Leu Gly
        50                  55                  60

Leu Thr Phe Glu Val Ala His Glu Ser Leu Met Lys Leu Arg Ala Ile
65                  70                  75                  80

Glu Pro Arg Phe Val Glu Pro Pro Ile Ala Arg Arg Phe Met Leu Lys
                85                  90                  95

Trp Glu Glu Met Arg Gly Lys Leu Glu Leu Val Glu Phe Asp Arg Glu
            100                 105                 110

Gly Ala Ile Ala Ser Leu Asp Ala Gly Gln Pro Val Ile Pro Val Trp
        115                 120                 125

Leu Glu Gln Ile Tyr Ser Lys Leu Ser Asn Lys Ile Ser Pro Asn
    130                 135                 140

<210> SEQ ID NO 36
<211> LENGTH: 158
<212> TYPE: PRT
<213> ORGANISM: Cyanothece sp.

<400> SEQUENCE: 36

Met Glu Glu Met Phe Phe Thr Ser Thr Glu Ala Ser Lys Leu Thr Gly
1               5                   10                  15

Cys Ser Arg Arg Gln Leu Gln Tyr Trp Arg Glu Lys Gly Val Val Val
            20                  25                  30

Pro Thr Val Asn Ala Ser Gly Lys Gly Arg Asn Val Tyr Tyr Ser Val
            35                  40                  45

Ser Asp Leu Leu Lys Leu Met Val Met Glu Tyr Leu Leu Ser Val Gly
        50                  55                  60

Leu Ser Phe Glu Thr Ala Gln Glu Ser Leu Glu Met Leu Lys Lys Ala
65                  70                  75                  80

His Pro Glu Met Phe Lys Ala Asp Val Ser Ser Glu Asp Leu Lys Arg
                85                  90                  95

Leu Met Ile Leu Pro Ser Pro Lys Arg Leu Glu Leu Lys Asp Phe Asp
            100                 105                 110

Pro Glu Glu Ala Phe Lys Arg Ile Asn Thr Tyr Ala Met Pro Leu Val
        115                 120                 125

Pro Phe Ser Gly Glu Met Ile His Glu Arg Leu Lys Glu Ser Leu Gln
    130                 135                 140

Gly Phe Ser Gly Asn Asn His Leu Lys Ser Ser Glu Asn Ser
145                 150                 155

-continued

```
<210> SEQ ID NO 37
<211> LENGTH: 142
<212> TYPE: PRT
<213> ORGANISM: Anabaena cylindrica

<400> SEQUENCE: 37

Met Gln Glu Thr Phe Phe Thr Ser Lys Glu Ala Ala Gln Leu Thr Gly
1               5                   10                  15

Cys Thr Leu Arg Gln Ile Gln Tyr Trp Arg Glu Lys Gly Ile Val Val
                20                  25                  30

Pro Ile Ile Ser Asp Thr Gly Thr Gly Arg Ser Ile Tyr Tyr Ser Arg
            35                  40                  45

Ser Asn Leu Val Glu Leu Ala Ala Leu Val Tyr Trp Leu Ser Thr Gly
        50                  55                  60

Ile Ser Phe Asp Ile Ala Cys Glu Thr Leu Lys Arg Leu Lys Ala Gln
65                  70                  75                  80

Glu Pro Glu Leu Phe Ile Ser Gly Lys Gly Lys Arg Phe Met Leu Leu
                85                  90                  95

Leu Ser Ala Gln Asn Glu Ser Leu Ser Leu Val Glu Phe Asp Arg Lys
                100                 105                 110

Ser Ala Ile Ala Ser Leu Asp Glu Gly Lys Ala Val Ile Pro Val Trp
            115                 120                 125

Leu Asp Ile Ile Tyr Gln Lys Leu Ala Ser Arg Leu Ala Gln
        130                 135                 140

<210> SEQ ID NO 38
<211> LENGTH: 549
<212> TYPE: PRT
<213> ORGANISM: Alkalinema sp.

<400> SEQUENCE: 38

Met Ile Val Thr Thr Leu Ser Pro Asp Glu Arg Lys Ile Lys Val
1               5                   10                  15

Leu Gln Pro Leu Ile Glu Pro Cys Asp Arg Ala Thr Tyr Gly Lys Arg
                20                  25                  30

Leu Arg Tyr Ala Ala Glu Gln Leu Gly Ile Ser Val Arg Ser Val Gln
                35                  40                  45

Arg Glu Ile Gln Arg Trp Glu Lys Asn Gly Ile Ala Gly Ile Thr Arg
        50                  55                  60

Asn Cys Arg Ala Asp Lys Gly Lys His Arg Ile Ser Asp Phe Trp Gln
65                  70                  75                  80

Asn Phe Ile Ile Lys Thr Tyr Lys Glu Gly Asn Thr Gly Ser Lys Arg
                85                  90                  95

Met Thr Pro Lys Gln Val Ala Val Arg Val Gln Ala Lys Ala His Glu
                100                 105                 110

Met Arg Asp Glu Asn Pro Pro His Tyr Arg Thr Val Leu Arg Val Leu
            115                 120                 125

Lys Pro Ile Ile Glu Arg Gln Glu Lys Thr Lys Ser Ile Arg Ser Pro
        130                 135                 140

Gly Trp Lys Gly Ser Thr Leu Ser Val Lys Thr Arg Ser Gly Glu Asp
145                 150                 155                 160

Leu Val Ile Ala His Ser Asn His Val Trp Gln Cys Asp His Thr Pro
                165                 170                 175

Val Asp Val Met Leu Val Asp Gln Tyr Gly Glu Lys Arg Lys Arg Pro
            180                 185                 190

Trp Leu Thr Ile Val Ile Asp Ser Tyr Ser Arg Cys Ile Met Gly Ile
```

```
                195                 200                 205
Asn Leu Gly Phe Asp Ala Pro Ser Ser Gln Val Val Ala Leu Ala Leu
210                 215                 220

Arg His Ala Ile Leu Pro Lys His Tyr Gly Ala Glu Tyr Lys Leu Asn
225                 230                 235                 240

Cys Glu Trp Gly Thr Tyr Gly Lys Pro Val His Phe Tyr Thr Asp Gly
                245                 250                 255

Gly Lys Asp Phe Arg Ser Asn His Val Gln Gln Ile Gly His Asp Leu
                260                 265                 270

Gly Phe Thr Cys His Leu Arg Asp Arg Pro Ser Glu Gly Gly Ile Val
                275                 280                 285

Glu Arg Pro Phe Lys Thr Leu Asn Glu Gln Leu Phe Ser Thr Leu Pro
                290                 295                 300

Gly Tyr Thr Asp Ser Asn Val Gln Lys Arg Pro Lys Asp Val Glu Lys
305                 310                 315                 320

Asp Ala Arg Leu Thr Leu Arg Asp Leu Glu Arg Leu Val Val Arg Phe
                325                 330                 335

Ile Cys Asp Cys Tyr Asn Gln Ser Ile Asp Ala Arg Ile Gly Asp Gln
                340                 345                 350

Thr Arg Phe Gln Arg Trp Glu Ala Gly Leu Pro Gly Val Pro Asp Val
                355                 360                 365

Ile Gly Glu Arg Leu Leu Asp Pro Cys Leu Met Asn Val Ser Arg Arg
                370                 375                 380

Thr Ile Gln Arg Gly Gly Tyr Leu Gln Phe Lys Asn Leu Met Tyr Arg
385                 390                 395                 400

Gly Glu Tyr Leu Ala Gly Tyr Ala Gly Glu Ile Val Ser Val Arg Phe
                405                 410                 415

Asn Pro Asp Asp Ile Thr Thr Leu Leu Val Tyr Arg Arg Glu Asn Asn
                420                 425                 430

Arg Glu Val Phe Leu Thr Arg Ala Phe Ala Gln Gly Leu Glu Thr Glu
                435                 440                 445

Gln Leu Ser Leu Ser Glu Ala Gln Ala Ser Ser Ser Arg Arg Lys Glu
450                 455                 460

Ala Gly Lys Ser Leu Ser Asn Thr Ala Ile Phe Gln Glu Val Leu Asp
465                 470                 475                 480

Arg Asp Ala Leu Val Asn Ser Lys Lys Ser Arg Lys Gln Arg His Lys
                485                 490                 495

Glu Glu Gln Lys Ile Ala Arg Ser Glu Thr Glu Thr Pro Lys Thr Gly
                500                 505                 510

Ala Val Ser Val Glu Gln Pro Glu Thr Ala Pro Thr Glu Leu Glu Val
                515                 520                 525

Ala Leu Asp Leu Glu Thr Glu Thr Phe Glu Pro Ile Asp Phe Glu Glu
                530                 535                 540

Leu Gln Gly Gly Trp
545

<210> SEQ ID NO 39
<211> LENGTH: 582
<212> TYPE: PRT
<213> ORGANISM: Anabaena sp.

<400> SEQUENCE: 39

Met Asn Arg Asp Glu Asn Ser Asp Leu Asn Thr Ser Ala Ile Pro Val
1               5                   10                  15
```

Glu Ser Ile Ser Glu Gly Asp Asn Thr Pro Pro Glu Thr Asn Val Ile
                20                  25                  30

Ala Thr Glu Leu Ser Glu Ser Gln Leu Lys Leu Glu Val Leu Gln
            35                  40                  45

Ser Leu Leu Glu Pro Cys Asp Arg Thr Thr Tyr Gly Gln Lys Leu Lys
50                      55                  60

Glu Ala Ala Glu Lys Leu Ala Val Ser Val Arg Thr Val Gln Arg Leu
65                  70                  75                  80

Val Lys Lys Trp Glu Gln Asp Gly Leu Val Gly Leu Thr Gln Thr Gly
                85                  90                  95

Arg Thr Asp Lys Gly Lys His Arg Ile Gly Glu Phe Trp Glu Asp Phe
            100                 105                 110

Ile Val Lys Thr His Lys Glu Gly Asn Lys Gly Ser Lys Arg Met Ser
        115                 120                 125

Pro Lys Gln Val Ala Ile Arg Val Gln Ala Lys Ala His Glu Leu Ser
130                 135                 140

Asp Leu Lys Pro Pro Asn Tyr Arg Thr Val Leu Arg Val Leu Ala Pro
145                 150                 155                 160

Ile Leu Glu Lys Gln Glu Lys Thr Lys Ser Ile Arg Ser Pro Gly Trp
                165                 170                 175

Arg Gly Thr Thr Leu Ser Val Lys Thr Arg Glu Gly Lys Asp Leu Ser
            180                 185                 190

Val Asp Tyr Ser Asn His Val Trp Gln Cys Asp His Thr Pro Ala Asp
        195                 200                 205

Val Leu Leu Val Asp Gln His Gly Glu Leu Leu Ser Arg Pro Trp Leu
210                 215                 220

Thr Thr Val Ile Asp Thr Tyr Ser Arg Cys Ile Met Gly Ile Asn Leu
225                 230                 235                 240

Gly Phe Asp Ala Pro Ser Ser Glu Val Val Ala Leu Ala Leu Arg His
                245                 250                 255

Ala Ile Leu Pro Lys Arg Tyr Ser Leu Glu Tyr Lys Leu His Cys Glu
            260                 265                 270

Trp Gly Thr Tyr Gly Lys Pro Glu His Phe Tyr Thr Asp Gly Gly Lys
        275                 280                 285

Asp Phe Arg Ser Asn His Leu Ser Gln Ile Gly Ala Gln Leu Gly Phe
290                 295                 300

Val Cys His Leu Arg Asp Arg Pro Ser Glu Gly Ile Val Glu Arg
305                 310                 315                 320

Pro Phe Lys Thr Leu Asn Asp Gln Leu Phe Ser Thr Leu Pro Gly Tyr
                325                 330                 335

Thr Gly Ser Asn Val Gln Glu Arg Pro Glu Asp Ala Glu Lys Asp Ala
            340                 345                 350

Lys Leu Thr Leu Arg Glu Leu Glu Gln Leu Ile Val Arg Tyr Ile Val
        355                 360                 365

Asp Arg Tyr Asn Gln Ser Ile Asp Ala Arg Met Gly Asp Gln Thr Arg
370                 375                 380

Phe Gly Arg Trp Glu Ala Gly Leu Pro Ser Val Pro Val Pro Ile Glu
385                 390                 395                 400

Glu Arg Asp Leu Asp Ile Cys Leu Met Lys Gln Ser Arg Arg Val
                405                 410                 415

Gln Lys Gly Gly His Leu Gln Phe Gln Asn Leu Met Tyr Arg Gly Glu
            420                 425                 430

Tyr Leu Gly Gly Tyr Asp Gly Glu Thr Val Asn Leu Arg Phe Asn Pro

```
                435                 440                 445
Arg Asp Ile Thr Thr Val Leu Val Tyr Arg Gln Glu Asn Ser Gln Glu
450                 455                 460

Val Phe Leu Thr Arg Ala His Ala Gln Gly Leu Glu Thr Glu Gln Leu
465                 470                 475                 480

Ser Leu Asp Glu Ala Glu Ala Ser Arg Arg Leu Arg Asn Leu Gly
                485                 490                 495

Lys Thr Ile Ser Asn Gln Ala Leu Leu Gln Glu Val Leu Asp Arg Asp
                500                 505                 510

Ala Leu Val Ala Asn Lys Lys Ser Arg Lys Asp Arg Gln Lys Leu Glu
            515                 520                 525

Gln Glu Ile Leu Arg Ser Thr Ala Val Asn Asp Ser Lys Asn Glu Ser
530                 535                 540

Leu Ala Ser Pro Val Met Glu Ala Glu Asp Val Glu Phe Thr Thr Pro
545                 550                 555                 560

Val Gln Ser Ser Ser Pro Glu Leu Glu Val Trp Asp Tyr Glu Gln Leu
                565                 570                 575

Arg Glu Glu Tyr Gly Phe
            580

<210> SEQ ID NO 40
<211> LENGTH: 663
<212> TYPE: PRT
<213> ORGANISM: Anabaena variabilis

<400> SEQUENCE: 40

Met Asn Tyr Leu Asp Val Asp Asn Gln Phe Glu Leu Glu Asp Glu Asp
1               5                   10                  15

Asp Phe Leu Leu Asp Asp Glu Asp Ala Asp Ile Leu Asp Phe Ser Ile
                20                  25                  30

Glu Val Glu Ser Leu Ser Asn Asp Gly Asn Ser Val Ala Glu Asp Lys
            35                  40                  45

Leu Val Glu Phe Leu Asp Gln Arg Tyr Leu Glu Asp Ser Glu Leu Arg
50                  55                  60

Leu Ser Gly Glu Gln Arg Leu Lys Leu Glu Ile Ile Arg Asn Leu Arg
65                  70                  75                  80

Glu Pro Cys Asp Arg Leu Thr Tyr Gly Lys Arg Leu Glu Glu Ala Ala
                85                  90                  95

Lys Lys Leu Gly Lys Ser Glu Arg Thr Val Arg Arg Leu Ile Lys Ser
                100                 105                 110

Trp Glu Glu Lys Gly Ile Ala Ala Leu Ala Glu Val Pro Arg Ala Asp
            115                 120                 125

Lys Gly Gln Val Arg Lys Ser Glu Tyr Trp Tyr Asn Leu Ser Leu Lys
130                 135                 140

Ile Tyr Lys Gln Gly Asn Lys Gly Asp Lys Gly Asp Lys Gly Asp Lys
145                 150                 155                 160

Gly Ser Asp Arg Met Thr Arg Thr Gln Val Ala Glu Lys Val Glu Thr
                165                 170                 175

Lys Ala Tyr Glu Phe Ala Lys Lys Glu Leu Glu Ala Glu Ile Ser Lys
                180                 185                 190

Leu Glu Ser Gln Gly Phe Arg Gly Gln Asp Leu Asp Trp Glu Leu Lys
            195                 200                 205

Lys Leu Ile Lys Ile Lys Glu Lys Ala Glu Gly Phe Lys Tyr Trp Ser
210                 215                 220
```

-continued

```
Lys Tyr Gly Lys Pro Ser Thr Arg Thr Val Glu Arg Trp Leu Lys
225                 230                 235                 240

Pro Val Glu Glu Lys Arg His Lys Ser Arg Thr Ser Arg Ser Pro Gly
            245                 250                 255

Trp His Gly Ser Glu His Thr Ile Lys Thr Arg Asp Gly Gln Glu Ile
                260                 265                 270

Ser Ile Lys Tyr Thr Asn Gln Val Trp Gln Ile Asp His Thr Lys Ala
            275                 280                 285

Asp Ile Leu Leu Val Asp Glu Asp Gly Glu Ile Gly Arg Pro Gln
            290                 295                 300

Leu Thr Thr Val Ile Asp Cys Tyr Ser Arg Cys Ile Val Gly Phe Arg
305                 310                 315                 320

Leu Gly Phe Ala Ala Pro Ser Ser Gln Val Val Ala Leu Ala Leu Arg
                325                 330                 335

His Ala Ile Met Pro Lys Arg Tyr Ser Ser Glu Tyr Glu Leu Arg Cys
                340                 345                 350

Lys Trp Ser Ala Tyr Gly Val Pro Lys Tyr Val Tyr Thr Asp Gly Gly
            355                 360                 365

Lys Asp Phe Arg Ser Lys His Leu Val Glu Trp Ile Ala Asn Glu Leu
370                 375                 380

Asp Phe Glu Pro Ile Leu Arg Ser Lys Pro Ser Asp Gly Gly Ile Val
385                 390                 395                 400

Glu Arg Pro Phe Arg Thr Ile Ser Gly Leu Leu Ser Glu Met Pro Gly
                405                 410                 415

Tyr Thr Gly Ser Ser Val Lys Asp Arg Pro Glu Gly Ala Glu Lys Lys
            420                 425                 430

Ala Cys Ile Ser Leu Pro Glu Leu Glu Lys Leu Ile Val Gly Tyr Ile
            435                 440                 445

Val Asp Ser Tyr Asn Gln Lys Pro Asp Ala Arg Ser Gln Ala Asn Pro
            450                 455                 460

Leu Thr Pro Lys Gln Ser Arg Ile Glu Arg Trp Glu Lys Gly Leu Gln
465                 470                 475                 480

Met Pro Pro Thr Leu Leu Asn Asp Arg Glu Leu Asp Ile Cys Leu Met
                485                 490                 495

Lys Ala Ala Glu Arg Val Val Tyr Asp Asn Gly Tyr Leu Asn Phe Ser
            500                 505                 510

Gly Leu Arg Tyr Arg Gly Glu Asn Leu Gly Ala Tyr Ala Gly Asp Lys
            515                 520                 525

Val Ile Leu Arg Phe Asp Pro Arg Asp Ile Thr Met Val Leu Val Tyr
530                 535                 540

Gly Arg Lys Asn Asn Lys Glu Ile Phe Leu Ala Arg Ala Tyr Ala Ile
545                 550                 555                 560

Gly Leu Glu Ala Ala Ser Leu Ser Val Glu Glu Val Lys Tyr Ala Arg
                565                 570                 575

Lys Lys Ala Glu Asn Ser Gly Lys Gly Ile Asn Asn Ile Ser Ile Leu
            580                 585                 590

Glu Glu Ala Leu Arg Arg Arg Asn Phe Leu Gln Gln Lys Lys Asn Lys
            595                 600                 605

Thr Lys Ala Glu Arg Arg Arg Ser Glu Glu Lys Arg Ile Glu Lys Ile
            610                 615                 620

Pro Gln Val Leu Thr Glu Lys Lys Asn Glu Gln Val Ala Val Leu Ile
625                 630                 635                 640

Ser Gln Pro Glu Asp Asp Glu Pro Ile Glu Lys Leu Asp Leu Lys Leu
```

-continued

```
                     645                 650                 655
Leu Arg Glu Glu Leu Gly Leu
            660

<210> SEQ ID NO 41
<211> LENGTH: 560
<212> TYPE: PRT
<213> ORGANISM: Anabaena variabilis

<400> SEQUENCE: 41

Met Leu Asp Asp Pro Asp Lys Gly Asn Gln Glu Pro Glu Thr His Glu
1               5                   10                  15

Ile Val Thr Glu Leu Ser Leu Asp Glu Gln His Leu Leu Glu Met Ile
            20                  25                  30

Gln Lys Leu Ile Glu Pro Cys Asp Arg Ile Thr Tyr Gly Glu Arg Gln
        35                  40                  45

Arg Glu Val Ala Gly Lys Leu Gly Lys Ser Val Arg Thr Val Arg Arg
    50                  55                  60

Leu Val Lys Lys Trp Glu Gln Glu Gly Leu Thr Ala Leu Gln Thr Ala
65                  70                  75                  80

Thr Arg Thr Asp Lys Gly Thr His Arg Ile Asp Ser Asp Trp Gln Asp
                85                  90                  95

Phe Ile Ile Lys Thr Tyr Lys Glu Asn Asn Lys Asp Gly Lys Arg Met
            100                 105                 110

Ser Pro Lys Gln Val Ala Leu Arg Val Gln Thr Lys Ala Glu Glu Leu
        115                 120                 125

Gly Gln Gln Lys Tyr Pro Ser Tyr Arg Thr Val Tyr Arg Val Leu Gln
    130                 135                 140

Pro Ile Ile Glu Gln Lys Glu Gln Lys Glu Gly Ile Arg His Arg Gly
145                 150                 155                 160

Trp His Gly Ser Arg Leu Ser Val Lys Thr Arg Asp Gly Lys Asp Leu
                165                 170                 175

Phe Val Glu His Ser Asn His Val Trp Gln Cys Asp His Thr Arg Val
            180                 185                 190

Asp Leu Leu Leu Val Asp Gln His Gly Glu Leu Leu Ser Arg Pro Trp
        195                 200                 205

Leu Thr Ile Val Val Asp Thr Tyr Ser Arg Cys Ile Met Gly Ile Asn
    210                 215                 220

Leu Gly Phe Asp Ala Pro Ser Ser Gln Val Ile Ala Leu Ala Leu Arg
225                 230                 235                 240

His Ala Ile Leu Pro Lys Arg Tyr Gly Ser Glu Tyr Gly Leu His Glu
                245                 250                 255

Glu Trp Gly Thr Tyr Gly Lys Pro Glu His Phe Tyr Thr Asp Gly Gly
            260                 265                 270

Lys Asp Phe Arg Ser Asn His Leu Gln Gln Ile Gly Val Gln Leu Gly
        275                 280                 285

Phe Val Cys His Leu Arg Asp Arg Pro Ser Glu Gly Gly Ile Val Glu
    290                 295                 300

Arg Pro Phe Gly Thr Phe Asn Thr Asp Leu Phe Ser Thr Leu Pro Gly
305                 310                 315                 320

Tyr Thr Gly Ser Asn Val Gln Glu Arg Pro Glu Gln Ala Glu Lys Glu
                325                 330                 335

Ala Cys Ile Thr Leu Arg Glu Leu Glu Arg Leu Leu Val Arg Tyr Ile
            340                 345                 350
```

```
Val Asp Lys Tyr Asn Gln Ser Ile Asp Ala Arg Leu Gly Asp Gln Thr
        355                 360                 365

Arg Tyr Gln Arg Trp Glu Ala Gly Leu Ile Val Ala Pro Asn Leu Ile
    370                 375                 380

Ser Glu Glu Leu Arg Ile Cys Leu Met Lys Gln Thr Arg Arg Ser
385                 390                 395                 400

Ile Tyr Arg Gly Gly Tyr Val Gln Phe Glu Asn Leu Thr Tyr Arg Gly
                405                 410                 415

Glu Asn Leu Ala Gly Tyr Ala Gly Glu Asn Val Val Leu Arg Tyr Asp
                420                 425                 430

Pro Lys Asp Ile Thr Thr Leu Leu Val Tyr Arg Gln Lys Gly Asn Gln
                435                 440                 445

Glu Glu Phe Leu Ala Arg Ala Tyr Ala Gln Asp Leu Glu Thr Glu Glu
                450                 455                 460

Leu Ser Val Asp Glu Ala Lys Ala Met Ser Arg Arg Ile Arg Gln Ala
465                 470                 475                 480

Gly Lys Ala Ile Ser Asn Arg Ser Ile Leu Ala Glu Val Arg Asp Arg
                485                 490                 495

Glu Thr Phe Val Asn Gln Lys Lys Thr Lys Lys Glu Arg Gln Lys Ala
                500                 505                 510

Glu Gln Thr Ile Val Gln Lys Ala Lys Lys Pro Val Pro Val Glu Pro
                515                 520                 525

Glu Glu Glu Ile Glu Val Ala Ser Val Asp Ser Glu Pro Glu Tyr Gln
                530                 535                 540

Met Pro Glu Val Phe Asp Tyr Glu Gln Met Arg Glu Asp Tyr Gly Trp
545                 550                 555                 560

<210> SEQ ID NO 42
<211> LENGTH: 546
<212> TYPE: PRT
<213> ORGANISM: Aphanocapsa montana

<400> SEQUENCE: 42

Met Glu Leu Val Asn Pro Asp Asp Leu Asn Ser Val Glu Ser Arg Leu
1               5                   10                  15

Lys Leu Glu Ile Ile Glu Lys Leu Ser Glu Pro Cys Asp Arg Lys Thr
                20                  25                  30

Tyr Gly Glu Arg Leu Arg Ser Ala Ala Gln Gln Leu Lys Cys Ser Val
            35                  40                  45

Arg Thr Val Gln Arg Leu Met Lys Lys Trp Glu Glu Glu Gly Leu Ala
50                  55                  60

Ala Leu Ile Asp Ser Gly Arg Ile Asp Lys Gly Lys Pro Arg Ile Ala
65                  70                  75                  80

Glu Asp Trp Gln Gln Phe Ile Lys Lys Val Tyr Ser Asn Asp Lys Cys
                85                  90                  95

Thr Pro Ala Gln Val Phe Thr Lys Val Arg Asn Lys Ala Arg Gln Glu
            100                 105                 110

Gly Leu Lys Asp Tyr Pro Ser His Met Thr Val Tyr Arg Ile Leu Arg
        115                 120                 125

Leu Val Lys Glu Ala Lys Glu Lys Glu Ser Ile Arg Asn Leu Gly
        130                 135                 140

Trp Lys Gly Ser Arg Leu Ala Leu Lys Thr Arg Asp Gly Glu Val Leu
145                 150                 155                 160

Glu Ile Asp Tyr Ser Asn Gln Val Trp Gln Cys Asp His Thr Arg Ala
                165                 170                 175
```

-continued

```
Asp Ile Leu Leu Val Asp Lys Tyr Gly His Gln Met Gly Arg Pro Trp
            180                 185                 190

Leu Thr Thr Val Ile Asp Thr Tyr Ser Arg Ala Ile Val Gly Ile Asn
        195                 200                 205

Leu Gly Tyr Asp Ala Pro Ser Ser Val Val Ala Leu Ala Leu Arg
    210                 215                 220

Asn Ala Ile Met Pro Lys Gln Tyr Gly Val Glu Tyr Lys Leu Tyr Ala
225                 230                 235                 240

Asp Trp Pro Thr Cys Gly Thr Pro Asp His Leu Phe Thr Asp Gly Gly
                245                 250                 255

Lys Asp Phe Arg Ser Asn His Leu Arg Gln Ile Gly Leu Gln Leu Gly
            260                 265                 270

Phe Ile Cys His Leu Arg Asp Arg Pro Ser Glu Gly Ile Val Glu
        275                 280                 285

Arg Pro Phe Gly Thr Ile Asn Thr Gln Phe Leu Ser Thr Leu Pro Gly
    290                 295                 300

Tyr Thr Gly Ser Asn Val Gln Asp Arg Pro Glu Ala Glu Ala Glu
305                 310                 315                 320

Ala Cys Leu Thr Leu Gln Glu Leu Glu Lys Leu Leu Val Ala Tyr Ile
                325                 330                 335

Val Asn Thr Tyr Asn Gln Arg Leu Asp Ala Arg Met Gly Asp Gln Thr
            340                 345                 350

Arg Ile Gln Arg Trp Glu Ala Gly Leu Leu Lys Gln Pro Arg Val Ile
        355                 360                 365

Pro Glu His Glu Leu His Ile Cys Leu Met Arg Gln Thr Arg Arg Thr
    370                 375                 380

Ile Tyr Arg Gly Gly Tyr Leu Gln Phe Glu Asn Leu Ala Tyr Arg Gly
385                 390                 395                 400

Glu Ala Leu Ala Glu His Ala Gly Glu Asn Ile Val Leu Arg Tyr Asp
                405                 410                 415

Pro Arg Asn Ile Ala Gln Val Leu Val Tyr Arg His Asp Pro Asp Arg
            420                 425                 430

Glu Val Tyr Leu Gly Val Ala Gln Ala Leu Glu Phe Glu Gly Glu Val
        435                 440                 445

Leu Ala Leu Asp Asp Ala Lys Ala His Ser Arg Arg Ile Arg Glu Asp
    450                 455                 460

Gly Lys Ala Val Ser Asn Asp Ala Met Leu Asp Glu Met Arg Asp Arg
465                 470                 475                 480

Glu Ala Phe Val Asp Gln Lys Asn Lys Ser Arg Lys Asp Arg Gln Lys
                485                 490                 495

Asp Glu Gln Ala Asp Leu Arg Pro Thr Thr Pro Ile Ile Gly Pro
            500                 505                 510

Asp Ser Ser Asp Glu Pro Ser Val Asp Val Gln Pro Asp Glu Ser Pro
        515                 520                 525

Glu Glu Leu Asp Ile Pro Glu Phe Asp Ile Trp Asp Phe Asp Asp
    530                 535                 540

Asp Ala
545
```

<210> SEQ ID NO 43
<211> LENGTH: 496
<212> TYPE: PRT
<213> ORGANISM: Calothrix sp.

```
<400> SEQUENCE: 43

Met Gly Glu Thr Leu Asn Ser Asp Asn Ile Asn Ala Leu Gln Val Phe
1               5                   10                  15

Asp Asp Ser Gly Glu Leu Glu Ile Ser Glu Ser Asp Asp Thr Glu
            20                  25                  30

Ser Lys Asn Thr Ile Val Thr Glu Leu Ser Ala Glu Ala Lys Leu Arg
            35                  40                  45

Met Glu Val Leu Gln Ser Leu Leu Glu Pro Cys Asp Arg Lys Thr Tyr
        50                  55                  60

Gly Ile Lys Leu His Asp Ala Ala Glu Lys Leu Gly Lys Thr Ile Arg
65                  70                  75                  80

Thr Val Gln Arg Leu Val Lys Lys Tyr Gln Glu Gly Leu Ser Ala
                85                  90                  95

Ile Thr Glu Ala Glu Arg Ser Asp Lys Gly Asp Tyr Arg Ile Asp Lys
                100                 105                 110

Glu Trp Gln Glu Phe Ile Phe Lys Thr Tyr Lys Glu Gly Asn Lys Asn
            115                 120                 125

Gly Arg Lys Met Thr Pro Ala Gln Val Ala Ile Arg Val Gln Val Lys
130                 135                 140

Ala Glu Gln Leu Ala Leu Ser Asn Tyr Pro Ser His Met Thr Val Tyr
145                 150                 155                 160

Arg Val Leu Asn Pro Ile Ile Glu Arg Lys Glu Gln Lys Gln Lys Val
                165                 170                 175

Arg Asn Ile Gly Trp Arg Gly Ser Arg Val Ser His Lys Thr Arg Asp
            180                 185                 190

Gly Gln Thr Leu Glu Pro Arg Tyr Ser Asn His Thr Trp Gln Cys Asp
        195                 200                 205

His Thr Lys Leu Asp Ile Met Leu Val Asp Gln Tyr Gly Glu Thr Leu
    210                 215                 220

Ala Arg Pro Trp Leu Thr Lys Ile Thr Asp Ser Tyr Ser Arg Cys Ile
225                 230                 235                 240

Met Gly Ile Asn Leu Gly Phe Asp Ala Pro Ser Ser Leu Val Val Ala
                245                 250                 255

Leu Ala Met Arg His Ala Ile Leu Pro Lys Ser Tyr Gly Ser Glu Tyr
            260                 265                 270

Lys Leu His Cys Lys Trp Glu Thr Tyr Gly Val Pro Glu Asn Leu Phe
        275                 280                 285

Thr Asp Gly Gly Lys Asp Phe Arg Ser Glu His Leu Lys Gln Ile Gly
    290                 295                 300

Phe His Leu Gly Phe Glu Cys His Leu Arg Asp Arg Pro Glu Gly
305                 310                 315                 320

Gly Ile Glu Glu Arg Gly Phe Gly Thr Ile Asn Thr Asp Phe Leu Ala
                325                 330                 335

Gly Phe Tyr Gly Tyr Leu Gly Ser Asn Leu Gln Gln Arg Pro Glu Glu
            340                 345                 350

Ala Glu Ser Glu Ala Cys Ile Thr Leu Arg Glu Leu His Leu Leu Leu
        355                 360                 365

Val Arg Tyr Ile Val Asp Asn Tyr Asn Gln Arg Ile Asp Ala Arg Ser
    370                 375                 380

Gly Asn Gln Thr Arg Phe Gln Arg Trp Glu Ala Gly Leu Pro Ala Leu
385                 390                 395                 400

Ala Pro Leu Ile Asp Glu Arg Gln Leu Asp Ile Cys Leu Met Lys Lys
                405                 410                 415
```

```
Thr His Arg Ser Ile Tyr Lys Gly Gly Tyr Val Ser Phe Glu Asn Ile
            420                 425                 430

Thr Tyr Arg Gly Glu Tyr Leu Ala Ala Tyr Ala Gly Glu Ser Val Ile
            435                 440                 445

Leu Arg Phe Asp Pro Arg Asp Glu Trp His Leu Leu Lys Gly Lys Arg
450                 455                 460

Ile Gly Met Ile Gly Phe His Ala Leu Val Met Ala Ile Asn Thr Val
465                 470                 475                 480

Gly Ala Tyr Ile Asn Thr Asn Thr Tyr Gln Leu His Ile His Val Asn
                485                 490                 495

<210> SEQ ID NO 44
<211> LENGTH: 567
<212> TYPE: PRT
<213> ORGANISM: Cyanothece sp.

<400> SEQUENCE: 44

Met Ser Leu Ser Leu Ser Ile Pro Asp Asp Ser Pro His Ser His Arg
1               5                   10                  15

Leu Pro Ser Asp Glu Met Ile Thr Asp Glu Val Lys Ala Lys Ile Asp
            20                  25                  30

Ile Ile Gln Ser Leu Ile Glu Pro Cys Asp Arg Ile Thr Tyr Arg Gln
        35                  40                  45

Arg Lys Glu Gln Ala Ala Lys Gln Leu Gly Val Thr Ile Arg Ser Val
    50                  55                  60

Glu Arg Leu Leu Lys Lys Tyr Arg Glu Gln Gly Leu Ile Ala Leu Met
65                  70                  75                  80

Lys Thr Arg Ser Asp Lys Gly Lys Thr Arg Ile Asp Asp Glu Trp Lys
                85                  90                  95

Glu Phe Ile Leu Asn Thr Tyr Lys Glu Gly Asn Lys Gly Ser Lys Arg
            100                 105                 110

Ile Thr Arg His Gln Val Phe Leu Lys Val Lys Gly Arg Ala Lys Gln
        115                 120                 125

Leu Gly Leu Asn Lys Glu Glu Phe Pro Ser His Gln Thr Val Tyr Arg
    130                 135                 140

Ile Leu Asp Lys Phe Ile Glu Glu Asn Glu Arg Lys Lys Lys Ala Arg
145                 150                 155                 160

Ser Pro Gly Tyr Ser Gly Ser Arg Leu Thr His Ile Thr Arg His Gly
                165                 170                 175

Arg Glu Leu Glu Val Glu Gly Ser Asn Asp Val Trp Gln Cys Asp His
            180                 185                 190

Thr Cys Leu Asp Ile Arg Leu Val Asp Glu Phe Gly Val Leu Ser Arg
        195                 200                 205

Pro Trp Leu Thr Ile Ile Ile Asp Ser Tyr Ser Arg Cys Val Met Gly
    210                 215                 220

Phe Phe Leu Gly Phe Tyr Ala Pro Ser Ser His Ile Asp Ala Leu Ala
225                 230                 235                 240

Leu Arg His Ala Ile Leu Pro Lys Ser Tyr Ser Ser Asp Tyr Gln Leu
                245                 250                 255

Lys Asn Glu Trp Asn Thr Tyr Gly Ile Pro Thr Tyr Tyr Tyr Thr Asp
            260                 265                 270

Gly Gly Lys Asp Phe Arg Ser Ile His Val Thr Glu Gln Val Ala Val
        275                 280                 285

Ser Leu Gly Phe Asn Cys Phe Leu Arg Ser Arg Pro Ser Asp Gly Gly
```

```
                290                 295                 300
Ile Val Glu Arg Phe Phe Lys Thr Leu Asn Asn Ser Val Leu Cys Glu
305                 310                 315                 320

Leu Pro Gly Tyr Thr Gly Ser Asn Val Gln Gln Arg Pro Lys Asn Val
                325                 330                 335

Asp Lys Asp Ala Cys Leu Ser Leu Lys Asp Leu Glu Lys Ile Leu Val
            340                 345                 350

Lys Tyr Ile Val Asp Glu Tyr Asn Gln Lys Pro Asp Ala Arg Met Lys
        355                 360                 365

Asn Gln Ser Arg Ile Thr Arg Trp Glu Ala Gly Leu Leu Thr Glu Pro
    370                 375                 380

Tyr Leu Tyr Asp Glu Arg Glu Leu Asp Ile Ala Leu Met Lys Glu Ala
385                 390                 395                 400

Lys Arg Thr Leu Gln Lys Ser Gly Thr Leu Gln Phe Glu Asn Leu Thr
                405                 410                 415

Tyr Arg Ser Pro Leu Leu Lys Gly Arg Glu Gly Glu Arg Val Ala Ile
            420                 425                 430

Arg Tyr Asp Pro Asp Asp Val Thr Thr Ile Leu Val Tyr Glu Tyr Leu
        435                 440                 445

Asp Asp Gly Thr Glu Ala Phe Leu Asp Tyr Ala His Ala Gln Asn Leu
    450                 455                 460

Glu Thr Glu Lys Leu Ser Tyr Arg Glu Leu Lys Ala Ile Asn Lys Gln
465                 470                 475                 480

Leu Asn Gln Glu Glu Glu Ala Ile Asn Asn Asp Lys Ile Leu Asp Ala
                485                 490                 495

Met Met Glu Arg Met Glu Met Thr Glu Glu Leu Val Lys Lys Asn Arg
            500                 505                 510

Gln Gln Arg Gln Gln Asn Ala His Glu Ala Val Asn Ser Arg Pro Ser
        515                 520                 525

Val Thr Glu Lys Leu Ser Ile Ser Gln Pro Asp Glu Glu Asp Trp Glu
    530                 535                 540

Asp Asp Ser Glu Asp Glu Pro Leu Pro Thr Tyr Lys Val Gln Tyr Met
545                 550                 555                 560

Asp Asp Leu Phe Glu Asp Asp
                565

<210> SEQ ID NO 45
<211> LENGTH: 555
<212> TYPE: PRT
<213> ORGANISM: Geminocystis sp.

<400> SEQUENCE: 45

Met Thr Ile Glu Asn Gln Ile Ser Glu Ser Gln Glu Leu Ile Ser Gln
1               5                   10                  15

Leu Ser Pro Glu Glu Gln Ala Ile Ala Asp Val Ile Glu Asp Leu Val
                20                  25                  30

Gln Pro Cys Asp Arg Lys Thr Tyr Gly Ala Lys Leu Lys Ala Ala
            35                  40                  45

Glu Thr Leu Asn Lys Ser Val Arg Thr Val Gln Arg Tyr Ile Lys Glu
        50                  55                  60

Trp Glu Glu Lys Gly Leu Leu Ala Ile Lys Lys Gly Asn Arg Ser Asp
65              70                  75                  80

Gln Gly Thr Tyr Arg Ile Glu Lys Arg Leu Gln Asp Phe Ile Val Lys
                85                  90                  95
```

-continued

```
Thr Tyr Arg Glu Gly Asn Lys Gly Ser Lys Arg Ile Ser Pro Lys Gln
                100                 105                 110
Val Tyr Leu Arg Thr Met Ala Gln Ala Lys Glu Trp Ser Ile Asp Pro
            115                 120                 125
Pro Ser His Met Thr Val Tyr Arg Ile Leu Asn Pro Ile Ile Glu Glu
        130                 135                 140
Lys Glu Asn Lys Lys Arg Val Arg Asn Pro Gly Trp Arg Gly Thr Lys
145                 150                 155                 160
Leu Ala Val Ser Thr Arg Ser Gly Asn Glu Ile Asn Val Glu Tyr Ser
                165                 170                 175
Asn His Ala Trp Gln Cys Asp His Thr Arg Ala Asp Ile Leu Leu Val
            180                 185                 190
Asp Gln Phe Gly Gln Leu Leu Gly Arg Pro Trp Leu Thr Thr Val Val
        195                 200                 205
Asp Thr Tyr Ser Arg Cys Ile Met Gly Ile Asn Leu Gly Phe Asp Ala
    210                 215                 220
Pro Ser Ser Gln Val Val Ser Leu Ala Leu Arg His Ala Met Leu Leu
225                 230                 235                 240
Lys Ser Tyr Ser Ser Asp Tyr Gly Leu His Glu Glu Trp Gly Thr Tyr
                245                 250                 255
Gly Lys Pro Glu Tyr Phe Tyr Thr Asp Gly Gly Lys Asp Phe Arg Ser
            260                 265                 270
Asn His Leu Gln Gln Ile Gly Leu Gln Leu Gly Phe Thr Cys His Leu
        275                 280                 285
Arg Ser Arg Pro Ser Glu Gly Gly Val Val Glu Arg Pro Phe Lys Thr
    290                 295                 300
Leu Asn Thr Glu Val Phe Ser Thr Leu Pro Gly Tyr Thr Gly Gly Asn
305                 310                 315                 320
Val Gln Glu Arg Ser Glu Asp Ala Glu Lys Asp Ala Ser Leu Thr Leu
                325                 330                 335
Arg Gln Leu Glu Arg Ile Ile Val Arg Tyr Ile Val Asp Asn Tyr Asn
            340                 345                 350
Gln Arg Met Asp Ala Arg Met Gly Glu Gln Thr Arg Phe Gln Arg Trp
        355                 360                 365
Asp Ser Gly Leu Leu Ser Ile Pro Asp Leu Leu Ser Glu Arg Asp Leu
    370                 375                 380
Asp Ile Cys Leu Met Lys Gln Ser Arg Arg Val Gln Lys Gly Gly
385                 390                 395                 400
Tyr Leu Gln Phe Glu Asn Leu Met Tyr Gln Gly Glu Tyr Leu Ala Gly
                405                 410                 415
Tyr Glu Gly Glu Thr Val Ile Leu Arg Tyr Asp Pro Arg Asp Ile Thr
            420                 425                 430
Ala Ile Leu Val Tyr Arg Asn Glu Gly Asn Lys Glu Val Phe Leu Thr
        435                 440                 445
Arg Ala Tyr Gly Leu Asp Leu Glu Thr Glu Ser Met Ser Trp Glu Asp
    450                 455                 460
Ala Lys Ala Ser Ala Lys Lys Val Arg Glu Ser Gly Lys Asn Leu Ser
465                 470                 475                 480
Asn Arg Ser Ile Leu Ala Glu Val Lys Glu Arg His Thr Phe Ser Asp
                485                 490                 495
Lys Lys Thr Lys Lys Glu Arg Gln Arg Gln Glu Gln Glu Val Lys
            500                 505                 510
Pro Tyr Ile Pro Ser Pro Val Leu Lys Glu Val Lys Glu Gln Thr Asp
```

```
                515                 520                 525
Lys Ala Thr Asp Thr Asp Met Ser Glu Glu Pro Ile Val Glu Val Phe
        530                 535                 540

Asp Tyr Ser Gln Leu Gln Asp Tyr Gly Phe
545                 550                 555

<210> SEQ ID NO 46
<211> LENGTH: 569
<212> TYPE: PRT
<213> ORGANISM: Leptolyngbya boryana

<400> SEQUENCE: 46

Met Gln Leu Pro Ile Glu Phe Pro Glu Ser Glu Gln Val Ser Arg Glu
1               5                   10                  15

Leu Val Glu Gln Asn Gln Ile Val Thr Glu Leu Ser Asp Glu Ala Lys
            20                  25                  30

Leu Lys Ile Glu Val Ile Gln Ser Leu Leu Glu Pro Cys Asp Arg Ala
        35                  40                  45

Thr Tyr Gly Asn Arg Leu Arg Asp Ala Ala Thr Arg Leu Gly Lys Ser
    50                  55                  60

Val Arg Thr Val Gln Arg Met Val Lys Ser Trp Gln Glu Glu Gly Ile
65                  70                  75                  80

Ala Gly Leu Ser Asn Gly Glu Arg Thr Asp Lys Gly Glu His Arg Ile
                85                  90                  95

Glu Gln Glu Trp Gln Asp Phe Ile Ile Lys Thr Tyr Gln Glu Gly Asn
            100                 105                 110

Lys Asn Gly Lys Arg Met Thr Pro Ala Gln Val Ala Ile Arg Val Lys
        115                 120                 125

Val Lys Ala Gln Gln Glu Gly Ile Thr Lys Tyr Pro Ser His Met Thr
130                 135                 140

Val Tyr Arg Val Leu Asn Pro Leu Ile Gln Arg Lys Thr Glu Lys Gln
145                 150                 155                 160

Asn Val Arg Ser Ile Gly Trp Gln Gly Ser Arg Leu Ser Leu Lys Thr
                165                 170                 175

Arg Asp Gly Asn Ser Leu Ser Val Glu Tyr Ser Asn Gln Val Trp Gln
            180                 185                 190

Cys Asp His Thr Arg Ala Asp Ile Leu Leu Val Asp Gln His Gly Glu
        195                 200                 205

Leu Ile Gly Arg Pro Trp Leu Thr Thr Val Val Asp Thr Tyr Ser Arg
    210                 215                 220

Cys Ile Val Gly Val Asn Leu Gly Phe Asp Ala Pro Ser Ser Asp Val
225                 230                 235                 240

Val Ala Leu Ala Leu Arg His Ala Ile Leu Pro Lys Thr Tyr Pro Asp
                245                 250                 255

Arg Tyr Gln Leu Asn Cys Asp Trp Gly Thr Tyr Gly Lys Pro Glu His
            260                 265                 270

Phe Phe Thr Asp Gly Gly Lys Asp Phe Arg Ser Asn His Leu Gln Gln
        275                 280                 285

Ile Ala Val Gln Ile Gly Phe Thr Cys His Leu Arg Asn Arg Pro Ser
    290                 295                 300

Glu Gly Gly Val Val Glu Arg Pro Phe Gly Thr Leu Asn Thr Glu Phe
305                 310                 315                 320

Phe Ser Ile Leu Pro Gly Tyr Thr Gly Ser Asn Val Gln Lys Arg Pro
                325                 330                 335
```

Glu Glu Ala Glu Ser Ala Ser Leu Thr Leu Arg Glu Leu Gln
            340                 345                 350

Phe Leu Val Arg Tyr Ile Thr Asp Arg Tyr Asn Gln Gly Ile Asp Ala
        355                 360                 365

Arg Met Gly Asp Gln Thr Arg Phe Gln Arg Trp Glu Ala Gly Leu Leu
    370                 375                 380

Ala Asn Pro Ser Val Leu Thr Glu Arg Glu Leu Asp Ile Cys Leu Met
385                 390                 395                 400

Lys Gln Thr Arg Arg Thr Val Tyr Arg Glu Gly Tyr Leu Arg Phe Glu
                405                 410                 415

Asn Leu Ile Tyr Arg Gly Glu Asn Leu Ala Gly Tyr Ala Gly Glu Thr
            420                 425                 430

Val Thr Leu Arg Tyr Glu Pro Arg Asp Ile Thr Thr Val Phe Val Tyr
        435                 440                 445

His Gln Glu Gln Gly Lys Glu Val Phe Leu Thr Arg Ala His Ala Gln
    450                 455                 460

Asp Leu Glu Thr Glu Thr Ile Ser Leu Tyr Glu Ala Lys Ala Ser Ser
465                 470                 475                 480

Arg Arg Ile Arg Asp Val Gly Lys Thr Ile Ser Asn Arg Ser Ile Leu
                485                 490                 495

Glu Glu Val Arg Asp Arg Asp Leu Phe Val Gln Lys Lys Thr Arg Lys
            500                 505                 510

Glu Arg Gln Lys Ala Glu Gln Ala Glu Val Lys Ile Asp Gln Val Pro
        515                 520                 525

Ser Pro Pro Gln Val Leu His Leu Asp Glu Ala Ser Gln Phe Glu Thr
530                 535                 540

Glu Ile Val Glu Thr Gln Cys Val Glu Ile Ser Glu Ile Glu Asp Tyr
545                 550                 555                 560

Glu Lys Leu Arg Asp Asp Phe Gly Trp
                565

<210> SEQ ID NO 47
<211> LENGTH: 563
<212> TYPE: PRT
<213> ORGANISM: Myxosarcina sp.

<400> SEQUENCE: 47

Met Asn Ser Glu Ser Thr Ser Glu Thr Asn Ser Lys Leu Ala Ile Ser
1               5                   10                  15

Asp Leu Glu Asp Asp Arg Glu Ile Val Ile Thr Ser Gln Leu Glu Gly
            20                  25                  30

Lys Ala Lys Glu Arg Leu Glu Val Ile Gln Ser Leu Leu Glu Pro Cys
        35                  40                  45

Asp Arg Ala Thr Tyr Gly Glu Arg Leu Arg Ala Gly Ala Lys Lys Leu
    50                  55                  60

Asp Ile Ser Val Arg Ser Val Gln Arg Leu Phe Lys Lys Tyr Gln Glu
65                  70                  75                  80

Gln Gly Leu Thr Ala Leu Val Ser Thr Asn Arg Val Asp Lys Gly Asn
                85                  90                  95

Arg Arg Ile Ser Ser Phe Trp Gln Asp Phe Ile Leu Gln Thr Tyr Ile
            100                 105                 110

Gln Gly Asn Lys Gly Ser Lys Arg Met Ser Pro Lys Gln Val Ala Ile
        115                 120                 125

Arg Val Gln Ala Lys Ala Ser Glu Ile Lys Asp Asn Lys Pro Pro Ser
    130                 135                 140

```
Tyr Lys Thr Val Leu Arg Leu Leu Lys Pro Ile Gln Lys Lys Glu
145                 150                 155                 160

Arg Thr Ile Arg Ser Pro Gly Trp Gln Gly Thr Thr Leu Ser Val Lys
            165                 170                 175

Thr Arg Asp Gly Gln Asp Ile Gln Ile Asn His Ser Asn Gln Val Trp
            180                 185                 190

Gln Cys Asp His Thr Leu Val Asp Val Leu Val Asp Arg His Gly
            195                 200                 205

Glu Leu Ile Gly Arg Pro Trp Leu Thr Thr Val Val Asp Ser Tyr Ser
210                 215                 220

Arg Cys Val Met Gly Ile Asn Leu Gly Phe Asp Ala Pro Ser Ser Leu
225                 230                 235                 240

Val Val Ala Leu Ala Leu Arg His Ser Ile Leu Pro Lys Asn Tyr Ser
            245                 250                 255

Gln Asp Phe Gln Leu Tyr Cys Asp Trp Gly Val Phe Gly Leu Pro Glu
            260                 265                 270

Cys Leu Phe Thr Asp Gly Gly Lys Asp Phe Arg Ser Asn His Leu Glu
            275                 280                 285

Glu Ile Ala Thr Gln Leu Gly Phe Ile Arg Lys Leu Arg Asp Arg Pro
290                 295                 300

Ser Glu Gly Gly Ile Val Glu Arg Pro Phe Lys Thr Leu Asn Gln Ser
305                 310                 315                 320

Leu Phe Ser Thr Leu Pro Gly Tyr Thr Gly Ser Asn Val Gln Glu Arg
            325                 330                 335

Pro Lys Asp Ala Glu Lys Asp Ala Arg Leu Thr Leu Arg Asp Leu Glu
            340                 345                 350

Met Leu Ile Val Arg Phe Ile Val Asp Lys Tyr Asn Gln Ser Thr Ile
            355                 360                 365

Ala Gly Lys Asp Glu Gln Thr Arg Tyr Gln Arg Trp Glu Ala Gly Leu
370                 375                 380

Ile Lys Asp Pro Lys Ile Ile Ser Glu Arg Glu Leu Asp Ile Cys Leu
385                 390                 395                 400

Met Lys Ser Lys Arg Arg Thr Val Gln Arg Gly Gly His Leu Gln Phe
            405                 410                 415

Glu Asn Ile Ile Tyr Arg Gly Glu Tyr Leu Ala Gly Tyr Glu Gly Asp
            420                 425                 430

Ile Val Asn Val Arg Tyr Asn Pro Ile Asn Ile Thr Thr Ile Leu Val
            435                 440                 445

Tyr Arg Arg Glu Gln Gly Lys Glu Val Phe Leu Thr Arg Ala His Ala
450                 455                 460

Leu Gly Trp Glu Thr Glu Ile His Ser Leu Ser Glu Ala Arg Ala Ser
465                 470                 475                 480

Val Lys Arg Leu Arg Gln Ala Lys Lys Ile Ser Asn Glu Ser Ile
            485                 490                 495

His Gln Glu Ile Leu Leu Arg Asp Ser Ala Val Asp Lys Lys Ser
            500                 505                 510

Arg Lys Gln Arg Gln Lys Glu Glu Gln Ser Tyr Lys Leu Ile Thr Ser
            515                 520                 525

Pro Lys Val Val Ala Gln Asp Ile Glu Ser Gln Glu Ile Glu Arg Asp
            530                 535                 540

Ile Ser Ala Glu Ile Ala Asp Val Glu Val Trp Asp Phe Asp Glu Leu
545                 550                 555                 560
```

Glu Asp Glu

<210> SEQ ID NO 48
<211> LENGTH: 584
<212> TYPE: PRT
<213> ORGANISM: Nostoc punctiforme

<400> SEQUENCE: 48

```
Met Asn Ser Gln Gln Asn Pro Asp Leu Ala Val His Pro Ser Ala Ile
1               5                  10                  15

Pro Ile Glu Gly Leu Leu Gly Glu Ser Asp Ile Thr Leu Glu Lys Asn
            20                  25                  30

Val Ile Ala Thr Gln Leu Ser Glu Ala Gln Leu Lys Leu Glu Val
        35                  40                  45

Ile Gln Ser Leu Leu Glu Pro Cys Asp Arg Thr Thr Tyr Gly Gln Lys
    50                  55                  60

Leu Arg Glu Ala Ala Glu Lys Leu Gly Val Ser Leu Arg Thr Val Gln
65                  70                  75                  80

Arg Leu Val Lys Asn Trp Glu His Asp Gly Leu Val Gly Leu Thr Gln
                85                  90                  95

Thr Gly Arg Ala Asp Lys Gly Lys His Arg Ile Gly Glu Phe Trp Glu
            100                 105                 110

Lys Phe Ile Thr Lys Thr Tyr Asn Glu Gly Asn Lys Gly Ser Lys Arg
        115                 120                 125

Met Thr Pro Lys Gln Val Ala Leu Arg Val Glu Ala Lys Ala Arg Glu
130                 135                 140

Leu Lys Asp Ser Lys Pro Pro Asn Tyr Lys Thr Val Leu Arg Val Leu
145                 150                 155                 160

Ala Pro Ile Leu Glu Lys Gln Glu Lys Ala Lys Ser Ile Arg Ser Pro
                165                 170                 175

Gly Trp Arg Gly Thr Thr Leu Ser Val Lys Thr Arg Glu Gly Lys Asp
            180                 185                 190

Leu Ser Val Asp Tyr Ser Asn His Val Trp Gln Cys Asp His Thr Arg
        195                 200                 205

Val Asp Val Leu Val Asp Gln His Gly Glu Leu Leu Ser Arg Pro
210                 215                 220

Trp Leu Thr Thr Val Ile Asp Thr Tyr Ser Arg Cys Ile Met Gly Ile
225                 230                 235                 240

Asn Leu Gly Phe Asp Ala Pro Ser Ser Gly Val Val Ala Leu Ala Leu
                245                 250                 255

Arg His Ala Ile Leu Pro Lys Gln Tyr Gly Phe Glu Tyr Lys Leu His
            260                 265                 270

Cys Glu Trp Gly Thr Tyr Gly Lys Pro Glu His Phe Tyr Thr Asp Gly
        275                 280                 285

Gly Lys Asp Phe Arg Ser Asn His Leu Ser Gln Ile Gly Ala Gln Leu
290                 295                 300

Gly Phe Val Cys His Leu Arg Asp Arg Pro Ser Glu Gly Gly Val Val
305                 310                 315                 320

Glu Arg Pro Phe Lys Thr Leu Asn Asp Gln Leu Phe Ser Thr Leu Pro
                325                 330                 335

Gly Tyr Thr Gly Ser Asn Val Gln Glu Arg Pro Lys Asp Ala Glu Lys
            340                 345                 350

Asp Ala Arg Leu Thr Leu Arg Glu Leu Glu Gln Leu Leu Ile Arg Tyr
        355                 360                 365
```

```
Ile Val Asp Arg Tyr Asn Gln Ser Ile Asp Ala Arg Met Gly Asp Gln
    370                 375                 380

Thr Arg Phe Glu Arg Trp Glu Ala Gly Leu Pro Thr Val Pro Val Pro
385                 390                 395                 400

Ile Pro Glu Arg Asp Leu Asp Ile Cys Leu Met Lys Gln Ser Arg Arg
                405                 410                 415

Thr Val Gln Arg Gly Gly Cys Leu Gln Phe Gln Asn Leu Met Tyr Arg
            420                 425                 430

Gly Glu Tyr Leu Ala Gly Tyr Ala Gly Glu Thr Val Asn Leu Arg Phe
            435                 440                 445

Asp Pro Arg Asp Ile Thr Thr Ile Leu Val Tyr Arg Gln Glu Asn Asn
450                 455                 460

Gln Glu Val Phe Leu Thr Arg Ala His Ala Gln Gly Leu Glu Thr Glu
465                 470                 475                 480

Gln Leu Ala Leu Asp Glu Ala Glu Ala Ser Arg Arg Leu Arg Asn
                485                 490                 495

Ala Gly Lys Thr Ile Ser Asn Gln Ser Leu Leu Gln Glu Val Val Asp
            500                 505                 510

Arg Asp Ala Leu Val Ala Thr Lys Lys Ser Arg Lys Glu Arg Gln Lys
            515                 520                 525

Leu Glu Gln Ala Val Leu Arg Ser Ala Gly Val Asp Glu Ser Lys Thr
530                 535                 540

Glu Ser Leu Ser Ser Gln Val Val Glu Pro Asp Glu Val Glu Ser Thr
545                 550                 555                 560

Glu Thr Val His Ser Gln Tyr Glu Asp Met Glu Val Trp Asp Tyr Glu
                565                 570                 575

Gln Leu Arg Glu Glu Tyr Gly Phe
            580

<210> SEQ ID NO 49
<211> LENGTH: 537
<212> TYPE: PRT
<213> ORGANISM: Nostoc sp.

<400> SEQUENCE: 49

Met Ile Gln Thr Leu Leu Glu Pro Cys Asp Arg Thr Thr Tyr Gly Gln
1               5                   10                  15

Lys Leu Lys Glu Ala Ala Asp Thr Leu Gly Val Thr Val Arg Thr Val
            20                  25                  30

Gln Arg Leu Val Lys Lys Trp Glu Glu Asp Gly Leu Val Gly Phe Ile
        35                  40                  45

Gln Thr Gly Arg Ala Asp Lys Gly Lys His Arg Ile Gly Glu Phe Trp
    50                  55                  60

Glu Asn Phe Ile Ile Lys Thr Tyr Lys Glu Gly Asn Lys Gly Ser Lys
65                  70                  75                  80

Arg Met Thr Pro Lys Gln Val Ala Leu Arg Val Gln Ala Lys Ala Arg
                85                  90                  95

Glu Leu Gly Asp Ser Lys Pro Pro Asn Tyr Arg Thr Val Leu Arg Val
            100                 105                 110

Leu Ala Pro Ile Leu Glu Gln Lys Glu Lys Thr Lys Ser Ile Arg Ser
        115                 120                 125

Pro Gly Trp Arg Gly Thr Thr Leu Ser Val Lys Thr Arg Glu Gly Gln
    130                 135                 140

Asp Leu Ser Val Asp Tyr Ser Asn His Val Trp Gln Cys Asp His Thr
145                 150                 155                 160
```

Arg Val Asp Val Leu Leu Val Asp Gln His Gly Glu Leu Leu Ser Arg
            165                 170                 175

Pro Trp Leu Thr Thr Val Ile Asp Thr Tyr Ser Arg Cys Ile Met Gly
            180                 185                 190

Ile Asn Leu Gly Phe Asp Ala Pro Ser Ser Val Val Ala Leu Ala
            195                 200                 205

Leu Arg His Ala Ile Leu Pro Lys Lys Tyr Gly Ala Glu Tyr Lys Leu
            210                 215                 220

His Cys Glu Trp Gly Thr Tyr Gly Lys Pro Glu His Phe Tyr Thr Asp
225                 230                 235                 240

Gly Gly Lys Asp Phe Arg Ser Asn His Leu Ser Gln Ile Gly Ala Gln
            245                 250                 255

Leu Gly Phe Val Cys His Leu Arg Asp Arg Pro Ser Glu Gly Gly Ile
            260                 265                 270

Val Glu Arg Pro Phe Lys Thr Leu Asn Asp Gln Leu Phe Ser Thr Leu
            275                 280                 285

Pro Gly Tyr Thr Gly Ser Asn Val Gln Glu Arg Leu Glu Asp Ala Glu
            290                 295                 300

Lys Asp Ala Lys Leu Thr Leu Arg Glu Leu Glu Gln Leu Leu Val Arg
305                 310                 315                 320

Tyr Ile Val Asp Arg Tyr Asn Gln Ser Ile Asp Ala Arg Met Gly Asp
            325                 330                 335

Gln Thr Arg Phe Gly Arg Trp Glu Ala Gly Leu Pro Ser Val Pro Val
            340                 345                 350

Pro Ile Glu Glu Arg Asp Leu Asp Ile Cys Leu Met Lys Gln Ser Arg
            355                 360                 365

Arg Thr Val Gln Arg Gly Gly Cys Leu Gln Phe Gln Asn Val Met Tyr
            370                 375                 380

Arg Gly Glu Tyr Leu Ala Gly Tyr Ala Gly Glu Thr Val Asn Leu Arg
385                 390                 395                 400

Tyr Asp Pro Arg Asp Ile Thr Thr Val Leu Val Tyr Arg Gln Glu Lys
            405                 410                 415

Ser Gln Glu Val Phe Leu Thr Arg Thr His Ala Gln Gly Leu Glu Thr
            420                 425                 430

Glu Gln Leu Ser Leu Asp Glu Ala Glu Ala Ser Arg Arg Leu Arg
            435                 440                 445

Asn Ala Gly Lys Thr Val Ser Asn Gln Ala Leu Leu Gln Glu Val Leu
450                 455                 460

Glu Arg Asp Ala Met Val Ala Asn Lys Lys Ser Arg Lys Glu Arg Gln
465                 470                 475                 480

Lys Leu Glu Gln Ala Ile Leu Arg Ser Ala Val Asn Glu Ser Lys
            485                 490                 495

Thr Glu Ser Leu Ala Ser Ser Val Met Glu Ala Glu Val Glu Ser
            500                 505                 510

Thr Thr Glu Val Gln Ser Ser Ser Glu Leu Glu Val Trp Asp Tyr
            515                 520                 525

Glu Gln Leu Arg Glu Glu Tyr Gly Phe
            530                 535

<210> SEQ ID NO 50
<211> LENGTH: 566
<212> TYPE: PRT
<213> ORGANISM: Nostoc sp.

-continued

```
<400> SEQUENCE: 50

Met Thr Arg Gln Gln His Thr Ser Ser Pro Pro Glu Thr Asn Leu Ile
1               5                   10                  15

Val Thr Glu Leu Ser Glu Glu Ala Gln Leu Lys Leu Glu Val Ile Gln
            20                  25                  30

Thr Leu Leu Glu Pro Cys Asp Arg Thr Thr Tyr Gly Gln Lys Leu Lys
        35                  40                  45

Glu Ala Ala Asp Thr Leu Gly Val Thr Val Arg Thr Val Gln Arg Leu
    50                  55                  60

Val Lys Lys Trp Glu Glu Asp Gly Leu Val Gly Phe Ile Gln Thr Gly
65                  70                  75                  80

Arg Ala Asp Lys Gly Lys His Arg Ile Gly Glu Phe Trp Glu Asn Phe
                85                  90                  95

Ile Ile Lys Thr Tyr Lys Glu Gly Asn Lys Gly Ser Lys Arg Met Thr
            100                 105                 110

Pro Lys Gln Val Ala Leu Arg Val Gln Ala Lys Ala Arg Glu Leu Gly
        115                 120                 125

Asp Ser Lys Pro Pro Asn Tyr Arg Thr Val Leu Arg Val Leu Ala Pro
    130                 135                 140

Ile Leu Glu Gln Lys Glu Lys Thr Lys Ser Ile Arg Ser Pro Gly Trp
145                 150                 155                 160

Arg Gly Thr Thr Leu Ser Val Lys Thr Arg Glu Gly Gln Asp Leu Ser
                165                 170                 175

Val Asp Tyr Ser Asn His Val Trp Gln Cys Asp His Thr Arg Val Asp
            180                 185                 190

Val Leu Leu Val Asp Gln His Gly Glu Leu Leu Ser Arg Pro Trp Leu
        195                 200                 205

Thr Thr Val Ile Asp Thr Tyr Ser Arg Cys Ile Met Gly Ile Asn Leu
    210                 215                 220

Gly Phe Asp Ala Pro Ser Ser Val Val Ala Leu Ala Leu Arg His
225                 230                 235                 240

Ala Ile Leu Pro Lys Lys Tyr Gly Ala Glu Tyr Lys Leu His Cys Glu
                245                 250                 255

Trp Gly Thr Tyr Gly Lys Pro Glu His Phe Tyr Thr Asp Gly Gly Lys
            260                 265                 270

Asp Phe Arg Ser Asn His Leu Ser Gln Ile Gly Ala Gln Leu Gly Phe
        275                 280                 285

Val Cys His Leu Arg Asp Arg Pro Ser Glu Gly Ile Val Glu Arg
    290                 295                 300

Pro Phe Lys Thr Leu Asn Asp Gln Leu Phe Ser Thr Leu Pro Gly Tyr
305                 310                 315                 320

Thr Gly Ser Asn Val Gln Glu Arg Leu Glu Asp Ala Glu Lys Asp Ala
                325                 330                 335

Lys Leu Thr Leu Arg Glu Leu Glu Gln Leu Leu Val Arg Tyr Ile Val
            340                 345                 350

Asp Arg Tyr Asn Gln Ser Ile Asp Ala Arg Met Gly Asp Gln Thr Arg
        355                 360                 365

Phe Gly Arg Trp Glu Ala Gly Leu Pro Ser Val Pro Val Pro Ile Glu
    370                 375                 380

Glu Arg Asp Leu Asp Ile Cys Leu Met Lys Gln Ser Arg Arg Thr Val
385                 390                 395                 400

Gln Arg Gly Gly Cys Leu Gln Phe Gln Asn Val Met Tyr Arg Gly Glu
                405                 410                 415
```

```
Tyr Leu Ala Gly Tyr Ala Gly Glu Thr Val Asn Leu Arg Tyr Asp Pro
                420                 425                 430

Arg Asp Ile Thr Thr Val Leu Val Tyr Arg Gln Glu Lys Ser Gln Glu
            435                 440                 445

Val Phe Leu Thr Arg Thr His Ala Gln Gly Leu Glu Thr Glu Gln Leu
    450                 455                 460

Ser Leu Asp Glu Ala Glu Ala Ser Arg Arg Leu Arg Asn Ala Gly
465                 470                 475                 480

Lys Thr Val Ser Asn Gln Ala Leu Leu Gln Glu Val Leu Glu Arg Asp
                485                 490                 495

Ala Met Val Ala Asn Lys Lys Ser Arg Lys Glu Arg Gln Lys Leu Glu
            500                 505                 510

Gln Ala Ile Leu Arg Ser Ala Ala Val Asn Glu Ser Lys Thr Glu Ser
        515                 520                 525

Leu Ala Ser Ser Val Met Glu Ala Glu Val Glu Ser Thr Thr Glu
530                 535                 540

Val Gln Ser Ser Ser Glu Leu Glu Val Trp Asp Tyr Glu Gln Leu
545                 550                 555                 560

Arg Glu Glu Tyr Gly Phe
                565

<210> SEQ ID NO 51
<211> LENGTH: 580
<212> TYPE: PRT
<213> ORGANISM: Nostoc sp.

<400> SEQUENCE: 51

Met Tyr Gln Lys Leu Lys Asn Ser Cys Leu Ser Ser Glu Asp Asp Ala
1               5                   10                  15

Val Glu Leu Gln Gln His Gln Asn Ser Thr Lys Pro His Lys Leu Pro
                20                  25                  30

Ser Glu Glu Leu Ile Thr Glu Gln Val Lys Leu Arg Met Glu Val Ile
            35                  40                  45

Gln Ser Leu Thr Glu Pro Cys Asp Arg Lys Thr Tyr Arg Ala Lys Lys
        50                  55                  60

Ile Glu Ala Ala Gln Lys Leu Gly Val Ser Ile Arg Gln Val Glu Arg
65                  70                  75                  80

Leu Leu Gln Lys Trp Arg Glu Gln Gly Leu Val Gly Leu Thr Thr Thr
                85                  90                  95

Arg Ser Asp Lys Gly Lys Tyr Arg Leu Glu Gln Glu Trp Ile Asp Phe
            100                 105                 110

Ile Ile Asn Thr Tyr Lys Glu Gly Asn Lys Gly Ser Lys Arg Met Thr
        115                 120                 125

Arg Asn Gln Val Phe Leu Lys Val Lys Gly Arg Ala Lys Gln Leu Ser
    130                 135                 140

Leu Asn Lys Ser Glu His Pro Ser His Gln Ser Val Tyr Arg Ile Leu
145                 150                 155                 160

Asp Glu His Ile Glu Gln Lys Glu Arg Lys Glu Lys Ala Arg Ser Pro
                165                 170                 175

Gly Tyr Leu Gly Glu Arg Leu Thr His Met Thr Arg Asp Gly Arg Glu
            180                 185                 190

Leu Glu Val Glu Gly Ser Asn Asp Val Trp Gln Cys Asp His Thr Arg
        195                 200                 205

Leu Asp Val Arg Leu Val Asp Glu Tyr Gly Val Leu Asp Arg Pro Trp
```

```
            210                 215                 220
Leu Thr Ile Val Ile Asp Ser Tyr Ser Arg Cys Leu Val Gly Phe Tyr
225                 230                 235                 240

Val Gly Phe Asp His Pro Ser Ser Gln Ile Asp Thr Leu Ala Leu Gly
                245                 250                 255

His Ala Ile Leu Pro Lys Ser Tyr Gly Ser Glu Tyr Gln Leu Arg Asn
                260                 265                 270

Glu Trp Gln Ala Tyr Gly Lys Pro Asn Tyr Phe Tyr Thr Asp Gly Gly
            275                 280                 285

Lys Asp Phe Thr Ser Ile His Thr Thr Glu Gln Val Ala Val Gln Ile
            290                 295                 300

Gly Phe Asn Cys Ala Leu Arg Arg Pro Ser Asp Gly Ile Val
305                 310                 315                 320

Glu Arg Phe Phe Lys Thr Leu Asn Leu Gln Val Leu Asn Thr Leu Pro
                325                 330                 335

Gly Tyr Thr Gly Ser Asn Val Gln Glu Arg Pro Glu Asn Val Asp Lys
                340                 345                 350

Asp Ala Cys Leu Thr Leu Lys Asp Leu Glu Leu Leu Val Arg Phe
            355                 360                 365

Ile Val Asn Glu Tyr Asn Pro His Thr Asp Ala Arg Met Lys Gly Gln
            370                 375                 380

Ser Arg Ile Gly Arg Trp Glu Ala Gly Leu Met Ala Asp Pro Tyr Leu
385                 390                 395                 400

Tyr Asp Gln Leu Asp Leu Ala Ile Cys Leu Met Lys Gln Glu Arg Arg
                405                 410                 415

Lys Val Gln Lys Tyr Gly Cys Ile Gln Phe Glu Asn Leu Thr Tyr Arg
                420                 425                 430

Ala Glu His Leu Arg Gly Arg Asp Gly Glu Thr Val Ala Phe Arg Tyr
            435                 440                 445

Asp Pro Ala Asp Ile Thr Thr Leu Leu Val Tyr Lys Met Asn Ala Asp
            450                 455                 460

Gly Thr Glu Glu Phe Met Asp Tyr Ala His Ala Gln Ala Leu Glu Thr
465                 470                 475                 480

Glu Cys Leu Ser Leu Arg Glu Leu Lys Ala Ile Asn Lys Arg Leu Asn
                485                 490                 495

Glu Ala Ser Gln Glu Ile Asn Asn Asp Ser Ile Leu Glu Ala Met Ile
            500                 505                 510

Asp Arg Gln Ala Phe Val Glu Glu Thr Val Lys Arg Asn Arg Lys Gln
            515                 520                 525

Arg Arg Gln Ala Ala Asn Glu Gln Val Asn Pro Val Glu Gln Val Ala
            530                 535                 540

Lys Lys Phe Ala Thr Pro Glu Gln Lys Glu Val Glu Pro Glu Ser Glu
545                 550                 555                 560

Ala Asp Ile Glu Leu Pro Lys Tyr Glu Val Arg Tyr Met Asp Glu Phe
                565                 570                 575

Phe Glu Glu Asp
            580

<210> SEQ ID NO 52
<211> LENGTH: 584
<212> TYPE: PRT
<213> ORGANISM: Scytonema hofmanni

<400> SEQUENCE: 52
```

```
Met Asn Ser Gln Gln Asn Pro Asp Leu Ala Val His Pro Leu Ala Ile
1               5                   10                  15

Pro Met Glu Gly Leu Leu Gly Glu Ser Ala Thr Thr Leu Glu Lys Asn
            20                  25                  30

Val Ile Ala Thr Gln Leu Ser Glu Glu Ala Gln Val Lys Leu Glu Val
            35                  40                  45

Ile Gln Ser Leu Leu Glu Pro Cys Asp Arg Thr Thr Tyr Gly Gln Lys
        50                  55                  60

Leu Arg Glu Ala Ala Glu Lys Leu Asn Val Ser Leu Arg Thr Val Gln
65                  70                  75                  80

Arg Leu Val Lys Asn Trp Glu Gln Asp Gly Leu Val Gly Leu Thr Gln
                85                  90                  95

Thr Ser Arg Ala Asp Lys Gly Lys His Arg Ile Gly Glu Phe Trp Glu
            100                 105                 110

Asn Phe Ile Thr Lys Thr Tyr Lys Glu Gly Asn Lys Gly Ser Lys Arg
        115                 120                 125

Met Thr Pro Lys Gln Val Ala Leu Arg Val Glu Ala Lys Ala Arg Glu
    130                 135                 140

Leu Lys Asp Ser Lys Pro Pro Asn Tyr Lys Thr Val Leu Arg Val Leu
145                 150                 155                 160

Ala Pro Ile Leu Glu Lys Gln Gln Lys Ala Lys Ser Ile Arg Ser Pro
                165                 170                 175

Gly Trp Arg Gly Thr Thr Leu Ser Val Lys Thr Arg Glu Gly Lys Asp
            180                 185                 190

Leu Ser Val Asp Tyr Ser Asn His Val Trp Gln Cys Asp His Thr Arg
        195                 200                 205

Val Asp Val Leu Leu Val Asp Gln His Gly Glu Ile Leu Ser Arg Pro
    210                 215                 220

Trp Leu Thr Thr Val Ile Asp Thr Tyr Ser Arg Cys Ile Met Gly Ile
225                 230                 235                 240

Asn Leu Gly Phe Asp Ala Pro Ser Ser Gly Val Val Ala Leu Ala Leu
                245                 250                 255

Arg His Ala Ile Leu Pro Lys Arg Tyr Gly Ser Glu Tyr Lys Leu His
            260                 265                 270

Cys Glu Trp Gly Thr Tyr Gly Lys Pro Glu His Phe Tyr Thr Asp Gly
        275                 280                 285

Gly Lys Asp Phe Arg Ser Asn His Leu Ser Gln Ile Gly Ala Gln Leu
    290                 295                 300

Gly Phe Val Cys His Leu Arg Asp Arg Pro Ser Glu Gly Gly Val Val
305                 310                 315                 320

Glu Arg Pro Phe Lys Thr Leu Asn Asp Gln Leu Phe Ser Thr Leu Pro
                325                 330                 335

Gly Tyr Thr Gly Ser Asn Val Gln Glu Arg Pro Glu Asp Ala Glu Lys
            340                 345                 350

Asp Ala Arg Leu Thr Leu Arg Glu Leu Glu Gln Leu Leu Val Arg Tyr
        355                 360                 365

Ile Val Asp Arg Tyr Asn Gln Ser Ile Asp Ala Arg Met Gly Asp Gln
    370                 375                 380

Thr Arg Phe Glu Arg Trp Glu Ala Gly Leu Pro Thr Val Pro Val Pro
385                 390                 395                 400

Ile Pro Glu Arg Asp Leu Asp Ile Cys Leu Met Lys Gln Ser Arg Arg
                405                 410                 415

Thr Val Gln Arg Gly Gly Cys Leu Gln Phe Gln Asn Leu Met Tyr Arg
```

```
                   420                 425                 430
Gly Glu Tyr Leu Ala Gly Tyr Ala Gly Glu Thr Val Asn Leu Arg Phe
            435                 440                 445

Asp Pro Arg Asp Ile Thr Thr Ile Leu Val Tyr Arg Gln Glu Asn Asn
450                 455                 460

Gln Glu Val Phe Leu Thr Arg Ala His Ala Gln Gly Leu Glu Thr Glu
465                 470                 475                 480

Gln Leu Ala Leu Asp Glu Ala Glu Ala Ser Arg Arg Leu Arg Thr
            485                 490                 495

Ala Gly Lys Thr Ile Ser Asn Gln Ser Leu Leu Gln Glu Val Val Asp
            500                 505                 510

Arg Asp Ala Leu Val Ala Thr Lys Lys Ser Arg Lys Glu Arg Gln Lys
            515                 520                 525

Leu Glu Gln Thr Val Leu Arg Ser Ala Ala Val Asp Glu Ser Asn Arg
            530                 535                 540

Glu Ser Leu Pro Ser Gln Ile Val Glu Pro Asp Glu Val Glu Ser Thr
545                 550                 555                 560

Glu Thr Val His Ser Gln Tyr Glu Asp Ile Glu Val Trp Asp Tyr Glu
            565                 570                 575

Gln Leu Arg Glu Glu Tyr Gly Phe
            580

<210> SEQ ID NO 53
<211> LENGTH: 579
<212> TYPE: PRT
<213> ORGANISM: Scytonema sp.

<400> SEQUENCE: 53

Met Gly Glu Thr Leu Asn Ser Asn Glu Val Asp Glu Ser Leu Val Leu
1               5                   10                  15

Tyr Asp Gly Ser Asp Glu Val Asp Glu Ile Ser Glu Ser Glu Asp Thr
            20                  25                  30

Lys Gln Ser Asn Val Ile Val Thr Glu Leu Ser Glu Glu Ala Lys Leu
        35                  40                  45

Arg Met Gln Val Leu Gln Ser Leu Ile Glu Pro Cys Asp Arg Lys Thr
    50                  55                  60

Tyr Gly Ile Lys Leu Lys Gln Ala Ala Glu Lys Leu Gly Lys Thr Val
65                  70                  75                  80

Arg Thr Val Gln Arg Leu Val Lys Lys Tyr Gln Glu Gln Gly Leu Ser
                85                  90                  95

Gly Val Thr Glu Val Glu Arg Ser Lys Gly Gly Tyr Arg Ile Asp
            100                 105                 110

Asp Asp Trp Gln Asp Phe Ile Val Lys Thr Tyr Lys Glu Gly Asn Lys
        115                 120                 125

Gly Gly Arg Lys Met Thr Pro Ala Gln Val Ala Ile Arg Val Gln Val
130                 135                 140

Arg Ala Gly Gln Leu Gly Leu Glu Lys Tyr Pro Cys His Met Thr Val
145                 150                 155                 160

Tyr Arg Val Leu Asn Pro Ile Ile Glu Arg Lys Glu Gln Lys Gln Lys
                165                 170                 175

Val Arg Asn Ile Gly Trp Arg Gly Ser Arg Val Ser His Gln Thr Arg
            180                 185                 190

Asp Gly Gln Thr Leu Asp Val His His Ser Asn His Val Trp Gln Cys
        195                 200                 205
```

```
Asp His Thr Lys Leu Asp Val Met Leu Val Asp Gln Tyr Gly Glu Thr
    210                 215                 220

Leu Ala Arg Pro Trp Leu Thr Lys Ile Thr Asp Ser Tyr Ser Arg Cys
225                 230                 235                 240

Ile Met Gly Ile His Leu Gly Phe Asp Ala Pro Ser Ser Leu Val Val
                245                 250                 255

Ala Leu Ala Met Arg His Ala Met Leu Arg Lys Gln Tyr Ser Ser Glu
            260                 265                 270

Tyr Lys Leu His Cys Glu Trp Gly Thr Tyr Gly Val Pro Glu Asn Leu
        275                 280                 285

Phe Thr Asp Gly Gly Lys Asp Phe Arg Ser Glu His Leu Lys Gln Ile
    290                 295                 300

Gly Phe Gln Leu Gly Phe Glu Cys His Leu Arg Asp Arg Pro Pro Glu
305                 310                 315                 320

Gly Gly Ile Glu Glu Arg Gly Phe Gly Thr Ile Asn Thr Ser Phe Leu
                325                 330                 335

Ser Gly Phe Tyr Gly Tyr Leu Asp Ser Asn Val Gln Lys Arg Pro Glu
            340                 345                 350

Gly Ala Glu Glu Glu Ala Cys Ile Thr Leu Arg Glu Leu His Leu Leu
        355                 360                 365

Ile Val Arg Tyr Ile Val Asp Asn Tyr Asn Gln Arg Ile Asp Ala Arg
    370                 375                 380

Ser Gly Asn Gln Thr Arg Phe Gln Arg Trp Glu Ala Gly Leu Pro Ala
385                 390                 395                 400

Leu Pro Asn Leu Val Asn Glu Arg Glu Leu Asp Ile Cys Leu Met Lys
                405                 410                 415

Lys Thr Arg Arg Ser Ile Tyr Lys Gly Gly Tyr Val Ser Phe Glu Asn
            420                 425                 430

Ile Met Tyr Arg Gly Asp Tyr Leu Ser Ala Tyr Ala Gly Glu Ser Val
        435                 440                 445

Leu Leu Arg Tyr Asp Pro Arg Asp Ile Ser Thr Val Phe Val Tyr Arg
    450                 455                 460

Gln Asp Ser Gly Lys Glu Val Leu Leu Ser Gln Ala His Ala Ile Asp
465                 470                 475                 480

Leu Glu Thr Glu Gln Ile Ser Leu Glu Glu Thr Lys Ala Ala Ser Arg
                485                 490                 495

Lys Ile Arg Asn Ala Gly Lys Gln Leu Ser Asn Lys Ser Ile Leu Ala
            500                 505                 510

Glu Val Gln Asp Arg Asp Thr Phe Ile Lys Lys Lys Lys Ser His
        515                 520                 525

Lys Gln Arg Lys Lys Glu Glu Gln Ala Gln Val His Ser Val Lys Ser
    530                 535                 540

Phe Gln Thr Lys Glu Pro Val Glu Thr Val Glu Glu Ile Pro Gln Pro
545                 550                 555                 560

Gln Lys Arg Arg Pro Arg Val Phe Asp Tyr Glu Gln Leu Arg Lys Asp
                565                 570                 575

Tyr Asp Asp

<210> SEQ ID NO 54
<211> LENGTH: 555
<212> TYPE: PRT
<213> ORGANISM: Spirulina major

<400> SEQUENCE: 54
```

```
Met Asn Thr Gly Asn Gln Glu Ala His Ala Val Ile Thr Asp Phe Ser
1               5                   10                  15
Glu Glu Glu Arg Leu Lys Leu Glu Val Ile Gln Ser Leu Met Glu Pro
            20                  25                  30
Cys Asp His Ala Thr Tyr Gly Gln Lys Leu Lys Asp Ala Ala Gln Lys
        35                  40                  45
Leu Gly Lys Ser Lys Arg Thr Val Gln Arg Leu Val Gln Gln Trp Glu
    50                  55                  60
Glu Met Gly Leu Ala Ala Val Thr Ser Lys Ala Arg Ala Asp Lys Gly
65                  70                  75                  80
Lys His Arg Ile Ser Gln Glu Trp Gln Asp Phe Ile Val Lys Thr Tyr
                85                  90                  95
Arg Leu Gly Asn Lys Gly Ser Lys Arg Met Ser Arg Lys Gln Val Ala
            100                 105                 110
Leu Arg Val Gln Ala Arg Ala Ala Glu Leu Gly Glu Lys Met Tyr Pro
        115                 120                 125
Asn Glu Arg Thr Val Tyr Arg Val Leu Gln Pro Ile Ile Glu Ala Gln
    130                 135                 140
Glu Gln Lys Lys Ser Val Arg Ser Ala Gly Trp Arg Gly Asp Arg Leu
145                 150                 155                 160
Ser Val Lys Thr Arg Thr Gly Asn Asp Leu Val Val Glu Tyr Thr Asn
                165                 170                 175
Gln Val Trp Gln Cys Asp His Thr Trp Val Asp Val Leu Val Val Asp
            180                 185                 190
Val Glu Gly Asn Ile Ile Gly Arg Pro Trp Leu Thr Thr Val Ile Asp
            195                 200                 205
Thr Tyr Ser Arg Cys Ile Leu Gly Ile Arg Leu Gly Phe Asp Ala Pro
    210                 215                 220
Ser Ser Gln Val Val Ala Leu Ala Leu Arg His Ala Met Leu Pro Lys
225                 230                 235                 240
Gln Tyr Pro Pro Thr Phe Gly Leu Gln Cys Glu Trp Gly Thr Tyr Gly
                245                 250                 255
Lys Pro Glu Tyr Phe Tyr Thr Asp Gly Gly Lys Asp Phe Arg Ser Glu
            260                 265                 270
His Leu Arg Gln Ile Gly Ile Gln Leu Gly Phe Thr Cys Glu Leu Arg
        275                 280                 285
Asp Arg Pro Ser Glu Gly Gly Ala Val Glu Arg Pro Phe Gly Thr Leu
    290                 295                 300
Asn Thr Glu Leu Phe Ser Thr Leu Pro Gly Tyr Thr Gly Ser Asn Ile
305                 310                 315                 320
Gln Glu Arg Pro Glu Asp Ala Glu Lys Asp Ala Arg Met Thr Leu Arg
                325                 330                 335
Asp Leu Glu Gln Leu Ile Val Arg Tyr Leu Val Asp Asn Tyr Asn Gln
            340                 345                 350
Arg Leu Asp Lys Arg Met Gly Asp Gln Thr Arg Tyr Gln Arg Trp Glu
        355                 360                 365
Ser Gly Leu Leu Ala Thr Pro Ala Leu Leu Ser Glu Arg Glu Leu Asp
    370                 375                 380
Ile Cys Leu Met Lys Gln Thr Asn Arg Ser Ile Tyr Arg Glu Gly Tyr
385                 390                 395                 400
Ile Arg Phe Glu Asn Leu Met Tyr Lys Gly Glu Tyr Leu Ala Gly Tyr
                405                 410                 415
Val Gly Glu Arg Val Val Leu Arg Tyr Asp Pro Arg Asp Ile Thr Thr
```

```
                420              425              430
Val Leu Val Tyr Arg Arg Glu Lys Ser Gln Glu Val Phe Leu Ala Arg
            435              440              445
Ala Tyr Ala Gln Asp Leu Glu Thr Glu Gln Leu Thr Leu Glu Asp Ala
    450              455              460
Lys Ala Ile Asn Lys Ile Arg Glu Lys Gly Lys Thr Ile Ser Asn
465              470              475              480
Arg Ser Ile Leu Asp Glu Val Arg Asp Arg Asp Leu Phe Val Ser Lys
                485              490              495
Lys Lys Thr Lys Lys Glu Arg Gln Lys Glu Gln Thr Arg Leu Phe
            500              505              510
Thr Pro Val Thr Thr Pro Asn Ser Lys Gln Glu Thr Glu Glu Glu
            515              520              525
Ile Glu Pro Val Glu Lys Ile Asp Glu Leu Pro Gln Val Glu Ile Leu
            530              535              540
Asp Tyr Asp Glu Leu Asn Asp Tyr Gly Trp
545              550              555
```

<210> SEQ ID NO 55
<211> LENGTH: 565
<212> TYPE: PRT
<213> ORGANISM: Geminocystis sp.

<400> SEQUENCE: 55

```
Met Leu Glu Glu Lys His Asn Ile Glu Asp His Val Ala Arg Ser Arg
1               5                  10                  15
Leu Glu Asp Ser Ser Asn Asn Thr Ile Val Ser Glu Leu Pro Val Glu
                20                  25                  30
Ala Gln Gln Lys Leu Lys Ile Ile Gln Ser Leu Leu Glu Pro Cys Asp
            35                  40                  45
Arg Ala Thr Tyr Gly Asp Arg Leu Arg Glu Gly Ala Lys Glu Leu Gly
    50                  55                  60
Ile Ser Val Arg Ser Val Gln Arg Leu Phe Lys Arg Tyr Gln Glu Glu
65                  70                  75                  80
Gly Leu Asn Ala Leu Thr Ile Asn Asp Gln Arg Asp Lys Gly Lys His
                85                  90                  95
Arg Ile Lys Asp Phe Trp Glu Ser Phe Ile Leu Lys Thr Tyr Lys Glu
            100                 105                 110
Gly Asn Lys Gly Ser Lys Arg Met Asn Val Lys Gln Val Ala Ile Arg
        115                 120                 125
Val Gln Ala Lys Ala Leu Glu Leu Asn Glu Thr Asn Pro Pro Ser Tyr
130                 135                 140
Arg Thr Val Leu Arg Val Leu Asn Pro Ile Ile Asn Gln Glu Lys Lys
145                 150                 155                 160
Thr Ile Arg Ser Pro Gly Trp Glu Gly Ser Thr Leu Ser Val Lys Thr
                165                 170                 175
Arg Asp Gly Val Asp Leu Asn Ile Ser Tyr Ser Asn Gln Val Trp Gln
            180                 185                 190
Cys Asp His Thr Lys Val Asp Val Leu Leu Val Asp Lys Asn Glu Val
        195                 200                 205
Leu Leu Asp Arg Pro Trp Leu Thr Thr Val Ile Asp Ser Tyr Ser Arg
    210                 215                 220
Cys Ile Val Gly Val Asn Ile Gly Phe Asp Ala Pro Ser Ser Asn Val
225                 230                 235                 240
```

Val Gly Leu Ala Leu Arg His Ala Ile Leu Pro Lys His Tyr Pro Glu
            245                 250                 255

Glu Tyr Arg Leu Asn Cys Glu Trp Gly Thr Tyr Gly Leu Pro Gln Tyr
        260                 265                 270

Leu Phe Thr Asp Gly Gly Lys Asp Phe Arg Ser Asn His Leu Glu Glu
        275                 280                 285

Ile Ala Thr Gln Leu Gly Phe Val Leu Lys Leu Arg Asp Arg Pro Ser
        290                 295                 300

Glu Gly Gly Ile Val Glu Arg Pro Phe Lys Thr Leu Asn Gln Ser Leu
305                 310                 315                 320

Phe Ser Thr Leu Pro Gly Tyr Thr Gly Ser Asn Val Gln Glu Arg Pro
                325                 330                 335

Glu Asp Ala Glu Lys Asp Ala Gln Leu Thr Leu Gln Glu Leu Glu Arg
                340                 345                 350

Leu Ile Val Arg Phe Ile Val Asp Lys Tyr Asn Gln Ser Ile Asp Ala
                355                 360                 365

Arg Met Gly Asp Gln Thr Arg Phe Gln Arg Trp Glu Ala Gly Leu Arg
        370                 375                 380

Ala Ile Pro Glu Val Met Ser Glu Arg Asp Leu Asp Ile Cys Leu Met
385                 390                 395                 400

Lys Gln Ala Arg Arg Gln Val Gln Arg Gly Gly Tyr Leu Leu Phe Glu
                405                 410                 415

Asn Ile His Tyr Lys Gly Glu Tyr Leu Glu Gly Phe Ala Gly Lys Thr
                420                 425                 430

Val Ser Leu Arg Tyr Asp Pro Arg Asp Ile Thr Thr Ile Trp Val Tyr
        435                 440                 445

Gln His Ser Arg Gly Gln Glu Glu Phe Leu Thr Arg Ala Tyr Ala Gln
        450                 455                 460

Gly Leu Glu Thr Glu Ser Leu Ser Leu Ala Asp Ala Lys Ala Ser Ala
465                 470                 475                 480

Lys Arg Leu Arg Glu Lys Glu Lys Asn Ile Ser Asn Glu Ala Ile Leu
                485                 490                 495

Gln Glu Val Ile Asp Arg Glu Val Thr Ile Lys Asn Lys Ser Arg Lys
                500                 505                 510

Gln Arg Gln Lys Glu Glu Gln Ser Tyr Lys Lys Thr Pro Ser Leu Pro
        515                 520                 525

Val Ile Glu Lys Glu Gln Gly Ser Phe Glu Gln Val Glu Glu Ile Leu
        530                 535                 540

Leu Asp Thr Asp Asp Asp Phe Glu Val Trp Asp Leu Asp Glu Met Lys
545                 550                 555                 560

Asp Asp Tyr Gly Trp
                565

<210> SEQ ID NO 56
<211> LENGTH: 618
<212> TYPE: PRT
<213> ORGANISM: Nostoc sp.

<400> SEQUENCE: 56

Met Pro Asp Lys Glu Phe Gly Leu Thr Gly Glu Leu Thr Gln Ile Thr
1               5                   10                  15

Glu Ala Ile Phe Leu Ser Glu Ser Asn Phe Val Val Asp Pro Leu His
            20                  25                  30

Ile Ile Leu Glu Ser Ser Asp Ser Gln Lys Leu Lys Phe Asn Leu Ile
        35                  40                  45

```
Gln Trp Leu Ala Glu Ser Pro Asn Arg Gln Ile Lys Ser Gln Arg Lys
 50                  55                  60

Gln Ala Val Ala Asp Thr Leu Gly Val Ser Thr Arg Gln Val Glu Arg
 65                  70                  75                  80

Leu Leu Lys Glu Tyr Asn Gly Asp Arg Leu Asn Glu Thr Ala Gly Val
                 85                  90                  95

Gln Arg Cys Asp Lys Gly Lys His Arg Val Ser Glu Tyr Trp Gln Gln
                100                 105                 110

Tyr Ile Lys Thr Ile Tyr Glu Asn Ser Leu Lys Glu Lys His Pro Met
            115                 120                 125

Ser Pro Ala Ser Val Val Arg Glu Val Lys Arg His Ala Ile Val Asp
130                 135                 140

Leu Gly Leu Glu His Gly Asp Tyr Pro His Pro Ala Thr Val Tyr Arg
145                 150                 155                 160

Ile Leu Asn Pro Leu Ile Glu Gln Gln Lys Arg Lys Lys Lys Ile Arg
                165                 170                 175

Asn Pro Gly Ser Gly Ser Trp Leu Thr Val Glu Thr Arg Asp Gly Lys
            180                 185                 190

Gln Leu Lys Ala Glu Phe Ser Asn Gln Ile Ile Gln Cys Asp His Thr
        195                 200                 205

Glu Leu Asp Ile Arg Ile Val Asp Ser Asn Gly Val Leu Leu Pro Glu
210                 215                 220

Arg Pro Trp Leu Thr Thr Val Asp Thr Phe Ser Ser Cys Val Leu
225                 230                 235                 240

Gly Phe His Leu Trp Ile Lys Gln Pro Gly Ser Ala Glu Val Ala Leu
                245                 250                 255

Ala Leu Arg His Ser Ile Leu Pro Lys Gln Tyr Pro His Asp Tyr Glu
            260                 265                 270

Leu Ser Lys Pro Trp Gly Tyr Gly Pro Pro Phe Gln Tyr Phe Phe Thr
        275                 280                 285

Asp Gly Gly Lys Asp Phe Arg Ser Lys His Leu Lys Ala Ile Gly Lys
290                 295                 300

Lys Leu Arg Phe Gln Cys Glu Leu Arg Asp Arg Pro Asn Gln Gly Gly
305                 310                 315                 320

Ile Val Glu Arg Ile Phe Lys Thr Ile Asn Thr Gln Val Leu Lys Asp
                325                 330                 335

Leu Pro Gly Tyr Thr Gly Ser Asn Val Gln Glu Arg Pro Glu Asn Ala
            340                 345                 350

Glu Lys Glu Ala Cys Leu Gly Ile Gln Asp Ile Asp Lys Ile Leu Ala
        355                 360                 365

Ser Phe Phe Cys Asp Ile Tyr Asn His Glu Pro Tyr Pro Lys Asp Pro
370                 375                 380

Arg Glu Thr Arg Phe Glu Arg Trp Phe Lys Gly Met Gly Gly Lys Leu
385                 390                 395                 400

Pro Glu Pro Leu Asp Glu Arg Glu Leu Asp Ile Cys Leu Met Lys Glu
                405                 410                 415

Thr Gln Arg Val Val Gln Ala His Gly Ser Ile Gln Phe Glu Asn Leu
            420                 425                 430

Ile Tyr Arg Gly Glu Ser Leu Arg Ala Tyr Lys Gly Glu Tyr Val Thr
        435                 440                 445

Leu Arg Tyr Asp Pro Asp His Ile Leu Thr Leu Tyr Val Tyr Ser Cys
450                 455                 460
```

```
Asp Ala Asn Asp Asp Ile Gly Asp Phe Leu Gly Tyr Val His Ala Val
465                 470                 475                 480

Asn Met Asp Thr Gln Glu Leu Ser Ile Glu Glu Leu Lys Ser Leu Asn
            485                 490                 495

Lys Glu Arg Ser Lys Ala Arg Arg Glu His Ser Asn Tyr Asp Ala Leu
        500                 505                 510

Leu Ala Leu Gly Lys Arg Lys Glu Leu Val Lys Glu Arg Lys Gln Glu
            515                 520                 525

Lys Lys Glu Arg Arg Gln Ala Glu Gln Lys Arg Leu Arg Ser Gly Ser
530                 535                 540

Lys Lys Asn Ser Asn Val Val Glu Leu Arg Lys Ser Arg Ala Lys Asn
545                 550                 555                 560

Tyr Val Lys Asn Asp Asp Pro Ile Glu Val Leu Pro Glu Arg Val Ser
                565                 570                 575

Arg Glu Glu Ile Gln Val Pro Lys Thr Glu Val Gln Ile Glu Val Ser
            580                 585                 590

Glu Gln Ala Asp Asn Leu Lys Gln Glu Arg His Gln Leu Val Ile Ser
        595                 600                 605

Arg Arg Lys Gln Asn Leu Lys Asn Ile Trp
    610                 615

<210> SEQ ID NO 57
<211> LENGTH: 558
<212> TYPE: PRT
<213> ORGANISM: Cyanothece sp.

<400> SEQUENCE: 57

Met Asn Thr Phe Pro Asn Glu Gln Ser Asn Ala Ile Val Leu Lys Asn
1               5                   10                  15

Thr Ile Val Ser Asp Leu Pro Glu Thr Ala Arg Thr Lys Met Glu Val
            20                  25                  30

Ile Gln Thr Leu Leu Glu Pro Cys Asp Arg Ile Thr Tyr Gly Glu Arg
        35                  40                  45

Leu Arg Glu Gly Ala Lys Lys Leu Gly Val Ser Val Arg Thr Val Gln
50                  55                  60

Arg Leu Phe Lys Gln Tyr Gln Glu Gln Gly Leu Ala Ala Leu Val Ser
65                  70                  75                  80

Thr Glu Arg Ser Asp Lys Gly Lys His Arg Ile Asn Glu Phe Trp Gln
                85                  90                  95

Asp Phe Ile Val Lys Thr Tyr Gln Gln Gly Asn Lys Gly Ser Lys Arg
            100                 105                 110

Met Thr Pro Lys Gln Val Ala Leu Lys Val Gln Ala Lys Ala Leu Glu
        115                 120                 125

Ile Gly Asp Glu Gln Pro Pro Thr Tyr Arg Thr Val Leu Arg Val Leu
130                 135                 140

Lys Pro Ile Gln Glu Lys Gln Glu Lys Thr Lys Ser Ile Arg Ser Pro
145                 150                 155                 160

Gly Trp Arg Gly Ser Thr Leu Ser Val Lys Thr Arg Asp Gly Asp Asp
                165                 170                 175

Leu Glu Ile Asn Tyr Ser Asn Gln Val Trp Gln Cys Asp His Thr Arg
            180                 185                 190

Ala Asp Val Leu Leu Val Asp Arg His Gly Glu Leu Ile Gly Arg Pro
        195                 200                 205

Trp Leu Thr Thr Val Ile Asp Ser Tyr Ser Arg Cys Ile Met Gly Ile
210                 215                 220
```

```
Asn Leu Gly Phe Asp Ala Pro Ser Ser Gln Val Val Ala Leu Ala Leu
225                 230                 235                 240

Arg His Ala Ile Leu Pro Lys Arg Tyr Gly Asp Glu Tyr Lys Leu His
                245                 250                 255

Cys Glu Trp Glu Thr Ser Gly Thr Pro Glu Tyr Phe Tyr Thr Asp Gly
            260                 265                 270

Gly Lys Asp Phe Arg Ser Asn His Leu Ala Gln Ile Gly Ser Gln Leu
        275                 280                 285

Gly Phe Val His Lys Leu Arg Asp Arg Pro Ser Glu Gly Gly Ile Val
    290                 295                 300

Glu Arg Pro Phe Lys Thr Leu Asn Gln Ser Leu Phe Ser Thr Leu Pro
305                 310                 315                 320

Gly Tyr Thr Gly Ser Asn Val Gln Glu Arg Pro Lys Glu Ala Glu Lys
                325                 330                 335

Glu Ala Ser Leu Thr Leu Arg Glu Leu Glu Gln Leu Ile Val Arg Phe
            340                 345                 350

Ile Val Asp Lys Tyr Asn Gln Ser Ile Asp Ala Arg Met Gly Asp Gln
        355                 360                 365

Thr Arg Tyr Gln Arg Trp Glu Ala Gly Leu Arg Arg Gln Pro Glu Pro
    370                 375                 380

Ile Ser Glu Arg Glu Leu Asp Ile Cys Leu Met Lys Ala Ala Arg Arg
385                 390                 395                 400

Thr Val Gln Arg Gly Gly Tyr Leu Gln Phe Glu Asn Val Met Tyr Arg
                405                 410                 415

Gly Glu Tyr Leu Glu Gly Tyr Ala Gly Asp Thr Val Ile Leu Arg Tyr
            420                 425                 430

Glu Pro Arg Asp Ile Thr Thr Ile Trp Val Tyr Arg Gln Lys Lys His
        435                 440                 445

Gln Glu Val Phe Leu Thr Arg Ala His Ala Gln Asp Leu Glu Thr Glu
    450                 455                 460

Gln Leu Ser Val Asp Glu Ala Lys Ala Ser Ala Lys Lys Leu Arg Asp
465                 470                 475                 480

Ala Gly Lys Thr Ile Ser Asn Gln Ser Ile Leu Gln Glu Val Ile Glu
                485                 490                 495

Arg Glu Ala Leu Val Glu Lys Lys Ser Arg Lys Gln Arg Gln Lys Ala
            500                 505                 510

Glu Gln Ala Tyr Lys Gln Glu Lys Gln Pro Ser Ile Ile Glu Thr Val
        515                 520                 525

Glu Pro Ile Glu Pro Glu Pro Leu Thr Gln Thr Glu Val Asp Asp Ile
    530                 535                 540

Glu Val Trp Asp Tyr Asp Gln Leu Arg Asp Asp Tyr Gly Trp
545                 550                 555

<210> SEQ ID NO 58
<211> LENGTH: 628
<212> TYPE: PRT
<213> ORGANISM: Calothrix sp.

<400> SEQUENCE: 58

Met Ser Val Phe Ala Leu Met Ala Asp Lys Lys Phe Glu Leu Thr Glu
1               5                   10                  15

Lys Phe Thr Gln Leu Pro Glu Ala Val Phe Leu Gly Glu Asn Asn Phe
                20                  25                  30

Val Ile Asp Pro Ser Gln Ile Ile Leu Glu Thr Ser Asp Lys His Lys
```

```
            35                  40                  45
Leu Thr Phe Asn Leu Met Gln Trp Leu Ala Glu Ser Pro Asn Arg Thr
 50                  55                  60

Ile Lys Ser Gln Arg Lys Gln Ala Ile Ala Ser Thr Leu Gly Val Ser
 65                  70                  75                  80

Thr Arg Gln Val Glu Arg Leu Leu Lys Gln Tyr Asp Glu Asp Arg Leu
                 85                  90                  95

Ser Glu Thr Ser Gly Leu Gln Arg Ser Asp Lys Gly Lys Tyr Arg Val
                100                 105                 110

Ser Asp Tyr Trp Gln Glu Phe Ile Lys Thr Thr Tyr Glu Lys Ser Leu
            115                 120                 125

Lys Asp Lys His Pro Ile Ser Pro Ala Ser Ile Val Arg Glu Val Lys
130                 135                 140

Arg His Ala Ile Val Asp Leu Lys Leu Glu Gln Gly Asn Tyr Pro His
145                 150                 155                 160

Pro Ala Thr Val Tyr Arg Ile Leu Asn Pro Leu Ile Glu Gln Gln Glu
                165                 170                 175

Arg Lys Lys Lys Val Arg Asn Pro Gly Ser Gly Ser Trp Met Thr Val
                180                 185                 190

Glu Thr Arg Asp Gly Lys Gln Leu Lys Val Asp Phe Ser Asn Gln Ile
            195                 200                 205

Ile Gln Cys Asp His Thr Lys Leu Asp Ile Arg Ile Val Asp Ser Asp
210                 215                 220

Gly Ile Leu Leu Thr Glu Arg Pro Trp Leu Thr Thr Val Val Asp Thr
225                 230                 235                 240

Phe Ser Ser Cys Val Asn Gly Phe His Leu Trp Ile Lys Gln Pro Gly
                245                 250                 255

Ser Ala Glu Val Ala Ile Ala Leu Arg His Ala Ile Leu Pro Lys Gln
                260                 265                 270

Tyr Pro Asp Asp Tyr Glu Leu Gly Lys Pro Trp Lys Ile Tyr Gly His
            275                 280                 285

Pro Phe Gln Tyr Phe Phe Thr Asp Gly Gly Lys Asp Phe Arg Ser Lys
290                 295                 300

His Leu Lys Ala Ile Gly Lys Lys Leu Gly Phe Gln Cys Glu Leu Arg
305                 310                 315                 320

Asp Arg Pro Ile Gln Gly Gly Ile Val Glu Arg Ile Phe Asn Thr Ile
                325                 330                 335

Asn Thr Gln Val Leu Lys Asp Leu Pro Gly Tyr Thr Gly Pro Asn Val
                340                 345                 350

Gln Glu Arg Pro Glu Asn Ala Glu Lys Glu Ala Cys Leu Ser Ile His
            355                 360                 365

Asp Leu Asp Lys Ile Leu Ala Ser Phe Phe Cys Asp Ile Tyr Asn His
370                 375                 380

Glu Pro Tyr Pro Lys Asp Thr Arg Ile Thr Arg Phe Glu Arg Trp Phe
385                 390                 395                 400

Lys Gly Met Gly Glu Lys Leu Pro Glu Pro Leu Asn Glu Arg Glu Leu
                405                 410                 415

Asp Ile Cys Leu Met Lys Glu Ala Gln Arg Val Val Gln Ala His Gly
                420                 425                 430

Ser Ile Gln Phe Glu Asn Leu Val Tyr Arg Gly Glu Ser Leu Asn Ala
            435                 440                 445

His Lys Gly Glu Tyr Val Thr Leu Arg Tyr Asp Pro Asp His Ile Leu
450                 455                 460
```

Thr Leu Tyr Val Tyr Ser Tyr Asp Val Asn Asp Glu Leu Glu Asn Phe
465                 470                 475                 480

Leu Gly Tyr Val His Ala Ile Asn Met Asp Thr Gln Asp Leu Ser Leu
                485                 490                 495

Glu Glu Leu Lys Ser Leu Asn Lys Glu Arg Ser Lys Ala Arg Arg Glu
            500                 505                 510

His Ser Asn Tyr Asp Ala Leu Leu Ala Leu Ser Lys Arg Lys Glu Leu
                515                 520                 525

Val Glu Glu Arg Lys Gln Gly Lys Glu Lys Arg Gln Ala Glu Gln
    530                 535                 540

Lys Arg Leu Arg Ala Ala Ser Lys Asn Ser Asn Val Val Glu Leu
545                 550                 555                 560

Arg Gln Asn Arg Ala Ser Ser Ser Asn Lys Asp Glu Lys Asp Glu
                565                 570                 575

Lys Ile Glu Leu Leu Pro Glu Arg Val Ser Arg Glu Glu Leu Lys Val
            580                 585                 590

Glu Lys Ile Glu Pro Gln Leu Glu Ile Leu Asp Lys Ala Glu Thr Pro
            595                 600                 605

Pro Gln Glu Arg His Lys Leu Val Ile Ser Ser Arg Lys Gln His Leu
    610                 615                 620

Lys Lys Ile Trp
625

<210> SEQ ID NO 59
<211> LENGTH: 555
<212> TYPE: PRT
<213> ORGANISM: Anabaena cylindrica

<400> SEQUENCE: 59

Met Lys Glu Ser Gln Val Ala Ile Gln Thr Leu Asp Ile Asp His Leu
1               5                   10                  15

Gly Ile Val Ala Gly Ile Ile Asp Glu Met Glu Leu Val Glu Glu Val
            20                  25                  30

Asn Lys Ile Val Gly Ile Lys Thr Lys Glu Thr Leu Thr Pro Gly Gln
            35                  40                  45

Val Val Lys Ala Met Ile Leu Asn Gly Leu Gly Phe Leu Ser Ala Pro
50                  55                  60

Leu Tyr Leu Phe Gly Glu Phe Phe Val Gly Lys Ala Thr Glu His Leu
65                  70                  75                  80

Ile Gly Glu Gly Val Leu Pro Glu His Leu Asn Asp Asp Lys Leu Gly
                85                  90                  95

Arg Glu Leu Asp Lys Tyr His Gln Ile Gly Thr Thr Lys Ile Phe Thr
            100                 105                 110

Ala Val Ala Ile Lys Ala Ala His Lys Phe Gln Val Glu Met Asp Ser
        115                 120                 125

Ile His Leu Asp Gly Thr Ser Met Ser Val Gly Glu Tyr Lys Lys
    130                 135                 140

Glu Ile Lys Glu Ile Asp Glu Ile Lys Gln Thr Glu Glu Asn Lys
145                 150                 155                 160

Leu Glu Ile Glu Pro Glu Met Lys Ala Ile Glu Ile Val His Gly Tyr
                165                 170                 175

Ser Arg Asp Lys Arg Pro Asp Leu Lys Gln Phe Ile Ile Asp Met Ile
            180                 185                 190

Val Thr Gly Asp Gly Asp Ile Pro Leu Tyr Leu Lys Val Asp Ser Gly

```
                195                 200                 205
Asn Val Asp Asp Lys Ser Val Phe Val Glu Arg Leu Lys Glu Phe Lys
        210                 215                 220
Lys Gln Trp Thr Phe Glu Gly Ile Ser Val Ala Asp Ser Ala Leu Tyr
225                 230                 235                 240
Thr Ala Glu Asn Leu Ala Ala Met Arg Glu Leu Lys Trp Ile Thr Arg
                245                 250                 255
Val Pro Leu Ser Ile Lys Glu Ala Lys Asn Lys Ile Val Asp Ile Lys
                260                 265                 270
Glu Ala Glu Trp Lys Asp Ser Gln Ile Ser Gly Tyr Lys Ile Ala Ala
                275                 280                 285
Lys Glu Ser Glu Tyr Ala Gly Ile Lys Gln Arg Trp Ile Ile Val Glu
                290                 295                 300
Ser Glu Ile Arg Lys Lys Ser Ile Gln Gln Val Glu Lys Gln Val
305                 310                 315                 320
Lys Lys Gln Glu Ala Lys Ala Lys Ala Leu Ser Lys Leu Ser Arg
                325                 330                 335
Gln Glu Phe Ala Cys Gln Pro Asp Ala Lys Ile Val Ile Glu Lys Leu
                340                 345                 350
Ser Lys Ser Trp Lys Tyr His Gln Ile Lys Glu Ile Glu Tyr Ile Glu
                355                 360                 365
Lys Leu Glu Tyr Lys Thr Ala Gly Arg Pro Ser Lys Leu Thr Glu Pro
                370                 375                 380
Ser Gln Ile Lys Tyr Gln Ile Lys Gly Gln Ile Glu Thr Arg Glu Glu
385                 390                 395                 400
Val Ile Glu Thr Glu Lys Ile Asn Ala Gly Arg Phe Ile Leu Ala Thr
                    405                 410                 415
Asn Val Leu Asp Arg Asn Glu Leu Ser Asp Glu Lys Val Leu Glu Glu
                420                 425                 430
Tyr Lys Ala Gln Gln Ser Asn Glu Arg Gly Phe Arg Phe Leu Lys Asp
                435                 440                 445
Pro Leu Phe Phe Thr Ser Ser Val Phe Val Lys Thr Pro Glu Arg Val
        450                 455                 460
Glu Ala Ile Ala Met Ile Met Gly Leu Cys Leu Leu Val Tyr Asn Leu
465                 470                 475                 480
Ala Gln Arg Lys Leu Arg Gln Glu Leu Ala Lys Phe Asp Asp Gly Ile
                485                 490                 495
Arg Asn Gln Val Lys Lys Ile Thr Asn Lys Pro Thr Met Arg Trp Val
                500                 505                 510
Phe Gln Met Phe Gln Ala Val His Leu Val Ile Asn Gly Gln Lys
                515                 520                 525
Gln Met Ser Asn Leu Thr Glu Arg Glu Lys Ile Val Arg Tyr Leu
        530                 535                 540
Gly Lys Ser Cys Ser Lys Tyr Tyr Leu Ile Thr
545                 550                 555

<210> SEQ ID NO 60
<211> LENGTH: 621
<212> TYPE: PRT
<213> ORGANISM: Anabaena cylindrica

<400> SEQUENCE: 60

Met Ala Asp Glu Glu Phe Glu Phe Glu Thr Glu Gly Thr Thr Gln Val Pro
1               5                   10                  15
```

```
Asp Ala Ile Leu Leu Asp Lys Ser Asn Phe Val Asp Pro Ser Gln
            20                  25                  30

Ile Ile Leu Ala Thr Ser Asp Arg His Lys Leu Thr Phe Asn Leu Ile
        35                  40                  45

Gln Trp Leu Ala Glu Ser Pro Asn Arg Thr Ile Lys Ser Gln Arg Lys
    50                  55                  60

Gln Ala Val Ala Asn Thr Leu Asp Val Ser Thr Arg Gln Val Glu Arg
65                  70                  75                  80

Leu Leu Lys Gln Tyr Asp Glu Asp Lys Leu Arg Glu Thr Ala Gly Ile
                85                  90                  95

Glu Arg Ala Asp Lys Gly Lys Tyr Arg Val Ser Glu Tyr Trp Gln Asn
            100                 105                 110

Phe Ile Thr Thr Ile Tyr Glu Lys Ser Leu Lys Glu Lys His Pro Ile
        115                 120                 125

Ser Pro Ala Ser Ile Val Arg Glu Val Lys Arg His Ala Ile Val Asp
    130                 135                 140

Leu Glu Leu Lys Leu Gly Glu Tyr Pro His Gln Ala Thr Val Tyr Arg
145                 150                 155                 160

Ile Leu Asp Pro Leu Ile Glu Gln Gln Lys Arg Lys Thr Arg Val Arg
                165                 170                 175

Asn Pro Gly Ser Gly Ser Trp Met Thr Val Val Thr Arg Asp Gly Glu
            180                 185                 190

Leu Leu Arg Ala Asp Phe Ser Asn Gln Ile Ile Gln Cys Asp His Thr
        195                 200                 205

Lys Leu Asp Val Arg Ile Val Asp Asn His Gly Asn Leu Leu Ser Asp
210                 215                 220

Arg Pro Trp Leu Thr Thr Ile Val Asp Thr Phe Ser Ser Cys Val Val
225                 230                 235                 240

Gly Phe Arg Leu Trp Ile Lys Gln Pro Gly Ser Thr Glu Val Ala Leu
                245                 250                 255

Ala Leu Arg His Ala Ile Leu Pro Lys Asn Tyr Pro Glu Asp Tyr Gln
            260                 265                 270

Leu Asn Lys Ser Trp Asp Val Cys Gly His Pro Tyr Gln Tyr Phe Phe
        275                 280                 285

Thr Asp Gly Gly Lys Asp Phe Arg Ser Lys His Leu Lys Ala Ile Gly
    290                 295                 300

Lys Lys Leu Gly Phe Gln Cys Glu Leu Arg Asp Arg Pro Glu Gly
305                 310                 315                 320

Gly Ile Val Glu Arg Ile Phe Lys Thr Ile Asn Thr Gln Val Leu Lys
                325                 330                 335

Glu Leu Pro Gly Tyr Thr Gly Ala Asn Val Gln Glu Arg Pro Glu Asn
            340                 345                 350

Ala Glu Lys Glu Ala Cys Leu Thr Ile Gln Asp Leu Asp Lys Ile Leu
        355                 360                 365

Ala Ser Phe Phe Cys Asp Ile Tyr Asn His Glu Pro Tyr Pro Lys Glu
    370                 375                 380

Pro Arg Asp Thr Arg Phe Glu Arg Trp Phe Lys Gly Met Gly Gly Lys
385                 390                 395                 400

Leu Pro Glu Pro Leu Asp Glu Arg Glu Leu Asp Ile Cys Leu Met Lys
                405                 410                 415

Glu Ala Gln Arg Val Val Gln Ala His Gly Ser Ile Gln Phe Glu Asn
            420                 425                 430

Leu Ile Tyr Arg Gly Glu Phe Leu Lys Ala His Lys Gly Glu Tyr Val
```

```
                435                 440                 445
Thr Leu Arg Tyr Asp Pro Asp His Ile Leu Ser Leu Tyr Ile Tyr Ser
450                 455                 460
Gly Glu Thr Asp Asp Asn Ala Gly Glu Phe Leu Gly Tyr Ala His Ala
465                 470                 475                 480
Val Asn Met Asp Thr His Asp Leu Ser Ile Glu Glu Leu Lys Ala Leu
                485                 490                 495
Asn Lys Glu Arg Ser Asn Ala Arg Lys Glu His Phe Asn Tyr Asp Ala
            500                 505                 510
Leu Leu Ala Leu Gly Lys Arg Lys Glu Leu Val Glu Glu Arg Lys Glu
        515                 520                 525
Asp Lys Lys Ala Lys Arg Asn Ser Glu Gln Lys Arg Leu Arg Ser Ala
    530                 535                 540
Ser Lys Lys Asn Ser Asn Val Ile Glu Leu Arg Lys Ser Arg Thr Ser
545                 550                 555                 560
Lys Ser Leu Lys Lys Gln Glu Asn Gln Glu Val Leu Pro Glu Arg Ile
                565                 570                 575
Ser Arg Glu Glu Ile Lys Leu Glu Lys Ile Glu Gln Gln Pro Gln Glu
            580                 585                 590
Asn Leu Ser Ala Ser Pro Asn Thr Gln Glu Glu Arg His Lys Leu
        595                 600                 605
Val Phe Ser Asn Arg Gln Lys Asn Leu Asn Lys Ile Trp
    610                 615                 620

<210> SEQ ID NO 61
<211> LENGTH: 623
<212> TYPE: PRT
<213> ORGANISM: Anabaena sp.

<400> SEQUENCE: 61

Met Ala Asp Arg Glu Ile Glu Phe Thr Glu Glu Ser Thr Gln Asp Ser
1               5                   10                  15
Asp Ala Ile Leu Leu Asp Asn Ser Asn Phe Val Val Asp Pro Ser Gln
            20                  25                  30
Ile Ile Leu Ala Thr Ser Asp Lys His Lys Leu Thr Phe Asn Leu Ile
        35                  40                  45
Gln Trp Leu Ala Gln Ser Pro Thr Arg Thr Val Lys Ser Glu Arg Lys
    50                  55                  60
Gln Ala Ile Ala Asn Thr Leu Ser Val Ser Thr Arg Gln Val Glu Arg
65                  70                  75                  80
Leu Leu Lys Gln Tyr Asn Glu Asp Lys Leu Arg Glu Thr Ala Gly Thr
                85                  90                  95
Glu Arg Ala Asp Lys Gly Lys His Arg Val Ser Glu Tyr Trp Gln Glu
            100                 105                 110
Phe Ile Lys Thr Thr Tyr Glu Lys Ser Leu Lys Asp Lys His Pro Ile
        115                 120                 125
Ser Pro Ala Ser Ile Val Arg Glu Val Lys Arg His Ala Ile Val Asp
    130                 135                 140
Leu Gly Leu Lys Pro Gly Asp Tyr Pro His Gln Ala Thr Val Tyr Arg
145                 150                 155                 160
Ile Leu Glu Pro Leu Ile Ala Gln His Lys Arg Lys Thr Arg Val Arg
                165                 170                 175
Asn Pro Gly Ser Gly Ser Trp Met Thr Val Val Thr Arg Asp Gly Gln
            180                 185                 190
```

-continued

Leu Leu Arg Ala Asp Phe Ser Asn Gln Ile Ile Gln Cys Asp His Thr
            195                 200                 205

Lys Leu Asp Ile Arg Ile Val Asp Ile His Gly Asp Leu Leu Ser Glu
    210                 215                 220

Arg Pro Trp Leu Thr Thr Val Asp Thr Tyr Ser Ser Cys Val Leu
225                 230                 235                 240

Gly Phe Arg Leu Trp Ile Lys Gln Pro Gly Ser Thr Glu Val Ala Leu
                245                 250                 255

Ala Leu Arg His Ala Ile Leu Pro Lys Gln Tyr Pro Asp Asp Tyr Gln
            260                 265                 270

Leu Asn Lys Ser Trp Asn Val Tyr Gly Asn Pro Phe Gln Tyr Phe Phe
        275                 280                 285

Thr Asp Gly Gly Lys Asp Phe Arg Ser Lys His Leu Lys Ala Ile Gly
    290                 295                 300

Lys Lys Leu Gly Phe Gln Cys Glu Leu Arg Asp Arg Pro Pro Glu Gly
305                 310                 315                 320

Gly Ile Val Glu Arg Ile Phe Lys Thr Ile Asn Thr Gln Val Leu Lys
                325                 330                 335

Asp Leu Pro Gly Tyr Thr Gly Ala Asn Val Gln Glu Arg Pro Glu Asn
            340                 345                 350

Ala Glu Lys Glu Ala Cys Leu Thr Ile Gln Asp Leu Asp Lys Ile Leu
        355                 360                 365

Ala Ser Phe Phe Cys Asp Ile Tyr Asn His Glu Pro Tyr Pro Lys Glu
    370                 375                 380

Pro Arg Asp Thr Arg Phe Glu Arg Trp Phe Lys Gly Met Gly Glu Lys
385                 390                 395                 400

Leu Pro Glu Arg Leu Asp Glu Arg Glu Leu Asp Ile Cys Leu Met Lys
                405                 410                 415

Glu Thr Gln Arg Val Val Gln Ala His Gly Ser Ile Gln Phe Glu Asn
            420                 425                 430

Leu Ile Tyr Arg Gly Glu Ser Leu Lys Ala His Lys Gly Glu Tyr Val
        435                 440                 445

Thr Leu Arg Tyr Asp Pro Asp His Ile Leu Thr Leu Phe Val Tyr Ser
    450                 455                 460

Cys Glu Thr Asp Asp Asn Leu Glu Glu Phe Leu Gly Tyr Ala His Ala
465                 470                 475                 480

Val Asn Met Asp Thr His Asp Leu Ser Leu Glu Glu Leu Lys Thr Leu
                485                 490                 495

Asn Lys Glu Arg Ser Lys Ala Arg Lys Glu His Phe Asn Tyr Asp Ala
            500                 505                 510

Leu Leu Ala Leu Gly Lys Arg Lys Glu Leu Val Asp Glu Arg Lys Ala
        515                 520                 525

Asp Lys Lys Glu Lys Arg His Ser Glu Gln Lys Arg Leu Arg Ser Ala
    530                 535                 540

Ser Lys Lys Asp Ser Asn Ile Ile Glu Leu Arg Lys Ser Arg Val Ser
545                 550                 555                 560

Lys Ser Leu Arg Lys Gln Glu Thr Gln Glu Ile Leu Pro Glu Arg Val
                565                 570                 575

Ser Arg Glu Glu Ile Lys Phe Glu Lys Ile Glu Leu Glu Pro Gln Glu
            580                 585                 590

Thr Leu Ser Ala Ser Pro Lys Pro Asn Pro Gln Glu Glu Gln Arg His
        595                 600                 605

Lys Leu Val Leu Ser Lys Arg Gln Lys Asn Leu Lys Asn Ile Trp

-continued

```
              610                 615                 620
```

<210> SEQ ID NO 62
<211> LENGTH: 164
<212> TYPE: PRT
<213> ORGANISM: Alkalinema sp.

<400> SEQUENCE: 62

```
Met Thr Ile Asp Ser Gly Ile Gln Pro Trp Leu Phe Gln Val Glu Pro
1               5                  10                  15

Tyr Glu Gly Glu Ser Leu Ser His Phe Leu Gly Arg Phe Arg Arg Pro
            20                  25                  30

Asn His Leu Thr Pro Ser Gly Leu Gly Gln Leu Ala Gly Ile Gly Ala
        35                  40                  45

Val Val Ala Arg Trp Glu Arg Phe His Trp Asn Pro Pro Pro Ser Arg
    50                  55                  60

Gln Glu Leu Glu Ala Leu Ala Lys Val Val Arg Val Ser Val Glu Gln
65                  70                  75                  80

Leu Ile Ala Met Leu Pro Pro Pro Gly Val Gly Met Gln Cys Ser Pro
                85                  90                  95

Ile Arg Leu Cys Ser Ala Cys Tyr Gly Glu Thr Pro Cys His Arg Met
            100                 105                 110

Glu Trp Gln Tyr Lys His Ile Trp Lys Cys Asn Arg His Ser Leu Lys
        115                 120                 125

Leu Leu Ala Lys Cys Pro Val Cys Ser Ala Leu Phe Lys Ala Pro Ala
    130                 135                 140

Gln Trp Gln Asp Gly Met Cys Arg Arg Cys Leu Thr Pro Phe Gly Gln
145                 150                 155                 160

Met Gln Gln Gln
```

<210> SEQ ID NO 63
<211> LENGTH: 159
<212> TYPE: PRT
<213> ORGANISM: Anabaena sp.

<400> SEQUENCE: 63

```
Met Ile Gln Pro Tyr Glu Gly Glu Ser Leu Ser His Phe Leu Gly Arg
1               5                  10                  15

Phe Arg Arg Ala Asn His Leu Ser Ala Ala Gly Leu Gly Asn Leu Ala
            20                  25                  30

Gly Ile Gly Ala Val Ile Ala Arg Trp Glu Arg Phe His Phe Asn Pro
        35                  40                  45

Arg Pro Ser Gln Lys Glu Leu Glu Ala Ile Ala Ser Val Val Glu Val
    50                  55                  60

Asp Ala Gln Arg Leu Ala Glu Met Leu Pro Pro Ala Gly Val Ser Met
65                  70                  75                  80

Gln His Glu Pro Ile Arg Leu Cys Gly Ala Cys Tyr Ala Glu Thr Pro
                85                  90                  95

Cys His Gln Ile Lys Trp Gln Phe Lys Glu Thr Gly Gly Cys Asp Arg
            100                 105                 110

His Tyr Leu Arg Leu Leu Ser Lys Cys Pro Asn Cys Asp Ala Arg Phe
        115                 120                 125

Lys Ile Pro Ala Leu Trp Glu Leu Gly Val Cys Gln Arg Cys Leu Met
    130                 135                 140

Thr Phe Ala Glu Met Ala Gly Tyr Gln Lys Ser Ile Asn Gly Thr
145                 150                 155
```

<210> SEQ ID NO 64
<211> LENGTH: 170
<212> TYPE: PRT
<213> ORGANISM: Anabaena variabilis

<400> SEQUENCE: 64

Met Pro Glu Glu Ile Tyr Asn Phe Glu Ala Trp Ile Asn Val Val Glu
1               5                   10                  15

Pro Leu Pro Gly Glu Ser Ile Ser His Phe Leu Gly Arg Phe Glu Arg
            20                  25                  30

Ala Asn Leu Leu Thr Gly Tyr Gln Val Gly Arg Glu Val Gly Val Gly
        35                  40                  45

Ala Ile Val Thr Arg Trp Lys Lys Leu Tyr Leu Asn Pro Phe Pro Thr
    50                  55                  60

Leu Gln Glu Leu Glu Ala Leu Ala Arg Phe Val Glu Val Glu Val Glu
65                  70                  75                  80

Lys Leu Lys Glu Met Leu Pro Ser Gln Gly Met Thr Met Lys Pro Arg
                85                  90                  95

Pro Ile Lys Ile Cys Ala Ala Cys Tyr Ala Glu Val Pro Cys His Arg
            100                 105                 110

Ile Glu Trp Gln Tyr Lys Asp Asn Met Lys Cys Asp Arg His Asn Leu
        115                 120                 125

Arg Leu Leu Thr Lys Cys Thr Asn Cys Glu Thr Pro Phe Pro Ile Pro
    130                 135                 140

Ala Asp Trp Leu Gln Gly Glu Cys Pro Arg Cys Phe Leu Pro Phe Ala
145                 150                 155                 160

Lys Met Ala Lys Arg Gln Lys Leu Asn Ser
                165                 170

<210> SEQ ID NO 65
<211> LENGTH: 173
<212> TYPE: PRT
<213> ORGANISM: Anabaena variabilis

<400> SEQUENCE: 65

Met Arg Glu Ser Ile Asn Glu Asn Lys Gln Phe Trp Leu Ile Arg Val
1               5                   10                  15

Glu Pro Leu Glu Gly Ser Ile Ser His Phe Leu Gly Arg Phe Arg
            20                  25                  30

Arg Glu Lys Gly Asn Lys Phe Ser Ala Pro Ser Gly Leu Gly Asp Val
        35                  40                  45

Ala Gly Leu Gly Ala Val Leu Ala Arg Trp Glu Lys Phe Tyr Phe Asn
    50                  55                  60

Pro Phe Pro Thr His Gln Glu Leu Glu Ala Leu Ala Ser Val Val Gln
65                  70                  75                  80

Val Asp Val Asp Arg Leu Arg Gln Met Leu Pro Pro Leu Gly Val Ser
                85                  90                  95

Met Lys His Ser Pro Ile Arg Leu Cys Gly Ala Cys Tyr Ala Glu Ser
            100                 105                 110

Pro Cys His Lys Ile Glu Trp Gln Phe Lys Thr Val Gly Cys Asp
        115                 120                 125

Arg His Gln Leu Arg Leu Leu Ser Lys Cys Pro Val Cys Glu Lys Pro
    130                 135                 140

Phe Pro Val Pro Ala Leu Trp Val Asp Gly Ile Cys Asn Arg Cys Phe
145                 150                 155                 160

Thr Pro Phe Ala Glu Met Ala Gln Tyr Gln Lys His Tyr
            165                 170

<210> SEQ ID NO 66
<211> LENGTH: 167
<212> TYPE: PRT
<213> ORGANISM: Anabaena variabilis

<400> SEQUENCE: 66

Met Glu Val Pro Gln Ile Gln Pro Trp Leu Phe Gln Ile Glu Pro Leu
1               5                   10                  15

Glu Gly Glu Ser Leu Ser His Phe Leu Gly Arg Phe Arg Arg Ala Asn
            20                  25                  30

Asp Leu Thr Pro Thr Gly Leu Gly Lys Ala Ala Gly Leu Gly Gly Ala
        35                  40                  45

Ile Ala Arg Trp Glu Lys Phe Arg Phe Asn Pro Pro Ser Arg Gln
    50                  55                  60

Gln Leu Glu Ala Leu Ala Asn Val Val Gly Val Asp Ala Asp Arg Leu
65                  70                  75                  80

Ala Gln Met Leu Pro Ser Ala Gly Val Gly Met Lys Met Glu Pro Ile
                85                  90                  95

Arg Leu Cys Ala Ala Cys Tyr Ala Glu Ser Pro Cys His Lys Ile Glu
            100                 105                 110

Trp Gln Phe Lys Val Thr Arg Gly Cys Ala Arg His Lys Ile Thr Leu
        115                 120                 125

Leu Ser Glu Cys Pro Asn Cys Lys Ala Arg Phe Lys Val Pro Ala Leu
130                 135                 140

Trp Val Asp Gly Trp Cys Asn Arg Cys Phe Leu Arg Phe Glu Glu Met
145                 150                 155                 160

Ala Lys Tyr Gln Lys Gly Leu
                165

<210> SEQ ID NO 67
<211> LENGTH: 165
<212> TYPE: PRT
<213> ORGANISM: Aphanocapsa montana

<400> SEQUENCE: 67

Met Val Ile Pro Gln Ile Pro Ala Trp Val Phe Pro Val Glu Pro Ser
1               5                   10                  15

Pro Gly Glu Ser Leu Ser His Phe Leu Gly Arg Phe Cys Arg Glu Asn
            20                  25                  30

His Thr Thr Leu Asn Gln Leu Gly Glu Lys Thr Gly Leu Gly Ala Val
        35                  40                  45

Leu Gly Arg Trp Glu Lys Phe Arg Phe Ile Pro Gln Pro Ser Asp Ala
    50                  55                  60

Gln Leu Ala Ala Leu Ala Lys Leu Val Arg Leu Glu Val Asp Gln Ile
65                  70                  75                  80

Lys Gln Met Leu Pro Gln Glu Thr Met Gln Asn Arg Val Ile Arg Leu
                85                  90                  95

Cys Ala Ala Cys Tyr Ala Glu Glu Pro Tyr His Arg Ile Glu Trp Gln
            100                 105                 110

Tyr Lys Leu Ala Asn Arg Cys Asp Arg His His Leu Leu Leu Leu Leu
        115                 120                 125

Glu Cys Pro Asn Cys Lys Ala Lys Leu Pro Met Pro Ser Lys Trp Ala
130                 135                 140

```
Asn Gly Thr Cys Lys Arg Cys Leu Thr Pro Phe Glu Gln Met Ala Asp
145                 150                 155                 160

Leu Gln Lys Gly Ile
            165

<210> SEQ ID NO 68
<211> LENGTH: 163
<212> TYPE: PRT
<213> ORGANISM: Calothrix sp.

<400> SEQUENCE: 68

Met Asn Glu Pro Arg Phe Phe Glu Ile Glu Pro Phe Glu Cys Glu Ser
1               5                   10                  15

Leu Ser His Phe Leu Gly Arg Phe Arg Arg Glu Asn Tyr Leu Thr Ala
            20                  25                  30

Thr Gln Leu Gly Lys Leu Thr Gly Leu Gly Ala Val Ile Ser Arg Trp
        35                  40                  45

Glu Asn Cys Tyr Phe Asn Pro Phe Pro Thr Gln Gln Glu Leu Glu Ala
    50                  55                  60

Leu Ala Ser Val Val Gly Ala Glu Val Glu Lys Leu Arg Glu Met Leu
65                  70                  75                  80

Pro Pro Ile Gly Val Thr Met Lys Pro Arg Pro Ile Arg Leu Cys Ala
                85                  90                  95

Ala Cys Tyr Ala Glu Ser Pro Tyr His His Ile Glu Trp Gln Phe Lys
            100                 105                 110

Asp Val Met Lys Cys Ser Tyr His Gln Met Arg Leu Leu Thr Lys Cys
            115                 120                 125

Thr Asn Cys Gly Ala Val Phe Pro Ile Pro Ala Asp Trp Val Thr Gly
        130                 135                 140

Glu Cys Pro His Cys Cys Leu Pro Phe Val Thr Met Val Arg Lys Gln
145                 150                 155                 160

Gln Lys Gly

<210> SEQ ID NO 69
<211> LENGTH: 167
<212> TYPE: PRT
<213> ORGANISM: Cyanothece sp.

<400> SEQUENCE: 69

Met Asp Lys Glu Tyr Trp Leu Thr Lys Val Glu Pro Tyr Glu Gly Glu
1               5                   10                  15

Ser Ile Ser His Phe Leu Gly Arg Phe Arg Arg Thr Lys Gly Asn Arg
            20                  25                  30

Phe Ser Ala Ala Ser Gly Leu Gly Gln Val Ala Gly Leu Gly Ala Ile
            35                  40                  45

Leu Ala Arg Trp Glu Lys Leu Tyr Phe Asn Pro Phe Pro Asn Glu Gln
50                  55                  60

Glu Leu Glu Ala Leu Gly Lys Val Val Met Leu Asp Val Glu Asp Leu
65                  70                  75                  80

Arg Lys Met Leu Pro Gln Lys Gly Met Val Thr Gln Pro Lys Pro Ile
                85                  90                  95

Met Leu Cys Ala Val Cys Tyr Gly Glu Lys Pro Tyr His Arg Met Val
            100                 105                 110

Trp Gln Asp Lys His Gln Arg Gly Cys Glu Val His Gly Leu Glu Leu
            115                 120                 125
```

Leu Ser Arg Cys Ile Asn Cys Lys Arg Leu Phe Pro Ile Pro Ser Lys
130                 135                 140

Trp Glu Glu Gly Lys Cys Leu Leu Cys Gly Leu Ala Phe Ala Lys Ile
145                 150                 155                 160

Ala Lys His Gln Lys Pro Ile
                165

<210> SEQ ID NO 70
<211> LENGTH: 160
<212> TYPE: PRT
<213> ORGANISM: Geminocystis sp.

<400> SEQUENCE: 70

Met Asp Leu Gln Ile Gln Asn Trp Leu Phe Ile Leu Val Pro Tyr Glu
1               5                   10                  15

Gly Glu Ser Ile Ser His Phe Leu Gly Arg Phe Arg Arg Ala Asn Ser
                20                  25                  30

Leu Ser Cys Gly Gly Leu Gly Gln Ala Thr Gly Leu Tyr Ser Ala Ile
            35                  40                  45

Ala Arg Trp Glu Lys Phe Arg Phe Asn Pro Pro Ser Leu Lys Gln
50                  55                  60

Leu Glu Lys Leu Ser Glu Ile Val Gln Val Glu Met Ala Thr Leu Gln
65                  70                  75                  80

Thr Met Phe Pro Ser Ala Pro Met Lys Met Thr Pro Ile Arg Ile Cys
                85                  90                  95

Ser Ala Cys Tyr Gly Glu Asn Pro Tyr His Gln Met Ser Trp Gln Tyr
            100                 105                 110

Lys Glu Ile Tyr Arg Cys Asp Arg His Asn Leu Asn Ile Leu Ser Glu
        115                 120                 125

Cys Pro Asn Cys Ala Ala Arg Phe Lys Phe Pro Asn Leu Trp Phe Glu
    130                 135                 140

Gly Phe Cys His Arg Cys Phe Thr Pro Phe Glu Gln Met Pro Gln Ser
145                 150                 155                 160

<210> SEQ ID NO 71
<211> LENGTH: 172
<212> TYPE: PRT
<213> ORGANISM: Leptolyngbya boryana

<400> SEQUENCE: 71

Met Ile Glu His Ser Glu Ile Gln Pro Trp Phe Phe His Val Glu Ala
1               5                   10                  15

Leu Glu Gly Glu Ser Ile Ser His Phe Leu Gly Arg Phe Arg Gln Ala
                20                  25                  30

Asn Glu Leu Thr Pro Ser Gly Val Gly Lys Ile Ser Gly Leu Gly Gly
            35                  40                  45

Ala Ile Ala Arg Trp Glu Lys Phe Arg Phe Asn Pro Tyr Pro Thr Gln
50                  55                  60

Gln Gln Phe Glu Lys Leu Ser Thr Ala Thr Gly Ile Ser Val Glu Gln
65                  70                  75                  80

Leu Trp Lys Met Met Pro Pro Glu Gly Val Gly Met Gln Leu Glu Pro
                85                  90                  95

Ile Arg Leu Cys Ala Ser Cys Tyr Ala Glu Leu Pro Cys His Gln Ile
            100                 105                 110

Gln Trp Gln Phe Lys Asp Thr Gln Gly Cys Glu Val His Gly Leu Arg
        115                 120                 125

Leu Leu Ser Glu Cys Pro Asn Cys Lys Ala Arg Phe Lys Pro Pro Ala
            130                 135                 140

Thr Trp Ser Asp Ser Lys Cys His Arg Cys Phe Met Leu Phe Ser Glu
145                 150                 155                 160

Met Arg Asn Arg Gln Lys Arg His Ser Phe Ser Arg
                165                 170

<210> SEQ ID NO 72
<211> LENGTH: 171
<212> TYPE: PRT
<213> ORGANISM: Leptolyngbya boryana

<400> SEQUENCE: 72

Met Glu His Ser Glu Ile Gln Pro Trp Phe His Val Glu Ala Leu
1               5                   10                  15

Glu Gly Glu Ser Ile Ser His Phe Leu Gly Arg Phe Arg Gln Ala Asn
            20                  25                  30

Glu Leu Thr Pro Ser Gly Val Gly Lys Ile Ser Gly Leu Gly Gly Ala
        35                  40                  45

Ile Ala Arg Trp Glu Lys Phe Arg Phe Asn Pro Tyr Pro Thr Gln Gln
50                  55                  60

Gln Phe Glu Lys Leu Ser Thr Ala Thr Gly Ile Ser Val Glu Gln Leu
65                  70                  75                  80

Trp Lys Met Met Pro Pro Glu Gly Val Gly Met Gln Leu Glu Pro Ile
                85                  90                  95

Arg Leu Cys Ala Ser Cys Tyr Ala Glu Leu Pro Cys His Gln Ile Gln
            100                 105                 110

Trp Gln Phe Lys Asp Thr Gln Gly Cys Glu Val His Gly Leu Arg Leu
        115                 120                 125

Leu Ser Glu Cys Pro Asn Cys Lys Ala Arg Phe Lys Pro Pro Ala Thr
130                 135                 140

Trp Ser Asp Ser Lys Cys His Arg Cys Phe Met Leu Phe Ser Glu Met
145                 150                 155                 160

Arg Asn Arg Gln Lys Arg His Ser Phe Ser Arg
                165                 170

<210> SEQ ID NO 73
<211> LENGTH: 140
<212> TYPE: PRT
<213> ORGANISM: Myxosarcina sp.

<400> SEQUENCE: 73

Met Asn Asn Thr Lys Glu Ala Gln Leu Trp Leu Phe Pro Val Glu Pro
1               5                   10                  15

Ser Asn Gly Glu Ser Leu Ser His Phe Leu Gly Arg Phe Arg Arg Ser
            20                  25                  30

Asn His Leu Ser Pro Ser Ala Leu Gly Asp Leu Ala Gly Ile Gly Gly
        35                  40                  45

Val Val Ala Arg Trp Glu Arg Phe His Leu Asn Phe Pro Thr Asp
50                  55                  60

Glu Gln Phe Gln Ala Leu Ala Glu Val Val Asp Val Asp Ser Ser Thr
65                  70                  75                  80

Leu Arg Glu Met Leu Pro Pro Lys Gly Thr Gly Met Lys Cys Asp Arg
                85                  90                  95

His Asn Leu Lys Leu Ile Ser Lys Cys Pro Asn Cys Arg Ala Lys Phe
            100                 105                 110

```
Lys Met Pro Ala Leu Trp Glu Tyr Gly Cys Cys His Arg Cys Arg Leu
        115                 120                 125

Pro Phe Ala Ala Ile Ala Gln Tyr Gln Gln Ser Val
    130                 135                 140

<210> SEQ ID NO 74
<211> LENGTH: 166
<212> TYPE: PRT
<213> ORGANISM: Nostoc punctiforme

<400> SEQUENCE: 74

Met Thr Thr Pro Asp Val Lys Pro Trp Leu Phe Ile Ile Glu Pro Tyr
1               5                   10                  15

Pro Gly Glu Ser Leu Ser His Phe Leu Gly Arg Phe Arg Arg Ala Asn
            20                  25                  30

His Leu Ser Pro Ala Gly Leu Gly Gly Leu Ala Gly Ile Gly Ala Val
        35                  40                  45

Val Ala Arg Trp Glu Arg Phe His Phe Asn Pro Arg Pro Ser Gln Lys
50                  55                  60

Glu Leu Glu Ala Ile Ala Ser Val Val Glu Val Asp Ala Gln Arg Leu
65                  70                  75                  80

Ala Gln Met Leu Pro Pro Ala Gly Val Gly Met Gln His Glu Pro Ile
                85                  90                  95

Arg Leu Cys Gly Ala Cys Tyr Ala Glu Ala Pro Cys His Arg Ile Glu
            100                 105                 110

Trp Gln Tyr Lys Ser Val Trp Lys Cys Asp Arg His Gln Leu Lys Ile
        115                 120                 125

Leu Ala Lys Cys Pro Asn Cys Gln Ala Pro Phe Lys Met Pro Ala Leu
    130                 135                 140

Trp Glu Asp Gly Cys Cys His Arg Cys Arg Thr Leu Phe Ala Glu Met
145                 150                 155                 160

Ala Lys Gln Gln Lys Ser
                165

<210> SEQ ID NO 75
<211> LENGTH: 168
<212> TYPE: PRT
<213> ORGANISM: Nostoc sp.

<400> SEQUENCE: 75

Met Met Ala Ala Pro Asp Val Lys Pro Trp Leu Phe Ile Ile Gln Pro
1               5                   10                  15

Tyr Glu Gly Glu Ser Leu Ser His Phe Leu Gly Arg Phe Arg Arg Ala
            20                  25                  30

Asn His Leu Ser Ala Ser Gly Leu Gly Lys Leu Ala Gly Ile Gly Ala
        35                  40                  45

Val Val Ala Arg Trp Glu Arg Phe His Phe Asn Pro Arg Pro Ser Gln
    50                  55                  60

Lys Glu Leu Glu Ala Ile Ala Ser Leu Val Glu Val Asp Ala Asp Arg
65                  70                  75                  80

Leu Ala Gln Met Leu Pro Pro Leu Gly Val Gly Met Gln His Glu Pro
                85                  90                  95

Ile Arg Leu Cys Gly Ala Cys Tyr Ala Glu Ala Pro Cys His Arg Ile
            100                 105                 110

Glu Trp Gln Tyr Lys Ser Val Trp Lys Cys Asp Arg His Glu Leu Lys
        115                 120                 125
```

```
Ile Leu Ala Lys Cys Pro Asn Cys Glu Ala Pro Phe Lys Ile Pro Ala
            130                 135                 140

Leu Trp Glu Asp Lys Cys Cys His Arg Cys Arg Thr Pro Phe Ala Glu
145                 150                 155                 160

Met Thr Lys Tyr Gln Lys Ile Thr
                165

<210> SEQ ID NO 76
<211> LENGTH: 167
<212> TYPE: PRT
<213> ORGANISM: Nostoc sp.

<400> SEQUENCE: 76

Met Ala Ala Pro Asp Val Lys Pro Trp Leu Phe Ile Ile Gln Pro Tyr
1               5                   10                  15

Glu Gly Glu Ser Leu Ser His Phe Leu Gly Arg Phe Arg Arg Ala Asn
            20                  25                  30

His Leu Ser Ala Ser Gly Leu Gly Lys Leu Ala Gly Ile Gly Ala Val
        35                  40                  45

Val Ala Arg Trp Glu Arg Phe His Phe Asn Pro Arg Pro Ser Gln Lys
50                  55                  60

Glu Leu Glu Ala Ile Ala Ser Leu Val Glu Val Asp Ala Asp Arg Leu
65                  70                  75                  80

Ala Gln Met Leu Pro Pro Leu Gly Val Gly Met Gln His Glu Pro Ile
                85                  90                  95

Arg Leu Cys Gly Ala Cys Tyr Ala Glu Ala Pro Cys His Arg Ile Glu
            100                 105                 110

Trp Gln Tyr Lys Ser Val Trp Lys Cys Asp Arg His Glu Leu Lys Ile
        115                 120                 125

Leu Ala Lys Cys Pro Asn Cys Glu Ala Pro Phe Lys Ile Pro Ala Leu
    130                 135                 140

Trp Glu Asp Lys Cys Cys His Arg Cys Arg Thr Pro Phe Ala Glu Met
145                 150                 155                 160

Thr Lys Tyr Gln Lys Ile Thr
                165

<210> SEQ ID NO 77
<211> LENGTH: 173
<212> TYPE: PRT
<213> ORGANISM: Nostoc sp.

<400> SEQUENCE: 77

Met Glu Glu Asn Ile Asp Glu Lys Arg Gln Ile Trp Leu Thr Arg Val
1               5                   10                  15

Glu Pro Phe Asp Gly Glu Ser Ile Ser His Phe Leu Gly Arg Phe Arg
            20                  25                  30

Arg Glu Lys Gly Asn Lys Phe Ser Ala Pro Ser Gly Leu Gly Asp Val
        35                  40                  45

Ala Gly Leu Gly Val Val Leu Ala Arg Trp Glu Lys Phe Tyr Phe Asn
    50                  55                  60

Pro Phe Pro Thr His Gln Glu Leu Asp Ala Leu Ala Thr Val Val Glu
65                  70                  75                  80

Leu Asp Ala Glu Arg Leu Arg Gln Met Leu Pro Pro Glu Gly Val Gly
                85                  90                  95

Met Lys His Ser Pro Ile Arg Leu Cys Gly Ala Cys Tyr Ala Glu Ser
            100                 105                 110
```

Val Cys His Lys Ile Glu Trp Gln Phe Lys Lys Arg Val Gly Cys Asp
                115                 120                 125

Arg His Leu Leu Arg Leu Leu Ser Lys Cys Pro Val Cys Glu Lys Pro
            130                 135                 140

Phe Pro Val Pro Ala Leu Trp Met Asp Gly Gln Cys Gln Arg Cys Phe
145                 150                 155                 160

Thr Ser Phe Ala Glu Met Ala Glu His Gln Lys His Tyr
                165                 170

<210> SEQ ID NO 78
<211> LENGTH: 167
<212> TYPE: PRT
<213> ORGANISM: Scytonema hofmanni

<400> SEQUENCE: 78

Met Ile Glu Ala Pro Asp Val Lys Pro Trp Leu Phe Leu Ile Lys Pro
1               5                   10                  15

Tyr Glu Gly Glu Ser Leu Ser His Phe Leu Gly Arg Phe Arg Arg Ala
                20                  25                  30

Asn His Leu Ser Ala Ser Gly Leu Gly Thr Leu Ala Gly Ile Gly Ala
            35                  40                  45

Ile Val Ala Arg Trp Glu Arg Phe His Phe Asn Pro Arg Pro Ser Gln
50                  55                  60

Gln Glu Leu Glu Ala Ile Ala Ser Val Val Glu Val Asp Ala Gln Arg
65                  70                  75                  80

Leu Ala Gln Met Leu Pro Pro Ala Gly Val Gly Met Gln His Glu Pro
                85                  90                  95

Ile Arg Leu Cys Gly Ala Cys Tyr Ala Glu Ser Pro Cys His Arg Ile
            100                 105                 110

Glu Trp Gln Tyr Lys Ser Val Trp Lys Cys Asp Arg His Gln Leu Lys
        115                 120                 125

Ile Leu Ala Lys Cys Pro Asn Cys Gln Ala Pro Phe Lys Met Pro Ala
130                 135                 140

Leu Trp Glu Asp Gly Cys Cys His Arg Cys Arg Met Pro Phe Ala Glu
145                 150                 155                 160

Met Ala Lys Leu Gln Lys Val
                165

<210> SEQ ID NO 79
<211> LENGTH: 175
<212> TYPE: PRT
<213> ORGANISM: Scytonema sp.

<400> SEQUENCE: 79

Met Glu Ile Pro Ala Glu Gln Pro Arg Phe Phe Gln Val Glu Pro Leu
1               5                   10                  15

Glu Gly Glu Ser Leu Ser His Phe Leu Gly Arg Phe Arg Arg Glu Asn
                20                  25                  30

Tyr Leu Thr Ala Thr Gln Leu Gly Lys Leu Thr Gly Ile Gly Ala Val
            35                  40                  45

Ile Ser Arg Trp Glu Lys Phe Tyr Leu Asn Pro Phe Pro Thr Pro Gln
50                  55                  60

Glu Leu Glu Ala Leu Ala Ala Val Val Glu Val Lys Val Asp Arg Leu
65                  70                  75                  80

Ile Glu Met Leu Pro Pro Lys Gly Val Thr Met Lys Pro Arg Pro Ile
                85                  90                  95

```
Arg Leu Cys Gly Ala Cys Tyr Gln Glu Ser Pro Cys His Arg Val Glu
                100                 105                 110

Trp Gln Phe Lys Asp Lys Leu Lys Cys Val Ser Glu Ala His Pro Lys
            115                 120                 125

Asp Ala Arg His Gln Leu Gly Leu Leu Thr Lys Cys Thr Asn Cys Glu
        130                 135                 140

Thr Pro Phe Pro Ile Pro Ala Asp Trp Val Gln Gly Glu Cys Pro His
145                 150                 155                 160

Cys Phe Leu Pro Phe Ala Lys Met Ala Arg Arg Gln Lys Arg Tyr
                165                 170                 175

<210> SEQ ID NO 80
<211> LENGTH: 167
<212> TYPE: PRT
<213> ORGANISM: Spirulina major

<400> SEQUENCE: 80

Met Asn Asp Trp Glu Ile Gln Pro Trp Leu Phe Val Val Glu Pro Tyr
1               5                   10                  15

Glu Gly Glu Ser Leu Ser His Phe Leu Gly Arg Phe Arg Arg Glu Asn
            20                  25                  30

Asp Leu Thr Pro Ala Gly Leu Gly Arg Glu Ala Glu Ile Gly Ala Val
        35                  40                  45

Val Ser Arg Trp Glu Lys Phe Arg Leu Ile Pro Phe Pro Ser Gln Arg
50                  55                  60

Glu Leu Glu Lys Leu Ala Gln Val Val Gln Val Asp Ala Ala Arg Leu
65                  70                  75                  80

Arg Val Met Leu Pro Pro Asp Gly Val Gly Met Lys Met Thr Pro Ile
                85                  90                  95

Arg Leu Cys Gly Ala Cys Tyr Arg Glu Val Arg Cys His Arg Met Glu
                100                 105                 110

Trp Gln Tyr Lys Thr Ser Asp Arg Cys Asp Lys His Pro Leu Arg Leu
            115                 120                 125

Leu Ser Glu Cys Pro Asn Cys Gly Ala Arg Phe Pro Ile Pro Ser Leu
        130                 135                 140

Trp Gln Asp Gly Trp Cys Thr Arg Cys Phe Thr Thr Phe Gly Glu Met
145                 150                 155                 160

Ala Glu Ser Gln Lys Pro Leu
                165

<210> SEQ ID NO 81
<211> LENGTH: 109
<212> TYPE: PRT
<213> ORGANISM: Geminocystis sp.

<400> SEQUENCE: 81

Met Leu Asp Thr Asp Ile Asn Thr Trp Leu Leu Pro Ile Glu Pro Leu
1               5                   10                  15

Glu Gly Glu Ser Leu Ser His Phe Leu Gly Arg Val Arg Arg Arg Asn
            20                  25                  30

Tyr Leu Ser Ala Ser Ala Leu Gly Glu Leu Ala Gly Ile Gly Gly Ala
        35                  40                  45

Ile Thr Arg Trp Glu Lys Phe Arg His Tyr Pro Phe Pro Ser Asp Glu
50                  55                  60

Glu Leu Thr Ala Leu Gly Asn Leu Leu Gly Leu Glu Leu Phe Gln Leu
65                  70                  75                  80
```

```
Lys Ala Met Leu Pro Ser Glu Pro Met Lys Leu Glu Pro Ile Arg Leu
             85                  90                  95

Cys Gly Ala Cys Tyr Gly Glu Ile Pro Ser Ser Ser Tyr
            100                 105
```

<210> SEQ ID NO 82
<211> LENGTH: 184
<212> TYPE: PRT
<213> ORGANISM: Nostoc sp.

<400> SEQUENCE: 82

```
Met Glu Lys Asp Thr Phe Pro Pro Lys Thr Glu Ile Arg Ile His Asp
1               5                   10                  15

Asn His Glu Ala Leu Pro Arg Leu Gly Tyr Val Glu Pro Tyr Glu Gly
            20                  25                  30

Glu Ser Ile Ser His Tyr Leu Gly Arg Leu Arg Arg Phe Lys Ala Asn
        35                  40                  45

Ser Leu Pro Ser Gly Tyr Ser Leu Gly Lys Ile Ala Gly Ile Gly Ala
    50                  55                  60

Val Thr Thr Arg Trp Glu Lys Leu Tyr Phe Asn Pro Phe Pro Ser Ser
65                  70                  75                  80

Glu Glu Leu Glu Ala Leu Gly Lys Leu Ile Gly Val Pro Ala Asn Arg
                85                  90                  95

Ile Tyr Glu Met Leu Pro Pro Lys Gly Val Thr Met Lys Pro Arg Pro
            100                 105                 110

Ile Arg Leu Cys Ala Ala Cys Tyr Ala Glu Val Pro Cys His Arg Ile
        115                 120                 125

Glu Trp Gln Tyr Lys Asp Lys Leu Lys Cys Asn His His Asn Leu Gly
    130                 135                 140

Leu Leu Thr Lys Cys Thr Asn Cys Glu Thr Pro Phe Pro Ile Pro Ala
145                 150                 155                 160

Asp Trp Val Gln Gly Glu Cys Pro His Cys Phe Leu Pro Phe Ala Lys
                165                 170                 175

Met Ala Lys Arg Gln Lys Pro Arg
            180
```

<210> SEQ ID NO 83
<211> LENGTH: 188
<212> TYPE: PRT
<213> ORGANISM: Calothrix sp.

<400> SEQUENCE: 83

```
Met Ala Glu Asp Ile Tyr Leu Pro Lys Arg Glu Ile Ile Ser Asn Lys
1               5                   10                  15

Glu Ile Asn Lys Gly Asp Glu Ile Leu Pro Arg Leu Gly Phe Val Glu
            20                  25                  30

Pro Tyr Glu Cys Glu Ser Ile Ser His Tyr Leu Gly Arg Val Arg Arg
        35                  40                  45

Phe Lys Ala Asn Ser Leu Pro Ser Gly Tyr Ser Leu Gly Lys Ile Ala
    50                  55                  60

Gly Ile Gly Ala Val Thr Thr Arg Trp Glu Lys Leu Tyr Leu Asn Pro
65                  70                  75                  80

Phe Pro Ser Glu Thr Glu Leu Glu Ala Leu Ala Lys Val Ile Glu Val
                85                  90                  95

Glu Val Glu Arg Leu Arg Gln Met Leu Pro Pro Lys Gly Met Thr Met
            100                 105                 110
```

```
Lys Pro Arg Pro Ile Arg Leu Cys Ala Ala Cys Tyr Ala Glu Ser Pro
            115                 120                 125

His His Arg Ile Glu Trp Gln Phe Lys Asp Val Met Val Cys Asp Arg
    130                 135                 140

His Gln Leu Pro Leu Ser Thr Lys Cys Lys Asn Cys Gly Thr Pro Phe
145                 150                 155                 160

Pro Ile Pro Ala Asp Trp Val Arg Gly Glu Cys Pro His Cys Cys Leu
                165                 170                 175

Ser Phe Thr Lys Met Ala Lys Arg Gln Lys Ser Gly
            180                 185

<210> SEQ ID NO 84
<211> LENGTH: 167
<212> TYPE: PRT
<213> ORGANISM: Anabaena cylindrica

<400> SEQUENCE: 84

Met Glu Val Gly Glu Ile Asn Pro Trp Leu Phe Gln Val Glu Pro Tyr
1               5                   10                  15

Leu Gly Glu Ser Leu Ser His Phe Leu Gly Arg Phe Arg Arg Ala Asn
            20                  25                  30

Asp Leu Thr Thr Thr Gly Leu Gly Lys Ala Ala Gly Val Gly Gly Ala
        35                  40                  45

Ile Ser Arg Trp Glu Lys Phe Arg Phe Asn Pro Pro Ser Arg Gln
    50                  55                  60

Gln Leu Glu Ala Leu Ala Lys Val Val Gly Val Asp Ala Asp Arg Leu
65                  70                  75                  80

Glu Gln Met Leu Pro Pro Ala Gly Val Gly Met Asn Leu Glu Pro Ile
                85                  90                  95

Arg Leu Cys Ala Ala Cys Tyr Val Glu Ser Pro Cys His Arg Ile Glu
            100                 105                 110

Trp Gln Phe Lys Val Thr Gln Gly Cys Gln His His His Leu Ser Leu
        115                 120                 125

Leu Ser Glu Cys Pro Asn Cys Gly Ala Arg Phe Lys Val Pro Ala Leu
    130                 135                 140

Trp Val Asp Gly Trp Cys Gln Arg Cys Phe Leu Pro Phe Gly Glu Met
145                 150                 155                 160

Ile Glu His Gln Lys Arg Ile
                165

<210> SEQ ID NO 85
<211> LENGTH: 184
<212> TYPE: PRT
<213> ORGANISM: Anabaena cylindrica

<400> SEQUENCE: 85

Met Ala Gln Asn Ile Phe Leu Ser Lys Thr Glu Ile Gly Ile Asp Glu
1               5                   10                  15

Asp Asp Glu Ile Arg Pro Lys Leu Gly Tyr Val Glu Pro Tyr Glu Glu
            20                  25                  30

Glu Ser Ile Ser His Tyr Leu Gly Arg Leu Arg Arg Phe Lys Ala Asn
        35                  40                  45

Ser Leu Pro Ser Gly Tyr Ser Leu Gly Lys Ile Ala Gly Leu Gly Ala
    50                  55                  60

Met Ile Ser Arg Trp Glu Lys Leu Tyr Phe Asn Pro Pro Thr Leu
65                  70                  75                  80
```

Gln Glu Leu Glu Ala Leu Ser Ser Val Val Gly Val Asn Ala Asp Arg
                85                  90                  95

Leu Ile Glu Met Leu Pro Ser Gln Gly Met Thr Met Lys Pro Arg Pro
            100                 105                 110

Ile Arg Leu Cys Gly Ala Cys Tyr Ala Glu Ser Pro Cys His Arg Ile
            115                 120                 125

Glu Trp Gln Cys Lys Asp Arg Met Lys Cys Asp Arg His Asn Leu Arg
            130                 135                 140

Leu Leu Ile Lys Cys Thr Asn Cys Glu Thr Pro Phe Pro Ile Pro Ala
145                 150                 155                 160

Asp Trp Val Lys Gly Gln Cys Pro His Cys Ser Leu Pro Phe Ala Lys
            165                 170                 175

Met Ala Lys Arg Gln Arg Arg Asp
            180

<210> SEQ ID NO 86
<211> LENGTH: 171
<212> TYPE: PRT
<213> ORGANISM: Anabaena sp.

<400> SEQUENCE: 86

Met Asn Glu Asp Asp Glu Ile Arg Pro Lys Leu Gly Tyr Val Glu Pro
1               5                   10                  15

Tyr Glu Gly Glu Ser Ile Ser His Tyr Leu Gly Arg Leu Arg Arg Phe
                20                  25                  30

Lys Ala Asn Ser Leu Pro Ser Gly Tyr Ser Leu Gly Lys Ile Ala Gly
            35                  40                  45

Leu Gly Ala Val Thr Thr Arg Trp Glu Lys Leu Tyr Phe Asn Pro Phe
50                  55                  60

Pro Asn Arg Gln Glu Leu Glu Ala Leu Ala Ser Val Val Gly Val Ser
65                  70                  75                  80

Ala Glu Arg Phe Ile Glu Met Leu Pro Pro Lys Gly Val Thr Met Lys
                85                  90                  95

Pro Arg Pro Ile Arg Leu Cys Ala Ala Cys Tyr Ala Glu Val Pro Cys
            100                 105                 110

His Arg Ile Asp Trp Gln Phe Lys Asp Lys Met Lys Cys Asp Arg His
            115                 120                 125

Asn Leu Arg Leu Leu Thr Lys Cys Thr Asn Cys Glu Thr Pro Phe Pro
            130                 135                 140

Ile Pro Ala Asp Trp Ala Gln Gly Glu Cys Pro His Cys Ser Leu Ser
145                 150                 155                 160

Phe Ala Lys Met Val Lys Arg Gln Lys Leu Arg
            165                 170

<210> SEQ ID NO 87
<211> LENGTH: 276
<212> TYPE: PRT
<213> ORGANISM: Alkalinema sp.

<400> SEQUENCE: 87

Met Thr Gln Ala Lys Glu Trp Ala Glu Val Leu Gly Glu Phe Gln Pro
1               5                   10                  15

Asp Asp Asp Trp Leu Lys Ala Glu Ile Ala Arg Leu Arg Lys Lys Thr
                20                  25                  30

Val Met Pro Leu Ala Gln Val Ser Gln Leu His Asp Trp Leu Asp Gly
            35                  40                  45

Lys Arg Lys Ser Arg Gln Ser Cys Arg Ile Val Gly Glu Ser Arg Thr
        50                  55                  60

Gly Lys Ser Val Ala Cys Glu Ala Tyr Phe Tyr Arg Asn Lys Pro Gln
65                  70                  75                  80

Gln Glu Ala Gly Lys Lys Pro Ile Val Pro Val Tyr Val Gln Pro
                85                  90                  95

Pro Gln Lys Cys Gly Pro Lys Glu Leu Phe Lys Glu Ile Ile Glu Phe
                100                 105                 110

Leu Lys His Arg Ala Thr Arg Gly Thr Val Ser Asp Leu Arg Gly Arg
        115                 120                 125

Ala Ile Glu Val Leu Gln Ala Cys Gly Val Glu Met Leu Ile Ile Asp
        130                 135                 140

Glu Ala Asp Arg Leu Lys Pro Glu Thr Phe Ala Asp Val Arg Asp Ile
145                 150                 155                 160

Tyr Asp Lys Leu Gly Ile Ala Val Val Leu Val Gly Thr Asp Arg Leu
                165                 170                 175

Asp Ala Val Ile Lys Arg Asp Glu Gln Val Tyr Asn Arg Phe Arg Ala
                180                 185                 190

Cys His Arg Phe Gly Lys Leu Ser Gly Glu Glu Phe Lys Lys Thr Ile
        195                 200                 205

Ala Leu Trp Glu Gln Lys Ile Leu Asn Leu Pro Val Ala Ser Asn Leu
        210                 215                 220

Ile Ser Lys Asp Met Leu Arg Ile Leu Thr Thr Gly Thr Glu Gly Tyr
225                 230                 235                 240

Ile Gly Arg Met Asp Glu Ile Leu Arg Glu Ala Ala Ile Arg Ser Leu
                245                 250                 255

Ser Phe Gly Tyr Lys Lys Val Glu Lys Lys Cys Leu Glu Glu Val Ala
                260                 265                 270

Lys Glu Tyr Lys
        275

<210> SEQ ID NO 88
<211> LENGTH: 278
<212> TYPE: PRT
<213> ORGANISM: Anabaena sp.

<400> SEQUENCE: 88

Met Thr Asp Asp Ala Gln Ala Ile Ala Lys Gln Leu Gly Gly Val Lys
1               5                   10                  15

Pro Asp Glu Glu Trp Leu Gln Ala Glu Ile Thr His Leu Thr Ser Lys
                20                  25                  30

Ser Ile Val Pro Leu Gln Gln Val Ile Thr Leu His Asp Trp Leu Asp
        35                  40                  45

Gly Lys Arg Lys Ala Arg Gln Ser Cys Arg Val Val Gly Glu Ser Arg
        50                  55                  60

Thr Gly Lys Thr Val Ala Cys Asp Ala Tyr Arg Tyr Arg His Lys Pro
65                  70                  75                  80

Arg Gln Glu Met Gly Lys Thr Pro Ile Val Pro Val Val Tyr Ile Gln
                85                  90                  95

Pro Pro Ser Lys Cys Gly Ala Lys Asp Leu Phe Gln Glu Ile Ile Glu
                100                 105                 110

Tyr Leu Lys Phe Lys Ala Thr Arg Gly Thr Ile Ser Asp Phe Arg Gly
        115                 120                 125

Arg Thr Met Glu Val Leu Lys Gly Cys Arg Val Glu Met Ile Ile Ile
        130                 135                 140

Asp Glu Ala Asp Arg Ile Lys Pro Asp Thr Phe Ala Asp Val Arg Asp
145                 150                 155                 160

Ile Tyr Asp Lys Leu Gly Ile Ala Ile Val Leu Val Gly Thr Asp Arg
            165                 170                 175

Leu Glu Ala Val Ile Lys Arg Asp Glu Gln Val Tyr Asn Arg Phe Arg
        180                 185                 190

Ala Cys His Arg Phe Gly Lys Leu Ala Gly Lys Asp Phe Gln Asp Thr
    195                 200                 205

Val Gln Ala Trp Glu Asp Lys Ile Leu Lys Leu Pro Leu Pro Ser Asn
210                 215                 220

Leu Ile Ser Lys Asp Met Leu Arg Ile Leu Thr Ser Ala Thr Glu Gly
225                 230                 235                 240

Tyr Ile Gly Gly Leu Asp Glu Ile Leu Arg Glu Ala Ala Ile Arg Ser
            245                 250                 255

Leu Ser Arg Gly Leu Lys Lys Ile Asp Lys Ala Val Leu Gln Glu Val
        260                 265                 270

Val Gln Glu Phe Lys Leu
        275

<210> SEQ ID NO 89
<211> LENGTH: 268
<212> TYPE: PRT
<213> ORGANISM: Anabaena variabilis

<400> SEQUENCE: 89

Met Thr Asn Glu Glu Ile Gln Gln Glu Ile Glu Arg Leu Arg Gln Pro
1               5                   10                  15

Asp Ile Leu Asn Leu Glu Gln Val Lys Arg Phe Ser Ser Trp Leu Asp
            20                  25                  30

Glu Arg Arg Lys Leu Arg Lys Pro Gly Arg Ala Val Gly Glu Ser Gly
        35                  40                  45

Leu Gly Lys Thr Thr Ala Ser Leu Phe Tyr Thr Tyr Gln Asn Arg Ala
    50                  55                  60

Ala Lys Ile Pro Asn Gln Asn Pro Val Ala Pro Val Leu Tyr Val Glu
65                  70                  75                  80

Leu Ile Gly Ser Ser Cys Ser Pro Ser Leu Leu Phe Lys Thr Ile Ile
                85                  90                  95

Glu Thr Leu Lys Phe Lys Ala Lys Gly Gly Thr Glu Asn Gln Leu Arg
            100                 105                 110

Glu Arg Ala Trp Tyr Leu Ile Lys Gln Cys Lys Val Glu Met Leu Ile
        115                 120                 125

Ile Asp Glu Ala His Arg Leu Gln Phe Lys Thr Leu Thr Asp Val Thr
    130                 135                 140

Asp Leu Ser Asp Lys Val Lys Ile Ile Pro Ile Leu Val Gly Thr Ser
145                 150                 155                 160

Ser Arg Leu Asp Ala Leu Ile Ser Lys Asn Glu Gln Val Gly Gly Arg
                165                 170                 175

Phe Ala Ala Tyr Phe Ser Phe Glu Gln Leu Ser Gly Ala Asn Phe Ile
            180                 185                 190

Lys Thr Val Lys Ile Trp Glu Gln Gln Ile Leu Lys Leu Pro Glu Pro
        195                 200                 205

Ser Asn Leu Ala Glu Asn Gln Glu Ile Ile Thr Ile Leu Gln Ala Lys
    210                 215                 220

Thr Ala Gly Gln Ile Arg Leu Leu Asp Gln Ile Leu Arg Asp Ala Ala

```
                    225                 230                 235                 240
Val Lys Ala Leu Glu Ser Gly Val Asn Lys Ile Asp Lys Ser Leu Leu
                245                 250                 255

Asn Ser Ile Glu Gly Asp Tyr Ser Leu Val Ala Ser
                260                 265
```

<210> SEQ ID NO 90
<211> LENGTH: 275
<212> TYPE: PRT
<213> ORGANISM: Anabaena variabilis

<400> SEQUENCE: 90

```
Met Thr Asp Ala Lys Pro Leu Asp Phe Ile Gln Glu Pro Thr Arg Glu
1               5                   10                  15

Ile Gln Ala His Ile Glu Arg Leu Ser Arg Ala Pro Tyr Leu Glu Leu
                20                  25                  30

Asn Gln Val Lys Ser Cys His Thr Trp Met Tyr Glu Leu Val Ile Ser
                35                  40                  45

Arg Met Thr Gly Leu Leu Val Gly Glu Ser Arg Ser Gly Lys Thr Val
        50                  55                  60

Thr Cys Lys Ala Phe Arg Asn Asn Tyr Asn Asn Leu Arg Gln Gly Gln
65                  70                  75                  80

Glu Gln Arg Ile Lys Pro Val Val Tyr Ile Gln Ile Ser Lys Asn Cys
                85                  90                  95

Gly Ser Arg Glu Leu Phe Val Lys Ile Leu Lys Ala Leu Asn Lys Pro
                100                 105                 110

Ser Asn Gly Thr Ile Ala Asp Leu Arg Glu Arg Thr Leu Asp Ser Leu
                115                 120                 125

Glu Ile His Gln Val Glu Met Leu Ile Ile Asp Glu Ala Asn His Leu
        130                 135                 140

Lys Ile Glu Thr Phe Ser Asp Val Arg His Ile Tyr Asp Glu Asp Ser
145                 150                 155                 160

Leu Lys Ile Ser Val Leu Leu Val Gly Thr Thr Ser Arg Leu Leu Ala
                165                 170                 175

Val Val Lys Arg Asp Glu Gln Val Asn Arg Phe Leu Glu Lys Phe
                180                 185                 190

Glu Ile Asp Lys Leu Glu Glu Asn Gln Phe Lys Gln Met Ile Gln Val
                195                 200                 205

Trp Glu Arg Asp Val Leu Arg Leu Pro Glu Glu Ser Lys Leu Ala Ser
        210                 215                 220

Gly Glu Ser Phe Lys Leu Leu Lys Gln Ser Thr Asn Lys Leu Ile Gly
225                 230                 235                 240

Arg Leu Asp Met Ile Leu Arg Lys Ala Ala Ile Arg Ser Leu Leu Arg
                245                 250                 255

Gly Tyr Lys Lys Val Asp Gln Gly Val Leu Lys Glu Ile Ile Thr Ala
                260                 265                 270

Thr Lys Phe
        275
```

<210> SEQ ID NO 91
<211> LENGTH: 278
<212> TYPE: PRT
<213> ORGANISM: Anabaena variabilis

<400> SEQUENCE: 91

```
Met Thr Ser Lys Gln Ala Gln Ala Val Ala Gln Gln Leu Gly Asp Ile
```

```
            1               5               10              15
        Pro Val Asn Asp Glu Lys Ile Gln Ala Glu Ile Gln Arg Leu Asn Arg
                        20              25              30
        Lys Ser Phe Ile Pro Leu Glu Gln Val Gln Met Leu His Asp Trp Leu
                        35              40              45
        Asp Gly Lys Arg Gln Ser Arg Gln Ser Gly Arg Val Val Gly Glu Ser
                50              55                      60
        Arg Thr Gly Lys Thr Met Gly Cys Asp Ala Tyr Arg Leu Arg His Lys
        65              70                      75                  80
        Pro Lys Gln Glu Pro Gly Arg Pro Thr Val Pro Val Ala Tyr Ile
                        85              90              95
        Gln Ile Pro Gln Glu Cys Gly Ala Lys Glu Leu Phe Gly Val Leu Leu
                        100             105             110
        Glu His Leu Lys Tyr Gln Met Thr Lys Gly Thr Val Ala Glu Ile Arg
                        115             120             125
        Asp Arg Thr Leu Arg Val Leu Lys Gly Cys Gly Val Glu Met Leu Ile
                        130             135             140
        Ile Asp Glu Ala Asp Arg Leu Lys Pro Lys Thr Phe Ala Glu Val Pro
        145                     150             155                 160
        Asp Ile Phe Asp Lys Leu Glu Ile Ala Val Ile Leu Val Gly Thr Asp
                        165                     170             175
        Arg Leu Asp Ala Val Ile Lys Arg Asp Glu Gln Val Tyr Asn Arg Phe
                        180             185                     190
        Arg Ala Cys His Arg Phe Gly Lys Phe Ser Gly Asp Glu Phe Lys Lys
                        195             200             205
        Ile Val Asp Ile Trp Glu Lys Lys Val Leu Gln Leu Pro Val Ala Ser
                        210             215             220
        Asn Leu Ser Ser Lys Thr Met Leu Lys Thr Leu Gly Glu Thr Thr Gly
        225                     230             235                 240
        Gly Tyr Ile Gly Leu Leu Asp Met Ile Leu Arg Glu Ser Ala Ile Arg
                        245                     250             255
        Ala Leu Lys Lys Gly Leu Arg Lys Val Asp Leu Ala Thr Leu Lys Glu
                        260             265             270
        Val Thr Glu Glu Tyr Lys
                        275

<210> SEQ ID NO 92
<211> LENGTH: 270
<212> TYPE: PRT
<213> ORGANISM: Aphanocapsa montana

<400> SEQUENCE: 92

Met Ile Ala Leu Gln Asp Gln Glu Val Gln Ala His Ile Glu Arg Leu
        1               5                       10                  15
        Arg Arg Asp Lys Thr Val Ala Leu Asp Ser Val Lys Gln Ala His Thr
                        20              25              30
        Trp Leu Lys Arg Lys Arg Asn Ala Arg Gln Cys Gly Arg Leu Thr Gly
                        35              40              45
        Asp Ser Arg Thr Gly Lys Thr Lys Thr Cys Glu Ser Phe Leu Lys Leu
                50              55                      60
        Tyr Gly Glu Pro Asp Leu Ser Gly Arg Val Pro Ile Ile Pro Ile Ser
        65                      70                      75              80
        Tyr Val His Pro Lys Gln Glu Cys Thr Ser Arg Glu Leu Phe Arg Glu
                        85              90                      95
```

```
Ile Leu Glu Gln Tyr Gly Asp Asp Leu Pro Arg Gly Thr Val Gly Asp
                100                 105                 110

Ala Arg Ser Arg Thr Leu Lys Val Leu Arg Ala Cys Lys Thr Glu Met
            115                 120                 125

Leu Met Ile Asp Glu Ala Asp Arg Leu Lys Pro Lys Thr Phe Ala Asp
        130                 135                 140

Val Arg Asp Ile Phe Asp Lys Leu Glu Ile Ser Val Ile Leu Ile Gly
145                 150                 155                 160

Thr Lys Gln Arg Leu Asp Pro Ala Val Lys Asp Glu Gln Val Phe
                165                 170                 175

Asn Arg Phe Arg Ser Ser Tyr Arg Ile Gly Thr Ile Pro Ser Asn Gln
            180                 185                 190

Leu Lys Thr Ile Val Gly Leu Trp Glu Arg Asp Ile Leu Lys Leu Pro
        195                 200                 205

Val Pro Ser Asn Leu Thr Ser Glu Ala Met Leu Lys Glu Leu Arg Lys
210                 215                 220

Ala Thr Gly Val Ser Arg Lys Gly Tyr Tyr Ile Gly Leu Ile Asp Met
225                 230                 235                 240

Val Leu Arg Glu Ala Ala Ile Arg Ala Leu Glu Lys Gly Gln Ser Lys
                245                 250                 255

Ile Glu Leu Glu Thr Leu Lys Glu Val Ala Lys Glu Tyr Ser
            260                 265                 270

<210> SEQ ID NO 93
<211> LENGTH: 278
<212> TYPE: PRT
<213> ORGANISM: Calothrix sp.

<400> SEQUENCE: 93

Met Ala Asp Glu Tyr Leu Arg Lys Trp Val Gln Asn Leu Trp Gly Asp
1               5                   10                  15

Asp Pro Ile Pro Glu Glu Leu Met Pro Gln Ile Glu Arg Leu Ile Thr
            20                  25                  30

Pro Ser Ile Val Glu Leu Asp His Ile Gln Lys Ile His Asp Trp Leu
        35                  40                  45

Asp Ser Leu Arg Leu Ser Lys Gln Cys Gly Arg Ile Val Ala Pro Pro
50                  55                  60

Arg Ala Gly Lys Ser Val Thr Cys Asp Val Tyr Lys Leu Leu Asn Lys
65                  70                  75                  80

Pro Gln Lys Arg Thr Gly Lys Arg Asp Ile Val Pro Val Leu Tyr Met
                85                  90                  95

Gln Val Pro Gly Asp Cys Ser Ala Gly Glu Leu Leu Thr Leu Ile Leu
            100                 105                 110

Glu Ser Leu Lys Tyr Glu Ala Thr Ser Gly Lys Leu Thr Asp Leu Arg
        115                 120                 125

Arg Arg Val Gln Arg Leu Leu Lys Glu Ser Lys Val Glu Met Leu Ile
130                 135                 140

Ile Asp Glu Ala Asn Phe Leu Lys Leu Asn Thr Phe Ser Glu Ile Ala
145                 150                 155                 160

Arg Ile Tyr Asp Leu Leu Lys Val Ser Ile Val Leu Val Gly Thr Asp
                165                 170                 175

Gly Leu Asp Asn Leu Ile Lys Lys Glu Pro Tyr Ile His Asp Arg Phe
            180                 185                 190

Ile Glu Cys Tyr Arg Leu Gln Leu Val Ser Glu Lys Lys Phe Ser Glu
        195                 200                 205
```

```
Leu Val Gln Ile Trp Glu Asp Val Leu Cys Leu Pro Val Pro Ser
    210                 215                 220

Asn Leu Val Lys Arg Glu Thr Leu Ile Pro Leu Tyr Gln Lys Thr Gly
225                 230                 235                 240

Gly Lys Ile Gly Leu Val Asp Arg Val Leu Arg Arg Ala Ala Ile Leu
                245                 250                 255

Ser Leu Arg Lys Gly Leu Ser Ile Ile Asp Lys Ile Thr Leu Asp Glu
            260                 265                 270

Val Leu Glu Trp Phe Glu
        275

<210> SEQ ID NO 94
<211> LENGTH: 290
<212> TYPE: PRT
<213> ORGANISM: Cyanothece sp.

<400> SEQUENCE: 94

Met Thr Asp Ser Ser Val Ile Asp Lys Leu Ala Glu Phe Gly Gly
1               5                   10                  15

Phe Ala Thr Pro Ser Pro Glu Ile Gln Ala Glu Ile Gln Arg Leu Ser
                20                  25                  30

Arg Gln Pro Tyr Leu Glu Tyr Glu Gln Val Lys Asn Cys His Gly Trp
            35                  40                  45

Leu Tyr Glu Leu Val Leu Ser Arg Met Thr Gly Leu Leu Val Gly Glu
    50                  55                  60

Ser Arg Ser Gly Lys Thr Val Thr Cys Lys Ser Phe Glu Lys Arg Tyr
65                  70                  75                  80

Asn Lys Ile Lys Thr Gly Asn Lys Lys Arg Ile Lys Pro Ile Val Tyr
                85                  90                  95

Ile Gln Ser Pro Gln Asn Cys Gly Ala Arg Glu Phe Phe Thr Lys Ile
                100                 105                 110

Leu Lys Ala Leu Asn Lys Pro Thr Asn Gly Asn Val Ser Asp Leu Arg
            115                 120                 125

Glu Arg Thr Leu Asp Gly Leu Gln Ile His Glu Cys Glu Met Leu Ile
130                 135                 140

Ile Asp Glu Ala Asn His Leu Lys Gln Glu Thr Phe Ala Glu Val Arg
145                 150                 155                 160

His Val Tyr Asp Glu Glu Leu Asn Met Ala Val Leu Leu Val Gly
                165                 170                 175

Thr Arg His Arg Leu Glu Ala Val Val Lys Arg Asp Glu Gln Val Leu
            180                 185                 190

Asn Arg Phe Met Glu Glu Tyr Glu Leu Asp Arg Leu Asp Asp Lys Glu
        195                 200                 205

Phe Lys Gln Leu Ile Lys Ile Trp Glu Gln Ser Val Leu Cys Leu Pro
    210                 215                 220

Glu Leu Ser Asn Leu Asp Thr Gly Asp Asn Leu Lys Leu Leu Lys Lys
225                 230                 235                 240

Thr Thr Arg Lys Leu Ile Gly Arg Leu Asp Met Ile Leu Arg Lys Ser
                245                 250                 255

Ala Ile Arg Ala Leu Arg Glu Gly Lys Gln Ser Ile Ser Pro Glu Leu
            260                 265                 270

Leu Lys Gln Val Ile Ser Ser Ile Lys Trp Ser Glu Gly Arg Lys Gly
        275                 280                 285

Asn Gly
```

<210> SEQ ID NO 95
<211> LENGTH: 275
<212> TYPE: PRT
<213> ORGANISM: Geminocystis sp.

<400> SEQUENCE: 95

Met Glu Ala Lys Ala Ile Ala Gln Glu Leu Gly Asn Ile Glu Ile Pro
1               5                   10                  15

Glu Glu Lys Leu Gln Met Glu Ile Glu Arg Leu Asn Ser Lys Thr Leu
            20                  25                  30

Val Ser Leu Glu Gln Val Ala Lys Leu His Glu Tyr Phe Glu Gly Lys
        35                  40                  45

Arg Gln Ser Lys Gln Ser Cys Arg Val Gly Glu Ser Arg Thr Gly
    50                  55                  60

Lys Thr Met Ala Cys Asp Ser Tyr Arg Leu Arg His Lys Pro Ile Gln
65              70                  75                  80

Lys Val Gly His Pro Pro Gln Val Pro Val Tyr Ile Gln Ile Pro
            85                  90                  95

Gln Asp Cys Gly Thr Lys Glu Leu Phe Gln Gly Ile Ile Glu Tyr Leu
            100                 105                 110

Lys Tyr Gln Met Thr Lys Gly Thr Ile Ala Glu Ile Arg Gln Arg Ala
        115                 120                 125

Ile Lys Val Leu Gln Gly Cys Gly Val Glu Met Ile Ile Asp Glu
130                 135                 140

Ala Asp Arg Phe Lys Pro Lys Thr Phe Ala Glu Val Arg Asp Ile Phe
145                 150                 155                 160

Asp Arg Leu Asn Ile Pro Ile Val Leu Val Gly Thr Asp Arg Leu Asp
                165                 170                 175

Thr Val Ile Lys Arg Asp Glu Gln Val Tyr Asn Arg Phe Arg Ser Cys
            180                 185                 190

Tyr Arg Phe Gly Lys Leu Ser Gly Ala Asp Phe Gln Asn Thr Val Asn
        195                 200                 205

Ile Trp Glu Lys Gln Val Leu Lys Leu Pro Val Ala Ser Asn Leu Ile
210                 215                 220

Gln Thr Lys Met Leu Lys Leu Ile Ala Glu Ala Thr Gly Gly Tyr Ile
225                 230                 235                 240

Gly Leu Met Asp Thr Ile Leu Arg Glu Ser Ala Ile Arg Ser Leu Lys
                245                 250                 255

Arg Gly Leu Asn Lys Ile Thr Phe Glu Ile Leu Lys Glu Val Thr Gln
                260                 265                 270

Glu Phe Lys
        275

<210> SEQ ID NO 96
<211> LENGTH: 278
<212> TYPE: PRT
<213> ORGANISM: Leptolyngbya boryana

<400> SEQUENCE: 96

Met Met Ala Asn Glu Ala Gln Ser Ile Ala Gln Thr Leu Gly Ser Leu
1               5                   10                  15

Pro Leu Thr Ser Glu Leu Leu Gln Ala Glu Ile His Arg Leu Thr Lys
            20                  25                  30

Lys Ser Val Val Ser Leu Ser Gln Val Gln Ser Leu His Asn Trp Leu

```
                35                  40                  45
Glu Gly Lys Arg Gln Ala Arg Gln Ser Cys Arg Val Gly Glu Ser
    50                  55                  60

Arg Thr Gly Lys Thr Leu Ala Cys Asp Ala Tyr Arg Leu Arg His Lys
 65                  70                  75                  80

Pro Thr Gln Gln Ala Gly Lys Pro Pro Ile Val Pro Val Tyr Ile
                85                  90                  95

Gln Val Pro Gln Glu Cys Gly Ser Lys Glu Leu Phe Gln Ile Ile Ile
                100                 105                 110

Glu His Leu Lys Tyr Gln Met Val Lys Gly Thr Val Ala Glu Ile Arg
                115                 120                 125

Glu Arg Thr Met Arg Val Leu Lys Gly Cys Gly Val Glu Met Leu Ile
                130                 135                 140

Ile Asp Glu Ala Asp Arg Leu Lys Pro Lys Thr Phe Ala Asp Val Arg
145                 150                 155                 160

Asp Ile Phe Asp Lys Leu Glu Ile Ser Val Val Leu Val Gly Thr Asp
                165                 170                 175

Arg Leu Asp Ala Val Ile Lys Arg Asp Glu Gln Val Tyr Asn Arg Phe
                180                 185                 190

Arg Ala Cys His Arg Phe Gly Lys Leu Ala Gly Glu Glu Phe Arg Arg
                195                 200                 205

Thr Ile Glu Ile Trp Gly Lys Gln Ile Leu Lys Leu Pro Val Ala Ser
                210                 215                 220

Asn Leu Thr Ser Lys Ala Ala Leu Lys Ile Leu Gly Glu Thr Thr Ala
225                 230                 235                 240

Gly Tyr Ile Gly Leu Leu Asp Met Val Leu Arg Glu Ala Ala Ile Arg
                245                 250                 255

Ala Leu Lys Gln Gly Lys Thr Lys Ile Asp Leu Glu Ile Leu Lys Glu
                260                 265                 270

Val Ser Thr Glu Tyr Arg
                275

<210> SEQ ID NO 97
<211> LENGTH: 282
<212> TYPE: PRT
<213> ORGANISM: Myxosarcina sp.

<400> SEQUENCE: 97

Met Thr Glu Ala Lys Ala Ile Ala Asp Lys Leu Gly Lys Ile Glu Leu
1                5                  10                  15

Asp Glu Glu Trp Val Gln Lys Glu Ile Ala Arg Leu Asn Arg Lys Ser
                20                  25                  30

Thr Val Ala Leu Glu His Ile Lys Glu Leu His Asp Trp Leu Asp Gly
                35                  40                  45

Lys Arg Lys Ser Arg Arg Ser Cys Arg Ile Val Gly Lys Ser Arg Thr
    50                  55                  60

Gly Lys Thr Val Ala Cys Glu Ala Tyr Val Met Arg Asn Lys Leu Asn
 65                  70                  75                  80

Lys Pro Pro Gln Glu Arg Gln Thr Lys Asn Gln Ile Pro Ile Glu Pro
                85                  90                  95

Val Ile Met Ile Met Pro Pro Gln Lys Cys Gly Ala Lys Glu Leu Phe
                100                 105                 110

Arg Glu Ile Ile Glu Cys Leu Lys Phe Arg Ala Val Lys Gly Thr Ile
                115                 120                 125
```

```
Ser Glu Phe Arg Ser Arg Ala Met Asp Val Leu Gln Lys Cys Gln Val
    130                 135                 140

Glu Met Leu Ile Ile Asp Glu Ala Asp Arg Leu Lys Pro Glu Thr Phe
145                 150                 155                 160

Ser Glu Val Arg Asp Ile Tyr Asp Lys Leu Glu Ile Ala Val Val Leu
                165                 170                 175

Val Gly Thr Glu Arg Leu Asp Thr Ala Val Lys Arg Asp Glu Gln Val
            180                 185                 190

Glu Asn Arg Phe Arg Ala Asn Arg Arg Phe Gly Thr Leu Glu Gly Ile
        195                 200                 205

Asn Phe Lys Lys Thr Val Glu Ile Trp Glu Gly Lys Ile Leu Lys Leu
210                 215                 220

Pro Val Ala Ser Asn Leu Thr Asn Lys Thr Thr Trp Lys Ile Leu Leu
225                 230                 235                 240

Ile Ala Thr Glu Gly Phe Ile Gly Arg Leu Asp Glu Ile Leu Arg Glu
                245                 250                 255

Ala Ala Ile Ala Ser Leu Ser Gln Gly His Lys Val Asp Pro Lys
            260                 265                 270

Ile Leu Lys Glu Ile Ala Arg Glu Tyr Ser
        275                 280

<210> SEQ ID NO 98
<211> LENGTH: 276
<212> TYPE: PRT
<213> ORGANISM: Nostoc punctiforme

<400> SEQUENCE: 98

Met Thr Glu Ala Gln Ala Ile Ala Lys Gln Leu Gly Gly Val Lys Pro
1               5                   10                  15

Asp Asp Glu Trp Leu Gln Ala Glu Ile Ala Arg Leu Lys Gly Lys Ser
            20                  25                  30

Ile Val Pro Leu Gln Gln Val Lys Thr Leu His Asp Trp Leu Asp Gly
        35                  40                  45

Lys Arg Lys Ala Arg Gln Ser Cys Arg Val Val Gly Glu Ser Arg Thr
50                  55                  60

Gly Lys Thr Val Ala Cys Asp Ala Tyr Arg Tyr Arg Gln Lys Pro Gln
65                  70                  75                  80

Gln Glu Val Gly Arg Pro Pro Ile Val Pro Val Tyr Ile Gln Pro
            85                  90                  95

Pro Gln Lys Cys Gly Ser Lys Asp Leu Phe Lys Glu Met Ile Glu Tyr
        100                 105                 110

Leu Lys Phe Arg Ala Thr Lys Gly Thr Val Ser Asp Phe Arg Gly Arg
        115                 120                 125

Ala Met Glu Val Leu Lys Gly Cys Gly Val Glu Met Leu Ile Ile Asp
        130                 135                 140

Glu Ala Asp Arg Leu Lys Pro Glu Thr Phe Ala Glu Val Arg Asp Ile
145                 150                 155                 160

Tyr Asp Lys Leu Gly Ile Ala Val Val Leu Val Gly Thr Asp Arg Leu
                165                 170                 175

Glu Ala Val Ile Lys Arg Asp Glu Gln Val Tyr Asn Arg Phe Arg Ala
            180                 185                 190

Cys His Arg Phe Gly Lys Leu Ser Gly Lys Asp Phe Gln Asp Thr Val
        195                 200                 205

Gln Ala Trp Glu Asp Arg Val Leu Lys Leu Pro Val Ser Ser Asn Leu
210                 215                 220
```

```
Thr Ser Lys Asp Met Leu Arg Ile Leu Thr Ser Ala Thr Glu Gly Tyr
225                 230                 235                 240

Ile Gly Arg Leu Asp Glu Ile Leu Arg Glu Thr Ala Ile Arg Ser Leu
                245                 250                 255

Ser Lys Gly Phe Lys Lys Ile Asp Lys Ala Val Leu Gln Glu Val Ala
                260                 265                 270

Lys Glu Tyr Lys
        275

<210> SEQ ID NO 99
<211> LENGTH: 276
<212> TYPE: PRT
<213> ORGANISM: Nostoc sp.

<400> SEQUENCE: 99

Met Thr Asp Ala Lys Ala Ile Ala Gln Gln Leu Gly Gly Val Lys Pro
1               5                   10                  15

Asp Glu Glu Trp Leu Gln Ala Glu Ile Ala Arg Leu Lys Gly Lys Ser
                20                  25                  30

Ile Val Pro Leu Gln Gln Val Arg Ser Leu His Asp Trp Leu Asp Gly
            35                  40                  45

Lys Arg Lys Ala Arg Gln Phe Cys Arg Val Val Gly Glu Ser Arg Thr
50                  55                  60

Gly Lys Thr Val Ala Cys Asp Ala Tyr Arg Tyr Arg Gln Lys Val Gln
65                  70                  75                  80

Ala Glu Val Gly Arg Pro Pro Ile Val Pro Val Val Tyr Ile Gln Pro
                85                  90                  95

Pro Gln Lys Cys Gly Ala Lys Asp Leu Phe Gln Glu Ile Ile Glu Tyr
            100                 105                 110

Leu Lys Phe Lys Ala Thr Lys Gly Thr Val Ser Asp Phe Arg Gly Arg
        115                 120                 125

Thr Met Glu Val Leu Lys Gly Cys Gly Val Glu Met Ile Ile Val Asp
    130                 135                 140

Glu Ala Asp Arg Leu Lys Pro Glu Thr Phe Ala Glu Val Arg Asp Ile
145                 150                 155                 160

Tyr Asp Lys Leu Gly Ile Ala Val Val Leu Val Gly Thr Asp Arg Leu
                165                 170                 175

Glu Ala Val Ile Lys Arg Asp Glu Gln Val Tyr Asn Arg Phe Arg Ala
            180                 185                 190

Cys His Arg Phe Gly Lys Leu Ser Gly Lys Asp Phe Gln Asp Thr Val
        195                 200                 205

Gln Ala Trp Glu Asp Lys Ile Leu Lys Leu Pro Leu Pro Ser Asn Leu
    210                 215                 220

Ile Ser Lys Asp Met Leu Arg Ile Leu Thr Ser Ala Thr Glu Gly Tyr
225                 230                 235                 240

Ile Gly Arg Leu Asp Glu Ile Leu Arg Glu Ala Ala Ile Arg Ser Leu
                245                 250                 255

Ser Arg Gly Leu Lys Lys Ile Asp Lys Pro Val Leu Gln Glu Val Ala
            260                 265                 270

Gln Glu Tyr Lys
        275

<210> SEQ ID NO 100
<211> LENGTH: 279
<212> TYPE: PRT
```

<213> ORGANISM: Nostoc sp.

<400> SEQUENCE: 100

Met Thr Asn Ala Met Ser Leu Ala Lys Gln Phe Gly Val Ile Gln Glu
1               5                   10                  15

Leu Thr Pro Glu Ile Gln Ala Glu Ile Glu Arg Leu Ser Arg Gln Pro
            20                  25                  30

Tyr Leu Glu Leu Asp Gln Val Lys Arg Cys His Ala Trp Met Tyr Glu
        35                  40                  45

Leu Val Ile Ser Arg Met Thr Gly Leu Leu Leu Gly Glu Ser Arg Cys
    50                  55                  60

Gly Lys Thr Val Thr Cys Lys Ala Phe Ala Asn Leu Tyr Asn Lys Leu
65                  70                  75                  80

Arg Gln Thr Lys Gly Gln Arg Met Lys Pro Val Val Tyr Ile Gln Val
                85                  90                  95

Gly Lys Asn Cys Gly Ser Arg Asp Phe Phe Met Lys Ile Leu Lys Ala
            100                 105                 110

Leu Asn Lys Pro Ser Asn Gly Thr Ile Ser Asp Leu Arg Glu Arg Thr
        115                 120                 125

Leu Asp Ser Leu Ala Ile His Gln Val Glu Met Leu Ile Ile Asp Glu
    130                 135                 140

Ala Asn His Leu Lys Phe Glu Thr Phe Ser Asp Val Arg His Ile Tyr
145                 150                 155                 160

Asp Asp Asp Glu Leu Lys Ile Ser Val Leu Leu Val Gly Thr Thr Ser
                165                 170                 175

Arg Leu Leu Ala Ile Val Lys Arg Asp Glu Gln Val Val Asn Arg Phe
            180                 185                 190

Leu Glu Gln Phe Glu Leu Asp Arg Leu Glu Asp Thr Gln Phe Lys Gln
        195                 200                 205

Met Ile Gln Ile Trp Glu Arg Asp Val Leu Arg Leu Pro Glu Glu Ser
    210                 215                 220

Lys Leu Ala Ser Gly Asp Asn Leu Lys Ile Leu Lys Gln Ala Thr Lys
225                 230                 235                 240

Lys Leu Ile Gly Arg Leu Asp Met Ile Leu Arg Lys Ala Ile Arg
                245                 250                 255

Ser Leu Leu Arg Gly Gln Lys Gln Val Asp Lys Asp Ile Leu Lys Glu
            260                 265                 270

Val Ile Ala Ala Ser Lys Leu
            275

<210> SEQ ID NO 101
<211> LENGTH: 276
<212> TYPE: PRT
<213> ORGANISM: Scytonema hofmanni

<400> SEQUENCE: 101

Met Thr Glu Ala Gln Ala Ile Ala Lys Gln Leu Gly Gly Val Lys Pro
1               5                   10                  15

Asp Asp Glu Trp Leu Gln Ala Glu Ile Ala Arg Leu Lys Gly Lys Ser
            20                  25                  30

Ile Val Pro Leu Gln Gln Val Lys Thr Leu His Asp Trp Leu Asp Gly
        35                  40                  45

Lys Arg Lys Ala Arg Lys Ser Cys Arg Val Val Gly Glu Ser Arg Thr
    50                  55                  60

Gly Lys Thr Val Ala Cys Asp Ala Tyr Arg Tyr Arg His Lys Pro Gln

```
            65                  70                  75                  80
    Gln Glu Ala Gly Arg Pro Pro Thr Val Pro Val Tyr Ile Arg Pro
                    85                  90                  95

His Gln Lys Cys Gly Pro Lys Asp Leu Phe Lys Lys Ile Thr Glu Tyr
                100                 105                 110

Leu Lys Tyr Arg Val Thr Lys Gly Thr Val Ser Asp Phe Arg Asp Arg
                115                 120                 125

Thr Ile Glu Val Leu Lys Gly Cys Gly Val Glu Met Leu Ile Ile Asp
    130                 135                 140

Glu Ala Asp Arg Leu Lys Pro Glu Thr Phe Ala Asp Val Arg Asp Ile
    145                 150                 155                 160

Ala Glu Asp Leu Gly Ile Ala Val Val Leu Val Gly Thr Asp Arg Leu
                    165                 170                 175

Asp Ala Val Ile Lys Arg Asp Glu Gln Val Leu Glu Arg Phe Arg Ala
                180                 185                 190

His Leu Arg Phe Gly Lys Leu Ser Gly Glu Asp Phe Lys Asn Thr Val
                195                 200                 205

Glu Met Trp Glu Gln Met Val Leu Lys Leu Pro Val Ser Ser Asn Leu
    210                 215                 220

Lys Ser Lys Glu Met Leu Arg Ile Leu Thr Ser Ala Thr Glu Gly Tyr
    225                 230                 235                 240

Ile Gly Arg Leu Asp Glu Ile Leu Arg Glu Ala Ala Ile Arg Ser Leu
                    245                 250                 255

Ser Arg Gly Leu Lys Lys Ile Asp Lys Ala Val Leu Gln Val Ala
                260                 265                 270

Lys Glu Tyr Lys
                275

<210> SEQ ID NO 102
<211> LENGTH: 278
<212> TYPE: PRT
<213> ORGANISM: Scytonema sp.

<400> SEQUENCE: 102

Met Ala Glu Asp Tyr Leu Arg Lys Trp Val Gln Asn Leu Trp Gly Asp
    1               5                   10                  15

Asp Pro Ile Pro Glu Glu Leu Leu Pro Ile Ile Glu Arg Leu Ile Thr
                    20                  25                  30

Pro Ser Val Val Glu Leu Glu His Ile Gln Lys Ile His Asp Trp Leu
                35                  40                  45

Asp Ser Leu Arg Leu Ser Lys Gln Cys Gly Arg Ile Val Ala Pro Pro
    50                  55                  60

Arg Ala Gly Lys Ser Val Thr Cys Asp Val Tyr Lys Leu Leu Asn Lys
    65                  70                  75                  80

Pro Gln Lys Arg Thr Gly Lys Arg Asp Ile Val Pro Val Leu Tyr Met
                    85                  90                  95

Gln Ala Pro Gly Asp Cys Ser Ala Gly Glu Leu Leu Thr Leu Ile Leu
                100                 105                 110

Glu Ser Leu Lys Tyr Asp Ala Thr Ser Gly Lys Leu Thr Asp Leu Arg
                115                 120                 125

Arg Arg Val Leu Arg Leu Lys Glu Ser Arg Val Glu Met Leu Val
    130                 135                 140

Ile Asp Glu Ala Asn Phe Leu Lys Leu Asn Thr Phe Ser Glu Ile Ala
    145                 150                 155                 160
```

```
Arg Ile Tyr Asp Leu Leu Lys Ile Ser Ile Val Leu Val Gly Thr Asp
            165                 170                 175

Gly Leu Asp Asn Leu Ile Lys Lys Glu Arg Tyr Ile His Asp Arg Phe
        180                 185                 190

Ile Glu Cys Tyr Lys Leu Pro Leu Val Ser Glu Asn Lys Phe Pro Glu
        195                 200                 205

Phe Val Gln Ile Trp Glu Asp Glu Val Leu Cys Leu Pro Val Pro Ser
    210                 215                 220

Asn Leu Ile Lys Ser Glu Thr Leu Lys Pro Leu Tyr Gln Lys Thr Ser
225                 230                 235                 240

Gly Lys Ile Gly Leu Val Asp Arg Val Leu Arg Arg Ala Ala Ile Leu
            245                 250                 255

Ser Leu Arg Lys Gly Leu Lys Asn Ile Asp Lys Ala Thr Leu Asp Glu
        260                 265                 270

Val Leu Glu Trp Phe Glu
        275

<210> SEQ ID NO 103
<211> LENGTH: 283
<212> TYPE: PRT
<213> ORGANISM: Spirulina major

<400> SEQUENCE: 103

Met Ala Ser Ala Glu Ser Lys Ala Lys Ala Glu Ala Val Ala Gln Gln
1               5                   10                  15

Leu Gly Asn Phe Glu Lys Thr Glu Glu Asp Leu Ala Lys Glu Ile Gln
            20                  25                  30

Arg Leu Arg Arg Arg Asn Val Val Gln Leu Glu Gln Val Lys Gln Leu
        35                  40                  45

His Asn Trp Leu Glu Gly Lys Arg Arg Ser Arg Gln Cys Cys Arg Val
    50                  55                  60

Val Gly Glu Ser Arg Thr Gly Lys Thr Ile Gly Cys Asn Ala Tyr Arg
65                  70                  75                  80

Leu Arg His Lys Pro Ile Gln Glu Thr Gly Lys Pro Pro Ile Val Pro
                85                  90                  95

Val Val Tyr Ile Glu Pro Pro Gln Asp Cys Gly Ser Ile Asp Leu Phe
            100                 105                 110

Arg Ala Ile Ile Glu Tyr Leu Lys Tyr Lys Val Gln Ser Arg Glu Lys
        115                 120                 125

Val Arg Glu Leu Arg Ser Arg Ala Met Lys Val Leu Glu Arg Cys Gln
    130                 135                 140

Val Glu Thr Leu Ile Ile Asp Glu Ala Asp Arg Leu Lys Pro Lys Thr
145                 150                 155                 160

Phe Ala Asp Val Arg Asp Ile Phe Asp Lys Arg Asn Ile Ser Val Val
                165                 170                 175

Leu Val Gly Thr Asp Arg Leu Asp Asn Val Ile Lys Arg Asp Glu Gln
            180                 185                 190

Val His Asn Arg Phe Arg Ala Cys Tyr Arg Phe Gly Lys Leu Thr Gly
        195                 200                 205

Thr Glu Phe Glu Gln Val Val Lys Ile Trp Arg Asp Ile Leu Arg
    210                 215                 220

Leu Pro Ile Pro Ser Asn Leu His Ala Lys Asn Met Leu Lys Ile Leu
225                 230                 235                 240

Gly Gln Ala Thr Gly Gly Tyr Ile Gly Leu Leu Asp Met Ile Leu Arg
                245                 250                 255
```

Glu Thr Ala Val Arg Ala Leu Glu Lys Gly Leu Gly Lys Ile Asn Leu
            260                 265                 270

Glu Thr Leu Lys Glu Val Ala Glu Tyr Ser
        275                 280

<210> SEQ ID NO 104
<211> LENGTH: 270
<212> TYPE: PRT
<213> ORGANISM: Geminocystis sp.

<400> SEQUENCE: 104

Met Thr Lys Ala Gln Ser Ile Ala Lys Glu Leu Gly Asp Leu Gly Gln
1               5                   10                  15

Asp Glu Gln Trp Leu His Gln Glu Ile Cys Arg Leu Asn Arg Ser Ser
            20                  25                  30

Ile Val Pro Leu Glu His Leu Lys Asp Leu His Asn Trp Leu Asp Glu
        35                  40                  45

Lys Arg Lys Ala Arg Gln Ser Cys Arg Ile Val Gly Glu Ser Arg Thr
    50                  55                  60

Gly Lys Thr Ile Ala Cys Glu Ser Tyr Lys Leu Arg Asn Lys Pro Ser
65                  70                  75                  80

Gln Lys Gly Gln Gln Thr Pro Ser Val Pro Val Val Tyr Ile Met Pro
                85                  90                  95

Pro Ala Lys Cys Ser Ala Lys Asp Phe Phe Arg Glu Ile Ile Glu Ala
            100                 105                 110

Leu Arg Tyr Arg Ala Val Lys Gly Thr Val Ser Asp Phe Arg Ser Arg
        115                 120                 125

Ala Met Asp Val Leu Lys Ala Cys Asp Val Glu Met Leu Ile Val Asp
    130                 135                 140

Glu Ala Asp Arg Leu Lys Pro Asp Thr Phe Pro Glu Val Arg Asp Ile
145                 150                 155                 160

Ser Asp Lys Leu Glu Met Leu Val Val Leu Val Gly Thr Asp Arg Leu
                165                 170                 175

Asp Ala Val Ile Lys Arg Asp Glu Gln Val Tyr Asn Arg Phe Arg Ser
            180                 185                 190

His Arg Arg Phe Gly Lys Leu Thr Gly Glu Asp Phe Lys Glu Thr Val
        195                 200                 205

Ser Ile Trp Glu Lys Glu Val Leu Asn Leu Pro Val Ala Ser Asn Leu
    210                 215                 220

Thr Lys Leu Asp Met Phe Lys Ile Ile Thr Lys Ala Thr Gly Gly Tyr
225                 230                 235                 240

Ile Gly Arg Leu Asp Glu Leu Leu Arg Glu Ala Ala Ile Lys Ser Leu
                245                 250                 255

Ser Arg Gly Lys Lys Ala Leu Lys Arg Ile Phe Tyr Arg Arg
            260                 265                 270

<210> SEQ ID NO 105
<211> LENGTH: 284
<212> TYPE: PRT
<213> ORGANISM: Nostoc sp.

<400> SEQUENCE: 105

Met Ala Gln Ser Gln Leu Val Ile Gln Pro Asn Val Glu Thr Leu Ala
1               5                   10                  15

Pro Gln Leu Glu Leu Asn Asn Gln Leu Ala Lys Val Val Glu Ile Glu
            20                  25                  30

Glu Ile Phe Ser Asn Cys Phe Ile Pro Thr Asp Arg Ala Cys Glu Tyr
            35                  40                  45

Phe Arg Trp Leu Asp Glu Leu Arg Ile Leu Lys Gln Cys Gly Arg Val
 50                  55                  60

Val Gly Pro Arg Asp Val Gly Lys Ser Arg Ala Ser Val His Tyr Arg
 65                  70                  75                  80

Glu Glu Asp Arg Lys Lys Val Ser Tyr Val Arg Ala Trp Ser Ala Ser
                 85                  90                  95

Ser Ser Lys Arg Leu Phe Ser Gln Ile Leu Lys Asp Ile Asn His Ala
                100                 105                 110

Ala Pro Thr Gly Lys Arg Glu Asp Leu Arg Pro Arg Leu Ala Gly Ser
                115                 120                 125

Leu Glu Leu Phe Gly Ile Glu Gln Val Ile Val Asp Asn Ala Asp Asn
130                 135                 140

Leu Gln Arg Glu Ala Leu Leu Asp Leu Lys Gln Leu Phe Asp Glu Ser
145                 150                 155                 160

Asn Val Ser Val Val Leu Val Gly Gly Gln Glu Leu Asp Lys Ile Leu
                165                 170                 175

His Asp Cys Asp Leu Leu Thr Ser Phe Pro Thr Leu Tyr Glu Phe Asp
                180                 185                 190

Thr Leu Glu Asp Asp Asp Phe Lys Lys Thr Leu Ser Thr Ile Glu Phe
                195                 200                 205

Asp Val Leu Ala Leu Pro Gln Ala Ser Asn Leu Cys Glu Gly Ile Thr
210                 215                 220

Phe Glu Ile Leu Val Gln Ser Thr Gly Gly Arg Ile Gly Leu Leu Val
225                 230                 235                 240

Lys Ile Leu Thr Lys Ala Val Leu His Ser Leu Lys Asn Gly Phe Gly
                245                 250                 255

Arg Val Asp Gln Asn Ile Leu Glu Lys Ile Ala Asn Arg Tyr Gly Lys
                260                 265                 270

Arg Tyr Ile Pro Pro Glu Asn Arg Asn Lys Asn Ser
                275                 280

<210> SEQ ID NO 106
<211> LENGTH: 276
<212> TYPE: PRT
<213> ORGANISM: Cyanothece sp.

<400> SEQUENCE: 106

Met Thr Gln Ala Gln Glu Ile Ala Gln Lys Leu Gly Asp Leu Asn Pro
1               5                   10                  15

Asp Glu Gln Trp Leu Gln Met Glu Ile Ala Arg Leu Asn Arg Gln Ser
                20                  25                  30

Ile Val Pro Leu Glu His Ile Arg Asp Leu His Glu Trp Leu Asp Gly
            35                  40                  45

Lys Arg Lys Ala Arg Gln Ser Cys Arg Leu Val Gly Glu Ser Arg Thr
 50                  55                  60

Gly Lys Thr Val Ala Cys Glu Ala Tyr Thr Leu Arg Asn Lys Pro Ile
 65                  70                  75                  80

Gln Gln Gly Arg Gln Thr Pro Ile Val Pro Val Tyr Ile Met Pro
                 85                  90                  95

Pro Thr Lys Cys Gly Ser Lys Asp Leu Phe Lys Glu Ile Ile Glu Tyr
                100                 105                 110

Leu Arg Tyr Lys Ala Val Lys Gly Thr Val Ser Glu Phe Arg Ser Arg

```
            115                 120                 125
Ala Met Glu Val Leu Lys Gly Cys Glu Val Glu Met Ile Ile Ile Asp
    130                 135                 140

Glu Ala Asp Arg Leu Lys Pro Asp Thr Phe Pro Asp Val Arg Asp Ile
145                 150                 155                 160

Asn Asp Lys Leu Glu Ile Ser Val Val Leu Val Gly Asn Asp Arg Leu
                165                 170                 175

Asp Ala Val Ile Lys Arg Asp Glu Gln Val Tyr Asn Arg Phe Arg Ala
            180                 185                 190

His Arg Arg Phe Gly Lys Leu Ala Gly Val Glu Phe Lys Lys Thr Val
        195                 200                 205

Ala Ile Trp Glu Glu Lys Val Leu Lys Leu Pro Val Ala Ser Asn Leu
    210                 215                 220

Thr Ser Ser Ala Leu Ile Lys Ile Leu Val Lys Ala Thr Glu Gly Tyr
225                 230                 235                 240

Ile Gly Arg Leu Asp Glu Ile Leu Arg Glu Ala Ala Ile Lys Ser Leu
                245                 250                 255

Met Lys Gly His Lys Arg Ile Glu Lys Glu Val Leu Gln Glu Val Ala
            260                 265                 270

Lys Glu Tyr Ser
        275

<210> SEQ ID NO 107
<211> LENGTH: 283
<212> TYPE: PRT
<213> ORGANISM: Calothrix sp.

<400> SEQUENCE: 107

Met Ala Arg Ser Gln Leu Ala Ile Gln Ser Ser Val Glu Val Leu Val
1               5                   10                  15

Pro Gln Leu Asp Leu Asn Ala Gln Leu Ala Lys Val Val Glu Val Glu
            20                  25                  30

Glu Ile Phe Ser Asn Tyr Phe Ile Pro Thr Asp Arg Ser Ser Glu Tyr
        35                  40                  45

Leu Arg Trp Leu Asp Glu Leu Arg Ile Leu Arg Gln Cys Gly Arg Val
    50                  55                  60

Ile Gly Pro Arg Asp Val Gly Lys Ser Arg Ala Ser Leu His Tyr Gln
65                  70                  75                  80

Gly Gln Asp Gln Lys Arg Ile Ser Tyr Val Arg Ala Trp Ser Ala Ser
                85                  90                  95

Ser Ser Lys Arg Leu Phe Ser Gln Ile Leu Lys Asp Ile Lys His Ala
            100                 105                 110

Ala Pro Met Gly Lys Arg Asp Asp Leu Arg Pro Arg Leu Ala Gly Ser
        115                 120                 125

Leu Glu Val Phe Gly Phe Glu Gln Val Ile Ile Asp Asn Ala Glu Asn
    130                 135                 140

Leu Gln Lys Glu Ala Leu Leu Asp Leu Lys Gln Leu Phe Asp Glu Cys
145                 150                 155                 160

His Val Pro Ile Val Leu Ile Gly Gly Gln Glu Leu Asp Thr Ile Leu
                165                 170                 175

Asp Glu Phe Asp Leu Leu Thr Cys Phe Pro Thr Leu Tyr Glu Phe Asp
            180                 185                 190

Gly Leu Asp Glu Asn Asp Phe Lys Lys Thr Leu Asn Thr Ile Glu Phe
        195                 200                 205
```

```
Asp Ile Leu Ala Leu Pro Glu Ala Ser Asn Leu Ser Glu Gly Ile Ile
    210                 215                 220

Phe Glu Leu Leu Ala Glu Ser Thr Gly Ala Arg Ile Gly Leu Leu Val
225                 230                 235                 240

Lys Ile Leu Thr Lys Ala Val Leu His Ser Leu Lys Asn Gly Phe Ser
                245                 250                 255

Lys Ile Asp Gln Asn Ile Leu Glu Lys Ile Ala Asn Arg Tyr Gly Arg
            260                 265                 270

Arg Tyr Ile Pro Pro Glu Lys Arg Asn Asn Lys
        275                 280
```

<210> SEQ ID NO 108
<211> LENGTH: 283
<212> TYPE: PRT
<213> ORGANISM: Anabaena cylindrica

<400> SEQUENCE: 108

```
Met Ala Gln Pro Gln Leu Ala Thr Gln Ser Ile Val Glu Val Leu Ala
1               5                   10                  15

Pro Arg Leu Asp Ile Lys Ala Gln Ile Ala Lys Thr Ile Asp Ile Glu
            20                  25                  30

Glu Ile Phe Arg Ala Cys Phe Ile Thr Thr Asp Arg Ala Ser Glu Cys
        35                  40                  45

Phe Arg Trp Leu Asp Glu Leu Arg Ile Leu Lys Gln Cys Gly Arg Ile
50                  55                  60

Ile Gly Pro Arg Asn Val Gly Lys Ser Arg Ala Ala Leu His Tyr Arg
65                  70                  75                  80

Asp Glu Asp Lys Lys Arg Val Ser Tyr Val Lys Ala Trp Ser Ala Ser
                85                  90                  95

Ser Ser Lys Arg Leu Phe Ser Gln Ile Leu Lys Asp Ile Asn His Ala
            100                 105                 110

Ala Pro Thr Gly Lys Arg Gln Asp Leu Arg Pro Arg Leu Ala Gly Ser
        115                 120                 125

Leu Glu Leu Phe Gly Leu Glu Leu Val Ile Ile Asp Asn Ala Glu Asn
130                 135                 140

Leu Gln Lys Glu Ala Leu Leu Asp Leu Lys Gln Leu Phe Glu Glu Cys
145                 150                 155                 160

Asn Val Pro Ile Val Leu Ala Gly Gly Lys Glu Leu Asp Asp Leu Leu
                165                 170                 175

His Asp Cys Asp Leu Leu Thr Asn Phe Pro Thr Leu Tyr Glu Phe Glu
            180                 185                 190

Arg Leu Glu Tyr Asp Asp Phe Lys Lys Thr Leu Thr Thr Ile Glu Leu
        195                 200                 205

Asp Val Leu Ser Leu Pro Glu Ala Ser Asn Leu Ala Glu Gly Asn Ile
210                 215                 220

Phe Glu Ile Leu Ala Val Ser Thr Glu Ala Arg Met Gly Ile Leu Ile
225                 230                 235                 240

Lys Ile Leu Thr Lys Ala Val Leu His Ser Leu Lys Asn Gly Phe His
                245                 250                 255

Arg Val Asp Glu Ser Ile Leu Glu Lys Ile Ala Ser Arg Tyr Gly Thr
            260                 265                 270

Lys Tyr Ile Pro Leu Lys Asn Arg Asn Arg Asp
        275                 280
```

<210> SEQ ID NO 109

```
<211> LENGTH: 284
<212> TYPE: PRT
<213> ORGANISM: Anabaena sp.

<400> SEQUENCE: 109

Met Ala Arg Ser Gln Leu Ala Asn Gln Pro Ile Val Glu Val Leu Ala
1               5                   10                  15

Pro Gln Leu Asp Leu Asn Ala Gln Ile Ala Lys Ala Ile Asp Ile Glu
            20                  25                  30

Glu Ile Phe Arg Asn Cys Phe Ile Thr Thr Asp Arg Val Ser Glu Cys
        35                  40                  45

Phe Arg Trp Leu Asp Glu Leu Arg Ile Leu Lys Gln Cys Gly Arg Ile
50                  55                  60

Ile Gly Pro Arg Asn Val Gly Lys Ser Arg Ala Ala Leu His Tyr Arg
65                  70                  75                  80

Asp Glu Asp Lys Lys Arg Ile Ser Tyr Val Lys Ala Trp Ser Ala Ser
                85                  90                  95

Ser Ser Lys Arg Ile Phe Ser Gln Ile Leu Lys Asp Ile Asn His Ala
            100                 105                 110

Ala Pro Thr Gly Lys Arg Gln Asp Leu Arg Pro Arg Leu Ala Gly Ser
        115                 120                 125

Leu Glu Leu Phe Gly Leu Glu Leu Val Ile Ile Asp Asn Ala Asp Asn
130                 135                 140

Leu Gln Lys Glu Ala Leu Ile Asp Leu Lys Gln Leu Phe Glu Glu Cys
145                 150                 155                 160

His Val Pro Ile Val Leu Ile Gly Gly Lys Glu Leu Asp Asn Ile Leu
                165                 170                 175

Gln Asp Cys Asp Leu Leu Thr Asn Phe Pro Thr Leu Tyr Glu Phe Glu
            180                 185                 190

Arg Leu Glu Tyr Asp Asp Phe Arg Lys Thr Leu Ser Thr Ile Glu Leu
        195                 200                 205

Asp Ile Leu Ser Leu Pro Glu Ser Ser His Leu Ala Glu Gly Asn Ile
210                 215                 220

Phe Glu Ile Leu Ala Val Ser Thr Ser Gly Arg Met Gly Ile Leu Val
225                 230                 235                 240

Lys Ile Leu Thr Lys Ala Val Leu His Ser Leu Lys Asn Gly Phe Gly
                245                 250                 255

Arg Val Asp Glu Ser Ile Leu Glu Lys Ile Ala Ser Arg Tyr Gly Thr
            260                 265                 270

Lys Tyr Val Pro Leu Glu Asn Arg Asn Arg Asn Glu
        275                 280

<210> SEQ ID NO 110
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 110
atcgcaacca actgtcctga agaagggcga ttgaaag                            37

<210> SEQ ID NO 111
<211> LENGTH: 37
<212> TYPE: DNA
<213> ORGANISM: Unknown
```

```
<220> FEATURE:
<221> NAME/KEY: source
<223> OTHER INFORMATION: /note="Description of Unknown:
      Direct repeat nucleotide sequence"

<400> SEQUENCE: 111
gtaacaacaa ccctcctagt acagggtggg ttgaaag                               37

<210> SEQ ID NO 112
<211> LENGTH: 36
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 112
gtttcaacga ccatcccggc tagggcggg ttgaaa                                 36

<210> SEQ ID NO 113
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 113
gtgacaatag cccttcccgt gttgagcggg ttgaaag                               37

<210> SEQ ID NO 114
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 114
gtttcaacac ccctcccgaa gtgggcggg ttgaaag                                37

<210> SEQ ID NO 115
<211> LENGTH: 28
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 115
ggtcgccaaa agcatttcag ggcagggc                                        28

<210> SEQ ID NO 116
<211> LENGTH: 36
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 116
gtgctgtaac ctaagatgtc gcaaggcgtt gagcag                               36
```

<210> SEQ ID NO 117
<211> LENGTH: 39
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 117
gagtttcatc aaccctcctg atgtgggatg ggttgaaag                                39

<210> SEQ ID NO 118
<211> LENGTH: 38
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 118
gtttcataca ggtttttgac ctcccattga ttgaaaga                                 38

<210> SEQ ID NO 119
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 119
gttgaaataa gaaaataacct tctctaggga ttgaaag                                 37

<210> SEQ ID NO 120
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 120
gtttcatcca ggtttgcggc aaggggggcga ttgaaag                                 37

<210> SEQ ID NO 121
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 121
gtttcaacga ccactttaag atgggtatgg ttgaaag                                  37

<210> SEQ ID NO 122
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

```
<400> SEQUENCE: 122
gtggcaacaa ccctccaggt actgggtggg ttgaaag                              37

<210> SEQ ID NO 123
<211> LENGTH: 38
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 123
cgttgcaacc ctccttccag taatgggagg gttgaaag                             38

<210> SEQ ID NO 124
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 124
gttgcaatga cccttcccgt gttgagcggg ttgaaag                              37

<210> SEQ ID NO 125
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 125
gtggcaacaa ccttccaggt actaggtggg ttgaaag                              37

<210> SEQ ID NO 126
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 126
gtttcaacaa ccatcccggc tagggtggg ttgaaag                               37

<210> SEQ ID NO 127
<211> LENGTH: 39
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 127
gtttcaatga ccatcccacg ttgggatgga ttgaaagag                            39

<210> SEQ ID NO 128
<211> LENGTH: 25
<212> TYPE: DNA
```

```
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 128
gattcttcgt aaactcagaa tgaca                                          25

<210> SEQ ID NO 129
<211> LENGTH: 36
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 129
gttgcagatg aatttacttc tctgtgcgat cgaaag                              36

<210> SEQ ID NO 130
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 130
gtttcaacga ccatcccggc tagggtggg ttgaaag                              37

<210> SEQ ID NO 131
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 131
gtttcaacga ccattcccaa cagggatggg ttgaaag                             37

<210> SEQ ID NO 132
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 132
gtttcaacta ccatcccgac tagggtggg ttgaaag                              37

<210> SEQ ID NO 133
<211> LENGTH: 37
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 133
gtttcaacac ccctcccgga gtggggcggg ttgaaag                             37
```

```
<210> SEQ ID NO 134
<211> LENGTH: 38
<212> TYPE: DNA
<213> ORGANISM: Unknown
<220> FEATURE:
<221> NAME/KEY: source
<223> OTHER INFORMATION: /note="Description of Unknown:
      Direct repeat nucleotide sequence"

<400> SEQUENCE: 134
gtttccaaag ccctctcgtt aggtggtggg ttgaaagt                           38

<210> SEQ ID NO 135
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 135
tctaacagat tgactgtcg                                               19

<210> SEQ ID NO 136
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 136
aataacactt tatttgtcg                                               19

<210> SEQ ID NO 137
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 137
attcgcaaat tcaatgtcg                                               19

<210> SEQ ID NO 138
<211> LENGTH: 29
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 138
tttggacaat aattctttaa aactggttt                                    29

<210> SEQ ID NO 139
<211> LENGTH: 19
<212> TYPE: DNA
<213> ORGANISM: Unknown
<220> FEATURE:
<221> NAME/KEY: source
<223> OTHER INFORMATION: /note="Description of Unknown:
```

Transposon end motif"

<400> SEQUENCE: 139
aatgatagaa tagctgtag                                          19

<210> SEQ ID NO 140
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 140
ggcagcaata cgggatgca                                          19

<210> SEQ ID NO 141
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 141
attgactcat taactgaca                                          19

<210> SEQ ID NO 142
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 142
cttgacaaat tatttgtca                                          19

<210> SEQ ID NO 143
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 143
attcgcaaat taaatgtcg                                          19

<210> SEQ ID NO 144
<211> LENGTH: 21
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 144
ggtgcatccg acttgtaagc g                                       21

<210> SEQ ID NO 145
<211> LENGTH: 19

```
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 145
agtgactaat tatatgtca                                              19

<210> SEQ ID NO 146
<211> LENGTH: 20
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 146
gagagtacat cgttgacata                                             20

<210> SEQ ID NO 147
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 147
agtgactaat tatatgtcg                                              19

<210> SEQ ID NO 148
<211> LENGTH: 20
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 148
gagagcgcta cgttgacatt                                             20

<210> SEQ ID NO 149
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 149
ttcgacaaat tagctgtca                                              19

<210> SEQ ID NO 150
<211> LENGTH: 18
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 150
```

```
gtagtaaatg cttgttat                                                  18

<210> SEQ ID NO 151
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 151
agtaacagat tatttgtcg                                                 19

<210> SEQ ID NO 152
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 152
agtaacaaat tatttgtca                                                 19

<210> SEQ ID NO 153
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 153
gttcgcaaat taaatgtcg                                                 19

<210> SEQ ID NO 154
<211> LENGTH: 18
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 154
taatcaacaa taaaacat                                                  18

<210> SEQ ID NO 155
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 155
agtgccacat taattgtca                                                 19

<210> SEQ ID NO 156
<211> LENGTH: 19
<212> TYPE: DNA
<213> ORGANISM: Unknown
<220> FEATURE:
<221> NAME/KEY: source
```

<223> OTHER INFORMATION: /note="Description of Unknown:
     Transposon end motif"

<400> SEQUENCE: 156
agcgacaaat aatttgtcg                                                19

<210> SEQ ID NO 157
<211> LENGTH: 19
<212> TYPE: DNA
<213> ORGANISM: Unknown
<220> FEATURE:
<221> NAME/KEY: source
<223> OTHER INFORMATION: /note="Description of Unknown:
     Transposon end motif"

<400> SEQUENCE: 157
ggcgcacttc gttcgggat                                                19

<210> SEQ ID NO 158
<211> LENGTH: 19
<212> TYPE: DNA
<213> ORGANISM: Unknown
<220> FEATURE:
<221> NAME/KEY: source
<223> OTHER INFORMATION: /note="Description of Unknown:
     Transposon end motif"

<400> SEQUENCE: 158
attcgcaaat tgaatgtcg                                                19

<210> SEQ ID NO 159
<211> LENGTH: 21
<212> TYPE: DNA
<213> ORGANISM: Unknown
<220> FEATURE:
<221> NAME/KEY: source
<223> OTHER INFORMATION: /note="Description of Unknown:
     Transposon end motif"

<400> SEQUENCE: 159
ggagcatcag actcttaatt t                                             21

<210> SEQ ID NO 160
<211> LENGTH: 19
<212> TYPE: DNA
<213> ORGANISM: Unknown
<220> FEATURE:
<221> NAME/KEY: source
<223> OTHER INFORMATION: /note="Description of Unknown:
     Transposon end motif"

<400> SEQUENCE: 160
gcaagtcctt ttatccgct                                                19

<210> SEQ ID NO 161
<211> LENGTH: 19
<212> TYPE: DNA
<213> ORGANISM: Unknown
<220> FEATURE:
<221> NAME/KEY: source
<223> OTHER INFORMATION: /note="Description of Unknown:
     Transposon end motif"

<400> SEQUENCE: 161
tttaacaaat taagtgtca                                                19

<210> SEQ ID NO 162

```
<211> LENGTH: 22
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 162
gatcagtagg tcgtgggttt aa                                            22

<210> SEQ ID NO 163
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 163
agtgactaat tatttgtca                                                19

<210> SEQ ID NO 164
<211> LENGTH: 22
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 164
aatgacaata atttgtcaca aa                                            22

<210> SEQ ID NO 165
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 165
aataactaat taaatgtcg                                                19

<210> SEQ ID NO 166
<211> LENGTH: 19
<212> TYPE: DNA
<213> ORGANISM: Unknown
<220> FEATURE:
<221> NAME/KEY: source
<223> OTHER INFORMATION: /note="Description of Unknown:
      Transposon end motif"

<400> SEQUENCE: 166
aatgacaaat tgtttgtcg                                                19

<210> SEQ ID NO 167
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 167
```

```
tgatatttat tgttctatc acatcttcat aaatatctgc cattgtcaaa gttaagttaa      60
ctgaatctaa atgtaattta tcatcttttc ctaaatacttc cgttgaccaa tttccttgat   120
catcttgacg acaaacctcc acttttattt gattttgcta aactagaaca tattcctttta  180 gactgtctat agtttgataa ttaatgcgtt tttcacgttt gtctattgtt gctgtggaat    240
tagataaaac ttcagaaatg ttgaatgtcg ttacaaaact ttacatattt aagtatagta   300
gtattatcaa gggtaaaaat gtcaacattt cataatatct tccatccaat gaacataact   360
gatttgttga cacatacaag attgaagata gcggaattta tctaacatct tttcacccca  420
ttctttcgga acagataaat gtacagtgac taattatatg tcatcgtgac aaattaatgt  480
catcttataa atccttgctg tagaaggatt ttagcaattt aacgatatta tacttcaatc  540
cagttagtga caaaataaat gtcgtttccc atgattgtga caaattaact gtcgcgttac  600
cgattaaaaa aagttttttgt atattttcat aatgacaaat tgactgtcgc tttccagtaa  660
gctagaataa catcatgttt ttataaaatc tgtttgattt                          700

<210> SEQ ID NO 168
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 168
aggtaaaatg gtgtgcgatc gcccaacaca gaattaggta acaacaaccc accctatggt    60
gggttgaaag gttatcatat tcttataaaa agagggttga aagagagtac atcgttgaca   120
tatcgctctg atatatcaat aaatgacatt aatttgtcac taccattaaa acgacaacaa   180
tttgtcctaa cgacactaaa ttgtcaccga cgacatataa ttagtcactg tacaaaaagt   240
atggacggta ttggactcga accaacgacc ccatcgatgt caacgatgta ctctaaccac   300
ctgagctaac cgtccttaat cccatagact aataacgtat cacataaaat ataatttgtc   360
aatccctaaa atccaaattt tattctacat atatctagtc aactgtaccc gatagcgatc   420
cttttttgtc accgcaattt cccccaacttc caaccgacct tttccccgaa tagcgattaa  480 atccctgtt ttcacttgag                                                 500

<210> SEQ ID NO 169
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 169
aaaaatgatg cagttatgaa ttttttcgctt ctttgtctat agctttacac aatttcttgg   60
cttgggtgaa tttttgagca acaacttagt ttttctgtgg tatcggggtg caaataagta   120
attcaagctc tagttaacta acaaaactca actacgcgaa gacggaaaaa acacagaata  180
agtaaggata agtctacaag gttatctgtt cttgcttcgc catcaccaaa aaagaccgcc  240
gcaccccttc aatttcgcgt ggagccaact gtagtgcata tcgcctagtt gtttctgaag  300
ttttggacaa taattcttta aaactggatt gatggctgaa agctaggaaa tacgtaaatt  360
```

```
atgcgtttag cactgtcaaa tggacaataa ttctttaaaa ctgacaataa ttatttaaag      420
tacatattgt acattcgcac attatatgtc gcaatttgca acaacgaca  ttagacgaca      480 ttagcatctt gagcatctaa acgcttatc  gtataaagct ttcaggaaat tgttaattaa      540
aaacgttaaa ttcctgactt cgcacattgt atgtcgctaa cattaaagct cgcaaattaa      600
tgtcgttaat ctaaattttg tcacattgca aattcaatgt cgcattttct tcagttaatg      660
gtacattaat actaccaata actacattct cctcgcttaa                            700
```

<210> SEQ ID NO 170
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 170

```
agtaagaaga atagaagtaa tttcctgaaa tcaactatat ttggacatat tttaggaata       60
taactaaatt atgggagggt tgaaaggagc gctgcgatca aacaaatgtt aaggtaaaat      120
aattcgtctg tagcaaatac cacagttaat gagtaagcca tacgacgtta atttgcgaaa      180
aactaatatg attgaattaa cgacgcgaat tagcgaaagt aatgttaatt acctaaaaac      240
gacatcaatt tgcgaaaagc gacaaataat gtgcgaatgt acacatatgg agaataggga      300
actcgaatcc ctgacctctg cggtgcgatc gcagcgctct accaactgag ctaattcccc      360
tgactttgtt gagtgttcag ttaatcacac tcgtccatca tagagtattt taacattcag      420
ttagggatgg ctgagatttg ttgccagaaa aaacttcttg tactcgctct agttctaatt      480
cgctcagata atccacagtc                                                  500
```

<210> SEQ ID NO 171
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 171

```
gtgttaattt acttacctga gattaacaaa cattctttga gaataatcac aaaaaatgta       60
aagactaaat aaaagcagtc acctataagt aaatgaccta tgggcgtaac ccaataatgt      120
cttcaagcac aagttccaac tggtaacttg cagtattaat acttaaatat tttttttgtat     180 tcaaaaaaat ataaactaaa cttaataaaa attaacttta cttattgtta acaataatga     240
aggaattctt gatagatgtt tttattgttt tttgagattt aaaatgcgat cgctcgtaat      300
tatatttgat ataagtata  atttgacaca gtaacaaaaa tctacctacc ctcgtagaga      360
cgttccgccg gaacgtcttt acatttatta tgtgttgccc aaaaccattg tagagaggta      420
gcattgctac gtctctacgt gtacagtgac taattatatg tcgttgtgac aaattattgt      480
catcagtaaa atccttatac agtatagatt atagcgcttt ggcagtttta gcataacctc      540
tttgcagtga caaaatagat gtcgttgtcc gtgattgtga caattagct  gtcgctttgc      600 aagataggaa aaagcttttg tgtattttca taatgacaaa ttgactgtcg ctttgtatat      660
agatagaata acaatatgtt tttataaaaa agttttatat                            700
```

<210> SEQ ID NO 172
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 172
aatcttttaa accgagatta gttttgggtt tcagtaacta ttaaacttag gggtgggttg      60
aaagcaagtc cttttatccg cttgttttaa ttgctttgta taataattgc agagcatatt     120
atattgatga catttaattt gtcatcaatt aattaagcaa cgctgatggg tcacgacgac     180
aattaaatag tcacaatgac attaatctgt caccgacgac agataaattg tcactgtaca     240
ctacgccttt tgtggagatg tctaataaac taaaaatttt tgatagtgcg gataaaagga     300
cttgaacctt cactcctttc ggaactagaa cctaaatcta gcgcgtctgc caatttcgcc     360
atatccgcat cagtttccta tattaccata acgaattatc tgtggcaata gggattcggg     420
actgggacaa ggaggaattc ccaatgcccc atgccccatg cccaatgccc catgcccaat     480
gccccatgcc ccatgcccaa                                                 500

<210> SEQ ID NO 173
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 173
ataaaatacc caaatcttta ttgatctcct taatataata attattcaaa tcaataaaca      60
catcacagcc ttctaacttc aaaaacttcc aaatatcccc cgttgttact gcaccataaa     120
tagttgtcga ataactaatt aaatgtcgtc ttaacaaatt aatgtcgctc aaaacgtaaa     180
ggctataatc gttactaagc aaggattata gccttttttga tttctattta gcattcctaa     240
atatttaact aattaaacgt cgtaatttgt aaatataaca aaataagtgt cgttttttca     300
aaaaatctct ttccaaagtt tttaacggct cataacaaaa taagtgtcgt cttttggaag     360
tgagtaaaaa atctaaaatt acgtgtcgct ttttggaata aagtagtagt atatttacta     420
ggtaatagta attatgtacg aataaggtgt tacgcattta attttttttgc ccaaaagcct     480 tgcagcaagg actttaggct gcaaaatatt acatttagat gcgcgtcagc ttacaaacat     540
agttgtactc aagtcttctt atttctctct acttgcaaag tcattcctca tattgcgtta     600
aaggttgatg tgagttgagg ctgtatactt tgcttttcg ctcttagact tgctgtaccg     660
tattggctaa ccaactagtt tcaagcgatg aagtttgttt                           700

<210> SEQ ID NO 174
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 174
gtcaagtttg cttgtgaggg ttgaaaggaa tgtcaccttc ccaatactag aagagtgtca      60

| | |
|---|---|
| aaagctatgc tggctaatgg aaggttgaaa ttaatcgcta ttttttttgca aagaaaagat | 120 |
| tctaccagtt ataaaaaagc aagagtgaca aacaattagt cgttcaaaca aatgacaaat | 180 |
| tgtttgtcgc tctaaagtat cctagattac ttgactatac gagtttattt tttagggatt | 240 |
| aagctcgggg aaaagtttgt gatctactga cattcaagta acactgacaa ataatttgtc | 300 |
| actgtacaat actcaataag agtcggctac attaaatgac tataagacaa ataatttgtc | 360 |
| gctttaccac ttttgacaaa taatttgtcg ccacggtcaa ataatttgtc gctctacatt | 420 |
| tgaaagcggg cgatgggact cgaacccacg acgttcacct tgggaaggtg acattctacc | 480 |
| actgaattac acccgcaaat | 500 |

<210> SEQ ID NO 175
<211> LENGTH: 700
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 175

| | |
|---|---|
| gtgttatgca gcaatatgag tagccgtcat gaactgcgta caccaaaacc tatgaaaaag | 60 |
| gcatcaaagg atttttcaaat cagaacaact ggaaaaaaac aactatgtta aatattgtaa | 120 |
| aaacaataag attgagttcg tagtaaggac tttaatcctt gtaaagttct cactacaagt | 180 |
| ctttaattat ccaccctgtt ctactcagtt catttaaggc taacaactta gacgcggtgg | 240 |
| taagttgaag ccatctctcc actgaaccat attgatatat aatgtagagc gacacattat | 300 |
| ttgaccactt cgacaaatta gctgtcacag cattatcttg aacgaaaatc catatatatc | 360 |
| aatactttct agcaatgaaa gctaaatcaa gctcattcag tcttggacga caaattacat | 420 |
| gacttttta aaagtccgcg acttattaga tgacaattat taattttgcg aaaaattacg | 480 |
| tgtcaattat tcgcagtttc atagtagtat aaatgtaccc aataatcaaa gacaaatcac | 540 |
| atctatgaat tatttagatg tagataacca gtttgaactg gaagatgaag atgactttct | 600 |
| tttggatgat gaggatgcag acatactcga ttttcaatt gaagttgagt cattgagtaa | 660 |
| tgatggaaac tctgtagcag aagacaaatt agtagagttt | 700 |

<210> SEQ ID NO 176
<211> LENGTH: 500
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 176

| | |
|---|---|
| aagttacagt tattaggtgg gttgaaagta gtaaatgctt gttattttag gtttagacct | 60 |
| caaaaaatt acagatataa cttcgagagc taatgtaacc aaaaataata cttagcccag | 120 |
| tggagtgcta ctatgtaact gcatagagga aaagacgatg acaaataatt tgtcgctatg | 180 |
| atatttatga caaatatttt gtcgctacag acaaataata tgtcgctcta catataacca | 240 |
| acaaaaaagg cttggtcggg ccaagccttt atgtatacca agcatttact acaccaagct | 300 |
| taatttaaac cctctagcac tttagttcat ctgtctttag actgtatgca aattctttca | 360 |
| aacctggtat gaactggcat atttacatac aaaaaaggct tggttcaaca ccaaacctcg | 420 |
| ataattgctg tgcttaacaa cgtactaaat taatttaaac tggattgttg tccttatcat | 480 | cttcctttag tatgtgttgc                                              500

<210> SEQ ID NO 177
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 177
ttcgggagtt tctgcaaatc ctggagtggg tggcgacgaa gaaggggaag cgggtggtct    60
atgttgagcg ctggttccct tcgagcaaga cctgttcaag ttgtggtcat attttggagc   120
atctggattt agagactcgc cattggcggt gtcccagttg ctcgacagag aatgaccggg   180
atgagaatgc ggcgatgaat attaaagtgg ctggggcttc agccattggg ttaggtgatg   240
tcagacaggc gttgcctgct attgctgttt gatcccagaa tccccgtttt tctaaacggg   300
ggagtaagtc aaagggttct taacgttgta cagtccctcg ttggcgtggt cgatcagttc   360
tgaactgtct gcccccacac tgcccccaaa atcttgattt taatgacatt ttttttccaa   420
ttttagggtg tgggtgtcga ttgactcatt aactgacatc ttgacaaatt atttgtcatt   480
gctatagaca agcctgcaac ccttactata cataaggttg tgggcttttt gcattggaaa   540
tttactcaaa agcaaaattg acaaattagg tgtcgtatat taggagtttg ccaaaatatg   600
tgtcgctttt catttagtcc agattttctg gcttttgac acattctgtg tcgctcaggg    660
taaaataaca acatgtttgt attaaacaca tttgttgtaa                         700

<210> SEQ ID NO 178
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 178
gtttgcctcg gagatgtttg ccctagtgag attggttgct gaaaccatcc caaggtggga    60
ttaggttgaa agagtaatac aagaattggg tggattgaaa gcaagtccca ccgtcccta   120 ctttagtgca atgcaagatt acacaacaaa cttgctctga atgtatggaa ggttcgtaaa   180
agtggtgaca ataatttgt caagatgaca tcaatttgac aacgatgaca ataattagt    240 caatcgacat gtgggcaaca ccgtcagaac aactcagaaa actctgaaac gatggggtg   300 gtgggacttg aacccacacg tcttttacg gacaacggat tttaagtccg cagcgtctac   360
cattccgcca caccccaag agcagtgaca gggttctagt ttagcagcaa atggcggcca   420
ctgcatggaa cagaaccctc agaaaatcta atcaatctgc ctcttgcgct ccgatgggtt   480
gaattgttta tgatgggagg                                              500

<210> SEQ ID NO 179
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 179

```
aacagattaa aaatttaata attaccgtaa tctttagcta actataatta tttacaacta      60
tgcagacaca ataaccgcaa taaaggttcc ttttcctcaa aaaagagctt agtaaaaatt     120
gccttatata gcagatgtta tttaaaatac ctgtgtgtgt tatgcagcaa tatgagtagc     180
cgtcatgaac tgcgtacacc aaaacctatg aaaaaggcat caaggatttt caaatcaga      240
acaactggaa aaaacaact atgttaaata ttgtaaaaac aataagattg agttcgtagt     300
aaggacttta atccttgtaa agttctcact acaagtcttt aattatccac cctgttctac     360
tcagttcatt taaggctaac aacttagacg cggtggtaag ttgaagccat ctctccactg    420
aaccatattg atatataatg tagagcgaca cattatttga ccacttcgac aaaattagctg   480
tcacagcatt atcttgaacg aaaatccata tatcaata ctttctagca atgaaagcta      540
aatcaagctc attcagtctt ggacgacaaa ttacatgact ttttaaaag tccgcgactt     600
attagatgac aattattaat tttgcgaaaa attacgtgtc aattattcgc agtttcatag    660
tagtataaat gtacccaata atcaaagaca aatcacatct                          700
```

<210> SEQ ID NO 180
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 180

```
actgcgccag caattcacca aactgccgca atttaatcaa acaggtgttg ggatcatctg     60
caaaatatcg ctcggctaga gtcgctaatc gaaccagttg tatgtcgtgg actgcaagga    120
atgagaagtt taatgactct ggcatactgg cttttgagag aatctgtcca gttagtttca    180
agttgtctca ataacctaa tcaagactcc tcttgttgta ggttgcccaa attaacttag    240
tcatagtcta gcagtaattc aagtctcata atatacatct aactaaaaat ttggaaaata    300
ttattaatct gtgaatatat agcaattccc aagctcatga aatacacccc acccgtgctg    360
tcgcgcaccg tagccttacc aaggggagga ttggggaggg gtaattttgt atctaactag    420
agtgagaaag gctattgtac gttcgcaaat taaatgtcgc ttttcgcaaa ttagtgtcgc    480
aactgctttt aaggactaaa acctttattc tataagcatc ataagctatt taccccctaca  540
aaagactaag ttacctaatt cgcatattgt atgtcgtaaa acctggtttc gcaaattaaa    600
tgtcgtttgt taagaatttg gtattttgca aattagatgt cgcatttttg agtaattcat    660
ggtacattag taccttaatt attcatgagt gggtttcact                          700
```

<210> SEQ ID NO 181
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 181

```
ataactagaa tttacttgcg ttaaccatta aaataaaatg gttgcaaaat agaaatgatc     60
atgggagggt tgaaaggagt gctgcgatcg aacacatatc aataatccaa taatgccctt    120
gcagcaataa tttattgtat agtaaatgtt aagttcatgc gacattaatt tgcgaaaact    180
```

```
tagaataatt aaattgactc tgaaaaacaa ccaccacgac attaatttgc gaataacgac    240
actaaattgc gaaaagcgac atttaatttg cgaatgtaca tatataatgg agaataggag    300
actcgaaccc ctgacctctg cggtgcgatc gcagcactct accaactgag ctaattcccc    360
ttgctagtct caagttacta actcagacag ccgtactata tgttaacact caggcagggt    420
agttttcacc tcttttgca aaaaaacttc ctgtacccgg tctaattcca aatcagtcag    480
ataatctact gtccagttag                                               500
```

<210> SEQ ID NO 182
<211> LENGTH: 700
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 182

```
tctcatccaa aaaccttaaa gatagttcaa gaaaaaatag aaaatgagtg ggagataaaa    60
ataagcaaag atacgataaa aagattagca aaaaaaaagg gcatggggtg gtatcggttc   120
aagaaaaggg taaaagggga agtatgccct gaattatacc aacaaaaaaa gagacaatta   180
gagcaactaa aaagagcaga aaatgaagga aaaatagata tatattatgg tgatgaaagt   240
ggatttagtt tagtaccttg tttaccttat ggatggcaag aaaaagggag aaaaatagaa   300
agagaaagta gcctaagtaa aagattaaat gtgttaggat ttatgaaaaa aataatgag   360 ttagaaagct atgtatttga gtcatcaatc aatagtgatg tcgtgatagc ttgtatagat   420
aacttgagta aaaaaataaa gaaggaaaca gtattagtaa tggataatgc ctcgattcac   480
caaaataaaa aattctggaa taagaagaa gaatgggaaa aaaaaggatt aaaaatattc   540
tttctaccac cctattcacc acaattaaac aaaatagaaa tactgtggag atttatgaaa   600
tataaatggt tagagaactc ctgttataaa agttatttag atttagtaaa aggagtagaa   660
aatattctta taaactttgg ttcaaaatat acaattaatt                        700
```

<210> SEQ ID NO 183
<211> LENGTH: 500
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 183

```
gatcattata agactgcaaa atacaaaaat agctataata gatatatatg tggattgaaa    60
gaggtcacga gttcaatcat aaaatgacat ttaatttgtt aacgatgatt cagcgacagg   120
aatttgttaa gacgacaatt aattcgttaa gatgacagat aaaatgttat tcgacaatac   180
ctgtaattta ccattgcaag gacattcaca cgaaagcctt tgacgaggat tgaactcgtg   240 acctcacccct taccaagggt gtgctctacc actgagctac aaaggcagtg ggccgagctg   300
gatttgaacc agcgtaggca tagccagcgg atttacagtc cgcccccatt aaccactcgg   360
gcatcgaccc atttgttttc acatttacta attatagctc atctttttt taatgccaa    420 cttttttgtt taatttttat ccagtttgcc caatgcgagg ttctgttcct gctataattc   480
gatcgatatt agtacgatga                                               500
```

<210> SEQ ID NO 184
<211> LENGTH: 700
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 184
actatttgaa acagccaatt acttttatct tcataagcta cggttgaatc tataacttct      60
aaaaactccg tgtcgtagaa atagagaaaa tcatcaatta acttttcttg ctttactctc     120
cccgtagtgt tggtataacc tctttcaata aaaaatttaa ttgccgagcg aagctattat     180
tgccaacata gaattacag cagcaatacc aatgacaatc aaagcgaaaa tcgccaagcc      240
atattgcagc gtgtatagct tgcgtaattg gctcattgcg ttcattaggt tatcaatatc     300
gttacctgaa gttttgacaa tgcgctgaaa gccgccagcc gctagtacat tccagcgtcc     360
tatcaacaga agtagaattc cctgaatgat gccactaatt ccactattaa taggaacctc     420 ttcttttga ataaatatgt acggtgacta attatttgac ataatgacaa attgttgtca      480
tgcaattcaa agctttatat gctaggcatc atagcatttt tattataata tttgattgac     540
ttatataatg acaaacaaaa tgtcgtttgt ttgcaaaatg actaattagc tgtcgtttat     600
tgaaaattca gttttaaaga aaagtgacaa gatctgtgtc acttttttat ttaaatatag     660
aattacatta tgtgtttttt aaaaaaacta atttactaaa                           700

<210> SEQ ID NO 185
<211> LENGTH: 500
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 185
cgtaattctt aggagtgggt gcaaaattta accccaggtt tcaatgacca ttttgtgatg     60
gcttgggttg aaagataaag gcttagtcat tgttattgat gaagcggaag tgccaacgac    120
cacacgcaaa ttttaattct caataactat cgtctaattc tcgctaagaa actgaaagta    180 atttttaaagt cttgttcttt ggttactcca agtaatttat tacttttagg cgatcgcctt    240
gcttgccgag tttaatttgt atcagcaatt gctgtataca gtctaaaacc aagtaaattc    300
gattaattat ttttgtgcg acgcagtaag tcgcttgatt taagtgaaaa tttcatgact    360
gaggttatgg atttctagta gatttcatcc tactattccc acgtaaagga gtctcgtact    420
ctggtcacat tgaaagtaaa taatgaactc aatggaatgc agaccatgaa tgtatccgaa    480
ggtggataac ctctatccag                                                500

<210> SEQ ID NO 186
<211> LENGTH: 700
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 186
cgaggacaat accggtatat ttcagcaagt ctgcactcaa aatactgggg ttgggctgtc     60

```
gaagcgcgat cgctgtcaaa agttctggaa tttcacaatt ctgcttcctt ttattttctt    120
gtatttataa gcacataagt aaaaataagt attctatgta tacctagtga tataagaata    180
cacatattta acaagatata tgaataaaat tttgataaat tttctgtaaa aacagtgaat    240
atacttaatt tttaattaaa ttttccaaat tcaggacttt caagatattg acatttctgt    300
ggttagtatt ataccgtccc aatattcaga ttccaaaaca ttagtttctc ttccattcgc    360
aaattgagga agcacagacg gcacaaaccg ataattatca gagtcaaaaa tcgacaaaag    420
gatgattgaa aagtgtacat tcgcaaatta aatgtcgctt ttcgcaaaca atgtcgcaac    480
tgtattgaat ggctgaaagc tacatcgtgt aaatattata ggtcatttat ctctaagaca    540
ggctaatttg cttgtttcgc atattatatg tcgcataatc acgttttgc aaattaaatg     600 tcgtttgtta aagttggtga cttttgcaaa ttaaatgtcg tattctttat gaatatatgg    660
tacattagta ccttaattac tcatgagtgg gtttcactct                          700

<210> SEQ ID NO 187
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 187
acttagataa tcaatcctag aaaaaacgct cttagtttat ccgtctttgc gctacaaaaa     60
tcttgtcaaa tggggtaggg ttgaaaggtg catccgactt gtaagcgtat taaaccttaa    120
aaacataaaa caaaaaatta aaacttattt aattctgatt ttttatatgt aagaattagg    180
ttctgcacaa ccatcaattc acttgttgaa gtaatattat tgtgttaaca cttgcttgta    240
agcaacactg taacaatcta gaaggaaaaa acgacattaa tgtgcgaaaa cctagcataa    300
ctaaattgat tataaaaaat agccgaagcg acatcaattt gagaaaaccg acactaaatt    360
gcgaaaagcg acatttaatt tgcgaatgta cagattgaaa agccagcagt cggatttgaa    420
ccgacgacct tccgattaca agtcggatgc actaccactg tgctatgctg gcaaattagg    480
tgatgcgttt gaatcattca                                                500

<210> SEQ ID NO 188
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 188
tttctagtaa ggtttctagc gcgatagaac agccgtggat atcactgatg gctagtgttc     60
tcatagcttt gcttttgttt ttctatgatg cctttgatcc tatcttgact aggttaaggt    120
ttatttaaga cagagaaact atagtaaaat ttttaaggct aaggtaaatc tttgaacgac    180
tgcttcaccg cttaaaatgg catcctctcg atattgagtc atcgaccat cttggcgata     240 aacaaacgct tgacgattaa tgcgatcgat taaccatcct aatttaaccc cattgtttct    300
atattcttgc attttttgtt taagtttact taaactatca gatttagaac gaatttcaat    360
aacaaaatct ggcgcaagat tgaaaaattc atcctcttcc tcatcccatc cttgaggtaa    420
```

```
tctttcctta gcaattgtac agtgacacat tatttgacat gatgacaaat tagtgtcatt    480
ctttaaaccc tttactcaat aaggcctaca gctattctat cattatttat aatcgttcag    540
ctaagtgaca aattaagcgt cgcttttttgc ttttatgaca aattaattgt cgttttttca    600
taaagcttca aaataattg tgacaaattc aatgtcactt tttctataaa tgtctgctaa    660
aataacatta tggtttttaa aatagtgttc taattatgag                          700
```

<210> SEQ ID NO 189
<211> LENGTH: 700
<212> TYPE: DNA
<213> ORGANISM: Unknown
<220> FEATURE:
<221> NAME/KEY: source
<223> OTHER INFORMATION: /note="Description of Unknown: Non-coding transposon end sequence"

<400> SEQUENCE: 189

```
atgattataa aaatattagt atggattgaa aggcagcaat acgggatgca aaatgatgac     60
atttaatttg tcactaaagc ttaaacgaca acaattggtc acaacgacaa ttaaattgtc    120
tccatgacac taatctgtca tcgatgacaa ataatctgtc actgtacaat agttcgtcaa    180
aatgtaaagg cccggagtct aagcctatca caagcatccc gtattgctgc taccttccag    240
tcctgacaag atttgggcgt tgtaatcgca taggtccgag ccaattacta ggataacaca    300
gaactgaggc actcactctt gatcgttgtt cataatttga ggtacgcgga aaaagtcgcc    360
ctcttgttct ggggcacttt taagcaatga ttcgcgatcg ccataggttt ctgtgcgatc    420
gctgcgggta atattgctca attcgatcgc gcgtgtcatt gggggacat tttcggtgtc    480 aagttcgctt aactgatcga aatattgcaa aatgctattt aattggggggg caaacgcttc    540 ttcttcggct ggtgtaatct ccagtcgggc taaatgggcg atttttttcaa cttgttggcg    600 atcaatcatc gatggtttct cactctgatt taaaagaaga catccatttc agaacgtcca    660
gtcaccttga gccaattttg ggcttcaata tagttattgg                          700
```

<210> SEQ ID NO 190
<211> LENGTH: 700
<212> TYPE: DNA
<213> ORGANISM: Unknown
<220> FEATURE:
<221> NAME/KEY: source
<223> OTHER INFORMATION: /note="Description of Unknown: Non-coding transposon end sequence"

<400> SEQUENCE: 190

```
gaaccagctt ccgtaggcaa agattattca gacgaagcag tattaaggga ttttttcttt     60
catgattgtc aaccggatgt agcacagtgg gcaatctcga aaagtcgtcc gcaacaatct    120
atggcatata tatttgaaac gaatcctcta aaagctttgc cgcatgttga gcgtaaatat    180
attgtttgta gcaacgatcg cataatatct cctacatggt cgcgctacgc tgcacgcaag    240
cgcttaggag tcgatgccat tgagctacct tctggacatt gcccacatct gtctcgtcct    300
gaccttcttg cctcaatatt aactagtaat taattttttg atccatatt taggaaatta    360 accgaagcgt attgagtgtg aacaagggaa tatctttgaa attttaattc ggcatagacg    420
aacgatatta tctaattaat aacgacatga atttgcaaat tgcgacattg aatttgcgaa    480
tgtacacatg gtgtccatta ataattatt gtcactttta agaattatt gtccagtttt    540 acgatatctg tataacaggc tcaaaggctt accaaacaag tctttgagct atatttatac    600
ttttattatt ctctagccag ttttaaagta aatgatgtca ttttttctgat aaatttttaa    660
```
agtaaatgat gtcattttc ttggaagacg ggtcaagtgt 700

<210> SEQ ID NO 191
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 191

```
tatgatcccc gaagtaggcg ctttggttat ataattttgt attagggtgg tttgaaagga      60
gtgctgcgat cgcacgtaaa acgcagctat gtagcagtgg agcctctgct tgggtgaaaa     120
cagcaaaaca agaggtagta tatttttgta attagactgc aaataaaggg ctttaaagct     180
actcttgtaa ttcaataacc ttgagcctgc tgtaataaat taaattagta accatatatt     240
tagccgagtt ttacaggctg attttggaca ataattcttt aaaactggtt tcaactctgg     300
acaataattc tttaaaactg atttaattgc tgaaagccgc gaaaatacgt aacttatgcc     360
cctgaacttg gaaaaaatgg acattaattc tttaaaagtg acaataatta tttaatggac     420
acatggagaa taacggattt gaaccgatgg cctctgcggt gcgatcgcag cgctctacca     480
actgagctaa ttccccttga                                                 500
```

<210> SEQ ID NO 192
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 192

```
gttttctcat cctaatcaac ggggctaaat atactatatt ataatatcta taactaaagt      60
gtgggtacaa taaataagct aaagtccatt taagtttaat actaactgac gataagccgt     120
cttgaatttt tgtaactcat tcataccttc ttgaagagtt ttaatatatg agagtctatg     180
attaatgtta aataagaatg ccacttagcc acttagtttt tgatctaatt tcaattaaag     240
gtaatttgag agaaaaacac acactatcag aaagtggacg agaagctcta ttttgctatc     300
cttgttttaa ttttggcagt aattgtttga ctacttatta aaataaaatt gatggaaaag     360
ttaaaaatca gtctgaaaat gcttttgaat aactttgata aaaaatcttg tacagtaaca     420
gattatttgt cgtgataaca aattcgtgtc atctaaaaat aagactctta aaatccttat     480
atatcaacaa ttataactta tccttaccct aaaatcacac tcgattgtat cttaaaatag     540
attaacaaat taagtgtcat tttccctaaa aataacaaat tagatgtcgc cttcggaaaa     600 ggcgatttt tttgttttg agtggcaatt cacagattaa atgtcataga ataataagta     660
cacatcaact ttgattttat taaacataaa aatatcagct                          700
```

<210> SEQ ID NO 193
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

```
<400> SEQUENCE: 193
gcttttattt tgaactaaaa ctctactaat tagaatctgt catcgagacg aaacaaaacg    60
atcatatttt cttttaaag ttataatttc aatagtgccg tagatcaagt tttaacaacc   120
tctgttctat gaaaaatgag gagtagttta cttttacaa gaagtttgct ttcggctcct   180
gctaactact tgccctgatg ctgtctatct taggatagag aaactaggcg cactcccagc   240
aataagggtg caggtgtact gctatagcgg ttagcaaatc actttcgatc gaggaagaat   300
tctctttgag aattgaaagc gagtcctgtc gcacccaatc atttagacga cattaatctg   360
ttatcacgtc atctaatttg ttaagacgac actaatctgt taccgatgac aaataatttg   420
ttactgtaca tcaatttaaa atacgagcca acggctaagt aatacacggg tgcgacagga   480
ctcgaacctg tgaccgactg                                              500

<210> SEQ ID NO 194
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 194
tcatattcct gttgataaga caggcgttct cttgctgctg actcccctg agattgcttt    60 aaatcgtcaa ttaacgcctt taaaacctt ttaatcaccg tagccgtcac attttcatcc   120
tcttccggct cataactcgc cacctcttgc gctgactcca ccgcttcact taactcccct   180
tgcgctgcac taatttact ctctaactct tcaatttgcg cctcctcagc ttgaaaaaag   240
gcagttaaca gatattcatc aggaataagg gtgtgatgcc aacctgtatt aataatcgtc   300
ttcaaatcat agcgaatctg ttgccaccag ttaacaaaca cccccgcaga cttaaactca   360
tccaacaccc ccaaaggaat aagctgctgt ttcagactgt ctagtaactc ttgccggtgt   420
acattcacta attaagtgtc gcaatttgac agattaatgt cgcaaaataa ataagctgta   480
aaccttacac gacaagcatt ctagcatttt tcagggactg tatacaaaaa tgcttgattt   540
aacggataat ctgtcgtaaa ttagattctt aatgtttat ctgtcgtttc ttggatagat   600
agtcaaattg ctggtcaaca ttttttcata cattaattgt cgtttcttgg aaaagagtct   660
atactatggt tagttcgttt gttggattct atgctaactc                        700

<210> SEQ ID NO 195
<211> LENGTH: 320
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 195
ttgggatggg ttggattcat gatcatgttc aaacatcgag aaggattgaa aggcgcactt    60
cgttcgggat cgtagactta taaaaatatt cgatcccaaa atagcgacac ttaatgtctg   120
aacaattgtc cattaaataa ttattgtcac aattaaaaaa ttaatgtcac ttttttgaga   180
gagttttaag ataccgcaag gttctgttaa ataaagcttt cagcgattga aaagagttat   240
atcctgtcaa ttgtcatttt aaactaaaat gtgtcactta ttaaaaagcc ttgctagaat   300 cttttaaagta aaatatgtca                                             320
```

<210> SEQ ID NO 196
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 196

```
ttatcagcta attctaaacg aataccatca ggagttttaa ttttttttgcc ttgagaaggt      60
tgccatatct cctgcaacca atcacaaata agttgagaat tagggttagg aatttctaaa     120
tataaaattt cttttagttt catttatata agtacttgat aaaaatattt agttattaat     180
gagatgattt gatttattat ctaataatag gagtctcttc gccaagagaa caatatctga     240
agataaacag ccaggattaa gaaatagctg atccagaaat gatccagttt tctaattttg     300
aatgaaaaca aaaatatgag aatagcaaat attaataaat aataaatgat ctagcaatta     360
tccagttttt taatcaacaa taaaacatca aagaaaataa tcaacaataa aaccttaaag     420
tgtagagatg gatgatgtac agtgccaaat taaatgacat gaagccaaat tagtgtcgtt     480
gggtttaatc cttattatct ctacattata gtcttttttct ctaatttacg aagctaattt     540
taaatgacaa attcaatgtc gtctttatat ttagtgacag attaaatggc atcttttcaa     600
atattctttt tttttgacgg tgacaaattc atcgtcattt tttatttact gtgttaagat     660
aacattatgt ttttatttaa caattatact atttagagtg                          700
```

<210> SEQ ID NO 197
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 197

```
tataataaat tacaggaagg acgtatagct cagttggtta gagtacatcg ttgacatcga      60
tggggtctcg tgttcgagtc acgatacgtc catttattt tgtacagtgc cacattaatt     120
gtcatcggtg acaaattaat gtcgttatgc caaattcttg tcttttaata agcagtgaca     180
aattaaatgt cgtctaataa atttgccttg tggtttgttt cgatggtggg gaaatttaat     240
ttttatttgt gaccccattg atgtcctttc aatctatcct aagtcgatta tactgtattg     300
atttatttcg gctcgatcga tcattaattt tttgtcttac cctaatttga tcgttgctca     360
gatattttca atcaacccca aagggaaaac ttgattgaaa ccatcaatgg aggcaatatt     420
ccccgattag ataatttttc aatcaacccc aaagggaaaa cttgattgaa accccgtgct     480
tcggaagcct tatacagtaa                                                500
```

<210> SEQ ID NO 198
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 198

| | |
|---|---|
| tccgaattaa ggatggagca attgtcgcgg caagagtaga tacacaaacg accctgaagt | 60 |
| atttctaccg acaaggaagc gaagtcattt tgaaacctgc aaatgctgct tacgaaccca | 120 |
| ccgtagttga agcgaaccaa gtagatatcc aagggatgta cgtaggactg atacggcgac | 180 |
| tttgggagaa cggtgagcca tgacttatag tgcttgcaat atcgatattg atctgcctga | 240 |
| tgaagaggcg gcagtcgatt tcgaagactg tggcgatgca gaatacgagg attggctcgc | 300 |
| tgattattac tcggattggg cagatttcta tcaacaggtg tccgatgcag aagatgcctt | 360 |
| tcgacacaat ttaatagtga agaattatga gtttcaggca cgcggtggct tttaccggg | 420 |
| ggacactgta atggcggaag tcgaaccagg gtattggcat cactgcaccg tcctcttagt | 480 |
| agggatatcg acgttagtgg ttagtgccga gcgatctaca accgttcaag tcataactca | 540 |
| actcaacacg tattggctcg actagatctg attttggaat tcgctcgtct tgcgatcgct | 600 |
| tcaaatagtt aatttgtatt aattttcctg tctaacagat tgactgtcgc tatttcttcc | 660 |
| tcataggatt agtgcagttc ctgataggac ttatgtactt | 700 |

```
<210> SEQ ID NO 199
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 199
```

| | |
|---|---|
| agtaacttag tcttttgaca actttaatag gcacaatctt tcggttaaca gtgggtggat | 60 |
| tgaaaggact gcctgactcg gggttttaat ttagaaatat ttgcccctcg ctataacgag | 120 |
| cagagttagc attcgttttta actgggtaga gtctgtactg taaaatgttg aagtggataa | 180 |
| gaatttgaat gagcattcaa ctgcttgaag ctctgatgac aagaatttgt taacgaatga | 240 |
| tttcttaccc ctcgacgaca agaagctgtt aaaacgacac taaattgtta acgacgacat | 300 |
| caatccgtta acgacgacaa ataaagtgtt attcgacaac aatcacacga atttaaacaa | 360 |
| aaaattgcct gactcttaaa agcccccaga gtcaggcagt ctacctgtaa ggcacgcctt | 420 |
| taaccggata caccaaacaa acttagttgc cccctagttg cttagctttt ccgagtgcgt | 480 |
| tcctcagatt tgaatctatt | 500 |

```
<210> SEQ ID NO 200
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 200
```

| | |
|---|---|
| tttttatctc catgggaaat ccagcaactg ggggaagatt ctgcggcgaa gcggagtggc | 60 |
| tggtgcgggc tgctaccatc ttaaccaaga gccacaagtc ttttttgcccg taccagccac | 120 |
| cgcagaatct agcgcagcgt tccacagttg cgtcaatgtt aagagtaccg gtttttttgtt | 180 |
| aacgatcgct tgacttttaa gacagtcgct acagaactta aggtttttat ggctaactaa | 240 |
| accgtattgg ttttttagttg aaatcgtgtc cgcttaatca acctgagtaa aaatgtccta | 300 |
| cttttagcat gaactttctg aattccttga tatccttttat caccaaagta ttcaatattt | 360 |
| tctcttaacc gaactttact gttttttaagt atgcaaaaat tattgtacat taactaatta | 420 |

```
tttgtcattg tacaaaaatg tacagtgact aattatatgt cgtcgagaca aattaatgtc    480
atccattaaa atcttgctcg gtataggtta cagcgtttta gtagtattag gataacatct    540
tgacagtgac agattagctg tcattttggg taatagtgac aaattagctg tcgcttcatc    600
agagataaaa aagcttttgt gtattttcat aatgacaaat tgactgtcgc tttctgttta    660
agtagaataa caatatgttt ttataaaaaa gcttcgcatt                          700
```

<210> SEQ ID NO 201
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 201

```
gcaaatctga aatcattacg cacgcataca aaaatgtttt aataacctgc caggtactag     60
gtgggttatc ataattttta ttagggaggg ttgaaagaga gcgctacgtt gacattatcg    120
ctatagtctc tgtaaataaa tgacattaat ctgtcactgg cacctaaacg acatcaattc    180
gtcccgacga cagttaatta gtcccaacga cattaatctg tcaccgacga caaataatta    240
gtcactgtac aaaaaaaatg gacgtaactg gattcgaacc agtgacctct acgatgtcaa    300
cgtagcgctc taaccaactg agctatacgt ccttaaccac acgaatattg atagtagcat    360
atacttttgc gatcgcacaa gataaagacc caagcttttt aagggggttt tagattttga    420
gtgcgtaaat cctaatttca aataaaatcc ttattatttc gttacaatca gcttgtgcgt    480
taagcattca agagttatca                                                500
```

<210> SEQ ID NO 202
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 202

```
caatggtggc ttgcgacaaa tagtcattaa tctgctacac aacagcctca agtttacagc     60
caatggtggt cgagtgtggg tgagagctag agtccaaggc gaatacgtca tactagaaat    120
tcgtgacaca ggtatcggta ttgctgaaag cgaaattccc aaaatattcg actgctttta    180
tcgtgtgcga tcgggactaa ttgatgagac gaatggcgca ggtttaggac tcacaattgt    240
ccagagattg ttatggcatt gtggtggttc tgttaatgtg agaagcaagg ttgatgaagg    300
tactatggta atagtgcaaa tgaagatagg aagcacctcg ccaacttaga tccggaaaac    360
ggggtgaagc gatcgcctgt tggttgacaa ctgcacttgt agagcgacaa ataatttgtc    420
gttctacaat tgtcgattgc caaattatat gaccacttga caagttaatg tcattcaaaa    480
tattatcctc aaaaccccttg ccaagcaagg gttttgttat tttaggctca aaatacccag    540
aaacttattg ccaaaatagc tgtcctcttt tgaaaagttg acgaaatatc tgtccttgct    600
tgaaaaggga cttgagggaa gattttttaca gaaattgaca aaataaatgt cctccaagta    660
gtacaataca actacgtttt tattgaacat ttatgtaaat                          700
```

<210> SEQ ID NO 203

```
<211> LENGTH: 500
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 203
accttcatgc aaggatataa aaaattttag gtgggttgaa aggcgcactt cgttcgggat    60
tttccctgac cgaaacagta ccaataaatc aaagctatta taataacagc ttctaatgcc   120
aatacacctt gatgactaag taatttggca acgcggacaa caacttggca atacggacaa   180
caatttgtca acgcagacaa agaatttggc aatcgacaac aataatcggg atgactggat   240
tcgaaccagc ggccccttcg tcccgaacga agtgcgctac caagctgcgc tacatcccgt   300
taaaaatttt atacgccttt tttagcataa cataaataat agtcaataca gaaaagacat   360
ctacatctat atatatagat gaatcggaac gggatttgct tgctaggatt agatttgtat   420
aacattcagt ggtaaaagcg gattgtgact gtaaaaccag actggttgcg ggtaaaagcg   480
cctcaatggg agcgcgttgg                                              500

<210> SEQ ID NO 204
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 204
aaagcagtag gactattatc tgcccatatc cacagtaatc cttgtaatac ttgagtcgga    60
tatgtggtaa tttgcgatcg ctcgctttta caagcagttt ctaaagcctt ttcatcgctc   120
aacatgggaa tatttgtaca tgttcctgtc ccatcaaaac accaaccatg atggcgacac   180
atgatgttgc cattttttgtc aatacttcct aaagataact gcgctaattt atggggacaa   240
acatcatcca ttgccaccca tttttgctgc ttatctctcc aaattaccag attttttaccc   300 agcaaagtaa ttgcagtggg atgagagggt tctagatagc tgataggagt tacaggatac   360
cactgtttag tccaggaaaa gttagtcatc atcaaattaa ctaatttatt cgactcaaat   420
ttgaaaaatg agtaaaaagc ggcatttaat gtgcgaatgt tgtacattcg cacattatat   480
gtcgcttttc gcaagttagg tcgcaaccgc atttaactgc tataaaccct attttacaaa   540
ggtttgatgc tcttagcaca tcaagcccac gaatttactt aattcgcata ttccatgtcg   600
caaactaaat attcgcaaat tgaatgtcgt ttattaaaat ttgtcacttc gcaaattgtt   660
tgtcgtatta ttgagcgatt catggtacat tggtactcta                        700

<210> SEQ ID NO 205
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 205
ttgaaaatct aagagcaact acactataga tttatttaga gggttgaaag gagcatcaga    60
ctcttaattt aagtgataga gataatatttt aagcacagat atatttctta ctcagcaata   120
```

```
gcatttagta tttgcatgga aataaatagc tttgagacaa cattaatttg ttaacgatgt    180
ctttgaggat ttaggggaca tcaatttgtt aaaaaagaca ttaattttgt taacgacgac    240
aaattatttg taatcgactt taggacaaat aatttgtcgc tttatgtact ttgacaaata    300
atgtgtcgct ctacatcagt taatcgacaa taaccaagcg acgttaattt gcgaaaacct    360
ataatcatca atatagtaca caaatctgtc gaaagcgaca ctaatttgct aataacgaca    420
ctaatgtgcg aaaagcgaca tttaatgtgc gaaagtacaa atgtacaaaa tgggcgacct    480
ggggctcgaa cccagaacca gcagattaag agtctgatgc tctaccattg agctagtcgc    540
cctcaccatt tactactata gcaaattatt tgaacaatag ttaaccttta tcggaaaatc    600
ttcatataac tagttgacat tagcaaacac ataccctctg atgcggataa aacttgctca    660
tacaaaatca aaactaggta atagcaccac taattatact                         700
```

<210> SEQ ID NO 206
<211> LENGTH: 700
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 206

```
agtcaggagt caggagtcag aaagaagaat tagaaggaga tcagaatatt ctcaaatctg     60
ggtaaatgaa ctatttttga tgctttcatc gcttatttct tgcaccttct ccaacttttt   120
cagcctgaga ctgttgatat atctatgttt ttggtttatt aagcaaaccc taagtactat   180
ctgcaagggt tcaggcatg atagacccct taaattgtca ttacgagcgg agcgaagtaa    240
tcacataatg cgatcgcacc acctcaagct agatgatgaa accaagtact agtaggaatt   300
ttaagacttg tgtgtacacc gtagattatt gagtaggggc atctaacgat aacgaataat   360
gataaatacc gtagtgcaat attatgctac aggaaactta atcagtgttt acataatttg   420
tgtacattaa ctaattattt gacaatttaa caaaatattg tcaaaaatca taaaaatacc   480
ttaaaacctt ctacagcaaa gattgtagga ggtttttatt tatctaattt gtgaacatcc   540
tccagacata tatttaacaa attaagtgtc aaaagccaga taattatcaa tttatttgtc   600
aatttgccaa atacaggtaa attactatat ttctgaaaat ttcacacatt aaatgtcact   660
tttactctat actatacaaa tatgttgtaa ttaaacatta                         700
```

<210> SEQ ID NO 207
<211> LENGTH: 500
<212> TYPE: DNA
<213> ORGANISM: Unknown
<220> FEATURE:
<221> NAME/KEY: source
<223> OTHER INFORMATION: /note="Description of Unknown:
    Non-coding transposon end sequence"

<400> SEQUENCE: 207

```
acattaatgc aagtagaata aaaaatatct aggtgggttg aaagatcagt aggtcgtggg     60
tttaactctg aaaacacttg aaaacactat ataaatacag tgttgcttgt gacatttagg   120
gacaattaat ttgttaacag tgacacgaat tagttaaaaa tgacattaat ttgttaacag   180
tgacaaataa attgttaatg tacagacata tagtgtgcga atgtacacca aagccgatga   240
tgggatttga acccacgacc tactgattac gaatcagttg ctctacccct gagccacatc   300
```

```
ggcatacaca gtttgatatc atagcattat ttacctatga tagacccaaa ttcccaaaat    360
cgtcttaact ctaaacaata tgcccacctg aaagctgaaa tagcagcccc ttatcgtggt    420
ttgcggcaat ttatctatat aggtgttggt gcttctggtt ttatcggcgc attcaccttc    480 tttttttcaac tgcttgctgg                                               500
```

<210> SEQ ID NO 208
<211> LENGTH: 700
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 208

```
cattggaaaa cagcgaacag tgctttagcc agaatcagaa cagcatttga tcggcacagt     60
cttaagccat atactttttt tgtgggatct gctatagaaa aaagcatggc agaagaaatt    120
tggcatcaac taaattctgg cattcttact aatgcagcaa acctcactca gcctgaccaa    180
gttgcctctt tgtgcgcttg gtttattcaa ctttgatgta cagtgactaa ttatttgtca    240
ctgtacacaa gatgtacagt gactaattat ttgtcactgt acacaagatg tacagtgact    300
aattgtttgt cgtcgtgaca aattaatgtc gtcgaatgaa tccttgcaat acaaaggttt    360
tagctattta agagttatta cattatttct catacgtgac taaataaatg tcgttttccg    420
caaaaatgac aaattaactg tcgcttcagt aattacaaaa aaggttttgt atattttcat    480
aatgacaaat tgactgtcgt tttctccacg tttagaataa cattatgtat ttataaatta    540
cctttgtttc atgaacaaaa aatcttatgt ctgatttac tgttcatacc gcagtggata     600
ctgcggaagc tttattacaa gacaacaaca cacctcctca cctcctgaga cgaatctgat    660
tgttacagaa ctctcagagg aagcccaact caagctagag                          700
```

<210> SEQ ID NO 209
<211> LENGTH: 1300
<212> TYPE: DNA
<213> ORGANISM: Unknown
<220> FEATURE:
<221> NAME/KEY: source
<223> OTHER INFORMATION: /note="Description of Unknown:
      Non-coding transposon end sequence"

<400> SEQUENCE: 209

```
acatggtgaa aacaaattgg atatgaaact gccttacgtt gtctgatggt gtaattaatt     60
tccaagaagt agagggttga aagcaaatcc cgtcatcggc ttgtaactaa agttattcag    120
gataagctac tcatagaagt gattaaaaga gcttttttgaa tgcaaacgct tataataggg    180
gctaaatata tagagaaact ccatatataa attgttgctt ttccgaaaaa tgacaataat    240
ttgtcacaaa tatatatgga agcgagttac taagttggat gacaataatt tgtcacaacg    300
acatcaattt gtcaccgacg acaaataaga gaccatttat aaagtaaatc tttagacgac    360
tagacgacgt agcataatac gagtcataac ggcatatatg gcagcctcac tcatttctgg    420
gagacgctca taatccttac tgagacgacg gtactggttt aaccagccaa atgttctttc    480
tactacccac cgtttgggca aaacctgaaa ttcttgatta gtacgccgga ttacctcaac    540
atgagcttga atcatcagcc aaacagagag cgcaaattta tcaccgtcat agccggaatc    600
aacccagatg acttcaactt tttccagtaa ttctggacgc tcttctaaca gttccatcaa    660
agtataggcg gcaagtaatc tttctccagc atttgcttca cttacaacca cttttaacaa    720
```

```
aagtcccaga ctatcaacca aagtttgccg ctttcgtcct tttaccttct tgccaccatc    780
aaaaccgtac acatccccct tttttcagtc gtttttaccg actggctgtc tgccgcgatc    840
gccgtgggtt gagttgactt ccccattttt tgacgaactt gatcgcgcaa agtatgattc    900
atttgctccc agatacctcg tttttgccat ttacgatagt agctgtaaac agttgaacta    960
ggaggaaaat cccctggaag catatcccac tgacaacctg ttttcagatg gtagtagata   1020
gcgttgcata cttctcgcat atcagttgtt cggggatgcc caccgcattt agcgggtgga   1080
atcaaaggag ctaaaattgc ccattctgag tcattaaggt ctgtagaata agactttcgt   1140
ctcattgttt cctatgtaaa tacactctac aaacagtatc ttatcgctgc cttttttatct  1200 gatagctctc ctttagattt actttataaa tagcctctaa tttgtcactg tacacaagaa   1260
ttagtcaaga caaaaatatg attttatgaa aaccaagccg                         1300
```

CRISPR-ASSOCIATED TRANSPOSON SYSTEMS AND COMPONENTS

CROSS REFERENCE TO RELATED APPLICATIONS

This application claims the benefit of priority of U.S. Application No. 62/580,880, filed on Nov. 2, 2017; and U.S. Application No. 62/587,381, filed on Nov. 16, 2017. The content of each of the foregoing applications is hereby incorporated by reference in its entirety.

SEQUENCE LISTING

The instant application contains a Sequence Listing which has been submitted electronically in ASCII format and is hereby incorporated by reference in its entirety. Said ASCII copy, created May 1, 2020, is named 51451-003003_Sequence_Listing_5.1.20_ST25 and is 432,713 bytes in size.

FIELD OF THE INVENTION

The present disclosure relates to novel CRISPR systems and components, systems for detecting CRISPR systems, and methods and compositions for use of the CRISPR systems in, for example, nucleic acid targeting and manipulation.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consist of a single effector protein that complexes with the crRNA to target DNA or RNA substrates. The single-subunit effector composition of the Class 2 systems provides a simpler component set for engineering and application translation, and have thus far been an important source of programmable effectors. Thus, the discovery, engineering, and optimization of novel Class 2 systems may lead to widespread and powerful programmable technologies for genome engineering and beyond.

Citation or identification of any document in this application is not an admission that such document is available as prior art to the present invention.

SUMMARY

The present disclosure provides methods for computational identification of new CRISPR-Cas systems from genomic databases, together with the development of the natural loci into an engineered system, and experimental validation and application translation.

In one aspect, provided herein is an engineered, non-naturally occurring Clustered Interspaced Short Palindromic Repeat (CRISPR)—Cas system of CLUST.004377 including a Guide consisting of a direct repeat sequence and a spacer sequence capable of hybridizing to a target nucleic acid, wherein the Guide is CRISPR RNA (crRNA) or DNA, and any one of the following: a CRISPR-associated protein containing charged N-terminal residues that are capable of binding to the Guide, either as a monomer or multimer, and of targeting the target nucleic acid sequence complementary to the Guide spacer; a CRISPR-associated protein containing charged N-terminal residues and an HTH domain-containing protein that together are capable of binding to the Guide and of targeting the target nucleic acid sequence complementary to the spacer sequence; a CRISPR-associated protein containing charged N-terminal residues and a transposase module that together are capable of binding to the Guide and of targeting the target nucleic acid sequence complementary to the spacer sequence; a CRISPR-associated protein containing charged N-terminal residues, an HTH domain-containing protein, and a transposase module that together are capable of binding to the Guide and of targeting the target nucleic acid sequence complementary to the spacer sequence; and a payload nucleic acid flanked by transposon end sequences.

In some embodiments, the target nucleic acid is a DNA or an RNA. In some embodiments, the target nucleic acid is double-stranded DNA.

In some embodiments, the targeting of the target nucleic acid by the protein and the Guide results in a modification in the target nucleic acid.

In some embodiments, the modification in the target nucleic acid is a double-stranded cleavage event. In some embodiments, the modification in the target nucleic acid is a single-stranded cleavage event.

In some embodiments, the system further comprises a donor template nucleic acid. In some embodiments, the donor template nucleic acid is a DNA. In some embodiments, the target nucleic acid is a double stranded DNA and the targeting of the double stranded DNA results in scarless DNA insertion.

In some embodiments, the modification results in cell toxicity.

In some embodiments, the systems described herein are located within a cell. In some embodiments, the cell comprises a prokaryotic or eukaryotic cell.

In yet another aspect, the disclosure provides methods of targeting and editing a target nucleic acid, wherein the methods include contacting the target nucleic acid with one or more of the systems described herein.

In another aspect, the disclosure provides methods of targeting the insertion of a payload nucleic acid at a site of the target nucleic acid, wherein the methods include contacting the target nucleic acid with one or more of the systems described herein.

In another aspect, the disclosure provides methods of targeting the excision of a payload nucleic acid from a site at a target nucleic acid, wherein the methods include contacting the target nucleic acid with one or more systems described herein.

In some embodiments, the transposase module comprises Mu-transposase, TniQ, and/or TniB.

In some embodiments, the CRISPR-associated protein comprises an amino acid sequence having at least 85%, 90%, 95%, 96%, 97%, 98%, 99%, or 100% similarity to an amino acid sequence provided in any one of Tables 2-6.

In some embodiments, the crRNA or Guide comprises a nucleic acid sequence having at least 85%, 90%, 95%, 96%, 97%, 98%, 99%, or 100% similarity to a nucleic acid sequence provided in Table 7.

In some embodiments, the payload nucleic acid is flanked by transposon end sequences comprising a nucleic acid sequence having at least 85%, 90%, 95%, 96%, 97%, 98%, 99%, or 100% similarity to a nucleic acid sequence provided in Table 8.

In some embodiments, the payload nucleic acid is flanked by transposon end sequences comprising a nucleic acid sequence having at least 85%, 90%, 95%, 96%, 97%, 98%, 9, or 100%/o similarity to a nucleic acid sequence contained in Table 9.

In some embodiments, the CRISPR-associated protein comprises at least one nuclear localization signal.

In some embodiments, the CRISPR-associated protein comprises at least one nuclear export signal.

In some embodiments, at least one component of the system is encoded by a codon-optimized nucleic acid for expression in a cell.

In some embodiments, the codon-optimized nucleic acid is present within at least one vector.

In some embodiments, the at least one vector comprise one or more regulatory elements operably-linked to a nucleic acid encoding the component of the system.

In some embodiments, the one or more regulatory elements comprise at least one promoter.

In some embodiments, the at least one promoter comprises an inducible promoter or a constitutive promoter.

In some embodiments, the at least one vector comprises a plurality of vectors.

In some embodiments, the at least one vector comprises a viral vector.

In some embodiments, the viral vector is selected from the group consisting of a retroviral vector, a lentiviral vector, an adenoviral vector, an adeno-associated vector, and a herpes simplex vector.

In some embodiments, the system is present in a delivery system.

In some embodiments, the delivery system comprises a delivery vehicle selected from the group consisting of a liposome, an exosome, a microvesicle, and a gene-gun.

In yet another aspect, the disclosure provides a cell comprising the system described herein.

In some embodiments, the cell is a eukaryotic cell.

In some embodiments, the eukaryotic cell is a mammalian cell or a plant cell.

In some embodiments, the mammalian cell is a human cell.

In some embodiments, the cell is a prokaryotic cell.

In some embodiments, the method results in an insertion or substitution of DNA to correct a native locus.

In some embodiments, the method results in a targeted insertion of a DNA payload into a specific genomic target site.

In some embodiments, the method results in a targeted deletion of DNA to correct a native locus.

The term "CRISPR-associated transposon" as used herein refers to a mobile genetic element having terminal transposon ends on both sides, which is acted upon by a CRISPR system described herein. In some embodiments, the CRISPR-associated transposon includes a gene encoding a CRISPR-associated transposase that is capable of facilitating the mobility (e.g., excision or deletion) of the CRISPR-associated transposon from a first site in a nucleic acid to a second site in a nucleic acid.

The term "CRISPR-associated transposase" as used herein refers to a protein including one or more transposase domains that is encoded by a gene that in nature is present in a CRISPR-associated transposon. In some embodiments, the CRISPR-associated transposase is capable of facilitating the mobility of a CRISPR-associated transposon from a first site in a nucleic acid to a second site in a nucleic acid. In some embodiments, the CRISPR-associated transposase has integration activity. In some embodiments, the CRISPR-associated transposase has excision activity. In some embodiments, the CRISPR-associated transposase specifically targets a CRISPR-associated transposon for mobilization via an RNA guide.

The term "Guide" for a CRISPR-associated transposase system refers to either an RNA or DNA sequence that includes one or more direct repeat and spacer sequences, and that is capable of hybridizing to a target nucleic acid and to the proteins and/or nucleic acid of the CRISPR-associated transposon complex.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR system" as used herein refers to nucleic acids and/or proteins involved in the expression of, or directing the activity of, CRISPR-effectors, including sequences encoding CRISPR effectors, RNA guides, and other sequences and transcripts from a CRISPR locus.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The term "CRISPR repeat," or "CRISPR direct repeat," or "direct repeat," as used herein, refers to multiple short direct repeating sequences, which show very little or no sequence variation within a CRISPR array.

The term "CRISPR RNA" or "crRNA" as used herein refers to an RNA molecule comprising a guide sequence used by a CRISPR effector to specifically target a nucleic acid sequence. Typically crRNAs contains a sequence that mediates target recognition and a sequence that forms a duplex with a tracrRNA. The crRNA: tracrRNA duplex binds to a CRISPR effector. The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR effector," "effector," "CRISPR-associated protein," or "CRISPR enzyme" as used herein refers to a protein that carries out an enzymatic activity or that binds to a target site on a nucleic acid specified by an RNA guide. In some embodiments, a CRISPR effector has endonuclease activity, nickase activity, exonuclease activity, transposase activity, and/or excision activity.

The term "guide RNA" or "gRNA" as used herein refers to an RNA molecule capable of directing a CRISPR effector having nuclease activity to target and cleave a specified target nucleic acid.

The term "RNA guide" as used herein refers to any RNA molecule that facilitates the targeting of a protein described herein to a target nucleic acid. Exemplary "RNA guides" include, but are not limited to, tracrRNAs, and crRNAs.

The term "mobile genetic element" as used herein refers to a nucleic acid capable of being specifically recognized and mobilized from a nucleic acid. In some embodiments, the mobile genetic element comprises nucleic acid sequences at flanking terminal ends that are specifically recognized by a CRISPR-associated transposase.

The term "origin of replication," as used herein, refers to a nucleic acid sequence in a replicating nucleic acid molecule (e.g., a plasmid or a chromosome) at which replication is initiated.

As used herein, the term "target nucleic acid" refers to a specific nucleic acid sequence that is to be modified by a CRISPR system described herein. In some embodiments, the target nucleic acid comprises a gene. In some embodiments, the target nucleic acid comprises a non-coding region (e.g., a promoter). In some embodiments, the target nucleic acid is single-stranded. In some embodiments, the target nucleic acid is double-stranded.

The terms "trans-activating crRNA" or "tracrRNA" as used herein refer to an RNA including a sequence that forms a structure required for a CRISPR effector to bind to a specified target nucleic acid.

A "transcriptionally-active site" as used herein refers to a site in a nucleic acid sequence comprising promoter regions at which transcription is initiated and actively occurring.

The term "collateral RNAse activity," as used herein in reference to a CRISPR enzyme, refers to non-specific RNAse activity of a CRISPR enzyme after the enzyme has modified a specifically-targeted nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

FIG. 1A-B shows the conserved effectors and CRISPR array elements by bacterial genome accession and species for representative CLUST.004377 loci.

FIGS. 2A-D show the left (A, labeled TER-L) and right (B, labeled TER-R) transposon ends by bacterial genome accession and species for representative CLUST.004377 loci.

FIG. 5 shows PFAM domains identified within CLUST.004377 effector A proteins.

FIG. 8 shows PFAM domains identified within CLUST.004377 effector B proteins.

FIG. 11 shows PFAM domains identified within CLUST.004377 effector C1 proteins.

FIG. 14 shows PFAM domains identified within CLUST.004377 effector C2 proteins.

FIG. 17 shows PFAM domains identified within CLUST.004377 effector C3 proteins.

Figure 21:
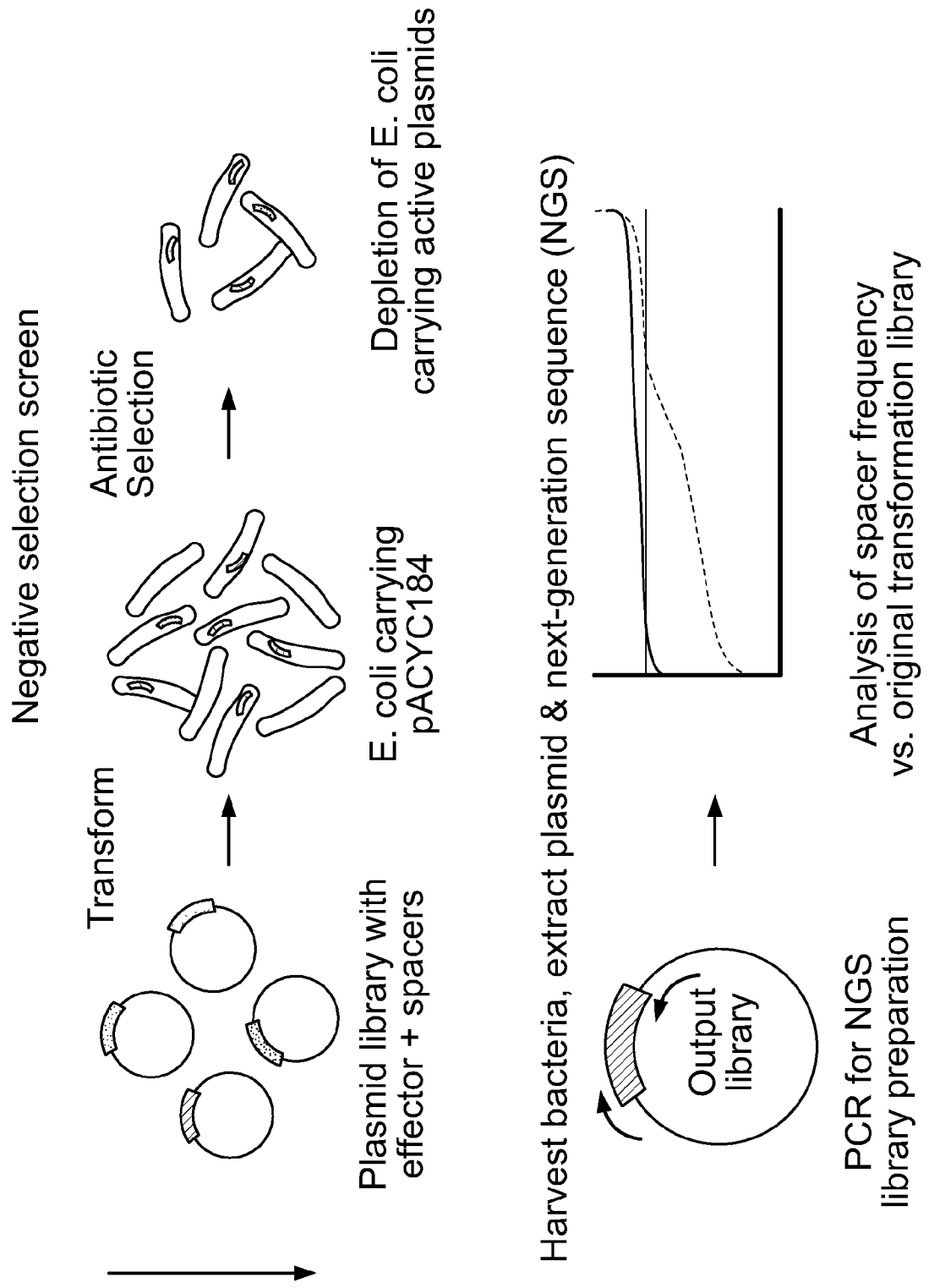
Figure 22:
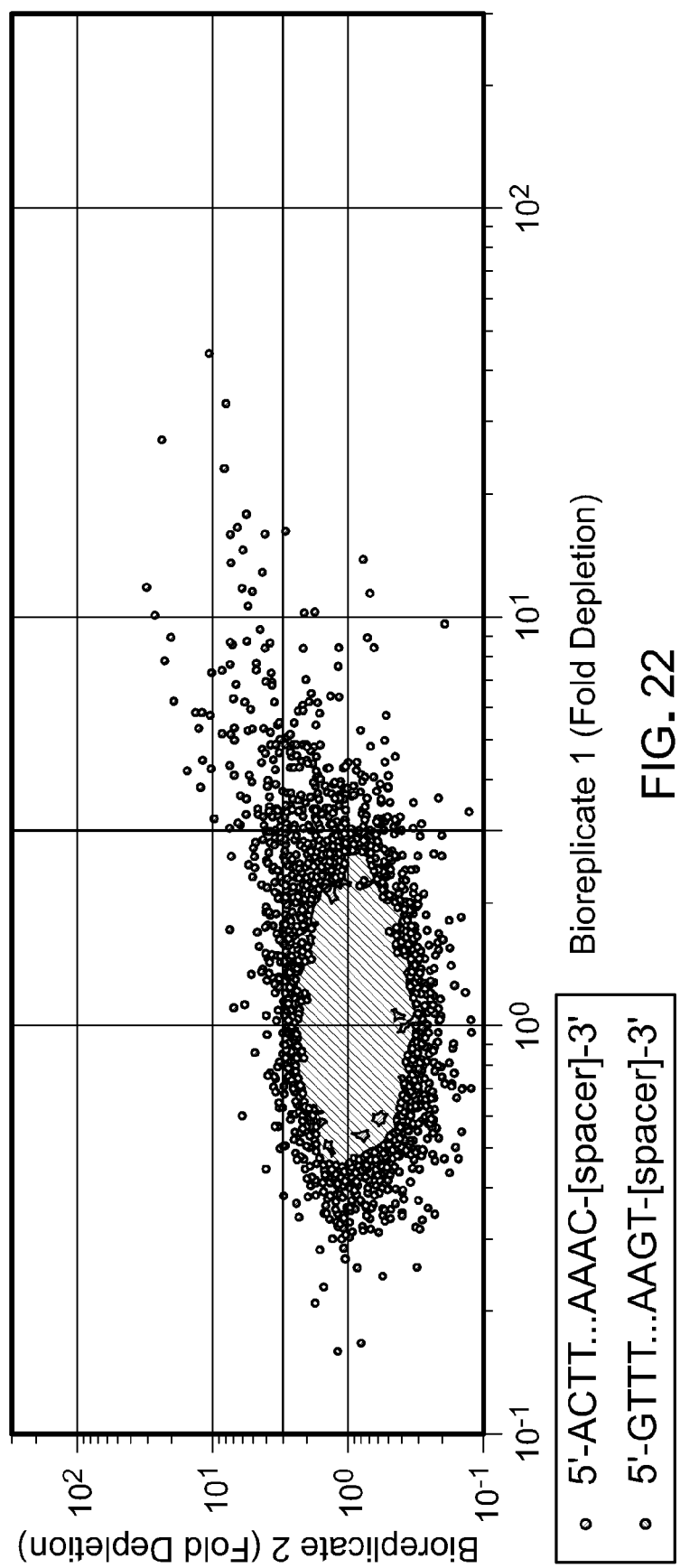
Figure 23:
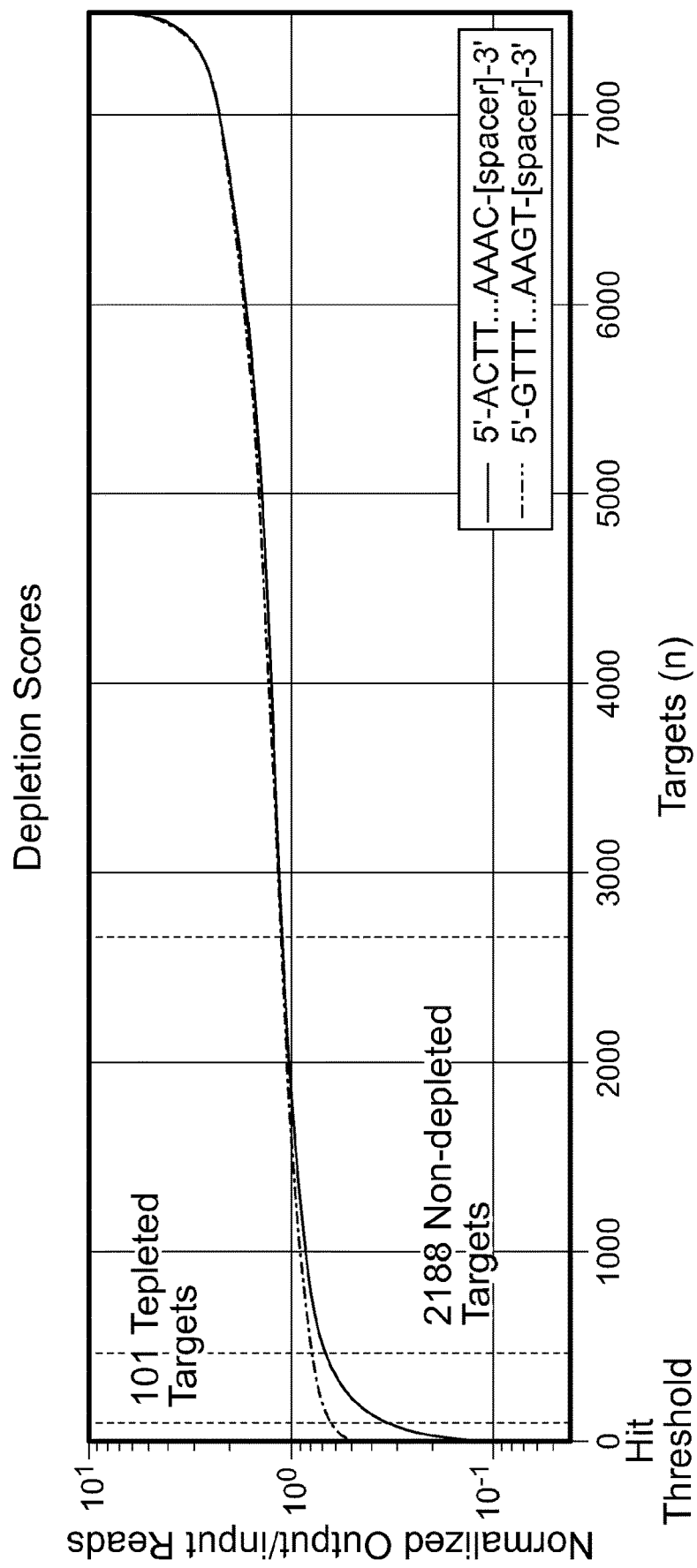

FIG. 21 shows a schematic CRISPR negative selection screening FIGS. 22 and 23 show depletion distributions for direct repeats and spacers targeting pACYC and *E. coli* essential genes. To quantify depletion, a fold-depletion ratio was calculated as $R_{treated}/R_{input}$ for each direct repeat and spacer. The normalized input read count is computed as:

$$R_{input} = \text{\# reads containing } DR+\text{spacer/total reads}$$

without expressing the CLUST.004377 system and RNA guide. The treated read count is computed as $$R_{treated} = (1+\text{\# reads containing } DR+\text{spacer})/\text{total \# reads}$$

with expression of the CLUST.004377 system and RNA guide. A strongly depleted target has a fold depletion greater than 3, which is marked by the red lines.

Figure 24A:
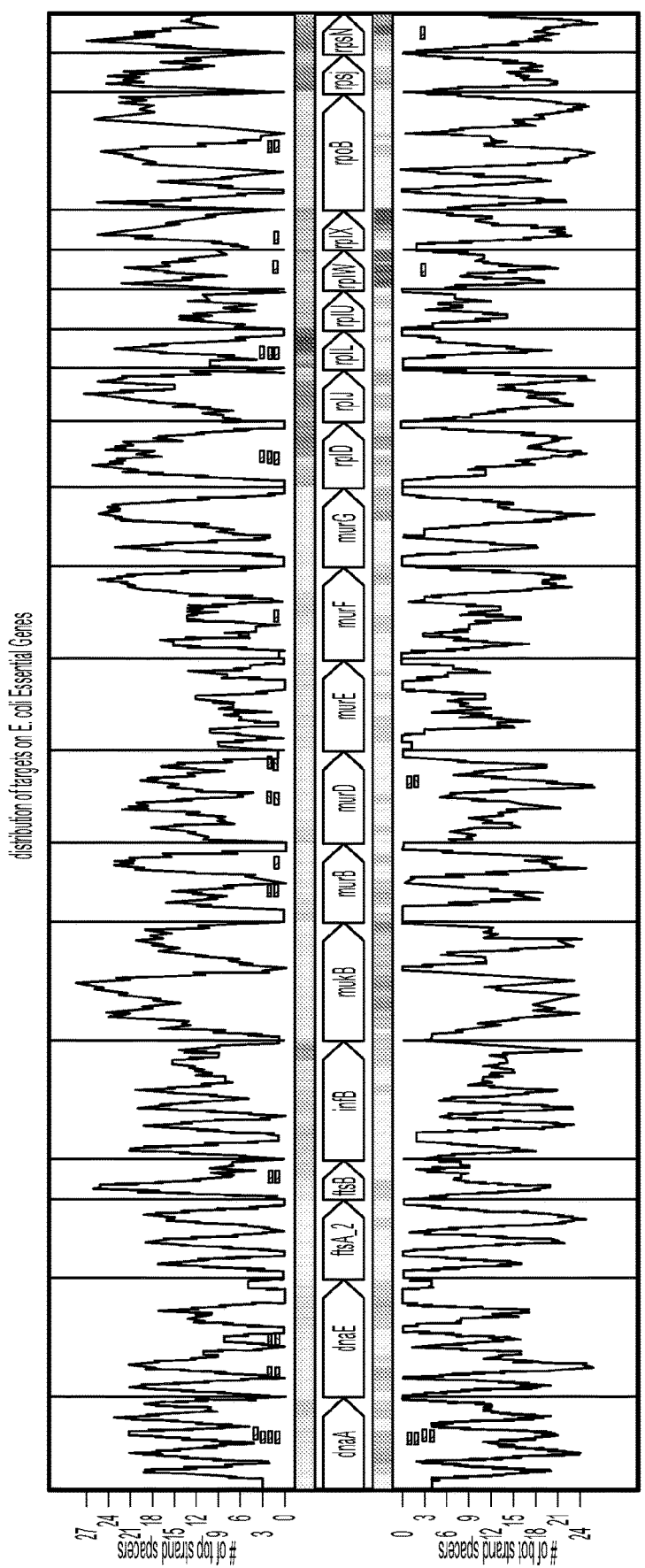
Figure 24B:
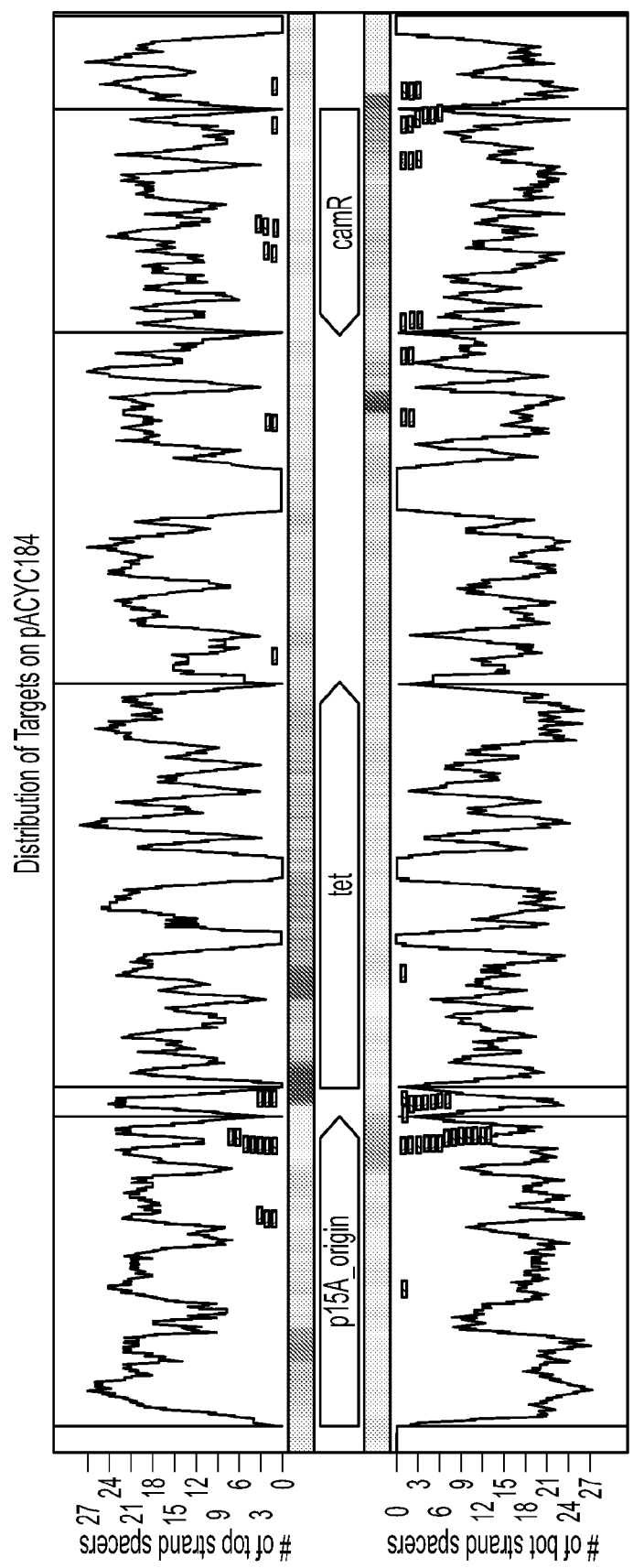

FIGS. 24A and 24B show the target site mapping of depleted RNA guides targeting pACYC (A) and *E. coli* essential genes (B).

Figure 25A:
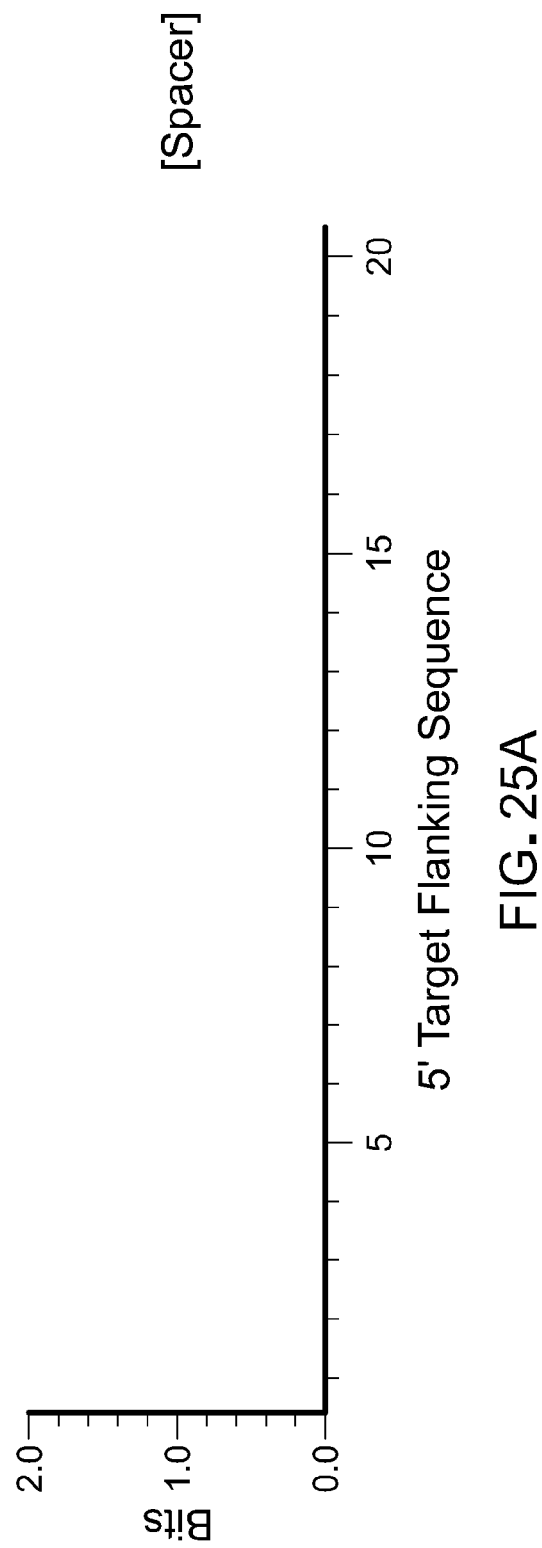
Figure 25B:
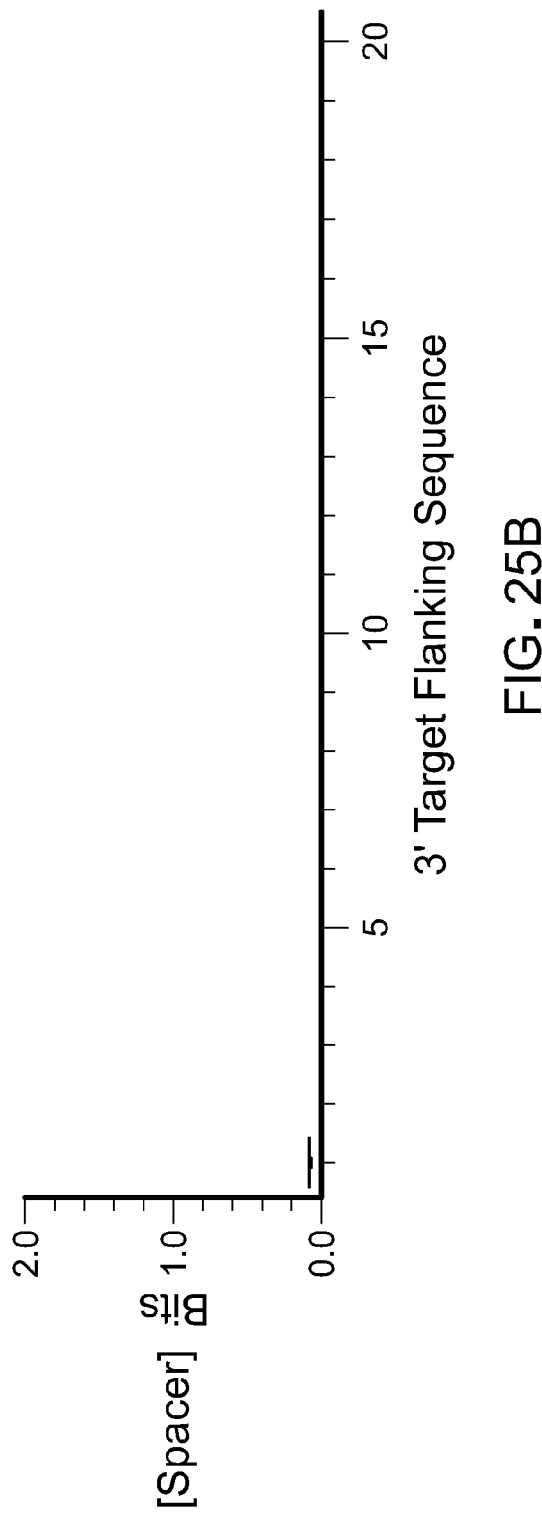
Figure 25C:
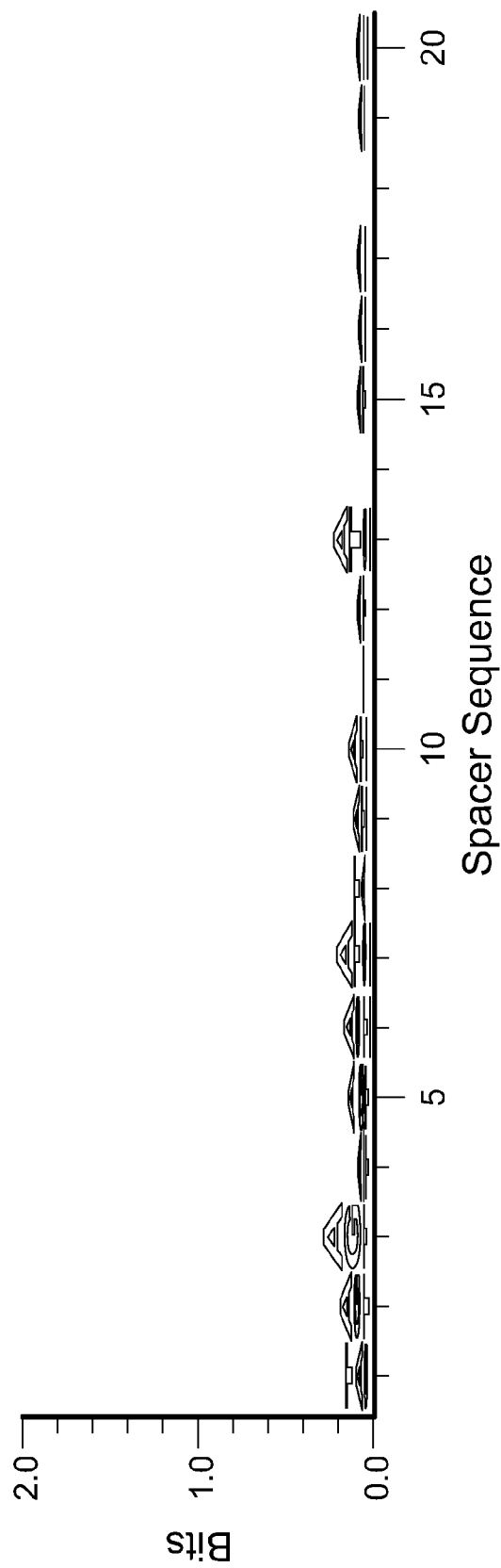

FIGS. 25A-C shows a weblogo of the sequences flanking the left (A) and right (B) sides of depleted targets for the KV757663 CLUST.004377 CRISPR-Cas system.

DETAILED DESCRIPTION

The disclosure relates to the use of computational methods and algorithms to predict new CRISPR-Cas systems and identify their components.

In one embodiment, the disclosure includes new computational methods for identifying novel CRISPR loci by:
  detecting all potential CRISPR arrays in prokaryotic data sources (contig, scaffold, or complete genome);
  identifying all predicted protein coding genes in close proximity to a CRISPR array (e.g. 10 kb);
  forming protein clusters (putative protein families) around identified genes, using, for example, mmseqs2;
  selecting clusters of proteins of unknown function, and identifying homologs in the wider prokaryotic set of proteins using, e.g., BLAST or UBLAST;
  identifying clusters of proteins with a large percentage of homologs co-occurring with CRISPR arrays; and
  predicting the functional domains of the proteins in the identified cluster, e.g., by using hmmsearch on each member of the cluster individually, or by, for example, using a profile hidden Markov model (HMM) constructed from the multiple alignment.

External databases of functional domains include, for example, Pfam and Uniprot. Multiple alignment can be done using, e.g., mafft.

In another aspect, the disclosure relates to defining the minimal elements of novel CRISPR systems by:
  identifying conserved elements (both coding genes and non-coding) in the loci surrounding each cluster (in one aspect, this can be done manually by inspection on a case by case analysis);
  identifying specific conserved non-coding elements that may be terminal repeats required for transposon activity;
  identifying the RNA guide associated with each protein (identify conserved direct repeat structures and then attach a non-natural spacer sequence to the direct repeat. The effect of the non-natural spacer is to induce the effector to target a novel DNA or RNA substrate);
  identifying the minimal RNA or DNA target (identify RNA and DNA targeting a by testing targeting activity of the effector(s) in combination with crRNAs containing multiple different engineered spacer sequences targeting a high diversity of DNA and RNA substrates);
  identifying the minimal system necessary to achieve activity, and
  testing all conserved elements together and then systematically removing different proteins while preserving activity.

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein can be used to discover additional mechanisms and parameters within single subunit Class 2 effector systems that can be more effectively harnessed for programmable biotechnologies.

Pooled-Screening

To efficiently validate the activity of the engineered novel CRISPR-Cas systems and simultaneously evaluate in an unbiased manner different activity mechanisms and functional parameters, we used a new pooled-screening approach in *E. coli*. First, from the computational identification of the conserved protein and noncoding elements of the novel CRISPR-Cas system, DNA synthesis and molecular cloning was used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers were replaced with a library of unprocessed crRNAs containing non-natural spacers targeting the essential genes of the host *E. coli*, or a second plasmid bearing antibiotic resistance, pACYC184. This crRNA library was cloned into the vector backbone containing the protein effectors and noncoding elements (e.g. pET-28a+), and then subsequently transformed the library into *E. coli* along with the pACYC184 plasmid target. Consequently, each resulting *E. coli* cell contains no more than one targeting spacer.

Third, the *E. coli* were grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Examining the population of surviving cells at a later time point compared to an earlier time point results in a depleted signal compared to the inactive crRNAs.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

The key advantages of the in vivo pooled-screen described herein include:
(1) Versatility—Plasmid design allows multiple effectors and/or noncoding elements to be expressed; library cloning strategy enables both transcriptional directions of the computationally predicted crRNA to be expressed;
(2) Comprehensive tests of activity mechanisms & functional parameters—Evaluates diverse interference mechanisms, including DNA or RNA cleavage; DNA excision and/or insertion via transposition; examines co-occurrence of features such as transcription, plasmid DNA replication; and flanking sequences for crRNA library can be used to reliably determine PAMs with complexity equivalence of 4N's;
(3) Sensitivity—by using as targets the low copy number of pACYC184 and the single copy of the *E. coli* genome, this screen design enables high sensitivity for CRISPR-Cas activity since even modest interference rates can result in loss of cell viability through loss of antibiotic resistance or essential gene targeting; and
(4) Efficiency—Optimized molecular biology steps to enable greater speed and throughput, as RNA-sequencing and protein expression samples can be directly harvested from the surviving cells in the screen.

The novel CRISPR-Cas families described herein were evaluated using this in vivo pooled-screen to evaluate their operational elements, mechanisms and parameters, as well as their ability to be active and reprogrammed in an engineered system outside of their natural cellular environment.

CRISPR Enzymes Associated with Mobile Genetic Elements

This disclosure provides mobile genetic elements (e.g., CRISPR-associated transposons) associated with CRISPR systems described herein. These mobile genetic elements can be genetically-altered to delete and/or add one or more components (e.g., a gene encoding a therapeutic product), thereby resulting in mobile genetic elements that can be readily inserted into or removed from a target nucleic acid. In some embodiments, the CRISPR systems encoded by these mobile genetic elements include one or more effector proteins, referred to herein as "CRISPR-associated transposases," which facilitate the movement of the mobile genetic elements from a first site in a nucleic acid to a second site in a nucleic acid. As described in further detail below, in some embodiments, the activity (e.g., excision activity or integration activity) of the CRISPR-associated transposases can be directed to a particular site on a target nucleic acid using a RNA guide that is complementary to a nucleic acid sequence on the target nucleic acid. In some embodiments, the RNA guides are engineered to specifically target the insertion, excision, and/or mobilization of the mobile genetic element to any site in a target nucleic acid of interest.

In some embodiments, the disclosure provides CRISPR-associated transposons that include one or more genes encoding a CRISPR-associated transposase and an RNA guide. In some embodiments, the CRISPR-associated transposons include a payload nucleic acid. In some embodiments, the payload nucleic acid includes a gene of interest. In some embodiments, the gene of interest is operably linked to a promoter (e.g., a constitutive promoter or an inducible promoter). In some embodiments, the gene of interest encodes a therapeutic protein.

This disclosure further provides a class of CRISPR effectors, referred to herein as CRISPR-associated transposases, capable of facilitating the movement of a mobile genetic element (e.g., a CRISPR-associated transposon), wherein the targeting of the mobile genetic element is facilitated by RNA guides. Mobile genetic elements in CLUST.004377, CLUST.009467, and CLUST.009925 comprise CRISPR-associated transposons, including genes encoding CRISPR-associated transposases having a rve integrase domain (also referred to herein as rve integrase domain-containing effectors).

RNA-Guided DNA Insertion

In some embodiments, a CRISPR system described herein mediates the insertion of a nucleotide payload into a target nucleic acid sequence. This activity is facilitated by one or more CRISPR-associated transposases present in the CRISPR system. In some embodiments, the CRISPR-associated transposase comprises one or more of a rve integrase domain a TniQ domain, a TniB domain, or a TnpB domain. In some embodiments, the site of the target nucleic acid where the nucleotide payload is to be inserted is specified by a guide RNA.

RNA-Guided DNA Excision

In some embodiments, a CRISPR system described herein mediates the excision of a nucleotide payload from a target nucleic acid sequence. This activity is facilitated by one or more CRISPR-associated transposases present in the CRISPR system. In some embodiments, the CRISPR-associated transposase comprises one or more of a rye domain a TniQ domain, a TniB domain, or a TnpB domain. In some embodiments, the site of the target nucleic acid where the nucleotide payload is to be excised is specified by a guide RNA.

RNA-Guided DNA Mobilization

In some embodiments, a CRISPR system described herein mediates the excision of a nucleotide payload from a first site in a target nucleic acid, mobilization of the nucleotide payload, and insertion of the nucleotide payload at a second site in a target nucleic acid. This activity is facilitated by one or more CRISPR-associated transposases present in the CRISPR system. In some embodiments, the CRISPR-associated transposase comprises one or more of a rye domain a TniQ domain, a TniB domain, or a TnpB domain. In some embodiments, the first site of the target nucleic acid where the nucleotide payload is to be excised is specified by a guide RNA. In some embodiments, the second site in the target nucleic acid where the nucleotide payload is to be inserted is specified by a guide RNA.

Transposase Activity

In some embodiments, a CRISPR effector described herein (e.g., a CRISPR-associated transposase) comprises transposase activity. DNA transposition is one of the mechanisms by which genome rearrangement and horizontal gene transfer occurs in prokaryotic and eukaryotic cells. Transposons are DNA sequences that are capable of being moved within a genome. During DNA transposition a transposase recognizes transposon-specific sequences that flank an intervening DNA sequence. The transposase recognizes the transposon, excises the transposon from one location in a nucleic acid sequence, and inserts it (including the inverted repeat sequences with the intervening sequence) into another location. In some instances, the end sequences of the transposon comprise short inverted terminal repeats comprising duplications of a short segment of the sequence flanking the insertion sites that are characteristic for each transposon.

The mechanisms involved in transposition mediated by several transposon systems including Tc1, Tol2, Minos, Himar1, Hsmar1, Mos1, Frog Prince, Piggyback, and Sleeping Beauty have been characterized (see, e.g., Chitilian et al. (2014) *Stem Cells* 32: 204-15; Ivics et al. (1997) *Cell* 91: 501-10; Miskey et al. (2003) *Nucleic Acids Res.* 31: 6873-81; Urschitz et al. (2013) *Mob. Genet. Elements* 3: e25167; Jursch et al. (2013) *Mob. DNA* 4: 15; Pflieger et al. (2014) *J. Biol. Chem.* 289: 100-11); and Hou et al. (2015) *Cancer Biol. Ther.* 16(1): 8-16). For example, the Sleeping Beauty transposase (SBase) functions through a "cut-and-paste" process (see, e.g., Yant et al. (2004) *Mol. Cell. Biol.* 4: 9239-47). In some embodiments, a CRISPR-associated transposase described herein comprise a transposase domain or a transposase-like domain. For example, in some embodiments, the CRISPR-associated transposase comprises a Mu-transposase domain or module. In some embodiments, the CRISPR-associated transposase comprises a TniQ transposase domain. In some embodiments, the CRISPR-associated transposase comprises a TniB transposase domain. In some embodiments, the transposase domain is a OrfB_IS605 domain.

In some embodiments, the transposase domain of a CRISPR-associated transposase described herein is capable of one or more of the following activities: (a) excising a nucleic acid fragment from its situs on in a genome (i.e., excision activity); (b) mediating the integration of a nucleic acid fragment into a situs in a genome (i.e., integration activity); and/or (c) specifically recognizing a transposon element (e.g., a specific inverted repeat sequence). In some embodiments, a transposase domain of a CRISPR-associated transposase described herein is modified to eliminate one or more activities. In some embodiments, a transposase domain of a CRISPR-associated transposase described herein may be mutated such that the transposase domain comprises excision activity, but does not comprise integration activity. In some embodiments, a transposase domain of a CRISPR-associated transposase described herein is mutated such that a transpose domain comprises integration activity, but does not comprise excision activity. In some embodiments, a transposase domain of a CRISPR-associated transposase described herein is mutated such that the transposase domain comprises integration activity and excision activity, but lacks the ability to recognize a specific nucleic acid sequence. In some embodiments, a transposase domain of a CRISPR-associated transposase described herein is mutated such that the transposase domain comprises integration activity, but lacks excision activity and the ability to recognize a specific nucleic acid sequence. In some embodiments, a transposase domain of a CRISPR-associated transposase described herein is mutated such that the transposase domain comprises excision activity, but lacks integration activity and the ability to recognize a specific nucleic acid sequence.

In some embodiments, the CRISPR-associated transposases described herein can be used to facilitate the random insertion of a nucleic acid sequence into the genome of a cell. In some embodiments, the CRISPR-associated transposases described herein may be used to facilitate the targeted insertion or excision of a nucleic acid sequence into or out of the genome of a cell. In some embodiments, the nucleic acid sequence that is inserted into the cell is flanked by inverted repeat sequences that are specifically recognized by a transposase domain of the CRISPR-associated transposase. In some embodiments, the intervening nucleic acid sequence between these inverted repeat sequences is at least 10 bp, at least 20 bp, at least 30 bp, at least 40 bp, at least 50 bp, at least 60 bp, at least 70 bp, at least 80 bp, at least 90 bp, at least 100 bp, at least 150 bp, at least 200 bp, at least 250 bp, at least 300 bp, at least 400 bp, at least 500 bp, at least 600 bp, at least 700 bp, at least 800 bp, at least 900 bp, at least 1000 bp, at least 1,500 bp, at least 2,000 bp, at least 3,000 bp, at least 4,000 bp, at least 5,000 bp in length, at least 6,000 bp in length, at least 7,000 bp in length, at least 8,000 bp in length, at least 9,000 bp in length, or at least 10,000 bp in length. In some embodiments, the intervening nucleic acid sequence between these inverted repeat sequences is less than 10 bp, less than 20 bp, less than 30 bp, less than 40 bp, less than 50 bp, less than 60 bp, less than 70 bp, less than 80 bp, less than 90 bp, less than 100 bp, less than 150 bp, less than 200 bp, less than 250 bp, less than 300 bp, less than 400 bp, less than 500 bp, less than 600 bp, less than 700 bp, less than 800 bp, less than 900 bp, less than 1000 bp, less than 1,500 bp, less than 2,000 bp, less than 3,000 bp, less than 4,000 bp, less than 5,000 bp in length, or less than 10,000 bp in length.

Effectors Comprising Helix-Turn-Helix Domains

In some embodiments, effectors within the systems described herein may contain a helix-turn-helix (HTH) domain. HTH domains typically include or consist of two α-helices forming an internal angle of approximately 120 degrees that are connected by a short strand or turn of amino acid residues, and are present in a multitude of prokaryotic and eukaryotic DNA-binding proteins, such as transcription factors (see, e.g., Aravind et al. (2005) FEMS Microbiol. Rev. 29(2): 231-62). Beyond transcriptional regulation, HTH domains are involved in a wide range of functions including DNA repair and replication, RNA metabolism and protein-protein interactions. In some embodiments, an effector described herein comprises DNA-binding activity. In some embodiments, an effector described herein comprises RNA-binding activity. In some embodiments, an effector described herein comprises a HTH domain that mediates a protein-protein interaction.

CRISPR Enzyme Modifications

Modulating Insertion/Excision/Transposition Activity of CRISPR Enzymes

The activity of CRISPR-associated transposases may be altered in ways to change the relative efficiencies of insertion and excision. Altering these activities enable greater control in the different modes of transposase directed genome editing; for instance, CRISPR-associated transposases with predominantly insertion activity can be used for locus-specific insertion of transgenes to enable applications including, but not limited to, therapeutics (e.g., fetal hemoglobin expression for treatment of thalassemia), genetic engineering (e.g., trait stacking in plant genome engineering), or engineered cells (e.g., introducing control circuits or custom chimeric antigen receptors for CAR-T cell engineering). Alternatively, CRISPR-associated transposases with predominantly excision activity can also be used in applications, such as restoring the genome of engineered cells through excising inserted transcription factors. These CRISPR-associated transposases can be modified to have diminished excision or insertion activity, e.g., excision or insertion inactivation of at least 40%, at least 50%, at least 60%, at least 70%, at least 80%, at least 90%, at least 95%, at least 97%, or 100% as compared with the wild type CRISPR-associated transposases. Modulation of the insertion or excision activity can be done with several methods known in the art, such as introducing mutations into the catalytic core of the transposase. In some embodiments, catalytic residues for the transposase activities are identified, and these amino acid residues can be substituted by different amino acid residues (e.g., glycine or alanine) to diminish the transposase activity. An example in which modifications to the catalytic core of a transposase yielded differential effects on excision versus insertion is with the generation of an excision competent/integration defective variant of the piggyBac transposase (Exc+/Int− PB) Li, Xianghong et al. "piggyBac transposase tools for genome engineering," Proc. Nat'l. Acad. Sci., 1073.10 (2013): 2279-2287. In other embodiments, the variants to modulate excision/insertion activity can be combined with other CRISPR-associated transposase modifications, such as a mutations that relax or make more stringent the targeting space or PAM constraints. Furthermore, these mutations are not restricted to the protein effectors of the transposon, but may be found on the non-coding elements such as the transposase ends. Together, these may yield a set of mutations that enable the tuning of the enzymatic activities of the CRISPR-associated transposase.

Generation of Fusion Proteins

Additionally, CRISPR-associated transposases, whether in its native functional form or with mutations to modulation its activity, can provide a foundation from which fusion proteins with additional functional proteins can be created. The inactivated CRISPR enzymes can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding. In some embodiments, the functional domains are Kruippel associated box (KRAB), VP64, VP16, Fok1, P65, HSF1, MyoD1, and biotin-APEX.

The positioning of the one or more functional domains on the CRISPR transposase is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the CRISPR enzyme is modified to comprise a first functional domain at the N-terminus and a second functional domain at the C-terminus.

The addition of functional domains to the CRISPR-associated transposase or onto other effector proteins in the complex may provide an ability for the transposase system to modify the the physical DNA (e.g., methylation, etc.) or its regulation (e.g., transcriptional or repression) in situ.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the guide RNA recruits them into a ternary complex that recapitulates the activity of full-length CRISPR enzymes and catalyzes site-specific DNA cleavage. The use of a modified guide RNA abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can modify the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional guide RNA, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, guide RNAs, and guide RNAs that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45(13): e118).

Inducible CRISPR Enzymes

The CRISPR enzymes can be inducible, e.g., light inducible or chemically inducible. This mechanism allows for activation of the functional domain in the CRISPR enzymes. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," *Nature*, 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," *Nature Biotech.*, 33.2 (2015): 139-142).

Furthermore, expression of the CRISPR enzymes can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," *Nucl. Acids Res.*, 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues.

In some embodiments, at least one Nuclear Localization Signal (NLS) is attached to the nucleic acid sequences encoding the CRISPR enzyme. In some embodiments, at least one Nuclear Export Signal (NES) is attached to the nucleic acid sequences encoding the CRISPR enzyme. In a preferred embodiment a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its helicase activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a guide RNA. In some embodiments, the CRISPR enzyme is mutated at one or more amino acid residues to alter its ability to functionally associate with a target nucleic acid.

In some embodiments, the CRISPR enzymes described herein are capable of modifying a target nucleic acid molecule. In some embodiments, the CRISPR enzyme modifies both strands of the target nucleic acid molecule. However, in some embodiments, the CRISPR enzyme is mutated at one or more amino acid residues to alter its nucleic acid manipulation activity. For example, in some embodiments, the CRISPR enzyme may comprise one or more mutations which render the enzyme incapable of cleaving a target nucleic acid or inserting/excising a target sequence.

In some embodiments, a CRISPR enzyme described herein may be engineered to comprise a deletion in one or more amino acid residues to reduce the size of the enzyme while retaining one or more desired functional activities (e.g., nuclease activity and the ability to functionally interact with a guide RNA). The truncated CRISPR enzyme may be advantageously used in combination with delivery systems having load limitations.

In one aspect, the present disclosure provides nucleotide sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Guide RNA Modifications

Spacer Lengths

The spacer length of guide RNAs can range from about 15 to 50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the direct repeat length of the guide RNA is at least 16 nucleotides, or is from 16 to 20 nucleotides (e.g., 16, 17, 18, 19, or 20 nucleotides). In some embodiments, the direct repeat length of the guide RNA is 19 nucleotides.

The guide RNA sequences can be modified in a manner that allows for formation of the CRISPR complex and successful binding to the target, while at the same time not allowing for successful effector activity (i.e., without excision activity/without insertion activity/without nuclease activity). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active modification. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a guide RNA (gRNA) wherein the gRNA comprises a dead guide sequence whereby the gRNA is capable of hybridizing to a target sequence such that the CRISPR system is directed to a genomic locus of interest in a cell without detectable nucleic acid modification activity.

A detailed description of dead guides is described, e.g., in WO 2016094872, which is incorporated herein by reference in its entirety.

Inducible Guides

Guide RNAs can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of guide RNA can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical Modifications

Chemical modifications can be applied to the guide RNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized guide RNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the guide RNA includes one or more phosphorothioate modifications. In some embodiments, the guide RNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the guide RNAs, tracrRNAs, and crRNAs described herein can be optimized. In some embodiments, the optimized length of guide RNA can be determined by identifying the processed form of tracrRNA and/or crRNA, or by empirical length studies for guide RNAs, tracrRNAs, crRNAs, and the tracrRNA tetraloops.

The guide RNAs can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, Qj3, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.,* 2016 Nov. 16; 44(20):9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The guide RNAs can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. For CRISPR nucleases, modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR-associated transposon systems described herein have a wide variety of utilities including modifying (e.g., deleting, inserting, translocating, inactivating, or activating) a target polynucleotide in a multiplicity of cell types. The CRISPR transposon systems have a broad spectrum of applications in, e.g., tracking and labeling of nucleic acids, drug screening, and treating various genetic disorders.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Illumina system). CRISPR-associated transposases may enable more efficient preparation due to the ability to directly insert barcodes and adaptor sequences on a transposase payload.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, guide RNA sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae,*" *Yeast,* 2017 Sep. 8. doi: 10.1002/yea.3278; and Hlavova et al., "Improving microalgae for biotechnology—from genetics to synthetic biology," *Biotechnol. Adv.,* 2015 Nov. 1; 33:1194-203, both of which are incorporated herein by reference in the entirety.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 2011 June; 11(3):222-8, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). CRISPR-associated transposases may enable more efficient disruption due to the potential for inserting larger sequences. Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis (Bashing)

The CRISPR systems described herein can be used for in situ saturating mutagenesis. In some embodiments, a pooled guide RNA library can be used to perform in situ saturating mutagenesis for particular genes or regulatory elements. In other embodiments, a pooled library of DNA inserts containing a saturating mutagenesis library can be inserted by the CRISPR-associated transposase. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577): 192-7, which is incorporated herein by reference in its entirety.

RNA-Related Applications

The CRISPR systems described herein can have various RNA-related applications, e.g., modulating gene expression, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016205764 A1, which is incorporated herein by reference in its entirety.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the effector proteins and suitable guide RNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Therapeutic Applications

The CRISPR-associated transposon systems described herein can have diverse therapeutic applications. Without wishing to be limiting, one framework to organize the range of therapeutic applications enabled by CRISPR-associated transposon systems is determining whether the therapeutic genetic modification is a correction of a native locus, or locus-agnostic gene augmentation.

For therapeutic correction of a native locus, the new CRISPR systems can be used to correct mutations responsible for monogenic diseases (e.g., Duchenne Muscular Dystrophy, Cystic Fibrosis, etc.), or introduce beneficial mutations (e.g., Pcsk9 for lowered cardiovascular disease risk, BCL11a for increasing fetal hemoglobin expression in treating hemoglobinapthies, CCR5 for HIV resistance, etc.) Using CRISPR-associated transposons may have key advantages. The first advantage is the potential to use a single therapeutic construct to correct a diverse set of genetic mutations, whether in a single patient or across the patient population. This is due to the fact that transposition enables the replacement of a large gene fragment, rather than the short-range corrections enabled by homology directed repair following DNA cleavage or base editing. Second, using CRISPR-associated transposons may enable therapeutic modifications in a broad range of post-mitotic cells and tissues, given that the enzymatic mechanism of action of the transposon is anticipated to be independent from DNA repair mechanisms such as homologous recombination or homology directed repair.

For locus-agnostic gene augmentation, the new CRISPR systems can be used to introduce gene fragments that provide a therapeutic benefit. This includes gene therapies to replace missing or defective native enzymes, including, but not limited to, RPE65 in Leber's Congenital Amaurosis, adenosine de-aminase in Severe Combined Immunodeficiency (SCID), and any number of defective enzymes causing diseases of inborn errors of metabolism. In addition to supplementing defective enzymes, the CRISPR-associated transposons may provide augment existing cellular properties, such as the introduction of custom chimeric antigen T-cell receptors for the production of cell therapies. The CRISPR-associated transposons may have the advantages of greater therapeutic durability when the transgene is incorporated genomically (vs. episomal expression in some recombinant viral vectors), and of greater control in transgene insertion, to ensure that the transposon is directed towards chromosomal locations that are at once "safe harbors" for genome editing but still transcriptionally active. This is differentiated from the possible deleterious effects of pseudo-random insertion of integrating viruses, as well as the promiscuous insertion using transposases such as Tn5, piggyBac, and Sleeping Beauty.

Altogether, a programmable transposon would enable a range of genome modifications that may prove highly valuable to therapeutic development, whether directly via therapeutic gene corrections, or indirectly by enabling the engineering of cells and disease models.

Delivery

Through this disclosure and the knowledge in the art, the CRISPR systems described herein, or components thereof, nucleic acid molecules thereof, or nucleic acid molecules encoding or providing components thereof, can be delivered by various delivery systems such as vectors, e.g., plasmids, viral delivery vectors. The new CRISPR enzymes and/or any of the RNAs (e.g., guide RNAs) can be delivered using suitable vectors, e.g., plasmids or viral vectors, such as adeno-associated viruses (AAV), lentiviruses, adenoviruses, and other viral vectors, or combinations thereof. The proteins and one or more guide RNAs can be packaged into one or more vectors, e.g., plasmids or viral vectors.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least $1\times10^5$ particles (also referred to as particle units, pu) of adenoviruses. In some embodiments, the dose preferably is at least about $1\times10^6$ particles, at least about $1\times10^7$ particles, at least about $1\times10^8$ particles, and at least about $1\times10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR enzymes. In some embodiments, the CRISPR enzymes and/or guide RNAs are coupled to one or more CPPs to effectively transport them inside cells (e.g., plant protoplasts). In some embodiments, the CRISPR enzymes and/or guide RNA(s) are encoded by one or more circular or non-circular DNA molecules that are coupled to one or more CPPs for cell delivery.

CPPs are short peptides of fewer than 35 amino acids either derived from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hallbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.,* 2014 June; 24(6): 1020-7; and WO 2016205764 A1; each of which is incorporated herein by reference in its entirety.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

EXAMPLES

The invention is further described in the following examples, which do not limit the scope of the invention described in the claims.

Example 1—Identification of Minimal Components for a CLUST.004377 CRISPR System (FIGS. 1-17)

Figure 1A:
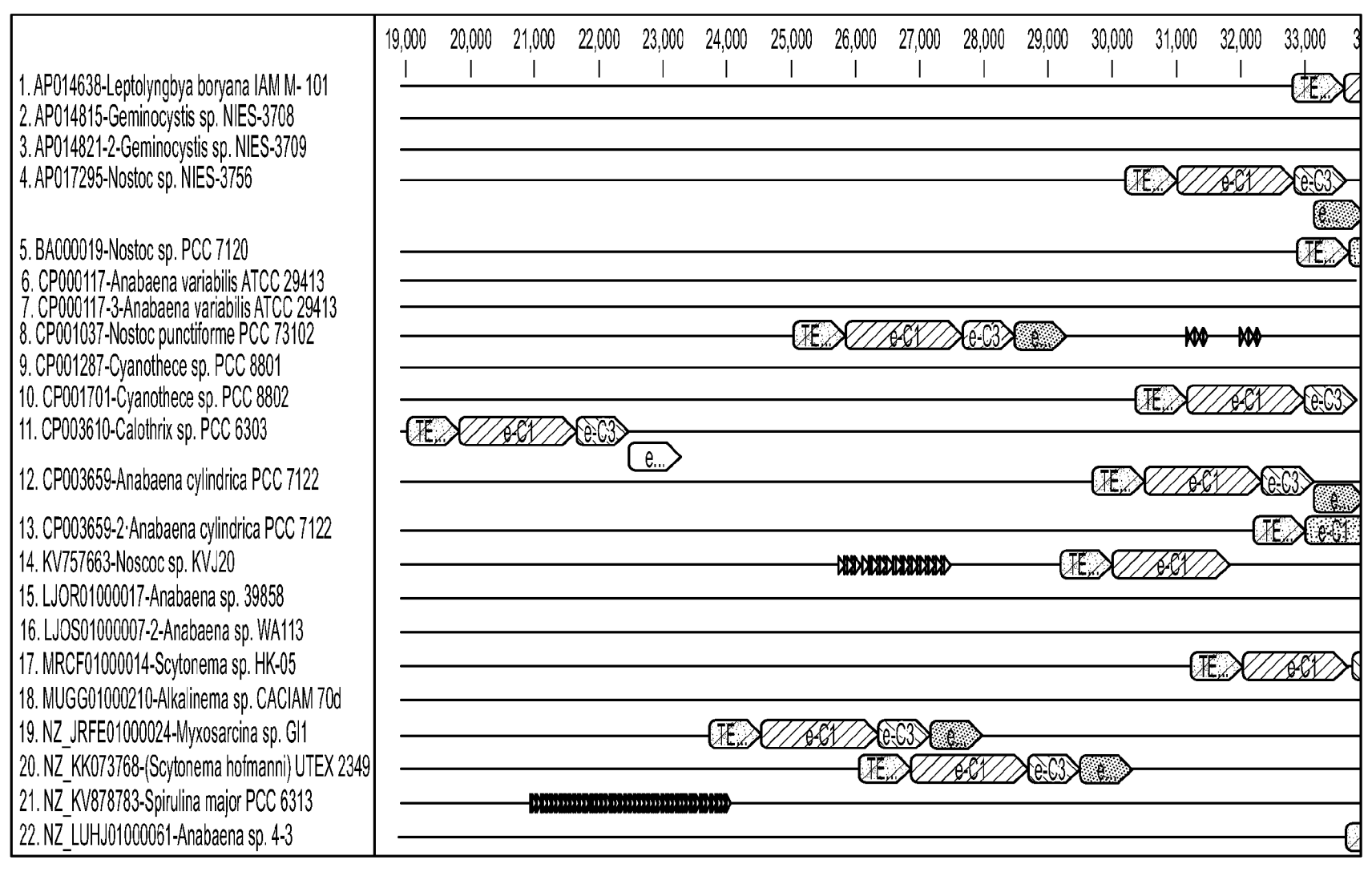
Figure 1B:
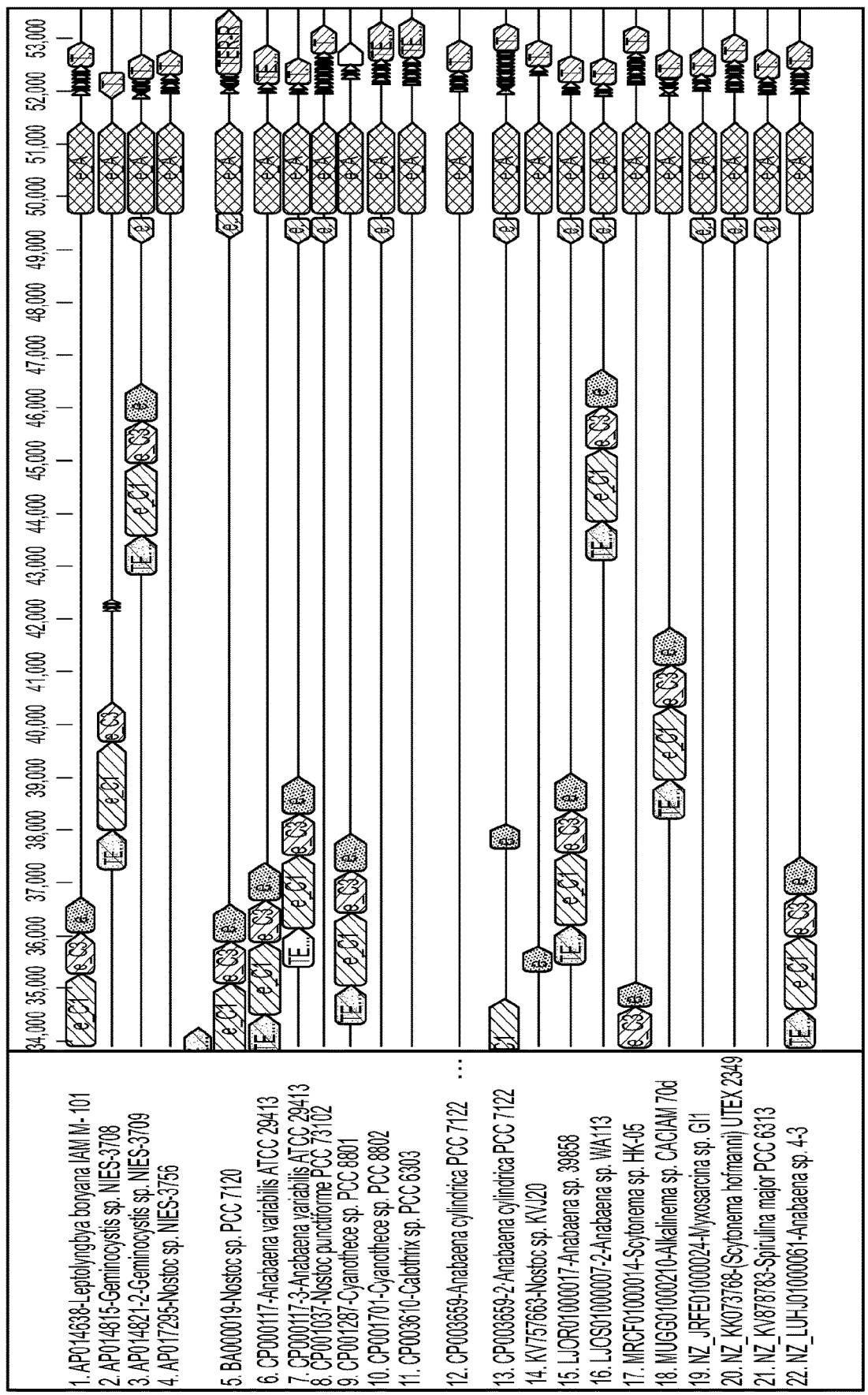

This protein family describes a mobile genetic element associated with CRISPR systems found in organisms including but not limited to *Anabaena* and *Cyanothece* (FIG. 1).

Figure 2A:
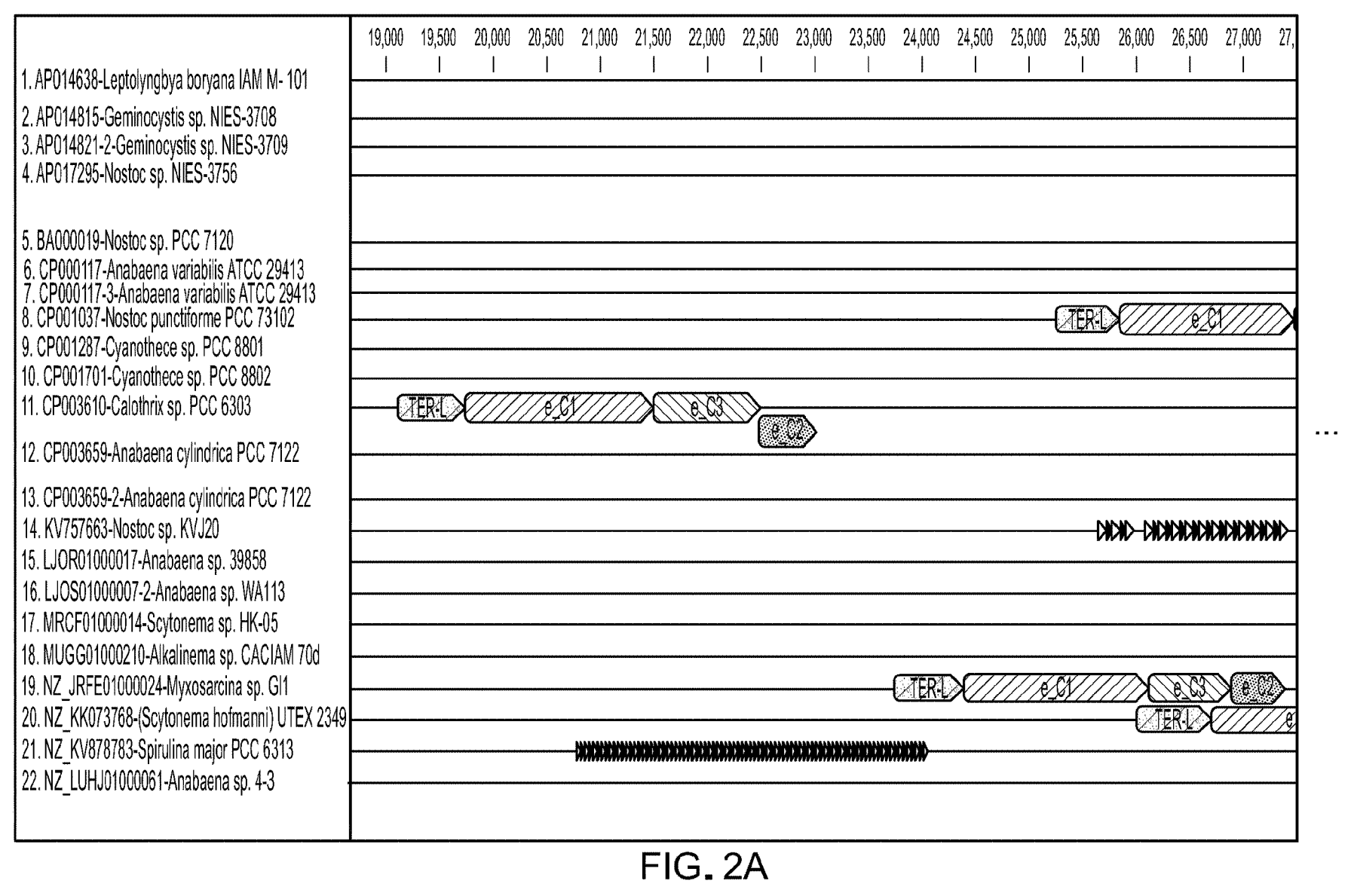
Figure 2B:
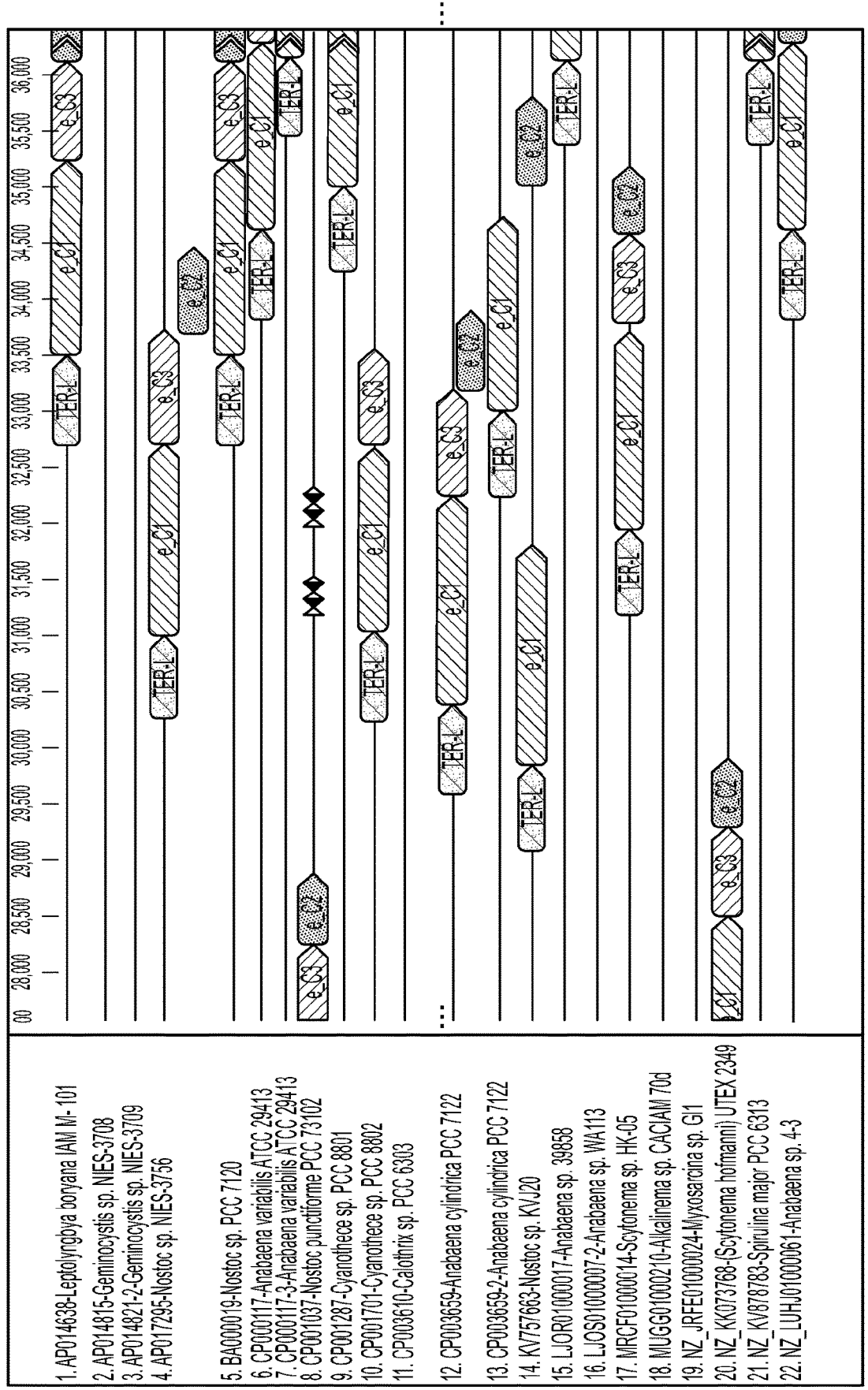
Figure 2C:
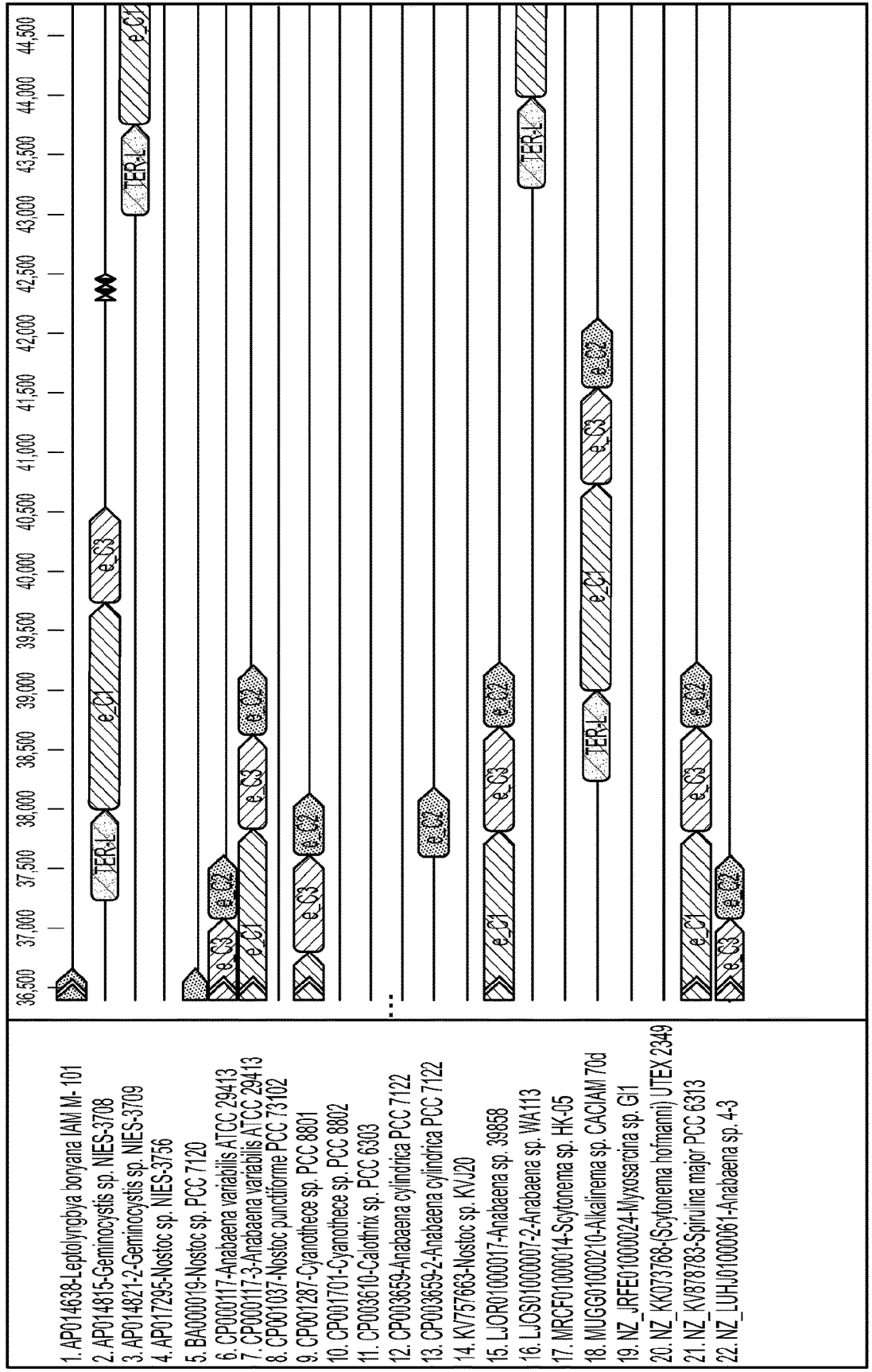
Figure 2D:
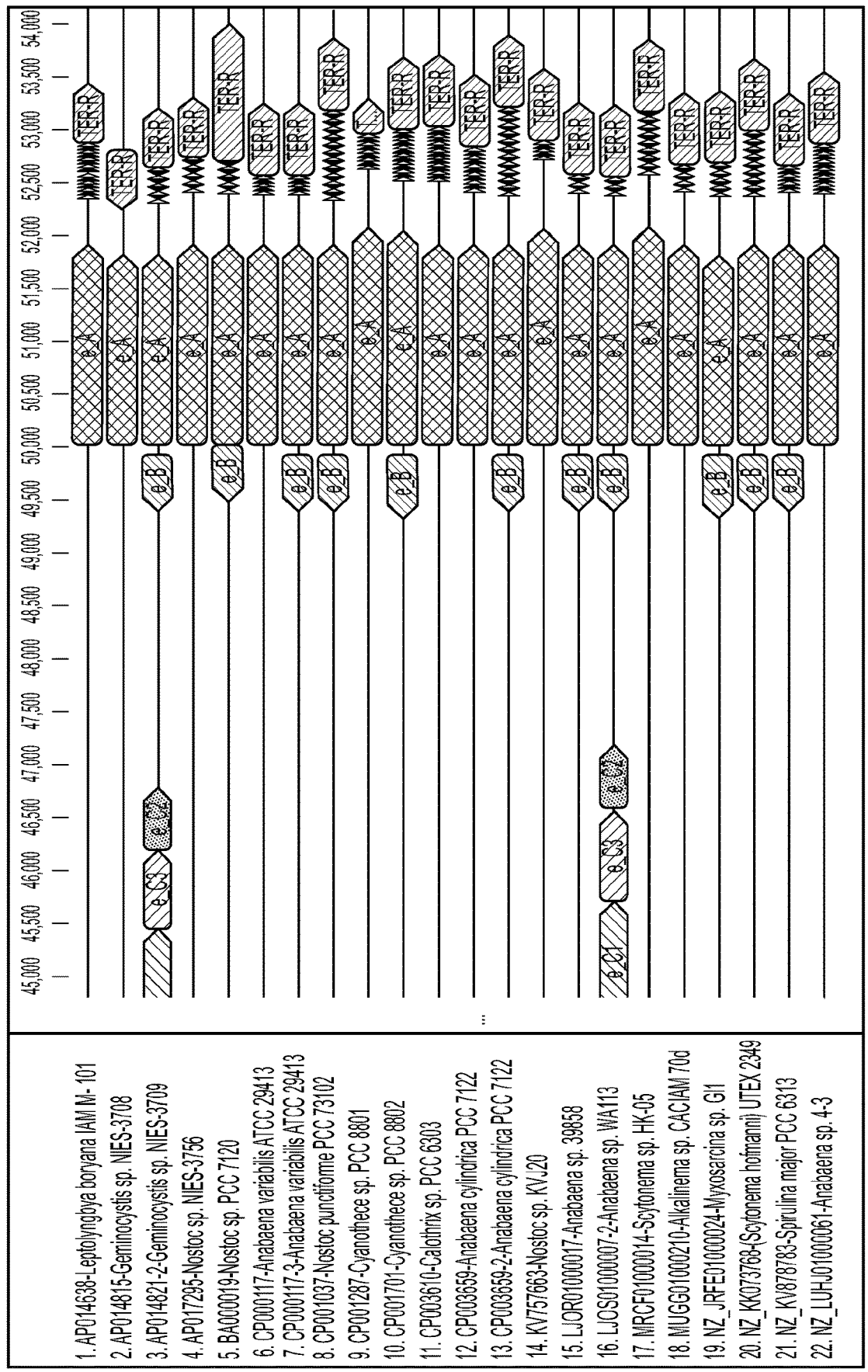

The naturally occurring loci containing this effector are depicted in FIGS. 1, 2A-2B, indicative that Effector A (~620 amino acids) has a high co-occurrence with Effectors C1, C2, and C3, as well as the effector protein Effector B (~140 aa). CLUST.004377 effectors include the exemplary effectors detailed in TABLES 1-9.

Figure 3:
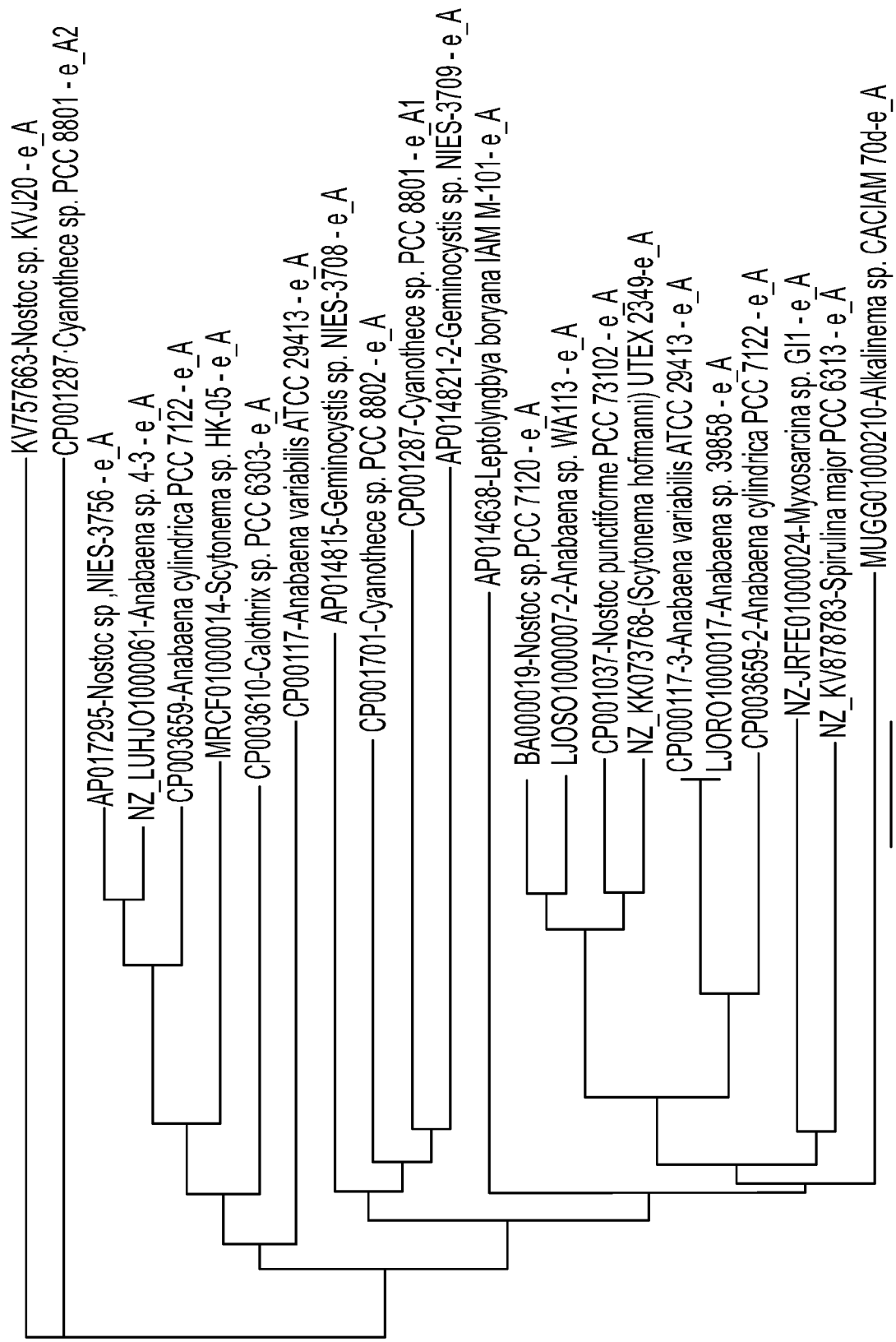
FIG. 3 shows a phylogenetic tree of CLUST.004377 effector A proteins.
Figure 4:
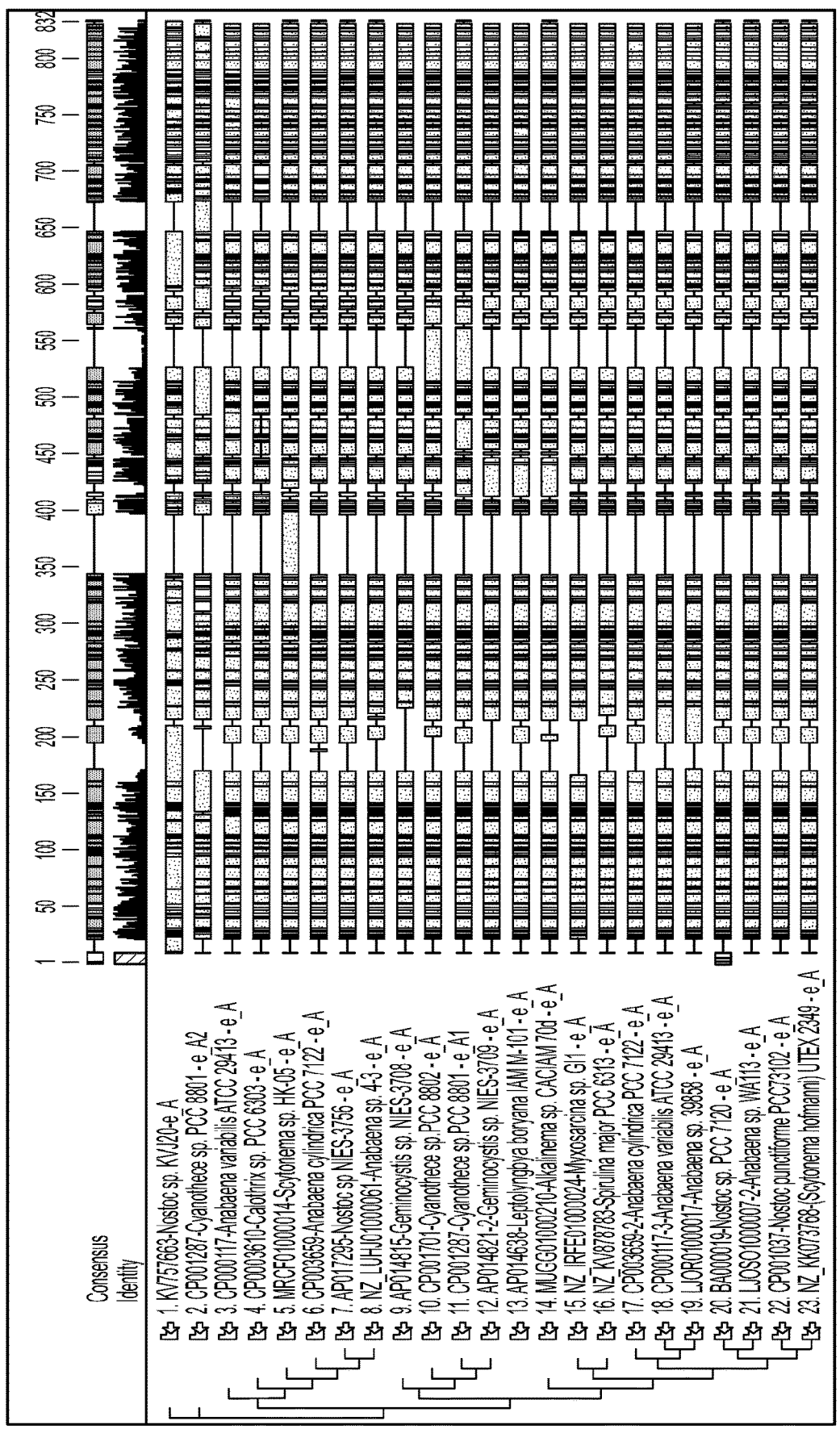
FIG. 4 shows an alignment of CLUST.004377 effector A proteins by genome accession and species, highlighting sequence location of conserved residues, with color denoting nucleotide polarity (Yellow: Non-polar side chain, Green: Polar side chain, Blue: Basic, Red: Acidic).

Effector A revealed an OrfB_IS605 domain, indicative that it is derived from the TnpB family of non-autonomous transposases (FIGS. 3-5).

Figure 6:
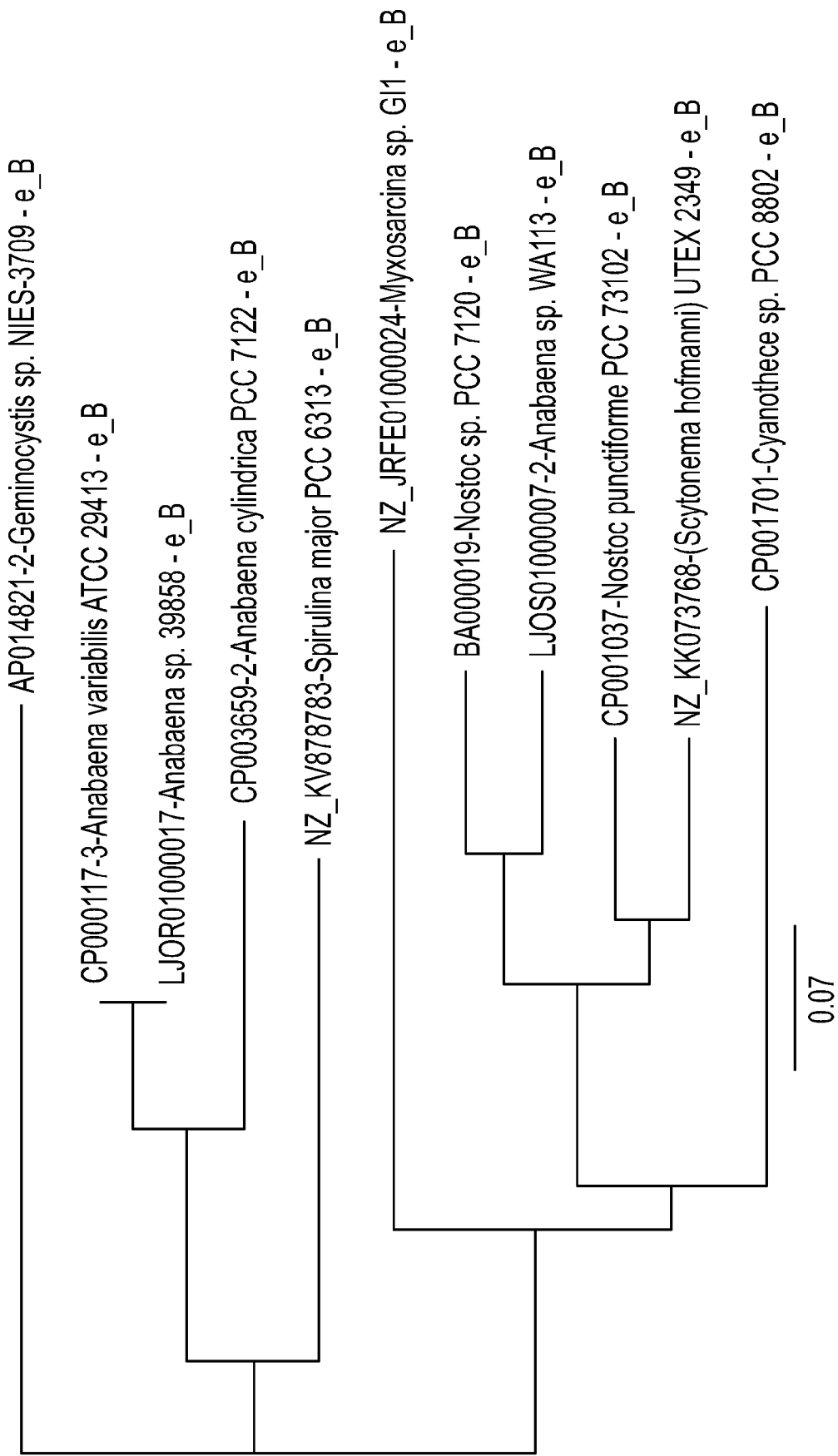
FIG. 6 shows a phylogenetic tree of CLUST.004377 effector B proteins.
Figure 7:
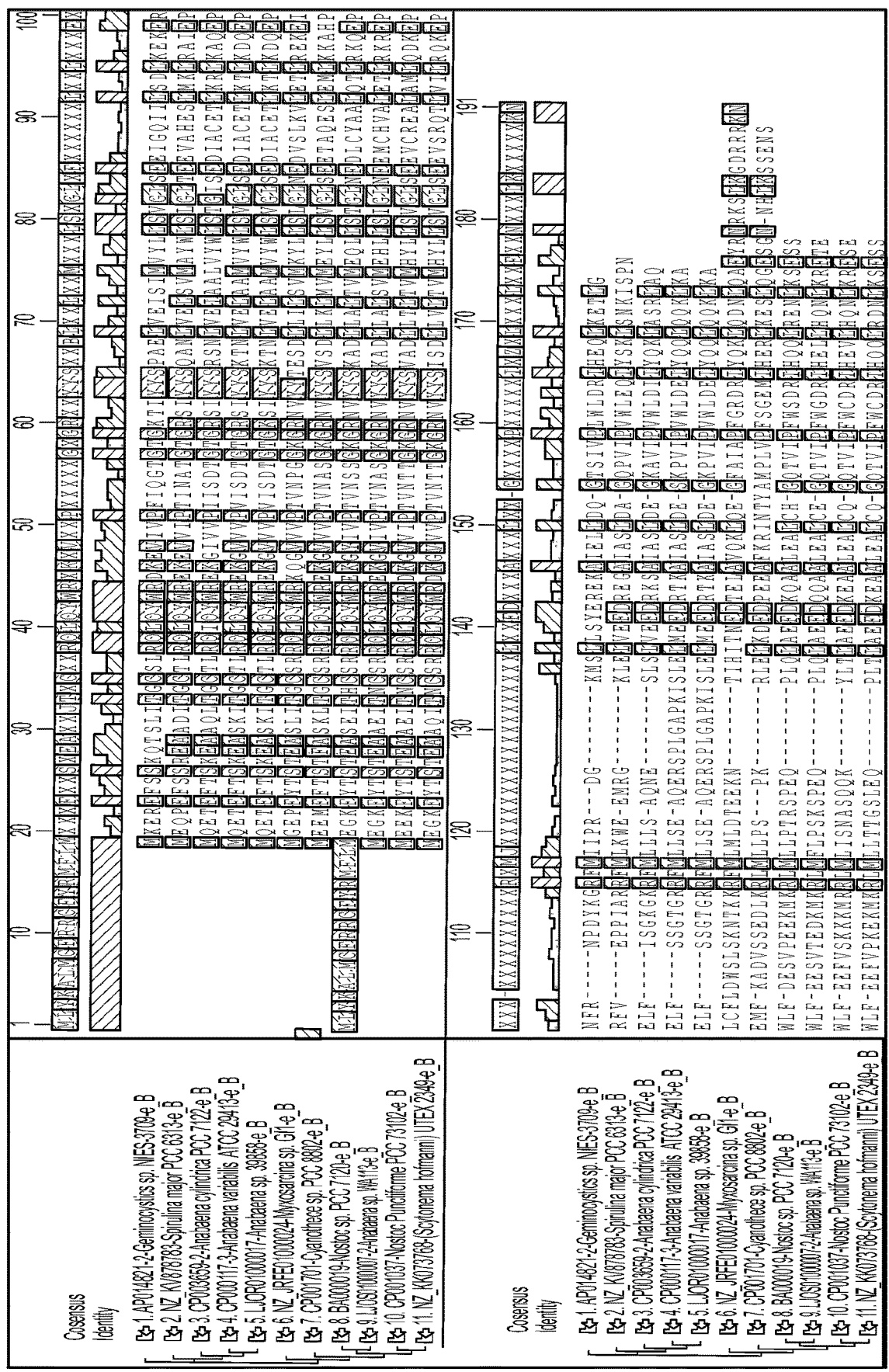
FIG. 7 shows an alignment of CLUST.004377 effector B proteins by genome accession and species, highlighting sequence location of conserved residues, with color denoting nucleotide polarity (Yellow: Non-polar side chain, Green: Polar side chain, Blue: Basic, Red: Acidic).

A domain search for Effector B revealed a MerR_1 domain indicative of transcriptional regulation (FIGS. 6-8).

Figure 9:
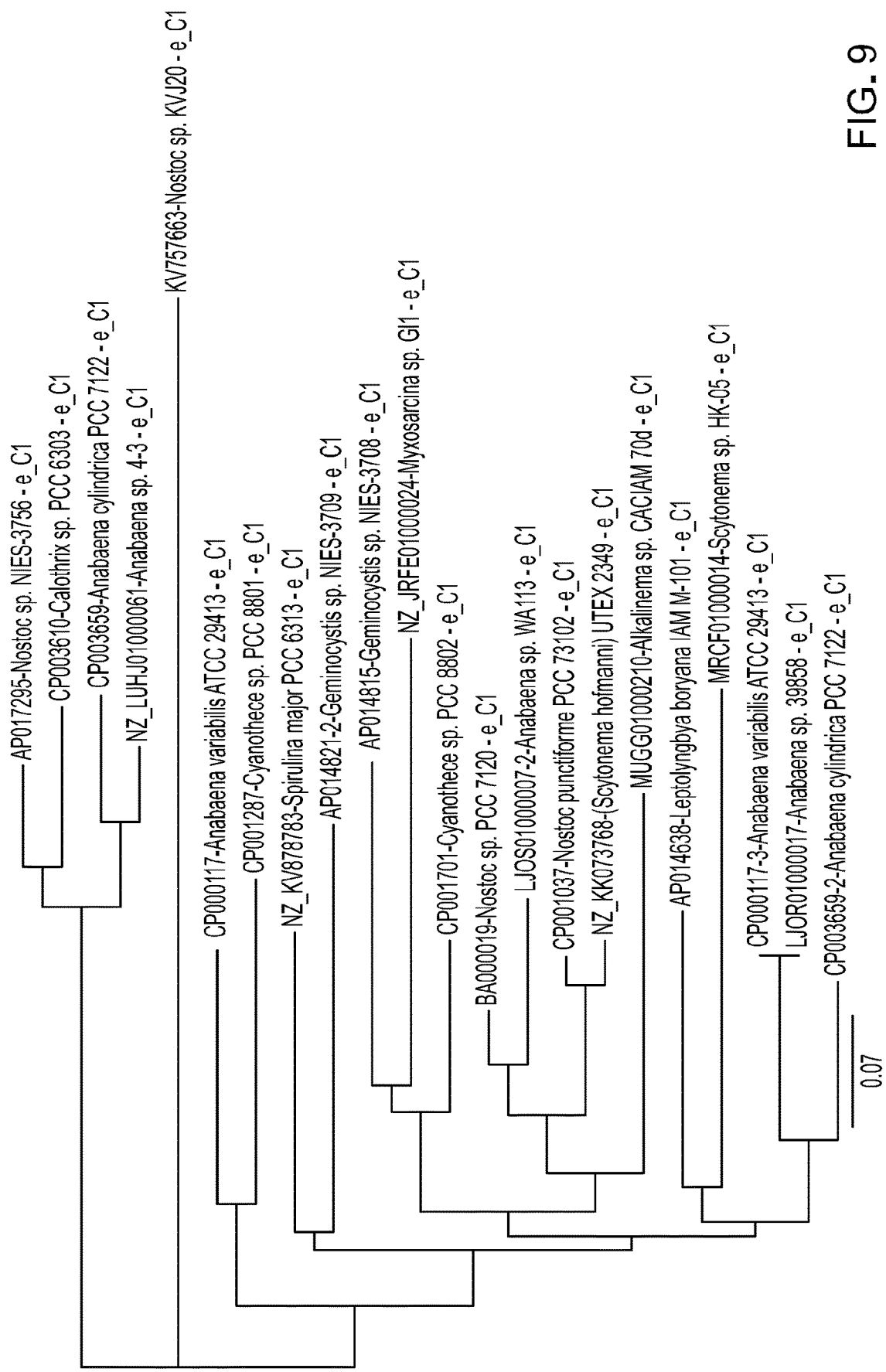
FIG. 9 shows a phylogenetic tree of CLUST.004377 effector C1 proteins.
Figure 10:
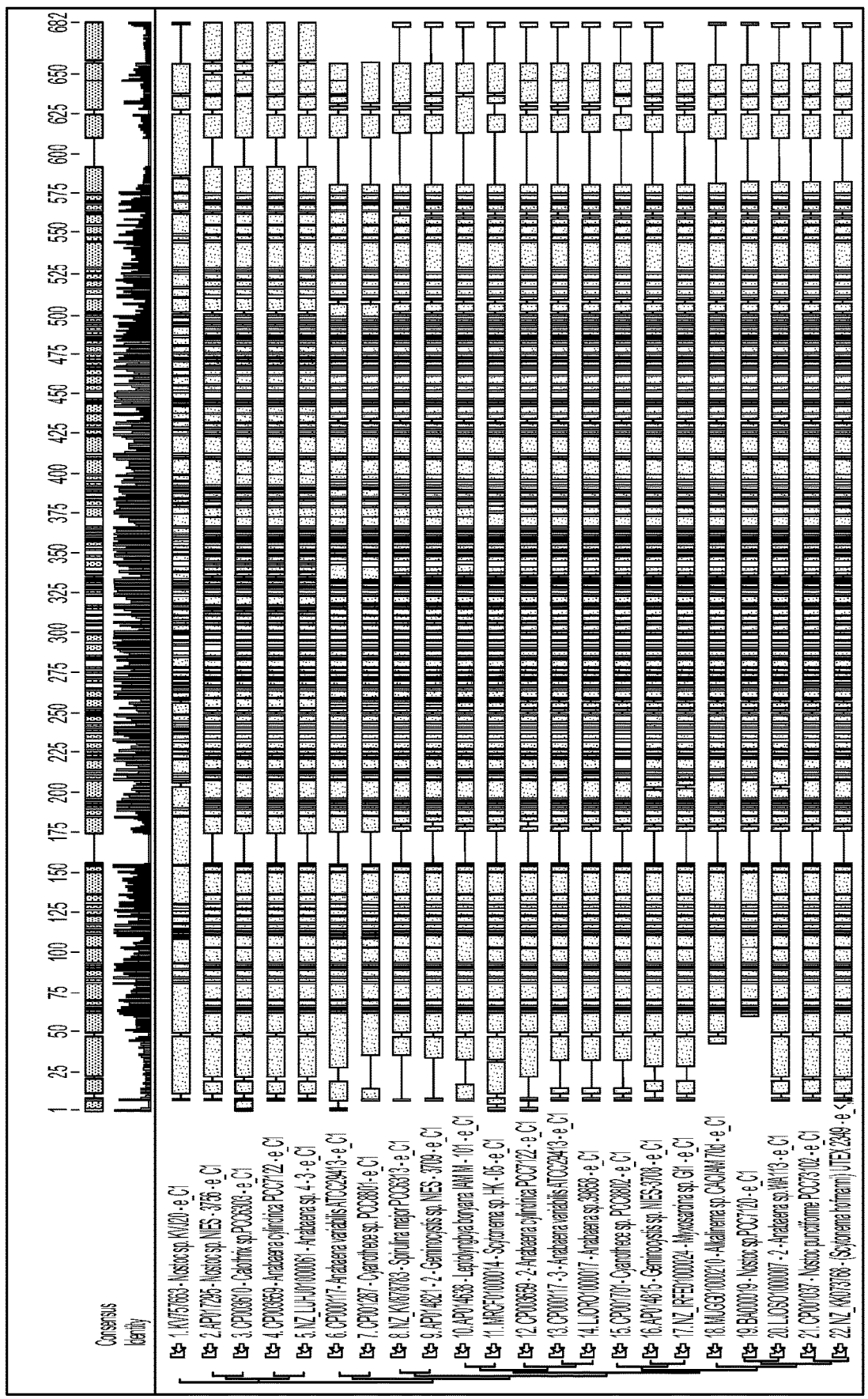
FIG. 10 shows an alignment of CLUST.004377 effector C1 proteins by genome accession and species, highlighting sequence location of conserved residues, with color denoting nucleotide polarity (Yellow: Non-polar side chain, Green: Polar side chain, Blue: Basic, Red: Acidic).
Figure 12:
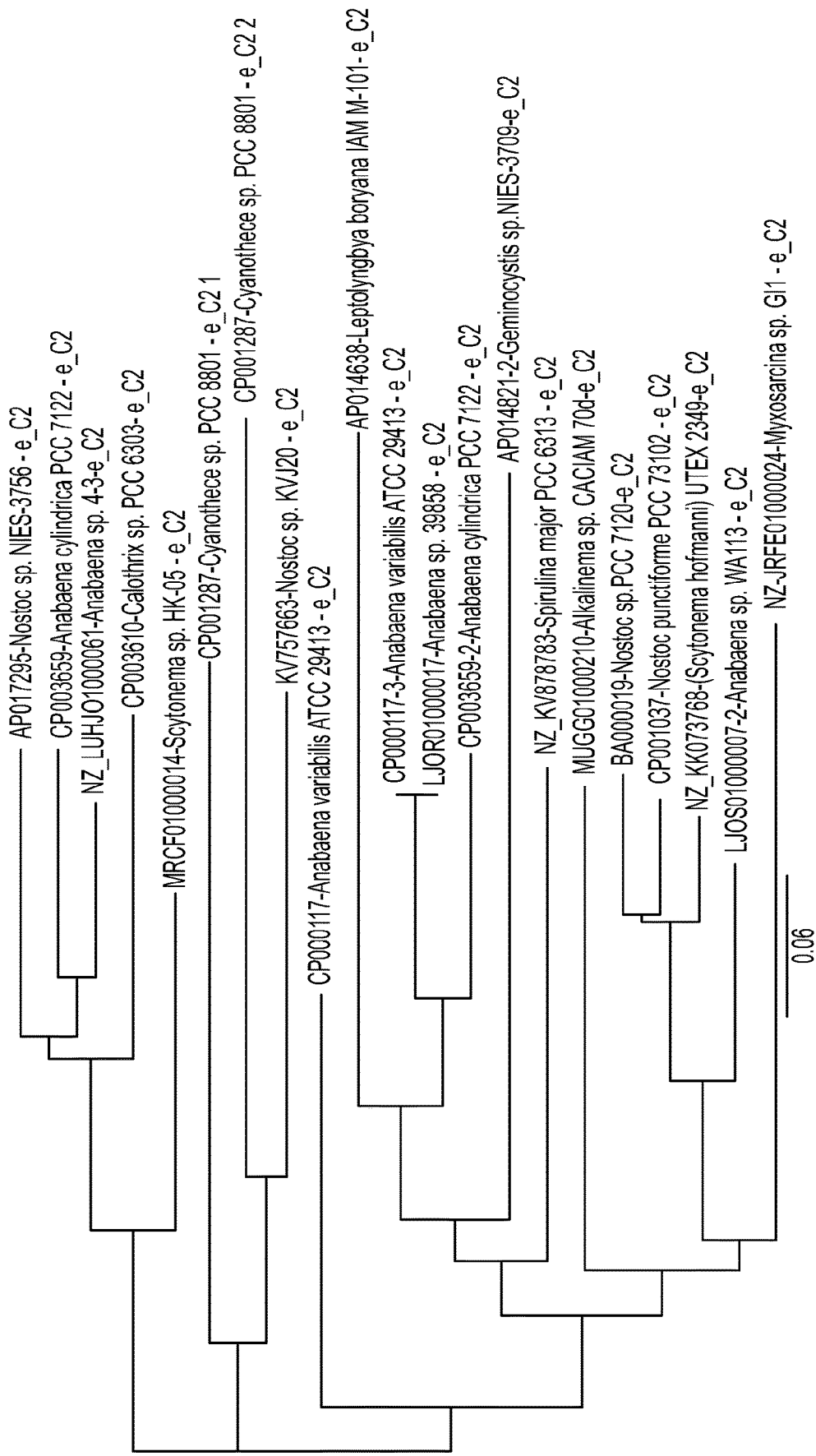
FIG. 12 shows a phylogenetic tree of CLUST.004377 effector C2 proteins.
Figure 13:
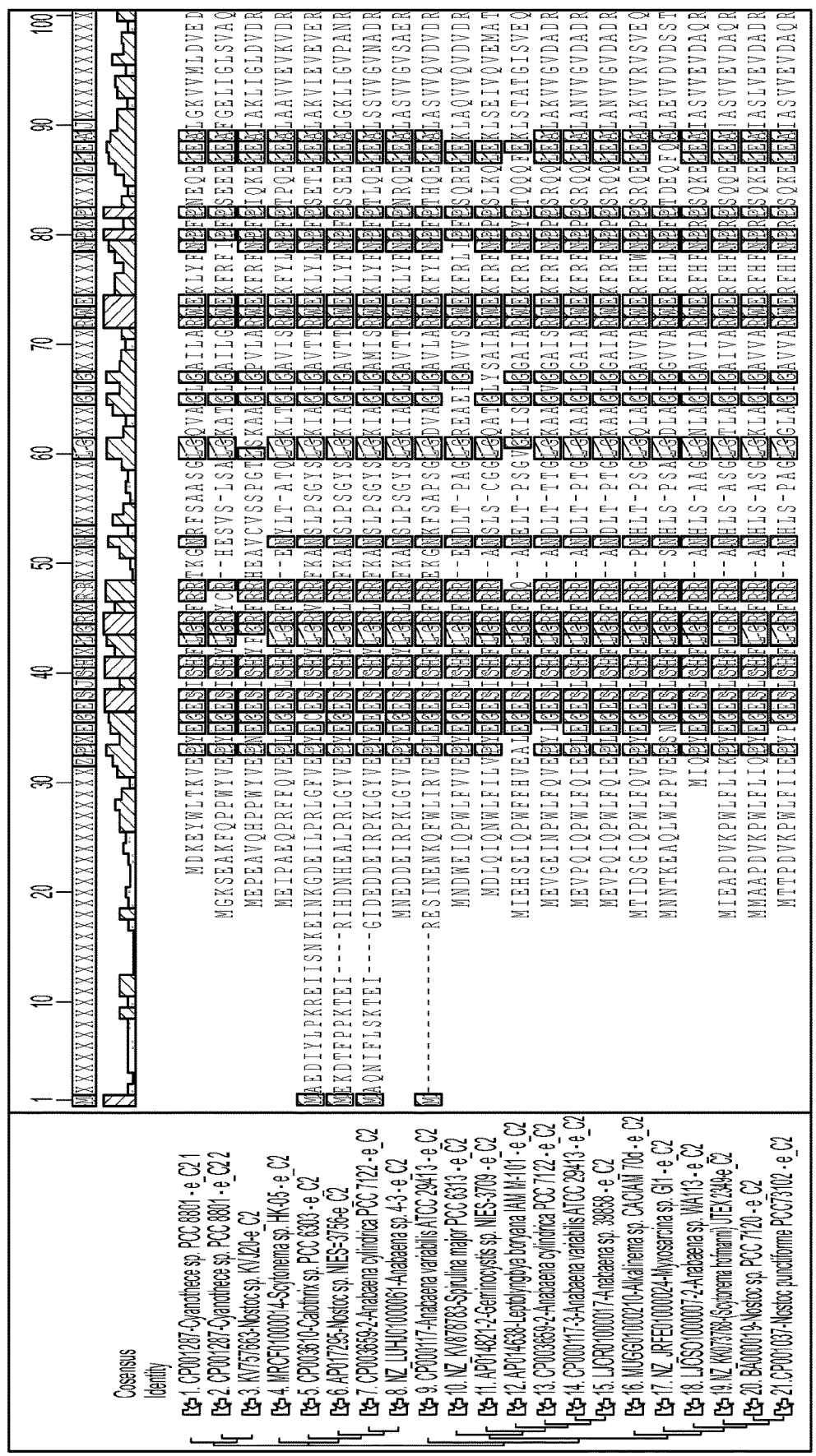
FIG. 13 shows an alignment of CLUST.004377 effector C2 proteins by genome accession and species, highlighting sequence location of conserved residues, with color denoting nucleotide polarity (Yellow: Non-polar side chain, Green: Polar side chain, Blue: Basic, Red: Acidic).
Figure 13:
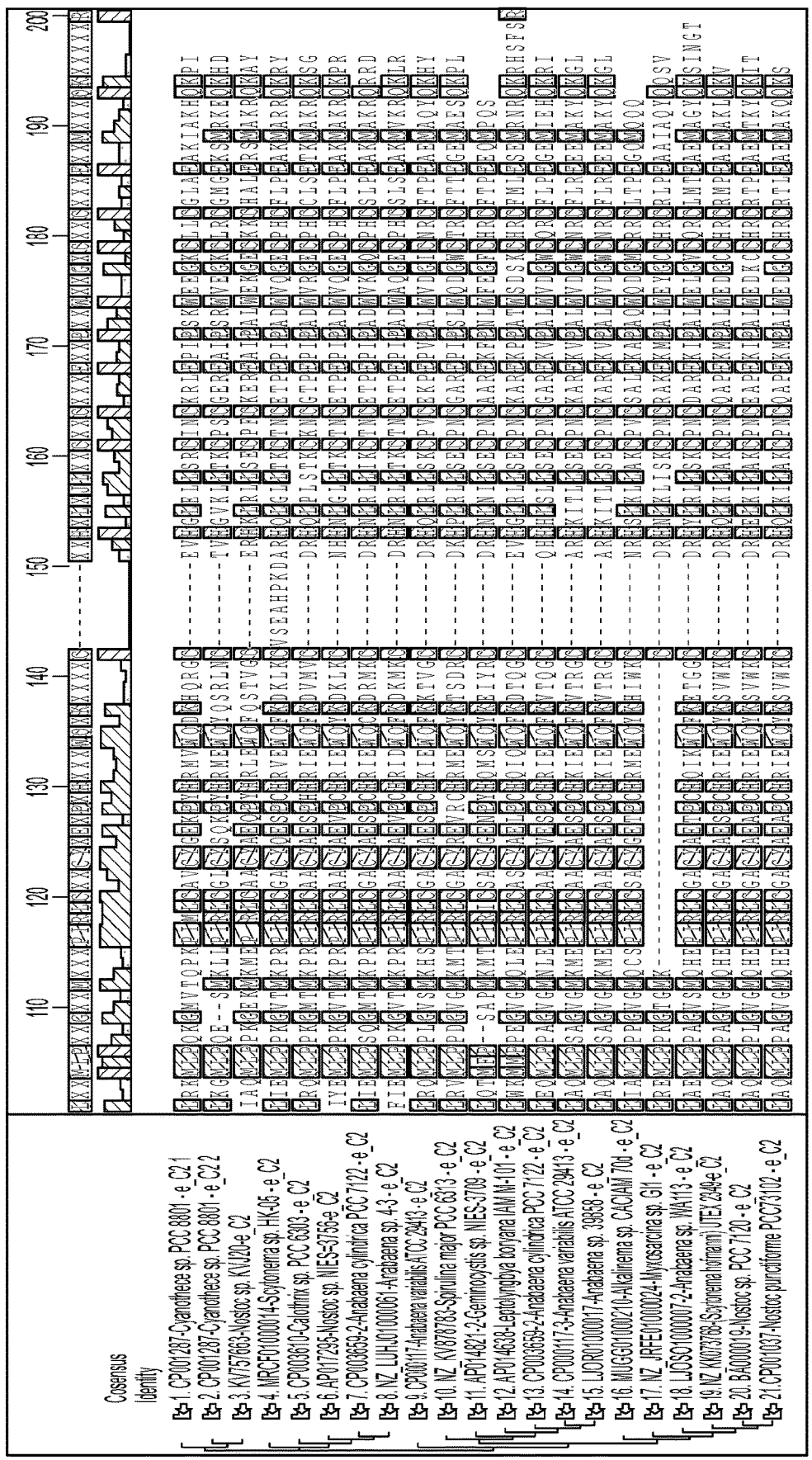
Figure 15:
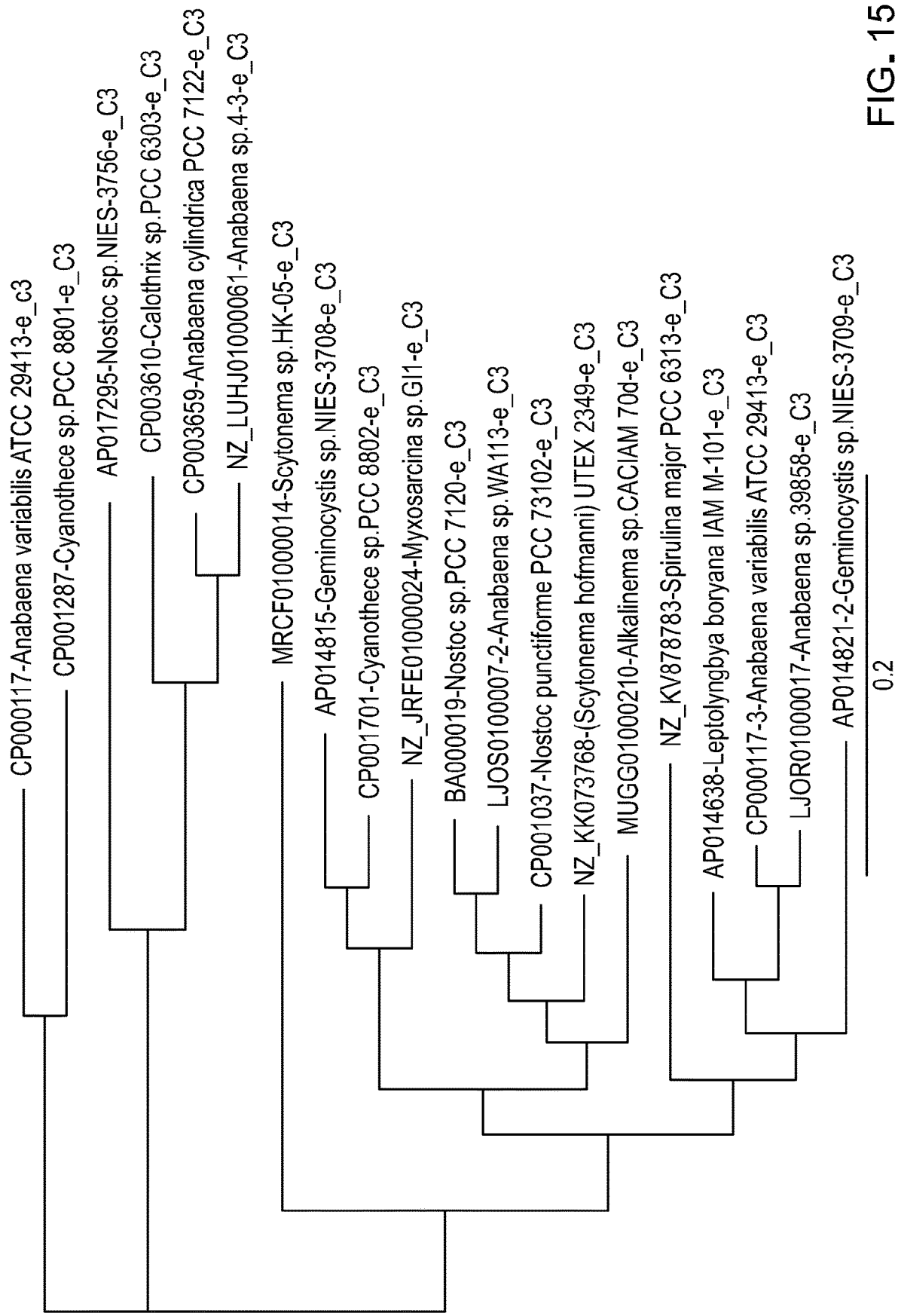
FIG. 15 shows a phylogenetic tree of CLUST.004377 effector C3 proteins.
Figure 16:
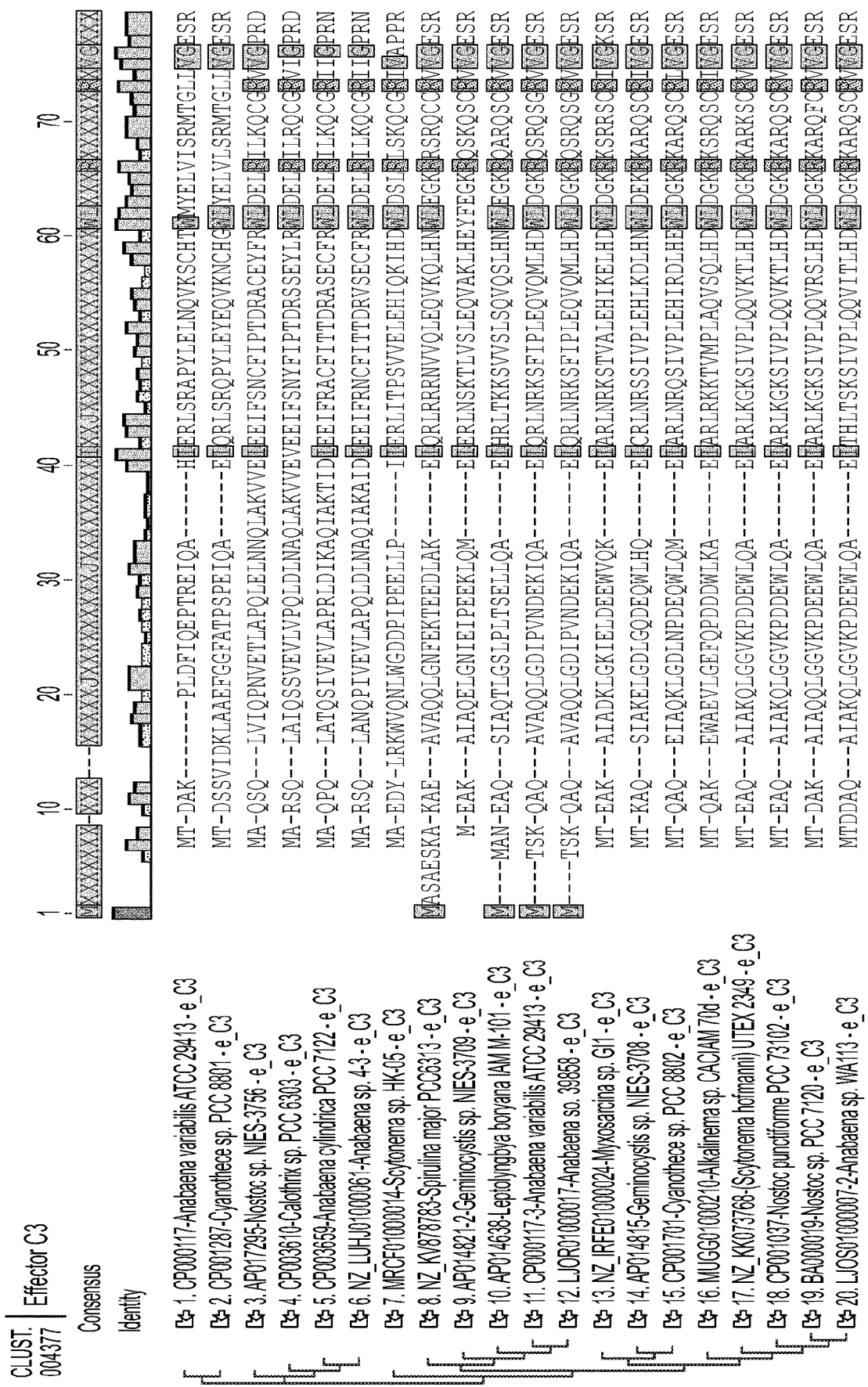
FIG. 16 shows an alignment of CLUST.004377 effector C3 proteins by genome accession and species, highlighting sequence location of conserved residues, with color denoting nucleotide polarity (Yellow: Non-polar side chain, Green: Polar side chain, Blue: Basic, Red: Acidic).
Figure 16:
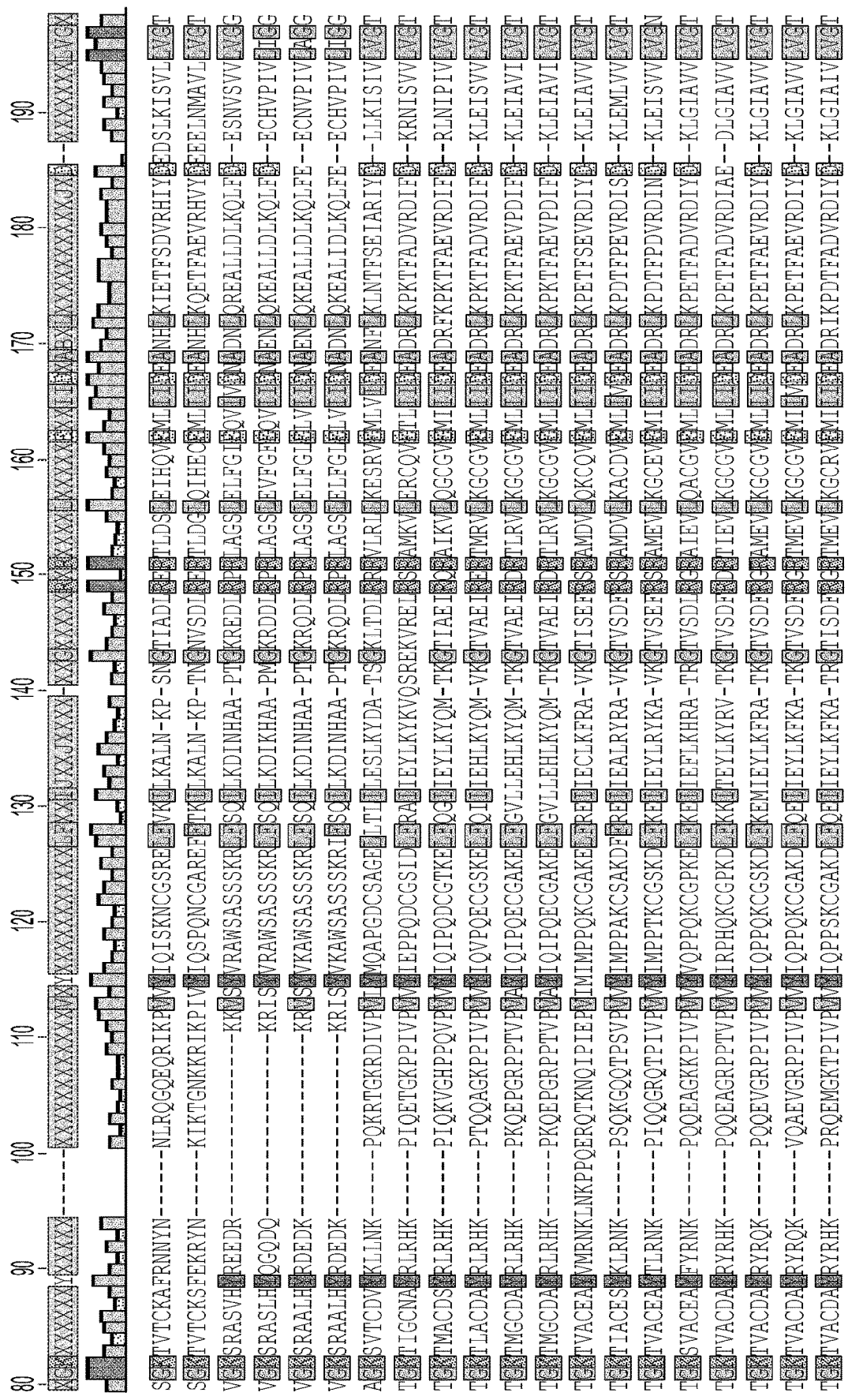
Figure 16:
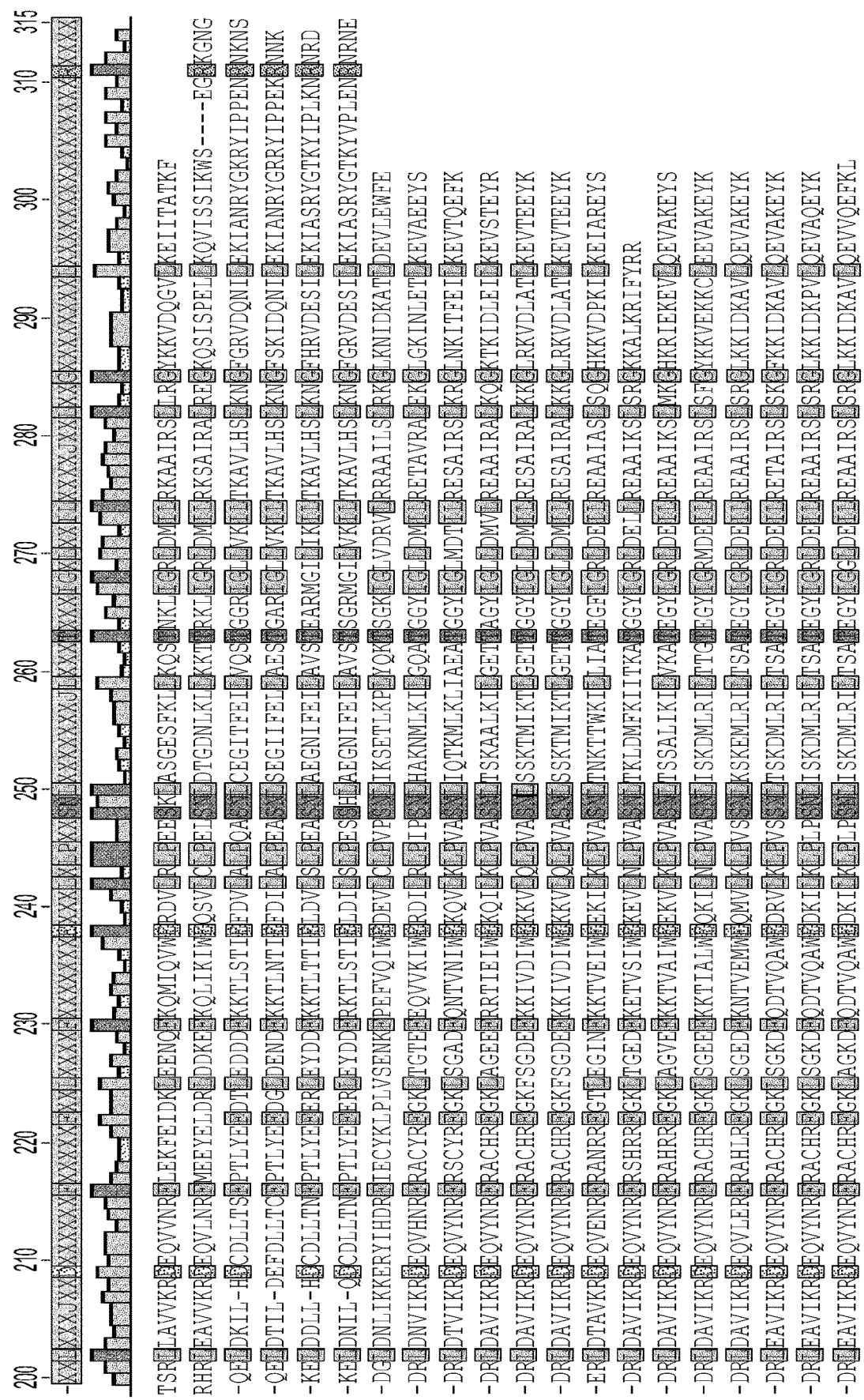

An HMM profile constructed from the multiple sequence alignment of Effector C1, and Pfam and Uniprot database searches revealed an rve domain indicative of integrase activity, as well as HTH, Mu-transposase, and DDE_2 domains, indicative of nucleic acid binding and transposition activity (FIGS. 9-11).

A domain search as described above for Effectors C2 and C3 revealed TniQ and TniB domains respectively, indicative of accessory functions to the transposition process (FIGS. 12-14, 15-17).

TABLE 1

Representative CLUST.004377 Effector Proteins

| Species | Effector A | Effector B | Effector C1 | Effector C2 |
|---|---|---|---|---|
| *Alkalinema* sp. CACIAM 70d (MUGG01000210) | OUC12050.1 | N/A | OUC12067.1 | OUC12055.1 |
| *Anabaena cylindrica* PCC 7122 (CP003659) | AFZ58287.1 | AFZ58288.1 | AFZ58294.1 | AFZ58293.1 |
| *Anabaena cylindrica* PCC 7122 (CP003659) | AFZ56196.1 | N/A | AFZ56182.1 | AFZ56184.1 |
| *Anabaena* sp. 4-3 (NZ_LUHJ01000061) | WP_066425713.1 | N/A | WP_066425682.1 | WP_066425687.1 |
| *Anabaena* sp. WA113 (LIOS01000007) | OBQ23770.1 | OBQ23832.1 | OBQ23776.1 | OBQ23833.1 |
| *Anabaena variabilis* ATCC 29413 (CP000117) | WP_011318157.1 | N/A | ABA20966.1 | WP_011318169.1 |
| *Anabaena variabilis* ATCC 29413 (CP000117) | WP_011318983.1 | N/A | WP_011318973.1 | WP_011318975.1 |
| *Anabaena variabilis* ATCC 29413 (CP000117) | WP_011318008.1 | WP_011318007.1 | WP_011317997.1 | WP_011317999.1 |
| *Aphanocapsa montana* BDHKU210001 (NZ_JTJD01000271) | WP_039730330.1 | N/A | WP_044151373.1 | WP_039728662.1 |
| *Calothrix* sp. PCC 6303 (CP003610) | AFZ00435.1 | N/A | AFZ00420.1 | AFZ00422.1 |
| *Calothrix* sp. PCC 7103 (NZ_KB217483) | WP_019497312.1 | N/A | WP_019497296.1 | WP_019497300.1 |
| *Cyanothece* sp. PCC 8801 (CP001287) | WP_012596241.1 | N/A | WP_012596233.1 | WP_012596235.1 |
| *Cyanothece* sp. PCC 8801 (CP001287) | WP_012596246.1 | N/A | WP_012596233.1 | WP_012596235.1 |
| *Cyanothece* sp. PCC 8802 (CP001701) | ACV01094.1 | ACV01093.1 | ACV01082.1 | N/A |
| *Geminocystis* sp. NIES-3708 (AP014815) | BAQ60380.1 | N/A | BAQ60391.1 | BAQ60389.1 |
| *Geminocystis* sp. NIES-3709 (AP014821) | BAQ63841.1 | BAQ63842.1 | BAQ63848.1 | BAQ63846.1 |
| *Geminocystis* sp. NIES-3709 (NZ_AP014821) | WP_066116114.1 | WP_066116116.1 | WP_066116124.1 | WP_066116120.1 |
| *Leptolyngbya boryana* dg5 (AP014642) | WP_017289534.1 | N/A | WP_017289545.1 | BAS55900.1 |
| *Leptolyngbya boryana* IAM M-101 (NZ_AP014638) | WP_017289534.1 | N/A | WP_017289545.1 | WP_026148796.1 |
| *Leptolyngbya boryana* PCC 6306 (NZ_KB731324) | WP_017289534.1 | N/A | WP_017289545.1 | WP_026148796.1 |
| *Lyngbya confervoides* BDU141951 (NZ_JTHE01000274) | WP_039730330.1 | N/A | WP_044151373.1 | WP_039728662.1 |
| *Myxosarcina* sp. GI1 (NZ_RFE01000024) | WP_036484397.1 | WP_052055737.1 | WP_036484426.1 | WP_036484423.1 |
| *Nostoc punctiforme* PCC 73102 (CP001037) | WP_012411901.1 | WP_012411902.1 | WP_012411919.1 | WP_012411917.1 |
| *Nostoc* sp. KVJ20 (KV757663) | ODH02164.1 | N/A | N/A | N/A |
| *Nostoc* sp. NIES-3756 (AP017295) | BAT55382.1 | N/A | BAT55397.1 | BAT55395.1 |
| *Nostoc* sp. PCC 7120 (BA000019) | BAB75312.1 | WP_010997761.1 | BAB75329.1 | BAB75327.1 |
| *Nostoc* sp. PCC 7120 (NC_003272) | WP_044521835.1 | WP_010997761.1 | WP_044521841.1 | WP_044521839.1 |
| *Nostoc* sp. 'Peltigera membranacea cyanobiont' 232 (NOLK01000067) | WP_094343940.1 | N/A | WP_094343929.1 | WP_094343931.1 |
| *Scytonema hofmanni* UTEX 2349 (NZ_KK073768) | WP_029636312.1 | WP_029636314.1 | WP_084763316.1 | WP_029636334.1 |
| *Scytonema* sp. HK-05 (NZ_MRCF01000014) | WP_073629970.1 | N/A | WP_073629994.1 | WP_073629990.1 |
| *Spirulina major* PCC 6313 (NZ_KV878783) | WP_072619878.1 | WP_072619877.1 | WP_072619869.1 | WP_072619870.1 |

| Species | Effector C3 | # spacers | cas1 | cas2 | effector size |
|---|---|---|---|---|---|
| *Alkalinema* sp. CACIAM 70d (MUGG01000210) | OUC12056.1 | 3 | N | N | 629 |
| *Anabaena cylindrica* PCC 7122 (CP003659) | N/A | 11 | N | N | 635 |
| *Anabaena cylindrica* PCC 7122 (CP003659) | AFZ56183.1 | 5 | N | N | 642 |
| *Anabaena* sp. 4-3 (NZ_LUHJ01000061) | WP_066425684.1 | 6 | N | N | 632 |

TABLE 1-continued

Representative CLUST.004377 Effector Proteins

| | | | | | |
|---|---|---|---|---|---|
| *Anabaena* sp. WA113 (LIOS01000007) | OBQ23775.1 | 4 | N | N | 639 |
| *Anabaena variabilis* ATCC 29413 (CP000117) | WP_011318170.1 | 2 | N | N | 635 |
| *Anabaena variabilis* ATCC 29413 (CP000117) | WP_011318974.1 | 2 | N | N | 643 |
| *Anabaena variabilis* ATCC 29413 (CP000117) | WP_011317998.1 | 2 | N | N | 642 |
| *Aphanocapsa montana* BDHKU210001 (NZ_JTJD01000271) | WP_044151374.1 | 2 | N | N | 641 |
| *Calothrix* sp. PCC 6303 (CP003610) | AFZ00421.1 | 7 | N | N | 639 |
| *Calothrix* sp. PCC 7103 (NZ_KB217483) | WP_019497299.1 | 16 | Y | Y | 649 |
| *Cyanothece* sp. PCC 8801 (CP001287) | WP_012596234.1 | 7 | N | N | 682 |
| *Cyanothece* sp. PCC 8801 (CP001287) | WP_012596234.1 | 7 | N | N | 660 |
| *Cyanothece* sp. PCC 8802 (CP001701) | ACV01083.1 | 6 | N | N | 667 |
| *Geminocystis* sp. NIES-3708 (AP014815) | BAQ60390.1 | 2 | N | N | 608 |
| *Geminocystis* sp. NIES-3709 (AP014821) | BAQ63847.1 | 4 | N | N | 646 |
| *Geminocystis* sp. NIES-3709 (NZ_AP014821) | WP_066116122.1 | 4 | N | N | 616 |
| *Leptolyngbya boryana* dg5 (AP014642) | WP_026148797.1 | 7 | N | N | 636 |
| *Leptolyngbya boryana* IAM M-101 (NZ_AP014638) | WP_026148797.1 | 7 | N | N | 636 |
| *Leptolyngbya boryana* PCC 6306 (NZ_KB731324) | WP_026148797.1 | 9 | N | N | 636 |
| *Lyngbya confervoides* BDU141951 (NZ_JTHE01000274) | WP_044151374.1 | 2 | N | N | 641 |
| *Myxosarcina* sp. GI1 (NZ_RFE01000024) | WP_036484424.1 | 4 | N | N | 615 |
| *Nostoc punctiforme* PCC 73102 (CP001037) | WP_012411918.1 | 15 | N | N | 639 |
| *Nostoc* sp. KVJ20 (KV757663) | N/A | 2 | N | N | 679 |
| *Nostoc* sp. NIES-3756 (AP017295) | BAT55396.1 | 4 | N | N | 635 |
| *Nostoc* sp. PCC 7120 (BA000019) | WP_010997774.1 | 4 | N | N | 648 |
| *Nostoc* sp. PCC 7120 (NC_003272) | WP_010997774.1 | 4 | N | N | 639 |
| *Nostoc* sp. 'Peltigera membranacea' cyanobiont' 232 (NOLK01000067) | WP_094343930.1 | 5 | N | N | 641 |
| *Scytonema hofmanni* UTEX 2349 (NZ_KK073768) | WP_029636336.1 | 28 | N | N | 639 |
| *Scytonema* sp. HK-05 (NZ_MRCF01000014) | WP_073629992.1 | 8 | N | N | 690 |
| *Spirulina major* PCC 6313 (NZ_KV878783) | WP_072622994.1 | 45 | N | N | 627 |

TABLE 2

Amino acid sequences of Representative CLUST.004377 Effector A Proteins

```
>OUC12050.1
[Alkalinema sp. CACIAM 70d]
MSQITIQCRLVAPPTARQHLWTLAAEKNTPLINTLIQEVANHEEFETWRLKGKHPTKIVSEICRRLRTEAPFSGQPARFYTSAE
KTVNYIFKSWFTLQSRLQRQLSRKQIWLSILKSDPELVELCGHPLETIQNKATQLLTQIEKTLADSNPEDPQSPCTNDLIRAQL
FKKYHGAKTPLIRCSIAYLIKNGGKLPKSPEIPHKFAQRRRKAEIQVQRLQDQLEGRLPKGRDLTGQAWLSTLITATSTVPKDN
HEQKQWNDRLLAKPCTTPFPILFETNEDLNWSKNHTGRICVRFNGLSEHTFQVYCDQRQLPWFQRFLEDQQTKHTSKNQHSSAL
FTLRSAHLAWQETHSNGAGWDNHYITLYCTVDVRLWTAEGTEEVHQEKAVDIAKQLTYLDQKEDLSETQAAFAQRLTSTLDRLN
KPFPRPHRHRAQQHSHIIVGLSVDWEAPLTLAIWNANTQEVLVYRSLRQLLGKDYPLFLQHRQEQQKQSHNRHKAQKRNKNCQF
GTSHLGEHIDRLLAKAVITIAQQYNAGSIAVPNLDNIRETLQATIDAKAEQKAPGCIEAQKRYTKQYKITIHRWSYGRLIDQII
SKAKQVGLGVEEAKQPLSGNVQEKAKLVAISAYNARLIVAF (SEQ ID NO: 1)

>OBQ23770.1
[Anabaena sp. WA113]
MSQITVQCRLIASESTRQQLWTLMAELNTPLINELLQQLSKHPDFEKWRKDGKFPSTVVSQLCQPLKTDPQFAGQPSRCYLSAI
HVVDYIYKSWLTIQKRLQQQLDGKIRWLEMLNSDAELVETSGYSLEAIRTKAAEILAMTTPESDTNVPLTKKRNTKKSKKSSAS
NPEPSLSHKLFNAYQETDDILSRSAISYLLKNGCKLNDKEEDTEKFAKRRRKVEIQIQRLTDKLTSRIPKGRDLTNSKWLETLF
TAITTVPEDNAEAKRWQDILSTRSSSLPFPLIFETNEDLKWSTNEKGRLCVHFNGLTDLTFEVYCDSRQLHWFKRFLEDQQTKR
KSKNQHSSGLFTLRNGRLAWQEGEGKGETWQIHRLTLSCCVDNRLWTAEGTEQVRQEKAEDITKFITKMKEKSDLSDTQQAFIQ
RKQSTLTRINNSFDRPCKPLYQGQSHILVGVSMGLEKPATVAVVDASANKVLTYRSIKQILGENYELLNRQRRQQRSSSHERHK
AQKSFSPNQFGTSELGQYIDRLLAKEIVAIAQTYKAGSIVLPKLGDMRENIQSEIQATAEIKCPGSVEIQQKYAKQYRINVHKW
SYGRLIQSIQSKAAQVGIVIEEGKQPVRDSPQDKAKELALSTYHLRLAKQS (SEQ ID NO: 2)

>WP_011318157.1
[Anabaena variabilis ATCC 29413]
MSVITIQCRLVAEEDILRQLWELMAEKNTPLINELLAQVGKHPEFETWLDKGRIPTELLKTLVNSFKTQERFADQPGRFYTSAI
ALVDYVYKSWFALQKRRKRQIEGKERWLTILKSDLQLEQESQCNLNVIRTKANEILTQFTPQSDQNKNPRKSKKAKKSAKLQKS
SLFQILLNTHEQTQETLTRCATAYLLKNNCQISERDEDPEEFNRNRRTKEIEIERLKDQLQSRIPKGRDLTGEEWLETLEIATV
NVPQNEKEAKAWQAALLRKTADVPFPVAYESNEDMTWLQNDKDRLFVRFNGLGKMTFEVYCDKRHLHYFKRFLEDQEIKRNSKN
QYSSSLFTLRSGRLAWLPKGQKGEPWKINQLHLYCTLDTRMWTAEGTGQVVNEKITKITETLTKAKQKDELNDKQQAFITRQQS
TLDRINNPFPRPSQPNYQGRPSILVGVSFGLEKPVTLAVVDVVKNEVQLAYRSVKQLLGKNYNLLNRQRQQQQRLSHERHKAQKQ
NAPNSFGESELGQYVDRLLADEIVAIAKTYQAGSIVIPKLRDMREQISSEIQSRAEKKCPGYKEVQQKYAKEYRMSVHRWSYGR
LIESIKSQAAKAGIFTEIGTQPIRGSPQEKARDLAVFAYQERQAALI (SEQ ID NO: 3)
```

TABLE 2-continued

Amino acid sequences of Representative CLUST.004377 Effector A Proteins

>WP_011318983.1
[Anabaena variabilis ATCC 29413]
MSVITIQCRLIASEATRSYLWQLMAQKNTPLINELIEQLGIHPEIEQWLKKGKLPDGVVKPLCDSLITQESFANQPKRFNKSAI
EVVEYIYKSWLALQKERQQTIDRKEHWLKMLKSDVELEQESKCTLDAIRSQATKILPKYLAQSEQNNNQTQSQNKKKSKKSKTK
NENSTLFDILFKAYDKAKNPLNRCTLAYLLKNNCQVSQKDEDPNQYALRRSKKEKEIERLKKQLQSRKPNGRDLTGREWQQTLI
MATSSVPESNDEANIWQKRLLKKDISLPFPIRFRTNEDLIWSKNEEGRICVSFSGEGLNDHIFETYCGNRQIHWFQRFLEDQNI
KNDNNDQHSSALFTLRSAILAWQENKQHKENSLPWNTRRLTLYCTLDTRLWTTDGTEKVKQEKVDEFTQQLANMEQKENLNQNQ
QNYVKRLQSTLNKLNNAYPRHNHDLYQGKPSILVGVSLGLEKPATLAIVDSSTNIVLAYRSIKQLLGDNYKLLNRQRQQQQRNS
HERHKAQKSNMPNKLSESDLGKYIDNLLAQATIALAKNYQAGSIVLPTMKNVRESIQSEIEARAVKRCPNYKEGQQQYAKQYRQ
SIHRWSYNRLMQFIQSQAVKANISIEQGPQPIRGSSQEKARDLAIAAYYLRQNKS (SEQ ID NO: 4)

>WP_011318008.1
[Anabaena variabilis ATCC 29413]
MSQITIQCRLVASEPSRHQLWKLMVDLNTPLINELLVQVAQHPEFETWRQKGKHPAKIVKELCEPLRTDPRFIGQPGRFYTSAI
ATVNYIYKSWFALMKRSQSQLEGKMRWWEMLKSDAELVEVSGVTLESLRTKAAEILSQFAPQPDTVEAQPAKGKKRKKTKKSDG
DCAERTLRERSISDYLFEAYRDTEEILTRCAINYLLKNGCKISNKEENAEKPAKRRRKLEIQIERLREKLEARIPKGRDLTDAK
WLETLLLATLNVPENEAEAKSWQDSLLKKSITVPFPVAYETNEDMTWFKNERGRICVKFSGLSEHTFQVYCDSRQLQWFQRFLE
DQQIKRNSKNQHSSLFTLRSGRIAWQEGEGKSEPWKVNRLILYCSVDTRLWTAEGTNLVREEKAEEIAKAIAQTKAKGKLNDK
QQAHIKRKNSSLARINNLFPRPSKPLYKGQSHILVGVSLGLEKPTTLAVVDGSIGKVLTYRNIKQLLGDNYRLLNRQRQQKHTL
SHQRQVAQILASPNQLGESELGQYVDRLLAKEIVAITQTYKAGSIVLPKLGDMREQVQSEIQAKAEQKSDLIEVQQKYSKQYRV
SVHQWSYGRLIASIRSSAAKVGIVIEESKQPIRGSPQEKARELAIAAYNSRRRT (SEQ ID NO: 5)

>WP_039730330.1
[Aphanocapsa montana BDHKU210001]
MSKITIQCRLVASEATRQYLWHLMADIYTPFVNEILRQIREDDNFEQWRQSGKIPASVFEDYRKTLKTESRFQGMPGRWYYAGR
EEVKRIYKSWLALRRRLRNQLAGQNRWLEVLQSDETLMEVSGLDLSALQAEASQLLNILGSKNKTSKNRSKKAKGKPKGKSAKD
PTLYQALWELYRETEDIAKKCVIAYLLKHKCQVPDKPEDPKKFRHRRREAEIRAERLNEQLIKTRLPKGRDLTNEQWLQVLEIA
TRQVPKDEDEAAIWQSRLLTDAAKFPFPVAYETNEDLKWFLNGKGRLCVSFNGLSEHTFEVYCGQRQLYWFNRFLEDQQIKKEN
QGERSAGLFTLRSGRLVWKPYSSDASRSDPWMANQLTLQCSVDTRLWTAEGTEQVRQEKATSIAKVIAGTKAKGNLNQKQQDFI
TKREKTLELLHNPFPRPSKPLYQGKPSIIAAVSFGLEKPATLAIVDIVTDKAITYRSIRQLLGQNYKLFTKHRLKQQQCAHQRH
QNQVESAENRISEGGLGEHLDSLIAKAILETAAEYGASSIVLPELGNIREIIHAEIQAKAERKIPGLKEKQDEYAAKFRASVHR
WSYGRLAQKVTTKASLHGLETESTRQSLQGTPQEKARNLAISAYESRKVAQRA (SEQ ID NO: 6)

>WP_019497312.1
[Calothrix sp. PCC 7103]
MSIITIQCRLVANDRTLQHLWELMAEKNTPLISELLEQLGKHPDFETWLKNGKVPKDTIKILCDSLKTQSRFAGQPGRFYTSAI
SQVKEIYKSWLTLQKRRQRQIEGKQRWLGMLKSDVELQEESNCSLEKIRAKGTEILAEFVSKFTKDTTKKSKTKIKSTKKSNKK
TKKDTEESNSTLFQALCDIYDKTEDTLSKCAIIYLLKNNCQVIDTEENPDTFLKRKRAKEIEIKRLQDQIVGRIPKGRDLTDKK
WLDTIKLASSQVPQDENEAKSWQNQLLKTSSSVPYSVDYETNTDIKWVKHNNGSIFVNFNGLGEHQFEVYCDSRQLPYFQRFCE
DMQIWHNDEEKYSSALFMLRSARLVWLEKKGRGKPWNVNYLYLTHCSLDTSLWTAEGTEQIRINKINETDEAIAKAKTKDKQELT
ENQLAYLQRQQSTRNKLNNSFPGRPSKPIYKGNSHILVGVSLGLEKPVTVAAVDVVSNKVLAYRSVKQLLGQNYKLLNRQRQQQ
KHLAQKRHESQKKQAPNQFGESELGLYVDRLLAKSIINFAKTYQASSIALPKLRDMREIIQSEIQAKAESKIPGYKEGQEKYAK
EYRMSVHRWSYGRLIGNIQAQAAQAGILIETSSGQIRGSPQEQAKHLAISAYIERQTILNK (SEQ ID NO: 7)

>WP_012596241.1
[Cyanothece sp. PCC 8801]
MTLKTLECRLYAPSDTLRYLWLLMAEKNTPLINEIINHLSEHPDFDQWFKAKQIPKSAISDICNDLKSQENYQNQPGRFYSSAI
SLTHYMPFKSWFAVHKQLQRRIEGKRRWLNLLKSDQELEQNCGQSLEIIIQKAEEILKLMDSEKSQSSSKPKKPKKPKKKKSSS
EETITLFDRLFKAYNQGNDSLESYALAYLLKNNGQIPEDDEDLDKFALRKRKKEIEIERLQQQLENRIPLGRDLTGELWQEMLT
IVNESIPQDENEASAWQAKLLKKSHNIPYPVAYETNTDLKWSKDSRGHLLVTFNGLVESLKKKLNLNPEFEIRCDRRHLPWFQRF
CKDQEIKANNDQHSSALFVLRSARLIWREGQGKEDPWKIHQLYLQCSVETQLWTEAGTKQVQSEKMVEFQLNQLRMKPELTFPI
FFRSQSLPTYFNLWKVITSYRILKFLEKGDFTKAQKNFQDAIKRTESCLENLQSSYLTSQKSLYQGNPEIIMGVAMGLSQPATI
AVVNVVTQEVLTYRSLKQLLGKNYNLLNRQRQQKQKLSHQRHKAQKKDAFNQYGESELGQYVDRLIAKAIVQVAKEYQADSIAV
PKIRQMREIIQSEVQARAERKIQGYKEGQKKYAQQYRENVHQWSYGRLIESIHQASAKFGIRVEIASQSYQGSFQEQAQNLAIA
AYTNRLEAVG (SEQ ID NO: 8)

>WP_012596246.1
[Cyanothece sp. PCC 8801]
MTHITVVQCRLIAPESTLQHIWKMMAQQQTPLINQLLHDINTHPDINTWLTANQLPSKLVETLAQPLKTQSPYQGLPGRFITSA
IILVKEMYASWFAIQTQKRLSLEGKKRFLTILKSDKQLIQDSQTDFLTLCYKAQQLLKRTQNKLKLDEPQHSEKAHWSIINALY
PAYNNAKTPISRAAFALLIKNNGQVPDTPENPDYYQQRRKRKEIQIRRLEEQLKASLPKGRILDSKHWENTLKLAQTPITTIEE
ITSLQTQLLQKYSHLPFPVFYGTNTDLTWFKNPQGRICVKFNGLNQYPFQIACNKRQYPWFQRFFTDYQSYKSHKQQVPTGLMV
LRSARLLWQPTNGQGEPWNTHHLSLHCAIDNDLWTISGIQQVKQQKILQTEQKIANFHSKALEKELTPNQQQRLKASQTSLNLL
KTFDINEFFPSKCSLYQGSPDIILGVSIGLENPATIAIINISTQEILTYRTTKQLLSRTRKVRNKKPNSNNSNQSLSSAYKQIS
NYELFLQYQQQKHHNQHQRHNAQINDANNNYGEANLGLYLNRLLAKAILELAQQYQVSLIILPSLKNKRELIESEIRAKAELKY
PGCKEKQDSYAKDYRTNVHQWSYQQLIKCIESKAAQIGIDTATGKQMNLETSQDQARNLVLNFCQKFSPTQV
(SEQ ID NO: 9)

>WP_066116114.1
[Geminocystis sp. NIES-3709]
MAHVTIQCRLIASRDTRQFLWQLMAQKNTPLINEILLRIKQHPDFPHWRTKKRLPKDFLARQIAELKNNYPFEEQPSRFYASVN
KVIDYIYKSWFEVQKALDWKLQGNLRWVEMLLPDTELIKHFDNSLESLQQQATLILDSIDSTVSHDRISTILFEKCGKTKKPEI
KSAIIYLLKNGCTIPKKPETTEKYQDLRKVEIKITKLHRQIESRIPKGRILGRDLEDKWLDTLITASTTAPIDQTEANTWFSILKQ
NQSSIPYPILYETNEDLKWSLNEKNRLSIRFSGLGEHSFQLCCDHRQLPYFQRFYEDQELKKASKDQLSSALFTLRSAMILWKE
DEGKGELWDRHKLYLHCTFETRCLTAEGTSTIVEEKQKEVTKIIDLMKAKEELSDSQQAFIRRKNSTLAKLNNTFPRPSKPVYQ
GKPNVHLGIAMGLEQPVTIAIVDIETDKVITYRNTKQLLREDYRLLRRRRIEKQKLSHQNHKARKRFNFQQKGESNLGEYLDRL
IAKAILTVAQEYQVSTILIPRLRDMRSITEAEIQLRAEKKIPEYKEGQKKYAQDYRVQVHQWSYGRLIENVKLICEKVGIVVVE
AKQPKQGTLTEKALQLVLSATEKNLKKK (SEQ ID NO: 10)

TABLE 2-continued

Amino acid sequences of Representative CLUST.004377 Effector A Proteins

>WP_017289534.1
[*Leptolyngbya boryana* dg5]
MSVITIQCKLVATEETRRALWHLMAEKHTPLINELLKHIAQDSRFEEWSLTGKLPRLVVSEACNQLKQDPQFSGQPGRFYSSAI
STVHRIFLSWLALQTRLRNQISGQTRWLAMLQSDNELTIASQTDINTLRLKASELLTHLNEPISESDQPEVKKTRSKKKNQTSN
QAGANVSRTLFKLYDETEDPLTRCAIAYLLKNGCKLPDQNENPEKFIKRRRKTEIRLERLMNTFQTTRIPRGRHLSWHSWIEAL
ETATSHIPENEEEAAGWQARLLTKPAILPFPVNYETNEDLRWSLNSQGRICVSFNGLSEHFFEVYCDQRDLHWFNRFLEDQETK
KASKNQHSSSLFSLRSGQIAWQEGKGDAEHWVVHRLVLSCSIETDTWTQEGTEEIRQKKASDCAKVIASTKAKENRSQNQDAFI
RRRERMLELLENQFPRPSYPLYQGQPSILAGVSYGLDKPATLAIVNIQTGKAITYRSIRQILGKNYKLLNRYRLNQQRNAHKRH
NNQRKGGSSQLRESNQGQYLDRLIAHEIVAIAQEYQVSSLALPDLGDIREIVQSEVQARAEQKILGSIEQQRKYARQYRASVHR
WRYAQLTQFIQSQAAQVGISIEITKQPLSGTPQEKARNLAIAAYQSRK (SEQ ID NO: 11)

>WP_017289534.1
[*Leptolyngbya boryana* IAM M-101]
MSVITIQCKLVATEETRRALWHLMAEKHTPLINELLKHIAQDSRFEEWSLTGKLPRLVVSEACNQLKQDPQFSGQPGRFYSSAI
STVHRIFLSWLALQTRLRNQISGQTRWLAMLQSDNELTIASQTDINTLRLKASELLTHLNEPISESDQPEVKKTRSKKKNQTSN
QAGANVSRTLFKLYDETEDPLTRCAIAYLLKNGCKLPDQNENPEKFIKRRRKTEIRLERLMNTFQTTRIPRGRHLSWHSWIEAL
ETATSHIPENEEEAAGWQARLLTKPAILPFPVNYETNEDLRWSLNSQGRICVSFNGLSEHFFEVYCDQRDLHWFNRFLEDQETK
KASKNQHSSSLFSLRSGQIAWQEGKGDAEHWVVHRLVLSCSIETDTWTQEGTEEIRQKKASDCAKVIASTKAKENRSQNQDAFI
RRRERMLELLENQFPRPSYPLYQGQPSILAGVSYGLDKPATLAIVNIQTGKAITYRSIRQILGKNYKLLNRYRLNQQRNAHKRH
NNQRKGGSSQLRESNQGQYLDRLIAHEIVAIAQEYQVSSLALPDLGDIREIVQSEVQARAEQKILGSIEQQRKYARQYRASVHR
WRYAQLTQFIQSQAAQVGISIEITKQPLSGTPQEKARNLAIAAYQSRK (SEQ ID NO: 11)

>WP_017289534.1
[*Leptolyngbya boryana* PCC 6306]
MSVITIQCKLVATEETRRALWHLMAEKHTPLINELLKHIAQDSRFEEWSLTGKLPRLVVSEACNQLKQDPQFSGQPGRFYSSAI
STVHRIFLSWLALQTRLRNQISGQTRWLAMLQSDNELTIASQTDINTLRLKASELLTHLNEPISESDQPEVKKTRSKKKNQTSN
QAGANVSRTLFKLYDETEDPLTRCAIAYLLKNGCKLPDQNENPEKFIKRRRKTEIRLERLMNTFQTTRIPRGRHLSWHSWIEAL
ETATSHIPENEEEAAGWQARLLTKPAILPFPVNYETNEDLRWSLNSQGRICVSFNGLSEHFFEVYCDQRDLHWFNRFLEDQETK
KASKNQHSSSLFSLRSGQIAWQEGKGDAEHWVVHRLVLSCSIETDTWTQEGTEEIRQKKASDCAKVIASTKAKENRSQNQDAFI
RRRERMLELLENQFPRPSYPLYQGQPSILAGVSYGLDKPATLAIVNIQTGKAITYRSIRQILGKNYKLLNRYRLNQQRNAHKRH
NNQRKGGSSQLRESNQGQYLDRLIAHEIVAIAQEYQVSSLALPDLGDIREIVQSEVQARAEQKILGSIEQQRKYARQYRASVHR
WRYAQLTQFIQSQAAQVGISIEITKQPLSGTPQEKARNLAIAAYQSRK (SEQ ID NO: 11)

>WP_039730330.1
[*Lyngbya confervoides* BDU141951]
MSKITIQCRLVASEATRQYLWHLMADIYTPFVNEILRQIREDDNFEQWRQSGKIPASVFEDYRKTLKTESRFQGMPGRWYYAGR
EEVKRIYKSWLALRRRLRNQLAGQNRWLEVLQSDETLMEVSGLDLSALQAEASQLLNILGSKNKTSKNRSKKAKGKPKGKSAKD
PTLYQALWELYRETEDIAKKCVIAYLLKHKCQVPDKPEDPKKFRHRRREAEIRAERLNEQLIKTRLPKGRDLTNEQWLQVLEIA
TRQVPKDEDEAAIWQSRLLTDAAKFPFPVAYETNEDLKWFLNGKGRLCVSFNGLSEHFFEVYCGQRQLYWFNRFLEDQQIKEM
QGERSAGLFTLRSGRLVWKPYSSDASRSDPWMANQLTLQCSVDTRLWTAEGTEQVRQEKATSIAKVIAGTKAKGNLNQKQQDFI
TKREKTLELLHNPFPRPSKPLYQGKPSIIAAVSFGLEKPATLAIVDIVTDKAITYRSIRQLLGQNYKLFTKHRLKQQQCAHQRH
QNQVESAENRISEGGLGEHLDSLIAKAILETAAEYGASSIVLPELGNIREIIHAEIQAKAERKIPGLKEKQDEYAAKFRASVHR
WSYGRLAQKVTTKASLHGLETESTRQSLQGTPQEKARNLAISAYESRKVAQRA (SEQ ID NO: 6)

>WP_036484397.1
[*Myxosarcina* sp. GI1]
MSQNAIQCRLIAPETTRRQQWQLMAEKNTPLINELLKQLAEHPELETWKRKGKIPPGTVKNLCQPLRTCPQYINQPGRFYSSVI
SLAEYIYRSWLKLQRRLIFRLNGQQRWLQMLKSDEELVAESGRSLKEIEAKASEALDRLNREENPSISNRLFDLYDETEDILIR
SAIVYLLKNGCKIRQKPEDPKKFARRRRKTEIRVKRLQEKLNGKAPQGRDLTGEKWLNTLFTATSQVPQDEAQAKSWQDILLTK
SKLVPYPIVYESNEDLTWSKNERGRLCVKFNGLSDHTFQIYCDRRQLKIFNRFYEDQQIKKASKNSHSSALFTLRSATIAWQEG
KGKGEPWNVNRLILYCTFDNLLLTTEGTEVVRQEKAEEAIANTLTKIKMKETRIRRKETSLSRINNPFPRPSRPLYKG
KSNILLGVAIRLDKPATVAIVDGATDKAIAYLSTKQLLGKNYHLLNRKRQQQHILSHQRNVAQRHHANNKFGESELGQYIDRLL
AKAIIQLAKDYRVGSIVVPYMEDTREIIQAEVQARAEAKIPGCIEKQKEYAKKYRTNIHKWSYGRLIDLIKAQAAKAGIVIEES
KQSIRGDPKKQAKEIAVCAYRDRIVPF (SEQ ID NO: 12)

>WP_012411901.1
[*Nostoc punctiforme* PCC 73102]
MSQITIQCRLIASESTRQKLWKLMATLNTPLINELIEQLGKHPDFENWRQQGKLPTTVVSQLCQPLKTDPRFVGQPSRLYMSAI
HIVDYIYKSWLAIQKRLQQQLDGKMRWLEMLNSDVELVETSGSSMGAIRTKASEILAKAMPTSDSDSSQPKTKKGKEAKKSSSS
SSDRSLSNKLFEAYQETEDILSRSAISYLLKNGCKLSDKEEDSEKFAKRRRQVEIQIQRLTEKLISRMPKGRDLTNRKWLETLF
TATTTFPEDNAEEAKRWQDILLTRPSSLPFPLVFETNEDMVWSKNQKGRLCVHFNGLSDLSFEVYCDNRQLHWFQRFLEDQQTKR
QSKSQYSSGLFTLRNGHLVWQEGEGKSEPWNLNRLNLYCCVDNRLWTADGTEQVRQEKAEEISKLITKMKEKSDLKDTQKAFIQ
RKESTLNRMNNSFERPSQPLYQGQSHILVGVSLGLEKPATVAVVDAIAGKVLAYRSIRQLLGDNYELLNRQRRQQRSSSHERHK
AQKSFSPNQFGTSELGQYVDRLLAKEIIAIAQTYKAGNIVLPKLGDMREIVQSEIQAIAEAKCPGSVEVQQKYAKQYRVNVHKW
SYGRLIQSIQSKGSQAGIVIEEGKQPVRGSPHEQAKELALSAYHDRLARRS (SEQ ID NO: 13)

>BAB75312.1
[*Nostoc* sp. PCC 7120]
MCFVWYFIFMSQKTIQCRLIASESTRQKLWKLMAESNTPLINELLQQLSKHPDFEKWRRNGKLPSTVVSQLCQPLKTDPSFTGQ
PSRFYISAIHIVDYIYKSWLTIQKRLQQQLDGKLRWIEMFNSDVELVEISGFSLEAIRTKASEILAITTPESDPKTLLTKRGKT
KQSKKSSASNPDRSLSRKLFDAYQETDDILSRSAISYLLKNGCKLNDKEENPEKFAKRRRKVEIQIQRLTDKLTSRIPKGRDLT
YSKWLETLFTATTTVPENNAEAKRWQDILLTRSSSIPFPVVFETNEDLVWSTNEKGRLCVHFNGLSDLIFEVYCDSRQLYWFQR
FLEDQQTKRKSKNQHSSGLFTLRNGRLAWQQGEGKGEPWNIGHLALYCCVDNRLWTAEGTEQVRQEKAEEITKFITKMKDKSDL
SETQRLAFIKRKESTLTRINNSFDRPSKPLYQGQSHILVGVSLGLEKPATIAVVDAIAGKVLTYRSLRQLLGDNYELLNRQRRQQ
RSLSHERHKAQKSFSPNQFGASELGQYVDRLLAKEIVAIAQTYKAGSIVLPKLGDIREIVQSEIQAIAEAKCPSSSEIQQKYAK
QYRVNVHQWSYGRLIQSIQSKAAQIGIVIEEGKQPIRGSPQDKAKELALYAYSLRLARRS (SEQ ID NO: 14)

TABLE 2-continued

Amino acid sequences of Representative CLUST.004377 Effector A Proteins

>WP_044521835.1
[Nostoc sp. PCC 7120]
MSQKTIQCRLIASESTRQKLWKLMAESNTPLINELLQQLSKHPDFEKWRRNGKLPSTVVSQLCQPLKTDPSFTGQPSRFYISAI
HIVDYIYKSWLTIQKRLQQQLDGKLRWIEMFNSDVELVEISGFSLEAIRTKASEILAITTPESDPKTLLTKRGKTKQSKKSSAS
NPDRSLSRKLFDAYQETDDILSRSAISYLLKNGCKLNDKEENPEKFAKRRRKVEIQIQRLTDKLTSRIPKGRDLTYSKWLETLF
TATTTVPENNAEAKRWQDILLTRSSSIPFPVVFETNEDLVWSTNEKGRLCVHFNGLSDLIFEVYCDSRQLYWFKRFLEDQQTKR
KSKNQHSSGLFTLRNGRLAWQQGEGKGEPWNIGHLALYCCVDNRLWTAEGTEQVRQEKAEEITKFITKMKDKSDLSETQLAFIK
RKESTLTRINNSFDRPSKPLYQGQSHILVGVSLGLEKPATIAVVDAIAGKVLTYRSLRQLLGDNYELLNRQRRQQRSLSHERHK
AQKSFSPNQFGASELGQYVDRLLAKEIVAIAQTYKAGSIVLPKLGDIREIVQSEIQAIAEAKCPSSSEIQQKYAQKQYRVNVHQW
SYGRLIQSIQSKAAQIGIVIEEGKQPIRGSPQDKAKELALYAYSLRLARRS (SEQ ID NO: 15)

>WP_094343940.1
[Nostoc sp. 'Peltigera membranacea cyanobiont' 232]
MSVITIQCRLVASEDTRRHLWQLMAEKNTPLINELLKQVRIHPDMEQWLKKGKLPDGVIKPLCDSLSTQECFVNQPKRFYKSAI
EVVEYIYKSWLALQKERQQKIDKKEHWLNMLKSDIELEQESNFSLNIIRAKAIKVLAHYIAKVEENHKQDITNKNVNKRKKSKS
KNNNYTLFDILFKAYDQAKVSLNRCAIAYLLKNNCQVSEEEEDPNRYALRRSKKLKEIERLKEQLKSRIPSGRDLTGQEWLQSL
LVATTNVPESENQFKIWQKHLLQNSSSIPFPVQFTSNEDLIWSKNEKGRICVSFSGEEFNNHIFEIYCDKKQIYWFQRFLEDQS
IKRNNKKQYSSSLFTLRSGRLAWQDNKGNDLPWKIHRLTLYCSVDTRLWTIEGTQEFRREKVDEITEKLADMEKKENLNKNQQI
YVKRLNSTLTKIDTAYPRPNQNLYQGKTSILIGVSLGLEKPATIAIVDCPTNKVLAYRSVKQLLGDNYNLLNRQRQQQRNSHE
RHKAQKSNTQIKLSELELGKHIDNLLAQAIITLAKSYQAGSIVLPTMKNVRESIQSEIEARAVKRCPNYKEGQQQYAKQYRQSI
HRWSYNRLIGCIKSQAAKANISIEQGPQPIRDSPQEKARDLAIAAYHFRQNKS (SEQ ID NO: 16)

>WP_029636312.1
[Scytonema hofmanni UTEX 2349]
MSQITIQARLISFESNRQQLWKLMADLNTPLINELLCQLGQHPDFEKWQQKGKLPSTVVSQLCQPLKTDPRFAGQPSRLYMSAI
HIVDYIYKSWLAIQKRLQQQLDGKTRWLEMLNSDAELVELSGDTLEAIRVKAAEILAIAMPASESDSASPKGKKGKKEKKPSSS
SPKRSLSKTLFDAYQETEDIKSRSAISYLLKNGCKLTDKEEDSEKFAKRRRQVEIQIQRLTEKLISRMPKGRDLTNAKWLETLL
TATTTVAEDNAQAKRWQDILLTRSSSLPFPLVFETNEDMVWSKNQKGRLCVHFNGLSDLIFEVYCGNRQLHWFQRFLEDQQTKR
KSKNQHSSGLFTLRNGHLVWLEGEGKGEPWNLHHLTLYCCVDNRLWTEEGTEIVRQEKADEITKFITNMKKKSDLSDTQQALIQ
RKQSTLTRINNSFERPSQPLYQGQSHILVGVSLGLEKPATVAVVDAIANKVLAYRSIKQLLGDNYELLNRQRRQQQYLSHERHK
AQKNFSPNQFGASELGQHIDRLLAKAIVALARTYKAGSIVLPKLGDMREVVQSEIQAIAEQKFPGYIEGQQKYAKQYRVNVHRW
SYGRLIQSIQSKAAQTGIVIEEGKQPIRGSPHDKAKELALSAYNLRLTRRS (SEQ ID NO: 17)

>WP_073629970.1
[Scytonema sp. HK-05]
MSVITIQCRLVAEENTLRQLWELMAEKNTPLINELLEQVGQHPNFEKWLKKGEVPEEAIDTIKKSLITQEPFAGQPGRFYTSAV
TLVKEIYKSWFALQQERQRKIEGKERWLKMLKSDIELQQESQCNLDIIRNKANEILTSFVANFTENRNQQFKKKGNKTKKNKKE
EEESTLFNALFKIYDKTKDCLSQCALAYLLKNNCQVSEIDEDPEEYVKRRRRKEIEIERLRKQLKSRKPKGRDLTGEKWLTALK
EATNQVPVDQLEAKSWQASLLKVTSDIPYPVDYESNTDLDWLIHSNDDDIKKKVILVWQIYFLKQLIKSGSYSFIKYLYFQRGC
LPKRDVNWLNLKNKAGRIFVKFNGLRKNIINPEFYICCDSRQRYPQRLCQDWQVWHDNEETYSSSLFFLRSARLLWQKRKGTG
APWKVNRLILQCSIETRLWTEEETELVRIEKINQAETEIRESEQKGKPKQKVLSHRQKLNNLFPNRPSKPIYKGKPNIIVGVSF
GLDKPATVAVVDVANKKVLAYRSTKQLLGKNYNLLNRQRQQQQRLSHERHKAQKRNAPNSFGESELGQYVDRLLADAIIAIAKT
YQAGSIVIPKLRDMREQITSEIQSRAEKKCPGYKRAQQKYAKEYRLSVHRWSYGRLIESIKSQAAKVGISTEIGTQPIRGSPEE
KARDLAVFAYQERQAALV (SEQ ID NO: 18)

>WP_072619878.1
[Spirulina major PCC 6313]
MSQITIQCRLVASEATRQVLWTLMAERNTPLINELLAQMAQHPDLEEWRQKGKPTPGVVKKLCDPLRQDPRFMGQPGRFYSSAI
ALVEYIYKSWLKLQQRLQRKLEGQQRWLGMLKSDPELCEENHCTLDTLRDKAAEILASLESPQPKQGKVKTKKAKAQSSPRQSL
FEMHDGAEDGFVKSAIAYLLKNGGKLPTHEEDPKKFAKRRRKAEVKVERLIHQITASLPKGRDLTGERWLETLLTASYTAPKDA
QQTKVWQSILLTKTKAVPYPINYETNEDLTWSKNEKGRLCVRFNGLSEHTFQIYCDQRQLKWFQRFYEDQEVKRTSKNQHSTSL
FTLRSGRIVWQESDRNDKPWTANHITLCCTLDTRLWSAEGTEEVRTEKAIDIAKTLTNMNEKGDLNDKQQAFIKRKTATLDRIN
NPYPRPSKPLYHGQSHILVGVALGLDKPATVAVVDGTTGKAITYRNLKQLLGENYKLVNRQRQQKQAQSHQRHKAQKRSGTDQF
GDSELGQHIDRLLAKAIVAFAHSQSAGSIVVPKLEDIREIVQSEIQARAEEKVPGYIEGQKQYAKRYRVQVHQWSYGRLIDSIK
SKATQQQVVIEEGKQPVRGSPEAQATELAISTYHLRASS (SEQ ID NO: 19)

>BAQ60380.1
[Geminocystis sp. NIES-3708]
MAVITIHCRLISSKSNRHQLWNLMVQKNTPLINELLLELSQHEDLEQWCELGKLPSGLISKLCDQLKQRAEFEGQPSRFYASAI
NLVDYIYKSYLRTQRRLRFRLQGQQRWFEMFKSDTEFKNETNFSLTDIRVKARELLDKDLKDSSPDDYFKTYESTSDLLTRSAI
SYLLKNGRKLPEKPEDYQKFQKRRRKLQIKEKLQKKIDSSPPMGRNLTNDSWLGMLNLVSNTIPQTDEEAKQWQDQLLRQSKS
VPYPVMFNTNEDLRWSKNKKGRLCVTFNGLGKLVFEIYCDQQQLKWFERFYEDQEVKRKGKNQHSSALFTLRSGMLLWQEHEGK
QEAWQNNHLTLYCSLDTCFETAEGTELVRQKKVKEVVNLIDAMNNKSERTKTQDAFIKRKQSTLARLDNSFPRPSKPLYQGNQN
IVVAVSMSLEYPATIAMFNMSSQEVLTYRSTKQLLDNNYHLLNRQRNQKQRLSHQRHKTQRQNSSDFFTQQESELGQYLDRLLA
QSIVSIAKQYQASTILLPNLKNIRDSIQAEIEAKAEAKIPNCKEAQKKYLKNYRINIHHWSYGRLIDSIQLQASKLDILIQEVK
QPIRGSPQEKAKQMAILTLE (SEQ ID NO: 20)

>BAQ63841.1
[Geminocystis sp. NIES-3709]
MAHVTIQCRLIASRDTRQFLWQLMAQKNTPLINEILLRIKQHPDFPHWRTKKRLPKDFLARQIAELKNNYPFEEQPSRFYASVN
KVIDYIYKSWFEVQKALDWKLQGNLRWVEMLLPDTELIKHFDNSLESLQQQATLILDSIDSTVSHDRISTILFEKCGKTKKPEI
KSAIIYLLKNGCTIPKKPETTEKYQDLKRKVEIKITKLHRQIESRIPLGRDLEDKKWLDTLITASTTAPIDQTEANTWFSILKQ
NQSSIPYPILYETNEDLKWSLNEKNRLSIRFSGLGEHSFQLCCDHRQLPYFQRFYEDQELKKASKDQLSSALFTLRSAMILWKE TABLE 2-continued Amino acid sequences of Representative CLUST.004377 Effector A Proteins

```
DEGKGELWDRHKLYLHCTFETRCLTAEGTSTIVEEKQKEVTKIIDLMKAKEELSDSQQAFIRRKNSTLAKLNNTFPRPSKPVYQ
GKPNVHLGIAMGLEQPVTIAIVDIETDKVITYRNTKQLLREDYRLLRRRRIEKQKLSHQNHKARKRFNFQQKGESNLGEYLDRL
IAKAILTVAQEYQVSTILIPRLRDMRSITEAEIQLRAEKKIPEYKEGQKKYAQDYRVQVHQWSYGRLIENVKLICEKVGIVVVE
AKQPKQGTLTEKALQLVLSATEKNLKKK (SEQ ID NO: 10)

>BAT55382.1

[Nostoc sp. NIES-3756]
MSVITIQCRLVAEEDTLRQVWELMTDKNTPLVNELLAQVGKHPEFETWLEKGKIPTEFLKTLVNSLKNQERFSDQPGRFYTSAI
ALVDYVYKSWFALQKRRKRQIEGKERWLIILKSDLQEQESQCSLNVIRTEANEILAKFTPQSDQNKNQRKSKRTRKSAKLQTP
SLFQNLLNTYEQTQETLTRCAIAYLLKNNCQISERDEDPEEFNRNRRKKEIEIERLKDQLQSRIPKGRDLTGEEWLKTLEIATT
NVPQNENEAKAWQAALLRKPADVPFPVAYESNEDMTWLQNDKGRLFVRFNGLGKLTFEIYCDKRHLHYFKRFLEDQELKRNSKN
QHSSSLFTLRSGRIAWSLGEEKGEPWKVNKLHLYCTLDRTMWTIEGTQQVVSEKTTKITETLNQAKRKDVLNDKQQAFVTRQQS
TLDRINNPFPRPSKPNYQGQPSILVGVSFGLEKPVTLAVVDVIKNEVLAYRTVKQLLGKNYNLLNRQRQQQQRLSHERHKVQKR
NAPNSFGESELGQYVDRLLADAIIAIAKTYQAGSIVIPKLRDMREQISSEIQSRAEKKCPGYKEVQQKYAKEYRMSVHRWGYGR
LIESIKSQAAKAGIFTEIGTQPIRGSPQEKARDLAVFAYQERQAALI (SEQ ID NO: 21)

>ACV01094.1
[Cyanothece sp. PCC 8802]
MSTITIQCRLVAPEATRQALWQLMAQKNTPLVSELLRQVAQHPDFETWRQQGKLEAGIIKKLCEPLKKDPRFNEQPARFYTSAI
ALVDYIYKSWLKLQQRLQRKLEGQNRWLAMLKSDDELIQISQTNIEIIQAKATEILSTLQPQDREQSSKKKAKKCKKSTNKNSL
FSQLDKLYNEINNNLTHCAIRYLLKNGGKIPQRPEDTEKFAQRRRKVEIKIERIIEQIESSIPQGRDLTGDSWLETLIIAANTA
TVEAEDVKSWQDKLLSQSKSIPYPVAYETNEDLTWSINEKGRLCVRFNGLGKHTFQIYCDQRQLKWFQRFYEDQQIKKDGKDHH
SSALFSLRSGRIVWQEGLGKGKPWNIHRLTLHCSLDTRFWTEEGTQQVQQEKSSKKFQTNRLRMKPELTFSIFFRSQTLETYLQV
WLVITAYRLQSFLDKGNVAKAHQEFQKAIKRNESSLQKITSSYNRPHKTLYQGKSHIFVGVAMGLEKPATVAVVDGTTGKAIAY
RSLKQLLGNNYHLFNRQGKQKQNTSHQRHKSQKHFADNQFGESQLGQYIDCLLAKAIISVAQTYCAGSIVVPKLKDMRELIQSE
IQAKAEAKIPGYVEGQAKYAKSYRVQVHQWSHGRLIDNITSQASKFNITVEEGEQPHQGNPQDKAKLLAIAAYHSRLCA
(SEQ ID NO: 22)

>AFZ00435.1
[Calothrix sp. PCC 6303]
MSVITIQCRLVADEETLRHLWTLMAEKNTPFANEILEQLAQHAEFESWVKNSRVPATVIKELCDSLKNQELFAGQPGRFYTSAT
TLVTYIYKSWLAVNKRLQRKIEGKKQWLDMLRSDTELEQESNSNLEKIRAKATEILDSFATRQINQVNSKSKTSKNNKNKQEKE
VKSLSIQSNILFETYRQTEDNLTKCAIVYLLKNNCEVNDVEEDIEEYEKNKRKKEIQIKRLEDQLKSRVPKGRDLTGEKWVEVL
EKAVNSVPESENEAKSWQASLLRKSSQIPFPVVYETNEDIKWSINEKGRIFVSFNGLGKLKFEIFCDKRHLHYFQRFLEDQDIK
RQGKNQHSSSLFTLRSGRISWLEQPGKGKPWNINRLLLFCSIDTRMLTAEGTQQVIEEKIADTQNKIAKAQEKCEGELNPNQQA
HINRKKSTLARINTPFPRPSKPLYQGKSHIVVGVSLGLKATATIAVFDAMNNQVLAYRSTKQLLGDNYKLLNRQQQQKQRLSQQ
RHKSQKQFASNSFGESELGQYVDRLLAKEIVAVAKNFGAGSIVLPKLGDMREIIQSEVQAKAEKKIPGFIELQKNYAKEYRKSA
HNWSYGRLIENIQSQATKEGIEIETGKQPTRGIPQEQARDLALFAYQCRIA (SEQ ID NO: 23)

>AFZ58287.1
[Anabaena cylindrica PCC 7122]
MSQITIQCRLVASETTRQQLWQLMAEKNTPLINELLSQIGKHPEFETWRQKGKHPTGIVKELCEPLKTDPRFIGQPARFYTSAT
ASVNYIYESWFALMKRYQSQLDGKLRWLEMFNSDAELVEHSGVSLDTLRATSAEILAQFAPQDTNRDTSNKGKKSKMGKKSQKS
DSEGNLSKKLFDAYSSAEDNLTRCAISHLLKNGCKVSNKEENSEKFTQRRRKLEIQIQRLTRLAARIPKGRDLTDTQWLETLF
TATYNVPEDETEAKLWQNSLLRKFSSLPFPVAYETNEDLVWSKNRFGRICLTFPTLREHIFQIYCDSRQLHWFQRFLEDQEIKK
NSKNQHSSALFTLRSGRIAWQEGEGKGEPWDIHHLTLYCCVDTRLWTEEGTNLVKEEKAEEIAKTITQTKAKGDLNDKQQAHLK
RKNSSLARINNPFPRPSQPLYKGQSHILLGVSLGLEKPATVAVVDGTTGKVLTYRNIKQLLGDNYKLLNRQRQQKHLLSHQRHI
AQRIAAPNNFGDSELGEYIDRLLAKEIIAIAQTYQAGSIVLPNLGDMREQIQSEIKAKAEQKSDLVEVQKKYAKQYPNSVHQWS
YGRLITNIQSQSKKAGIVIEEGKQQIRASPLEKAKELAINAYQSRKA (SEQ ID NO: 24)

>AFZ56196.1
[Anabaena cylindrica PCC 7122]
MSVITIQCRLVAEEDSLRQLWELMSEKNTPFINEILLQIGKHPEFETWLEKGRIPAELLKTLGNSLKTQEPFTGQPGRFYTSAI
TLVDYLYKSWFALQKRRKQQIEGKQRWLKMLKSDQELEQESQSSLEVIRNKATELFSKFTPQSDSEALRRNQNDKQKKVKKTKK
STKPKTSSIFKIFLSTYEEAEEPLTRCALAYLLKNNCQISELDENPEEFTRNKRRKEIEIERLKDQLQSRIPKGRDLTGEEWLE
TLEIATFNVPQNENEAKAWQAALLRKTANVPFPVAYESNEDMTWLKNDKGLKLTFEIYCDKRHLHYFQRFLEDQE
ILRNSKRQHSSSLFTLRSGRIAWLPGEEKGEHWKVNQLNFYCSLDTRMLTTEGTQQVVEEKVTAITEILNKTKQKDDLNDKQQA
FITRQQSTLARINNPFPRPSKPNYQGKSSILIGVSFGLEKPVTVAVVDVVKNKVIAYRSVKQLLGENYNLLNRQRQQQQRLSHE
RHKAQKQNAPNSFGESELGQYVDRLLADAIIAIAKKYQAGSIVLPKLRDMREQISSEIQSRAENQCPGYKEGQQKYAKEYRINV
HRWSYGRLIESIKSQAAQAGIAIETGKQSIRGSPQEKARDLAVFTYQERQAALI (SEQ ID NO: 25)

>ODH02164.1
[Nostoc sp. KVJ20]
MSSDRKKKSTIPVHRTIRCHLDASEDILRKVWEEMTQKNTPLILKLLKSVSEQPEFEANKEKGEITKKEIVKLRKNVTKNPELE
EQSGRLRSSAESFVKEVYSSWLTLYQKRKRQKEGKEYFLKNILKSDVELIDESNCDLETIRSKAQEVLSQPEEFIKQLTINDED
VKPTKSARKRVNKNINNKSTDAEQRKDSSSTNNVDKNKLETLTNILYEIHKQTQDILTRCTVAYLIKNHNKISNLEEDIQKLKK
RRNEKIVQIKRLENQIQDNRLPSGRDITGERYSEAFGNLINQVPKNNQEWEDWIANLSKKISHLPYPIDYLYGDLSWYKNDVGN
IFVYFNGWSEYHFKICCNKRQRHFFERFLEDYKAFKVSQKGEEKLSGSLITLRSAQLLWQQGEGKGEPWKVHKLALHCTYDSRL
WTAEGTEEVRKEKTDKAQKRVSKAEENEKLDDIQQTQLNKDKSSLSRLKNSFNRPGKLIYQSQSNIIVGISFHPIELATVAIVD
INTKKVLACNTVKQLLGNAFHLLSRRRQQVHLSKERKKAQKKDSPCNIGESKLGEYIDKLLAKRIVEIAKFYQAGCIILPRLK
DMKEIRTSAIQAKARAKIPGDVNAQKLYVKEYNRQIHNWSYNRLQESIKSKAAEFKISIEFGIQPHYGTLEEQAKDLAFYAYQS
RNHTLGR (SEQ ID NO: 26)

>WP_066425713.1
[Anabaena sp. 4-3]
MSVITIQCRLVAEEDTLRTLWELMADKNTPLINEILAQVGKHPEFETWLEKGKIPTELLKTLVNSLKTQERFASQPGRFYTSAI
ALVDYVYKSWFALQKRRKRQIEGKERWLTILKSDLELEQESQCSLNIIRTKATEIITEFTPQSDQNNSQKKRKKTTKSTKPSLF
QILLNNYEETQDILTRCALAYLLKNNCQISERDENPEEFTRNRRKKEIEIERLKDQLQSRIPKGRDLTGEEWLKTLEVVRANVT
```

TABLE 2-continued

Amino acid sequences of Representative CLUST.004377 Effector A Proteins

QNENEAKAWQAAILRKSADVPFPVAYESNEDMTWLQNDKGRLFVRFNGLGKLTFEIYCDKRHLHYFKRFLEDQELKRNSKNQYS
SSLFTLRSGRLAWSPGEEKGEPWKVNQLHLYCTLDTRMWTIEGTQQVVDEKSTKITETLTKAKQKDDLNDKQQAFVTRQQSTLN
RINNLFPRPSKSRYQGQPSILVGVSFGLENPVTLAVVDVVKNEVLAYRSVKQLLGKNYNLLNRQRQQQRLSHKRHKAQKRNAP
NSFGESELGQYVDRLLADAIIAIAKTYQAGSIVIPKLRDMREQISSEIQSRAEKKFPGYKRAQQKYAKEYRMSVHRWSYGRLIE
SIKSQAAKAGISTEIGTQPIRGSPQEKARDLAVFAYQERQAALI (SEQ ID NO: 27)

TABLE 3

Amino acid sequences of Representative CLUST.004377 Effector B Proteins

>OBQ23832.1
[Anabaena sp. WA113]
MEGKFYTSTEAAEITNCSRRQLQYWREKGVIVPTVNASGKGRNVYYSKADLLALSVMEHLLSIGLNFEMCHVALETLRKREPWL
FEESVTEDKMKRLMFLPSKSPEQPLQLAEFDQQAALEALCEGQTVIPFWGDRIHELLHQNLKRFTE (SEQ ID NO: 28)

>WP_011318007.1
[Anabaena variabilis ATCC 29413]
MQETFFTSKEASKITGCTLRQLQYWREKGVVVPVISDTGTGRSIYYSKTNLVELAAMVYWLSVGLSFDIACETLKTLKDQEPEL
FSSGTGRRFMLLSEAQERSPLGAPKISLELMEFDRTKAIASLDEGKPVIPVWLDEIYQQLQQKLKA (SEQ ID NO: 29)

>WP_066116116.1
[Geminocystis sp. NIES-3709]
MKERFFSSKQTSLITGCSLRQLQYWRDKEVIVPFIQGTGTGKTIYYSPAELVEISIMVYLLSVGLSFEIGQIILSDLKEKERNF
RNPDYKGRFMIIPRDGKMSLLSYEREKAIELLDQGTSIVPLWLDRIHEQLKETLG (SEQ ID NO: 30)

>WP_052055737.1
[Myxosarcina sp. GI1]
MGEPFYTSTEASLITGCSRRQLQYWRKQGVVVPTVNPGGKGRNVYYTESDLLILSVMKYLLSLGLNFDVSLKVLETLREKEILC
FLDWSLSKNTKKRFMLVLDTEEKNTIHITNFDTELAVQKLQEGFAIAPFGRDRIYQKLQDNLQAFYRNRKSLKGDRRTKN
(SEQ ID NO: 31)

>WP_012411902.1
[Nostoc punctiforme PCC 73102]
MEEKFYTSTEAAEITNCSRRQLQYWRDKGVVIPTVNTTGKGRNVYYSVADLLTLTVMHYLLSVGLSFEVCREALAMLQDKEPWL
FEEFVSKKKMRRLMLISNASQQKYLTLAEFDKEAALEALCQGQTVIPFWCDRIHEVLHQNLKRFSE (SEQ ID NO: 32)

>WP_010997761.1
[Nostoc sp. PCC 7120]
MLYKALMCFRRCFYRMFLMEGKFYTSTEASEITHCSRRQLQYWREKGVIVPTVNSSGKGRNVYYSKADLLALTVMEQLLSTGLN
FDLCYAALQTLRKQEPWLFDESVPEEKMKRLMLLPTRSPEQPLQLAEFDKQAALEALCHGQTVIPFWSDRIHQQLRENLKSFSS
(SEQ ID NO: 33)

>WP_029636314.1
[Scytonema hofmanni UTEX 2349]
MEGKFYTSTEAAQITNCSRRQLQYWRDKGVVVPTVNTTGKGRNVYYSISDLLVLTVMHYLLSVGLSFEVSRQTLVILRQKEPWL
FEEFVPKEKMKRLMLLTTCSLEQPLTLAEFDKEA.ALEALCQGQTVIPFWCDRIHQQLRDNLKSFSS (SEQ ID NO: 34)

>WP_072619877.1
[Spirulina major PCC 6313]
MEQPFFSSREAADITGCTLRQLQYWREKEVVIPTINATGTGRSIYYSQANLVELSVMAYWLSLGLTFEVAHESLMKLRAIEPRF
VEPPIARRFMLKWEEMRGKLELVEFDREGAIASLDAGQPVIPVWLEQIYSKLSNKISPN (SEQ ID NO: 35)

>ACV01093.1
[Cyanothece sp. PCC 8802]
MEEMFFTSTEASKLTGCSRRQLQYWREKGVVVPTVNASGKGRNVYYSVSDLLKLMVEYLLSVGLSFETAQESLEMLKKAHPEM
FKADVSSEDLKRLMILPSPKRLELKDFDPEEAFKRINTYAMPLVPFSGEMIHERLKESLQGFSGNNHLKSSENS
(SEQ ID NO: 36)

>AFZ58288.1
[Anabaena cylindrica PCC 7122]
MQETFFTSKEAAQLTGCTLRQLQYWREKGIVVPIISDTGTGRSIYYSRSNLVELAALVYWLSTGISFDIACETLKRLKAQEPEL
FISGKGKRFMLLLSAQNESLSLVEFDRKSAIASLDEGKAVIPVWLDIIYQKLASRLAQ (SEQ ID NO: 37)

TABLE 4

Amino acid sequences of Representative CLUST.004377 Effector C1 Proteins

>OUC12067.1
[Alkalinema sp. CACIAM 70d]
MIVTTLSPDEERKIKVLQPLIEPCDRATYGKRLRYAAEQLGISVRSVQREIQRWEKNGIAGITRNCRADKGKHRISDFWQNFII
KTYKEGNTGSKRMTPKQVAVRVQAKAHEMRDENPPHYRTVLRVLKPIIERQEKTKSIRSPGWKGSTLSVKTRSGEDLVIAHSNH
VWQCDHTPVDVMLVDQYGEKRKRPWLTIVIDSYSRCIMGINLGFDAPSSQVVALALRHAILPKHYGAEYKLNCEWGTYGKPVHF
YTDGGKDFRSNHVQQIGHDLGFTCHLRDRPSEGGIVERPFKTLNEQLFSTLPGYTDSNVQKRPKDVEKDARLTLRDLERLVVRF TABLE 4-continued Amino acid sequences of Representative CLUST.004377 Effector C1 Proteins ICDCYNQSIDARIGDQTRFQRWEAGLPGVPDVIGERLLDPCLMNVSRRTIQRGGYLQFKNLMYRGEYLAGYAGEIVSVRFNPDD
ITTLLVYRRENNREVFLTRAFAQGLETEQLSLSEAQASSSRRKEAGKSLSNTAIFQEVLDRDALVNSKKSRKQRHKEEQKIARS
ETETPKTGAVSVEQPETAPTELEVALDLETETFEPIDFEELQGGW (SEQ ID NO: 38)

>OBQ23776.1
[Anabaena sp. WA113]
MNRDENSDLNTSAIPVESISEGDNTPPETNVIATELSEESQLKLEVLQSLLEPCDRTTYGQKLKEAAEKLAVSVRTVQRLVKKW
EQDGLVGLTQTGRTDKGKHRIGEFWEDFIVKTHKEGNKGSKRMSPKQVAIRVQAKAHELSDLKPPNYRTVLRVLAPILEKQEKT
KSIRSPGWRGTTLSVKTREGKDLSVDYSNHVWQCDHTPADVLLVDQHGELLSRPWLTTVIDTYSRCIMGINLGFDAPSSEVVAL
ALRHAILPKRYSLEYKLHCEWGTYGKPEHFYTDGGKDFRSNHLSQIGAQLGFVCHLRDRPSEGGIVERPFKTLNDQLFSTLPGY
TGSNVQERPEDAEKDAKLTLRELEQLIVRYIVDRYNQSIDARMGDQTRFGRWEAGLPSVPVPIEERDLDICLMKQSRRRVQKGG
HLQFQNLMYRGEYLGGYDGETVNLRFNPRDITTVLVYRQENSQEVFLTRAHAQGLETEQLSLDEAEAASRRLRNLGKTISNQAL
LQEVLDRDALVANKKSRKDRQKLEQEILRSTAVNDSKNESLASPVMEAEDVEFTTPVQSSSPELEVWDYEQLREEYGF
(SEQ ID NO: 39)

>ABA20966.1
[Anabaena variabilis ATCC 29413]
MNYLDVDNQFELEDEDDFLLDDEDADILDFSIEVESLSNDGNSVAEDKLVEFLDQRYLEDSELRLSGEQRLKLEIIRNLREPCD
RLTYGKRLEEAAKKLGKSERTVRRLIKSWEEKGIAALAEVPRADKGQVRKSEYWYNLSLKIYKQGNKGDKGDKGDKGSDRMTRT
QVAEKVETKAYEFAKKELEAEISKLESQGFRGQDLDWELKKLIKIKEKAEGFKYWSKYGKPPSTRTVERWLKPVEEKRHKSRTS
RSPGWHGSEHTIKTRDGQEISIKYTNQVWQIDHTKADILLVDEDGEEIGRPQLTTVIDCYSRCIVGFRLGFAAPSSQVVALALR
HAIMPKRYSSEYELRCKWSAYGVPKYVYTDGGKDFRSKHLVEWIANELDFEPILRSKPSDGGIVERPFRTISGLLSEMPGYTGS
SVKDRPEGAEKKACISLPELEKLIVGYIVDSYNQKPDARSQANPLTPQKSRIERWEKGLQMPPTLLNDRELDICLMKAAERVVY
DNGYLNFSGLRYRGENLGAYAGDKVILRFDPRDITMVLVYGRKNNKEIFLARAYAIGLEAASLSVEEVKYARKKAENSGKGINN
ISILEEALRRRNFLQQKKNKTKAERRRSEEKRIEKIPQVLTEKKNEQVAVLISQPEDDEPIEKLDLKLLREELGL
(SEQ ID NO: 40)

>WP_011317997.1
[Anabaena variabilis ATCC 29413]
MLDDDPDKGNQEPETHEIVTELSLDEQHLLEMIQKLIEPCDRITYGERQREVAGKLGKSVRTVRRLVKKWEQEGLTALQTATRTD
KGTHRIDSDWQDFIIKTYKENNKDGKRMSPKQVALRVQTKAEELGQQKYPSYRTVYRVLQPIIEQKEQKEGIRHRGWHGSRLSV
KTRDGKDLFVEHSNHVWQCDHTRVDLLLVDQHGELLSRPWLTIVVDTYSRCIMGINLGFDAPSSQVIALALRHAILPKRYGSEY
GLHEEWGTYGKPEHFYTDGGKDFRSNHLQQIGVQLGFVCHLRDRPSEGGIVERPFGTFNTDLFSTLPGYTGSNVQERPEQAEKE
ACITLRELERLLVRYIVDKYNQSIDARLGDQTRYQRWEAGLIVAPNLISEEELRICLMKQTRRSIYRGGYVQFENLTYRGENLA
GYAGENVVLRYDPKDITTLLVYRQKGNQEEFLARAYAQDLETEELSVDEAKAMSRRIRQAGKAISNRSILAEVRDRETFVNQKK
TKKERQKAEQTIVQKAKKPVPVEPEEEIEVASVDSEPEYQMPEVFDYEQMREDYGW (SEQ ID NO: 41)

>WP_044151373.1
[Aphanocapsa montana BDHKU210001]
MELVNPDDLNSVESRLKLEIIEKLSEPCDRKTYGERLRSAAQQLKCSVRTVQRLMKKWEEEGLAALIDSGRIDKGKPRIAEDWQ
QFIKKVYSNDKCTPAQVFTKVRNKARQEGLKDYPSHMTVYRILRLVKEAKEKEESIRNLGWKGSRLALKTRDGEVLEIDYSNQV
WQCDHTRADILLVDKYGHQMGRPWLTTVIDTYSRAIVGINLGYDAPSSSVVALALRNAIMPKQYGVEYKLYADWPTCGTPDHLF
TDGGKDFRSNHLRQIGLQLGFICHLRDRPSEGGIVERPFGTINTQFLSTLPGYTGSNVQDRPPEAEAEACLTLQELEKLLVAYI
VNTYNQRLDARMGDQTRIQRWEAGLLKQPRVIPEHELHICLMRQTRRTIYRGGYLQFENLAYRGEALAEHAGENIVLRYDPRNI
AQVLVYRHDPDREVYLGVAQALEFEGEVLALDDAKAHSRRIREDGKAVSNDAMLDEMRDREAFVDQKNKSRKDRQKDEQADLRP
TTPPIIGPDSSDEPSVDVQPDESPEELDIPEFDIWDFDDDDA (SEQ ID NO: 42)

>WP_019497296.1
[Calothrix sp. PCC 7103]
MGETLNSDNINALQVFDDSGELEEISESDDTESKNTIVTELSAEAKLRMEVLQSLLEPCDRTYGIKLHDAAEKLGKTIRTVQR
LVKKYQEEGLSAITEAERSDKGDYRIDKEWQEFIFKTYKEGNKNGRKMTPAQVAIRVQVKAEQLALSNYPSHMTVYRVLNPIIE
RKEQKQKVRNIGWRGSRVSHKTRDGQTLEPRYSNHTWQCDHTKLDILVDKYGHQMGRPWLTIVIDTYSRLARPWLTIVIDTSYSRCIMGINLGFDAPSS
LVVALAMRHAILPKSYGSEYKLHCKWETYGVPENLFTDGGKDFRSEHLKQIGFHLGFECHLRDRPPEGGIEERGFGTINTDFLA
GFYGYLGSNLQQRPEEAESEACITLRELHLLLVRYIVDNYNQRIDARSGNQTRFQRWEAGLPALAPLIDERQLDICLMKKTHRS
IYKGGYVSFENITYRGEYLAAYAGESVILRFDPRDEWHLLKGKRIGMIGFRALVMAINTVGAYINTNTYQLHIHVN
(SEQ ID NO: 43)

>WP_012596233.1
[Cyanothece sp. PCC 8801]
MSLSLSIPDDSPHSHRLPSDEMITDEVKAKIDIIQSLIEPCDRITYRQRKEQAAKQLGVTIRSVERLLKKYREQGLIALMKTRS
DKGKTRIDDEWKEFILNTYKEGNKGSKRITRHQVFLKVKGRAKQLGLNKEEPPSHQTVYRILDKFIEENERKKKARSPGYSGSR
LTHITRHGRELEVEGSNDVWQCDHTCLDIRLVDEFGVLSRPWLTIIIDSYSRCVMGFFLGFYAPSSHIDALALRHAILPKSYSS
DYQLKNEWNTYGIPTYYYTDGGKDFRSIHVTEQVAVSLGFNCFLRSRPSDGGIVERFFKTLNNSVLCELPGYTGSNVQQRPKNV
DKDACLSLKDLEKILVKYIVDEYNQKPDARMKNQSRITRWEAGLLTEPYLYDERELDIALMKEAKRTLQKSGTLQFENLTYRSP
LLKGREGERVAIRYDPDDVTTILVYEYLDDGTEAFLDYAHAQNLETEKLSYRELKAINKQLNQEEEAINNDKILDAMMERMEMT
EELVKKNRQQRQQNAHEAVNSRPSVTEKLSISQPDEEDWEDDSEDEPLPTYKVQYMDDLFEDD (SEQ ID NO: 44)

>WP_066116124.1
[Geminocystis sp. NIES-3709]
MTIENQISESQELISQLSPEEQAIADVIEDLVQPCDRKTYGAKLKKAAETLNKSVRTVQRYIKEWEEKGLLAIKKGNRSDQGTY
RIEKRLQDFIVKTYREGNKGSKRISPKQVYLRTMAQAKEWSIDPPSHMTVYRILNPIIEEKENKKRVRNPGWRGTKLAVSTRSG
NEINVEYSNHAWQCDHTRADILLVDQFGQLLGRPWLTTVVDTYSRCIMGINLGFDAPSSQVVSLALRHAMLLKSYSSDYGLHEE
WGTYGKPEYFYTDGGKDFRSNHLQQIGLQLGFTCHLRSRPSEGGVVERPFKTLNTEVFSTLPGYTGGNVQERSEDAEKDASLTL
RQLERIIVRYIVDNYNQRMDARMGEQTRFQRWDSGLLSIPDLLSERDLDICLMKQSRRRVQKGGYLQFENLMYQGEYLAGYEGE
TVILRYDPRDITAILVYRNEGNKEVFLTRAYGLDLETESMSWEDAKASAKKVRESGKNLSNRSILAEVKERHTFSDKKTKKERQ
RQEQEQVKPYIPSPVLKEVKEQTDKATDTDMSEEPIVEVFDYSQLQDDYGF (SEQ ID NO: 45)

TABLE 4-continued

Amino acid sequences of Representative CLUST.004377 Effector C1 Proteins

>WP_017289545.1
[*Leptolyngbya boryana* dg5]
MQLPIEFPSEQVSRELVEQNQIVTELSDEAKLKIEVIQSLLEPCDRATYGNRLRDAATRLGKSVRTVQRMVKSWQEEGIAGLS
NGERTDKGEHRIEQEWQDFIIKTYQEGNKNGKRMTPAQVAIRVKVKAQQEGITKYPSHMTVYRVLNPLIQRKTEKQNVRSIGWQ
GSRLSLKTRDGNSLSVEYSNQVWQCDHTRADILLVDQHGELIGRPWLTTVVDTYSRCIVGVNLGFDAPSSDVVALALRHAILPK
TYPDRYQLNCDWGTYGKPEHFFTDGGKDFRSNHLQQIAVQIGFTCHLRNRPSEGGVVERPFGTLMKQTRRTVYREGYLRFENLIY
EEAEESASLTLRELEQFLVRYITDRYNQGIDARMGDQTRFQRWEAGLLANPSVLTERELDICLMKQTRRTVYREGYLRFENLIY
RGENLAGYAGETVTLRYEPRDITTVFVYHQEQGKEVFLTRAHAQDLETETISLYEAKASSRRIRDVGKTISNRSILEEVRDRDL
FVQKKTRKERQKAEQAEVKIDQVPSPPQVLHLDEASQFETEIVETQCVEISEIEDYEKLRDDFGW (SEQ ID NO: 46)

>WP_036484426.1
[*Myxosarcina* sp. GI1]
MNSESTSETNSKLAISDLEDDREIVITSQLEGKAKERLEVIQSLLEPCDRATYGERLRAGAKKLDISVRSVQRLFKKYQEQGLT
ALVSTNRVDKGNRRISSFWQDFILQTYIQGNKGSKRMSPKQVAIRVQAKASEIKDNKPPSYKTVLRLLKPIQKKKERTIRSPGW
QGTTLSVKTRDGQDIQINHSNQVWQCDHTLVDVLLVDRHGELIGRPWLTTVVDSYSRCVMGINLGFDAPSSLVVALALRHSILP
KNYSQDFQLYCDWGVFGLPECLFTDGGKDFRSNHLEEIATQLGFIRKLRDRPSEGGIVERPFKTLNQSLFSTLPGYTGSNVQER
PKDAEKDARLTLRDLEMLIVRFIVDKYNQSTIAGKDEQTRYQRWEAGLIKDPKIISERELDICLMKSKRRTVQRGGHLQFENII
YRGEYLAGYEGDIVNVRYNPINITTILVYRREQGKEVFLTRAHALGWETEIHSLSEARASVKRLRQAKKKISNESIHQEILLRD
SAVDKKKSRKQRQKEEQSYKLITSPKVVAQDIESQEIERDISAEIADVEVWDFDELEDE (SEQ ID NO: 47)

>WP_012411919.1
[*Nostoc punctiforme* PCC 73102]
MNSQQNPDLAVHPSAIPIEGLLGESDITLEKNVIATQLSEEAQLKLEVIQSLLEPCDRTTYGQKLREAAEKLGVSLRTVQRLVK
NWEHDGLVGLTQTGRADKGKHRIGEFWEKFITKTYNEGNKGSKRMTPKQVALRVEAKARELKDSKPPNYKTVLRVLAPILEKQE
KAKSIRSPGWRGTTLSVKTREGKDLSVDYSNHVWQCDHTRVDVLLVDQHGELLSRPWLTTVIDTYSRCIMGINLGFDAPSSGVV
ALALRHAILPKQYGFEYKLHCEWGTYGKPEHFYTDGGKDFRSNHLSQIGAQLGFVCHLRDRPSEGGVVERPFKTLNDQLFSTLP
GYTGSNVQERPKDAEKDARLTLRELEQLLIRYIVDRYNQSIDARMGDQTRFGRWEAGLPTVPVPIEPERDLDICLMKQSRRTVQR
GGCLQFQNLMYRGEYLAGYAGETVNLRFDPRDITTILVYRQENNQEVFLTRAHAQGLETEQLALDEAEAASRRLRNAGKTISNQ
SLLQEVVDRDALVATKKSRKERQKLEQAVLRSAGVDESKTESLSSQVVEPDEVESTETVHSQYEDMEVWDYEQLREEYGF
(SEQ ID NO: 48)

>BAB75329.1
[*Nostoc* sp. PCC 7120]
MIQTLLEPCDRTTYGQKLKEAADTLGVTVRTVQRLVKKWEEDGLVGFIQTGRADKGKHRIGEFWENFIIKTYKEGNKGSKRMTP
KQVALRVQAKARELGDSKPPNYRTVLRVLAPILEQKEKTKSIRSPGWRGTTLSVKTREGQDLSVDYSNHVWQCDHTRVDVLLVD
QHGELLSRPWLTTVIDTYSRCIMGINLGFDAPSSVVVALALRHAILPKKYGAELYKLHCEWGTYGKPEHFYTDGGKDFRSNHLSQ
IGAQLGFVCHLRDRPSEGGIVERPFKTLNDQLFSTLPGYTGSNVQERLEDAEKDAKLTLRELEQLLVRYIVDRYNQSIDARMGD
QTRFGRWEAGLPSVPVPIEERDLDICLMKQSRRTVQRGGCLQFQNVMYRGEYLAGYAGETVNLRYDPRDITTVLVYRQEKSQEV
FLTRTHAQGLETEQLSLDEARAASRRLRNAGKTVSNQALLQEVLERDAMVANKKSRKERQKLEQAILRSAAVNESKTESLASSV
MEAEEVESTTEVQSSSSELEVWDYEQLREEYGF (SEQ ID NO: 49)

>WP_044521841.1
[*Nostoc* sp. PCC 7120]
MTRQQHTSSPPETNLIVTELSEEAQLKLEVIQTLLEPCDRTTYGQKLKEAADTLGVTVRTVQRLVKKWEEDGLVGFIQTGRADK
GKHRIGEFWENFIIKTYKEGNKGSKRMTPKQVALRVQAKARELGDSKPPNYRTVLRVLAPILEQKEKTKSIRSPGWRGTTLSVK
TREGQDLSVDYSNHVWQCDHTRVDVLLVDQHGELSRPWLTTVIDTYSRCIMGINLGFDAPSSVVVALALRHAILPKKYGAEYK
LHCEWGTYGKPEHFYTDGGKDFRSNHLSQIGAQLGFVCHLRDRPSEGGIVERPFKTLNDQLFSTLPGYTGSNVQERLEDAEKDA
KLTLRELEQLLVRYIVDRYNQSIDARMGDQTRFGRWEAGLPSVPVPIEERDLDICLMKQSRRTVQRGGCLQFQNVMYRGEYLAG
YAGETVNLRYDPRDITTVLVYRQEKSQEVFLTRTHAQGLETEQLSLDEAEAASRRLRNAGKTVSNQALLQEVLERDAMVANKKS
RKERQKLEQAILRSAAVNESKTESLASSVMEAEEVESTTEVQSSSSELEVWDYEQLREEYGF (SEQ ID NO: 50)

>WP_094343929.1
[*Nostoc* sp. 'Peltigera membranacea cyanobiont' 232]
MYQKLKNSCLSSEDDAVELQQHQNSTKPHKLPSEELITEQVKLRMEVIQSLTEPCDRKTYRAKKIEAAQKLGVSIRQVERLLQK
WREQGLVGLTTTRSDKGKYRLEQEWIDFIINTYKEGNKGSKRMTRNQVFLKVKGRAKQLSLNKSEHPSHQSVYRILDEHIEQKE
RKEKARSPGYLGERLTHMTRDGRELEVEGSNDVWQCDHTRLDVRLVDEYGVLDRPWLTIVIDSYSRCLVGFYVGFDHPSSQIDT
LALGRAILPKSYGSEYQLRNEWQAYGKPNYFYTDGGKDFTSIHTTEQVAVQIGFNCALRRRPSDGGIVERFFKTLNLQVLNTLP
GYTGSNVQERPENVDKDACLTLKDLELLLVRFIVNEYNPHTDARMKGQSRIGRWEAGLMADPYLYDQLDLAICLMKQERRKVQK
YGCTQFENLTYRAEHLRGRDGETVAFRYDPADITTLLVYKMNADGTEEFMDYAHAQALETECLSLRELKAINKRLNEASQEINN
DSILEAMIDRQAFVEETVKRNRKQRRQAANEQVNPVEQVAKKFATPEQKEVEPESEADIELPKYEVRYMDEFFEED
(SEQ ID NO: 51)

>WP_084763316.1
[*Scytonema hofmanni* UTEX 2349]
MNSQQNPDLAVHPLAIPMEGLLGESATTLEKNVIATQLSEEAQVKLEVIQSLLEPCDRTTYGQKLREAAEKLNVSLRTVQRLVK
NWEQDGLVGLTQTSRADKGKHRIGEFWENFITKTYKEGNKGSKRMTPKQVALRVEAKARELKDSKPPNYKTVLRVLAPILEKQQ
KAKSIRSPGWRGTTLSVKTREGKDLSVDYSNHVWQCDHTRVDVLLVDQHGEILSRPWLTTVIDTYSRCIMGINLGFDAPSSGVV
ALALRHAILPKRYGSEYKLHCEWGTYGKPEHFYTDGGKDFRSNHLSQIGAQLGFVCHLRDRPSEGGVVERPFKTLNDQLFSTLP
GYTGSNVQERPEDAEKDARLTLRELEQLLVRYIVDRYNQSIDARMGDQTRFGRWEAGLPTVPVPIERDLDICLMKQSRRTVQR
GGCLQFQNLMYRGEYLAGYAGETVNLRFDPRDITTILVYRQENNQEVFLTRAHAQGLETEQLALDEAEAASRRLRTAGKTISNQ
SLLQEVVDRDALVATKKSRKERQKLEQTVLRSAAVDESNRESLPSQIVEPDEVESTETVHSQYEDIEVWDYEQLREEYGF
(SEQ ID NO: 52)

>WP_073629994.1
[*Scytonema* sp. HK-05]
MGETLNSNEVDESLVLYDGSDEVDEISESEDTKQSNVIVTELSEEAKLRMQVLQSLIEPCDRKTYGIKLKQAAEKLGKTVRTVQ
RLVKKYQEQGLSGVTEVERSDKGGYRIDDDWQDFIVKTYKEGNKGGRKMTPAQVAIRVQVRAGQLGLEKYPCHMTVYRVLNPII
ERKEQKQKVRNIGWRGSRVSHQTRDGQTLDVHHSNHVWQCDHTKLDVMLVDQYGETLARPWLTKITDSYSRCIMGIHLGFDAPS TABLE 4-continued Amino acid sequences of Representative CLUST.004377 Effector C1 Proteins SLVVALAMRHAMLRKQYSSEYKLHCEWGTYGVPENLFTDGGKDFRSEHLKQIGFQLGFECHLRDRPPEGGIEERGFGTINTSFL
SGFYGYLDSNVQKRPEGAEEEACITLRELHLLIVRYIVDNYNQRIDARSGNQTRFQRWEAGLPALPNLVNERELDICLMKKTRR
SIYKGGYVSFENIMYRGDYLSAYAGESVLLRYDPRDISTVFVYRQDSGKEVLLSQAHAIDLETEQISLEETKAASRKIRNAGKQ
LSNKSILAEVQDRDTFIKQKKKSHKQRKKEEQAQVHSVKSFQTKEPVETVEEIPQPQKRRPRVFDYEQLRKDYDD
(SEQ ID NO: 53)

>WP_072619869.1
[*Spirulina major* PCC 6313]
MNTGNQEAHAVITDFSEEERLKLEVIQSLMEPCDHATYGQKLKDAAQKLGKSKRTVQRLVQQWEEMGLAAVTSKARADKGKHRI
SQEWQDFIVKTYRLGNKGSKRMSRKQVALRVQARAAELGEKMYPNERTVYRLVQPIIEAQEQKKSVRSAGWRGDRLSVKTRTGN
DLVVEYTNQVWQCDHTWVDVLVVDVEGNIIGRPWLTTVIDTYSRCILGIRLGFDAPSSQVVALALRHAMLPKQYPPTFGLQCEW
GTYGKPEYFYTDGGKDFRSEHLRQIGIQLGFTCELRDRPSEGGAVERPFGTLNTELFSTLPGYTGSNIQERPEDAEKDARMTLR
DLEQLIVRYLVDNYNQRLDKRMGDQTRYQRWESGLLATPALLSERELDICLMKQTNRSIYREGYIRFENLMYKGEYLAGYVGER
VVLRYDPRDITTVLVYRREKSQEVFLARAYAQDLETEQLTLEDAKAINKKIREKGKTISNRSILDEVRDRDLFVSKKKTKKERQ
KEEQTRLFTPVTTPNSKQETEEEEIEPVEKIDELPQVEILDYDELNDDYGW (SEQ ID NO: 54)

>BAQ60391.1
[*Geminocystis* sp. NIES-3708]
MLEEKHNIEDHVARSRLEDSSNNTIVSELPVEAQQKLKIIQSLLEPCDRATYGDRLREGAKELGISVRSVQRLFKRYQEEGLNA
LTINDQRDKGKHRIKDFWESFILKTYKEGNKGSKRMNVKQVAIRVQAKALELNETNPPSYRTVLRVLNPIINQEKKTIRSPGWE
GSTLSVKTRDGVDLNISYSNQVWQCDHTKVDVLLVDKNEVLLDRPWLTTVIDSYSRCIVGVNIGFDAPSSNVVGLALRHAILPK
HYPEEYRLNCEWGTYGLPQYLFTDGGKDFRSNHLEEIATQLGFVLKDRPSEGGIVERPFKTLNQSLFSTLPGYTGSNVQERP
EDAEKDAQLTLQELERLIVRFIVDKYNQSIDARMGDQTRFQRWEAGLRAIPEVMSERDLDICLMKQARRQVQRGGYLLFENIHY
KGEYLEGFAGKTVSLRYDPRDITTIWVYQHSRGQEEFLTRAYAQGLETESLSLADAKASAKRLREKEKNISNEAILQEVIDREV
TIKNKSRKQRQKEEQSYKKTPSLPVIEKEQESFEQVEEILLDTDDDFEVWDLDEMKDDYGW (SEQ ID NO: 55)

>BAT55397.1
[*Nostoc* sp. NIES-3756]
MPDKEFGLTGELTQITEAIFLSESNFVVDPLHIILESSDSQKLKFNLIQWLAESPNRQIKSQRKQAVADTLGVSTRQVERLLKE
YNGDRLNETAGVQRCDKGKHRVSEYWQQYIKTIYENSLKEKHPMSPASVVREVKRHAIVDLGLEHGDYPHPATVYRILNPLIEQ
QKRKKKIRNPGSGSWLTVETRDGKQLKAEFSNQIIQCDHTELDIRIVDSNGVLLPERPWLTTVVDTFSSCVLGFHLWIKQPGSA
EVALALRHSILPKQYPHDYELSKPWGYGPPFQYFFTDGGKDFRSKHLKAIGKKLRFQCELRDRPNQGGIVERIFKTINTQVLKD
LPGYTGSNVQERPENAEKEACLGIQDIDKILASFFCDIYNHEPYPKDPRETRFERWFKGMGGKLPEPLDERELDICLMKETQRV
VQAHGSIQFENLIYRGESLRAYKGEYVTLRYDPDHILTLYVYSCDANDDIGDFLGYVHAVNMDTQELSIEELKSLNKERSKARR
EHSNYDALLALGKRKELVKERKQEKKERRQAEQKRLSGSKKNSNVVELRKSRAKNYVKNDDPIEVLPERVSREEIQVPKTEVQ
IEVSEQADNLKQERHQLVISRRKQNLKNIW (SEQ ID NO: 56)

>ACV01082.1
[*Cyanothece* sp. PCC 8802]
MNTFPNEQSNAIVLKNTIVSDLPETARTKMEVIQTLLEPCDRITYGERLREGAKKLGVSVRTVQRLFKQYQEQGLAALVSTERS
DKGKHRINEFWQDFIVKTYQQGNKGSKRMTPKQVALKVQAKALEIGDEQPPTYRTVLRVLKPIQEKQEKTKSIRSPGWRGSTLS
VKTRDGDDLEINYSNQVWQCDHTRADVLLVDRHGELIGRPWLTTVIDSYSRCIMGINLGFDAPSSQVVALALRHAILPKRYGDE
YKLHCEWETSGTPEYFYTDGGKDFRSNHLAQIGSQLGFVHKLRDRPSEGGIVERPFKTLNQSLFSTLPGYTGSNVQERPKEAEK
EASLTLRELEQLIVRFIVDKYNQSIDARMGDQTRYQRWEAGLRRQPEPISERELDICLMKAARRTVQRGGYLQFENVMYRGEYL
EGYAGDTVILRYEPRDITTIWVYRQKHQEVFLTRAHAQDLETEQLSVDEAKASAKKLRDAGKTISNQSILQEVIEREALVEKK
SRKQRQKAEQAYKQEKQPSIIETVEPIEPEPLTQTEVDDIEVWDYDQLRDDYGW (SEQ ID NO: 57)

>AFZ00420.1
[*Calothrix* sp. PCC 6303]
MSVFALMADKKFELTEKFTQLPEAVFLGENNFVIDPSQIILETSDKHKLTFNLMQWLAESPNRTIKSQRKQAIASTLGVSTRQV
ERLLKQYDEDRLSETSGLQRSDKGKYRVSDYWQEFIKTTYEKSLKDKHPISPASIVREVKRHAIVDLKLEQGNYPHPATVYRIL
NPLIEQQERKKKVRNPGSGSWMTVETRDGKQLKVDFSNQIIQCDHTKLDIRIVDSDGILLTERPWLTTVVDTFSSCVNGFHLWI
KQPGSAEVAIALRHAILPKQYPDDYELGKPWKIYGHPFQYFFTDGGKDFRSKHLKAIGKKLGFQCELRDRPIQGGIVERIFNTI
NTQVLKDLPGYTGPNVQERPENAEKEACLSIHDLDKILASFFCDIYNHEPYPKDTRITRFERWFKGMGEKLPEPLNERELDICL
MKEAQRVVQAHGSIQFENLVYRGESLNAHKGEYVTLRYDPDHILTLYVVSYDVNDELENFLGYVHAINMDTQDLSLEELKSLNK
ERSKARREHSNYDALLALSKRKELVEERKQGKKEKRQAEQKRLRAASKKNSNVVELRQNRASSSSNKDEKDEKIELLPERVSRE
ELKVEKIEPQLEILDKAETPPQERHKLVISSRKQHLKKIW (SEQ ID NO: 58)

>AFZ58294.1
[*Anabaena cylindrica* PCC 7122]
MKESQVAIQTLDIDHLGIVAGIIDEMELVEEVNKIVGIKTKETLTPGQVVKAMILNGLGFLSAPLYLFGEFFVGKATEHLIGEG
VLPEHLNDDKLGRELDKYHQIGTTKIFTAVAIKAAHKFQVEMDSIHLDGTSMSVEGEYKKEIKEIDEIKQETEENKLEIEPEMK
AIEIVHGYSRDKRPDLKQFIIDMIVTGDGDIPLYLKVDSGNVDDKSVFVERLKEFKKQWTFPEGISVADSALYTAENLAAMRELK
WITRVPLSIKEAKNKIVDIKEAEWKDSQIISGYKIAAAKESEYAGIKQRWIIVESEIRKKSSIQQVEKQVKKQEAKAKAALSKLSR
QEFACQPDAKIVIEKLSKSWKYHQIKEIEYIEKLEYKTAGRPSKLTEPSQIKYQIKGQIETREEVIETEKINAGRFILATNVLD
RNELSDEKVLEEYKAQQSNERGFRFLKDPLFFTSSVFVKTPERVEAIAMIMGLCLLVYNLAQRKLRQELAKFDDGIRNQVKKIT
NKPTMRWVFQMFQAVHLVIINGQKQMSNLTEEREKIVRYLGKSCSKYYLIT (SEQ ID NO: 59)

>AFZ56182.1
[*Anabaena cylindrica* PCC 7122]
MADEEFEFTEGTTQVPDAILLDKSNFVVDPSQIILATSDRHKLTFNLIQWLAESPNRTIKSQRKQAVANTLDVSTRQVERLLKQ
YDEDKLRETAGIERADKGKYRVSEYWQNFITTIYEKSLKEKHPISPASIVREVKRHAIVDLELKLGEYPHQATVYRILDPLIEQ
QKRKTRVRNPGSGSWMTVVTRDGELLRADFSNQIIQCDHTKLDVRIVDNHGNLLSDRPWLTTIVDTFSSCVVGFRLWIKQPGST
EVALALRHAILPKNYPEDYQLNKSWDVCGHPYQYFFTDGGKDFRSKHLKAIGKKLGFQCELRDRPPEGGIVERIFKTINTQVLK TABLE 4-continued Amino acid sequences of Representative CLUST.004377 Effector_C1 Proteins ELPGYTGANVQERPENAEKEACLTIQDLDKILASFFCDIYNHEPYPKEPRDTRFERWFKGMGGKLPEPLDERELDICLMKEAQR
VVQAHGSIQFENLIYRGEFLKAHKGEYVTLRYDPDHILSLYIYSGETDDNAGEFLGYAHAVNMDTHDLSIEELKALNKERSNAR
KEHFNYDALLALGKRKELVEERKEDKKAKRNSEQKRLRSASKKNSNVIELRKSRTSKSLKKQENQEVLPERISREEIKLEKIEQ
QPQENLSASPNTQEEERHKLVFSNRQKNLNKIW (SEQ ID NO: 60)

>WP_066425682.1
[*Anabaena* sp. 4-3]
MADREIEFTEESTQDSDAILLDNSNFVVDPSQIILATSDKHKLTFNLIQWLAQSPTRTVKSERKQAIANTLSVSTRQVERLLKQ
YNEDKLRETAGTERADKGKHRVSEYWQEFIKTTYEKSLKDKHPISPASIVREVKRHAIVDLGLKPGDYPHQATVYRILEPLIAQ
HKRKTRVRNPGSGSWMTVVTRDGQLLRADFSNQIIQCDHTKLDIRIVDIHGDLLSERPWLTTVVDTYSSCVLGFRLWIKQPGST
EVALALRHAILPKQYPDDYQLNKSWNVYGNPFQYFFTDGGKDFRSKHLKAIGKKLGFQCELRDRPPEGGIVERIFKTINTQVLK
DLPGYTGANVQERPENAEKEACLTIQDLDKILASFFCDIYNHEPYPKEPRDTRFERWFKGMGEKLPERLDERELDICLMKETQR
VVQAHGSIQFENLIYRGESLKAHKGEYVTLRYDPDHILTLFVYSCETDDNLEEFLGYAHAVNMDTHDLSEELKTLNKERSKAR
KEHFNYDALLALGKRKELVDERKADKKEKRHSEQKRLRSASKKDSNIIELRKSRVSKSLRKQETQEILPERVSREEIKFEKIEL
EPQETLSASPKPNPQEEQRHKLVLSKRQKNLKNIW (SEQ ID NO: 61)

TABLE 5

Amino acid sequences of Representative CLUST.004377 Effector_C2 Proteins

>OUC12055.1
[*Alkalinema* sp. CACIAM 70d]
MTIDSGIQPWLFQVEPYEGESLSHFLGRFRRPNHLTPSGLGQLAGIGAVVARWERFHWNPPPSRQELEALAKVVRVSVEQLIAM
LPPPGVGMQCSPIRLCSACYGETPCHRMEWQYKHIWKCNRHSLKLLAKCPVCSALFKAPAQWQDGMCRRCLTPFGQMQQQ
(SEQ ID NO: 62)

>OBQ23833.1
[*Anabaena* sp. WA113]
MIQPYEGESLSHFLGRFRRANHLSAAGLGNLAGIGAVIARWERFHFNPRPSQKELEAIASVVEVDAQRLAEMLPPAGVSMQHEP
IRLCGACYAETPCHQIKWQFKETGGCDRHYLRLLSKCPNCDARFKIPALWELGVCQRCLMTFAEMAGYQKSINGT
(SEQ ID NO: 63)

>WP_011318169.1
[*Anabaena variabilis* ATCC 29413]
MPEEIYNFEAWINVVEPLPGESISHFLGRFERANLLTGYQVGREVGVGAIVTRWKKLYLNPFPTLQELEALARFVEVEVEKLKE
MLPSQGMTMKPRPIKICAACYAEVPCHRIEWQYKDNMKCDRHNLRLLTKCTNCETPFPIPADWLQGECPRCFLPFAKMAKRQKL
NS (SEQ ID NO: 64)

>WP_011318975.1
[*Anabaena variabilis* ATCC 29413]
MRESINENKQFWLIRVEPLEGESISHFLGRFRREKGNKFSAPSGLGDVAGLGAVLARWEKFYFNPFPTHQELEALASVVQVDVD
RLRQMLPPLGVSMKHSPIRLCGACYAESPCHKIEWQFKKTVGCDRHQLRLLSKCPVCEKPFPVPALWVDGICNRCFTPFAEMAQ
YQKHY (SEQ ID NO: 65)

>WP_011317999.1
[*Anabaena variabilis* ATCC 29413]
MEVPQIQPWLFQIEPLEGESLSHFLGRFRRANDLTPTGLGKAAGLGGAIARWEKFRFNPPPSRQQLEALANVVGVDADRLAQML
PSAGVGMKMEPIRLCAACYAESPCHKIEWQFKVTRGCARHKITLLSECPNCKARFKVPALWVDGWCNRCFLRFEEMAKYQKGL
(SEQ ID NO: 66)

>WP_039728662.1
[*Aphanocapsa montana* BDHKU210001]
MVIPQIPAWVFPVEPSPGESLSHFLGRFCRENHTTLNQLGEKTGLGAVLGRWEKFRFIPQPSDAQLAALAKLVRLEVDQIKQML
PQETMQNRVIRLCAACYAEEPYHRIEWQYKLANRCDRHHLLLLLECPNCKAKLPMPSKWANGTCKRCLTPFEQMADLQKGI
(SEQ ID NO: 67)

>WP_019497300.1
[*Calothrix* sp. PCC 7103]
MNEPRFFEIEPFECESLSHFLGRFRRENYLTATQLGKLTGLGAVISRWENCYFNPFPTQQELEALASVVGAEVEKLREMLPPIG
VTMKPRPIRLCAACYAESPYHHIEWQFKDVMKCSYHQMRLLTKCTNCGAVFPIPADWVTGECPHCCLPFVTMVRKQQKG
(SEQ ID NO: 68)

>WP_012596235.1
[*Cyanothece* sp. PCC 8801]
MDKEYWLTKVEPYEGESISHFLGRFRRTKGNRFSAASGLGQVAGLGAILARWEKLYFNPFPNEQELEALGKVVMLDVEDLRKML
PQKGMVTQPKPIMLCAVCYGEKPYHRMVWQDKHQRGCEVHGLELLSRCINCKRLFPIPSKWEEGKCLLCGLAFAKIAKHQKPI
(SEQ ID NO: 69)

>WP_066116120.1
[*Geminocystis* sp. NIES-3709]
MDLQIQNWLFILVPYEGESISHFLGRFRRANSLSCGGLGQATGLYSAIARWEKFRFNPPPSLKQLEKLSEIVQVEMATLQTMFP
SAPMKMTPIRICSACYGENPYHQMSWQYKEIYRCDRHNLNILSECPNCAARFKFPNLWFEGFCHRCFTPFEQMPQS
(SEQ ID NO: 70)

TABLE 5-continued

Amino acid sequences of Representative CLUST.004377 Effector_C2 Proteins

>BA555900.1
[*Leptolyngbya boryana* dg5]
MIEHSEIQPWFFHVEALEGESISHFLGRFRQANELTPSGVGKISGLGGAIARWEKFRFNPYPTQQQFEKLSTATGISVEQLWKM
MPPEGVGMQLEPIRLCASCYAELPCHQIQWQFKDTQGCEVHGLRLLSECPNCKARFKPPATWSDSKCHRCFMLFSEMRNRQKRH
SFSR (SEQ ID NO: 71)

>WP_026148796.1
[*Leptolyngbya boryana* IAM M-101]
MEHSEIQPWFFHVEALEGESISHFLGRFRQANELTPSGVGKISGLGGAIARWEKFRFNPYPTQQQFEKLSTATGISVEQLWKMM
PPEGVGMQLEPIRLCASCYAELPCHQIQWQFKDTQGCEVHGLRLLSECPNCKARFKPPATWSDSKCHRCFMLFSEMRNRQKRHS
FSR (SEQ ID NO: 72)

>WP_036484423.1
[*Myxosarcina* sp. GI1]
MNNTKEAQLWLFPVEPSNGESLSHFLGRFRRSNHLSPSALGDLAGIGGVVARWERFHLNPFPTDEQFQALAEVVDVDSSTLREM
LPPKGTGMKCDRHNLKLISKCPNCRAKFKMPALWEYGCCHRCRLPFAAIAQYQQSV
(SEQ ID NO: 73)

>WP_012411917.1
[*Nostoc punctiforme* PCC 73102]
MTTPDVKPWLFIIEPYPGESLSHFLGRFRRANHLSPAGLGGLAGIGAVVARWERFHFNPRPSQKELEAIASVVEVDAQRLAQML
PPAGVGMQHEPIRLCGACYAEAPCHRIEWQYKSVWKCDRHQLKILAKCPNCQAPFKMPALWEDGCCHRCRTLFAEMAKQQKS
(SEQ ID NO: 74)

>BAB75327.1
[*Nostoc* sp. PCC 7120]
MMAAPDVKPWLFIIQPYEGESLSHFLGRFRRANHLSASGLGKLAGIGAVVARWERFHFNPRPSQKELEAIASLVEVDADRLAQM
LPPLGVGMQHEPIRLCGACYAEAPCHRIEWQYKSVWKCDRHELKILAKCPNCEAPFKIPALWEDKCCHRCRTPFAEMTKYQKIT
(SEQ ID NO: 75)

>WP_044521839.1
[*Nostoc* sp. PCC 7120]
MAAPDVKPWLFIIQPYEGESLSHFLGRFRRANHLSASGLGKLAGIGAVVARWERFHFNPRPSQKELEAIASLVEVDADRLAQML
PPLGVGMQHEPIRLCGACYAEAPCHRIEWQYKSVWKCDRHELKILAKCPNCEAPFKIPALWEDKCCHRCRTPFAEMTKYQKIT
(SEQ ID NO: 76)

>WP_094343931.1
[*Nostoc* sp. 'Peltigera membranacea cyanobiont' 232]
MEENIDEKRQIWLTRVEPFDGESISHFLGRFRREKGNKFSAPSGLGDVAGLGVVLARWEKFYFNPFPTHQELDALATVVELDAE
RLRQMLPPEGVGMKHSPIRLCGACYAESVCHKIEWQFKKRVGCDRHLLRLLSKCPVCEKPFPVPALWMDGQCQRCFTSFAEMAE
HQKHY (SEQ ID NO: 77)

>WP_029636334.1
[*Scytonema hofmanni* UTEX 2349]
MIEAPDVKPWLFLIKPYEGESLSHFLGRFRRANHLSASGLGTLAGIGAIVARWERFHFNPRPSQQELEAIASVVEVDAQRLAQM
LPPAGVGMQHEPIRLCGACYAESPCHRIEWQYKSVWKCDRHQLKILAKCPNCQAPFKMPALWEDGCCHRCRMPFAEMAKLQKV
(SEQ ID NO: 78)

>WP_073629990.1
[*Scytonema* sp. HK-05]
MEIPAEQPRFFQVEPLEGESLSHFLGRFRRENYLTATQLGKLTGIGAVISRWEKFYLNPFPTPQELEALAAVVEVKVDRLIEML
PPKGVTMKPRPIRLCGACYQESPCHRVEWQFKDKLKCVSEAHPKDARHQLGLLTKCTNCETPFPIPADWVQGECPHCFLPFAKM
ARRQKRY (SEQ ID NO: 79)

>WP_072619870.1
[*Spirulina major* PCC 6313]
MNDWEIQPWLFVVEPYEGESLSHFLGRFRRENDLTPAGLGREAEIGAVVSRWEKFRLIPFPSQRELEKLAQVVQVDAARLRVML
PPDGVGMKMTPIRLCGACYREVRCHRMEWQYKTSDRCDKHPLRLLSECPNCGARFPIPSLWQDGWCTRCFTTFGEMAESQKPL
(SEQ ID NO: 80)

>BAQ60389.1
[*Geminocystis* sp. NIES-3708]
MLDTDINTWLLPIEPLEGESLSHFLGRVRRRNYLSASALGELAGIGGAITRWEKFRHYPFPSDEELTALGNLLGLELFQLKAML
PSEPMKLEPIRLCGACYGEIPSSSY (SEQ ID NO: 81)

>BAT55395.1
[*Nostoc* sp. NIES-3756]
MEKDTFPPKTEIRIHDNHEALPRLGYVEPYEGESISHYLGRLRRFKANSLPSGYSLGKIAGIGAVTTRWEKLYFNPFPSSEELE
ALGKLIGVPANRIYEMLPPKGVTMKPRPIRLCAACYAEVPCHRIEWQYKDKLKCNHHNLGLLTKCTNCETPFPIPADWVQGECP
HCFLPFAKMAKRQKPR (SEQ ID NO: 82)

>AFZ00422.1
[*Calothrix* sp. PCC 6303]
MAEDIYLPKREIISNKEINKGDEILPRLGFVEPYECESISHYLGRVRRFKANSLPSGYSLGKIAGIGAVTTRWEKLYLNPFPSE
TELEALAKVIEVEVERLRQMLPPKGMTMKPRPIRLCAACYAESPHHRIEWQFKDVMVCDRHQLPLSTKCKNCGTPFPIPADWVR
GECPHCCLSFTKMAKRQKSG (SEQ ID NO: 83)

TABLE 5-continued

Amino acid sequences of Representative CLUST.004377 Effector_C2 Proteins

\>AFZ58293.1
[Anabaena cylindrica PCC 7122]
MEVGEINPWLFQVEPYLGESLSHFLGRFRRANDLTTTGLGKAAGVGGAISRWEKFRFNPPPSRQQLEALAKVVGVDADRLEQML
PPAGVGMNLEPIRLCAACYVESPCHRIEWQFKVTQGCQHHHLSLLSECPNCGARFKVPALWVDGWCQRCFLPFGEMIEHQKRI
(SEQ ID NO: 84)

\>AFZ56184.1
[Anabaena cylindrica PCC 7122]
MAQNIFLSKTEIGIDEDDEIRPKLGYVEPYEEESISHYLGRLRRFKANSLPSGYSLGKIAGLGAMISRWEKLYFNPFPTLQELE
ALSSVVGVNADRLIEMLPSQGMTMKPRPIRLCGACYAESPCHRIEWQCKDRMKCDRHNLRLLIKCTNCETPFPIPADWVKGQCP
HCSLPFAKMAKRQRRD (SEQ ID NO: 85)

\>WP_066425687.1
[Anabaena sp. 4-3]
MNEDDEIRPKLGYVEPYEGESISHYLGRLRRFKANSLPSGYSLGKIAGLGAVTTRWEKLYFNPFPNRQELEALASVVGVSAERF
IEMLPPKGVTMKPRPIRLCAACYAEVPCHRIDWQFKDKMKCDRHNLRLLTKCTNCETPFPIPADWAQGECPHCSLSFAKMVKRQ
KLR (SEQ ID NO: 86)

TABLE 6

Amino acid sequences of Representative CLUST.004377 Effector C3 Proteins

\>OUC12056.1
[Alkalinema sp. CACIAM 70d]
MTQAKEWAEVLGEFQPDDDWLKAEIARLRKKTVMPLAQVSQLHDWLDGKRKSRQSCRIVGESRTGKSVACEAYFYRNKPQQEAG
KKKPIVPVVYVQPPQKCGPKELFKEIIEFLKHRATRGTVSDLRGRAIEVLQACGVEMLIIDEADRLKPETFADVRDIYDKLGIAV
VLVGTDRLDAVIKRDEQVYNRFRACHRFGKLSGEEFKKTIALWEQKILNLPVASNLISKDMLRILTTGTEGYIGRMDEILREAA
IRSLSFGYKKVEKKCLEEVAKEYK (SEQ ID NO: 87)

\>OBQ23775.1
[Anabaena sp. WA113]
MTDDAQAIAKQLGGVKPDEEWLQAEITHLTSKSIVPLQQVITLHDWLDGKRKARQSCRVVGESRTGKTVACDAYRYRHKPRQEM
GKTPIVPVVYIQPPSKCGAKDLFQEIIEYLKFKATRGTISDFRGRTMEVLKGCRVEMIIIDEADRIKPDTFADVRDIYDKLGIA
IVLVGTDRLEAVIKRDEQVYNRFRACHRFGKLAGKDFQDTVQAWEDKILKLPLPSNLISKDMLRILTSATEGYIGGLDEILREA
AIRSLSRGLKKIDKAVLQEVVQEFKL (SEQ ID NO: 88)

\>WP_011318170.1
[Anabaena variabilis ATCC 29413]
MTNEEIQQEIERLRQPDILNLEQVKRFSSWLDERRKLRKPGRAVGESGLGKTTASLFYTYQNRAAKIPNQNPVAPVLYVELIGS
SCSPSLLFKTIIETLKFKAKGGTENQLRERAWYLIKQCKVEMLIIDEAHRLQFKTLTDVTDLSDKVKIIPILVGTSSRLDALIS
KNEQVGGRFAAYFSFEQLSGANFIKTVKIWEQQILKLPEPSNLAENQEIITILQAKTAGQIRLLDQILRDAAVKALESGVNKID
KSLLNSIEGDYSLVAS (SEQ ID NO: 89)

\>WP_011318974.1
[Anabaena variabilis ATCC 29413]
MTDAKPLDFIQEPTREIQAHIERLSRAPYLELNQVKSCHTWMYELVISRMTGLLVGESRSGKTVTCKAFRNNYNNLRQGQEQRI
KPVVYIQISKNCGSRELFVKILKALNKPSNGTIADLRERTLDSLEIHQVEMLIIDEANHLKIETFSDVRHIYDEDSLKISVLLV
GTTSRLLAVVKRDEQVVNRFLEKFEIDKLEENQFKQMIQVWERDVLRLPEESKLASGESFKLLKQSTNKLIGRLDMILRKAAIR
SLLRGYKKVDQGVLKEIITATKF (SEQ ID NO: 90)

\>WP_011317998.1
[Anabaena variabilis ATCC 29413]
MTSKQAQAVAQQLGDIPVNDEKIQAEIQRLNRKSFIPLEQVQMLHDWLDGKRQSRQSGRVVGESRTGKTMGCDAYRLRHKPKQE
PGRPPTVPVAYIQIPQECGAKELFGVLLEHLKYQMTKGTVAEIRDRTLRVLKGCGVEMLIIDEADRLKPKTFAEVPDIFDKLEI
AVILVGTDRLDAVIKRDEQVYNRFRACHRFGKFSGDEFKKIVDIWEKKVLQLPVASNLSSKTMLKTLGETTGGYIGLLDMILRE
SAIRALKKGLRKVDLATLKEVTEEYK (SEQ ID NO: 91)

\>WP_044151374.1
[Aphanocapsa montana BDHKU210001]
MIALQDQEVQAHIERLRRDKTVALDSVKQAHTWLKRKRNARQCGRLTGDSRTGKTKTCESFLKLYGEPDLSGRVPIIPISYVHP
KQECTSRELFREILEQYGDDLPRGTVGDARSRTLKVLRACKTEMLMIDEADRLKPKTFADVRDIFDKLEISVILIGTKQRLDPA
VKKDEQVFNRFRSSYRIGTIPSNQLKTIVGLWERDILKLPVPSNLTSEAMLKELRKATGVSRKGYYIGLIDMVLREAAIRALEK
GQSKIELETLKEVAKEYS (SEQ ID NO: 92)

\>WP_019497299.1
[Calothrix sp. PCC 7103]
MADEYLRKWVQNLWGDDPIPEELMPQIERLITPSIVELDHIQKIHDWLDSLRLSKQCGRIVAPPRAGKSVTCDVYKLLNKPQKR
TGKRDIVPVLYMQVPGDCSAGELLTLILESLKYEATSGKLTDLRRRVQRLLKESKVEMLIIDEANFLKLNTFSEIARIYDLLKV
SIVLVGTDGLDNLIKKEPYIHDRFIECYRLQLVSEKKFSELVQIWEDDVLCLPVPSNLVKRETLIPLYQKTGGKIGLVDRVLRR
AAILSLRKGLSIIDKITLDEVLEWFE (SEQ ID NO: 93)

\>WP_012596234.1
[Cyanothece sp. PCC 8801]
MTDSSVIDKLAAEFGGFATPSPEIQAEIQRLSRQPYLEYEQVKNCHGWLYELVLSRMTGLLVGESRSGKTVTCKSFEKRYNKIK
TGNKKRIKPIVYIQSPQNCGAREFFTKILKALNKPTNGNVSDLRERTLDGLQIHECEMLIIDEANHLKQETFAEVRHVYDEEEL TABLE 6-continued Amino acid sequences of Representative CLUST.004377 Effector C3 Proteins NMAVLLVGTRHRLEAVVKRDEQVLNRFMEEYELDRLDDKEFKQLIKIWEQSVLCLPELSNLDTGDNLKLLKKTTRKLIGRLDMI
LRKSAIRALREGKQSISPELLKQVISSIKWSEGRKGNG (SEQ ID NO: 94)

>WP_066116122.1
[*Geminocystis* sp. NIES-3709]
MEAKAIAQELGNIEIPEEKLQMEIERLNSKTLVSLEQVAKLHEYFEGKRQSKQSCRVVGESRTGKTMACDSYRLRHKPIQKVGH
PPQVPVVYIQIPQDCGTKELFQGIIEYLKYQMTKGTIAEIRQRAIKVLQGCGVEMIIIDEADRFKPKTFAEVRDIFDRLNIPIV
LVGTDRLDTVIKRDEQVYNRFRSCYRFGKLSGADFQNTVNIWEKQVLKLPVASNLIQTKMLKLIAEATGGYIGLMDTILRESAI
RSLKRGLNKITFEILKEVTQEFK (SEQ ID NO: 95)

>WP_026148797.1
[*Leptolyngbya boryana* dg5]
MMANEAQSIAQTLGSLPLTSELLQAEIHRLTKKSVVSLSQVQSLHNWLEGKRQARQSCRVVGESRTGKTLACDAYRLRHKPTQQ
AGKPPIVPVVYIQVPQECGSKELFQIIIEHLKYQMVKGTVAEIRERTMRVLKGCGVEMLIIDEADRLKPKTFADVRDIFDKLEI
SVVLVGTDRLDAVIKRDEQVYNRFRACHRFGKLAGEEFRRTIEIWEKQILKLPVASNLTSKAALKILGETTAGYIGLLDMVLRE
AAIRALKQGKTKIDLEILKEVSTEYR (SEQ ID NO: 96)

>WP_036484424.1
[*Myxosarcina* sp. GI1]
MTEAKAIADKLGKIELDEEWVQKEIARLNRKSTVALEHIKELHDWLDGKRKSRRSCRIVGKSRTGKTVACEAYVMRNKLNKPPQ
ERQTKNQIPIEPVIMIMPPQKCGAKELFREIIECLKFRAVKGTISEFRSRAMDVLQKCQVEMLIIDEADRLKPETFSEVRDIYD
KLEIAVVLVGTERLDTAVKRDEQVENRFRANRRFGTLEGINFKKTVEIWEEKILKLPVASNLTNKTTWKILLIATEGFIGRLDE
ILREAAIASLSQGHKKVDPKILKEIAREYS (SEQ ID NO: 97)

>WP_012411918.1
[*Nostoc punctiforme* PCC 73102]
MTEAQAIAKQLGGVKPDDEWLQAEIARLKGKSIVPLQQVKTLHDWLDGKRKARQSCRVVGESRTGKTVACDAYRYRQKPQQEVG
RPPIVPVVYIQPPQKCGSKDLFKEMIEYLKFRATKGTVSDFRGRAMEVLKGCGVEMLIIDEADRLKPETFAEVRDIYDKLGIAV
VLVGTDRLEAVIKRDEQVYNRFRACHRFGKLSGKDFQDTVQAWEDRVLKLPVSSNLTSKDMLRILTSATEGYIGRLDEILRETA
IRSLSKGFKKIDKAVLQEVAKEYK (SEQ ID NO: 98)

>WP_010997774.1
[*Nostoc* sp. PCC 7120]
MTDAKAIAQQLGGVKPDEEWLQAEIARLKGKSIVPLQQVRSLHDWLDGKRKARQFCRVVGESRTGKTVACDAYRYRQKVQAEVG
RPPIVPVVYIQPPQKCGAKDLFQEIIEYLKFKATKGTVSDFRGRTMEVLKGCGVEMIIVDEADRLKPETFAEVRDIYDKLGIAV
VLVGTDRLEAVIKRDEQVYNRFRACHRFGKLSGKDFQDTVQAWEDKILKLPLPSNLISKDMLRILTSATEGYIGRLDEILREAA
IRSLSRGLKKIDKPVLQEVAQEYK (SEQ ID NO: 99)

>WP_094343930.1
[*Nostoc* sp. 'Peltigera membranacea cyanobiont' 232]
MTNAMSLAKQFGVIQELTPEIQAEIERLSRQPYLELDQVKRCHAWMYELVISRMTGLLLGESRCGKTVTCKAFANLYNKLRQTK
GQRMKPVVYIQVGKNCGSRDFFMKILKALNKPSNGTISDLRERTLDSLAIHQVEMLIIDEANHLKFETFSDVRHIYDDDELKIS
VLLVGTTSRLLAIVKRDEQVVNRFLEQFELDRLEDTQFKQMIQIWERDVLRLPEESKLASGDNLKILKQATKKLIGRLDMILRK
AAIRSLLRGQKQVDKDILKEVIAASKL (SEQ ID NO: 100)

>WP_029636336.1
[*Scytonema hofmanni* UTEX 2349]
MTEAQAIAKQLGGVKPDDEWLQAEIARLKGKSIVPLQQVKTLHDWLDGKRKARKSCRVVGESRTGKTVACDAYRYRHKPQQEAG
RPPTVPVVYIRPHQKCGPKDLFKKITEYLKYRVTKGTVSDFRDRTIEVLKGCGVEMLIIDEADRLKPETFADVRDIAEDLGIAV
VLVGTDRLDAVIKRDEQVLERFRAHLRFGKLSGEDFKNTVEMWEQMVLKLPVSSNLKSKEMLRILTSATEGYIGRLDEILREAA
IRSLSRGLKKIDKAVLQEVAKEYK (SEQ ID NO: 101)

>WP_073629992.1
[*Scytonema* sp. HK-05]
MAEDYLRKWVQNLWGDDPIPEELLPIIERLITPSVVELEHIQKIHDWLDSLRLSKQCGRIVAPPRAGKSVTCDVYKLLNKPQKR
TGKRDIVPVLYMQAPGDCSAGELLTLILESLKYDATSGKLTDLRRRVLRLLKESRVEMLVIDEANFLKLNTFSEIARIYDLLKI
SIVLVGTDGLDNLIKKERYIHDRFIECYKLPLVSENKFPEFVQIWEDEVLCLPVPSNLIKSETLKPLYQKTSGKIGLVDRVLRR
AAILSLRKGLKNIDKATLDEVLEWFE (SEQ ID NO: 102)

>WP_072622994.1
[*Spirulina major* PCC 6313]
MASAESKAKAEAVAQQLGNFEKTEEDLAKEIQRLRRRNVVQLEQVKQLHNWLEGKRRSRQCCRVVGESRTGKTIGCNAYRLRHK
PIQETGKPPIVPVVYIEPPQDCGSIDLFRAIIEYLKYKVQSREKVRELRSRAMKVLERCQVETLIIDEADRLKPKTFADVRDIF
DKRNISVVLVGTDRLDNVIKRDEQVHNRFRACYRFGKLTGTEFEQVVKIWERDILRLPIPSNLHAKNMLKILGQATGGYIGLLD
MILRETAVRALEKGLGKINLETLKEVAEEYS (SEQ ID NO: 103)

>BAQ60390.1
[*Geminocystis* sp. NIES-3708]
MTKAQSIAKELGDLGQDEQWLHQEICRLNRSSIVPLEHLKDLHNWLDEKRKARQSCRIVGESRTGKTIACESYKLRNKPSQKGQ
QTPSVPVVYIMPPAKCSAKDFFREIIEALRYRAVKGTVSDFRSRAMDVLKACDVEMLIVDEADRLKPDTFPEVRDISDKLEMLV
VLVGTDRLDAVIKRDEQVYNRFRSHRRFGKLTGEDFKETVSIWEKEVLNLPVASNLTKLDMFKIITKATGGYIGRLDELLREAA
IKSLSRGKKALKRIFYRR (SEQ ID NO: 104)

TABLE 6-continued

Amino acid sequences of Representative CLUST.004377 Effector C3 Proteins

>BAT55396.1
[Nostoc sp. NIES-3756]
MAQSQLVIQPNVETLAPQLELNNQLAKVVEIEEIFSNCFIPTDRACEYFRWLDELRILKQCGRVVGPRDVGKSRASVHYREEDR
KKVSYVRAWSASSSKRLFSQILKDINHAAPTGKREDLRPRLAGSLELFGIEQVIVDNADNLQREALLDLKQLFDESNVSVVLVG
GQELDKILHDCDLLTSFPTLYEFDTLEDDDFKKTLSTIEFDVLALPQASNLCEGITFEILVQSTGGRIGLLVKILTKAVLHSLK
NGFGRVDQNILEKIANRYGKRYIPPENRNKNS (SEQ ID NO: 105)

>ACV01083.1
[Cyanothece sp. PCC 8802]
MTQAQEIAQKLGDLNPDEQWLQMEIARLNRQSIVPLEHIRDLHEWLDGKRKARQSCRLVGESRTGKTVACEAYTLRNKPIQQGR
QTPIVPVVYIMPPTKCGSKDLFKEIIEYLRYKAVKGTVSEFRSRAMEVLKGCEVEMIIDEADRLKPDTFPDVRDINDKLEISV
VLVGNDRLDAVIKRDEQVYNRFRAHRRFGKLAGVEFKKTVAIWEEKVLKLPVASNLTSSALIKILVKATEGYIGRLDEILREAA
IKSLMKGHKRIEKEVLQEVAKEYS (SEQ ID NO: 106)

>AFZ00421.1
[Calothrix sp. PCC 6303]
MARSQLAIQSSVEVLVPQLDLNAQLAKVVEVEEIFSNYFIPTDRSSEYLRWLDELRILRQCGRVIGPRDVGKSRASLHYQGQDQ
KRISYVRAWSASSSKRLFSQILKDIKHAAPMGKRDDLRPRLAGSLEVFGFEQVIIDNAENLQKEALLDLKQLFDECHVPIVLIG
GQELDTILDEFDLLTCFPTLYEFDGLDENDFKKTLNTIEFDILALPEASNLSEGIIFELLAESTGARIGLLVKILTKAVLHSLK
NGFSKIDQNILEKIANRYGRRYIPPEKRNNK (SEQ ID NO: 107)

>AFZ56183.1
[Anabaena cylindrica PCC 7122]
MAQPQLATQSIVEVLAPRLDIKAQIAKTIDIEEIFRACFITTDRASECFRWLDELRILKQCGRIIGPRNVGKSRAALHYRDEDK
KRVSYVKAWSASSSKRLFSQILKDINHAAPTGKRQDLRPRLAGSLELFGLELVIIDNAENLQKEALLDLKQLFEECNVPIVLAG
GKELDDLLHDCDLLTNFPTLYEFERLEYDDFKKTLTTIELDVLSLPEASNLAEGNIFEILAVSTEARMGILIKILTKAVLHSLK
NGFHRVDESILEKIASRYGTKYIPLKNRNRD (SEQ ID NO: 108)

>WP_066425684.1
[Anabaena sp. 4-3]
MARSQLANQPIVEVLAPQLDLNAQIAKAIDIEEIFRNCFITTDRVSECFRWLDELRILKQCGRIIGPRNVGKSRAALHYRDEDK
KRISYVKAWSASSSKRIFSQILKDINHAAPTGKRQDLRPRLAGSLELFGLELVIIDNADNLQKEALIDLKQLFEECHVPIVLIG
GKELDNILQDCDLLTNFPTLYEFERLEYDDFRKTLSTIEDILSLPESSHLAEGNIFEILAVSTSGRMGILVKILTKAVLHSLK
NGFGRVDESILEKIASRYGTKYVPLENRNRNE (SEQ ID NO: 109)

TABLE 7

Nucleotide sequences of Representative CLUST.004377 Direct Repeats

CLUST.004377 Effector_A Protein

| Accession | Direct Repeat Nucleotide Sequence |
| --- | --- |
| OUC12050.1 (SEQ ID NO: 1) | ATCGCAACCAACTGTCCTGAAGAAGGGCGATTGAAAG (SEQ ID NO: 110) |
| OBQ23770.1 (SEQ ID NO: 2) | GTAACAACAACCCTCCTAGTACAGGGTGGGTTGAAAG (SEQ ID NO: 111) |
| WP_011318157.1 (SEQ ID NO: 3) | GTTTCAACGACCATCCCGGCTAGGGGCGGGTTGAAA (SEQ ID NO: 112) |
| WP_011318983.1 (SEQ ID NO: 4) | GTGACAATAGCCCTTCCCGTGTTGAGCGGGTTGAAAG (SEQ ID NO: 113) |
| WP_011318008.1 (SEQ ID NO: 5) | GTTTCAACACCCCTCCCGAAGTGGGGCGGGTTGAAAG (SEQ ID NO: 114) |
| WP_039730330.1 (SEQ ID NO: 6) | GGTCGCCAAAAGCATTTCAGGGCAGGGC (SEQ ID NO: 115) |
| WP_019497312.1 (SEQ ID NO: 7) | GTGCTGTAACCTAAGATGTCGCAAGGCGTTGAGCAG (SEQ ID NO: 116) |
| WP_012596241.1 (SEQ ID NO: 8) | GAGTTTCATCAACCCTCCTGATGTGGGATGGGTTGAAAG (SEQ ID NO: 117) |
| WP_012596246.1 (SEQ ID NO: 9) | GTTTCATACAGGTTTTTGACCTCCCATTGATTGAAAGA (SEQ ID NO: 118) |
| WP_066116114.1 (SEQ ID NO: 10) | GTTGAAATAAGAAAATACCTTCTCTAGGGATTGAAAG (SEQ ID NO: 119) |
| WP_017289534.1 (SEQ ID NO: 11) | GTTTCATCCAGGTTTGCGGCAAGGGGGCGATTGAAAG (SEQ ID NO: 120) |

TABLE 7-continued

Nucleotide sequences of Representative CLUST.004377 Direct Repeats

| CLUST.004377 Effector_A Protein Accession | Direct Repeat Nucleotide Sequence |
|---|---|
| WP_017289534.1 (SEQ ID NO: 11) | GTTTCATCCAGGTTTGCGGCAAGGGGCGATTGAAAG (SEQ ID NO: 120) |
| WP_017289534.1 (SEQ ID NO: 11) | GTTTCATCCAGGTTTGCGGCAAGGGGCGATTGAAAG (SEQ ID NO: 120) |
| WP_039730330.1 (SEQ ID NO: 6) | GGTCGCCAAAAGCATTTCAGGGCAGGGC (SEQ ID NO: 115) |
| WP_036484397.1 (SEQ ID NO: 12) | GTTTCAACGACCACTTTAAGATGGGTATGGTTGAAAG (SEQ ID NO: 121) |
| WP_012411901.1 (SEQ ID NO: 13) | GTGGCAACAACCCTCCAGGTACTGGGTGGGTTGAAAG (SEQ ID NO: 122) |
| BAB75312.1 (SEQ ID NO: 14) | CGTTGCAACCCTCCTTCCAGTAATGGGAGGGTTGAAAG (SEQ ID NO: 123) |
| WP_044521835.1 (SEQ ID NO: 15) | CGTTGCAACCCTCCTTCCAGTAATGGGAGGGTTGAAAG (SEQ ID NO: 123) |
| WP_094343940.1 (SEQ ID NO: 16) | GTTGCAATGACCCTTCCCGTGTTGAGCGGGTTGAAAG (SEQ ID NO: 124) |
| WP_029636312.1 (SEQ ID NO: 17) | GTGGCAACAACCTTCCAGGTACTAGGTGGGTTGAAAG (SEQ ID NO: 125) |
| WP_073629970.1 (SEQ ID NO: 18) | GTTTCAACAACCATCCCGGCTAGGGGTGGGTTGAAAG (SEQ ID NO: 126) |
| WP_072619878.1 (SEQ ID NO: 19) | GTTTCAATGACCATCCCACGTTGGGATGGATTGAAAGAG (SEQ ID NO: 127) |
| BAQ60380.1 (SEQ ID NO: 20) | GATTCTTCGTAAACTCAGAATGACA (SEQ ID NO: 128) |
| BAQ63841.1 (SEQ ID NO: 10) | GTTGCAGATGAATTTACTTCTCTGTGCGATCGAAAG (SEQ ID NO: 129) |
| BAT55382.1 (SEQ ID NO: 21) | GTTTCAACGACCATCCCGGCTAGGGGTGGGTTGAAAG (SEQ ID NO: 130) |
| ACV01094.1 (SEQ ID NO: 22) | GTTTCAACGACCATTCCCAACAGGGATGGGTTGAAAG (SEQ ID NO: 131) |
| AFZ00435.1 (SEQ ID NO: 23) | GTTTCAACTACCATCCCGACTAGGGGTGGGTTGAAAG (SEQ ID NO: 132) |
| AFZ58287.1 (SEQ ID NO: 24) | GTTTCAACACCCCTCCCGGAGTGGGGCGGGTTGAAAG (SEQ ID NO: 133) |
| AFZ56196.1 (SEQ ID NO: 25) | GTTTCAACTACCATCCCGACTAGGGGTGGGTTGAAAG (SEQ ID NO: 132) |
| ODH02164.1 (SEQ ID NO: 26) | GTTTCCAAAGCCCTCTCGTTAGGTGGTGGGTTGAAAGT (SEQ ID NO: 134) |
| WP_066425713.1 (SEQ ID NO: 27) | GTTTCAACGACCATCCCGGCTAGGGGTGGGTTGAAAG (SEQ ID NO: 130) |

TABLE 8

Nucleotide sequences of Representative CLUST.004377 Transposon End Internal Repeat Motifs

| CLUST.004377 Effector_A Protein Accession | Left Tnp End Motif | Right Tnp End Motif |
|---|---|---|
| WP_017289534.1 (SEQ ID NO: 11) | TCTAACAGATTGACTGTCG (SEQ ID NO: 135) | AATAACACTTTATTTGTCG (SEQ ID NO: 136) |

TABLE 8-continued

Nucleotide sequences of Representative CLUST.004377 Transposon End Internal Repeat Motifs

| CLUST.004377 Effector_A Protein Accession | Left Tnp End Motif | Right Tnp End Motif |
|---|---|---|
| ODH02164.1 (SEQ ID NO: 26) | ATTCGCAAATTCAATGTCG (SEQ ID NO: 137) | TTTGGACAATAATTCTTTAAAACTGGTTT (SEQ ID NO: 138) |
| ACV01094.1 (SEQ ID NO: 22) | AATGATAGAATAGCTGTAG (SEQ ID NO: 139) | GGCAGCAATACGGGATGCA (SEQ ID NO: 140) |
| WP_072619878.1 (SEQ ID NO: 19) | ATTGACTCATTAACTGACA (SEQ ID NO: 141) | CTTGACAAATTATTTGTCA (SEQ ID NO: 142) |
| WP_066425713.1 (SEQ ID NO: 27) | ATTCGCAAATTAAATGTCG (SEQ ID NO: 143) | GGTGCATCCGACTTGTAAGCG (SEQ ID NO: 144) |
| OBQ23770.1 (SEQ ID NO: 2) | AGTGACTAATTATATGTCA (SEQ ID NO: 145) | GAGAGTACATCGTTGACATA (SEQ ID NO: 146) |
| WP_012411901.1 (SEQ ID NO: 13) | AGTGACTAATTATATGTCG (SEQ ID NO: 147) | GAGAGCGCTACGTTGACATT (SEQ ID NO: 148) |
| WP_011318983.1 (SEQ ID NO: 4) | TTCGACAAATTAGCTGTCA (SEQ ID NO: 149) | GTAGTAAATGCTTGTTAT (SEQ ID NO: 150) |
| WP_011318157.1 (SEQ ID NO: 3) | TTCGACAAATTAGCTGTCA (SEQ ID NO: 149) | GTAGTAAATGCTTGTTAT (SEQ ID NO: 150) |
| BAQ63841.1 (SEQ ID NO: 10) | AGTAACAGATTATTTGTCG (SEQ ID NO: 151) | AGTAACAAATTATTTGTCA (SEQ ID NO: 152) |
| AFZ58287.1 (SEQ ID NO: 24) | GTTCGCAAATTAAATGTCG (SEQ ID NO: 153) | ATTCGCAAATTAAATGTCG (SEQ ID NO: 143) |
| BAQ60380.1 (SEQ ID NO: 20) | TAATCAACAATAAAACAT (SEQ ID NO: 154) | AGTGCCACATTAATTGTCA (SEQ ID NO: 155) |
| WP_011318008.1 (SEQ ID NO: 5) | AGCGACAAATAATTTGTCG (SEQ ID NO: 156) | GGCGCACTTCGTTCGGGAT (SEQ ID NO: 157) |
| AFZ00435.1 (SEQ ID NO: 23) | ATTCGCAAATTGAATGTCG (SEQ ID NO: 158) | GGAGCATCAGACTCTTAATTT (SEQ ID NO: 159) |
| WP_029636312.1 (SEQ ID NO: 17) | AGTGACTAATTATATGTCG (SEQ ID NO: 147) | GCAAGTCCTTTTATCCGCT (SEQ ID NO: 160) |
| AFZ56196.1 (SEQ ID NO: 25) | TTTAACAAATTAAGTGTCA (SEQ ID NO: 161) | GATCAGTAGGTCGTGGGTTTAA (SEQ ID NO: 162) |
| BAB75312.1 (SEQ ID NO: 14) | AGTGACTAATTATTTGTCA (SEQ ID NO: 163) | AATGACAATAATTTGTCACAAA (SEQ ID NO: 164) |
| WP_073629970.1 (SEQ ID NO: 18) | AATAACTAATTAAATGTCG (SEQ ID NO: 165) | AATGACAAATTGTTTGTCG (SEQ ID NO: 166) |

TABLE 9

Non-coding Transposon End Sequences of Representative CLUST.004377 Systems

>Left Transposon End for OBQ23770.1
TGATATTTATTTGTTCTATCACATCTTCATAAATATCTGCCATTGTCAAAGTTAAGTTAACTGAATCTAAATGTAATTTATCAT
CTTTTCCTAATACTTCCGTTGACCAATTTCCTTGATCATCTTGACGACAAACCTCCACTTTTTATTTGATTTTGCTAAACTAGAA
CATATTCCTTTAGACTGTCTATAGTTTGATAATTAATGCGTTTTTCACGTTTGTCTATTGTTGCTGTGGAATTAGATAAACTTT
CAGAAATGTTGAATGTCGTTACAAAACTTTACATATTTAAGTATAGTAGTATTATCAAGGGTAAAAATGTCAACATTTCATAAT
ATCTTCCATCCAATGAACATAACTGATTTGTTGACACATACAAGATTGAAGATAGCGGAATTTATCTAACATCTTTTCACCCCA
TTCTTTCGGAACAGATAAATGTACAGTGACTAATTATATGTCATCGTGACAAATTAATGTCATCTTATAAATCCTTGCTGTAGA
AGGATTTTAGCAATTTAACGATATTATACTTCAATCCAGTTAGTGACAAAATAAATGTCGTTTCCCATGATTGTGACAAATTAA
CTGTCGCGTTACCGATTAAAAAAGTTTTTGTATATTTTCATAATGACAAATTGACTGTCGCTTTCCAGTAAGCTAGAATAACA
TCATGTTTTTATAAAATCTGTTTGATTT (SEQ ID NO: 167)

>Right Transposon End for OBQ23770.1
AGGTAAAATGGTGTGCGATCGCCCAACACAGAATTAGGTAACAACAACCCACCCTATGGTGGGTTGAAAGGTTATCATATTCTT
ATAAAAGAGGGTTGAAAGAGAGTACATCGTTGACATATCGCTCTGATATATCAATAAATGACATTAATTTGTCACTACCATTA
AAACGACAACAATTTGTCCTAACGACACTAAATTGTCACCGACGACATATAATTAGTCACTGTACAAAAAGTATGGACGGTATT
GGACTCGAACCAACGACCCCATCGATGTCAACGATGTACTCTAACCACCTGAGCTAACCGTCCTTAATCCCATAGACTAATAAC TABLE 9-continued Non-coding Transposon End Sequences of Representative CLUST.004377 Systems GTATCACATAAAATATAATTTGTCAATCCCTAAAATCCAAATTTTATTCTACATATATCTAGTCAACTGTACCCGATAGCGATC
CTTTTTTGTCACCGCAATTTCCCCAACTTCCAACCGACCTTTTCCCCGAATAGCGATTAAATCCCCTGTTTTCACTTGAG
(SEQ ID NO: 168)

>Left Transposon End for BAT55382.1
AAAAATGATGCAGTTATGAATTTTTCGCTTCTTTGTCTATAGCTTTACACAATTTCTTGGCTTGGGTGAATTTTTGAGCAACAA
CTTAGTTTTTCTGTGGTATCGGGGTGCAAATAAGTAATTCAAGCTCTAGTTAACTAACAAAACTCAACTACGCGAAGACGGAAA
AAACACAGAATAAGTAAGGATAAGTCTACAAGGTTATCTGTTCTTGCTTCGCCATCACCAAAAAAGACCGCCGCACCCCTTCAA
TTTCGCGTGGAGCCAACTGTAGTGCATATCGCCTAGTTGTTTCTGAAGTTTTGGACAATAATTCTTTAAAACTGGATTGATGGC
TGAAAGCTAGGAAATACGTAAATTATGCGTTTAGCACTGTCAAATGGACAATAATTCTTTAAAACTGACAATAATTATTTAAAG
TACATATTGTACATTCGCACATTATATGTCGCAATTTGCAAACAACGACATTAGACGACATTAGCATCTTGAGCATCTAAAACG
CTTATCGTATAAAGCTTTCAGGAAATTGTTAATTAAAAACGTTAAATTCCTGACTTCGCACATTGTATGTCGCTAACATTAAAG
CTCGCAAATTAATGTCGTTAATCTAAATTTTGTCACATTGCAAATTCAATGTCGCATTTTCTTCAGTTAATGGTACATTAATAC
TACCAATAACTACATTCTCCTCGCTTAA (SEQ ID NO: 169)

>Right Transposon End for BAT55382.1
AGTAAGAAGAATAGAAGTAATTTCCTGAAATCAACTATATTTGGACATATTTTAGGAATATAACTAAATTATGGGAGGGTTGAA
AGGAGCGCTGCGATCAAACAAATGTTAAGGTAAAATAATTCGTCTGTAGCAAATACCACAGTTAATGAGTAAGCCATACGACGT
TAATTTGCGAAAAACTAATATGATTGAATTAACGACGCGAATTAGCGAAAGTAATGTTAATTACCTAAAAACGACATCAATTTG
CGAAAAGCGACAAATAATGTGCGAATGTACACATATGGAGAATAGGGAACTCGAATCCCTGACCTCTGCGGTGCGATCGCAGCG
CTCTACCAACTGAGCTAATTCCCCTGACTTTGTTGAGTGTTCAGTTAATCACACTCGTCCATCATAGAGTATTTTAACATTCAG
TTAGGGATGGCTGAGATTTGTTGCCAGAAAAAACTTCTTGTACTCGCTCTAGTTCTAATTCGCTCAGATAATCCACAGTC
(SEQ ID NO: 170)

>Left Transposon End for WP_029636312.1
GTGTTAATTTACTTACCTGAGATTAACAAACATTCTTTGAGAATAATCACAAAAAATGTAAAGACTAAATAAAAGCAGTCACCT
ATAAGTAAATGACCTATGGGCGTAACCCAATAATGTCTTCAAGCACAAGTTCCAACTGGTAACTTGCAGTATTAATACTTAAAT
ATTTTTTTGTATTCAAAAAAATATAAACTAAACTTAATAAAAATTAACTTTACTTATTGTTAACAATAATGAAGGAATTCTTGA
TAGATGTTTTATTGTTTTTGAGATTTAAAATGCGATCGCTCGTAATTATATTTGATATAAAGTATAATTTGACACAGTAACA
AAAATCTACCTACCCTCGTAGAGACGTTCCGCCGGAACGTCTTTACATTTATTATGTGTTGCCCAAAACCATTGTAGAGAGGTA
GCATTGCTACGTCTCTACGTGTACAGTGACTAATTATATGTCGTTGTGACAAATTATTGTCATCAGTAAAATCCTTATACAGTA
TAGATTATAGCGCTTTGGCAGTTTTAGCATAACCTCTTTGCAGTGACAAAATAGATGTCGTTGTCCGTGATTGTGACAAATTAG
CTGTCGCTTTGCAAGATAGGAAAAAGCTTTTGTGTATTTTCATAATGACAAATTGACTGTCGCTTTGTATATAGATAGAATAAC
AATATGTTTTTATAAAAAGTTTTATAT (SEQ ID NO: 171)

>Right Transposon End for WP_029636312.1
AATCTTTTAAACCGAGATTAGTTTTGGGTTTCAGTAACTATTAAACTTAGGGGTGGGTTGAAAGCAAGTCCTTTTATCCGCTTG
TTTTAATTGCTTTGTATAATAATTGCAGAGCATATTATATTGATGACATTTAATTTGTCATCAATTAATTAAGCAACGCTGATG
GGTCACGACGACAATTAAATAGTCACAATGACATTAATCTGTCACCGACGACAGATAATTTGTCACTGTACACTACGCCTTTTG
TGGAGATGTCTAATAAACTAAAAATTTTTGATAGTGCGGATAAAAGGACTTGAACCTTCACTCCTTTCGGAACTAGAACCTAAA
TCTAGCGCGTCTGCCAATTTCGCCATATCCGCATCAGTTTCCTATATTACCATAACGAATTATCTGTGGCAATAGGGATTCGGG
ACTGGGACAAGGAGGAATTCCCAATGCCCCATGCCCCATGCCCAATGCCCCATGCCCAATGCCCCATGCCCCATGCCCAA
(SEQ ID NO: 172)

>Left Transposon End for WP_073629970.1
ATAAAATACCCAAAATCTTATTGATCTCCTTAATATAATAATTATTCAAATCAATAAACACATCACAGCCTTCTAACTTCAAAA
ACTTCCAAATATCCCCCGTTGTTACTGCACCATAAATAGTTGTCGAATAACTAATTAAATGTCGTCTTAACAAATTAATGTCGC
TCAAAACGTAAAGGCTATAATCGTTACTAAGCAAGGATTATAGCCTTTTTGATTTCTATTTAGCATTCCTAAATATTTAACTAA
TTAAACGTCGTAATTTGTAAATATAACAAAATAAGTGTCGTTTTTTCAAAAAATCTCTTTCCAAAGTTTTTAACGGCTCATAAC
AAAATAAGTGTCGTCTTTTGGAAGTGAGTAAAAAATCTAAAATTACGTGTCGCTTTTTGGAATAAAGTAGTAGTATATTTACTA
GGTAATAGTAATTATGTACGAATAAGGTGTTACGCATTTAATTTTTTTGCCCAAAAGCCTTGCAGCAAGGACTTTAGGCTGCAA
AATATTACATTTAGATGCGCGTCAGCTTACAAACATAGTTGTACTCAAGTCTTCTTATTTCTCTCTACTTGCAAAGTCATTCCT
CATATTGCGTTAAAGGTTGATGTGAGTTGAGGCTGTATACTTTGCTTTTTCGCTCTTAGACTTGCTGTACCGTATTGGCTAACC
AACTAGTTTCAAGCGATGAAGTTTGTTT (SEQ ID NO: 173)

>Right Transposon End for WP_073629970.1
GTCAAGTTTGCTTGTGAGGGTTGAAAGGAATGTCACCTTCCCAATACTAGAAGAGTGTCAAAAGCTATGCTGGCTAATGGAAGG
TTGAAATTAATCGCTATTTTTTTGCAAAGAAAAGATTCTACCAGTTATAAAAAAGCAAGAGTGACAAACAATTAGTCGTTCAAA
CAAATGACAAATTGTTTGTCGCTCTAAAGTATCCTAGATTACTTGACTATACGAGTTTATTTTTTAGGGATTAAGCTCGGGGAA
AAGTTTGTGATCTACTGACATTCAAGTAACACTGACAAATAATTTGTCACTGTACAATACTCAATAAGAGTCGGCTACATTAAA
TGACTATAAGACAAATAATTTGTCGCTTTACCACTTTTGACAAATAATTTGTCGCCACGGTCAAATAATTTGTCGCTCTACATT
TGAAAGCGGGCGATGGGACTCGAACCCACGACGTTCACCTTGGGAAGGTGACATTCTACCACTGAATTACACCCGCAAAT
(SEQ ID NO: 174)

>Left Transposon End for WP_011318157.1
GTGTTATGCAGCAATATGAGTAGCCGTCATGAACTGCGTACACCAAAACCTATGAAAAGGCATCAAAGGATTTTCAAATCAGA
ACAACTGGAAAAAAACAACTATGTTAAATATTGTAAAAACAATAAGATTGAGTTCGTAGTAAGGACTTTAATCCTTGTAAAGTT
CTCACTACAAGTCTTTAATTATCCACCCTGTTCTACTCAGTTCATTTAAGGCTAACAACTTAGACGCGGTGGTAAGTTGAAGCC
ATCTCTCCACTGAACCATATTGATATATAATGTAGAGCGACACATTATTTGACCACTTCGACAAATTAGCTGTCACAGCATTAT
CTTGAACGAAAATCCATATATATCAATACTTTCTAGCAATGAAAGCTAAATCAAGCTCATTCAGTCTTGGACGACAAATTACAT
GACTTTTTTAAAAGTCCGCGACTTATTAGATGACAATTATTAATTTTGCGAAAAATTACGTGTCAATTATTCGCAGTTTCATAG
TAGTATAAATGTACCCAATAATCAAAGACAAATCACATCTATGAATTATTTAGATGTAGATAACCAGTTTGAACTGGAAGATGA
AGATGACTTTCTTTTGGATGATGAGGATGCAGACATACTCGATTTTTCAATTGAAGTTGAGTCATTGAGTAATGATGGAAACTC
TGTAGCAGAAGACAAAATTAGTAGAGTTT (SEQ ID NO: 175)

>Right Transposon End for WP_011318157.1
AAGTTACAGTTATTAGGTGGGTTGAAAGTAGTAAATGCTTGTTATTTTAGGTTTAGACCTCAAAAAAAATTACAGATATAACTTC
GAGAGCTAATGTAACCAAAAATAATACTTAGCCCAGTGGAGTGCTACTATGTAACTGCATAGAGGAAAAGACGATGACAAATAA TABLE 9-continued Non-coding Transposon End Sequences of Representative CLUST.004377 Systems TTTGTCGCTATGATATTTATGACAAATATTTTGTCGCTACAGACAAATAATATGTCGCTCTACATATAACCAACAAAAAAGGCT
TGGTCGGGCCAAGCCTTTATGTATACCAAGCATTTACTACACCAAGCTTAATTTAAACCCTCTAGCACTTTAGTTCATCTGTCT
TTAGACTGTATGCAAATTCTTTCAAACCTGGTATGAACTGGCATATTTACATACAAAAAAGGCTTGGTTCAACACCAAACCTCG
ATAATTGCTGTGCTTAACAACGTACTAAATTAATTTAAACTGGATTGTTGTCCTTATCATCTTCCTTTAGTATGTGTTGC
(SEQ ID NO: 176)

>Left Transposon End for WP_072619878.1
TTCGGGAGTTTCTGCAAATCCTGGAGTGGGTGGCGACGAAGAAGGGGAAGCGGGTGGTCTATGTTGAGCGCTGGTTCCCTTCGA
GCAAGACCTGTTCAAGTTGTGGTCATATTTTGGAGCATCTGGATTTAGAGACTCGCCATTGGCGGTGTCCCAGTTGCTCGACAG
AGAATGACCGGGATGAGAATGCGGCGATGAATATTAAAGTGGCTGGGGCTTCAGCCATTGGGTTAGGTGATGTCAGACAGGCGT
TGCCTGCTATTGCTGTTTGATCCCAGAATCCCCCGTTTTCTAAACGGGGGAGTAAGTCAAAGGGTTCTTAACGTTGTACAGTCC
CTCGTTGGCGTGGTCGATCAGTTCTGAACTGTCTGCCCCCACACTGCCCCCAAAATCTTGATTTTAATGACATTTTTTTTCCAA
TTTTAGGGTGTGGGTGTCGATTGACTCATTAACTGACATCTTGACAAATTATTTGTCATTGCTATAGACAAGCCTGCAACCCTT
ACTATACATAAGGTTGTGGGCTTTTTGCATTGGAAATTTACTCAAAAGCAAAATTGACAAATTAGGTGTCGTATATTAGGAGTT
TGCCAAAATATGTGTCGCTTTTCATTTAGTCCAGATTTTCTGGCTTTTTGACACATTCTGTGTCGCTCAGGGTAAAATAACAAC
ATGTTTGTATTAAACACATTTGTTGTAA (SEQ ID NO: 177)

>Right Transposon End for WP_072619878.1
GTTTGCCTCGGAGATGTTTGCCCTAGTGAGATTGGTTGCTGAAACCATCCCAAGGTGGGATTAGGTTGAAAGAGTAATACAAGA
ATTGGGTGGATTGAAAGCAAGTCCCACCGTCCCCTACTTTAGTGCAATGCAAGATTACACAACAAACTTGCTCTGAATGTATGG
AAGGTTCGTAAAAGTGGTGACAAATAATTTGTCAAGATGACATCAATTTGACAACGATGACAAATAATTAGTCAATCGACATGT
GGGCAACACCGTCAGAACAACTCAGAAAACTCTGAAACGATGGGGGTGGTGGGACTTGAACCCACACGTCTTTTTACGGACAAC
GGATTTTAAGTCCGCAGCGTCTACCATTCCGCCACACCCCCAAGAGCAGTGACAGGGTTCTAGTTTAGCAGCAAATGGCGGCCA
CTGCATGGAACAGAACCCTCAGAAAATCTAATCAATCTGCCTCTTGCGCTCCGATGGGTTGAATTGTTTATGATGGGAGG
(SEQ ID NO: 178)

>Left Transposon End for WP_011318983.1
AACAGATTAAAAATTTAATAATTACCGTAATCTTTAGCTAACTATAATTATTTACAACTATGCAGACACAATAACCGCAATAAA
GGTTCCTTTTCCTCAAAAAAGAGCTTAGTAAAAATTGCCTTATATAGCAGATGTTATTTAAAATACCTGTGTGTTATGCAGC
AATATGAGTAGCCGTCATGAACTGCGTACACCAAAACCTATGAAAAAGGCATCAAAGGATTTTCAAATCAGAACAACTGGAAAA
AAACAACTATGTTAAATATTGTAAAAACAATAAGATTGAGTTCGTAGTAAGGACTTTAATCCTTGTAAAGTTCTCACTACAAGT
CTTTAATTATCCACCCTGTTCTACTCAGTTCATTTAAGGCTAACAACTTAGACGCGGTGGTAAGTTGAAGCCATCTCTCCACTG
AACCATATTGATATATAATGTAGAGCGACACATTATTTGACCACTTCGACAAATTAGCTGTCACAGCATTATCTTGAACGAAAA
TCCATATATATCAATACTTTCTAGCAATGAAAGCTAAATCAAGCTCATTCAGTCTTGGACGACAAATTACATGACTTTTTTAAA
AGTCCGCGACTTATTAGATGACAATTATTAATTTTGCGAAAAATTACGTGTCAATTATTCGCAGTTTCATAGTAGTATAAATGT
ACCCAATAATCAAAGACAAATCACATCT (SEQ ID NO: 179)

>Right Transposon End for WP_011318983.1
AAGTTACAGTTATTAGGTGGGTTGAAAGTAGTAAATGCTTGTTATTTTAGGTTTAGACCTCAAAAAAATTACAGATATAACTTC
GAGAGCTAATGTAACCAAAAATAATACTTAGCCCAGTGGAGTGCTACTATGTAACTGCATAGAGGAAAAGACGATGACAAATAA
TTTGTCGCTATGATATTTATGACAAATATTTTGTCGCTACAGACAAATAATATGTCGCTCTACATATAACCAACAAAAAAGGCT
TGGTCGGGCCAAGCCTTTATGTATACCAAGCATTTACTACACCAAGCTTAATTTAAACCCTCTAGCACTTTAGTTCATCTGTCT
TTAGACTGTATGCAAATTCTTTCAAACCTGGTATGAACTGGCATATTTACATACAAAAAAGGCTTGGTTCAACACCAAACCTCG
ATAATTGCTGTGCTTAACAACGTACTAAATTAATTTAAACTGGATTGTTGTCCTTATCATCTTCCTTTAGTATGTGTTGC
(SEQ ID NO: 176)

>Left Transposon End for AFZ58287.1
ACTGCGCCAGCAATTCACCAAACTGCCGCAATTTAATCAAACAGGTGTTGGGATCATCTGCAAAATATCGCTCGGCTAGAGTCG
CTAATCGAACCAGTTGTATGTCGTGGACTGCAAGGAATGAGAAGTTTAATGACTCTGGCATACTGGCTTTTGAGAGAATCTGTC
CAGTTAGTTTCAAGTTGTCTCAAATAACCTAATCAAGACTCCTCTTGTTGTAGGTTGCCCAAATTAACTTAGTCATAGTCTAGC
AGTAATTCAAGTCTCATAATATACATCTAACTAAAAATTTGGAAAATATTATTAATCTGTGAATATATAGCAATTCCCAAGCTC
ATGAAATACACCCCACCCGTGCTGTCGCGCACCGTAGCCTTACCAAGGGGAGGGTTGGGGAGGGGTAATTTTGTATCTAACTAG
AGTGAGAAAGGCTATTGTACGTTCGCAAATTAAATGTCGCTTTTCGCAAATTAGTGTCGCAACTGCTTTTAAGGACTAAAACCT
TTATTCTATAAGCATCATAAGCTATTTACCCCTACAAAAGACTAAGTTACCTAATTCGCATATTGTATGTCGTAAAACCTGGTT
TCGCAAATTAAATGTCGTTTGTTAAGAATTTGGTATTTTGCAAATTAGATGTCGCATTTTTGAGTAATTCATGGTACATTAGTA
CCTTAATTATTCATGAGTGGGTTTCACT (SEQ ID NO: 180)

>Right Transposon End for AFZ58287.1
ATAACTAGAATTTACTTGCGTTAACCATTAAAATAAAATGGTTGCAAAATAGAAATGATCATGGGAGGGTTGAAAGGAGTGCTG
CGATCGAACACATATCAATAATCCAATAATGCCCTTGCAGCAATAATTTATTGTATAGTAAATGTTAAGTTCATGCGACATTAA
TTTGCGAAAACTTAGAATAATTAAATTGACTCTGAAAAACAACCACCACGACGCATTAATTTGCGAATAACGACACTAAATTGCGA
AAAGCGACATTTAATTTGCGAATGTACATATATAATGGAGAATAGGAGACTCGAACCCCTGACCTCTGCGGTGCGATCGCAGCA
CTCTACCAACTGAGCTAATTCCCCTTGCTAGTCTCAAGTTACTAACTCAGACAGCCGTACTATATGTTAACACTCAGGCAGGGT
AGTTTTCACCTCTTTTTGCAAAAAAACTTCCTGTACCCGGTCTAATTCCAAATCAGTCAGATAATCTACTGTCCAGTTAG
(SEQ ID NO: 181)

>Left Transposon End for WP_066116114.1
TCTCATCCAAAAACCTTAAAGATAGTTCAAGAAAAAATAGAAATGAGTGGGAGATAAAAATAAGCAAAGATACGATAAAAAGA
TTAGCAAAAAAAAGGGCATGGGGTGGTATCGGTTCAAGAAAAGGGTAAAAGGGAAGTATGCCCTGAATTATACCAACAAAAA
AAGAGACAATTAGAGCAACTAAAAAGAGCAGAAAATGAAGGAAAAATAGATATATATTATGGTGATGAAAGTGGATTTAGTTTA
GTACCTTGTTTACCTTATGGATGCAAGAAAAAGGGAGAAAAATAGAAAGAGAAAGTAGCCTAAGTAAAAAGATTAAATGTGTTA
GGATTTATGAAAAAAAATAATGAGTTAGAAAGCTATGTATTTGAGTCATCAATCAATAGTGATGTCGTGATAGCTTGTATAGAT
AACTTGAGTAAAAAAATAAAGAAGGAAACAGTATTAGTAATGGATAATGCCTCGATTCACCAAAATAAAAAATTCTGGAATAAA
GAAGAAGAATGGGAAAAAAAGGATTAAAAATATTCTTTCTACCACCCTATTCACCACAATTAAACAAAATAGAAATACTGTGG
AGATTTATGAAATATAAATGGTTAGAGAACTCCTGTTATAAAAGTTATTTAGATTTAGTAAAAGGAGTAGAAAATATTCTTATA
AACTTTGGTTCAAAATATACAATTAATT (SEQ ID NO: 182)

TABLE 9-continued

Non-coding Transposon End Sequences of Representative CLUST.004377 Systems

>Right Transposon End for WP_066116114.1
GATCATTATAAGACTGCAAAATACAAAAATAGCTATAATAGATATATATGTGGATTGAAAGAGGTCACGAGTTCAATCATAAAA
TGACATTTAATTTGTTAACGATGATTCAGCGACAGGAATTTGTTAAGACGACAATTAATTCGTTAAGATGACAGATAAAATGTT
ATTCGACAATACCTGTAATTTACCATTGCAAGGACATTCACACGAAAGCCTTTGACGAGGATTGAACTCGTGACCTCACCCTTA
CCAAGGGTGTGCTCTACCACTGAGCTACAAAGGCAGTGGGCCGAGCTGGATTTGAACCAGCGTAGGCATAGCCAGCGGATTTAC
AGTCCGCCCCCATTAACCACTCGGGCATCGACCCATTTGTTTTCACATTTACTAATTATAGCTCATCTTTTTTTTTAATGCCAA
CTTTTTTGTTTAATTTTTATCCAGTTTGCCCAATGCGAGGTTCTGTTCCTGCTATAATTCGATCGATATTAGTACGATGA
(SEQ ID NO: 183)

>Left Transposon End for WP_036484397.1
ACTATTTGAAACAGCCAATTACTTTTATCTTCATAAGCTACGGTTGAATCTATAACTTCTAAAAACTCCGTGTCGTAGAAATAG
AGAAAATCATCAATTAACTTTTCTTGCTTTACTCTCCCCGTAGTGTTGGTATAACCTCTTTCAATAAAAAATTTAATTGCCGAG
CGAAGCTATTATTGCCAACATAGAAATTACAGCAGCAATACCAATGACAATCAAAGCGAAAATCGCCAAGCCATATTGCAGCGT
GTATAGCTTGCGTAATTGGCTCATTGCGTTCATTAGGTTATCAATATCGTTACCTGAAGTTTTGACAATGCGCTGAAAGCCGCC
AGCCGCTAGTACATTCCAGCGTCCTATCAACAGAAGTAGAATTCCCTGAAGATGCCACTAATTCCACTATTAATAGGAACCTC
TTCTTTTTGAATAAATATGTACGGTGACTAATTATTTGACATAATGACAAATTGTTGTCATGCAATTCAAAGCTTTATATGCTA
GGCATCATAGCATTTTTATTATAATATTTGATTGACTTATATAATGACAAACAAAATGTCGTTTGTTTGCAAAATGACTAATTA
GCTGTCGTTTATTGAAAATTCAGTTTTAAAGAAAAGTGACAAGATCTGTGTCACTTTTTATTTAAATATAGAATTACATTATG
TGTTTTTAAAAAAACTAATTTACTAAA (SEQ ID NO: 184)

>Right Transposon End for WP_036484397.1
CGTAATTCTTAGGAGTGGGTGCAAAATTTAACCCCAGGTTTCAATGACCATTTTGTGATGGCTTGGGTTGAAAGATAAAGGCTT
AGTCATTGTTATTGATGAAGCGGAAGTGCCAACGACCACAGCCAAATTTTAATTCTCAATAACTATCGTCTAATTCTCGCTAAG
AAACTGAAAGTAATTTTAAAGTCTTGTTCTTTGGTTACTCCAAGTAATTTATTACTTTTAGGCGATCGCCTTGCTTGCCGAGTT
TAATTTGTATCAGCAATTGCTGTATACAGTCTAAAACCAAGTAAATTCGATTAATTATTTTTTGTGCGACGCAGTAAGTCGCTT
GATTTAAGTGAAAATTTCATGACTGAGGTTATGGATTTCTAGTAGATTTCATCCTACTATTCCCACGTAAAGGAGTCTCGTACT
CTGGTCACATTGAAAGTAAATAATGAACTCAATGGAATGCAGACCATGAATGTATCCGAAGGTGGATAACCTCTATCCAG
(SEQ ID NO: 185)

>Left Transposon End for WP_066425713.1
CGAGGACAATACCGGTATATTTCAGCAAGTCTGCACTCAAAATACTGGGGTTGGGCTGTCGAAGCGCGATCGCTGTCAAAAGTT
CTGGAATTTCACAATTCTGCTTCCTTTTATTTTCTTGTATTTATAAGCACATAAGTAAAAATAAGTATTCTATGTATACCTAGT
GATATAAGAATACACATATTTAACAAGATATATGAATAAAATTTTGATAAATTTTCTGTAAAAACAGTGAATATACTTAATTTT
TAATTAAATTTTCCAAATTCAGGACTTTCAAGATATTGACATTTCTGTGGTTAGTATTATACCGTCCCAATATTCAGATTCCAA
AACATTAGTTTCTCTTCCATTCGCAAATTGAGGAAGCACAGACGGCACAAACCGATAATTATCAGAGTCAAAAATCGACAAAAG
GATGATTGAAAAGTGTACATTCGCAAATTAAATGTCGCTTTTCGCAAACAATGTCGCAATCGTGTATTGAATGGCTGAAAGCTACA
TCGTGTAAATATTATAGGTCATTTATCTCTAAGACAGGCTAATTTGCTTGTTTCGCATATTTATATGTCGCATAATCACGTTTTT
GCAAATTAAATGTCGTTTGTTAAAGTTGGTGACTTTTGCAAATTAAATGTCGTATTCTTTATGAATATATGGTACATTAGTACC
TTAATTACTCATGAGTGGGTTTCACTCT (SEQ ID NO: 186)

>Right Transposon End for WP_066425713.1
ACTTAGATAATCAATCCTAGAAAAAACGCTCTTAGTTTATCCGTCTTTGCGCTACAAAAATCTTGTCAAATGGGGTAGGGTTGA
AAGGTGCATCCGACTTGTAAGCGTATTAAACCTTAAAAACATAAAACAAAAAATTAAAACTTATTTAATTCTGATTTTTTATAT
GTAAGAATTAGGTTCTGCACAACCATCAATTCACTTGTTGAAGTAATATTATTGTGTTAACACTTGCTTGTAAGCAACACTGTA
ACAATCTAGAAGGAAAAAACGACATTAATGTGCGAAAACCTAGCATAACTAAATTGATTATAAAAAATAGCCGAAGCGACATCA
ATTTGAGAAAACCGACACTAAATTGCGAAAAGCGACATTTAATTTGCGAATGTACAGATTGAAAAGCCAGCAGTCGGATTTGAA
CCGACGACCTTCCGATTACAAGTCGGATGCACTACCACTGTGCTATGCTGGCAAATTAGGTGATGCGTTTGAATCATTCA
(SEQ ID NO: 187)

>Left Transposon End for ACV01094.1
TTTCTAGTAAGGTTTCTAGCGCGATAGAACAGCCGTGGATATCACTGATGGCTAGTGTTCTCATAGCTTTGCTTTTGTTTTCT
ATGATGCCTTTGATCCTATCTTGACTAGGTTAAGGTTTATTTAAGACAGAGAAACTATAGTAAAATTTTTAAGGCTAAGGTAAA
TCTTTGAACGACTGCTTCACCGCTTAAAATGGCATCCTCTCGATATTGAGTCATCGAACCATCTTGGCGATAAACAAACGCTTG
ACGATTAATGCGATCGATTAACCATCCTAATTTAACCCCATTGTTTCTATATTCTTGCATTTTTTGTTTAAGTTTACTTAAACT
ATCAGATTTAGAACGAATTTCAATAACAAAATCTGGCGCAAGATTGAAAAATTCATCCTCTTCCTCATCCCATCCTTGAGGTAA
TCTTTCCTTAGCAATTGTACAGTGACACATTATTTGACATGATGACAAATTAGTGTCATTCTTTAAACCCTTTACTCAATAAGG
CCTACAGCTATTCTATCATTATTTATAATCGTTCAGCTAAGTGACAAATTAAGCGTCGCTTTTTGCTTTTATGACAAATTAATT
GTCGTTTTTCATAAAGCTTCAAAAATAATTGTGACAAATTCAATGTCACTTTTTCTATAAATGTCTGCTAAAATAACATTATG
GTTTTTAAAATAGTGTTCTAATTATGAG (SEQ ID NO: 188)

>Right Transposon End for ACV01094.1
ATGATTATAAAAATATTAGTATGGATTGAAAGGCAGCAATACGGATGCAAAATGATGACATTTAATTTGTCACTAAAGCTTAA
ACGACAACAATTGGTCACAACGACAATTAAATTGTCTCCATGACACTAATCTGTCATCGATGACAAATAATCTGTCACTGTACA
ATAGTTCGTCAAAATGTAAAGGCCCGAGTCTAAGCCTATCACAAGCATCCCGTATTGCTGCTACCTTCCAGTCCTGACAAGAT
TTGGGCGTTGTAATCGCATAGGTCCGAGCCAATTACTAGGATAACACAGAACTGAGGCACTCACTCTTGATCGTTGTTCATAAT
TTGAGGTACGCGGAAAAAGTCGCCCTCTTGTTCTGGGGCACTTTTAAGCAATGATTCGCGATCGCCATAGGTTTCTGTGCGATC
GCTGCGGGTAATATTGCTCAATTCGATCGCGTGTCATTGGGGGGACATTTTCGGTGTCAAGTTCGCTTAACTGATCGAAATA
TTGCAAAATGCTATTTAATTGGGGGGCAAACGCTTCTTCTTCGGCTGGTGTAATCTCCAGTCGGGCTAAATGGGCGATTTTTC
AACTTGTTGGCGATCAATCATCGATGGTTTCTCACTCTGATTTAAAAGAAGACATCCATTTCAGAACGTCCAGTCACCTTGAGC
CAATTTTGGGCTTCAATATAGTTATTGG (SEQ ID NO: 189)

>Left Transposon End for ODH02164.1
GAACCAGCTTCCGTAGGCAAAGATTATTCAGACGAAGCAGTATTAAGGGATTTTTTCTTTCATGATTGTCAACCGGATGTAGCA
CAGTGGGCAATCTCGAAAAGTCGTCCGCAACAATCTATGGCATATATATTTGAAACGAATCCTCTAAAAGCTTTGCCGCATGTT
GAGCGTAAATATATTGTTTGTAGCAACGATCGCATAATATCTCCTACATGGTCGCGCTACGCTGCACGCAAGCGCTTAGGAGTC
GATGCCATTGAGCTACCTTCTGGACATTGCCCACATCTGTCTCGTCCTGACCTTCTTGCCTCAATATTAACTAGTAATTAATTT
TTTGATCCTATATTTTAGGAAATTAACCGAAGCGTATTGAGTGTGAACAAGGGAATATCTTTGAAATTTTAATTCGGCATAGACG
AACGATATTATCTAATTAATAACGACATGAATTTGCAAATTGCGACATTGAATTTGCGAATGTACACATGGTGTCCATTAAATA TABLE 9-continued Non-coding Transposon End Sequences of Representative CLUST.004377 Systems ATTATTGTCACTTTTAAAGAATTATTGTCCAGTTTTACGATATCTGTATAACAGGCTCAAAGGCTTACCAAACAAGTCTTTGAG
CTATATTTATACTTTTATTATTCTCTAGCCAGTTTTAAAGTAAATGATGTCATTTTTCTGATAAATTTTTAAAGTAAATGATGT
CATTTTTCTTGGAAGACGGGTCAAGTGT (SEQ ID NO: 190)

>Right Transposon End for ODH02164.1
TATGATCCCCGAAGTAGGCGCTTTGGTTATATAATTTTGTATTAGGGTGGTTTGAAAGGAGTGCTGCGATCGCACGTAAAACGC
AGCTATGTAGCAGTGGAGCCTCTGCTTGGGTGAAAACAGCAAAACAAGAGGTAGTATATTTTTGTAATTAGACTGCAAATAAAG
GGCTTTAAAGCTACTCTTGTAATTCAATAACCTTGAGCCTGCTGTAATAAATTAAATTAGTAACCATATATTTAGCCGAGTTTT
ACAGGCTGATTTTGGACAATAATTCTTTAAAACTGGTTTCAACTCTGGACAATAATTCTTTAAAACTGATTTAATTGCTGAAAG
CCGCGAAAATACGTAACTTATGCCCCTGAACTTGGAAAAAATGGACATTAATTCTTTAAAAGTGACAATAATTATTTAATGGAC
ACATGGAGAATAACGGATTTGAACCGATGGCCTCTGCGGTGCGATCGCAGCGCTCTACCAACTGAGCTAATTCCCCTTGA
(SEQ ID NO: 191)

>Left Transposon End for BAQ63841.1
GTTTTCTCATCCTAATCAACGGGGCTAAATATACTATATTATAATATCTATAACTAAAGTGTGGGTACAATAAATAAGCTAAAG
TCCATTTAAGTTTAATACTAACTGACGATAAGCCGTCTTGAATTTTTGTAACTCATTCATACCTTCTTGAAGAGTTTTAATATA
TGAGAGTCTATGATTAATGTTAAATAAGAATGCCACTTAGCCACTTAGTTTTTGATCTAATTTCAATTAAAGGTAATTTGAGAG
AAAAACACACACTATCAGAAAGTGGACGAGAAGCTCTATTTTGCTATCCTTGTTTTAATTTTGGCAGTAATTGTTTGACTACTT
ATTAAAATAAAATTGATGGAAAAGTTAAAAATCAGTCTGAAAATGCTTTTGAATAACTTTGATAAAAAATCTTGTACAGTAACA
GATTATTTGTCGTGATAACAAATTCGTGTCATCTAAAAATAAGACTCTTAAAATCCTTATATATCAACAATTATAACTTATCCT
TACCCTAAAATCACACTCGATTGTATCTTAAAATAGATTAACAAATTAAGTGTCATTTTCCCTAAAAATAACAAATTAGATGTC
GCCTTCGGAAAAGGCGATTTTTTTTGTTTTTGAGTGGCAATTCACAGATTAAATGTCATAGAATAATAAGTACACATCAACTTT
GATTTTATTAAACATAAAAATATCAGCT (SEQ ID NO: 192)

>Right Transposon End for BAQ63841.1
GCTTTTATTTTGAACTAAAACTCTACTAATTAGAATCTGTCATCGAGACGAAACAAAACGATCATATTTTCTTTTTAAAGTTAT
AATTTCAATAGTGCCGTAGATCAAGTTTTAACAACCTCTGTTCTATGAAAAATGAGGAGTAGTTTACTTTTTACAAGAAGTTTG
CTTTCGGCTCCTGCTAACTACTTGCCCTGATGCTGTCTATCTTAGGATAGAGAAACTAGGCGCACTCCCAGCAATAAGGGTGCA
GGTGTACTGCTATAGCGGTTAGCAAATCACTTTCGATCGAGGAAGAATTCTCTTTGAGAATTGAAAGCGAGTCCTGTCGCACCC
AATCATTTAGACGACATTAATCTGTTATCACGTCATCTAATTTGTTAAGACGACACTAATCTGTTACCGATGACAAATAATTTG
TTACTGTACATCAATTTAAAATACGAGCCAACGGCTAAGTAATACACGGGTGCGACAGGACTCGAACCTGTGACCGACTG
(SEQ ID NO: 193)

>Left Transposon End for WP_012596241.1
TCATATTCCTGTTGATAAGACAGGCGTTCTCTTGCTGCTGACTCCCCTTGAGATTGCTTTAAATCGTCAATTAACGCCTTTAAA
ACCTTTTTAATCACCGTAGCCGTCACATTTTCATCCTCTTCCGGCTCATAACTCGCCACCTCTTGCGCTGACTCCACCGCTTCA
CTTAACTCCCCTTGCGCTGCACTAATTTTACTCTCTAACTCTTCAATTTGCGCCTCCTCAGCTTGAAAAAAGGCAGTTAACAGA
TATTCATCAGGAATAAGGGTGTGATGCCAACCTGTATTAATAATCGTCTTCAAATCATAGCGAATCTGTTGCCACCAGTTAACA
AACACCCCCGCAGACTTAAACTCATCCAACACCCCCAAAGGAATAAGCTGCTGTTTCAGACTGTCTAGTAACTCTTGCCGGTGT
ACATTCACTAATTAAGTGTCGCAATTTGACAGATTAATGTCGCAAAATAAATAAGCTGTAAACCTTACACGACAAGCATTCTAG
CATTTTTCAGGGACTGTATACAAAAATGCTTGATTTAACGGATAATCTGTCGTAAATTAGATTCTTAATGTTTTATCTGTCGTT
TCTTGGATAGATAGTCAAATTGCTGGTCAACATTTTTTCATACATTAATTGTCGTTTCTTGGAAAAGAGTCTATACTATGGTTA
GTTCGTTTGTTGGATTCTATGCTAACTC (SEQ ID NO: 194)

>Right Transposon End for WP_012596241.1
TTGGGATGGGTTGGATTCATGATCATGTTCAAACATCGAGAAGGATTGAAAGGCGCACTTCGTTCGGGATCGTAGACTTATAAA
AATATTCGATCCCAAAATAGCGACACTTAATGTCTGAACAATTGTCCATTAAATAATTATTGTCACAATTAAAAAATTAATGTC
ACTTTTTTGAGAGAGTTTTAAGATACCGCAAGGTTCTGTTAAATAAAGCTTTCAGCGATTGAAAAGAGTTATATCCTGTCAATT
GTCATTTTAAACTAAAATGTGTCACTTATTAAAAAGCCTTGCTAGAATCTTTAAAGTAAAATATGTCA
(SEQ ID NO: 195)

>Left Transposon End for BAQ60380.1
TTATCAGCTAATTCTAAACGAATACCATCAGGAGTTTTAATTTTTTTGCCTTGAGAAGGTTGCCATATCTCCTGCAACCAATCA
CAAATAAGTTGAGAATTAGGGTTAGGAATTTCTAAATATAAAATTTCTTTTAGTTTCATTTATATAAGTACTTGATAAAAATAT
TTAGTTATTAATGAGATGATTTGATTTATTATCTAATAATAGGAGTCTCTTCGCCAAGAGAACAATATCTGAAGATAAACAGCC
AGGATTAAGAAATAGCTGATCCAGAAATGATCCAGTTTTCTAATTTTGAATGAAAACAAAAATATGAGAATAGCAAATATTAAT
AAATAATAAATGATCTAGCAATTATCCAGTTTTTTAATCAACAATAAAACATCAAAGAAAATAATCAACAATAAAACCTTAAAG
TGTAGAGATGGATGATGTACAGTGCCAAATTAAATGACATGAAGCCAAATTAGTGTCGTTGGGTTTAATCCTTATTATCTCTAC
ATTATAGTCTTTTTCTCTAATTTACGAAGCTAATTTTAAATGACAAATTCAATGTCGTCTTTATATTTAGTGACAGATTAAATG
GCATCTTTTCAAATATTCTTTTTTTTTGACGGTGACAAATTCATCGTCATTTTTTATTTACTGTGTTAAGATAACATTATGTTT
TTATTTAACAATTATACTATTTAGAGTG (SEQ ID NO: 196)

>Right Transposon End for BAQ60380.1
TATAATAAATTACAGGAAGGACGTATAGCTCAGTTGGTTAGAGTACATCGTTGACATCGATGGGGTCTCGTGTTCGAGTCACGA
TACGTCCATTTATTTTTGTACAGTGCCACATTAATTGTCATCGGTGACAAATTAATGTCGTTATGCCAAATTCTTGTCTTTTAA
TAAGCAGTGACAAATTAAATGTCGTCTAATAAATTTGCCTTGTGGTTTGTTTCGATGGTGGGAAATTTAATTTTTATTTGTGA
CCCCATTGATGTCCTTTCAATCTATCCTAAGTCGATTATACTGTATTGATTTATTTCGGCTCGATCGATCATTAATTTTTTGTC
TTACCCTAATTTGATCGTTGCTCAGATATTTTCAATCAACCCCAAAGGGAAACTTGATTGAAACCATCAATGGAGGCAATATT
CCCCGATTAGATAATTTTTCAATCAACCCCAAAGGGAAACTTGATTGAAACCCGTGCTTCGGAAGCCTTATACAGTAA
(SEQ ID NO: 197)

>Left Transposon End for WP_017289534.1
TCCGAATTAAGGATGGAGCAATTGTCGCGGCAAGAGTAGATACACAAACGACCCTGAAGTATTTCTACCGACAAGGAAGCGAAG
TCATTTTGAAACCTGCAAATGCTGCTTACGAACCCACCGTAGTTGAAGCGAACCAAGTAGATATCCAAGGGATGTACGTAGGAC
TGATACGGCGACTTTGGGAGAACGGTGAGCCATGACTTATAGTGCTTGCAATATCGATATTGATCTGCCTGATGAAGAGGCGGC
AGTCGATTTCGAAGACTGTGGCGATGCAGAATACGAGGATTGGCTCGCTGATTATTACTCGGATTGGGCAGATTTCTATCAACA
GGTGTCCGATGCAGAAGATGCCTTTCGACACAATTTAATAGTGAAGAATTATGAGTTTCAGGCACGCGGTGGCTTTTTACCGGG
GGACACTGTAATGGCGGAAGTCGAACCAGGGTATTGGCATCACTGCACCGTCCTCTTAGTAGGGATATCGACGTTAGTGGTTAG TABLE 9-continued Non-coding Transposon End Sequences of Representative CLUST.004377 Systems TGCCGAGCGATCTACAACCGTTCAAGTCATAACTCAACTCAACACGTATTGGCTCGACTAGATCTGATTTTGGAATTCGCTCGT
CTTGCGATCGCTTCAAATAGTTAATTTGTATTAATTTTCCTGTCTAACAGATTGACTGTCGCTATTTCTTCCTCATAGGATTAG
TGCAGTTCCTGATAGGACTTATGTACTT (SEQ ID NO: 198)

>Right Transposon End for WP_017289534.1
AGTAACTTAGTCTTTTGACAACTTTAATAGGCACAATCTTTCGGTTAACAGTGGGTGGATTGAAAGGACTGCCTGACTCGGGGT
TTTAATTTAGAAATATTTGCCCCTCGCTATAACGAGCAGAGTTAGCATTCGTTTTAACTGGGTAGAGTCTGTACTGTAAAATGT
TGAAGTGGATAAGAATTTGAATGAGCATTCAACTGCTTGAAGCTCTGATGACAAGAATTTGTTAACGAATGATTTCTTACCCCT
CGACGACAAGAAGCTGTTAAAACGACACTAAATTGTTAACGACGACATCAATCCGTTAACGACGACAAATAAAGTGTTATTCGA
CAACAATCACACGAATTTAAACAAAAAATTGCCTGACTCTTAAAAGCCCCCAGAGTCAGGCAGTCTACCTGTAAGGCACGCCTT
TAACCGGATACACCAAACAAACTTAGTTGCCCCCTAGTTGCTTAGCTTTTCCGAGTGCGTTCCTCAGATTTGAATCTATT
(SEQ ID NO: 199)

>Left Transposon End for WP_012411901.1
TTTTTATCTCCATGGGAAATCCAGCAACTGGGGGAAGATTCTGCGGCGAAGCGGAGTGGCTGGTGCGGGCTGCTACCATCTTAA
CCAAGAGCCACAAGTCTTTTTGCCCGTACCAGCCACCGCAGAATCTAGCGCAGCGTTCCACAGTTGCGTCAATGTTAAGAGTAC
CGGTTTTTTGTTAACGATCGCTTGACTTTTAAGACAGTCGCTACAGAACTTAAGGTTTTTATGGCTAACTAAACCGTATTGGTT
TTTAGTTGAAATCGTGTCCGCTTAATCAACCTGAGTAAAAATGTCCTACTTTTAGCATGAACTTTCTGAATTCCTTGATATCCT
TTATCACCAAAGTATTCAATATTTTCTCTTAACCGAACTTTACTGTTTTTAAGTATGCAAAAATTATTGTACATTAACTAATTA
TTTGTCATTGTACAAAAATGTACAGTGACTAATTATATGTCGTCGAGACAAATTAATGTCATCCATTAAAATCTTGCTCGGTAT
AGGTTACAGCGTTTTAGTAGTATTAGGATAACATCTTGACAGTGACAGATTAGCTGTCATTTTGGGTAATAGTGACAAATTAGC
TGTCGCTTCATCAGAGATAAAAAAGCTTTTGTGTATTTTCATAATGACAAATTGACTGTCGCTTTCTGTTTAAGTAGAATAACA
ATATGTTTTTATAAAAAAGCTTCGCATT (SEQ ID NO: 200)

>Right Transposon End for WP_012411901.1
GCAAATCTGAAATCATTACGCACGCATACAAAAATGTTTTAATAACCTGCCAGGTACTAGGTGGGTTATCATAATTTTTATTAG
GGAGGGTTGAAAGAGAGCGCTACGTTGACATTATCGCTATAGTCTCTGTAAATAAATGACATTAATCTGTCACTGGCACCTAAA
CGACATCAATTCGTCCCGACGACAGTTAATTAGTCCCAACGACATTAATCTGTCACCGACGACAAATAATTAGTCACTGTACAA
AAAAAATGGACGTAACTGGATTCGAACCAGTGACCTCTACGATGTCAACGTAGCGCTCTAACCAACTGAGCTATACGTCCTTAA
CCACACGAATATTGATAGTAGCATATACTTTTGCGATCGCACAAGATAAAGACCCAAGCTTTTTAAGGGGGTTTTAGATTTTGA
GTGCGTAAATCCTAATTTCAAATAAAATCCTTATTATTTCGTTACAATCAGCTTGTGCGTTAAGCATTCAAGAGTTATCA
(SEQ ID NO: 201)

>Left Transposon End for WP_011318008.1
CAATGGTGGCTTGCGACAAATAGTCATTAATCTGCTACACAACAGCCTCAAGTTTACAGCCAATGGTGGTCGAGTGTGGGTGAG
AGCTAGAGTCCAAGGCGAATACGTCATACTAGAAATTCGTGACACAGGTATCGGTATTGCTGAAAGCGAAATTCCCAAAATATT
CGACTGCTTTTATCGTGTGCGATCGGGACTAATTGATGAGACGAATGGCGCAGGTTTAGGACTCACAATTGTCCAGAGATTGTT
ATGGCATTGTGGTGGTTCTGTTAATGTGAGAAGCAAGGTTGATGAAGGTACTATGGTAATAGTGCAAATGAAGATAGGAAGCAC
CTCGCCAACTTAGATCCGGAAAACGGGGTGAAGCGATCGCCTGTTGGTTGACAACTGCACTTGTAGAGCGACAAATAATTTGTC
GTTCTACAATTGTCGATTGCCAAATTATATGACCACTTGACAAGTTAATGTCATTCAAAATATTATCCTCAAAACCCTTGCCAA
GCAAGGGTTTTGTTATTTTAGGCTCAAAATACCCAGAAACTTATTGCCAAAATAGCTGTCCTCTTTTGAAAAGTTGACGAAATA
TCTGTCCTTGCTTGAAAAGGGACTTGAGGGAAGATTTTTACAGAAATTGACAAAATAAATGTCCTCCAAGTAGTACAATACAAC
TACGTTTTTATTGAACATTTATGTAAAT (SEQ ID NO: 202)

>Right Transposon End for WP_011318008.1
ACCTTCATGCAAGGATATAAAAAATTTTAGGTGGGTTGAAAGGCGCACTTCGTTCGGGATTTTCCCTGACCGAAACAGTACCAA
TAAATCAAAGCTATTATAATAACAGCTTCTAATGCCAATACACCTTGATGACTAAGTAATTTGGCAACGCGGACAACAACTTGG
CAATACGGACAACAATTTGTCAACGCAGACAAAGAATTTGGCAATCAGCTCACATGTTACATGTTCTGTCCATCAAAACAGCGG
CCCCTTCGTCCCGAACGAAGTGCGCTACCAAGCTGCGCTACATCCCGTTAAAAAATTTATACGCCTTTTTTAGCATAACATAAA
TAATAGTCAATACAGAAAAGACATCTACATCTATATATATAGATGAATCGGAACGGGATTTGCTTGCTAGGATTAGATTTGTAT
AACATTCAGTGGTAAAAGCGGATTGTGACTGTAAAACCAGACTGGTTGCGGGTAAAAGCGCCTCAATGGGAGCGCGTTGG
(SEQ ID NO: 203)

>Left Transposon End for AFZ00435.1
AAAGCAGTAGGACTATTATCTGCCCATATCCACAGTAATCCTTGTAATACTTGAGTCGGATATGTGGTAATTTGCGATCGCTCG
CTTTTACAAGCAGTTTCTAAAGCCTTTTCATCGCTCAACATGGGAATATTTGTACATGTTCCTGTCCCATCAAAACACCAACCA
TGATGGCGACACATGATGTTGCCATTTTTGTCAATACTTCCTAAAGATAACTGCGCTAATTTATGGGGACAAACATCATCCATT
GCCACCCATTTTTGCTGCTTATCTCTCCAAATTACCAGATTTTTACCCAGCAAAGTAATTGCAGTGGGATGAGAGGGTTCTAGA
TAGCTGATAGGAGTTACAGGATACCACTGTTTAGTCCAGGAAAAGTTAGTCATCATCAAATTAACTAATTTATTCGACTCAAAT
TTGAAAAATGAGTAAAAAGCGGCATTTAATGTGCGAATGTTGTACATTCGCACATTATATGTCGCTTTTCGCAAGTTAGGTCGC
AACCGCATTTAACTGCTATAAACCCTATTTTACAAAGGTTTGATGCTCTTAGCACATCAAGCCCACGAATTTACTTAATTCGCA
TATTCCATGTCGCAAACTAAATATTCGCAAATTGAATGTCGTTTATTAAAATTTGTCACTTCGCAAATTGTTTGTCGTATTATT
GAGCGATTCATGGTACATTGGTACTCTA (SEQ ID NO: 204)

>Right Transposon End for AFZ00435.1
TTGAAAATCTAAGAGCAACTACACTATAGATTTATTTAGAGGGTTGAAAGGAGCATCAGACTCTTAATTTAAGTGATAGAGATA
ATATTTAAGCACAGATATATTTCTTACTCAGCAATAGCATTTAGTATTTGCATGGAAATAAATAGCTTTGAGACAACATTAATT
TGTTAACGATGTCTTTGAGGATTTAGGGGACATCAATTTGTTAAAAAAGACATTAATTTTGTTAACGACGACAAATTATTTGTA
ATCGACTTTAGGACAAATAATTTGTCGCTTTATGTACTTTGACAAATAATGTGTCGCTCTACATCAGTTAATCGACAATAACCA
AGCGACGTTAATTTGCGAAAACCTATAATCATCAATATAGTACACAAATCTGTCGAAAGCGACACTAATTTGCTAATAACGACA
CTAATGTGCGAAAAGCGACATTTAATGTGCGAAAGTACAAATGTACAAATGGGCGACCTGGGGCTCGAACCCAGAACCAGCAG
ATTAAGAGTCTGATGCTCTACCATTGAGCTAGTCGCCCTCACCATTTACTACTATAGCAAATTATTTGAACAATAGTTAACCTT
TATCGGAAAATCTTCATATAACTAGTTGACATTAGCAAACACATACCCTCTGATGCGGATAAAACTTGCTCATACAAAATCAAA
ACTAGGTAATAGCACCACTAATTATACT (SEQ ID NO: 205)

>Left Transposon End for AFZ56196.1
AGTCAGGAGTCAGGAGTCAGAAAGAAGAATTAGAAGGAGATCAGAATATTCTCAAATCTGGGTAAATGAACTATTTTTGATGCT
TTCATCGCTTATTTCTTGCACCTTCTCCAACTTTTTCAGCCTGAGACTGTTGATATATCTATGTTTTTGGTTTATTAAGCAAAC TABLE 9-continued Non-coding Transposon End Sequences of Representative CLUST.004377 Systems

```
CCTAAGTACTATCTGCAAGGGTTTCAGGCATGATAGACCCCTTAAATTGTCATTACGAGCGGAGCGAAGTAATCACATAATGCG
ATCGCACCACCTCAAGCTAGATGATGAAACCAAGTACTAGTAGGAATTTTAAGACTTGTGTGTACACCGTAGATTATTGAGTAG
GGGCATCTAACGATAACGAATAATGATAAATACCGTAGTGCAATATTATGCTACAGGAAACTTAATCAGTGTTTACATAATTTG
TGTACATTAACTAATTATTTGACAATTTAACAAAATATTGTCAAAAATCATAAAAATACCTTAAAACCTTCTACAGCAAAGATT
GTAGGAGGTTTTTATTTATCTAATTTGTGAACATCCTCCAGACATATATTTAACAAATTAAGTGTCAAAAGCCAGATAATTATC
AATTTATTTGTCAATTTGCCAAATACAGGTAAATTACTATATTTCTGAAAATTTCACACATTAAATGTCACTTTTACTCTATAC
TATACAAATATGTTGTAATTAAACATTA (SEQ ID NO: 206)

>Right Transposon End for AFZ56196.1
ACATTAATGCAAGTAGAATAAAAAATATCTAGGTGGGTTGAAAGATCAGTAGGTCGTGGGTTTAACTCTGAAAACACTTGAAAA
CACTATATAAATACAGTGTTGCTTGTGACATTTAGGGACAATTAATTTGTTAACAGTGACACGAATTAGTTAAAAATGACATTA
ATTTGTTAACAGTGACAAATAAATTGTTAATGTACAGACATATAGTGTGCGAATGTACACCAAAGCCGATGATGGGATTTGAAC
CCACGACCTACTGATTACGAATCAGTTGCTCTACCCCTGAGCCACATCGGCATACACAGTTTGATATCATAGCATTATTTACCT
ATGATAGACCCAAATTCCCAAAATCGTCTTAACTCTAAACAATATGCCCACCTGAAAGCTGAAATAGCAGCCCCTTATCGTGGT
TTGCGGCAATTTATCTATATAGGTGTTGGTGCTTCTGGTTTTATCGGCGCATTCACCTTCTTTTTTCAACTGCTTGCTGG
(SEQ ID NO: 207)

>Left Transposon End for BAB75312.1
CATTGGAAAACAGCGAACAGTGCTTTAGCCAGAATCAGAACAGCATTTGATCGGCACAGTCTTAAGCCATATACTTTTTTTGTG
GGATCTGCTATAGAAAAAAGCATGGCAGAAGAAATTTGGCATCAACTAAATTCTGGCATTCTTACTAATGCAGCAAACCTCACT
CAGCCTGACCAAGTTGCCTCTTTGTGCGCTTGGTTTATTCAACTTTGATGTACAGTGACTAATTATTTGTCACTGTACACAAGA
TGTACAGTGACTAATTATTTGTCACTGTACACAAGATGTACAGTGACTAATTGTTTGTCGTCGTGACAAATTAATGTCGTCGAA
TGAATCCTTGCAATACAAAGGTTTTAGCTATTTAAGAGTTATTACATTATTTCTCATACGTGACTAAATAAATGTCGTTTTCCG
CAAAAATGACAAATTAACTGTCGCTTCAGTAATTACAAAAAAGGTTTTGTATATTTTCATAATGACAAATTGACTGTCGTTTTC
TCCACGTTTAGAATAACATTATGTATTTATAAATTACCTTTGTTTCATGAACAAAAAATCTTATGTCTGATTTTACTGTTCATA
CCGCAGTGGATACTGCGGAAGCTTTATTACAAGACAACAACACACCTCCTCACCTCCTGAGACGAATCTGATTGTTACAGAACT
CTCAGAGGAAGCCCAACTCAAGCTAGAG (SEQ ID NO: 208)

>Right Transposon End for BAB75312.1
ACATGGTGAAAACAAATTGGATATGAAACTGCCTTACGTTGTCTGATGGTGTAATTAATTTCCAAGAAGTAGAGGGTTGAAAGC
AAATCCCGTCATCGGCTTGTAACTAAAGTTATTCAGGATAAGCTACTCATAGAAGTGATTAAAAGAGCTTTTTGAATGCAAACG
CTTATAATAGGGGCTAAATATATAGAGAAACTCCATATATAAATTGTTGCTTTTCCGAAAAATGACAATAATTTGTCACAAATA
TATATGGAAGCGAGTTACTAAGTTGGATGACAATAATTTGTCACAACGACATCAATTTGTCACCGACGACAAATAAGAGACCAT
TTATAAAGTAAATCTTTAGACGACTAGACGACGTAGCATAATACGAGTCATAACGGCATATATGGCAGCCTCACTCATTTCTGG
GAGACGCTCATAATCCTTACTGAGACGACGGTACTGGTTTAACCAGCCAAATGTTCTTTCTACTACCCACCGTTTGGGCAAAAC
CTGAAATTCTTGATTAGTACGCCGGATTACCTCAACATGAGCTTGAATCATCAGCCAAACAGAGAGCGCAAATTTATCACCGTC
ATAGCCGGAATCAACCCAGATGACTTCAACTTTTTCCAGTAATTCTGGACGCTCTTCTAACAGTTCCATCAAAGTATAGGCGGC
AAGTAATCTTTCTCCAGCATTTGCTTCACTTACAACCACTTTTAACAAAAGTCCCAGACTATCAACCAAAGTTTGCCGCTTTCG
TCCTTTTACCTTCTTGCCACCATCAAAACCGTACACATCCCCCTTTTTCAGTCGTTTTTACCGACTGGCTGTCTGCCGCGATC
GCCGTGGGTTGAGTTGACTTCCCCATTTTTTGACGAACTTGATCGCGCAAAGTATGATTCATTTGCTCCCAGATACCTCGTTTT
TGCCATTTACGATAGTAGCTGTAAACAGTTGAACTAGGAGGAAAATCCCCTGGAAGCATATCCCACTGACAACCTGTTTTCAGA
TGGTAGTAGATAGCGTTGCATACTTCTCGCATATCAGTTGTTCGGGGATGCCCACCGCATTTAGCGGGTGGAATCAAAGGAGCT
AAAATTGCCCATTCTGAGTCATTAAGGTCTGTAGAATAAGACTTTCGTCTCATTGTTTCCTATGTAAATACACTCTACAAACAG
TATCTTATCGCTGCCTTTTTATCTGATAGCTCTCCTTTAGATTTACTTTATAAATAGCCTCTAATTTGTCACTGTACACAAGAA
TTAGTCAAGACAAAAATATGATTTTATGAAAACCAAGCCG (SEQ ID NO: 209)
```

Figure 18:
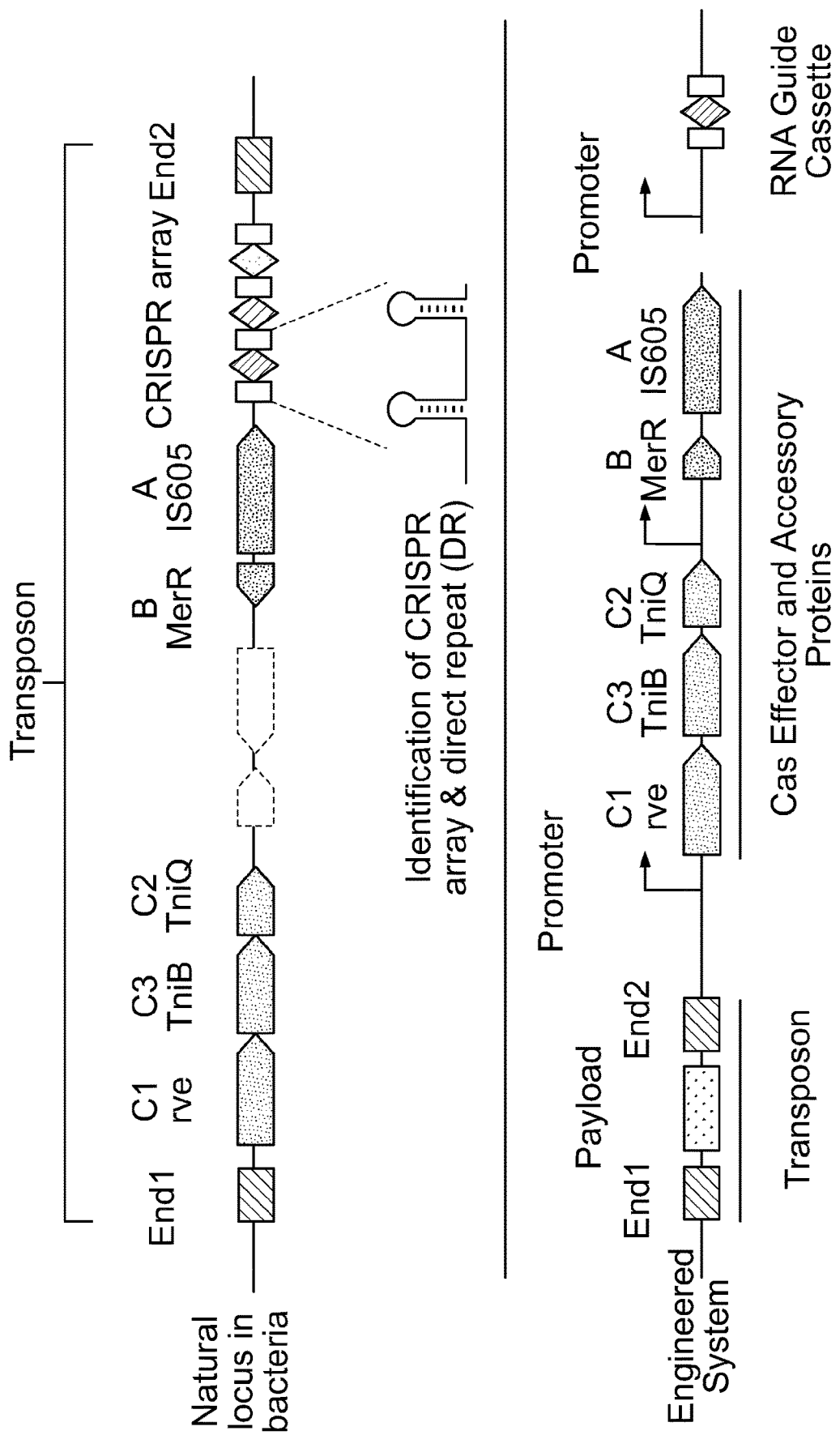
FIG. 18 shows a schematic of natural and engineered components for the CRISPR transposition system of CLUST.004377.

Example 2—Design of Engineered System for a CLUST.004377 CRISPR System (FIG. 18)

Having identified the minimal CLUST.004377 CRISPR-Cas system components, we composed an engineered system for transposon excision, mobilization, and programmable insertion (FIG. 18). Minimally, the natural locus consists of a left Tnp end flanked on the right side by effectors C1-C3, and a right Tnp end flanked on the left side by effectors A-B and the CRISPR array. Transposon cargoes ranging from approximately 2.5 kb to over 25 kb in length are located between effectors C1-C3 and effectors A-B. These cargoes are composed of CDS and non-coding sequences. In some embodiments, the Cas Effector Cassette of an engineered CLUST.004377 system is composed of effectors C1-C3 under the control of a single artificial promoter, followed by effectors A-B under the control of a second artificial promoter. In some embodiments, the Transposon Payload Cassette of an engineered CLUST.004377 system is composed of Tnp ends flanking nucleic acid cargoes ranging from approximately less than 100 nt to greater than 25 kb (FIG. 18). In some embodiments, the RNA Guide Cassette of an engineered CLUST.004377 system is expressed under the control of a single artificial promoter. In some embodiments, the RNA guide may consist of a minimal CRISPR array containing two or more direct repeats and one or more spacers. In some embodiments, the RNA guide may consist of one or more crRNAs containing processed direct repeat and spacer components, and optionally a 5 fused tracrRNA component. In some embodiments, the RNA guide cassette contains a tracrRNA expressed under a second artificial promoter.

We selected the KV757663 locus for functional validation of the engineered CLUST.004377 system.

DNA Synthesis & Effector Library Cloning

To test the activity of KV757663 CLUST.004377 CRISPR-Cas system, we designed and synthesized a minimal engineered system as described above into the pET28a (+) vector. The synthesized system consisting of an Effector Cassette and acceptor site for an RNA Guide Cassette were included as the cargo region of a Transposon Payload Cassette. The synthesized combined IPTG inducible T7 and lac promoters were used to drive expression of the Effector Cassette, and each CDS sequence was codon optimized for E. coli expression and preceded by an E. coli ribosome binding sequence. A J23119 (Registry of Standard Biological Parts: http://parts.igem.org/Part:BBa_J23119) promoter was used for expression of the RNA Guide Cassette.

In tandem with the effector gene synthesis, we first computationally designed an oligonucleotide library synthesis (OLS) pool containing "repeat-spacer-repeat" sequences, where "repeat" represents the consensus direct repeat sequence found in the CRISPR array associated with the effector, and "spacer" represents sequences tiling the pACYC184 plasmid and E. coli essential genes. The spacer length was determined by the mode of the spacer lengths found in the endogenous CRISPR array. The repeat-spacer-repeat sequence was appended with restriction sites enabling the bi-directional cloning of the fragment into the acceptor site for the RNA Guide Cassette, as well as unique PCR priming sites to enable specific amplification of a specific repeat-spacer-repeat library from a larger pool. The library synthesis was performed by Agilent Genomics.

We next cloned the CRISPR array library into the plasmid containing the minimal engineered CLUST.004377 system using the Golden Gate assembly method. In brief, we first amplified each repeat-spacer-repeat from the CRISPR array library using unique PCR primers, and pre-linearized the plasmid backbone using BsaI to reduce potential background. Both DNA fragments were purified with Ampure XP (Beckman Coulter) prior to addition to Golden Gate Assembly Master Mix (New England Biolabs) and incubated as per manufacturer's instructions. We further purified and concentrated the Golden Gate reaction to enable maximum transformation efficiency in the subsequent steps of the bacterial screen.

Example 3—Functional Screening of CLUST.004377 CRISPR System (FIGS. 19-25)

Functional Screening for CLUST.004377

To accelerate functional screening of CLUST.004377 systems, we developed a strategy to derive the following functional information in a single screen: 1) crRNA expression direction and processing, 2) nucleic acid substrate type, and 3) targeting requirements such as protospacer adjacent motif (PAM), protospacer flanking sequence (PFS), or target secondary structure. We designed minimal CRISPR array libraries consisting of two consensus direct repeats, each flanking a unique natural-length spacer sequence targeting either the pACYC184 vector, E. coli essential genes, or an absent GFP sequence as a negative control. We also designed a bidirectional array library cloning strategy to test both possible CRISPR array expression directions in parallel.

The CRISPR array library for the was cloned into the KV757663 CLUST.004377 CRISPR-Cas system expression plasmid RNA Guide Cassette acceptor site such that each element in the resulting plasmid library contained a single library element and orientation. The resulting plasmid libraries were transformed with pACYC184 into E. coli using electroporation, yielding a maximum of one plasmid library element per cell. Transformed E. coli cells were plated on bioassay plates containing Kanamycin (selecting for the library plasmid), Chloramphenicol (CAM; selecting for intact pACYC184 CAM expression), and Tetracycline (TET; selecting for intact pACYC184 TET expression).

Figure 19:
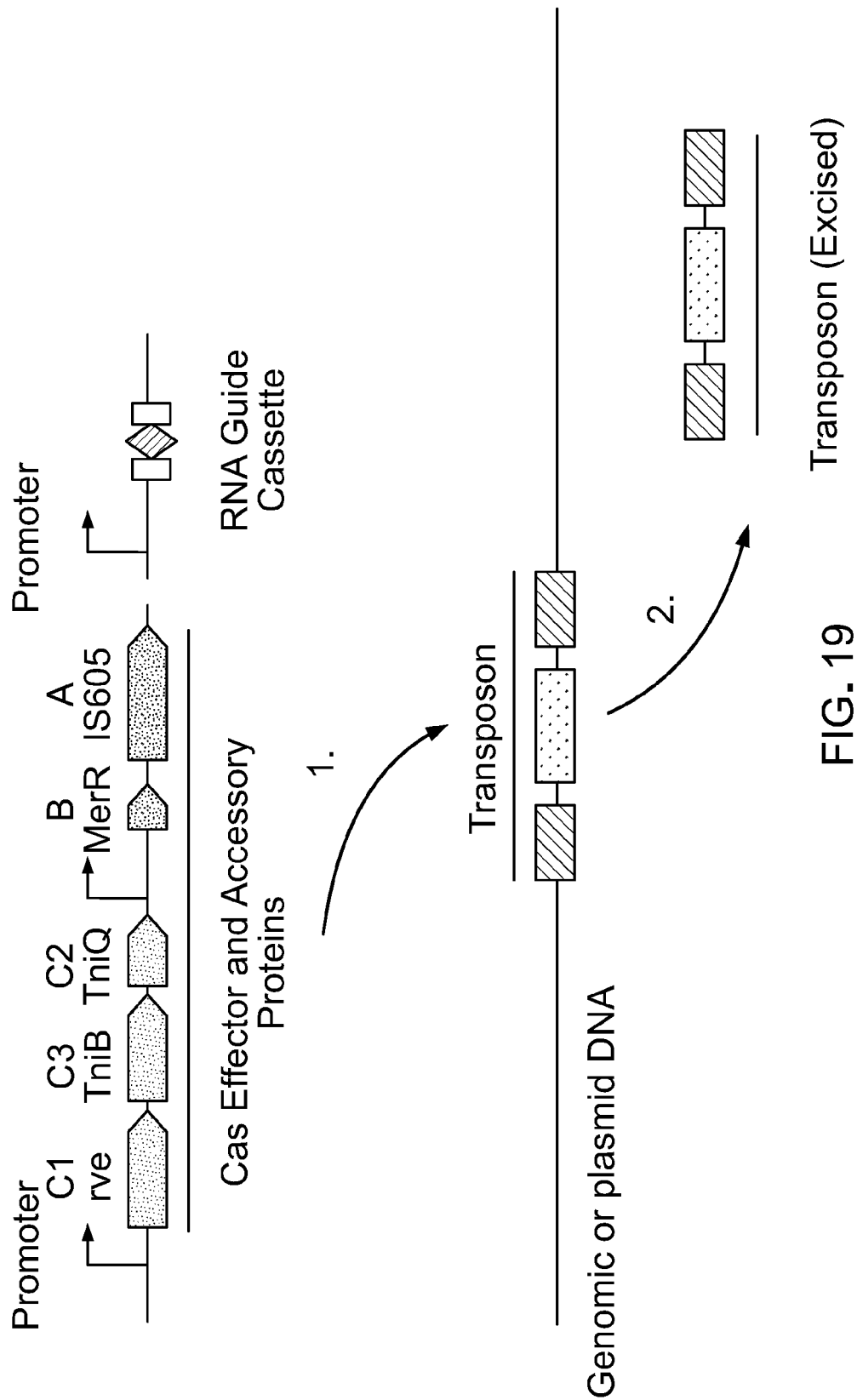
FIG. 19 shows a schematic of transposon excision in the engineered system of CLUST.004377.
Figure 20:
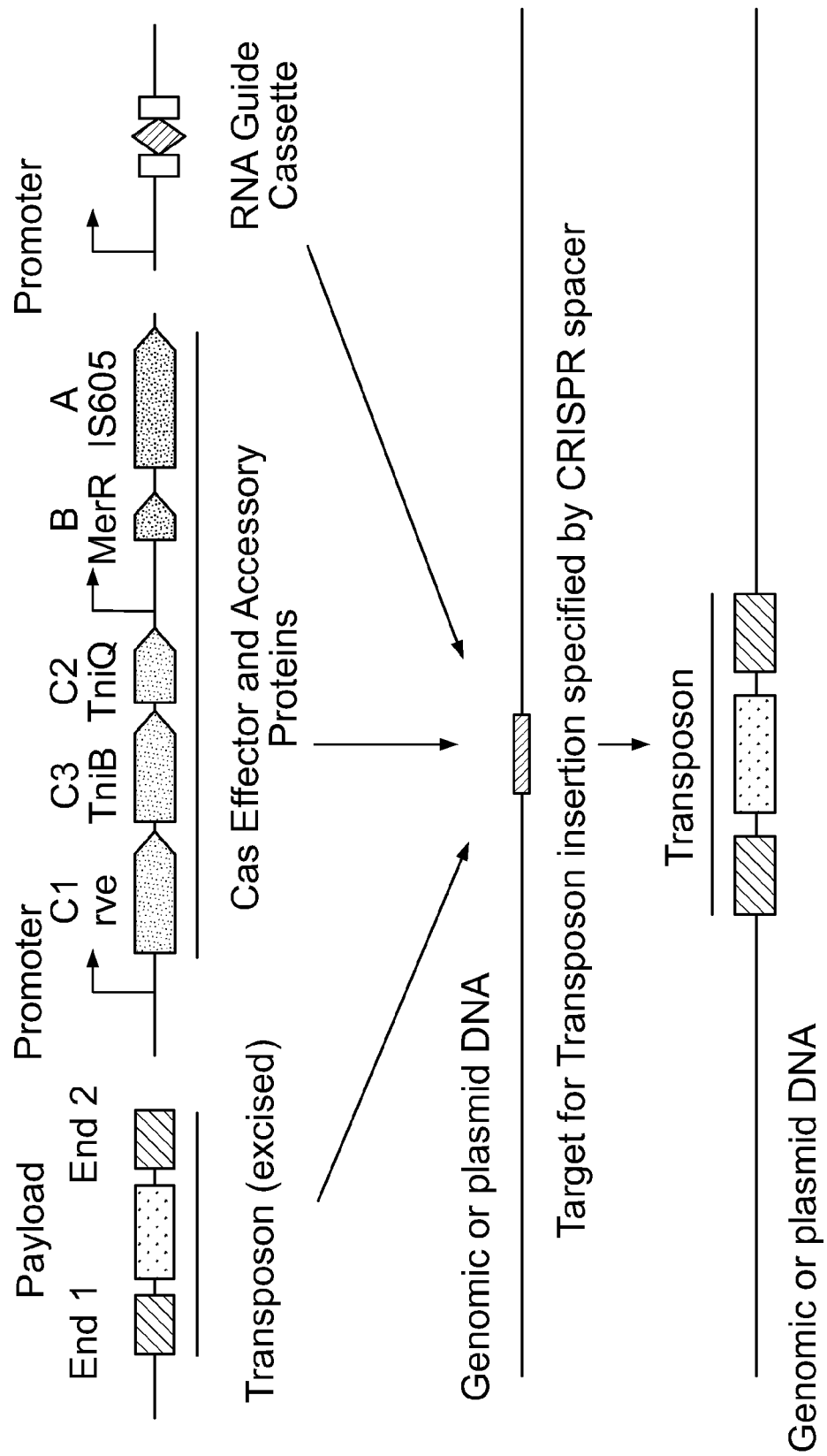
FIG. 20 shows a schematic of RNA guided transposon insertion in the engineered system of CLUST.004377.

Programmable mobilization and insertion of the KV757663 CLUST.004377 Transposon Payload Cassette was assessed as follows. Following transformation, the CLUST.004377 system mobilizes the Transposon Payload Cassette by excising it from the donor plasmid followed by programmable insertion of the mobilized cassette at a target site specified by the spacer sequence of the expressed RNA guide (FIGS. 19-20). Interruption of pACYC184 antibiotic resistance genes or E. coli essential genes by targeted insertion of the Transposon Payload Cassette by the CLUST.004377 CRISPR-Cas system results in bacterial cell death and depletion of the targeting RNA guide (FIG. 21). To investigate negative selection of RNA guides resulting from programmable transposon insertion, bacteria were harvested 12 h after plating, and plasmid DNA 5 was extracted. We PCR amplified the CRISPR array region of the input plasmid library prior to transformation and the output plasmid library after bacterial selection on antibiotic plates and compared the frequency of RNA guide elements in these samples to identify depleted elements (FIG. 21).

Bacterial Screen Transformation

The plasmid library containing the distinct repeat-spacer-repeat elements and Cas proteins was electroporated into Endura or E. coli electrocompetent E. coli (Lucigen) using a Gene Pulser Xcell (Bio-rad) following the protocol recommended by Lucigen. The library was either co-transformed with purified pACYC184 plasmid, or directly transformed into pACYC184-containing electrocompetent E. coli (Lucigen), plated onto agar containing Chloramphenicol (Fisher), Tetracycline (Alfa Aesar), and Kanamycin (Alfa Aesar) in BioAssay dishes (Thermo Fisher), and incubated for 10-12 h. After estimation of approximate colony count to ensure sufficient library representation on the bacterial plate, the bacteria were harvested and DNA plasmid extracted using a QIAprep Spin Miniprep Kit (Qiagen) to create the 'output library'. By performing a PCR using custom primers containing barcodes and sites compatible with Illumina sequencing chemistry, we generated a barcoded next generation sequencing library from both the pre-transformation 'input library' and the post-harvest 'output library', which were then pooled and loaded onto a Nextseq 550 (Illumina) to evaluate the effectors. At least two independent biological replicates were performed for each screen to ensure consistency.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source plasmid pACYC184 or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR of the input and output plasmid libraries. We define the array depletion ratio as the normalized output read count divided by the normalized input read count. An array was considered to be strongly depleted if the fold to depletion was at least than 3. When calculating the array depletion ratio across biological replicates, we took the maximum depletion ratio value for a given CRISPR array across all experiments (i.e. a strongly depleted array must be strongly depleted in all biological replicates). We generated a matrix including array depletion ratios and the following features for each spacer target: target strand, transcript targeting, ORI targeting, target sequence motifs, flanking sequence motifs, and target secondary structure. We investigated the degree to which different features in this matrix explained target depletion for CLUST.004377 systems, thereby yielding a broad survey of functional parameters within a single screen.

Bacterial Screening Indicates Programmable DNA Interference by the CLUST.004377 System Comparison of two bioreplicate screens for the KV757663 CLUST.004377 CRISPR-Cas system showed replication of depleted RNA guide elements for a single direct repeat expression direction (5' ACTT . . . AAAC-[spacer] . . . 3'). This indicates a specific interaction of the KV757663 CLUST.004377 effector proteins with a specific direct repeat orientation, and accompanying modification of targeted pACYC and E. coli essential gene target sequences (FIGS. 22-23). Targeting of both strands of pACYC and E. coli essential genes indicates DNA targeting is not confined to a specific strand orientation (FIGS. 24A-B). Additionally, localization of depleted targets to sequences either within or in close proximity to gene coding sequences is indicative of coding DNA interruption associated interference consistent with the interference arising from mobilization and programmable insertion of the Transposon Payload Cassette at or in close proximity to target sites (FIGS. 24A-B). In an attempt to understand targeting requirements for the CLUST.004377 system, we compiled all target and target-flanking sequences associated with depleted RNA guide elements (FIGS. 25A-C). Interestingly, while flanking sequences showed no evidence of PAM or PFS elements required for targeting, the KV757663 CLUST.004377 system shows a targeting preference for A and T-rich sequences.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Interspaced Short Palindromic Repeat (CRISPR)-Cas system comprising:
   (a) a Guide consisting of a direct repeat sequence and a spacer sequence capable of hybridizing to a target nucleic acid, wherein the Guide is CRISPR RNA (crRNA) or DNA;
   (b) a CRISPR-associated protein comprising an amino acid sequence that is at least 90% identical to SEQ ID NO: 19;
   (c) a CRISPR-associated protein comprising an rve integrase domain;
   (d) a CRISPR-associated protein comprising a TniQ domain; and
   (e) a CRISPR-associated protein comprising a TniB domain.

2. The system of claim 1, wherein the target nucleic acid is a DNA or an RNA.

3. The system of claim 2, wherein the target nucleic acid is double-stranded DNA.

4. A method of targeting and editing a target nucleic acid, the method comprising contacting the target nucleic acid with a system of claim 1, wherein optionally the method results in an insertion or substitution of DNA to correct a native locus.

5. A method of targeting the insertion of a payload nucleic acid at a site of a target nucleic acid, the method comprising contacting the target nucleic acid with a system of claim 1, wherein optionally the method results in a targeted insertion or deletion of a DNA payload into a specific genomic target site.

6. A method of targeting the excision of a payload nucleic acid from a site at a target nucleic acid, the method comprising contacting the target nucleic acid with a system of claim 1, wherein optionally the method results in a targeted deletion of DNA to correct a native locus.

7. The system of claim 1, wherein the system comprises a Mu-transposase.

8. The system of claim 1, wherein the CRISPR-associated protein comprises at least one nuclear localization signal or at least one nuclear export signal.

9. The system of claim 1, wherein at least one component of the system is encoded by a codon-optimized nucleic acid for expression in a cell, which optionally is present within at least one vector, which optionally comprises one or more regulatory elements operably-linked to a nucleic acid encoding the component of the system, wherein the one or more regulatory elements optionally comprises at least one promoter, which optionally comprises an inducible promoter or a constitutive promoter.

10. The system of claim 9, wherein the at least one vector comprises a plurality of vectors, and/or is a viral vector that is optionally selected from the group consisting of a retroviral vector, a lentiviral vector, an adenoviral vector, an adeno-associated vector, and a herpes simplex vector.

11. The system of claim 1, wherein the system is present in a delivery system, which optionally comprises a delivery vehicle selected from the group consisting of a liposome, an exosome, a microvesicle, and a gene-gun.

12. A cell comprising the system of claim 1, wherein optionally the cell is a eukaryotic cell, which optionally is a mammalian cell, such as a human cell, or a plant cell; or is a prokaryotic cell.

13. The system of claim 1, wherein:
   (a) the CRISPR-associated protein comprising an rve integrase domain comprises an amino acid sequence having at least 90% identity to SEQ ID NO: 54;
   (b) the CRISPR-associated protein comprising a TniQ domain comprises an amino acid sequence having at least 90% identity to SEQ ID NO: 80; and
   (c) the CRISPR-associated protein comprising a TniB domain comprises an amino acid sequence having at least 90% identity to SEQ ID NO: 103.

14. The system of claim 1, further comprising a payload nucleic acid flanked by transposon end sequences.

15. The system of claim 14, wherein at least one of the transposon end sequences comprises SEQ ID NO: 142.

16. The system of claim 14, wherein at least one of the transposon end sequences comprises SEQ ID NO: 141.

17. The system of claim 14, wherein at least one of the transposon end sequences comprises at least 100 contiguous nucleotides of SEQ ID NO: 177.

18. The system of claim 1, wherein:
   (a) the CRISPR-associated protein comprising an rve integrase domain comprises an amino acid sequence having at least 95% identity to SEQ ID NO: 54;
   (b) the CRISPR-associated protein comprising a TniQ domain comprises an amino acid sequence having at least 95% identity to SEQ ID NO: 80; and
   (c) the CRISPR-associated protein comprising a TniB domain comprises an amino acid sequence having at least 95% identity to SEQ ID NO: 103.

19. The system of claim 1, wherein:
(a) the CRISPR-associated protein comprising an rve integrase domain comprises the amino acid sequence of SEQ ID NO: 54;
(b) the CRISPR-associated protein comprising a TniQ domain comprises the amino acid sequence of SEQ ID NO: 80; and
(c) the CRISPR-associated protein comprising a TniB domain comprises the amino acid sequence of SEQ ID NO: 103.

20. The system of claim 1, comprising a CRISPR-associated protein comprising an amino acid sequence that is 100% identical to SEQ ID NO: 19.

21. The system of claim 1, comprising:
(a) the CRISPR-associated protein comprising an rve integrase domain comprises an amino acid sequence that is 100% identical to SEQ ID NO: 19;
(b) the CRISPR-associated protein comprising an amino acid sequence that is 100% identical to SEQ ID NO: 54;
(c) the CRISPR-associated protein comprising a TniQ domain comprises an amino acid sequence that is 100% identical to SEQ ID NO: 80; and
(d) the CRISPR-associated protein comprising a TniB domain comprises an amino acid sequence that is 100% identical to SEQ ID NO: 103.

* * * * *